United States Patent
Movassaghi et al.

(10) Patent No.: US 12,030,888 B2
(45) Date of Patent: Jul. 9, 2024

(54) HIMASTATIN DERIVATIVES, AND PROCESSES OF PREPARATION THEREOF, AND USES THEREOF

(71) Applicant: Massachusetts Institute of Technology, Cambridge, MA (US)

(72) Inventors: Mohammad Movassaghi, Lincoln, MA (US); Bradley L. Pentelute, Cambridge, MA (US); Carly Schissel, Cambridge, MA (US); Kyan Anthony D'Angelo, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/561,680

(22) Filed: Dec. 23, 2021

(65) Prior Publication Data

US 2022/0289750 A1     Sep. 15, 2022

Related U.S. Application Data

(60) Provisional application No. 63/153,286, filed on Feb. 24, 2021.

(51) Int. Cl.
| | |
|---|---|
| *C07D 519/00* | (2006.01) |
| *C07D 209/86* | (2006.01) |
| *C07D 487/04* | (2006.01) |
| *C07D 487/14* | (2006.01) |
| *C07D 487/22* | (2006.01) |
| *C07D 498/22* | (2006.01) |

(52) U.S. Cl.
CPC .......... *C07D 487/04* (2013.01); *C07D 209/86* (2013.01); *C07D 487/14* (2013.01); *C07D 487/22* (2013.01); *C07D 498/22* (2013.01); *C07D 519/00* (2013.01); *C07B 2200/05* (2013.01); *C07B 2200/07* (2013.01)

(58) Field of Classification Search
CPC .............................. C07D 519/00; C07D 209/86
USPC ........................................................ 540/460
See application file for complete search history.

(56) References Cited

U.S. PATENT DOCUMENTS

| | | |
|---|---|---|
| 4,197,311 A | 4/1980 | Wepplo et al. |
| 4,816,397 A | 3/1989 | Boss et al. |
| 4,816,567 A | 3/1989 | Cabilly et al. |
| 4,906,562 A | 3/1990 | Hellström et al. |
| 4,935,495 A | 6/1990 | Hellström et al. |
| 4,940,726 A | 7/1990 | Pettit et al. |
| 4,946,778 A | 8/1990 | Ladner et al. |
| 4,996,237 A | 2/1991 | Pettit et al. |
| 5,225,539 A | 7/1993 | Winter et al. |
| 5,242,824 A | 9/1993 | Hellström et al. |
| 5,338,845 A | 8/1994 | Barrow et al. |
| 5,409,953 A | 4/1995 | Pettit et al. |
| 5,423,753 A | 6/1995 | Fowles et al. |
| 5,430,062 A | 7/1995 | Cushman et al. |
| 5,475,092 A | 12/1995 | Chari et al. |
| 5,504,074 A | 4/1996 | D'Amato et al. |
| 5,525,632 A | 6/1996 | Obsumi et al. |
| 5,545,806 A | 8/1996 | Lonberg et al. |
| 5,561,122 A | 10/1996 | Pettit |
| 5,569,786 A | 10/1996 | Pettit et al. |
| 5,569,825 A | 10/1996 | Lonberg et al. |
| 5,585,089 A | 12/1996 | Queen |
| 5,625,126 A | 4/1997 | Lonberg et al. |
| 5,633,425 A | 5/1997 | Lonberg et al. |
| 5,646,176 A | 7/1997 | Golik et al. |
| 5,661,016 A | 8/1997 | Lonberg et al. |
| 5,661,143 A | 8/1997 | D'Amato et al. |
| 5,674,906 A | 10/1997 | Hatanaka et al. |
| 5,731,353 A | 3/1998 | Ohsumi et al. |
| 5,821,337 A | 10/1998 | Carter et al. |
| 5,877,158 A | 3/1999 | Bosslet et al. |
| 5,886,025 A | 3/1999 | Pinney |
| 5,892,069 A | 4/1999 | D'Amato et al. |

(Continued)

FOREIGN PATENT DOCUMENTS

| | | |
|---|---|---|
| CN | 105198885 A | 12/2015 |
| CN | 104447755 B | 6/2016 |

(Continued)

OTHER PUBLICATIONS

Rehse, et al., Deutsche Apotheker Zeitung (1973), 113(40), 1568-71. (Year: 1973).*
Rosenkranz, et al., Helvetica Chimica Acta (1974), 57(3), 887-916. (Year: 1974).*
Weiner, et al., Journal of Macromolecular Science, Chemistry (1977), A11(6), 1191-2000. (Year: 1977).*
Erra-Balsells, Rosa; Phytochemistry (1988), 27(12), 3945-7. (Year: 1988).*
Leet, et al., Journal of Antibiotics (1996), 49(3), 299-311. (Year: 1996).*
International Search Report and Written Opinion for PCT/US2021/065161, dated Apr. 25, 2022.

(Continued)

*Primary Examiner* — Jeffrey H Murray
(74) *Attorney, Agent, or Firm* — Wolf, Greenfield & Sacks, P.C.

(57) ABSTRACT

The present disclosure provides compounds of Formula I, methods of preparing the compounds, compositions, kits, and methods of using the compounds for treating or preventing microbial infections.

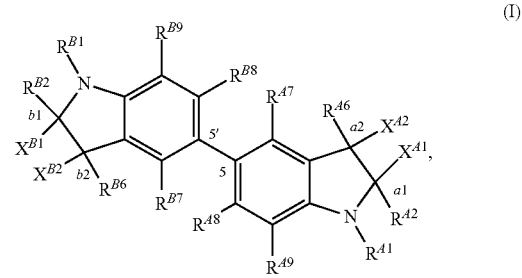

40 Claims, 37 Drawing Sheets

(56) References Cited

U.S. PATENT DOCUMENTS

| | | |
|---|---|---|
| 5,929,211 A | 7/1999 | Ashkenazi et al. |
| 5,985,837 A | 11/1999 | Ritter et al. |
| 6,054,297 A | 4/2000 | Carter et al. |
| 6,103,236 A | 8/2000 | Suzawa et al. |
| 6,147,076 A | 11/2000 | Danishefsky et al. |
| 6,150,407 A | 11/2000 | Tuséet al. |
| 6,162,810 A | 12/2000 | Carson et al. |
| 6,162,930 A | 12/2000 | Pinney et al. |
| 6,169,104 B1 | 1/2001 | Tuséet al. |
| 6,201,001 B1 | 3/2001 | Wang et al. |
| 6,214,345 B1 | 4/2001 | Firestone et al. |
| 6,232,327 B1 | 5/2001 | Nickel et al. |
| 6,262,094 B1 | 7/2001 | Hoefle et al. |
| 6,268,488 B1 | 7/2001 | Barbas, III et al. |
| 6,271,220 B1 | 8/2001 | Garst |
| 6,329,420 B1 | 12/2001 | Uckun et al. |
| 6,335,364 B1 | 1/2002 | Uckun et al. |
| 6,350,777 B2 | 2/2002 | Pinney et al. |
| 6,358,957 B1 | 3/2002 | Fukumoto et al. |
| 6,407,213 B1 | 6/2002 | Carter et al. |
| 6,423,753 B1 | 7/2002 | Dougherty |
| 6,433,012 B1 | 8/2002 | Tuséet al. |
| 6,528,676 B1 | 3/2003 | D'Amato et al. |
| 6,582,928 B1 | 6/2003 | Ashkenazi et al. |
| 6,620,976 B2 | 9/2003 | Sakanoue et al. |
| 6,639,055 B1 | 10/2003 | Carter et al. |
| 6,677,435 B2 | 1/2004 | Barbas, III et al. |
| 6,759,509 B1 | 7/2004 | King et al. |
| 6,815,530 B2 | 11/2004 | Ekwuribe et al. |
| 6,835,802 B2 | 12/2004 | Ekwuribe et al. |
| 6,855,689 B2 | 2/2005 | Firestone et al. |
| 6,858,580 B2 | 2/2005 | Ekwuribe et al. |
| 6,870,033 B1 | 3/2005 | Hsei et al. |
| 6,897,034 B2 | 5/2005 | Bebbington et al. |
| 7,018,809 B1 | 3/2006 | Carter |
| 7,030,082 B2 | 4/2006 | Soltero et al. |
| 7,087,840 B2 | 8/2006 | Herring et al. |
| 7,091,186 B2 | 8/2006 | Senter et al. |
| 7,115,573 B2 | 10/2006 | Pickford et al. |
| 7,119,162 B2 | 10/2006 | Ekwuribe et al. |
| 7,122,636 B2 | 10/2006 | Hsei et al. |
| 7,183,076 B2 | 2/2007 | Arathoon et al. |
| 7,214,663 B2 | 5/2007 | Bebbington et al. |
| 7,214,776 B2 | 5/2007 | Hsei et al. |
| 7,223,837 B2 | 5/2007 | de Groot et al. |
| 7,256,257 B2 | 8/2007 | Doronina et al. |
| 7,304,032 B2 | 12/2007 | Bebbington et al. |
| 7,319,139 B2 | 1/2008 | Brasalawsky et al. |
| 7,375,078 B2 | 5/2008 | Feng |
| 7,427,399 B2 | 9/2008 | Jakobovits et al. |
| 7,479,544 B2 | 1/2009 | Clark et al. |
| 7,494,646 B2 | 2/2009 | Jakobovits et al. |
| 7,507,405 B2 | 3/2009 | Hsei et al. |
| 7,521,541 B2 | 4/2009 | Eigenbrot et al. |
| 7,541,442 B2 | 6/2009 | Gudas et al. |
| 7,547,768 B2 | 6/2009 | Dowd et al. |
| 7,553,816 B2 | 6/2009 | Senter et al. |
| 7,585,834 B2 | 9/2009 | Wender et al. |
| 7,595,379 B2 | 9/2009 | Gudas et al. |
| 7,659,241 B2 | 2/2010 | Senter et al. |
| 7,662,936 B2 | 2/2010 | Kadkhodayan et al. |
| 7,691,962 B2 | 4/2010 | Boyd et al. |
| 7,696,313 B2 | 4/2010 | Pickford et al. |
| 7,705,045 B2 | 4/2010 | de Groot et al. |
| 7,714,016 B2 | 5/2010 | Gangwar et al. |
| 7,723,485 B2 | 5/2010 | Junutula et al. |
| 7,745,394 B2 | 6/2010 | Doronina et al. |
| 7,749,504 B2 | 7/2010 | Cairns et al. |
| 7,750,116 B1 | 7/2010 | Doronina et al. |
| 7,754,441 B2 | 7/2010 | de Sauvage et al. |
| 7,754,681 B2 | 7/2010 | Feng |
| 7,803,915 B2 | 9/2010 | Cairns et al. |
| 7,811,565 B2 | 10/2010 | Jakobovits et al. |
| 7,816,317 B2 | 10/2010 | Bebbington et al. |
| 7,829,531 B2 | 11/2010 | Senter et al. |
| 7,834,154 B2 | 11/2010 | Koch et al. |
| 7,842,789 B2 | 11/2010 | Hsei et al. |
| 7,846,893 B2 | 12/2010 | Sinko et al. |
| 7,851,437 B2 | 12/2010 | Senter et al. |
| 7,855,275 B2 | 12/2010 | Eigenbrot et al. |
| 7,858,759 B2 | 12/2010 | Brandt et al. |
| 7,888,536 B2 | 2/2011 | Davis et al. |
| 7,893,023 B2 | 2/2011 | Trouet et al. |
| 7,964,566 B2 | 6/2011 | Doronina et al. |
| 7,964,567 B2 | 6/2011 | Doronina et al. |
| 7,968,090 B2 | 6/2011 | Raitano et al. |
| 7,989,434 B2 | 8/2011 | Feng |
| 7,989,595 B2 | 8/2011 | Dennis et al. |
| 8,012,978 B2 | 9/2011 | Zhao et al. |
| 8,158,590 B2 | 4/2012 | Beusker et al. |
| 8,337,856 B2 | 12/2012 | Blättler et al. |
| 9,353,150 B2 | 5/2016 | Movassaghi et al. |
| 9,434,736 B2 | 9/2016 | Movassaghi et al. |
| 9,464,093 B2 | 10/2016 | Tun et al. |
| 9,962,383 B2 | 5/2018 | Movassaghi et al. |
| 10,220,099 B2 | 3/2019 | Movassaghi et al. |
| 10,640,508 B2 | 5/2020 | Movassaghi et al. |
| 10,918,627 B2 | 2/2021 | Movassaghi et al. |
| 10,918,735 B2 | 2/2021 | Movassaghi et al. |
| 11,535,634 B2 | 12/2022 | Movassaghi et al. |
| 2003/0096743 A1 | 5/2003 | Senter et al. |
| 2003/0130189 A1 | 7/2003 | Senter et al. |
| 2003/0149003 A1 | 8/2003 | Chaplin et al. |
| 2005/0143429 A1 | 6/2005 | Danishefsky et al. |
| 2008/0050310 A1 | 2/2008 | Ebens et al. |
| 2008/0267981 A1 | 10/2008 | Janda et al. |
| 2009/0068202 A1 | 3/2009 | Chen et al. |
| 2009/0203584 A1 | 8/2009 | Cuthbertson et al. |
| 2009/0280056 A1 | 11/2009 | Dennis et al. |
| 2010/0125065 A1 | 5/2010 | Moon et al. |
| 2010/0210543 A1 | 8/2010 | Rabuka et al. |
| 2010/0215669 A1 | 8/2010 | Chen et al. |
| 2011/0118480 A1 | 5/2011 | Vijayaraghavan et al. |
| 2011/0124844 A1 | 5/2011 | Davis et al. |
| 2011/0135667 A1 | 6/2011 | Chen et al. |
| 2011/0137017 A1 | 6/2011 | Eigenbrot et al. |
| 2011/0142859 A1 | 6/2011 | Ebens, Jr. et al. |
| 2011/0195021 A1 | 8/2011 | Deckert et al. |
| 2011/0195022 A1 | 8/2011 | Deckert et al. |
| 2011/0269972 A1 | 11/2011 | Loh et al. |
| 2012/0183566 A1 | 7/2012 | Barfield et al. |
| 2014/0187500 A1 | 7/2014 | Movassaghi et al. |
| 2015/0080405 A1 | 3/2015 | Movassaghi et al. |
| 2015/0274742 A1 | 10/2015 | Tun et al. |
| 2016/0354483 A1 | 12/2016 | Movassaghi et al. |
| 2017/0143708 A1 | 5/2017 | Movassaghi et al. |
| 2017/0333405 A1 | 11/2017 | Movassaghi et al. |
| 2017/0342077 A1 | 11/2017 | Movassaghi et al. |
| 2018/0360830 A1 | 12/2018 | Movassaghi et al. |
| 2019/0119286 A1 | 4/2019 | Movassaghi et al. |
| 2019/0252623 A1* | 8/2019 | Layek ............... C07F 7/0814 |
| 2019/0255187 A1 | 8/2019 | Movassaghi et al. |
| 2020/0062771 A1 | 2/2020 | Movassaghi et al. |
| 2020/0385407 A1 | 12/2020 | Movassaghi et al. |
| 2021/0329919 A9 | 10/2021 | Movassaghi et al. |
| 2023/0212195 A1 | 7/2023 | Movassaghi et al. |

FOREIGN PATENT DOCUMENTS

| | | | |
|---|---|---|---|
| CN | 109021080 A | 12/2018 | |
| EP | 0105360 A | 4/1984 | |
| EP | 0217577 A | 4/1987 | |
| EP | 0375562 A | 6/1990 | |
| FR | 2438034 A1 | 4/1980 | |
| JP | 2019085484 * | 6/2019 | ........... C07D 209/08 |
| WO | WO 88/03145 A2 | 5/1988 | |
| WO | WO 92/016486 A1 | 10/1992 | |
| WO | WO 94/14787 A1 | 7/1994 | |
| WO | WO 95/04535 A1 | 2/1995 | |
| WO | WO 98/039323 A1 | 9/1998 | |
| WO | WO 99/02166 A1 | 1/1999 | |
| WO | WO 99/02514 A2 | 1/1999 | |
| WO | WO 99/034788 A1 | 7/1999 | |
| WO | WO 99/035150 A1 | 7/1999 | |

(56) References Cited

FOREIGN PATENT DOCUMENTS

| | | |
|---|---|---|
| WO | WO 99/35164 A1 | 7/1999 |
| WO | 99/048495 A1 | 9/1999 |
| WO | WO 99/051224 A1 | 10/1999 |
| WO | WO 99/051246 A1 | 10/1999 |
| WO | WO 2000/000514 A2 | 1/2000 |
| WO | WO 2000/006556 A1 | 2/2000 |
| WO | WO 2000/026229 A1 | 5/2000 |
| WO | WO 2000/035865 A2 | 6/2000 |
| WO | WO 2000/040529 A1 | 7/2000 |
| WO | WO 2000/041669 A2 | 7/2000 |
| WO | WO 2000/048590 A1 | 8/2000 |
| WO | WO 2000/073264 A1 | 12/2000 |
| WO | WO 2001/009103 A2 | 2/2001 |
| WO | WO 2001/012579 A2 | 2/2001 |
| WO | WO 2001/019794 A2 | 3/2001 |
| WO | WO 2001/022954 A2 | 4/2001 |
| WO | WO 2001/024763 A2 | 4/2001 |
| WO | WO 2001/030803 A1 | 5/2001 |
| WO | WO 2001/040268 A2 | 6/2001 |
| WO | WO 2001/040309 A2 | 6/2001 |
| WO | WO 2001/068654 A2 | 9/2001 |
| WO | WO 2001/081288 A1 | 11/2001 |
| WO | WO 2001/081355 A1 | 11/2001 |
| WO | WO 2001/082909 A2 | 11/2001 |
| WO | WO 2001/084929 A1 | 11/2001 |
| WO | WO 2001/092224 A2 | 12/2001 |
| WO | WO 2002/004434 A1 | 1/2002 |
| WO | WO 2002/006267 A2 | 1/2002 |
| WO | WO 2002/008213 A1 | 1/2002 |
| WO | WO 2002/012228 A1 | 2/2002 |
| WO | WO 2002/014329 A1 | 2/2002 |
| WO | WO 2002/022576 A2 | 3/2002 |
| WO | WO 2002/022626 A1 | 3/2002 |
| WO | WO 2002/042319 A2 | 5/2002 |
| WO | WO 2002/047604 A2 | 6/2002 |
| WO | WO 2002/050007 A2 | 6/2002 |
| WO | WO 2002/060872 A1 | 8/2002 |
| WO | WO 2002/088172 A2 | 11/2002 |
| WO | WO 2002/098883 A1 | 12/2002 |
| WO | WO 2003/026577 A2 | 4/2003 |
| WO | WO 2003/043583 A2 | 5/2003 |
| WO | WO 2003/068144 A2 | 8/2003 |
| WO | WO 2004/010957 A2 | 2/2004 |
| WO | WO 2004/013093 A2 | 2/2004 |
| WO | WO 2004/016801 A2 | 2/2004 |
| WO | WO 2004/032828 A2 | 4/2004 |
| WO | WO 2004/043344 A2 | 5/2004 |
| WO | WO 2004/043493 A1 | 5/2004 |
| WO | WO 2004/050867 A1 | 6/2004 |
| WO | WO 2004/106343 A2 | 12/2004 |
| WO | WO 2005/001038 A2 | 1/2005 |
| WO | WO 2005/009369 A2 | 2/2005 |
| WO | WO 2005/037992 A2 | 4/2005 |
| WO | WO 2005/081711 A2 | 9/2005 |
| WO | WO 2005/082023 A2 | 9/2005 |
| WO | WO 2005/084390 A2 | 9/2005 |
| WO | WO 2006/055578 A2 | 5/2006 |
| WO | WO 2006/065533 A2 | 6/2006 |
| WO | WO 2006/086733 A2 | 8/2006 |
| WO | WO 2006/132670 A2 | 12/2006 |
| WO | WO 2007/008603 A1 | 1/2007 |
| WO | WO 2007/008848 A2 | 1/2007 |
| WO | WO 2007/011968 A2 | 1/2007 |
| WO | WO 2007/019232 A2 | 2/2007 |
| WO | WO 2007/024222 A1 | 3/2007 |
| WO | WO 2007/024536 A2 | 3/2007 |
| WO | WO 2007/030642 A2 | 3/2007 |
| WO | WO 2007/062138 A1 | 5/2007 |
| WO | WO 2007/089149 A2 | 8/2007 |
| WO | WO 2007/103288 A2 | 9/2007 |
| WO | WO 2007/137170 A2 | 11/2007 |
| WO | WO 2008/070593 A2 | 6/2008 |
| WO | WO 2008/078109 A2 | 7/2008 |
| WO | WO 2009/017394 A2 | 2/2009 |
| WO | WO 2009/048967 A1 | 4/2009 |
| WO | WO 2009/052431 A2 | 4/2009 |
| WO | WO 2009/080830 A1 | 7/2009 |
| WO | WO 2009/080831 A1 | 7/2009 |
| WO | WO 2009/080832 A1 | 7/2009 |
| WO | WO 2009/117531 A1 | 9/2009 |
| WO | WO 2009/134870 A1 | 11/2009 |
| WO | WO 2009/134952 A2 | 11/2009 |
| WO | WO 2009/134976 A1 | 11/2009 |
| WO | WO 2009/134977 A1 | 11/2009 |
| WO | WO 2009/135181 A2 | 11/2009 |
| WO | WO 2010/008726 A1 | 1/2010 |
| WO | WO 2010/025272 A1 | 3/2010 |
| WO | WO 2010/062171 A2 | 6/2010 |
| WO | WO 2010/081004 A1 | 7/2010 |
| WO | WO 2010/111018 A1 | 9/2010 |
| WO | WO 2010/126551 A1 | 11/2010 |
| WO | WO 2010/126552 A1 | 11/2010 |
| WO | WO 2010/128087 A2 | 11/2010 |
| WO | WO 2010/141566 A1 | 12/2010 |
| WO | WO 2011/038159 A2 | 3/2011 |
| WO | WO 2011/050180 A1 | 4/2011 |
| WO | WO 2011/091286 A1 | 7/2011 |
| WO | WO 2011/100398 A1 | 8/2011 |
| WO | WO 2011/100403 A1 | 8/2011 |
| WO | WO 2011/106528 A1 | 9/2011 |
| WO | WO 2011/112978 A1 | 9/2011 |
| WO | WO 2011/130613 A1 | 10/2011 |
| WO | WO 2011/133039 A2 | 10/2011 |
| WO | WO 2011/162933 A1 | 12/2011 |
| WO | WO 2012/019024 A2 | 2/2012 |
| WO | WO 2012/047724 A1 | 4/2012 |
| WO | WO 2012/054748 A2 | 4/2012 |
| WO | WO 2012/058592 A2 | 5/2012 |
| WO | WO 2012/061590 A1 | 5/2012 |
| WO | WO 2012/078688 A2 | 6/2012 |
| WO | WO 2012/112687 A1 | 8/2012 |
| WO | WO 2012/112708 A1 | 8/2012 |
| WO | WO 2012/128868 A2 | 9/2012 |
| WO | WO 2012/135517 A2 | 10/2012 |
| WO | WO 2012/135522 A2 | 10/2012 |
| WO | WO 2012/135740 A2 | 10/2012 |
| WO | WO 2012/138537 A2 | 10/2012 |
| WO | WO 2012/138749 A2 | 10/2012 |
| WO | WO 2012/145112 A2 | 10/2012 |
| WO | WO 2012/149412 A2 | 11/2012 |
| WO | WO 2012/177837 A2 | 12/2012 |
| WO | WO 2013/055990 A1 | 4/2013 |
| WO | WO 2013/055993 A1 | 4/2013 |
| WO | WO 2014/059314 A1 | 4/2014 |
| WO | WO 2014/089177 A2 | 6/2014 |

OTHER PUBLICATIONS

Leet et al., Himastatin, a new antitumor antibiotic from Streptomyces hygroscopicus. III. Structural elucidation. J Antibiot (Tokyo). Mar. 1996;49(3):299-311. doi: 10.7164/antibiotics.49.299.

Kamenecka et al., Discovery through total synthesis: a retrospective on the himastatin problem. Chemistry. Jan. 5, 2001;7(1):41-63. doi: 10.1002/1521-3765(20010105)7:1<41::aid-chem41>3.0.co;2-d.

Yu et al., Total synthesis of chloptosin, a potent apoptosis-inducing cyclopeptide. Org Lett. Mar. 5, 2010;12(5):1124-7. doi: 10.1021/ol100135a.

Matsumoto et al., Catalytic and Aerobic Oxidative Biaryl Coupling of Anilines Using a Recyclable Heterogeneous Catalyst for Synthesis of Benzidines and Bicarbazoles. J Org Chem. Dec. 4, 2020;85(23):15154-15166. doi: 10.1021/acs.joc.0c02020. Epub Nov. 23, 2020.

Funes-Ardoiz et al., Oxidative Coupling Mechanisms: Current State of Understanding. ACS Catal. Dec. 22, 2017;8(2):1161-72. doi: 10.1021/acscatal.7b02974.

Grzybowski et al., Synthetic Applications of Oxidative Aromatic Coupling-From Biphenols to Nanographenes. Angew Chem Int Ed Engl. Feb. 17, 2020;59(8):2998-3027. doi: 10.1002/anie.201904934. Epub Dec. 3, 2019.

Yang et al., Oxidative C—H/C—H Coupling Reactions between Two (Hetero)arenes. Chem Rev. Jul. 12, 2017;117(13):8787-8863. doi: 10.1021/acs.chemrev.6b00567. Epub Jan. 13, 2017.

(56) References Cited

OTHER PUBLICATIONS

International Search Report and Written Opinion for PCT/US2013/073062, dated May 20, 2014.
International Preliminary Report on Patentability for PCT/US2013/073062, dated Jun. 18, 2015.
International Search Report and Written Opinion for PCT/US2014/056263, dated Dec. 4, 2014.
International Preliminary Report on Patentability for PCT/US2014/056263, dated Mar. 31, 2016.
International Search Report and Written Opinion for PCT/US2017/032040, dated Aug. 11, 2017.
International Preliminary Report on Patentability for PCT/US2017/032040, dated Nov. 22, 2018.
International Search Report and Written Opinion for PCT/US2017/034327, dated Sep. 1, 2017.
International Preliminary Report on Patentability for PCT/US2017/034327, dated Dec. 6, 2018.
Invitation to Pay Additional Fees for PCT/US2018/032327, dated Jul. 23, 2018.
International Search Report and Written Opinion for PCT/US2018/032327, dated Sep. 21, 2018.
International Preliminary Report on Patentability for PCT/US2018/032327, dated Nov. 21, 2019.
Invitation to Pay Additional Fees for PCT/US2020/026415, dated Jul. 1, 2020.
International Search Report and Written Opinion for PCT/US2020/026415, dated Sep. 7, 2020.
International Preliminary Report on Patentability for PCT/US2020/026415, dated Dec. 16, 2021.
Abouelhassan et al., Discovery of quinoline small molecules with potent dispersal activity against methicillin-resistant *Staphylococcus aureus* and *Staphylococcus epidermidis* biofilms using a scaffold hopping strategy. Bioorg Med Chem Lett. Nov. 1, 2014;24(21):5076-80. doi: 10.1016/j.bmcl.2014.09.009. Epub Sep. 15, 2014.
Adam et al., Photochemistry of the Azoalkanes 2,3-Diazabicyclo[2.2.1]hept-2-ene and Spiro[cyclopropane-1, 7-[2,3]diazabicyclo[2.2.1]hept-2-ene]: On the Questions of One-Bond vs. Two-Bond Cleavage during the Denitrogenation, Cyclization vs. Rearrangement of the 1,3-Diradicals, and Double Inversion, J. Org. Chem. 1985, 50, pp. 3303-3312.
Adams et al., Concise Total Synthesis of (+)-Luteoalbusins A and B. Organic Letters Aug. 2015;17(17):4268-4271. DOI: 10.1021/acs.orglett.5b02059.
Adjibade et al., In Vitro Cytotoxicity of Polyindolenine Alkaloids on Rat Hepatoma Cell Lines. Structure Activity Relationships, Journal of Ethnopharmacology 1990, 29, pp. 127-136.
Albin et al., Efficient flow synthesis of human antimicrobial peptides. Aust J Chem. Apr. 2020;73(4):380-388. doi: 10.1071/CH20043. Epub Apr. 8, 2020.
Aleksandrzak et al., Antimitotic activity of diaryl compounds with structural features resembling combretastatin A-4. Anticancer Drugs. Jul. 1998; 9(6):545-50.
Aliev et al., A concise approach to the epidithiodiketopiperazine (ETP) core. Tetrahedron Lett. 2006; 47(14):2387-2390.
Amador et al., Antinociceptive Profile of Hodgkinsine, Planta Med 2000, 66, pp. 770-772.
Amir et al., Self-immolative dendrimers. Angew Chem Int Ed Engl. Sep. 29, 2003; 42(37):4494-9.
Amsberry et al., The lactonization of 2'-hydroxyhydrocinnamic acid amides: a potential prodrug for amines. J. Org. Chem. 1990; 55(23):5867-5877.
Andersen et al., Penicillium expansum: consistent production of patulin, chaetoglobosins, and other secondary metabolites in culture and their natural occurrence in fruit products. J Agric Food Chem. Apr. 21, 2004;52(8):2421-8.
Anderson et al., Studies on Total Synthesis of the Cytotoxic Marine Alkaloid Agelastatin A, J. Org. Chem., 63:7594-7595 (1998).
Andres et al., "Combretatropones"—hybrids of combretastatin and colchicine. Synthesis and biochemical evaluation Bioorganic. Med. Chem. Lett. 1993; 3(4):571-576.
Anet et al., Hodgkinsine, the Alkaloid of Hodgkinsonia Frutescens F. Muell, J. Chem. 1961, 14, pp. 173-174.
Anthon I, U. et al., Naturally Occurring Cyclotryptophans and Cyclotryptamines, Alkaloids: Chemical and Biological Perspectives, Pelletier, S. W., Ed.; Pergamon: London, 1999; vol. 13, pp. 163-236.
Aoyagi et al., Mild and Efficient One-Step Synthesis of Trithiocarbonates Using Minimum Amount of CS2. Synlett. 2006;636-638.
Bacher et al., D-24851, a novel synthetic microtubule inhibitor, exerts curative antitumoral activity in vivo, shows efficacy toward multidrug-resistant tumor cells, and lacks neurotoxicity. Cancer Res. Jan. 1, 2001; 61(1):392-9.
Bai et al., Interaction of dolastatin 10 with tubulin: induction of aggregation and binding and dissociation reactions. Molecular Pharmacology May 1995; 47(5):965-976.
Baldwin et al., Azo Anions in Synthesis. Use of Trityl- and Diphenyl-4-Pyridylmenthylhydrazones for Reductive C—C Bond Formation, Tetrahedron 1986, vol. 42, No. 15, pp. 4235-4246.
Banwell et al., Synthesis, X-Ray Crystal Structure and Tubulin-Binding Properties of a Benzofuran Analogue of the Potent Cytotoxic Agent Combretastatin A4. Australian Journal of Chemistry 1999; 52(8):767-774.
Barrow et al., WIN 64821, a new competitive antagonist to substance P, isolated from an *Aspergillus* species: structure determination and solution conformation. J. Org. Chem. 1993; 58(22):6016-6021.
Beck et al., Mild Aerobic Oxidative Palladium (II) Catalyzed C—H Bond Functionalization: Regioselective and Switchable C—H Alkenylation and Annulation of Pyrroles. J. Am. Chem. Soc. 2006; 128(8):2528-2529.
Bedford et al., Synthesis of water-soluble prodrugs of the cytotoxic agent Combretastatin A4. Bioorganic. Med. Chem. Lett. 1996; 6(2):157-160.
Behenna et al., Confirmation of the absolute configuration of (−)-aurantioclavine. Tetrahedron Letters Apr. 2011;52(17):2152-2154.
Belmar et al., Total Synthesis of (±)-Communesin F via a Cycloaddition with Indol-2-one. J. Am. Chem. Soc., 2012;134(41):16941-16943. DOI: 10.1021/ja307277w.
Belmar et al., Total Synthesis of (±)-isophellibiline and (±)-communesin F, and Design, Synthesis and Pharmacological Evaluation of Dihydro-β-erythroidine (DHBE) Analogs. Pennsylvania State University Dissertation 2012.
Benco et al., Synthesis of an ammonium ionophore and its application in a planar ion-selective electrode. Anal Chem. Jan. 1, 2003;75(1):152-6. doi: 10.1021/ac0257851.
Benkovics et al., Oxaziridine-mediated oxyamination of indoles: an approach to 3-aminoindoles and enantiomerically enriched 3-aminopyrroloindolines. Angew Chem Int Ed Engl. Nov. 22, 2010;49(48):9153-7. doi: 10.1002/anie.201004635.
Beretz et al., Polyindolinic Alkaloids from Psychotria forsteriana. Potent Inhibitors of the Aggregation of Human Platelets, Planta Med. 1985, 51, pp. 300-303.
Bernardo et al., A Novel Redox Mechanism for the Glutathione-dependent Reversible Uptake of a Fungal Toxin in Cells. J Biol. Chem. 2003; 278(47):46549-46555.
Bertling et al., Candida albicans and its metabolite gliotoxin inhibit platelet function via interaction with thiols. Thromb Haemost. Aug. 2010;104(2):270-8.
Bhattacharyya et al., Rapid identification and phylogenetic classification of diverse bacterial pathogens in a multiplexed hybridization assay targeting ribosomal RNA. Sci Rep. Mar. 19, 2019;9(1):4516. doi: 10.1038/s41598-019-40792-3.
Blokhin et al., Characterization of the interaction of the marine cyanobacterial natural product curacin A with the colchicine site of tubulin and initial structure-activity studies with analogues. Molecular Pharmacology Sep. 1995; 48(3):523-531.
Boger et al., Synthesis of the lower subunit of rhizoxin. J. Org. Chem. 1992; 57(8):2235-2244.

(56) References Cited

OTHER PUBLICATIONS

Boucher et al., Bad bugs, no drugs: no Eskape! An update from the Infectious Diseases Society of America. Clin Infect Dis. Jan. 1, 2009;48(1):1-12. doi: 10.1086/595011.
Boyer et al., Concise Total Synthesis of (+)-Gliocladins B and C. Chem Sci. Jan. 1, 2012;3(6):1798-1803. Epub Mar. 30, 2012.
Boyer et al., Synthesis and Anticancer Activity of Epipolythiodiketopiperazine Alkaloids. Chem Sci. 2013;4(4):1646-1657. doi:10.1039/C3SC50174D.
Brak et al., Total Synthesis of (−)-Aurantioclavine. Org. Lett., 2010;12(9):2004-2007. DOI: 10.1021/o1100470g.
Brown et al., Investigation of various N-heterocyclic substituted piperazine versions of 5/7-{[2-(4-aryl-piperazin-1-yl)-ethyl]-propyl-amino }-5,6,7,8-tetrahydro-naphthalen-2-ol: effect on affinity and selectivity for dopamine D3 receptor. Bioorg Med Chem. Jun. 1, 2009;17(11):3923-33.
Bundgaard, H., (C) Means to enhance penetration: (1) Prodrugs as a means to improve the delivery of peptide drugs. Advanced Drug Delivery Revieivs. 1992; 8(1):1-38.
Canham et al., Stereocontrolled enantioselective total synthesis of the [2+2] quadrigeminealkaloids, Tetrahedron 2015, 71, pp. 6424-6436.
Chaib et al., Anti-leukemia activity of chaetocin via death receptor-dependent apoptosis and dual modulation of the histone methyltransferase SUV39H1. Leukemia. Apr. 2012;26(4):662-74.
Chang et al., Heterocyclic Compounds. Part 15. NN'-Di-t-Butylthiadiaziridine 1, 1-Dioxide:Synthesis and Reactions, J. Chem. Soc., Perkin Trans. 1, 1977, pp. 1601-1605.
Chen et al., Ecology-based screen identifies new metabolites from a Cordyceps-colonizing fungus as cancer cell proliferation inhibitors and apoptosis inducers. Cell Prolif. Dec. 2009;42(6):838-47.
Cherblanc et al., On the Determination of the Stereochemistry of Semisynthetic Natural Product Analogues using Chiroptical Spectroscopy: Desulfurization of Epidithiodioxopiperazine Fungal Metabolites. Chem.-Eur. J. 2011; 17(42):11868-11875.
Choi et al., Agelastatin A (AgA), a Marine Sponge Derived Alkaloid, Inhibits Wnt/Beta-Catenin Signaling and Selectively Induces Apoptosis in Chronic Lymphocytic Leukemia Independently of p53, Blood (ASH Annual Meeting Abstracts), 118:Abstract1786, 2 (2011).
Choi et al., Lights, Camera, Action! Antimicrobial Peptide Mechanisms Imaged in Space and Time. Trends Microbiol. Feb. 2016;24(2):111-122. doi: 10.1016/j.tim.2015.11.004. Epub Dec. 13, 2015.
Chou et al., Therapeutic Cure against Human Tumor Xenografts inNude Mice by a Microtubule Stabilization Agent,Fludelone, via Parenteral or Oral Route. Cancer Res. 2005; 65(20):9445-9454.
Ciufolini et al., Synthesis, Chemistry and Conformational Properties of Piperazic Acids. Chem Soc Rev. 1998(27):437-45. doi: 10.1039/A827437Z.
Codelli et al., Enantioselective Total Synthesis of (−)-Acetylaranotin, a Dihydrooxepine Epidithiodiketopiperazine. J. Am. Chem. Soc. 2012; 134(4):1930-1933.
Coffen et al., A short synthesis of aromatic analogues of the aranotins. J. Org. Chem. Mar. 18, 1977;42(6):948-52.
Cogan et al., Asymmetric synthesis of chiral amines by highly diastereoselective 1,2-additions of organometallic reagents to N-tert-butanesulfinyl imines. Tetrahedron Jul. 1999;55(29):8883-8904.
Coleman et al., Antifungal activity of microbial secondary metabolites. PLoS One. 2011;6(9):e25321.
Collet et al., Catalytic C—H amination: recent progress and future directions, Chem. Commun. 2009, pp. 5061-5074.
Combeau et al., RPR112378 and RPR115781: Two Representatives of a New Family of Microtubule Assembly Inhibitors. Molecular Pharmacology Mar. 2000; 57(3):553-563.
Connelly et al., Chemical Redox Agents for Organometallic Chemistry. Chem Rev. Mar. 28, 1996;96(2):877-910. doi: 10.1021/cr940053x.
Cook et al., Epidithiodiketopiperazines Block the Interaction between Hypoxia-inducible Factor-1α (HIF-1α) and p300 by a Zinc Ejection Mechanism. J Biol. Chem. 2009; 284:26831-26838.
Cordell et al., Bisindole Alkaloids, The Alkaloids: Chemistry and Physiology, Manske R. H. F., Rodrigo, R. G. A., Ed.; Academic Press: New York, 1981; vol. 20, pp. 3-295.
Coretese et al., Podophyllotoxin as a probe for the colchicine binding site of tubulin. J Biol Chem. Feb. 25, 1977;252(4):1134-40.
Corey et al., Enantioselective Total Synthesis of Ecteinascidin 743, J. Am. Chem. Soc. 1996, 118, pp. 9202-9203.
Coste et al., Concise Total Synthesis of (+)-Bionectins A and C. Chem Sci. 2013;4(8):3191-3197. doi:10.1039/C3SC51150B.
Crawley et al., A Synthetic Approach to Nomofungin/Communesin B. Org. Lett., 2003, 5 (18), pp. 3169-3171. DOI: 10.1021/01034407v.
Crich et al., 2,4,6-Tri-tert-butylpyrimidine (TTBP): A Cost Effective, Readily Available Alternative to the Hindered Base 2,6-Di-tert-butylpyridine and its 4-Substituted Derivatives in Glycosylation and Other Reactions. Synthesis. 2001;2001(2):0323-6. doi: 10.1055/s-2001-10798.
Crich et al., Chemistry of the Hexahydropyrrolo[2,3-b]indoles: Configuration, Conformation, Reactivity, and Applications in Synthesis, Acc. Chem. Res. 2007, 40, pp. 151-161.
Crich et al., Expedient Synthesis of threo-β-Hydroxy-α-amino Acid Derivatives: Phenylalanine, Tyrosine, Histidine, and Tryptophan. J. Org. Chem. 2006; 71(18):7106-7109.
Cushman et al., Synthesis and evaluation of stilbene and dihydrostilbene derivatives as potential anticancer agents that inhibit tubulin polymerization. J. Med. Chem. 1991; 34(8):2579-2588.
Cushman et al., Synthesis of Analogs of 2-Methoxyestradiol with Enhanced Inhibitory Effects on Tubulin Polymerization and Cancer Cell Growth. J. Med. Chem. 1997; 40(15):2323-2334.
D'Ambrosia et al., Agelastatin A, a New Skeleton Cytotoxic Alkaloid of the Oroidin Family. Isolation from the Axinellid Sponge Agelas dendromorpha of the Coral Sea, J. Chem. Soc., Chem. Commun., pp. 1305-1306 (1993).
D'Ambrosio et al., The Active Centres of Agelastatin A, a Strongly Cytotoxic Alkaloid of the Coral Sea Axinellid Sponge Agelas dendromorpha, as Determined by Comparative Bioassays with Semisynthetic Derivatives, Helv. Chem. Acta, 79:727-735(1996).
D'Angelo et al., Concise Total Synthesis of (−)-Himastatin via a Bioinspired Final-Stage Dimerization. Feb. 17, 2021. 8 pages.
D'Costa et al. Inactivation of the lipopeptide antibiotic daptomycin by hydrolytic mechanisms. Antimicrob Agents Chemother. Feb. 2012;56(2):757-64. doi: 10.1128/AAC.05441-11. Epub Nov. 14, 2011.
Dalsgaard et al., Communesins G and H, new alkaloids from the psychrotolerant fungus *Penicillium rivulum*. J Nat Prod. Feb. 2005;68(2):258-61. doi: 10.1021/np0496461.
Davis et al., Adventures in Sulfur-Nitrogen Chemistry, J. Org. Chem. 2006, 71, pp. 8993-9003.
Davis et al., Asymmetric synthesis of amino acids using sulfinimines (thiooxime S-oxides), Chem. Soc. Rev. 1998, 27, pp. 13-18.
Davis et al., Formation of raloxifene homo-dimer in CYP3A4, evidence for multi-substrate binding in a single catalytically competent P450 active site. Arch Biochem Biophys. Sep. 15, 2011;513(2):110-8. doi: 10.1016/j.abb.2011.06.016. Epub Jul. 13, 2011.
De Groot et al., Cascade-release dendrimers liberate all end groups upon a single triggering event in the dendritic core. Angew Chem Int Ed Engl. Sep. 29, 2003; 42(37):4490-4.
De Groot et al., Design, Synthesis, and Biological Evaluation of a Dual Tumor-specific Motive Containing Integrin-targeted Plasmin-cleavable Doxorubicin Prodrug. Molecular Cancer Therapeutics 2002; 1(11):901-911.
De Groot et al., Synthesis and Biological Evaluation of Novel Prodrugs of Anthracyclines for Selective Activation by the Tumor-Associated Protease Plasmin. J. Med. Chem. 1999; 42(25):5277-5283.
De Loera et al., Efficient Aziridine Synthesis in Metastable Crystalline Phases by Photoinduced Denitrogenation of Crystalline Triazolines, Org. Lett. 2012, vol. 14, No. 15, pp. 3874-3877.

(56) References Cited

OTHER PUBLICATIONS

De Loera et al., Photoinduced and Thermal Denitrogenation of Bulky Triazoline Crystals: Insights into Solid-to-Solid Transformation, J. Am. Chem. Soc. 2013, 135, pp. 6626-6632.

Delfourne, Marine natural products and other derivatives as potent indoleamine 2,3-dioxygenase inhibitors. Mini Rev Med Chem. 2012;12(10):988-996. doi: 10.2174/138955712802762374.

Delorbe et al., Enantioselective Total Synthesis of (+)-Gliocladine C: Convergent Construction of Cyclotryptamine-Fused Polyoxopiperazines and a General Approach for Preparing Epidithiodioxopiperazines from Trioxopiperazine Precursors. J Am Chem Soc. Apr. 7, 2011;133(17):6549-52.

Delorbe et al., General Approach for Preparing Epidithiodioxopiperazines from Trioxopiperazine Precursors: Enantioselective Total Syntheses of (+)- and (−)-Gliocladine C, (+)-Leptosin D, (+)-T988C, (+)-Bionectin A, and (+)-Gliocladin A. J. Am. Chem. Soc. 2013; 135(10):4117-4128.

Denmark et al., Palladium-Catalyzed Cross-Coupling Reactions of 2-Indolyldimethylsilanols with Substituted Aryl Halides. Org. Lett. 2004; 6(20):3649-3652.

Depew et al., Total Synthesis of 5-N-Acetylardeemin and Amauromine: Practical Routes to Potential MDR Reversal Agents. J. Am. Chem. Soc.1999; 121(51):11953-11963.

DePorter et al., N-Nosyl oxaziridines as terminal oxidants in copper(II)-catalyzed olefinoxyaminations, Tetrahedron 2010, 51, pp. 5223-5225.

Dong et al., Nematicidal epipolysulfanyldioxopiperazines from Gliocladium roseum. J Nat Prod. Oct. 2005;68(10):1510-3.

Dorr et al., Antitumor activity of combretastatin-A4 phosphate, a natural product tubulin inhibitor. Invest. New Drugs Jun. 1996; 14(2):131-137.

Du Bois, J., Rhodium-Catalyzed C—H Amination. An Enabling Method for Chemical Synthesis, Org. Process Res. Dev. 2011, 15, pp. 758-762.

Dubey et al., Direct organocatalytic coupling of carboxylated piperazine-2,5-diones with indoles through conjugate addition of carbon nucleophiles to indolenine intermediates. Tetrahedron Lett. 2010;51(4):609-612. doi:10.1016/j.tetlet.2009.11.068.

Dubowchik et al., Monomethoxytrityl (MMT) as a versatile amino protecting group for complex prodrugs of anticancer compounds sensitive to strong acids, bases and nucleophiles. Tetrahedron Letters 1997; 38(30):5257-60.

Dubs et al., Eine neue Methode zur Herstellung gemischter Disulfide. Vorläufige Mitteilung Helv. Chim. Acta 1976; 59(4):1307-1311.

Ducki et al., Potent antimitotic and cell growth inhibitory properties of substituted chalcones. Bioorg Med Chem Lett. May 5, 1998; 8(9):1051-6.

Dörwald, F.Z., Preface. In: Side Reactions in Organic Synthesis. 2005, Wiley-VCH Verlag GmbH & Co. KGaA, Weinheim, p. IX.

Engel et al., Thermolysis of Free-Radical Initiators: tert-Butylazocumene and Its 1,3- and 1,4-Bisazo and 1,3,5-Trisazo Analogues, J. Am. Chem. Soc. 2001, 123, pp. 3706-3715.

Engel, P. S., Mechanism of the Thermal and Photochemical Decomposition of Azoalkanes, Chemical Reviews Apr. 1980, vol. 80, No. 2, 52.

Engel, P. S., Photochemistry of Aliphatic Azo Compounds in Solution, Accounts of Chemical Research 1973, vol. 6, pp. 275-281.

Erkel et al., Induction of differentiation in acute promyelocytic leukemia cells (HL-60) by the verticillin derivative Sch 52900. Z Naturforsch C J Biosci. Jul.-Aug. 2002;57(7-8):759-67. doi: 10.1515/znc-2002-7-834.

Espino et al., A Rh-Catalyzed C—H Insertion Reaction for the Oxidative Conversion of Carbamates to Oxazolidinones, Angew. Chem. Int. Ed. 2001, 40:3, pp. 598-600.

Espino et al., Expanding the Scope of C—H Amination through Catalyst Design, J. Am. Chem. Soc. 2004, 126, pp. 15378-15379.

Eto et al., Conformation of aromatic rings in isolable atropisomers of 2-arylindoline derivatives and kinetic evidences for π-π interaction. Tetrahedron Lett. Jan. 23, 2010;66(4):898-903.

Fan et al., Alkaloids with Cardiovascular Effects from the Marine-Derived Fungus *Penicillium expansum* Y32. Mar Drugs. Oct. 22, 2015;13(10):6489-504. doi: 10.3390/md13106489.

Fang et al., Dimerization of a 3-Substituted Oxindole at C-3 and Its Application to the Synthesis of (±)-Folicanthine, J. Am. Chem. Soc. 1994, 116, pp. 9480-9486.

Fernandez-Lopez et al., Antibacterial agents based on the cyclic D,L-alpha-peptide architecture. Nature. Jul. 26, 2001;412(6845):452-5. doi: 10.1038/35086601. Erratum in: Nature Nov. 15, 2001;414(6861):329.

Fink et al., Mercaptoacyl Dipeptides as Orally Active Dual Inhibitors of Angiotensin-Converting Enzyme and Neutral Endopeptidase. J. Med. Chem. 1996; 39(16):3158-3168.

Fiori et al., A mechanistic analysis of the Rh-catalyzed intramolecular C—H amination reaction, Tetrahedron 2009, 65, pp. 3042-3051.

Fiori et al., Catalytic Intermolecular Amination of C—H Bonds: Method Development and Mechanistic Insights, J. Am. Chem. Soc. 2007, 129, pp. 562-568.

Firouzabadi et al., Bispyridinesilver permanganate[Ag(C5H5N)2]MnO4: an efficient oxidizing reagent for organic substrates. Tetrahedron Lett. 1982; 23(17): 1847-1850.

Flynn et al., The synthesis and tubulin binding activity of thiophene-based analogues of combretastatin A-4. Bioorg Med Chem Lett. Sep. 3, 2001; 11(17):2341-3.

Foo et al., Total Synthesis-Guided Structure Elucidation of (+)-Psychotetramine, Angew. Chem. Int. Ed. Engl. 2011, 50(12), pp. 2716-2719.

Fotsis et al., The endogenous oestrogen metabolite 2-methoxyoestradiol inhibits angiogenesis and suppresses tumour growth. Nature. Mar. 17, 1994; 368(6468):237-9.

Frisch et al., Synthesis of Short Polyoxyethylene-Based Heterobifunctional Cross-Linking Reagents. Application to the Coupling of Peptides to Liposomes. Bioconjugate Chem., 1996, 7 (2), pp. 180-186.

Fuchs et al., Total Synthesis of (±)-Perophoramidine, J. Am. Chem. Soc. 2004, 126, pp. 5068-5069.

Fukuyama et al., A total synthesis of gliotoxin. J. Am. Chem. Soc. 1976; 98(21):6723-6724.

Furst, L. et al., Total Synthesis of (+)-Gliocladin C Enabled by Visible-Light Photoredox Catalysis, Angew. Chem. Int. Ed. 2011, 50, pp. 9655-9659.

Gardiner et al., The epipolythiodioxopiperazine (ETP) class of fungal toxins: distribution, mode of action, functions and biosynthesis. Microbiology. Apr. 2005; 151(Pt 4):1021-32.

Gardner et al., Understanding C—H bond oxidations: H. and H-transfer in the oxidation of toluene by permanganate. Science. Sep. 29, 1995; 269(5232):1849-51.

Gassman et al., Chemistry of Nitrenium Ions. XXI. Nucleophilic Aromatic Substitution of Anilines via Aryl Nitrenium Ions (Anilenium Ions). J Am Chem Soc. 1972;94:3884-91.

Gastpar et al., Methoxy-Substituted 3-Formyl-2-phenylindoles Inhibit Tubulin Polymerization. J. Med. Chem. 1998; 41(25):4965-4972.

Gerwick et al., Structure of Curacin A, a Novel Antimitotic, Antiproliferative and Brine Shrimp Toxic Natural Product from the Marine Cyanobacterium Lyngbya majuscula. J. Org. Chem.1994; 59(6):1243-1245.

Getahun et al., Synthesis of alkoxy-substituted diaryl compounds and correlation of ring separation with inhibition of tubulin polymerization: differential enhancement of inhibitory effects under suboptimal polymerization reaction conditions. J. Med. Chem. 1992; 35(6):1058-1067.

Gilow et al., Sulfenylation of some pyrroles and indoles. J Heterocyclic Chem. 1991, 28(4):1025-1034.

Golitz et al., A New Method for the Introduction of Trifluoromethyl Groups, Angew. Chem. Int. Ed. Engl. 1977, 16, No. 12, pp. 854-855.

Govek et al., Total Synthesis of (+)-asperazine, Tetrahedron 2007, 63, pp. 8499-8513.

Grandner et al., Mechanism of the P450-Catalyzed Oxidative Cyclization in the Biosynthesis of Griseofulvin. ACS Catal. Jul. 1, 2016;6(7):4506-4511. doi: 10.1021/acscatal.6b01068. Epub May 31, 2016.

(56) References Cited

OTHER PUBLICATIONS

Greene et al., Greene's Protective Groups in Organic Synthesis, Fifth Edition, Wiley, New York, NY 2014, Chapter 7, Protection for the Amino Group, 299 (Parts 1 & 2).
Greenman et al., Synthesis of phakellistatin 13 and oxidation to phakellistatin 3 and isophakellistatin 3. Org Lett. May 27, 2004;6(11):1713-6. doi: 10.1021/ol049614p.
Greiner et al., Identification of a specific inhibitor of the histone methyltransferase SU(VAR)3-9. Nat Chem Biol. Aug. 2005;1(3):143-5.
Gueritte-Voegelein et al., Alkaloids From Psychotria Oleoides with Activity on Growth Hormone Release, J. Nat. Prod. 1992, 55, pp. 923-930.
Guo et al., Design and Biosynthesis of Dimeric Alboflavusins with Biaryl Linkages via Regiospecific C—C Bond Coupling. J Am Chem Soc. Dec. 26, 2018;140(51):18009-18015. doi: 10.1021/jacs.8b10136. Epub Dec. 14, 2018.
Guo et al., NW-G01, a novel cyclic hexadepsipeptide antibiotic, produced by Streptomyces alboflavus 313: I. Taxonomy, fermentation, isolation, physicochemical properties and antibacterial activities. J Antibiot (Tokyo). Apr. 2009;62(4):201-5. doi: 10.1038/ja.2009.15. Epub Mar. 6, 2009.
Guo et al., NW-G01, a novel cyclic hexapeptide antibiotic, produced by Streptomyces alboflavus 313: II. Structural elucidation. J Antibiot (Tokyo). May 2010;63(5):231-5. doi: 10.1038/ja.2010.24. Epub Apr. 9, 2010. Erratum in: J Antibiot (Tokyo). Dec. 2010;63(12):733.
Gwaltney et al., Novel sulfonate derivatives: potent antimitotic agents. Bioorg Med Chem Lett. Jul. 9, 2001; 11(13):1671-3.
Hadimani et al., Synthesis, in vitro, and in vivo evaluation of phosphate ester derivatives of combretastatin A-4. Bioorg. Med. Chem. Lett. 2003; 13(9):1505-1508.
Hale et al., Enantiospecific Formal Total Synthesis of the Tumor and GSK-3b Inhibiting Alkaloid, (−)-Agelastatin A, Org. Lett., 5(16):2927-2930 (2003).
Hall et al., Biogenetic-Type Synthesis of the Calycanthaceous Alkaloids, Tetrahedron 1967, 23, pp. 4131-4141.
Hamada et al., Selective removal of electron-accepting p-toluene- and naphthalenesulfonyl protecting groups for amino function via photoinduced donor acceptor ion pairs with electron-donating aromatics. J. Am. Chem. Soc. 1986; 108(1):140-145.
Hammonds et al., Studies to show that with podophyllotoxin the early replicative stages of herpes simplex virus type 1 depend upon functional cytoplasmic microtubules. J Med Microbiol. Sep. 1996; 45(3):167-72.
Han et al., A Diastereodivergent Synthetic Strategy for the Syntheses of Communesin F andPerophoramidine, Org. Lett. 2014, 16, pp. 3316-3319.
Han et al., Evolution of a Unified, Sterodivergent Approach to the Synthesis of Communesin F and Perophoramidine, J. Org. Chem. 2015, 80, pp. 528-547.
Han et al., Synthesis and Anticancer Activity of All Known (−)-Agelastatin Alkaloids, The Journal of Organic Chemistry, 78, p. 11970-11984 (2013).
Hand et al., Anodic Oxidation Pathways of N-Alkylanilines. J Am Chem Soc. Feb. 6, 1974;96(3): 850-60.
Hansen et al., A stereoselective synthetic approach to (2S,3R)-N-(1′,1′-dimethyl-2′,3′-epoxypropyl)-3-hydroxytryptophan, a component of cyclomarin A. Tetrahedron: Asymmetry 2006; 17(1):15-21.
Hatanaka et al., Novel B-ring modified combretastatin analogues: syntheses and antineoplastic activity. Bioorg Med Chem Lett. Dec. 1, 1998; 8(23):3371-4.
Hay et al., A 2-nitroimidazole carbate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT. Bioorg. Med. Chem. Lett. 1999; 9:2237-2242.
Hayashi et al., New insecticidal compounds, communesins C, D and E, from Penicillium expansum link MK-57. Biosci Biotechnol Biochem. Mar. 2004;68(3):753-6. doi: 10.1271/bbb.68.753.

He et al., Total Syntheses of (−)-Asperlicin and (−)-Asperlicin C. J Am Chem Soc. Jun. 11, 1998;120(25):6417-8.
Hegedus et al., Palladium-Catalyzed Reactions in the Synthesis of 3- and 4-Substituted Indoles. 3. Total Synthesis of(±)-Aurantioclavine, J. Org. Chem. 1987, 52, pp. 3319-3322.
Hendrickson et al., Total Synthesis of the Calycanthaceous Alkaloids, Tetrahedron 1964, vol. 20, pp. 565-579.
Hendrickson et al., Total Synthesis of the Calycanthaceous Alkaloids. Chimonanthine, R. Proc. Chem. Soc. 1962, pp. 383-384.
Herscheid et al., Biosynthesis of gliotoxin. Synthesis of sulfur-bridged dioxopiperazines from N-hydroxyamino acids. J. Org. Chem. 1980; 45(10):1885-1888.
Herzon et al., Enantioselective Synthesis of Stephacidin B, J. Am. Chem. Soc. 2005, 127, pp. 5342-5344.
Higuchi et al., First Total Synthesis of Hinckdentine A. Org Lett. 2009;11(1):197-9.
Higuchi et al., Preparation of 2,2-disubstituted 1,2-dihydro-3H-indol-3-ones via oxidation of 2-substituted indoles and Mannich-type reaction. Tetrahedron Lett. Feb. 6, 2010;66(6):1236-43.
Hino et al., Chemistry and Reactions of Cyclic Tautomers of Tryptamines and Tryptophans, The Alkaloids: Chemistry and Pharmacology, Brossi, A., Ed.; Academic Press: New York, 1989; vol. 34, pp. 1-75.
Hino et al., Oxidative Dimerization of Nb-Methoxycarbonyltryptamines by Dye-Sensitized Photooxygenation in Formic Acid. Synthesis of (±)-Folicanthine and (±)-Chimonanthine, Tetrahedron Letters 1978, 49, pp. 4913-4916.
Hino et al., Synthesis of 3,6-diethoxycarbonyl-3,6-epipolythia-2,5-piperazinedione derivatives. Tetrahedron Lett. 1971; 12(33):3127-3129.
Hino et al., Total Synthesis of (±)-Folicanthine, Tetrahedron Letters 1963, 25, pp. 1757-1760.
Hoffmann et al., A Powerful Br0nsted Acid Catalyst for the Organocatalytic Asymmetric Transfer Hydrogenation of Imines, Angew. Chem. Int. Ed. 2005, 44, pp. 7424-7427.
Hoijemberg et al., Photolysis of an asymmetrically substituted diazene in solution and in the crystalline state, Photochem. Photobiol. Sci. 2009, 8, pp. 961-969.
Holwell et al., Anti-vascular effects of vinflunine in the MAC 15A transplantable adenocarcinoma model. Br. J. Cancer., 2001; 84:290-295.
Hong et al., Bidirectional synthesis of the central amino acid of chloptosin. Org Lett. Oct. 12, 2006;8(21):4919-22. doi: 10.1021/ol0620139.
Hossain, T. Md et al., Synthesis of Bisbicyclo[1.1.1]pentyldiazene. The Smallest Brigehead Diazene, J. Org. Chem. 2001, 66, pp. 6282-6285.
Hsieh et al., Structure-activity and crystallographic analysis of benzophenone derivatives-the potential anticancer agents. Bioorg Med Chem Lett. 2002; 13(1):101-105.
Huang et al., Diketopiperazines from Marine Organisms. Chem. Biodiv. 2010; 7(12):2809-2829.
Huard et al., N-Tosyloxycarbamates as Reagents in Rhodium-Catalyzed C—H Amination Reactions, Chem. Eur. J. 2008, 14, pp. 6222-6230.
Ikeda et al., Evidence for Significant Through-Space and Through-Bond Electronic Coupling in the 1,4-Diphenylcyclohexane-1,4-diyl Radical Cation Gained by Absorption Spectroscopy and OFT Calculations, Chem. Eur. J. 2007, 13, DD. 9207-9215.
Isham et al., Chaetocin: a promising new antimyeloma agent with in vitro and in vivo activity mediated via imposition of oxidative stress. Blood. Mar. 15, 2007;109(6):2579-88.
Isham et al., The anticancer effects of chaetocin are independent of programmed cell death and hypoxia, and are associated with inhibition of endothelial cell proliferation. Br J Cancer. Jan. 17, 2012;106(2):314-23.
Ishikawa et al., Dimerization of indole derivatives with hypervalent iodines(III): a new entry for the concise total synthesis of rac- and meso-chimonanthines, Tetrahedron Lett. 2002, 43, pp. 5637-5639.
Ivashenko et al., Oxidative electrochemical aryl C—C coupling of spiropyrans. Chem Commun (Camb). Aug. 4, 2013;49(60):6737-9. doi: 10.1039/c3cc42396d.

(56) References Cited

OTHER PUBLICATIONS

Iwasa et al., Total Synthesis of (+)-Chaetocin and its Analogues: Their Histone Methyltransferase G9a Inhibitory Activity. J. Am. Chem. Soc. 2010; 132(12):4078-4079.
Iwasa, et al., Epipolythiodiketopiperazine Alkaloids: Total Syntheses and Biological Activities. Isr. J Chem. 2011; 51(3-4):420-433.
Jabri et al., Enantioselective Total Synthesis of Plectosphaeroic Acid B and C. J. Org. Chem. Aug. 27, 2013;78(17):8766-8788. doi: 10.1021/jo4015479.
Jadulco et al., New communesin derivatives from the fungus *Penicillium* sp. derived from the Mediterranean sponge Axinella verrucosa. J Nat Prod. Jan. 2004;67(1):78-81. doi: 10.1021/np030271y.
Jadulco et al., New Communesin Derivatives from the Fungus *Penicillium* sp. Derived from theMediterranean Sponge *Axinella verrucosa*, J. Nat. Prod. 2004, 67, pp. 78-81.
Jadulco, Isolation and Structure Elucidation of Bioactive Secondary Metabolites from Marine Sponges and Sponge-derived Fungi, 2002, 88.
Jamison et al., Enantioselective Synthesis of Polypyrrolo-indolines by Controlled Oligomerization, Nat. Chem. 2017, doi: 10.1038/nchem.2825, 1 page.
Janik et al., Synthesis and antimicrobtubule activity of combretatropone derivatives. Bioorg. Med. Chem. Lett. 2002; 10:1895-1903.
Jannic et al., Pyrrolidinoindoline alkaloids from Psychotria oleoides and Psychotria lyciiflora. J Nat Prod. Jun. 1999;62(6):838-43.
Jiang et al., Disulfide- and Multisulfide-Containing Metabolites from Marine Organisms. Chem. Rev. 2012; 112(4):2179-2207.
Jiang et al., Epipolythiodioxopiperazines from fungi: chemistry and bioactivities. Mini Rev Med Chem. Aug. 2011;11(9):728-45.
Jiang et al., Synthesis and biological evaluation of 2-styrylquinazolin-4(3H)-ones, a new class of antimitotic anticancer agents which inhibit tubulin polymerization. J. Med. Chem.1990; 33(6):1721-1728.
Jordan et al., Fungal epipolythiodioxopiperazine toxins have therapeutic potential and roles in disease. Trends Pharmacol. Sci. 8, 144-149.
Jouanneau et al., Derivatization of agelastatin a leading to bioactive analogs and a trifunctional probe, Bioorganic & Medicinal Chemistry Letters, 26, p. 2092-2097 (2016).
Kakeya, et al., Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid. Chem. Pharm. Bull. 1984 32(2):692-698.
Kamenecka et al., Studies in the Total Synthesis of Himastatin: A Revision of the Stereochemical Assignment. Angew Chem Int Ed Engl. Nov. 16, 1998;37(21):2993-2995. doi: 10.1002/(SICI)1521-3773(19981116)37:21<2993::AID-ANIE2993>3.0.CO;2-I.
Kaneko et al., New hydrazone derivatives of Adriamycin and their immunoconjugates—a correlation between acid stability and cytotoxicity. Bioconjugate Chem. 1991; 2(3):133-141.
Kanoh et al., (−)-Phenylahistin arrests cells in mitosis by inhibiting tubulin polymerization. J Antibiot (Tokyo). Feb. 1999; 52(2):134-41.
Karaman et al., Preparation and properties of quaternary ammonium and phosphonium permanganates. J. Org. Chem.1984; 49(23):4509-4516.
Kerzaon et al., Structural investigation and elucidation of new communesins from a marine-derived Penicillium expansum Link by liquid chromatography/electrospray ionization mass spectrometry. Rapid Commun Mass Spectrom. Dec. 2009;23(24):3928-38. doi: 10.1002/rcm.4330.
Kieffer et al., Copper-Catalyzed Diastereoselective Arylation of Tryptophan Derivatives: Total Synthesis of (+)-Naseseazines A and B, J. Am. Chem. Soc. 2013, 135(15), pp. 5557-5560.
Kim et al., Alkylthiolation of allylic sulfides. [2,3] Sigmatropic rearrangement of thiosulfonium ions. J. Org. Chem. 1979; 44(12):1897-1904.

Kim et al., Biogenetically inspired syntheses of alkaloid natural products. Chem Soc Rev. Nov. 2009;38(11):3035-50. doi: 10.1039/b819925f. Epub Sep. 23, 2009.
Kim et al., Biogenetically-Inspired Total Synthesis of Epidithiodiketopiperazines, Acc. Chem. Res. 2015, 48, pp. 1159-1171.
Kim et al., Concise Total Synthesis and Stereochemical Revision of (+)-Naseseazines A and B: Regioselective Arylative Dimerization of Diketopiperazine Alkaloids. J. Am. Chem. Soc. 2011; 133(38):14940-14943.
Kim et al., General approach to epipolythiodiketopiperazine alkaloids: total synthesis of (+)- chaetocins A and C and (+)-12,12'-dideoxychetracin A. J Am Chem Soc. Oct. 20, 2010;132(41):14376-8. doi: 10.1021/ja106869s.
Kim et al., Total synthesis of (+)-11,11'-dideoxyverticillin A. Science. Apr. 10, 2009;324(5924):238-41. doi: 10.1126/science.1170777.
Kim et al., Transition-Metal-Mediated Direct C—H Amination of Hydrocarbons with Amine Reactants: The Most Desirable but Challenging C—N Bond-Formation Approach, ACS Catal. 2016, 6, pp. 2341-2351.
King et al., Facile synthesis of maleimide bifuntional linkers, Tetrahedron Lett. 2002; 43:1987-1990.
Kingsbury et al., A novel peptide delivery system involving peptidase activated prodrugs as antimicrobial agents. Synthesis and biological activity of peptidyl derivatives of 5-fluorouracil. J. Med. Chem. 1984; 27:1447-1451.
Kingston et al., The Chemistry of Taxol, a Clinically Useful Anticancer Agent. J. Nat. Prod. 1990; 53(1):1-12.
Kirchgessner et al., Understanding reactivity patterns of the dialkylaniline radical cation. J Org Chem. Dec. 22, 2006;71(26):9849-52. doi: 10.1021/jo061809i.
Kishi et al., Total synthesis of dehydrogliotoxin. J. Am. Chem. Soc. 1973; 95(19):6492-6493.
Kitir et al., Total synthesis and structural validation of cyclodepsipeptides solonamide A and B, Tetrahedron 2014, 70, pp. 7721-7732.
Kobayashi et al., Synthetic study on an antitumor antibiotic rhizoxin by using an enzymatic process on prochiral β-substituted glutarates. Pure Appl. Chem. 1992; 64(8):1121-1124.
Kodanko et al., Enantioselective Total Syntheses of the Cyclotryptamine Alkaloids Hodgkinsine and Hodgkinsine B, Angew. Chem. Int. Ed. 2003, 42, pp. 2528-2531.
Kodanko et al., Synthesis of All Low-energy Stereoisomers of the Tris(pyrrolidinoindoline) Alkaloid Hodgkinsine and Preliminary Assessment of Their Antinociceptive Activity, J. Org. Chem. 2007, 72, pp. 7909-7914.
Kosower, E. M., Monosubstituted Diazenes (Diimides). Suprising Intermediates, Accounts ofChemical Research 1971, vol. 1, No. 6, pp. 193-198.
Kricheldorf, H.R. Synthese von Isothiocyanatocarbonsäurechloriden aus Lactamen. Angew. Chem. 1975; 87(14):517.
Krishnan et al., Pd-Catalyzed Enantioselective Aerobic Oxidation of Secondary Alcohols:Applications to the Total Synthesis of Alkaloids, J. Am. Chem. Soc. 2008, 130, pp. 13745-13754.
Kroutil et al., First preparative biocatalytic hydrolysis and S-methylation of cyclic trithiocarbonates. Tetrahedron 2002; 58(13):2589-2592.
Ksander et al., Chemie der α-Aminonitrile 1. Mitteilung Einleitung und Wege zu Uroporphyrinogen-octanitrilen. Helv Chim Acta. Jul. 8, 1987;70(4):1115-72.
Kung et al., Small molecule blockade of transcriptional coactivation of the hypoxia-inducible factor pathway. Cancer Cell. Jul. 2004;6(1):33-43.
Kurokawa et al., Synthesis of 1,3-Diamines Through Rhodium-Catalyzed C—H Insertion, Angew. Chem. Int. Ed. 2009, 48, pp. 2777-2779.
Laguzza et al., New antitumor monoclonal antibody-vinca conjugates LY203725 and related compounds: design, preparation, and representative in vivo activity. J. Med. Chem. 1989; 32(3):548-555.
Lam et al., Himastatin, a new antitumor antibiotic from Streptomyces hygroscopicus. I. Taxonomy of producing organism, fermentation and biological activity. J Antibiot (Tokyo). Aug. 1990;43(8):956-60. doi: 10.7164/antibiotics.43.956.

(56) References Cited

OTHER PUBLICATIONS

Larumbe et al., Anodic Oxidation of Some Tertiary Amines. J Electroanal Chem. 1991;304:241-7.

Lathrop et al., Application of diazene-directed fragment assembly to the total synthesis and stereochemical assignment of (+)-desmethyl-meso-chimonanthine and related heterodimeric alkaloids, Chem. Sci. 2014, 5, DD. 333-340.

Lathrop et al., Convergent and Biomimetic Enantioselective Total Synthesis of (−)- Communesin F. J Am Chem Soc. Jun. 22, 2016;138(24):7763-9. doi: 10.1021/jacs.6b04072. Epub Jun. 14, 2016.

Lathrop et al., Radical-mediated dimerization and oxidation reactions for the synthesis of complex alkaloids. Chimia (Aarau). 2012;66(6):389-93. doi: 10.2533/chimia.2012.389.

Lavielle et al., New .alpha.-amino phosphonic acid derivatives of vinblastine: chemistry and antitumor activity. J. Med. Chem. 1991; 34(7):1998-2003.

Lawrence et al., The interaction of chalcones with tubulin. Anticancer Drug Des. Apr. 2000; 15(2):135-41.

Lebsack et al., Enantioselective Total Synthesis of Quadrigemine C and Psycholeine, J. Am. Chem. Soc. 2002, 124, pp. 9008-9009.

Lee et al., Antihepatoma activity of chaetocin due to deregulated splicing of hypoxia-inducible factor 1α pre-mRNA in mice and in vitro. Hepatology. Jan. 2011;53(1):171-80.

Leet et al., Himastatin, a new antitumor antibiotic from Streptomyces hygroscopicus. II. Isolation and characterization. J Antibiot (Tokyo). Aug. 1990;43(8):961-6. doi: 10.7164/antibiotics.43.961.

Leoni et al., Indanocine, a microtubule-binding indanone and a selective inducer of apoptosis in multidrug-resistant cancer cells. J Natl Cancer Inst. Feb. 2, 2000;92(3):217-24.

Li et al., An integrated approach to the discovery of potent agelastatin A analogues for brain tumors: chemical synthesis and biological, physicochemical and CNS pharmacokinetic analyses, Med. Chem. Commun., 4, p. 1093-1098 (2013).

Li et al., Consequences of Depsipeptide Substitution on the ClpP Activation Activity of Antibacterial Acyldepsipeptides. ACS Med Chem Lett. Oct. 19, 2017;8(11):1171-1176. doi: 10.1021/acsmedchemlett.7b00320.

Li et al., Cytotoxic metabolites from the antarctic psychrophilic fungus Oidiodendron truncatum. J Nat Prod. May 25, 2012;75(5):920-7. doi: 10.1021/np3000443. Epub May 14, 2012.

Li et al., General Approach for the Synthesis of Ajmaline/Sarpagine Indole Alkaloids: Enantiospecific Total Synthesis of (+)-Ajmaline, Alkaloid G, and Norsuaveoline via the Asymmetric Pictet-Spengler Reaction. J Am Chem Soc. Jul. 16, 1999;121(30):6998-7010.

Li et al., Ligand-based targeted therapy: a novel strategy for hepatocellular carcinoma. Int J Nanomedicine. Oct. 31, 2016;11:5645-5669. eCollection 2016.

Li et al., Pharmacokinetics of Agelastatin A in the central nervous system. Med. Chem. Commun. 2012;3:233-237.

Liang et al., Organocatalytic stereoselective conjugate addition of 3-substituted oxindoles with in situ generated ortho-quinone methides. Tetrahedron Lett. May 2, 2018;59(18):1742-7.

Libot et al., Biomimetic Transformation of Hodgkinsine, a Pyrrolidinoindoline Alkaloids, Heterocycles 1988, 27, pp. 2381-2386.

Libot et al., Rubiacees D'Oceanie: Alcalo'ldes de Psychotria Oleoides de Nouvelle-Caledonie et de Calycodendron Milnei du Vanuatu (Nouvelles-Hebrides), Journal of Natural Products 1987, vol. 50, No. 3, pp. 468-473.

Lim et al., Novel Route to Azobenzenes via Pd-Catalyzed Coupling Reactions of Aryl Hydrazides with Aryl Halides, Followed by Direct Oxidations, Org. Lett. 2003, vol. 5, No. 7, pp. 979-982.

Lin et al., Antimitotic natural products combretastatin A-4 and combretastatin A-2: studies on the mechanism of their inhibition of the binding of colchicine to tubulin. Biochemistry 1989; 28(17):6984-6991.

Lin et al., Elucidation of the Concise Biosynthetic Pathway of the Communesin Indole Alkaloids, Angew. Chem. Int. Ed. 2015, 54, pp. 3004-3007.

Lin et al., P450-Mediated Coupling of Indole Fragments to Forge Communesin and Unnatural Isomers. J Am Chem Soc. Mar. 30, 2016;138(12):4002-5. doi: 10.1021/jacs.6b01413. Epub Mar. 18, 2016.

Lindovska et al., Concise Synthesis of (−)-Hodgkinsine, (−)-Calycosidine, (−)-Hodgkinsine B, (−)- Quadrigemine C, and (−)-Psycholeine via Convergent and Directed Modular Assembly of Cyclotryptamines, https://www.ncbi.nlm.nih.gov/m/pubmed/29058431, 2017, 7 pages.

Ling et al., A new antibiotic kills pathogens without detectable resistance. Nature. Jan. 22, 2015;517(7535):455-9. doi: 10.1038/nature14098. Epub Jan. 7, 2015. Erratum in: Nature. Apr. 16, 2015;520(7547):388.

Ling et al., Synthesis of benzidine derivatives via $FeCl_3 \cdot 6H_2O$-promoted oxidative coupling of anilines. J Org Chem. Jun. 7, 2013;78(11):5218-26. doi: 10.1021/jo4002504. Epub May 28, 2013.

Link et al., Stereocontrolled Total Syntheses of meso-Chimonanthine and meso-Calycanthine via a Novel Samarium Mediated Reductive Dialkylation, J. Am. Chem. Soc. 1996, 118, pp. 8166-8167.

Little et al., Total Synthesis of the Marine Natural Product il9(121-Capnellene. Reversal ofRegiochemistry in the Intramolecular 1,3-Diyl Trapping Reaction, J. Am. Chem. Soc. 1983, 105, pp. 928-932.

Little, R. D., Diyl Trapping and Electroreductive Cyclization Reactions, Chem. Rev. 1996, 96, pp. 93-114.

Liu et al., Total Synthesis of the Polycyclic Fungal Metabolite (±)-Communesin F, Angew. Chem. Int. Ed. 2010, 49, pp. 2000-2003.

Liu et al., Verticillin A overcomes apoptosis resistance in human colon carcinoma through DNA methylation-dependent upregulation of BNIP3. Cancer Res. Nov. 1, 2011;71(21):6807-16.

Loach et al., Concise Total Synthesis of (+)-Asperazine, (+)-Pestalazine A, and (+)-iso-Pestalazine A. Structure Revision of (+)-Pestalazine A. J Am Chem Soc. Jan. 27, 2016;138(3):1057-64. doi: 10.1021/jacs.5b12392. Epub Jan. 19, 2016.

Lopez et al., Mechanistic insights into the stereocontrolled synthesis of hexahydropyrrolo[2,3-blindoles by electrophilic activation of tryptophan derivatives. Org Lett. Jan. 3, 2008;10(1):77-80. doi: 10.1021/01702732j. Epub Dec. 11, 2007.

Ma et al., Biosynthesis of himastatin: assembly line and characterization of three cytochrome P450 enzymes involved in the post-tailoring oxidative steps. Angew Chem Int Ed Engl. Aug. 16, 2011;50(34):7797-802. doi: 10.1002/anie.201102305. Epub Jul. 1, 2011.

Mahboobi et al., Synthetic 2-Aroylindole Derivatives as a New Class of Potent Tubulin-Inhibitory, Antimitotic Agents. J. Med. Chem. 2001; 44(26):4535-4553.

Mamber et al., Inhibition of antibacterial activity of himastatin, a new antitumor antibiotic from Streptomyces hygroscopicus, by fatty acid sodium salts. Antimicrob Agents Chemother. Nov. 1994;38(11):2633-42. doi: 10.1128/AAC.38.11.2633.

Mannila et al., Combretastatin Analogs via Hydration of Stilbene Derivatives. Liebigs. Ann. Chem. 1993; 1993(9):1037-1039.

Mascitti et al., Total Synthesis of (±)-Pentacycloanammoxic Acid, J. Am. Chem. Soc. 2004, 126, pp. 15664-15665.

Mason et al., Agelastatin A: a novel inhibitor of osteopontin-mediated adhesion, invasion, and colony formation, Mol. Cancer Ther., 7:548-558 (2008).

Matano et al., Synthesis and Charge-Carrier Transport Properties of Poly(phosphole P-alkanesulfonylimide)s, Org. Lett., 2013, 15 (4), pp. 932-935.

Matsuda et al., Total Synthesis and Structure Reinvestigation of So-Called Isochimonanthine, Heterocycles 2005, 65, pp. 1031-1033.

May, J. A. et al., Biomimetic approach to communesin B (a.k.a. nomofungin), Tetrahedron Letters 2003, 44, pp. 1203-1205.

May, J. A. et al., The structural and synthetic implications of the biosynthesis of the calycanthaceous alkaloids, the communesins, and nomofungin, Tetrahedron 2006, 62, pp. 5262-5271.

McMahon, VEGF receptor signaling in tumor angiogenesis. Oncologist. 2000;5 Suppl 1:3-10. doi: 10.1634/theoncologist.5-suppl_1-3. PMID: 10804084.

(56) References Cited

OTHER PUBLICATIONS

Medarde et al., Synthesis and antineoplastic activity of combretastatin analogues: Heterocombretastatins. Eur. J. Med. Chem., 1998; 33(1)71-77.
Medarde et al., Synthesis and pharmacological activity of combretastatin analogues. Naphthylcombretastatins and related compounds. Bioorganic. Med. Chem. Lett. 1995; 5(3):229-232.
Medarde et al., Synthesis and pharmacological activity of diarylindole derivatives. Cytotoxic agents based on combretastatins. Bioorg Med Chem Lett. Aug. 1, 1999; 9(16):2303-2308.
Medina et al., Novel antineoplastic agents with efficacy against multidrug resistant tumor cells. Bioorg Med Chem Lett. Oct. 6, 1998; 8(19):2653-6.
Michaelis, D. J. et al., Oxaziridine-mediated enantioselective aminohydroxylation of styrenes catalyzed by copper(II) bis(oxazoline) complexes, Tetrahedron 2009, 65, pp. 5118-5124.
Miknis et al., Total synthesis of (.+--.)-aspirochlorine. J. Am. Chem. Soc. 1993; 115(2):536-547.
Miller et al., Specific Inhibition of Viral Ribonucleic Acid Replication by Gliotoxin. Science Jan. 26, 1968; 159(3813):431-432.
Miranda et al., Alkaloids of Aspidosperma melanocalyx Muell-Arg. Experientia. Jun. 15, 1969;25(6):575-6. doi: 10.1007/BF01896517.
Moody et al., Dirhodium(II) tetraacetate catalysed reactions of diazo thioamides: isolation and cycloaddition of anhydro-4-hydroxy-1,3-thiazolium hydroxides (thioisomünchnones), an approach to analogues of dehydrogliotoxin. Org. Biomol. Chem. 2003;1(15):2716-2722.
Morton, D. et al., Chiral non-racemic sulfinimines: versatile reagents for asymmetric synthesis, Tetrahedron 2006, 62, pp. 8869-8905.
Movassaghi et al., Concise total synthesis of (+)-WIN 64821 and (−)-ditryptophenaline. Angew Chem Int Ed Engl. 2008;47(8):1485-7. doi: 10.1002/anie.200704960.
Movassaghi et al., Concise total synthesis of (−)-calycanthine, (+)-chimonanthine, and (+)- folicanthine. Angew Chem Int Ed Engl. 2007;46(20):3725-8. doi: 10.1002/anie.200700705.
Movassaghi et al., Directed heterodimerization: stereocontrolled assembly via solvent-caged unsymmetrical diazene fragmentation. J Am Chem Soc. Aug. 24, 2011;133(33):13002-5. doi: 10.1021/ja2057852. Epub Aug. 1, 2011.
Movassaghi et al., Total Synthesis of All (−)-Agelastatin Alkaloids Asymmetric Synthesis Ii: More Methods and Applications. 2013;391-396. DOI: 10.1002/9783527652235.ch49.
Movassaghi et al., Total synthesis of all (−)-agelastatin alkaloids. Chem. Sci. 2010;1:561-66.
Mu et al., Synthesis, anticancer activity, and inhibition of tubulin polymerization by conformationally restricted analogues of lavendustin A. J Med Chem. Apr. 24, 2003; 46(9):1670-82.
Myers et al., A Concise, Stereocontrolled Synthesis of (−)-Saframycin A by the Directed Condensation of α-Amino Aldehyde Precursors. J Am Chem Soc. Nov. 5, 1999;121(46):10828-29.
Müllbacher et al., Structural relationship of epipolythiodioxopiperazines and their immunomodulating activity. Molec. Immunol. Feb. 1986; 23(2):231-235.
Nakada et al., The first total synthesis of the antitumor macrolide, rhizoxin. Tetrahedron Lett., 1993; 34(6):1039-1042.
Nakagawa et al., Oxidative Dimerization of Nb-Acyltryptophans Total Synthesis and Absolute Configuration of Ditryptophenaline, Tetrahedron Letters 1981, vol. 22, No. 52, pp. 5323-5326.
Nam et al., Combretastatin A-4 analogues as antimitotic antitumor agents. Curr Med Chem. Sep. 2003; 10(17):1697-722.
Nam et al., Synthesis and anti-tumor activity of novel combretastatins: combretocyclopentenones and related analogues. Bioorg Med Chem Lett. 2002; 12(15):1955-1958.
Nascimento et al., New Alkaloids from Margaritopsis carrascoana (Rubiaceae), J. Braz. Chem. Soc. 2015, vol. 26, No. 6, pp. 1152-1159.
Natali et al., Interaction studies between photochromic spiropyrans and transition metal cations: the curious case of copper. Org Biomol Chem. Feb. 14, 2012;10(6):1162-71. doi: 10.1039/c1ob06375h. Epub Dec. 7, 2011.

Nelsen et al., Azocumene. I. Preparation and Decomposition of Azocumene. Unsymmetrical Coupling Products of the Cumyl Radical, Journal of the American Chemical Society, Jan. 5, 1966, 88:1, pp. 137-143.
Nelson et al., Chiral Anion Phase Transfer of Aryldiazonium Cations: An EnantioselectiveSynthesis of C3-Diazenated Pyrroloindolines, Angew. Chem. Int. Ed. 2014, 53, pp. 5600-5603.
Nelson et al., Concise total synthesis of (+)-asperazine A and (+)-pestalazine B. Org Biomol Chem. Jan. 3, 2018;16(2):202-207. doi: 10.1039/c7ob02985c.
Neuman et al., cis-Diazenes. Viscosity Effects, One-Bond Scission, and Cis-Trans Isomerization, J. Org. Chem. 1990, 55, pp. 2682-2688.
Nguyen et al., A general solid phase method for the synthesis of depsipeptides. Org Biomol Chem. Feb. 21, 2013;11(7):1167-70. doi: 10.1039/c2ob26893k.
Nguyen-Hai et al., Combretoxazolones: synthesis, cytotoxicity and antitumor activity. Bioorg. Med. Chem. Lett. 2001; 11(23):3073-3076.
Nicolaou et al., A Practical Sulfenylation of 2,5-Diketopiperazines. Angem. Chem. Int. Ed. 2012; 51(3):728-732.
Nicolaou et al., Synthesis of epothilones A and B in solid and solution phase. Nature. May 15, 1997;387(6630):268-72.
Nicolaou et al., Total Synthesis of Epicoccin G. J. Am. Chem. Soc. 2011; 133(21):8150-8153.
Nielsen et al., Glycolamide Esters as Biolabile Prodrugs of Carboxylic Acid Agents: Synthesis, Stability, Bioconversion, and Physicochemical Properties. J. Pharma. Sciences. 1988; 77(4):285-298.
Nishida et al., Fungal metabolite gliotoxin targets flavocytochrome b558 in the activation of the human neutrophil NADPH oxidase. Infect Immun. Jan. 2005;73(1):235-44.
Numata et al., Communesins, cytotoxic metabolites of a fungus isolated from a marine alga. Tetrahedron Lett. Apr. 2, 1993;34(14):2355-8. doi: 10.1016/S0040-4039(00)77612-X.
Numata, A. et al., Communesins, Cytotoxic Metabolites of a Fungus Isolated from a Marine Alga, Tetrahedron Lett. 1993, 34, pp. 2355-2358.
Oelke et al., Total synthesis of chloptosin. Angew Chem Int Ed Engl. Aug. 16, 2010;49(35):6139-42. doi: 10.1002/anie.201002880.
Oelke et al., Total synthesis of chloptosin: a dimeric cyclohexapeptide. Chemistry. Apr. 4, 2011;17(15):4183-94. doi: 10.1002/chem.201003216. Epub Mar. 15, 2011.
Oguri et al., Amino Acids and Peptides. XXIX. A New Efficient Asymmetric Synthesis of α-Amino Acid Derivatives with Recycle of a Chiral Reagent-Asymmetric Alkylation of a Chiral Schiff Base from Glycine. Chem. Pharm. Bull. 1978; 26(3):803-808.
Ohme, R. et al., Preparation of Azo Compounds from N,N'-Dialkylsulfamides, Angew. Chem. Internat. Edit. 1965, vol. 4, No. 5, p. 433.
Ohsumi et al., Novel Combretastatin Analogues Effective against Murine Solid Tumors: Design and Structure-Activity Relationships. J. Med. Chem. 1998; 41(16):3022-3032.
Ohsumi et al., Syntheses and antitumor activity of cis-restricted combretastatins: 5-membered heterocyclic analogues. Bioorg Med Chem Lett. Nov. 17, 1998; 8(22):3153-8.
Okoth et al., End-labeled amino terminated monotelechelic glycopolymers generated by ROMP and Cu(I)-catalyzed azide-alkyne cycloaddition, Beilstein J. Org. Chem. 2013, 9, 608-612.
Olsson et al., Synthesis of Potent Cytotoxic Epidithiodiketopiperazines Designed for Derivatization. J Org Chem. Apr. 3, 2020;85(7):4648-4662. doi: 10.1021/acs.joc.9b03371. Epub Mar. 19, 2020. PMID: 32126173; PMCID: PMC7127967.
Ooi et al., XF-73, a novel antistaphylococcal membrane-active agent with rapid bactericidal activity. J Antimicrob Chemother. Oct. 2009;64(4):735-40. doi: 10.1093/jac/dkp299. Epub Aug. 18, 2009.
Ottenheijm et al., Approaches to analogs of dehydrogliotoxin. 6. An efficient synthesis of a gliotoxin analog with anti-reverse transcriptase activity. J. Org. Chem. 1976: 41(21):3433-3438.
Overman et al., Construction of Epithiodioxopiperazines by Directed Oxidation of Hydroxyproline-Derived Dioxopiperazines. Org. Lett. 2007; 9(25):5267-5270.

(56) References Cited

OTHER PUBLICATIONS

Overman et al., Direct Stereo- and Enantiocontrolled Synthesis of Vicinal Stereogenic Quaternary Carbon Centers. Total Synthesis of meso- and (−)-Chimonanthine and (+)-Calycanthine, J. Am. Chem. Soc. 1999, 121, pp. 7702-7703.
Overman et al., Enantioselective Construction of Vicinal Stereogenic Quaternary Centers by Dialkylation: Practical Total Syntheses of(+)- and meso-Chimonanthine, Angew. Chem. Int. Ed. 2000, vol. 39, No. 1, pp. 213-215.
Overman et al., Enantioselective synthesis of (−)-idiospermuline, Tetrahedron 2003, 59, pp. 6905-6919.
Overman et al., Enantioselective Total Synthesis of (+)-Gliocladin C, Org. Lett. 2007, 9(2), pp. 339-341.
Overman et al., Enantioselective Total Synthesis of the Cyclotryptamine Alkaloid Idiospermuline, Angew. Chem. Int. Ed. 2003, 42, pp. 2525-2528.
Overman et al., The cyanomethyl group for nitrogen protection and iminium ion generation in ring-enlarging pyrrolidine annulation. A short synthesis of the amaryllidaceae alkaloid d,1-crinine. Tetrahedron Lett. 1982;23(27):2741-4.
Owellen et al., Inhibition of tubulin-microtubule polymerization by drugs of the Vinca alkaloid class. Cancer Res. Apr. 1976; 36(4):1499-502.
Pahl et al., The immunosuppressive fungal metabolite gliotoxin specifically inhibits transcription factor NF-kappaB. J Exp Med. Apr. 1, 1996; 183(4): 1829-1840.
Palmisano et al., Aspidosperma Alkaloids. A New Didehydrodimerization Mode of β-Anilinoacrylic Alkaloids by Anodic Oxidation. Helv Chim Acta. 1992;75:813-24. doi: 10.1002/hlca.19920750316.
Patel et al., Straightforward access to protected syn alpha-amino-beta-hydroxy acid derivatives. Angew Chem Int Ed Engl. 2008; 47(22):4224-7.
Patron et al., Origin and distribution of epipolythiodioxopiperazine (ETP) gene clusters in filamentous ascomycetes. BMC Evolutionary Biology 2007; 7:174.
Perez-Balado et al., Expedient Total Synthesis of WIN 64745 and WIN 64821, Org. Lett. 2008, vol. 10, No. 17, pp. 3701-3704.
Perez-Balado et al., Stereocontrolled and Versatile Total Synthesis of Bispyrrolidinoindoline Diketopiperazine Alkaloids: Structural Revision of the Fungal Isolate (+)-Asperdimin, Chem. Eur. J. 2009, 15, pp. 9928-9937.
Peterson et al., Antibiotic Resistance Mechanisms in Bacteria: Relationships Between Resistance Determinants of Antibiotic Producers, Environmental Bacteria, and Clinical Pathogens. Front Microbiol. Nov. 30, 2018;9:2928. doi: 10.3389/fmicb.2018.02928.
Pettit et al., Antineoplastic agents 365. Dolastatin 10 SAR probes. Anticancer Drug Des. Jun. 1998; 13(4):243-77.
Pettit et al., Antineoplastic agents, 122. Constituents of Combretum caffrum. J. Nat. Prod. 1987; 50(3):386-391.
Pettit et al., Antineoplastic agents. 113. Synthesis of natural (−)-combretastatin. J. Org. Chem. 1985; 50(18):3404-3406.
Pettit et al., Antineoplastic agents. 257. Isolation and structure of spongistatin 1. J. Org. Chem.1993; 58(6):1302-1304.
Pettit et al., Antineoplastic Agents. 291. Isolation and Synthesis of Combretastatins A-4, A-5, and A-6. J. Med. Chem. 1995; 38(10):1666-1672.
Pettit et al., Antineoplastic Agents. 443. Synthesis of the Cancer Cell Growth Inhibitor Hydroxyphenstatin and Its Sodium Diphosphate Prodrug. J. Med. Chem. 2000; 43(14):2731-2737.
Pettit et al., Antineoplastic agents. 487. Synthesis and biological evaluation of the antineoplastic agent 3,4-methylenedioxy-5,4'-dimethoxy-3'-amino-Z-stilbene and derived amino acid amides. J Med Chem. Feb. 13, 2003; 46(4):525-31.
Pettit et al., cation salts, combretastatin A-3, diphosphate, prodrugs. Anti-Cancer Drug Design 2000: 15(6):397-403.
Pettit et al., Isolation and structure of combretastatin. Canadian Journal of Chemistry, 1982, 60(11): 1374-137.
Pettit et al., The isolation and structure of a remarkable marine animal antineoplastic constituent: dolastatin 10. J. Am. Chem. Soc.1987; 109(22):6883-6885.
Pinedo et al., Translational Research: the role of VEGF in tumor angiogenesis. Oncologist. Jan. 2000;5:1-2.
Pinney et al., A new anti-tubulin agent containing the benzo[b]thiophene ring system. Bioorg Med Chem Lett. Apr. 19, 1999; 9(8):1081-6.
Pinney et al., Synthesis and biological evaluation of aryl azide derivatives of combretastatin A-4 as molecular probes for tubulin. Bioorg Med Chem. Oct. 2000; 8(10):2417-25.
Pogliano et al., Daptomycin-mediated reorganization of membrane architecture causes mislocalization of essential cell division proteins. J Bacteriol. Sep. 2012;194(17):4494-504. doi: 10.1128/JB.00011-12. Epub Jun. 1, 2012.
Poisel et al., Syntheseversuche in der Reihe der 3.6-Epidithio-2.5-dioxo-piperazin-Antibiotika Gliotoxin, Sporidesmin, Aranotin und Chaetocin, II. Chem. Ber., 1971; 104(6):17141721.
Polaske et al., Enantioselective organocatalytic α-sulfenylation of substituted diketopiperazines. Tetrahedron: Asym. 2009; 20(23):2742-2750.
Pompeo et al., Total Synthesis and Anti-Cancer Activity of All Known Communesin Alkaloids and Related Derivatives. J Am Chem Soc. Sep. 11, 2019;141(36):14411-14420. doi: 10.1021/jacs.9b07397. Epub Aug. 30, 2019.
Porter et al., Diazenyl Radicals: A 15N CIDNP and Radical Trapping Study of Unsymmetric Diazenes, Journal of the American Chemical Society Feb. 1, 1978, 100:3, pp. 920-925.
Porter et al., Photolysis of Unsymmetric Azo Compounds. Cis Azo Compound Intermediates, Journal of the American Chemical Society Jun. 27, 1973, 95:13, pp. 4361-4367.
Pubchem CID 161244 deposited on Mar. 27, 2005, pp. 1-15.
Pubchem CID 18624123 deposited on Dec. 4, 2007, pp. 1-12.
Pubchem CID 69829071 deposited on Dec. 1, 2012, pp. 1-12.
Qian et al., Rhodium(II)- and copper(II)-catalyzed reactions of enol diazoacetates with nitrones: metal carbene versus Lewis acid directed pathways. Angew Chem Int Ed Engl. Jun. 11, 2012;51(24):5900-3. doi: 10.1002/anie.201202525. Epub May 4, 2012.
Rao et al., Radical mediated enantioselective construction of C-1 to C-9 segment of rhizoxin. Tetrahedron Lett. 1992; 33(27):3907-3910.
Rao et al., Studies directed towards the total synthesis of rhizoxin: Stereoselective synthesis of C-12 to C-18 segment. Tetrahedron Lett. 1993; 34(4):707-710.
Rasolonjanahary et al., Psycholeine, a natural alkaloid extracted from Psychotria oleoides, acts as a weak antagonist of somatostatin, European Journal of Pharmacology 1995, 285, pp. 19-23.
Reece et al., Epidithiodiketopiperazines (ETPs) exhibit in vitro antiangiogenic and in vivo antitumor activity by disrupting the HIF-1α/p300 complex in a preclinical model of prostate cancer. Mol Cancer. Apr. 28, 2014;13:91. doi: 10.1186/1476-4598-13-91.
Rezanka et al., Pharmacologically Active Sulfur-Containing Compounds. Anti-Infect. Agents Med. Chem., 2006; 5(2):187-224.
Ried et al., Uber Synthese und Reaktionen neuer vinyloger Chlorformamidine. Liebigs Ann Chem. 1986:389-394.
Rightsel et al., Antiviral Activity of Gliotoxin and Gliotoxin Acetate. Nature. Dec. 26, 1964;204:1333-4.
Robak et al., Synthesis and Applications of tert-Butanesulfinamide, Chem. Rev. 2010, 110, pp. 3600-3637 40 (Parts 1 & 2).
Robinson et al., Calcycanthine and Calycanthidine, Chem. Ind. 1954, 27, pp. 783-784.
Roch et al., Daptomycin Resistance in Clinical MRSA Strains Is Associated with a High Biological Fitness Cost. Front Microbiol. Dec. 5, 2017;8:2303. doi: 10.3389/fmicb.2017.02303.
Rodrigues et al., Synthesis and beta-lactamase-mediated activation of a cephalosporin-taxol prodrug. Chem Biol. Apr. 1995; 2(4):223-7.
Rodriguez-Vazquez et al., Membrane-targeted self-assembling cyclic peptide nanotubes. Curr Top Med Chem. 2014;14(23):2647-61. doi: 10.2174/1568026614666141215143431.
Roizen et al., Metal Catalyzed Nitrogen-Atom Transfer methods for the Oxidation of Aliphatic C—H Bonds, Accounts of Chemical Research, Jan. 10, 2012, vol. 45, No. 6, pp. 911-922.
Roizen et al., Selective Intermolecular Amination of C—H Bonds at Tertiary Carbon Centers, Angew. Chem. Int. Ed. 2013, 52, pp. 11343-11346.

(56) References Cited

OTHER PUBLICATIONS

Ross et al., The Chemistry of Methyl Vinyl Ketone. II. Reactions with Esters, β-Keto Esters, Malonic Ester, Amines, Tar Bases, and Inorganic Salts. J. Org. Chem. 1964; 29(8):2346-2350.
Ruff et al., Thiolation of symmetrical and unsymmetrical diketopiperazines. Org. Biomol. Chem. 2012; 10(5):935-940.
Ruiz-Sanchis et al., Orthogonal Protecting Groups in the Synthesis of Tryptophanyl-Hexahydropyrroloindoles. Eur J Org Chem. Jan. 2012;1:67-73. doi: 10.1002/ejoc.201101057.
Saad et al., Biological Activities of Pyrrolidinoindoline Alkaloids from Calycodendron milnei, Planta Med. 1995, 61, pp. 313-316.
Sakaitani et al., Syntheses and Reactions of Silyl Carbamates. 1. Chemoselective Transformation of Amino Protecting Groups via Tert-Butyldimethylsilyl Carbamates. J Org Chem. Feb. 1, 1990;55(3):870-6. doi: 10.1021/jo00290a015.
Sala et al., Tetrabutylammonium permanganate: an efficient oxidant for organic substrates. J. Chem. Soc., Chem. Commun. 1978; 253-254.
Salayova et al., Stereoselective synthesis of 1-methoxyspiroindoline phytoalexins and their amino analogues. Tetrahedron: Asymmetry. Sep. 15, 2014;24(16-17):1221-33.
Saruwatari et al., Cytochrome P450 as dimerization catalyst in diketopiperazine alkaloid biosynthesis. Chembiochem. Mar. 21, 2014;15(5):656-9. doi: 10.1002/cbic.201300751.
Schammel et al., Exploration of the interrupted Fischer indolization reaction, Tetrahedron 2010, 66, pp. 4687-4695.
Schiff et al., Promotion of microtubule assembly in vitro by taxol. Nature. 1979; 277:665-667.
Schmidt et al., New Strategies for the Synthesis of Hexahydropyrroloindole Alkaloids Inspired by Biosynthetic Hypotheses, Synlett 2008, 3, pp. 0313-0324.
Schumacher et al., Potent Antitumor Activity of 2-Methoxyestradiol in Human Pancreatic Cancer Cell Lines. Clin. Cancer Res. 1999; 5(3):493-499.
Scott et al., Reaction Pathways in the Photochemical Conversion of Diphenylamines toCarbazoles, J. Am. Chem. Soc. 1964, 86, pp. 302-303.
Senanayake et al., Enantiopure Sulfoxides and Sulfinamides: Recent Developments in Their Stereoselective Synthesis and Applications to Asymmetric Synthesis, Aldrichim. Acta 2005, 38, pp. 93-104.
Seo, J. H. et al., Synthetic Studies on Perophoramidine and the Communesins: Construction of the Vicinal Quaternary Stereocenters, J. Org. Chem. 2006, 71, pp. 8891-8900.
Sevier et al., Formation and transfer of disulphide bonds in living cells. Nat Rev Mol Cell Biol. Nov. 2002;3(11):836-47.
Shamis et al., Bioactivation of Self-Immolative Dendritic Prodrugs by Catalytic Antibody 38C2, J. Am. Chem. Soc. 2004; 126 (6):1726-1731.
Shan et al., Selective, covalent modification of β-tubulin residue Cys-239 by T138067, an antitumor agent with in vivo efficacy against multidrug-resistant tumors. Proc. Nat. Acad. Sci. USA May 11, 1999; 96(10):5686-5691.
Shende et al., Structure and Function of NzeB, a Versatile C—C and C—N Bond-Forming Diketopiperazine Dimerase. J Am Chem Soc. Oct. 14, 2020;142(41):17413-17424. doi: 10.1021/jacs.0c06312. Epub Sep. 30, 2020.
Shi et al., Distinct reactivity differences of metal oxo and its corresponding hydroxo moieties in oxidations: implications from a manganese(IV) complex having dihydroxide ligand. Angew Chem Int Ed Engl. Aug. 1, 2011; 50(32):7321-4.
Shi et al., Synthesis and Reactions of 2-(Alkylthio )-4,4-dimenthyl-1,3-thiazole-5( 4H)-thiones. Helvetica Chemica Acta. 1994;77:1903-1920.
Shin et al., Transition-Metal-Catalyzed C—N Bond Forming Reactions Using Organic Azides as the Nitrogen Source: A Journey for the Mild and Versatile C—H Amination. Acc. Chem. Res. 2015;48:1040-1052.
Shirai et al., Asymmetric synthesis of antimitotic combretadioxolane with potent antitumor activity against multi-drug resistant cells. Bioorg Med Chem Lett. Aug. 4, 1998; 8(15):1997-2000.

Shirai et al., Synthesis and nti-tubulin activity of aza-combretastatins. Bioorganic. Med. Chem. Lett. 1994; 4(5):699-704.
Shiraki et al., Solid-state photochemistry of crystalline pyrazolines: reliable generation and reactivity control of 1,3-biradicals and their potential for the green chemistry sysnthesis of substitutedcyclopropanes, Photochem. Photobiol. Sci. 2012, 11, pp. 1929-1937.
Shiraki et al., The synthesis and stereospecific solid-state photodecarbonylation of hexasubstituted mesa- and d,/-ketones. Photochem. Photobiol. Sci. 2011;10:1480-1487.
Singh et al., Antineoplastic agents. 166. Isolation, structure, and synthesis of combretastatin C-1. J. Org. Chem. 1989; 54(17):4105-4114.
Singh et al., Recent trends in targeted anticancer prodrug and conjugate design. Curr Med Chem. 2008;15(18):1802-26.
Snell et al., Catalytic Enantioselective Total Synthesis of Hodgkinsine B. Angew. Chem. Int. Ed. 2011;50:9116-9119.
Soledade et al., Minor phytotoxins from the blackleg fungus Phoma lingam. Phytonchem. 1990; 29(3):777-782.
Solladie-Cavallo et al., A Four-Step Diastereoselective Synthesis of D-erythro-Sphingosine by an Enantioselective Aldol Reaction Using a Titanium Enolate Derived from a Chiral Iminoglycinate. J. Org. Chem. 1994; 59(11):3240-3242.
Solladie-Cavallo et al., A four-step synthesis of erythro-m-chloro-3-hydroxytyrosine ethyl ester enantiomerically pure. Tetrahedron Lett., 1998; 39(15):2191-2194.
Solladie-Cavallo et al., Diastereoselective monoalkylation of lithium and potassium enolates of a chiral imine of ethyl glycinate: the role of added salts. Organometallics1993; 12(9):3743-3747.
Solladie-Cavallo et al., Enantioselective synthesis of optically pure natural S(+) or unnatural R(−) DABA. Tetrahedron Lett. 1989;30(44):6011-6014.
Somei et al., A novel reductive amino-cyclization method and its application for the total syntheses of (±)-aurantio-clavine and (±)-lophocerine, Heterocycles 2007, 7 4, pp. 943-950.
Somei et al., Preparations of melatonin and 1-hydroxymelatonin, and its novel nucleophilicdimerization to (±)-3a,3a'-bispyrrolo[2,3-b]indoles. Heterocycles. 1999;51(6):1237-1242.
Speth et al., Gliotoxin as putative virulence factor and immunotherapeutic target in a cell culture model of cerebral aspergillosis. Mol Immunol. Sep. 2011;48(15-16):2122-9.
Springer et al., The structure of ditryptophenaline—a new metabolite of aspergillusflavus. Tetrahedron Lett. 1977: 18(28):2403-2406.
Steinbuch et al., Mechanisms of Resistance to Membrane-Disrupting Antibiotics in Gram-Positive and Gram-Negative Bacteria. Med Chem Commun. Nov. 19, 2015;7:86-102. doi: 10.1039/C5MD00389J.
Steininger, Synthesis of 5-Chloromethyl-2,dinitrotetrahydrofuran. Angew. Chem. Internat. Edit.1965;4(5):433.
Stephens et al., Straightforward Access to Hexahydropyrrolo[2,3-b]indole Core by aRegioselective C3-Azo Coupling Reaction of Arenediazonium Compounds with Tryptamines, Eur. J. Org. Chem. 2014, pp. 3662-3670.
Steven et al., Total Synthesis of Complex Cyclotryptamine Alkaloids: Stereocontrolled Construction of Quaternary Carbon Stereocenters, Angew. Chem. Int. Ed. 2007, 46, pp. 5488-5508.
Stork, The stereospecific synthesis of reserpine. Pure Appl Chem. 1989;61(3):439-42.
Storm et al., Effect of small changes in orientation on reaction rate. J. Am. Chem. Soc. 1972; 94(16):5815-5825.
Stout et al., Potent Fluorinated Agelastatin Analogues for Chronic Lymphocytic Leukemia: Design, Synthesis, and Pharmacokinetic Studies, J. Med. Chem., 57, p. 5085-5093 (2014).
Strassner et al., Mechanism of Permanganate Oxidation of Alkanes: Hydrogen Abstraction and Oxygen "Rebound" J. Am. Chem. Soc. 2000; 122(32):7821-7822.
Stueber et al., Carbonates, Thiocarbonates, and the Corresponding Monoalkyl Derivatives. 1. Their Preparation and Isotropic 13C NMR Chemical Shifts. Inorg. Chem. 2001; 40(8):1902-1911.
Suetsugu et al., Asymmetric Synthesis of (−)-Aurantioclavine via Palladium-CatalyzedIntramolecular Allylic Amination, Org. Lett. 2014, 16, pp. 996-999.
Sugiyama et al., Syntheses of four unusual amino acids, constituents of cyclomarin A. Tetrahedron Lett. 2002: 43(19):3489-2492.

(56) References Cited

OTHER PUBLICATIONS

Sumiyoshi et al., Laser Flash Photolysis of Azocumenes. Direct Observation of StepwiseDecomposition, Bull. Chem. Soc. Jpn. 1987, 60, pp. 77-81.
Sun et al., Construction of 3-oxyindoles via hypervalent iodine mediated tandem cyclization-acctoxylation of o-acyl anilines. Chem Commun. 2010;46(36):6834-6.
Sun et al., Enabling ScFvs as multi-drug carriers: A dendritic approach, Bioorganic & Medicinal Chemistry Letters 2003; 11:1761-1768.
Sun et al., Syntheses of Dendritic Linkers Containing Chlorambucil Residues for the Preparation of Antibody-Multidrug Immunoconjugates, Bioorganic & Medicinal Chemistry Letters 2002; 12:2213-2215.
Szalai et al., Geometric disassembly of dendrimers: dendritic amplification. J Am Chem Soc. Dec. 24, 2003;125(51):15688-9.
Tabakovic et al., One pot electrochemical synthesis of 10,10'-bisvindoline by an oxidation-reduction sequence. Tetrahedron Lett. May 20, 1996;37(21):3659-62. doi: 10.1016/0040-4039(96)00655-7.
Tadano et al., Bio-Inspired Dimerization Reaction of Tryptophan Derivatives in Aqueous AcidicMedia: Three-Step Syntheses of (+)-WIN 64821, (−)-Ditryptophenaline, and (+)- Naseseazine B. Angew. Chem. Int. Ed. 2013;52:7990-7994.
Takahashi et al., Inhibition of histone H3K9 methyltransferases by gliotoxin and related epipolythiodioxopiperazines. J Antibiot (Tokyo). May 2012;65(5):263-5.
Takahashi et al., Novel Homodimer Metabolites of GDC-0994 via Cytochrome P450-Catalyzed Radical Coupling. Drug Metab Dispos. Jun. 2020;48(6):521-527. doi: 10.1124/dmd.119.090019. Epub Mar. 31, 2020.
Teng et al., Unnatural enantiomer of chaetocin shows strong apoptosis-inducing activity through caspase-8/caspase-3 activation. Bioorg. Med. Chem. Lett. 2010; 20(17):5085-5088.
Teniou et al., (+)(1R,2R,5R) 2-Hydroxy-3-pinanone as Chiral Auxiliary in Erythro-selective Aldol Reactions. Asian J Chem. 2006; 18:2487-2490.
Tibodeau et al., The anticancer agent chaetocin is a competitive substrate and inhibitor of thioredoxin reductase. Antioxid Redox Signal. May 2009; 11(5):1097-106.
Tilvi et al., Agelastatin E, Agelastatin F, and Benzosceptrin C from the Marine Sponge Agelas dendromorpha, J. Nat. Prod., 73, p. 720-723 (2010).
Timberlake et al., Thiadiaziridine 1, 1-Dioxides: Synthesis and Chemistry. J. Org. Chem. 1981;46:2082-2089.
Toki et al., Protease-Mediated Fragmentation of p-Amidobenzyl Ethers: A New Strategy for the Activation of Anticancer Prodrugs. J. Org. Chem. 2002; 67(6):1866-1872.
Tomasic et al., Some cyclic oligopeptides with S2n symmetry. Helv Chim Acta. Jul. 8, 1987;70(4):1012-6. doi: 10.1002/hlca.19870700413.
Trail et al., Cure of xenografted human carcinomas by BR96-doxorubicin immunoconjugates. Science Jul. 9, 1993; 261(5118):212-215.
Trail et al., Effect of Linker Variation on the Stability, Potency, and Efficacy of Carcinoma-reactive BR64-Doxornbicin Immunoconjugates. Cancer Research 1997; 57:100-105.
Traunecker et al., Bispecific single chain molecules (Janusins) target cytotoxic lymphocytes on HIV infected cells. EMBO J. Dec. 1991; 10(12): 3655-3659.
Trost et al., Recent Advances on the Total Syntheses of Communesin Alkaloids andPerophoramidine, Chem. Eur. J. 2015, 21, pp. 16318-16343.
Trown, P.W, Antiviral activity of N, N'-dimethyl-epidithiapiperazinedione, a synthetic compound related to the gliotoxins, LL-S88alpha and beta, chetomin and the sporidesmins. Biochem Biophys Res Commun. Nov. 8, 1968;33(3):402-7.
Tsuji et al., Diazenes. VI. Alkyldizenes, Journal of the American Chemical Society 1971, 93(8), pp. 1992-1999.

Uckun et al., Structure-based design of a novel synthetic spiroketal pyran as a pharmacophore for the marine natural product spongistatin 1. Bioorg Med Chem Lett. Mar. 20, 2000; 10(6):541-5.
Umezawa et al., Chloptosin, an apoptosis-inducing dimeric cyclohexapeptide produced by Streptomyces. J Org Chem. Jan. 28, 2000;65(2):459-63. doi: 10.1021/jo991314b.
Uraguchi et al., Catalytic Asymmetric Oxidation of N-Sulfonyl I mines with HydrogenPeroxide-Trichloroacetonitrile System, J. Am. Chem. Soc. 2013, 135, pp. 8161-8164.
Usami et al., Gliocladins A—C and Glioperazine; Cytotoxic Dioxo- or Trioxopiperazine Metabolites from a *Gliocladium* Sp. Separated from a Sea Hare. Heterocycles 2004; 63(5):2004:1123-1129.
Ventola, C.L., The antibiotic resistance crisis: part 1: causes and threats. P T. Apr. 2015;40(4):277-83.
Verbitski et al., Isolation, Structure Determination, and Biological Activity of a Novel Alkaloid, Perophoramidine, from the Philippine Ascidian Perophora namei, J. Org. Chem. 2002, 67, pp. 7124-7126.
Verdier-Pinard et al., A Steroid Derivative with Paclitaxel-Like Effects on Tubulin Polymerization. Molecular Pharmacology Mar. 2000: 57(3):568-575.
Verdier-Pinard et al., Biosynthesis of radiolabeled curacin A and its rapid and apparently irreversible binding to the colchicine site of tubulin. Arch Biochem Biophys. Oct. 1, 1999; 370(1):51-8.
Verotta et al., Pyrrolidinoindoline Alkaloids from Psychotria colorata, J. Nat. Prod. 1998, 61, pp. 392-396.
Verotta et al., Synthesis and Antinociceptive Activity of Chimonanthines and Pyrrolidinoindoline-Type Alkaloids, Bioorganic & Medicinal Chemistry 2002, 10, pp. 2133-2142.
Vingushin et al., Gliotoxin is a dual inhibitor of farnesyltransferase and geranylgeranyltransferase I with antitumor activity against breast cancer in vivo. Med Oncol. 2004;21(1):21-30.
Wade et al., All-D amino acid-containing channel-forming antibiotic peptides. Proc Natl Acad Sci U S A. Jun. 1990;87(12):4761-5. doi: 10.1073/pnas.87.12.4761.
Walker et al., A High Yielding Synthesis of N-Alkyl Maleimides Using a Novel Modification of the Mitsunobu Reaction. J. Org. Chem., 1995; 60(16):5352-5355.
Wang et al., Mirror Images of Antimicrobial Peptides Provide Reflections on Their Functions and Amyloidogenic Properties. J Am Chem Soc. May 4, 2016;138(17):5706-13. doi: 10.1021/jacs.6b02575. Epub Apr. 26, 2016.
Wang et al., Potent, Orally Active Heterocycle-Based Combretastatin A-4 Analogues: Synthesis, Structure-Activity Relationship, Pharmacokinetics, and In Vivo Antitumor Activity Evaluation. J. Med. Chem. 2002; 45(8):1697-1711.
Wang et al., Synthesis of B-ring homologated estradiol analogues that modulate tubulin polymerization and microtubule stability. J Med Chem. Jun. 15, 2000; 43(12):2419-29.
Wantanabe et al., Reaction of 1-Acyl and Aroyl-2-hydroxy-3,3-dimethylindolines with Arylamines Catalyzed by BF3•Etherate. Formation of Dihydroindolo[1,2-c]quinazoline. Heterocycles. 2007;71(2):343-59.
Waring et al., Gliotoxin and related epipolythiodioxopiperazines. Gen Pharmacol. Dec. 1996;27(8):1311-6.
Waring et al., The chemistry and biology of the immunomodulating agent gliotoxin and related epipolythiodioxopiperazines. Med Res Rev. Oct.-Dec. 1988;8(4):499-524.
Wen et al., Synthesis of a fully protected (2S,3R)-N-(1',1'-dimethyl-2'-propenyl)-3-hydroxytryptophan from tryptophan. Tetrahedron Lett. 2002: 43(30):5291-5294.
Wen et al., Total Synthesis of Cyclomarin C. Org. Lett. 2004; 6(16):2721-2724.
Wender et al., Practical Synthesis of Prostratin, OPP, and Their Analogs, Adjuvant Leads Against Latent HIV, Science May 8, 2008, 320(5876), pp. 649-652.
Wenkert et al., Five-membered aromatic heterocycles as dienophiles in Diels-Alder reactions. Furan, pyrrole, and indole. J. Am. Chem. Soc. 1988; 110(21):7188-7194.
White et al., Concise Total Syntheses of (+)-Haplocidine and (+)-Haplocine via Late-StageOxidation of ( +)-Fendleridine Derivatives, J. Am. Chem. Soc. 2016, 138(35), pp. 11383-11389.

(56) References Cited

OTHER PUBLICATIONS

Wiegand et al., Agar and broth dilution methods to determine the minimal inhibitory concentration (MIC) of antimicrobial substances. Nat Protoc. 2008;3(2):163-75. doi: 10.1038/nprot.2007.521.
Wigley, L. J. et al., Natural and directed biosynthesis of communesin alkaloids, Phytochemistry 2006, 67, pp. 561-569.
Wilen et al., Strategies in optical resolutions. Tetrahedron. 1977;33(21):2725-2736. doi: 10.1016/0040-4020(77)80264-0.
Williams et al., Divergent, generalized synthesis of unsymmetrically substituted 2,5-piperazinediones. J. Am. Chem. Soc. 1985; 107(11):3246-3253.
Williams et al., Syntheses of the fungal metabolites (.+--.)-gliovictin and (.+--.)-hyalodendrin. J. Org. Chem. 1980; 45(13):2625-2631.
Williamson et al., Iron Catalyzed Asymmetric Oxyamination of Olefins, J. Am. Chem. Soc. 2012, 134, pp. 12370-12373.
Williamson et al., Iron-Catalyzed Aminohydroxylation of Olefins, J. Am. Chem. Soc. 2010, 132, pp. 4570-4571.
Woods et al., The interaction with tubulin of a series of stilbenes based on combretastatin A-4. Br J Cancer. Apr. 1995; 71(4):705-11.
Woodward et al., Calycanthine: The Structure of the Alkaloid and its Degradation Product, Calycanine, Proc. Chem. Soc. 1960, pp. 76-78.
Wright, G.D., Bacterial resistance to antibiotics: enzymatic degradation and modification. Adv Drug Deliv Rev. Jul. 29, 2005;57(10):1451-70. doi: 10.1016/j.addr.2005.04.002.
Wright, G.D., Something old, something new: revisiting natural products in antibiotic drug discovery. Can J Microbiol. Mar. 2014;60(3):147-54. doi: 10.1139/cjm-2014-0063. Epub Jan. 22, 2014.
Wu-Wong et al., Identification and Characterization of A-105972, an Antineoplastic Agent. Cancer Res. 2001; 61:1486-1492.
Xi et al., Elevated Conformational Rigidity in Dipeptides Incorporating Piperazic Acid Derivatives. J Am Chem Soc. Jan. 14, 1998;120(1):80-6.
Xie et al., Highly Enantioselective Bromocyclization of Tryptamines and Its Application in the Synthesis of(−)-Chimonanthine, Angew. Chem. Int. Ed. 2013, 52, pp. 12924-12927.
Xu et al., Iridium(III)-Catalyzed Regioselective C7-Amination of N-Pivaloylindoles with Sulfonoazides, J. Org. Chem. 2016, 81, pp. 10476-10483.
Xu et al., Studies on the Alkaloids of the Calycanthaceae and Their Syntheses, Molecules 2015, 20, pp. 6715-6738.
Xu et al., Total Synthesis of Clavicipitic Acid and Aurantioclavine: Stereochemistry of Clavicipitic Acid Revisited, J. Org. Chem. 2010, 75, pp. 7626-7635.
Yamada et al., A Total and Practical Synthesis of Ergot Alkaloid, (±)-Aurantioclavine, Chem. Pharm. Bull. 1985, 33, pp. 2162-2163.
Yamada et al., Concise Synthesis of (±)-Aurantioclavine through a Base-Promoted Pictet-Spengler Reaction, Eur. J. Org. Chem. 2009, pp. 5752-5759.
Yanagihara et al., Leptosins isolated from marine fungus *Leptoshaeria* species inhibit DNA topoisomerases I and/or II and induce apoptosis by inactivation of Akt/protein kinase B. Cancer Sci. Nov. 2005;96(11):816-24.

Yang et al., Application of Rapid Scan Cyclic Voltammetry to a Study of the Oxidation and Dimerization of N,N-Dimethylaniline in Acetonitrile. J Electroanal Chem. 1992;331:913-24.
Yang et al., Total Synthesis of (±)-Communesin F, J. Am. Chem. Soc. 2007, 129, pp. 13794-13795.
Yano et al., Chetomin induces degradation of XIAP and enhances TRAIL sensitivity in urogenital cancer cells. Int J Oncol. Feb. 2011;38(2):365-74.
Yasir et al., Mode of action of the antimicrobial peptide Mel4 is independent of *Staphylococcus aureus* cell membrane permeability. PLoS One. Jul. 29, 2019;14(7):e0215703. doi: 10.1371/journal.pone.0215703.
Yu et al., A General Strategy for the Synthesis of Vincamajine-Related Indole Alkaloids: Stereocontrolled Total Synthesis of (+)-Dehydrovoachalotine, (−)-Vincamajinine, and (−)-11-Methoxy-17-epivincamajine as Well as the Related Quebrachidine Diol, Vincamajine Diol, and Vincarinol1. J Org Chem. Apr. 19, 2005;70(10):3963-79.
Yu et al., A new epipolythiodioxopiperazine with antibacterial and cytotoxic activities from the endophytic fungus *Chaetomium* sp. M336. Nat Prod Res. 2018;32(6):689-694. doi:10.1080/14786419.2017.1338285.
Yu et al., Stereocontrolled Total Synthesis of (−)-Vincamajinine and (−)-11-Methoxy-17-epivincamajine. J Am Chem Soc. Jan. 21, 2004;126(5):1358-9.
Zalatan et al., Metal-Catalyzed Oxidations of C—H to C—N Bonds, Top. Curr. Chem. 2010, 292, pp. 347-378.
Zalatan et al., Understanding the Differential Performance of Rh2(esp)2 as a Catalyst for C—H Amination, J. Am. Chem. Soc. 2009, 131, pp. 7558-7559.
Zhang et al., Microtubule effects of welwistatin, a cyanobacterial indolinone that circumvents multiple drug resistance. Molecular Pharmacology Feb. 1996; 49(2):288-294.
Zhang et al., Riboflavin Is Directly Involved in N-Dealkylation Catalyzed by Bacterial Cytochrome P450 Monooxygenases. Chembiochem. Aug. 17, 2020;21(16):2297-2305. doi: 10.1002/cbic.202000071. Epub Apr. 30, 2020.
Zhao et al., Binding of two flaviolin substrate molecules, oxidative coupling, and crystal structure of Streptomyces coelicolor A3(2) cytochrome P450 158A2. J Biol Chem. Mar. 25, 2005;280(12):11599-607. doi: 10.1074/jbc.M410933200. Epub Jan. 19, 2005.
Zheng et al., Bionectins A-C, Epidithiodioxopiperazines with Anti-MRSA Activity, from Bionectra byssicola F120, J. Nat. Prod., 2006, 69 (12), pp. 1816-1819.
Zhou et al., Recent advances in asymmetric reactions using sulfinimines (N-sulfinyl imines), Tetrahedron 2004, 60, pp. 8003-8030.
Zhu et al., Aptamer-Drug Conjugates. Bioconjug Chem. Nov. 18, 2015;26(11):2186-97. doi: 10.1021/acs.bioconjchem.5b00291. Epub Jul. 14, 2015.
Zuo, Z. et al., Enantioselective Total Syntheses of Communesins A and B, Angew. Chem. Int. Ed. 2011, 50, pp. 12008-12011.
Zuo, Z. et al., Total Synthesis and Absolute Stereochemical Assignment of (−)-Communesin F, J. Am. Chem. Soc. 2010, 132, pp. 13226-13228.
Antropow et al., Synthesis and Evaluation of Agelastatin Derivatives as Potent Modulators for Cancer Invasion and Metastasis. J Org Chem. Aug. 4, 2017;82(15):7720-7731. doi: 10.1021/acs.joc.7b01162. Epub Jul. 25, 2017.

\* cited by examiner

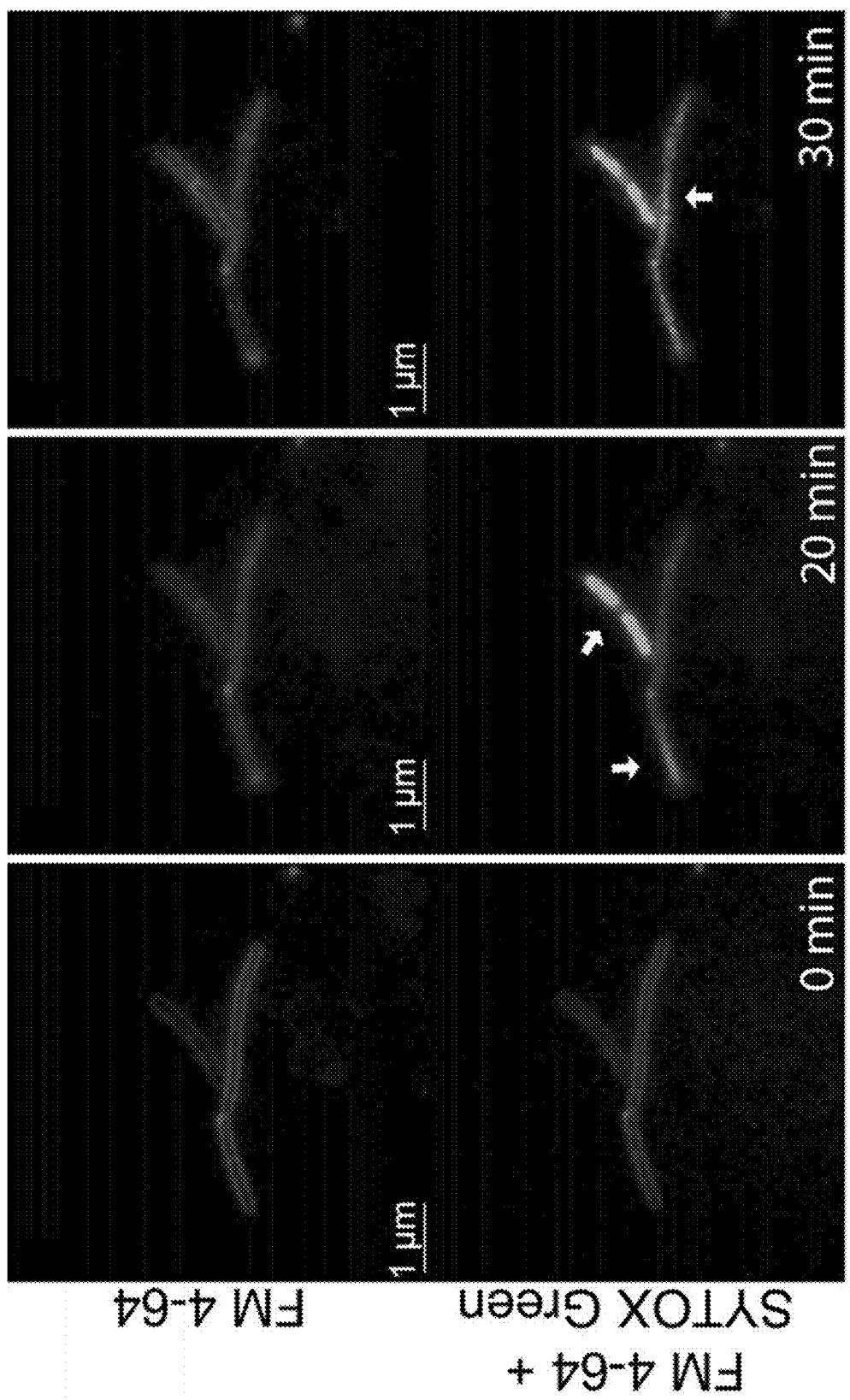

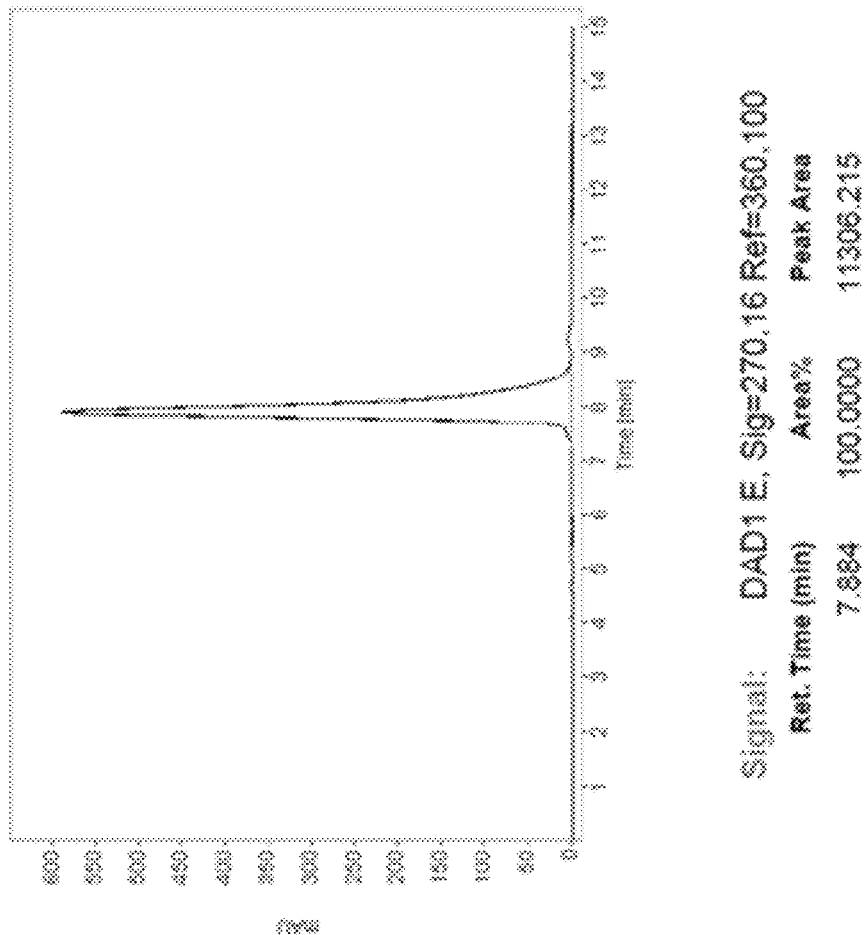
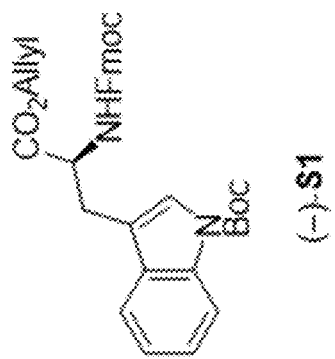
(−)-S1
HPLC conditions:
CHIRALPAK® IA, 4.6 mm × 250 mm
Lot# IA00CE-PD046
25% i-PrOH in hexanes
1.0 mL/min
λ = 270 nm
FIG. 15

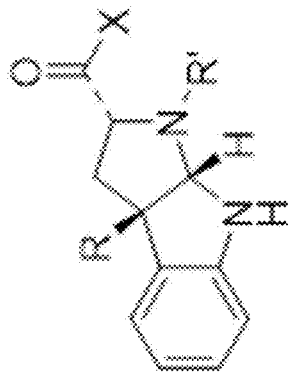
cyclotryptophan
X = NR$_2$, OR
11a-11b, 11e-11h
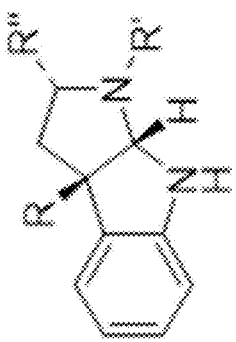
cyclotryptamine
where R'' is not a carbonyl group
11c-11d
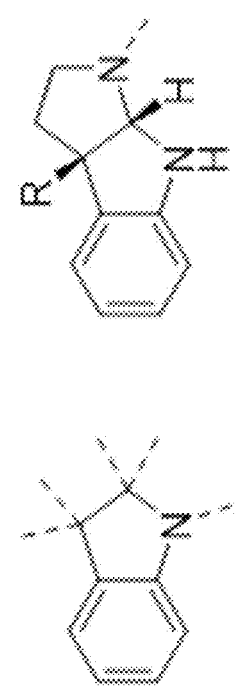
pyrroloindoline
11a-11h
indoline
11i-11k
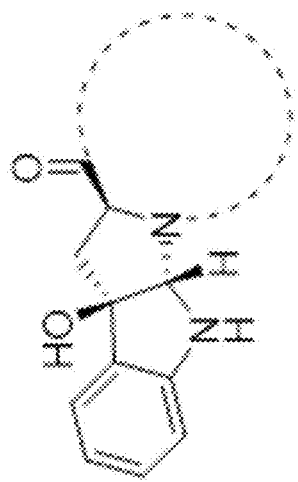
macrocyclic hydroxycyclotryptophan
where dashed line represents a chain of > 3 amino acids
1, 6, 25-32
FIG. 21

Single Electron Oxidants*

Inorganic: AgSbF$_6$, Cu(SbF$_6$)$_2$, Cu(OTf)$_2$, AgOTf, AgClO$_4$, Cu(ClO$_4$)$_2$, AgO, AgF$_2$
M(polypyridine)$_n$X$_m$ (M = Fe(3+), Ru(3+))

Organic:

X = BF$_4^-$, SbF$_6^-$, OTf$^-$, PF$_6^-$, ClO$_4^-$

Bases

Inorganic: Ag$_2$CO$_3$, Ag$_2$O

Organic:

R = Large Group (e.g., $t$-Bu, SiR$_3$)
R' = H, alkyl, aryl, halogen

Solvents 1,2-DCE, CH$_2$Cl$_2$, EtNO$_2$, MeNO$_2$, hexane, heptane, pentane, PhCF$_3$

*Some of these oxidants may be used as catalysts in conjunction with a sacrificial oxidant such as Ag$_2$CO$_3$

HIMASTATIN DERIVATIVES, AND PROCESSES OF PREPARATION THEREOF, AND USES THEREOF

RELATED APPLICATIONS

This application claims priority under 35 U.S.C. § 119(e) to U.S. Provisional Patent Application No. 63/153,286, filed Feb. 24, 2021, which is incorporated herein by reference.

GOVERNMENT SUPPORT

This invention was made with government support under Grant No. R01 GM089732 awarded by the National Institutes of Health. The government has certain rights in the invention.

BACKGROUND

The alarming proliferation of multi-drug resistant pathogenic bacteria is widely recognized as an eminent threat to global health.[i,ii] Since their discovery, natural products have served as the primary inspiration for new antibiotics to treat bacterial infections.[iii] (−)-Himastatin (1) is a member of a class of macrocyclic 3a-hydroxycyclotryptophan antibiotics isolated from *Streptomyces* soil bacteria.[iv,v,vi] Along with (−)-chloptosin (2),[vii] (−)-himastatin (1) is a homodimer linked via a central C5-C5' biaryl subunit (FIG. 1). This linkage is critical for the potent antibiotic activity of (−)-himastatin (1) against Gram positive bacteria,[viii] and is formed in the final step of its biosynthesis. It has been established that monomeric derivatives such as the related natural product NW-G01 have reduced activity that are improved upon dimerization.[ix,x,xi] Other notable structural features of (−)-himastatin (1) include the alternating sequence of D- and L-amino acids, a depsipeptide linkage, and a single piperazic acid residue with γ-hydroxylation.

Danishefsky's synthesis of (−)-himastatin (1), which clarified the Cα stereochemistry of the cyclotryptophan residue, featured an early-stage Stille coupling to form the central C5-C5' linkage followed by bidirectional elaboration of a dimeric cyclotryptophan.[viii,xii] This general approach was later utilized in total syntheses of (−)-chloptosin (2) by Ley and Yao.[xiii,xiv,xv,xvi] Though considered an attractive synthetic strategy, attempts at late-stage dimerization via cross-coupling were unsuccessful.[xvi] Other strategies were reported in Ling et al., *J. Org. Chem.* 2013, 78, 5218-5226; Natali et al., *Org. Biomol. Chem.*, 2012, 10, 1162-1171; Miranda-Gilbert, 1969 Article, Alkaloids Of Aspidosperma Melanoc; Tabakovic et al., *Tetrahedron Letters*, Vol. 37, No. 21, pp. 3659-3662, 1996; Chinese Patent Application Publication No. CN 109021080A.

SUMMARY OF THE DISCLOSURE

The concise total synthesis of (−)-himastatin via a biomimetic final-stage dimerization is described. Our synthesis relies on expedient synthesis of a macrocyclic dissipative monomer, followed by a newly developed silver(I)-promoted oxidative dimerization reaction to secure the central C5-C5' biaryl linkage critical for himastatin's potent antibiotic activity. Application of the oxidative dimerization methodology enabled the preparation of dimeric C5-C5' cyclotryptophans, cyclotryptamines, and indolines via a radical-radical coupling pathway supported by mechanistic studies. The modularity and convergence of our hybrid solution/solid-phase approach to the synthesis of macrocyclic peptide monomers enabled general access to several himastatin derivatives and their comparative biological evaluation. Our findings indicate that the depsipeptide linkage and piperazic acid residue of himastatin are important for bioactivity, but that the introduction of an alkyl azide functional handle in place of leucine has negligible impact. Direct observation of bacteria incubated at lethal and sublethal concentrations of himastatin provided evidence that himastatin targets and disrupts the bacterial membrane. An orthogonal synthetic probe of this mechanism of action, ent-(+)-himastatin, had identical bioactivity and biological phenotype to its natural enantiomer in *B. subtilis*, but was capable of evading the resistance mechanism utilized by the bacteria which produces (−)-himastatin. Collectively, our studies situate himastatin as a distinct member of the membrane-targeting class of antibiotics, whose strength in evading canonical mechanisms of resistance in bacteria is increasingly being recognized.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC), supercritical fluid chromatography (SFC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The present disclosure additionally encompasses compounds described herein as individual isomers substantially free of other isomers, and alternatively, as mixtures of various isomers.

In a formula, the bond ~~ is a single bond, the dashed line - - - is a single bond or absent, and the bond ≡≡≡ or === is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-12}$ alkyl (e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)). The attachment point of alkyl may be a single bond (e.g., as in —$CH_3$), double bond (e.g., as in =$CH_2$), or triple bond (e.g., as in ≡CH). The moieties =$CH_2$ and ≡CH are also alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more (e.g., two, three, or four, as valency permits) carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

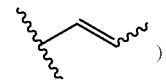

)

may be in the (E)- or (Z)-configuration.

"Alkynyl" refers to a radical of a straight-chain or branched hydrocarbon group having from 2 to 20 carbon atoms, one or more (e.g., two, three, or four, as valency permits) carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 13 ring carbon atoms ("$C_{3-13}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-4}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged, or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl may include zero, one, or more (e.g., two, three, or four, as valency permits) C=C double bonds in all the rings of the carbocyclic ring system that are not aromatic or heteroaromatic. Carbocyclyl including one or more (e.g., two or three, as valency permits) C=C double bonds in the carbocyclic ring is referred to as "cycloalkenyl." Carbocyclyl including one or more (e.g., two or three, as valency permits) C≡C triple bonds in the carbocyclic ring is referred to as "cycloalkynyl." "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl. In certain embodiments, the carbocyclyl is substituted or unsubstituted, 3- to 7-membered, and monocyclic. In certain embodiments, the carbocyclyl is substituted or unsubstituted, 5- to 13-membered, and bicyclic.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-4}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. In certain embodiments, the carbocyclyl includes oxo substituted thereon.

"Heterocyclyl" or "heterocyclic" refers to a radical of a 3- to 24-membered non-aromatic ring system having ring carbon atoms and 1 to 10 ring heteroatoms, wherein each heteroatom is independently selected from nitrogen, oxygen, and sulfur ("3-24 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"). A heterocyclyl group can be saturated or can be partially unsaturated. Heterocyclyl may include zero, one, or more (e.g., two, three, or four, as valency permits) double bonds in all the rings of the heterocyclic ring system that are not aromatic or heteroaromatic. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is 3- to 7-membered. In certain embodiments, the heterocyclyl group is 5- to 7-membered. In certain embodiments, the heterocyclyl group is 5-membered. In certain embodiments, the heterocyclyl group is 6-membered. In certain embodiments, the heterocyclyl group is 12- to 24-membered ("macrocyclic heterocyclyl"). In certain embodiments, the heterocyclyl group is 16- to 20-membered. In certain embodiments, the heterocyclyl group is 18-membered. In certain embodiments, the heterocyclyl group is 12- to 16-membered. In certain embodiments, the heterocyclyl group is 20- to 24-membered. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, and monocyclic. In certain embodiments, the heterocyclyl is substituted or unsubstituted, 5- to 13-membered, and bicyclic. In certain embodiments, the heterocyclyl includes oxo substituted thereon.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include azirdinyl, oxiranyl, or thiiranyl. Exemplary 4-membered heterocyclyl groups containing one heteroatom include azetidinyl, oxetanyl and thietanyl. Exemplary 5-membered heterocyclyl groups containing one heteroatom include tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include dioxolanyl, oxasulfuranyl, disulfuranyl, and oxazolidin-2-one. Exemplary 5-membered heterocyclyl groups containing three heteroatoms include triazolinyl, oxadiazolinyl, and thiadiazolinyl. Exemplary 6-membered heterocyclyl groups containing one heteroatom include piperidinyl, tetrahydropyranyl, dihydropyridinyl, and thianyl. Exemplary 6-membered heterocyclyl groups containing two heteroatoms include piperazinyl, morpholinyl, dithianyl, and dioxanyl. Exemplary 6-membered heterocyclyl groups containing two heteroatoms include triazinanyl. Exemplary 7-membered heterocyclyl groups containing one heteroatom include azepanyl, oxepanyl and thiepanyl. Exemplary 8-membered heterocyclyl groups containing one heteroatom include azocanyl, oxecanyl, and thiocanyl. Exemplary 5-membered heterocyclyl groups fused to a $C_6$ aryl ring (also referred to herein as a 5,6-bicyclic heterocyclic ring) include indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl. In certain embodiments, the heteroaryl group is 5-6 membered, monocyclic. In certain embodiments, the heteroaryl group is 8-14 membered, bicyclic.

Exemplary 5-membered heteroaryl groups containing one heteroatom include pyrrolyl, furanyl and thiophenyl. Exemplary 5-membered heteroaryl groups containing two heteroatoms include imidazolyl, pyrazolyl, oxazolyl, isoxazolyl, thiazolyl, and isothiazolyl. Exemplary 5-membered heteroaryl groups containing three heteroatoms include triazolyl, oxadiazolyl, and thiadiazolyl. Exemplary 5-membered heteroaryl groups containing four heteroatoms include tetrazolyl. Exemplary 6-membered heteroaryl groups containing one heteroatom include pyridinyl. Exemplary 6-membered heteroaryl groups containing two heteroatoms include pyridazinyl, pyrimidinyl, and pyrazinyl. Exemplary 6-membered heteroaryl groups containing three or four heteroatoms include triazinyl and tetrazinyl, respectively. Exemplary 7-membered heteroaryl groups containing one heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —N$^{bb}$CO$_2$R$^{aa}$, —N$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two RC groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=N(R$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=N$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O) SR$^{ee}$, —C(=S)SR$^{ee}$, —SC(=S)SR$^{ee}$, —P(=O) (OR$^{ee}$)$_2$, —P(=O)(R$^{ee}$)$_2$, —OP(=O)(R$^{ee}$), —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, C$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$^{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted C$_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, or —NO$_2$. In certain embodiments, the carbon atom substituents are independently halogen, substituted (e.g., substituted with one or more halogen moieties) or unsubstituted C$_{1-6}$ alkyl, —OR$^{aa}$, —SR$^{aa}$, —N(R$^{bb}$)$_2$, —CN, —SCN, or —NO$_2$, wherein R$^{aa}$ is hydrogen, substituted (e.g., substituted with one or more halogen) or unsubstituted C$_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted C$_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group. In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group, wherein R$^{aa}$ is hydrogen, substituted (e.g., substituted with one or more halogen) or unsubstituted C$_{1-6}$ alkyl, or an oxygen protecting group when attached to an oxygen atom; and each R$^{bb}$ is independently hydrogen, substituted (e.g., substituted with one or more halogen) or unsubstituted C$_{1-6}$ alkyl, or a nitrogen protecting group. In certain embodiments, the nitrogen atom substituents are independently substituted (e.g., substituted with one or more halogen) or unsubstituted C$_{1-6}$ alkyl or a nitrogen protecting group.

In certain embodiments, the substituent present on a nitrogen atom is a nitrogen protecting group (also referred to as an amino protecting group). Nitrogen protecting groups include —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$ R$^{aa}$) include p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy] methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl) methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or an oxygen protecting group. In certain embodiments, the oxygen atom substituents are independently substituted (e.g., substituted with one or more halogen) or unsubstituted $C_{1-6}$ alkyl, —C(=O)R$^{aa}$, —CO$_2$R$^{aa}$, —C(=O)N(R$^{bb}$)$_2$, or an oxygen protecting group, wherein R$^{aa}$ is hydrogen, substituted (e.g., substituted with one or more halogen) or unsubstituted $C_{1-6}$ alkyl, or an oxygen protecting group when attached to an oxygen atom; and each R$^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$) R$^{aa}$, —C(=NR$^{bb}$)OR$^{aa}$, —C(=NR$^{bb}$)N(R$^{bb}$)$_2$, —S(=O) R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O) (OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or a sulfur protecting group. In certain embodiments, the sulfur atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3{}^+X^-$, $—P(OR^{cc})_2$, $—P(OR^{cc})_3{}^+X^-$, $—P(=O)(R^{aa})_2$, $—P(=O)(OR^{cc})_2$, and $—P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in J. Pharmaceutical Sciences (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the subject is a mammal. The subject may be a male or female and at any stage of development. A non-human animal may be a transgenic animal.

The terms "administer," "administering," or "administration," refers to implanting, absorbing, ingesting, injecting, inhaling, or otherwise introducing a compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a provided compound refers to an amount sufficient to elicit the desired biological response, i.e., treating the condition. As will be appreciated by those of ordinary skill in this art, the effective amount of a provided compound may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of a compound may reduce the tumor burden or stop the growth or spread of a tumor.

A "therapeutically effective amount" of a provided compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a provided compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

BRIEF DESCRIPTION OF THE DRAWINGS

(FIGS. 5A-5C) Untreated *B. subtilis* cells or cells incubated with sublethal concentration (0.25 μg/mL) of (FIG. 5B) (−)-himastatin (1) or (FIG. 5C) ent-(+)-himastatin (1), stained with FM 4-64 (membrane, red). (D-E) Time-lapse of cells treated with a lethal concentration (2 μg/mL) of (−)-himastatin (1). (FIG. 5D) At the start of treatment, little to no green fluorescence is observed. (FIG. 5E) After 10 minutes, a small amount of SYTOX green has entered the cells. (FIG. 5F) By 35 minutes, some cells show bright green fluorescence, indicating that membrane integrity has been compromised.

FIGS. 12A-12C shows the himastatin treatment at a lethal concentration causes rapid loss of cell viability. (FIGS. 12A-12C) Confocal micrographs showing time-lapse of *B. subtilis* treated with a lethal concentration (2 μg/mL) of (−)-himastatin (1) and stained with FM 4-64 (membrane, red) and SYTOX Green (DNA, green). (FIG. 12A) At the start of treatment, little to no green fluorescence is observed as the membrane remains impermeable. (FIG. 12B) After 20 minutes, SYTOX Green has begun to enter the cells. (FIG. 12C) By 30 minutes, all cells show bright green fluorescence (white arrows), indicating that membrane integrity has been compromised. Top frames show FM 4-64 channel alone, while bottom frames show overlay of FM 4-64 and SYTOX Green channels.

FIG. 15 shows an HPLC chromatogram.

FIG. 21 shows exemplary compound scaffolds.

FIG. 23 shows exemplary single-electron oxidants.

(FIG. 27A) Substrate scope of our oxidative dimerization reaction. In the ORTEP representation of dimeric endo-diketopiperazine (+)-7h, the thermal ellipsoids are drawn at 30% probability and only selected hydrogen atoms are shown. (FIG. 27B) Mechanistic studies using equimolar mixtures of differentially substituted indolines provide evidence for a radical-radical coupling mechanism. Reagents and conditions: AgSbF$_6$, TTBP, ClCH$_2$CH$_2$Cl, 23° C.; * Copper(II)-catalyzed conditions: Cu(OTf)$_2$ (20 mol %), Ag$_2$CO$_3$, ClCH$_2$CH$_2$Cl, 23° C. TES=triethylsilyl; TTBP=2,4,6-tri-tert-butylpyrimidine.

FIGS. 29A-29C. Designed derivatives and probes of himastatin reveal critical structural elements for antibiotic activity. (FIG. 29A) Dimerization of unnatural himastatin derivatives with single-residue substitutions. (FIG. 29B) Synthesis of a heterodimeric fluorescent himastatin probe. (FIG. 29C) Antibiotic evaluation of himastatin derivatives and probes against Gram-positive bacteria. MIC values were determined using the broth-microdilution method; see Table S10. Reagents and conditions: (a) Cu(SbF$_6$)$_2$, DTBMP, ClCH$_2$CH$_2$Cl, 23° C.; (b) (i) PMe$_3$, H$_2$O, THF, 40° C., (ii) 5-TAMRA succinimidyl ester, i-Pr$_2$NEt, DMF, 23° C. Lys=lysine; MRSA=methicillin-resistant *Staphylococcus aureus*; MSSA=methicillin-sensitive *S. aureus*; Pro=proline; Ser=serine; TAMRA=carboxytetramethylrhodamine; Val=Valine; VRE=vancomycin-resistant *Enterococcus*; VSE=vancomycin-sensitive *Enterococcus*.

DETAILED DESCRIPTION OF CERTAIN EMBODIMENTS OF THE DISCLOSURE

Figure 1:
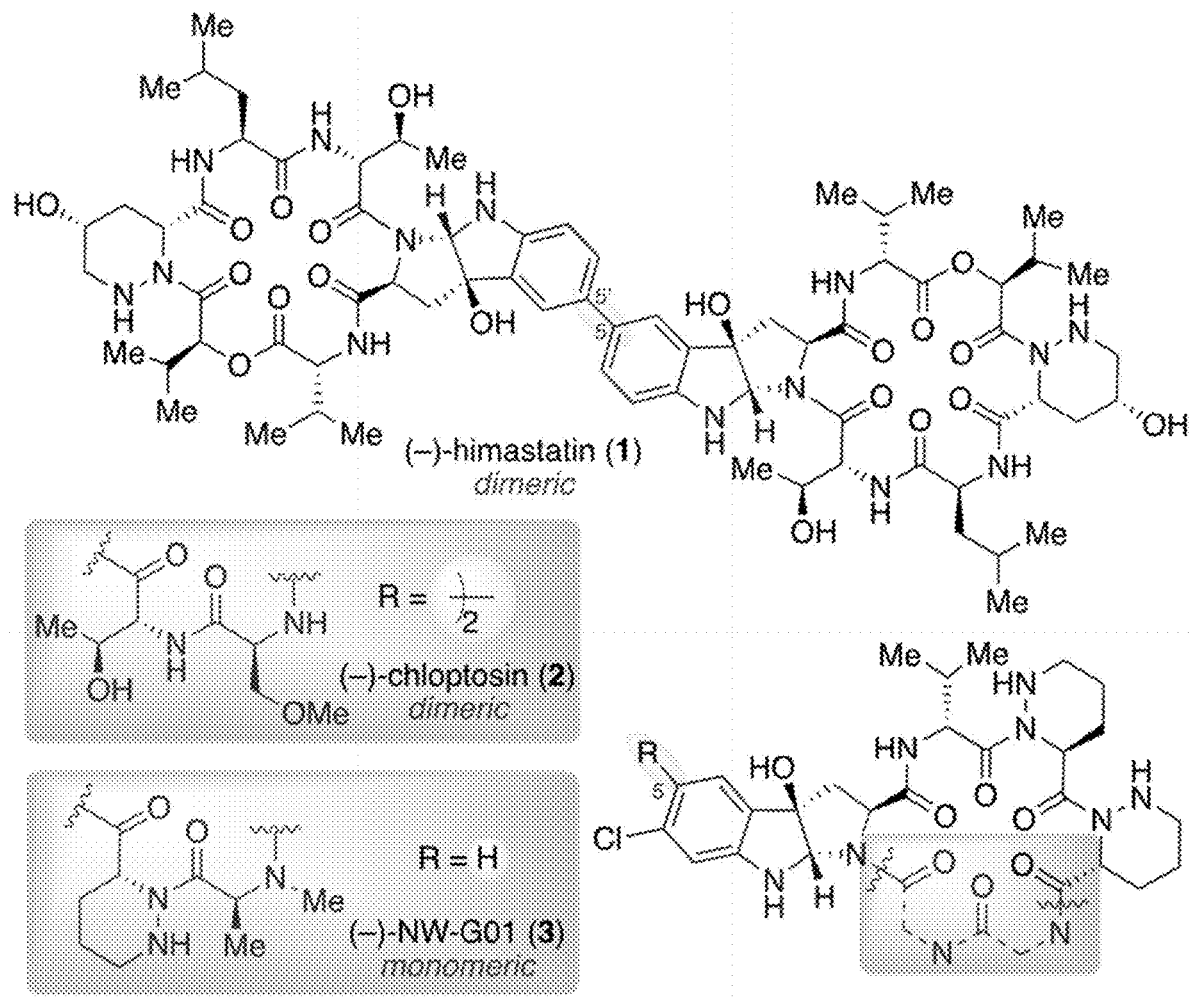
FIG. 1 shows structures shows of naturally occurring *Streptomyces* 3a-hydroxycyclotryptophan antibiotics (−)-himastatin (1), (−)-chloptosin (2), and (−)-NW-G01 (3).

The present disclosure provides compounds of Formula I, and tautomers and isotopically labeled compounds thereof, and salts (e.g., pharmaceutically acceptable salts) thereof (collectively the compounds described herein or compounds of the disclosure).

In one aspect, the present disclosure provides a compound of Formula I:

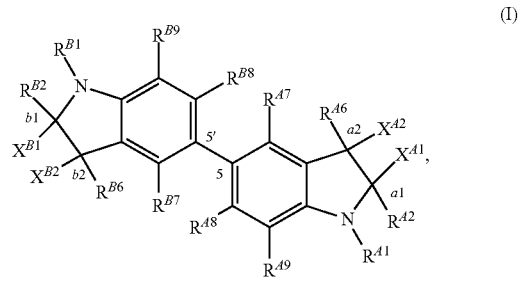

(I)

or a tautomer or isotopically labeled compound thereof, or a salt thereof, wherein:
the bond a1 and the bond a2 are syn or anti to each other;
the bond b1 and the bond b2 are syn or anti to each other;
each of $R^{A1}$ and $R^{B1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), —P(=O)(OR$^a$)$_2$, or a nitrogen protecting group;
each of $R^{A2}$, $R^{B2}$, $R^{A6}$, $R^{B6}$, $R^{A7}$, $R^{B7}$, $R^{A8}$, $R^{B8}$, $R^{A9}$, and $R^{B9}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$ NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —OS(=O)$_2$R$^a$, —OS(=O)$_2$OR$^a$, —OS(=O)$_2$N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), or —P(=O)(OR$^a$)$_2$;
each of $X^{A1}$, $X^{B1}$, $X^{A2}$, and $X^{B2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —N$^a$C(=NR$^a$)R$^a$, —NC(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —OS(=O)$_2$R$^a$, —OS(=O)$_2$OR$^a$, —OS(=O)$_2$N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), or —P(=O)(OR$^a$)$_2$;

or: $X^{A1}$ and $X^{A2}$ are joined with their intervening atoms to form substituted or unsubstituted carbocyclyl or substituted or unsubstituted heterocyclyl; and/or $X^{B1}$ and $X^{B2}$ are joined with their intervening atoms to form substituted or unsubstituted carbocyclyl or substituted or unsubstituted heterocyclyl;

or: $R^{A2}$, $X^{A1}$, and $X^{A2}$ are joined with their intervening atoms to form substituted or unsubstituted carbocyclyl or substituted or unsubstituted heterocyclyl; and/or $R^{B2}$, $X^{B1}$, and $X^{B2}$ are joined with their intervening atoms to form substituted or unsubstituted carbocyclyl or substituted or unsubstituted heterocyclyl;

or: $X^{A1}$, $X^{A2}$, and $R^{A6}$ are joined with their intervening atoms to form substituted or unsubstituted carbocyclyl or substituted or unsubstituted heterocyclyl; and/or $X^{B1}$, $X^{B2}$, and $R^{B6}$ are joined with their intervening atoms to form substituted or unsubstituted carbocyclyl or substituted or unsubstituted heterocyclyl; and each R$^a$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ on a nitrogen atom are joined with the nitrogen atom to form substituted or unsubstituted heterocyclyl or substituted or unsubstituted heteroaryl;

provided that the compound is not of the formula:

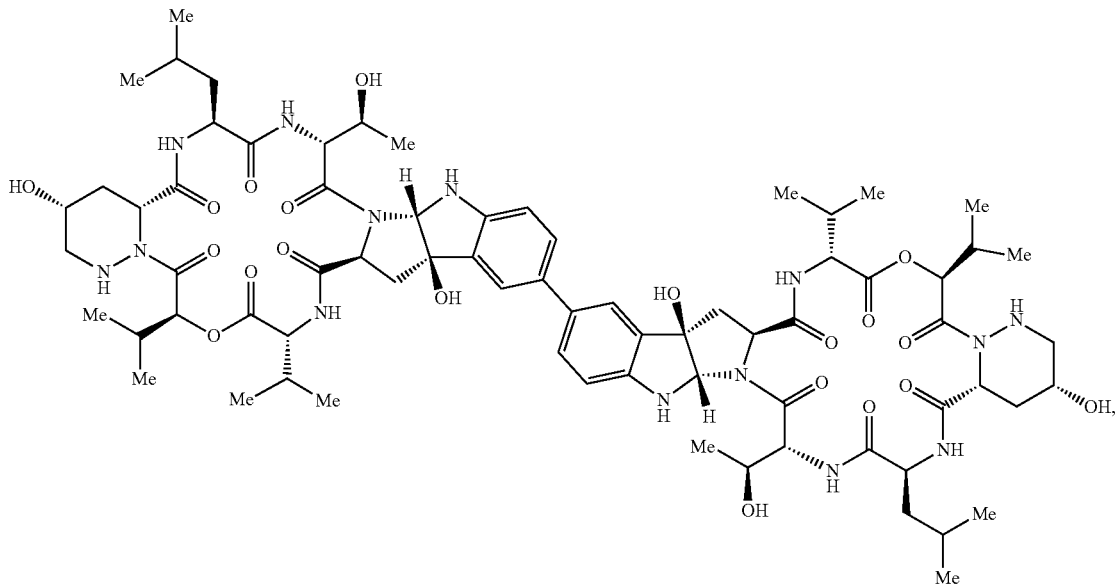

((-)-himastatin)

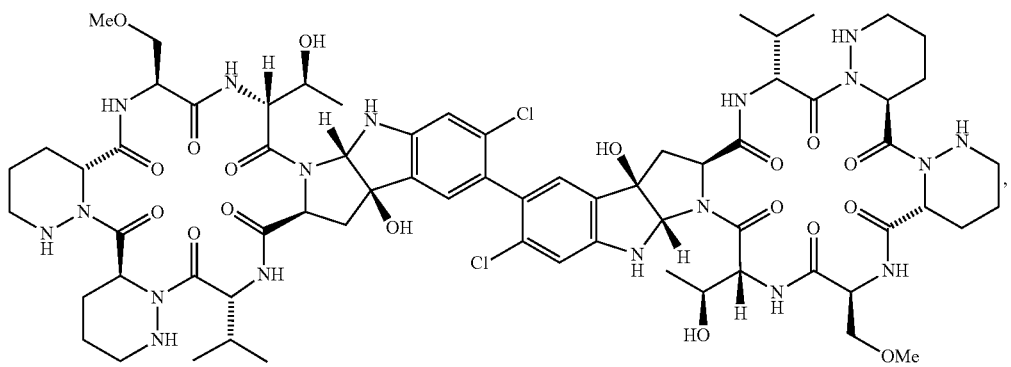

((-)-chloptosin)

-continued
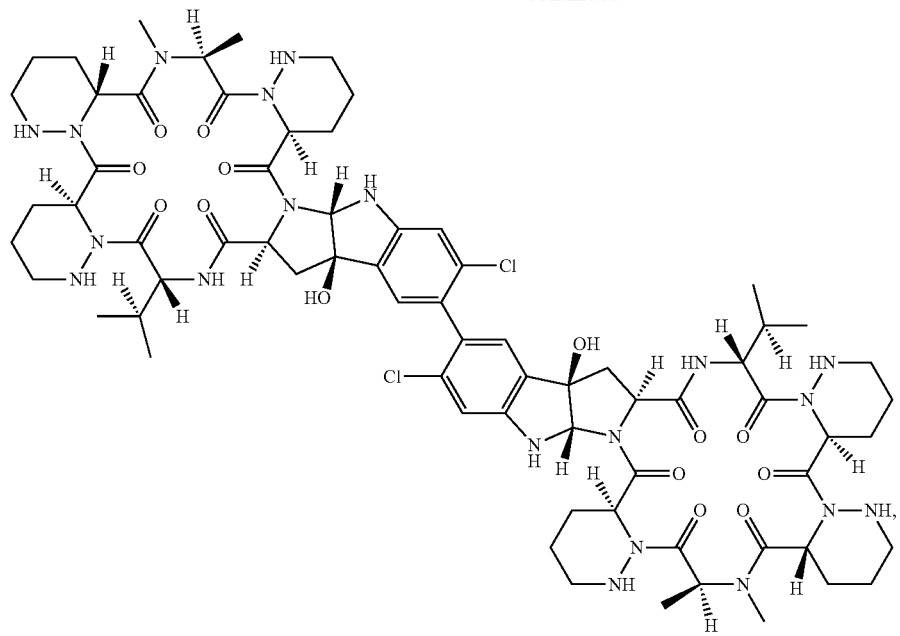
(NW-G01)
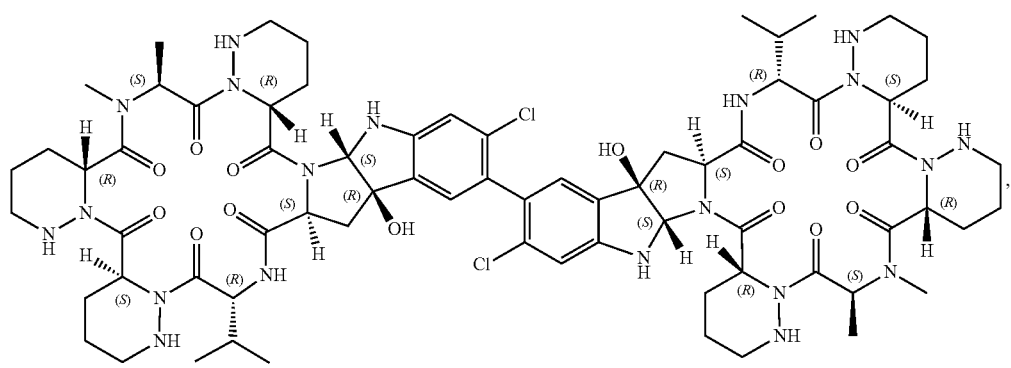
(dialboflavusin A)
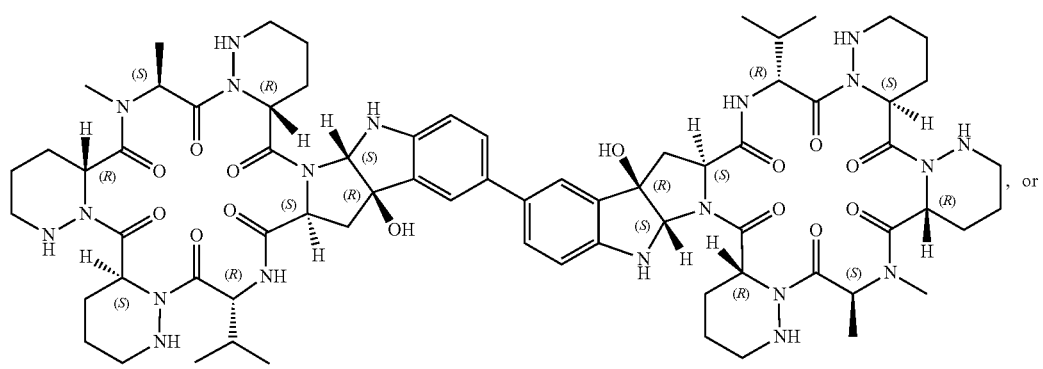
(de-Cl-dialboflavusin A)
, or

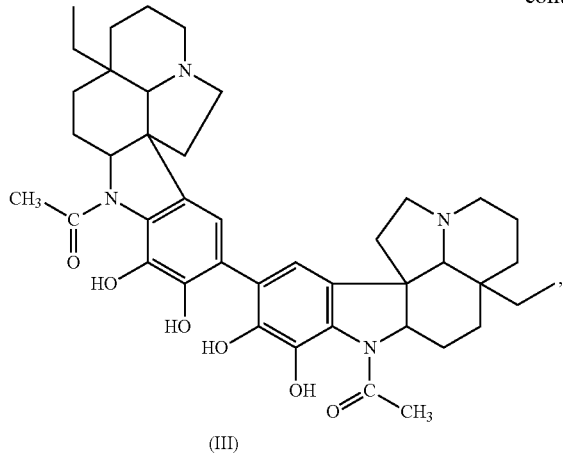

(III)

or a tautomer or isotopically labeled compound thereof, or a salt thereof.

In another aspect, the present disclosure provides a process of preparing a compound of Formula I:

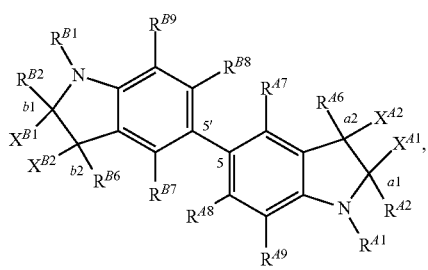

(I)

or a tautomer or isotopically labeled compound thereof, or a salt thereof, the process comprising reacting a compound of Formula A:

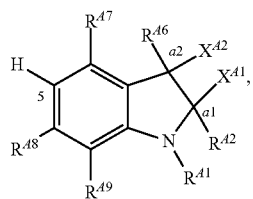

or a tautomer or isotopically labeled compound thereof, or a salt thereof, with a compound of Formula B:

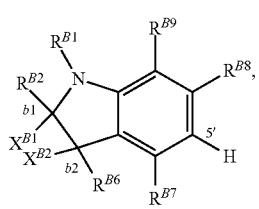

(B)

or a tautomer or isotopically labeled compound thereof, or a salt thereof, in the presence of a single-electron oxidant, a base, and a solvent, wherein:

the bond a1 and the bond a2 are syn or anti to each other;
the bond b1 and the bond b2 are syn or anti to each other;
each of $R^{A1}$ and $R^{B1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)O$R^a$, —C(=O)N($R^a$)$_2$, —C(=N$R^a$)$R^a$, —C(=N$R^a$)O$R^a$, —C(=N$R^a$)N($R^a$)$_2$, —S(=O)$R^a$, —S(=O)O$R^a$, —S(=O)N($R^a$)$_2$, —S(=O)$_2 R^a$, —S(=O)$_2$O$R^a$, —S(=O)$_2$N($R^a$)$_2$, —P(=O)($R^a$)$_2$, —P(=O)($R^a$)(O$R^a$), —P(=O)(O$R^a$)$_2$, or a nitrogen protecting group;

each of $R^{A2}$, $R^{B2}$, $R^{A6}$, $R^{B6}$, $R^{A7}$, $R^{B7}$, $R^{A8}$, $R^{B8}$, $R^{A9}$, and $R^{B9}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=O)$R^a$, —C(=O)O$R^a$, —C(=O)N($R^a$)$_2$, —C(=N$R^a$)$R^a$, —C(=N$R^a$)O$R^a$, —C(=N$R^a$)N($R^a$)$_2$, —NO$_2$, —N$_3$, —N$R^a$C(=O)$R^a$, —N$R^a$C(=O)O$R^a$ N$R^a$C(=O)N($R^a$), —N$R^a$C(=N$R^a$)$R^a$, —N$R^a$C(=N$R^a$)O$R^a$, —N$R^a$C(=N$R^a$)N($R^a$), —OC(=O)$R^a$, —OC(=O)O$R^a$, —OC(=O)N($R^a$)$_2$, —OC(=N$R^a$)$R^a$, —OC(=N$R^a$)O$R^a$, —OC(=N$R^a$)N($R^a$)$_2$, —N$R^a$S(=O)$R^a$, —N$R^a$S(=O)O$R^a$, —N$R^a$S(=O)N($R^a$)$_2$, —N$R^a$S(=O)$_2 R^a$, —N$R^a$S(=O)$_2$O$R^a$, —N$R^a$S(=O)$_2$N($R^a$), —OS(=O)$R^a$, —OS(=O)O$R^a$, —OS(=O)N($R^a$)$_2$, —OS(=O)$_2 R^a$, —OS(=O)$_2$O$R^a$, —OS(=O)$_2$N($R^a$)$_2$, —S(=O)$R^a$, —S(=O)O$R^a$, —S(=O)N($R^a$)$_2$, —S(=O)$_2 R^a$, —S(=O)$_2$O$R^a$, —S(=O)$_2$N($R^a$)$_2$, —P(=O)($R^a$)$_2$, —P(=O)($R^a$)(O$R^a$), or —P(=O)(O$R^a$)$_2$;

each of $X^{A1}$, $X^{B1}$, $X^{A2}$, and $X^{B2}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$), —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)R$^a$, —NR$^a$S(=O)OR$^a$, —NR$^a$S(=O)N(R$^a$), —NR$^a$S(=O)$_2$R$^a$, —NR$^a$S(=O)$_2$OR$^a$, —NR$^a$S(=O)$_2$N(R$^a$), —OS(=O)R$^a$, —OS(=O)OR$^a$, —OS(=O)N(R$^a$)$_2$, —OS(=O)$_2$R$^a$, —OS(=O)$_2$OR$^a$, —OS(=O)$_2$N(R$^a$)$_2$, —S(=O)R$^a$, —S(=O)OR$^a$, —S(=O)N(R$^a$), —S(=O)$_2$R$^a$, —S(=O)$_2$OR$^a$, —S(=O)$_2$N(R$^a$)$_2$, —P(=O)(R$^a$), —P(=O)(R$^a$)(OR$^a$), or —P(=O)(OR$^a$)$_2$;

or: X$^{A1}$ and X$^{A2}$ are joined with their intervening atoms to form substituted or unsubstituted carbocyclyl or substituted or unsubstituted heterocyclyl; and/or X$^{B1}$ and X$^{B2}$ are joined with their intervening atoms to form substituted or unsubstituted carbocyclyl or substituted or unsubstituted heterocyclyl;

or: R$^{A2}$, X$^{A1}$, and X$^{A2}$ are joined with their intervening atoms to form substituted or unsubstituted carbocyclyl or substituted or unsubstituted heterocyclyl; and/or R$^{B2}$, X$^{B1}$, and X$^{B2}$ are joined with their intervening atoms to form substituted or unsubstituted carbocyclyl or substituted or unsubstituted heterocyclyl;

or: X$^{A1}$, X$^{A2}$, and R$^{A6}$ are joined with their intervening atoms to form substituted or unsubstituted carbocyclyl or substituted or unsubstituted heterocyclyl; and/or X$^{B1}$, X$^{B2}$, and R$^{B6}$ are joined with their intervening atoms to form substituted or unsubstituted carbocyclyl or substituted or unsubstituted heterocyclyl; and each R$^a$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ on a nitrogen atom are joined with the nitrogen atom to form substituted or unsubstituted heterocyclyl or substituted or unsubstituted heteroaryl.

In certain embodiments,

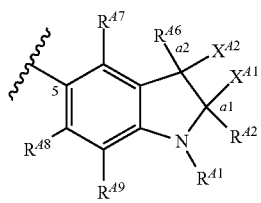

is the same as

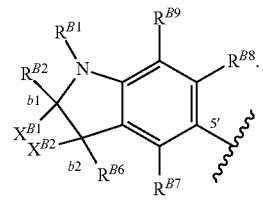

In certain embodiments, when

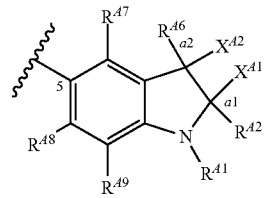

is the same as

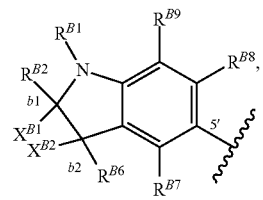

the compound is referred to as a homodimer. In certain embodiments, when

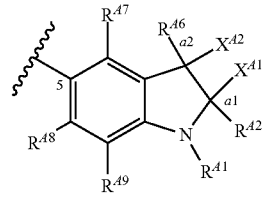

is different from

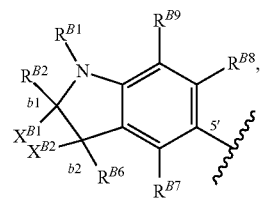

the compound is referred to as a heterodimer.

Any two variables (e.g., moieties) described herein may be the same or different from each other, unless provided otherwise.

In certain embodiments, the bond a1 and the bond a2 are syn to each other; and/or the bond b1 and the bond b2 are syn to each other. In certain embodiments, the bond a1 and the bond a2 are anti to each other; and/or the bond b1 and the bond b2 are anti to each other.

In certain embodiments, $X^{A1}$ and $X^{A2}$ are joined with their intervening atoms to form substituted or unsubstituted carbocyclyl; and/or $X^{B1}$ and $X^{B2}$ are joined with their intervening atoms to form substituted or unsubstituted carbocyclyl. In certain embodiments, $X^{A1}$ and $X^{A2}$ are joined with their intervening atoms to form substituted or unsubstituted cyclopentyl, substituted or unsubstituted cyclohexyl, or substituted or unsubstituted cycloheptyl; and/or $X^{B1}$ and $X^{B2}$ are joined with their intervening atoms to form substituted or unsubstituted cyclopentyl, substituted or unsubstituted cyclohexyl, or substituted or unsubstituted cycloheptyl.

In certain embodiments, $X^{A1}$ and $X^{A2}$ are joined with their intervening atoms to form substituted or unsubstituted heterocyclyl; and/or $X^{B1}$ and $X^{B2}$ are joined with their intervening atoms to form substituted or unsubstituted heterocyclyl. In certain embodiments, $X^{A1}$ and $X^{A2}$ are joined with their intervening atoms to form substituted or unsubstituted, bicyclic heterocyclyl; and/or $X^{B1}$ and $X^{B2}$ are joined with their intervening atoms to form substituted or unsubstituted, bicyclic heterocyclyl. In certain embodiments, $X^{A1}$ and $X^{A2}$ are joined with their intervening atoms to form substituted or unsubstituted, 5- to 7-membered, monocyclic heterocyclyl; and/or $X^{B1}$ and $X^{B2}$ are joined with their intervening atoms to form substituted or unsubstituted, 5- to 7-membered, monocyclic heterocyclyl. In certain embodiments, $X^{A1}$ and $X^{A2}$ are joined with their intervening atoms to form substituted or unsubstituted, 5-membered, monocyclic heterocyclyl; and/or $X^{B1}$ and $X^{B2}$ are joined with their intervening atoms to form substituted or unsubstituted, 5-membered, monocyclic heterocyclyl.

In certain embodiments, Formula I is:

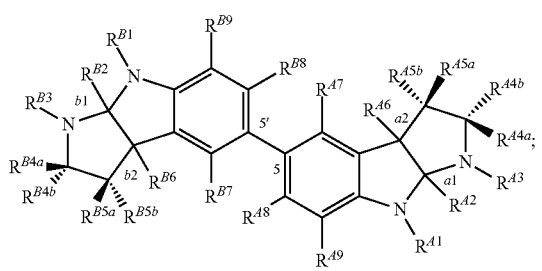

wherein:

each of $R^{A3}$ and $R^{B3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), —P(=O)(OR$^a$)$_2$, a nitrogen protecting group, a peptide, or a depsipeptide; and each of $R^{A4a}$, $R^{B4a}$, $R^{A4b}$, $R^{B4b}$, $R^{A5a}$, $R^{B5a}$, $R^{A5b}$, and $R^{B5b}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$), —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$), —OS(=O)R$^a$, —OS(=O)OR$^a$, —OS(=O)N(R$^a$)$_2$, —OS(=O)$_2$R$^a$, —OS(=O)$_2$OR$^a$, —OS(=O)$_2$N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), —P(=O)(OR$^a$)$_2$, a peptide, or a depsipeptide;

or: $R^{A3}$ and $R^{A4a}$ or $R^{A4b}$ are joined with their intervening atoms to form substituted or unsubstituted carbocyclyl or substituted or unsubstituted heterocyclyl; and/or $R^{B3}$ and $R^{B4a}$ or $R^{B4b}$ are joined with their intervening atoms to form substituted or unsubstituted carbocyclyl or substituted or unsubstituted heterocyclyl.

In certain embodiments, Formula I is:

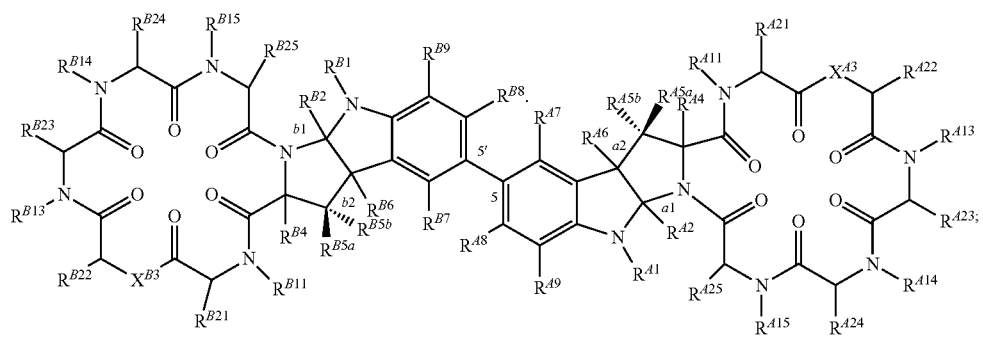

wherein:
R$^{A4}$ is R$^{A4a}$ or R$^{A4b}$;
R$^{B4}$ is R$^{B4a}$ or R$^{B4b}$;
X$^{A3}$ is O or NR$^{A12}$;
X$^{B3}$ is O or NR$^{B12}$;
each of R$^{A11}$, R$^{B11}$, R$^{A12}$, R$^{B12}$, R$^{A13}$, R$^{B13}$, R$^{A14}$, R$^{B14}$, R$^{A15}$, and R$^{B15}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), —P(=O)(OR$^a$)$_2$, or a nitrogen protecting group; and each of R$^{A21}$, R$^{B21}$, R$^{A22}$, R$^{B22}$, R$^{A23}$, R$^{B23}$, R$^{A24}$, R$^{B24}$, R$^{A25}$, and R$^{B25}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$), —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$), —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —OS(=O)$_2$R$^a$, —OS(=O)$_2$OR$^a$, —OS(=O)$_2$N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), or —P(=O)(OR$^a$)$_2$;

or:
R$^{A11}$ and R$^{A21}$ are joined with their intervening atoms to form substituted or unsubstituted heterocyclyl;
R$^{A21}$ and R$^{A12}$ are joined with their intervening atoms to form substituted or unsubstituted heterocyclyl;
R$^{A12}$ and R$^{A22}$ are joined with their intervening atoms to form substituted or unsubstituted heterocyclyl;
R$^{A22}$ and R$^{A13}$ are joined with their intervening atoms to form substituted or unsubstituted heterocyclyl;
R$^{A13}$ and R$^{A23}$ are joined with their intervening atoms to form substituted or unsubstituted heterocyclyl;
R$^{A23}$ and R$^{A14}$ are joined with their intervening atoms to form substituted or unsubstituted heterocyclyl;
R$^{A14}$ and R$^{A24}$ are joined with their intervening atoms to form substituted or unsubstituted heterocyclyl;
R$^{A24}$ and R$^{A15}$ are joined with their intervening atoms to form substituted or unsubstituted heterocyclyl;
R$^{A15}$ and R$^{A25}$ are joined with their intervening atoms to form substituted or unsubstituted heterocyclyl;
R$^{B11}$ and R$^{B21}$ are joined with their intervening atoms to form substituted or unsubstituted heterocyclyl;
R$^{B21}$ and R$^{B12}$ are joined with their intervening atoms to form substituted or unsubstituted heterocyclyl;
R$^{B12}$ and R$^{B22}$ are joined with their intervening atoms to form substituted or unsubstituted heterocyclyl;
R$^{B22}$ and R$^{B13}$ are joined with their intervening atoms to form substituted or unsubstituted heterocyclyl;
R$^{B13}$ and R$^{B23}$ are joined with their intervening atoms to form substituted or unsubstituted heterocyclyl;
R$^{B23}$ and R$^{B14}$ are joined with their intervening atoms to form substituted or unsubstituted heterocyclyl;
R$^{B14}$ and R$^{B24}$ are joined with their intervening atoms to form substituted or unsubstituted heterocyclyl;
R$^{B24}$ and R$^{B15}$ are joined with their intervening atoms to form substituted or unsubstituted heterocyclyl; and/or
R$^{B15}$ and R$^{B25}$ are joined with their intervening atoms to form substituted or unsubstituted heterocyclyl.

In certain embodiments, Formula I is:

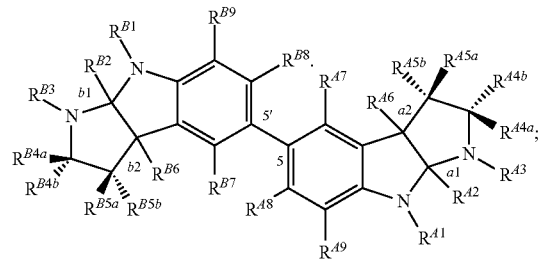

Formula A is:

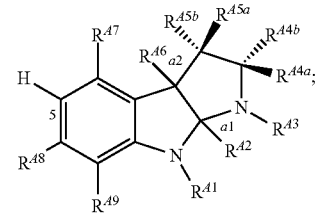

and
Formula B is:

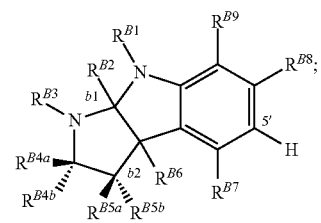

wherein:
each of R$^{A3}$ and R$^{B3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), —P(=O)(OR$^a$)$_2$, a nitrogen protecting group, a peptide, or a depsipeptide; and each of $R^{A4a}$, $R^{B4a}$, $R^{A4b}$, $R^{B4b}$, $R^{A5a}$, $R^{B5a}$, $R^{A5b}$, and $R^{B5b}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=O)$R^a$, —C(=O)$OR^a$, —C(=O)$N(R^a)_2$, —C(=$NR^a$)$R^a$, —C(=$NR^a$)$OR^a$, —C(=$NR^a$)$N(R^a)_2$, —$NO_2$, —$N_3$, —$NR^aC$(=O)$R^a$, —$N^aC$(=O)$OR^a$ $NR^aC$(=O)$N(R^a)_2$, —$NR^aC$(=$NR^a$)$R^a$, —$NR^aC$(=$NR^a$)$OR^a$, —$NR^aC$(=$NR^a$)$N(R^a)_2$, —OC(=O)$R^a$, —OC(=O)$OR^a$, —OC(=O)$N(R^a)_2$, —OC(=$NR^a$)$R^a$, —OC(=$NR^a$)$OR^a$, —OC(=$NR^a$)$N(R^a)_2$, —$NR^aS$(=O)$R^a$, —$NR^aS$(=O)$OR^a$, —$NR^aS$(=O)$N(R^a)_2$, —$NR^aS$(=O)$_2R^a$, —$NR^aS$(=O)$_2OR^a$, —$NR^aS$(=O)$_2N(R^a)_2$, —OS(=O)$R^a$, —OS(=O)$OR^a$, —OS(=O)$N(R^a)_2$, —OS(=O)$_2R^a$, —OS(=O)$_2OR^a$, —OS(=O)$_2N(R^a)_2$, —S(=O)$R^a$, —S(=O)$OR^a$, —S(=O)$N(R^a)_2$, —S(=O)$_2R^a$, —S(=O)$_2OR^a$, —S(=O)$_2N(R^a)_2$, —P(=O)$(R^a)_2$, —P(=O)$(R^a)(OR^a)$, —P(=O)$(OR^a)_2$, a peptide, or a depsipeptide;

or: $R^{A3}$ and $R^{A4a}$ or $R^{A4b}$ are joined with their intervening atoms to form substituted or unsubstituted carbocyclyl or substituted or unsubstituted heterocyclyl; and/or $R^{B3}$ and $R^{B4a}$ or $R^{B4b}$ are joined with their intervening atoms to form substituted or unsubstituted carbocyclyl or substituted or unsubstituted heterocyclyl.

Formula A is:

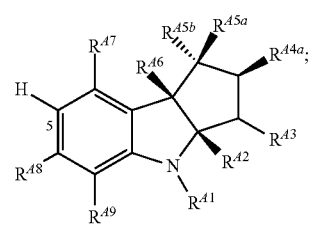

and

Formula B is:

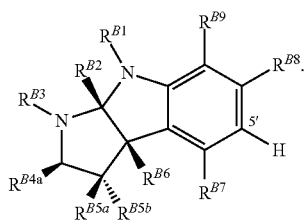

In certain embodiments, Formula I is:

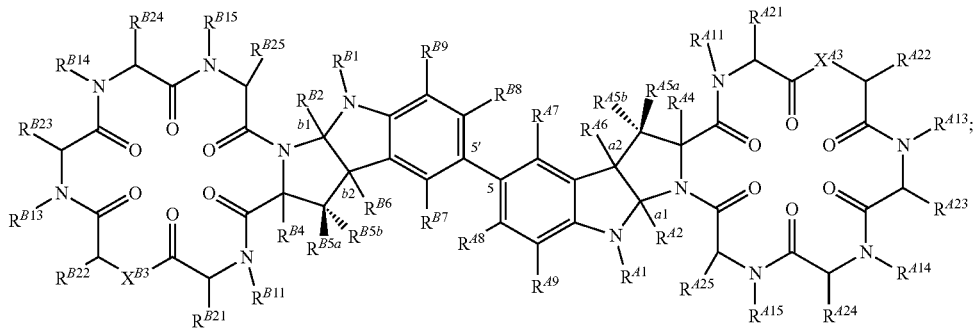

In certain embodiments, Formula I is:

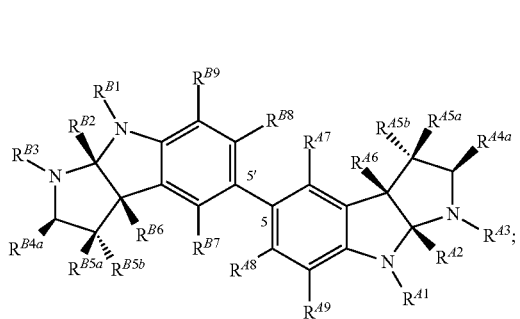

Formula A is:

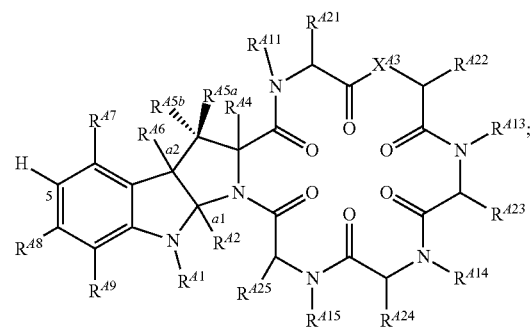

Formula B is:

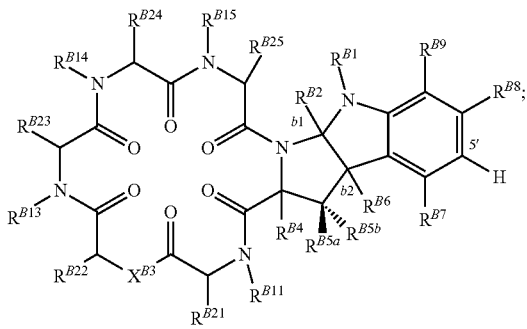

wherein:
$R^{A4}$ is $R^{A4a}$ or $R^{A4b}$;
$R^{B4}$ is $R^{B4a}$ or $R^{B4b}$;
$X^{A3}$ is O or $NR^{A12}$;
$X^{B3}$ is O or $NR^{B12}$;
each of $R^{A11}$, $R^{B11}$, $R^{A12}$, $R^{B12}$, $R^{A13}$, $R^{B13}$, $R^{A14}$, $R^{B14}$, $R^{A15}$ and $R^{B15}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)O$R^a$, —C(=O)N($R^a$)$_2$, —C(=N$R^a$)$R^a$, —C(=N$R^a$)O$R^a$, —C(=N$R^a$)N($R^a$)$_2$, —S(=O)$R^a$, —S(=O)O$R^a$, —S(=O)N($R^a$)$_2$, —S(=O)$_2$$R^a$, —S(=O)$_2$O$R^a$, —S(=O)$_2$N($R^a$)$_2$, —P(=O)($R^a$)$_2$, —P(=O)($R^a$)(O$R^a$), —P(=O)(O$R^a$)$_2$, or a nitrogen protecting group; and
each of $R^{A21}$, $R^{B21}$, $R^{A22}$, $R^{B22}$, $R^{A23}$, $R^{B23}$, $R^{A24}$, $R^{B24}$, $R^{A25}$, and $R^{B25}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=O)$R^a$, —C(=O)O$R^a$, —C(=O)N($R^a$)$_2$, —C(=N$R^a$)$R^a$, —C(=N$R^a$)O$R^a$, —C(=N$R^a$)N($R^a$)$_2$, —NO$_2$, —N$_3$, —N$R^a$C(=O)$R^a$, —N$R^a$C(=O)O$R^a$, —N$R^a$C(=O)N($R^a$)$_2$, —N$R^a$C(=N$R^a$)$R^a$, —N$R^a$C(=N$R^a$)O$R^a$, —N$R^a$C(=N$R^a$)N($R^a$)$_2$, —OC(=O)$R^a$, —OC(=O)O$R^a$, —OC(=O)N($R^a$)$_2$, —OC(=N$R^a$)$R^a$, —OC(=N$R^a$)O$R^a$, —OC(=N$R^a$)N($R^a$)$_2$, —N$R^a$S(=O)$R^a$, —N$R^a$S(=O)O$R^a$, —N$R^a$S(=O)N($R^a$)$_2$, —N$R^a$S(=O)$_2$$R^a$, —N$R^a$S(=O)$_2$O$R^a$, —N$R^a$S(=O)$_2$N($R^a$)$_2$, —OS(=O)$R^a$, —OS(=O)O$R^a$, —OS(=O)N($R^a$)$_2$, —OS(=O)$_2$$R^a$, —OS(=O)$_2$O$R^a$, —OS(=O)$_2$N($R^a$)$_2$, —S(=O)$R^a$, —S(=O)O$R^a$, —S(=O)N($R^a$)$_2$, —S(=O)$_2$$R^a$, —S(=O)$_2$O$R^a$, —S(=O)$_2$N($R^a$)$_2$, —P(=O)($R^a$)$_2$, —P(=O)($R^a$)(O$R^a$), or —P(=O)(O$R^a$)$_2$;
or:
$R^{A11}$ and $R^{A21}$ are joined with their intervening atoms to form substituted or unsubstituted heterocyclyl;
$R^{A21}$ and $R^{A12}$ are joined with their intervening atoms to form substituted or unsubstituted heterocyclyl;
$R^{A12}$ and $R^{A22}$ are joined with their intervening atoms to form substituted or unsubstituted heterocyclyl;
$R^{A22}$ and $R^{A13}$ are joined with their intervening atoms to form substituted or unsubstituted heterocyclyl;
$R^{A13}$ and $R^{A23}$ are joined with their intervening atoms to form substituted or unsubstituted heterocyclyl;
$R^{A23}$ and $R^{A14}$ are joined with their intervening atoms to form substituted or unsubstituted heterocyclyl;
$R^{A14}$ and $R^{A24}$ are joined with their intervening atoms to form substituted or unsubstituted heterocyclyl;
$R^{A24}$ and $R^{A15}$ are joined with their intervening atoms to form substituted or unsubstituted heterocyclyl;
$R^{A15}$ and $R^{A25}$ are joined with their intervening atoms to form substituted or unsubstituted heterocyclyl;
$R^{B11}$ and $R^{B21}$ are joined with their intervening atoms to form substituted or unsubstituted heterocyclyl;
$R^{B21}$ and $R^{B12}$ are joined with their intervening atoms to form substituted or unsubstituted heterocyclyl;
$R^{B12}$ and $R^{B22}$ are joined with their intervening atoms to form substituted or unsubstituted heterocyclyl;
$R^{B22}$ and $R^{B13}$ are joined with their intervening atoms to form substituted or unsubstituted heterocyclyl;
$R^{B13}$ and $R^{B23}$ are joined with their intervening atoms to form substituted or unsubstituted heterocyclyl;
$R^{B23}$ and $R^{B14}$ are joined with their intervening atoms to form substituted or unsubstituted heterocyclyl;
$R^{B14}$ and $R^{B24}$ are joined with their intervening atoms to form substituted or unsubstituted heterocyclyl;
$R^{B24}$ and $R^{B15}$ are joined with their intervening atoms to form substituted or unsubstituted heterocyclyl; and/or
$R^{B15}$ and $R^{B25}$ are joined with their intervening atoms to form substituted or unsubstituted heterocyclyl.

In certain embodiments, $R^{A4}$ is $R^{A4b}$ and/or $R^{B4}$ is $R^{B4b}$. In certain embodiments, $R^{A4}$ is $R^{A4a}$ and/or $R^{B4}$ is $R^{B4a}$.
In certain embodiments, $X^{A3}$ and/or $X^{B3}$ are O. In certain embodiments, $X^{A3}$ and/or $X^{B3}$ are NH.
In certain embodiments, $R^{A11}$ and/or $R^{B11}$ are hydrogen. In certain embodiments, $R^{A11}$ and/or $R^{B11}$ are unsubstituted $C_{1-6}$ alkyl (e.g., unsubstituted methyl).
In certain embodiments, $R^{A21}$ and/or $R^{B21}$ are substituted or unsubstituted alkyl. In certain embodiments, $R^{A21}$ and/or $R^{B21}$ are unsubstituted $C_{1-6}$ alkyl (e.g., unsubstituted isopropyl).
In certain embodiments, $R^{A12}$ and/or $R^{B12}$ are hydrogen. In certain embodiments, $R^{A12}$ and/or $R^{B12}$ are substituted or unsubstituted alkyl. In certain embodiments, $R^{A12}$ and/or $R^{B12}$ are unsubstituted $C_{1-6}$ alkyl (e.g., unsubstituted methyl).
In certain embodiments, $R^{A22}$ and/or $R^{B22}$ are substituted or unsubstituted alkyl. In certain embodiments, $R^{A22}$ and/or $R^{B22}$ are unsubstituted $C_{1-6}$ alkyl (e.g., unsubstituted isopropyl).
In certain embodiments, $R^{A13}$ and $R^{A23}$ are joined with their intervening atoms to form substituted or unsubstituted heterocyclyl, and/or $R^{B13}$ and $R^{B23}$ are joined with their intervening atoms to form substituted or unsubstituted heterocyclyl. In certain embodiments, $R^{A13}$ and $R^{A23}$ are joined with their intervening atoms to form substituted or unsubstituted, monocyclic, 6-membered heterocyclyl, and/or $R^{B13}$ and $R^{B23}$ are joined with their intervening atoms to form substituted or unsubstituted, monocyclic, 6-membered heterocyclyl.
In certain embodiments, $R^{A13}$ and/or $R^{B13}$ are hydrogen. In certain embodiments, $R^{A13}$ and/or $R^{B13}$ are unsubstituted $C_{1-6}$ alkyl (e.g., unsubstituted methyl).
In certain embodiments, $R^{A14}$ and/or $R^{B14}$ are hydrogen. In certain embodiments, $R^{A14}$ and/or $R^{B14}$ are unsubstituted $C_{1-6}$ alkyl (e.g., unsubstituted methyl).
In certain embodiments, $R^{A24}$ and/or $R^{B24}$ are substituted or unsubstituted alkyl. In certain embodiments, $R^{A24}$ and/or $R^{B24}$ are substituted or unsubstituted alkyl, wherein the molecular weight of $R^{A24}$ and/or the molecular weight of $R^{B24}$ are not more than 300 g/mol. In certain embodiments, $R^{A24}$ and/or $R^{B24}$ are substituted or unsubstituted alkyl, wherein the molecular weight of $R^{A24}$ and/or the molecular weight of $R^{B24}$ are between 2 and 10, between 10 and 50, between 50 and 100, between 100 and 200, between 200 and 300, g/mol, inclusive. In certain embodiments, $R^{A24}$ and/or $R^{B24}$ are substituted or unsubstituted alkyl, wherein the molecular weight of $R^{A24}$ and/or the molecular weight of $R^{B24}$ are between 300 and 400, between 400 and 500, between 500 and 600, or between 600 and 800, or between 800 and 1,000, g/mol, inclusive. In certain embodiments, $R^{A24}$ and/or $R^{B24}$ are unsubstituted $C_{1-6}$ alkyl (e.g., unsubstituted methyl, unsubstituted isopropyl). In certain embodiments, $R^{A24}$ and/or $R^{B24}$ are substituted $C_{1-6}$ alkyl (e.g., $C_{1-6}$ alkyl substituted with at least one —$OR^a$ or —$N_3$). In certain embodiments, $R^{A24}$ and/or $R^{B24}$ are -(substituted or unsubstituted alkylene or substituted or unsubstituted heteroalkylene)-(click chemistry handle). In certain embodiments, $R^{A24}$ and/or $R^{B24}$ are -(substituted or unsubstituted alkylene)-$N_3$.

In certain embodiments, $R^{A24}$ and/or $R^{B24}$ are -(substituted or unsubstituted alkylene or substituted or unsubstituted heteroalkylene)-fluorophore. In certain embodiments, at least one instance of the fluorophore is a xanthene derivative (e.g., fluorescein, rhodamine, Oregon green, eosin, or Texas red), cyanine derivative (e.g., cyanine, indocarbocyanine, oxacarbocyanine, thiacarbocyanine, or merocyanine), squaraine derivative or ring-substituted squaraine (e.g., a Seta or Square dye), squaraine rotaxane derivative, naphthalene derivative (dansyl or prodan derivative), coumarin derivative, oxadiazole derivative (e.g., pyridyloxazole, nitrobenzoxadiazole, or benzoxadiazole) anthracene derivative (e.g., anthraquinone, including DRAQ5, DRAQ7, or CyTRAK Orange) pyrene derivative (e.g., cascade blue), oxazine derivative (e.g., Nile red, Nile blue, cresyl violet, or oxazine 170), acridine derivative (e.g., proflavin, acridine orange, or acridine yellow), arylmethine derivative (e.g., auramine, crystal violet, or malachite green), tetrapyrrole derivative (e.g., porphin, phthalocyanine, or bilirubin), or dipyrromethene derivative (e.g., BODIPY or aza-BODIPY).

In certain embodiments, $R^{A15}$ and/or $R^{B15}$ are hydrogen. In certain embodiments, $R^{A15}$ and/or $R^{B15}$ are unsubstituted $C_{1-6}$ alkyl (e.g., unsubstituted methyl).

In certain embodiments, $R^{A25}$ and/or $R^{B25}$ are substituted or unsubstituted alkyl. In certain embodiments, $R^{A25}$ and/or $R^{B25}$ are unsubstituted $C_{1-6}$ alkyl. In certain embodiments, $R^{A25}$ and/or $R^{B25}$ are substituted $C_{1-6}$ alkyl (e.g., $C_{1-6}$ alkyl substituted with at least one —$OR^a$).

In certain embodiments, the bond a1 and the bond a2, and/or the bond b1 and the bond b2, are up bonds. In certain embodiments, the bond a1 and the bond a2, and/or the bond b1 and the bond b2, are down bonds.

In certain embodiments, $R^{A1}$ and/or $R^{B1}$ are hydrogen. In certain embodiments, $R^{A1}$ and/or $R^{B1}$ are substituted or unsubstituted alkyl. In certain embodiments, $R^{A1}$ and/or $R^{B1}$ are —$CH_3$.

In certain embodiments, $R^{A2}$ and/or $R^{B2}$ are hydrogen. In certain embodiments, $R^{A2}$ and/or $R^{B2}$ are unsubstituted $C_{1-6}$ alkyl (e.g., unsubstituted methyl). In certain embodiments, $R^{A2}$ and/or $R^{B2}$ are substituted or unsubstituted alkyl. In certain embodiments, $R^{A2}$ and/or $R^{B2}$ are —$CH_3$. In certain embodiments, $R^{A2}$ and/or $R^{B2}$ are substituted or unsubstituted phenyl.

In certain embodiments, $R^{A6}$ and/or $R^{B6}$ are —$OR^a$. In certain embodiments, $R^{A6}$ and/or $R^{B6}$ are —OH. In certain embodiments, $R^{A6}$ and/or $R^{B6}$ are substituted or unsubstituted alkyl. In certain embodiments, $R^{A6}$ and/or $R^{B6}$ are —$CH_3$. In certain embodiments, $R^{A6}$ and/or $R^{B6}$ are substituted or unsubstituted phenyl.

In certain embodiments, $R^{A7}$ and/or $R^{B7}$ are hydrogen. In certain embodiments, $R^{A7}$ and/or $R^{B7}$ are halogen or substituted or unsubstituted alkyl. In certain embodiments, $R^{A7}$ and/or $R^{B7}$ are halogen.

In certain embodiments, $R^{A8}$ and/or $R^{B8}$ are hydrogen. In certain embodiments, $R^{A8}$ and/or $R^{B8}$ are halogen or substituted or unsubstituted alkyl.

In certain embodiments, $R^{A9}$ and/or $R^{B9}$ are hydrogen. In certain embodiments, $R^{A9}$ and/or $R^{B9}$ are halogen or substituted or unsubstituted alkyl.

In certain embodiments, $R^{A3}$ and $R^{A4a}$ or $R^{A4b}$ rejoined with their intervening atoms to form substituted or unsubstituted heterocyclyl; and/or $R^{B3}$ and $R^{B4a}$ or $R^{B4b}$ are joined with their intervening atoms to form substituted or unsubstituted heterocyclyl. In certain embodiments, $R^{A3}$ and $R^{A4a}$ or $R^{A4b}$ are joined with their intervening atoms to form substituted or unsubstituted, 12- to 24-membered, monocyclic heterocyclyl optionally fused independently with one to four substituted or unsubstituted, 3- to 7-membered, monocyclic heterocyclyl; and/or $R^{B3}$ and $R^{B4a}$ or $R^{B4b}$ are joined with their intervening atoms to form substituted or unsubstituted, 12- to 24-membered, monocyclic heterocyclyl optionally fused independently with one to four substituted or unsubstituted, 3- to 7-membered, monocyclic heterocyclyl. In certain embodiments, the substituted or unsubstituted, 12- to 24-membered, monocyclic heterocyclyl optionally fused independently with one to four substituted or unsubstituted, 3- to 7-membered, monocyclic heterocyclyl is a cyclic peptide or cyclic depsipeptide.

In certain embodiments, $R^{A3}$ and $R^{A4a}$ or $R^{A4b}$ are joined with their intervening atoms to form substituted or unsubstituted, 5- to 7-membered, monocyclic heterocyclyl; and/or $R^{B3}$ and $R^{B4a}$ or $R^{B4b}$ are joined with their intervening atoms to form substituted or unsubstituted, 5- to 7-membered, monocyclic heterocyclyl. In certain embodiments, $R^{A3}$ and/or $R^{B3}$ are —C(=O)O (substituted or unsubstituted alkyl) or a nitrogen protecting group. In certain embodiments, $R^{A3}$ and/or $R^{B3}$ are a peptide or depsipeptide. In certain embodiments, $R^{A4a}$ and/or $R^{B4a}$ are —C(=O)O (substituted or unsubstituted alkyl). In certain embodiments, $R^{A4a}$ and/or $R^{B4a}$ are a peptide or depsipeptide. In certain embodiments, $R^{A4a}$ and/or $R^{B4a}$ are hydrogen. In certain embodiments, wherein:

$R^{A3}$ is different from $R^{B3}$; and/or $R^{A4a}$ is different from $R^{B4a}$.

In certain embodiments, $R^{A4b}$ and/or $R^{B4b}$ are hydrogen. In certain embodiments, $R^{A4b}$ and/or $R^{B4b}$ are —C(=O)O (substituted or unsubstituted alkyl). In certain embodiments, $R^{A4b}$ and/or $R^{B4b}$ are a peptide or depsipeptide.

In certain embodiments, $R^{A5a}$ and/or $R^{B5a}$ are hydrogen. In certain embodiments, $R^{A5b}$ and/or $R^{B5b}$ are hydrogen.

In certain embodiments, the compound of Formula A is the same as the compound of Formula B. In certain embodiments, the compound of Formula A is different from the compound of Formula B.

In certain embodiments, the compound is of the formula:
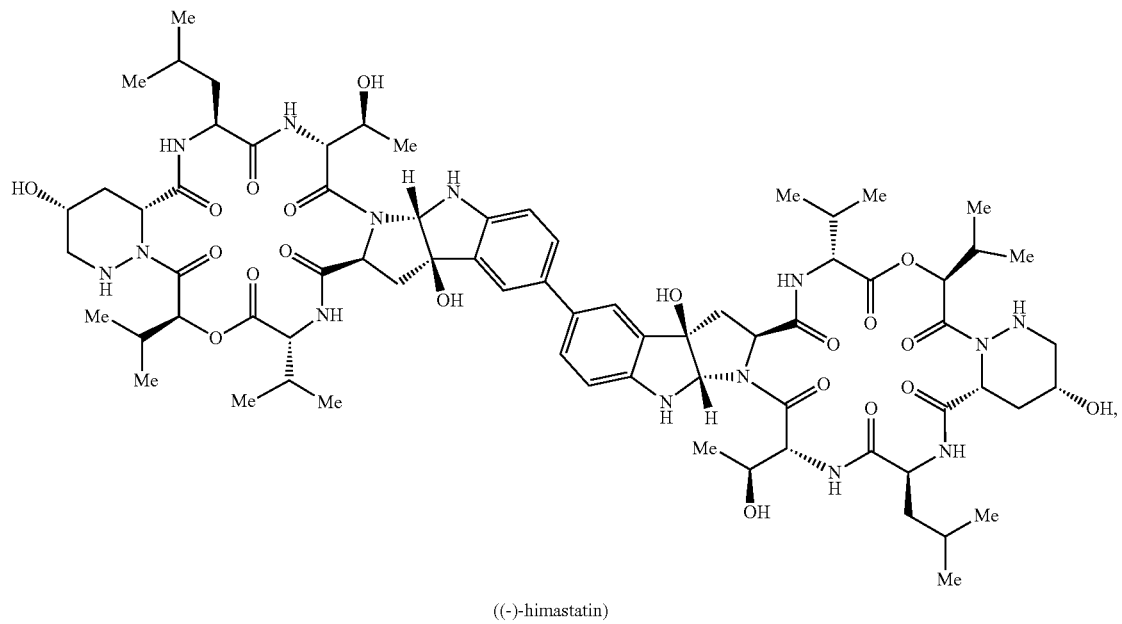
((−)-himastatin)
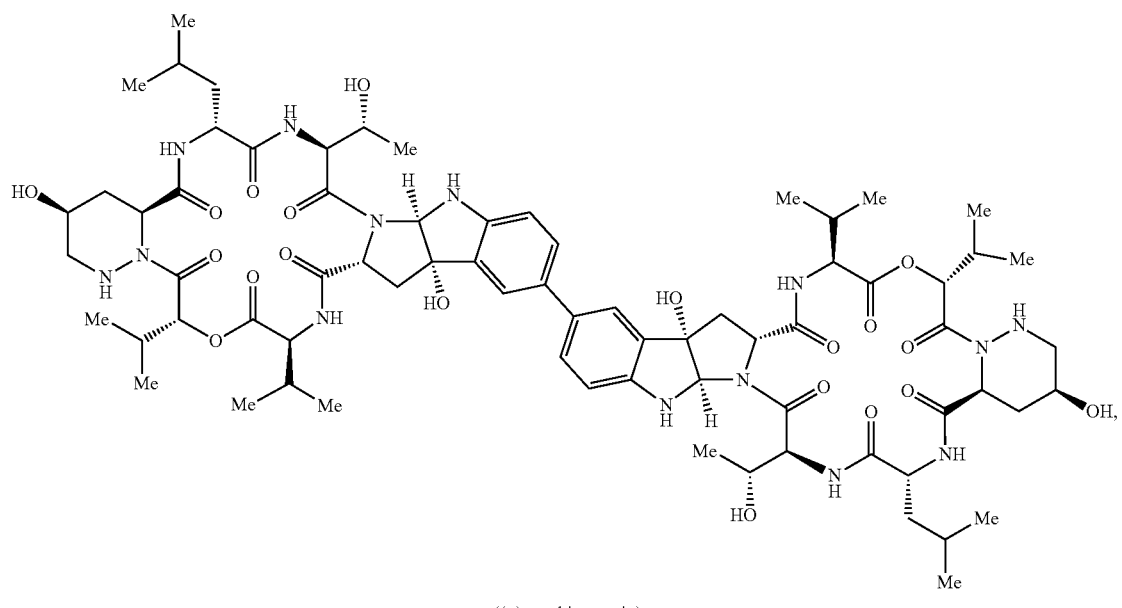
((+)-ent-himastatin)

-continued
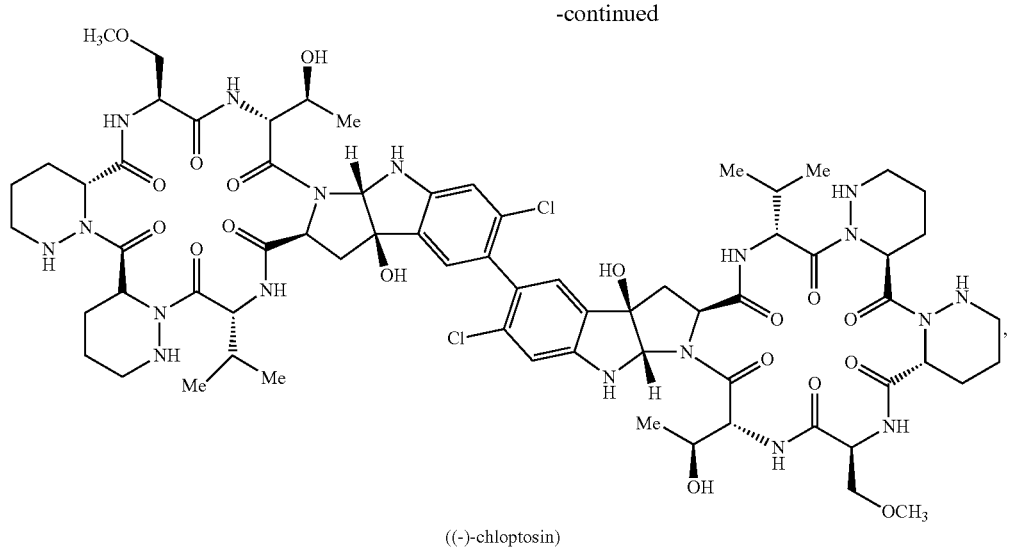
((-)-chloptosin)
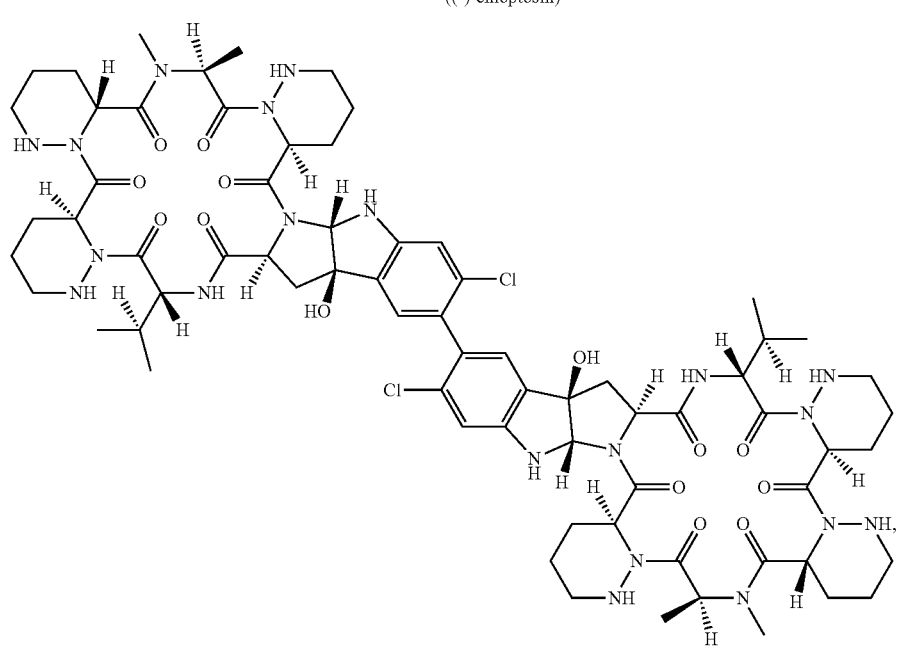
(NW-G01)
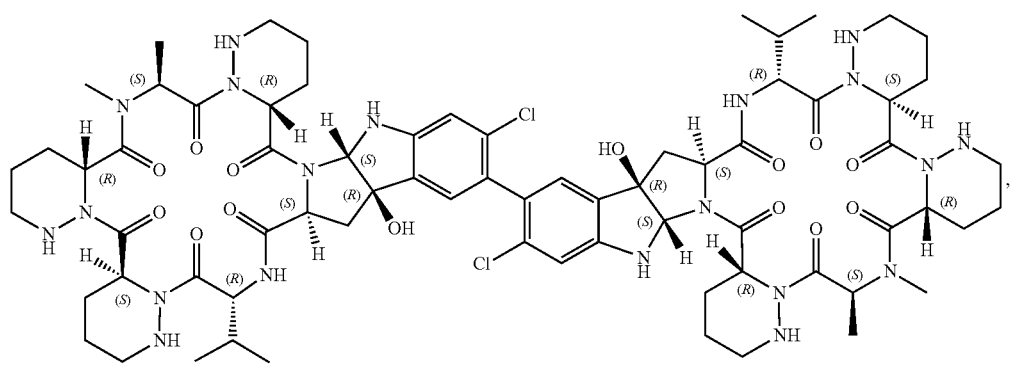
(dialboflavusin A)

-continued
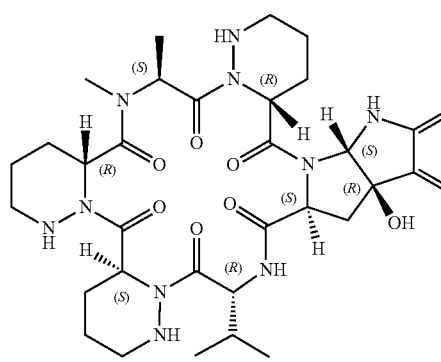
(de-Cl-dialboflavusin A)
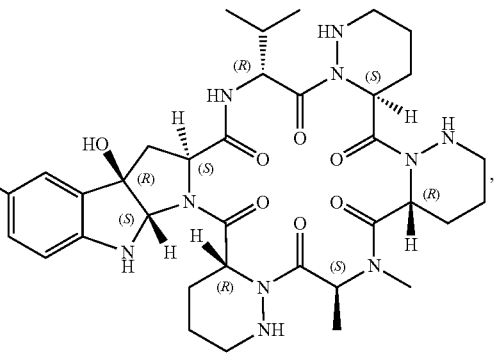
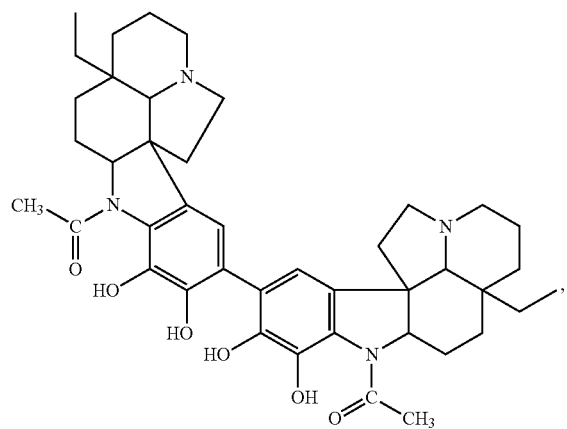
(Compound III)
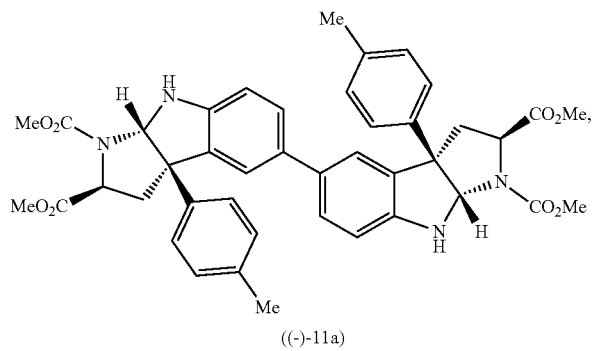
((-)-11a)
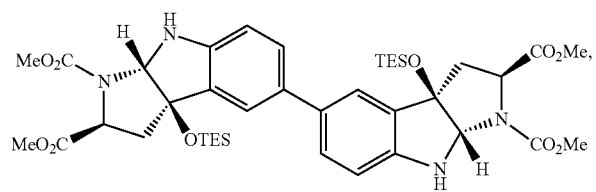
((-)-11b)
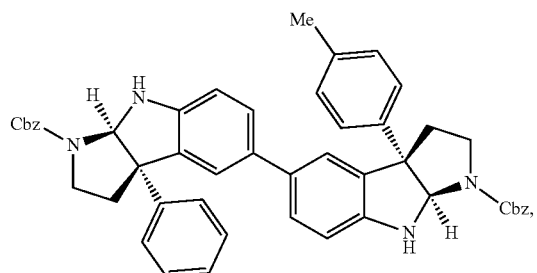
((-)-11c)
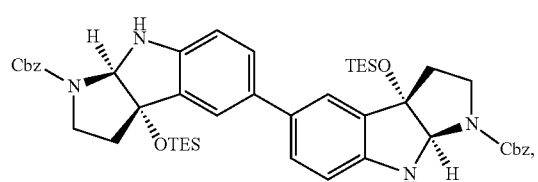
((+)-11d)
((-)-11d)
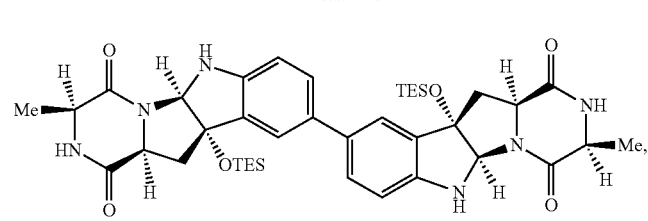
(endo-(+)-11e)
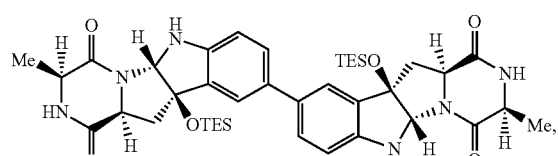
(endo-(+)-11f)
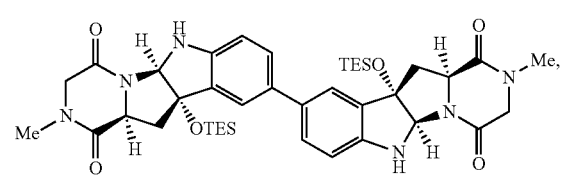
(endo-(+)-11g)

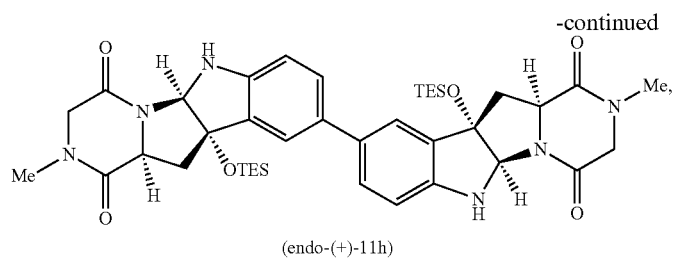
(endo-(+)-11h)
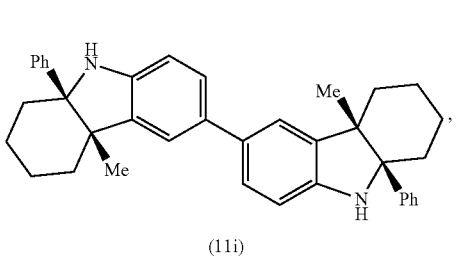
(11i)
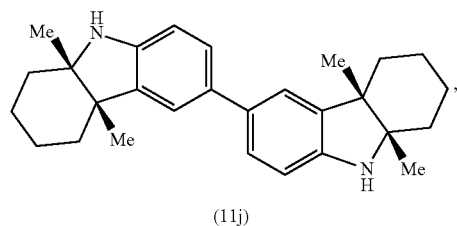
(11j)
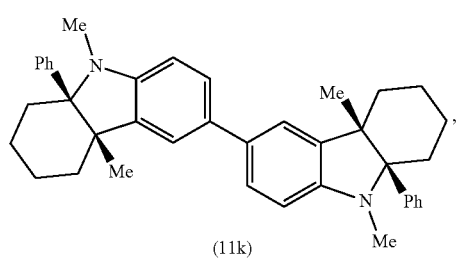
(11k)
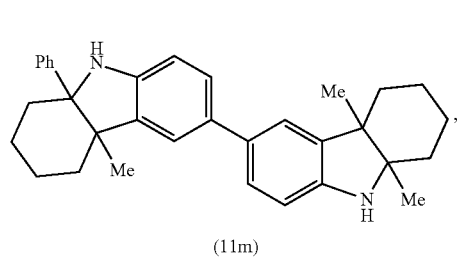
(11m)
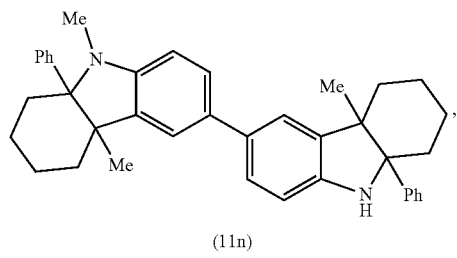
(11n)
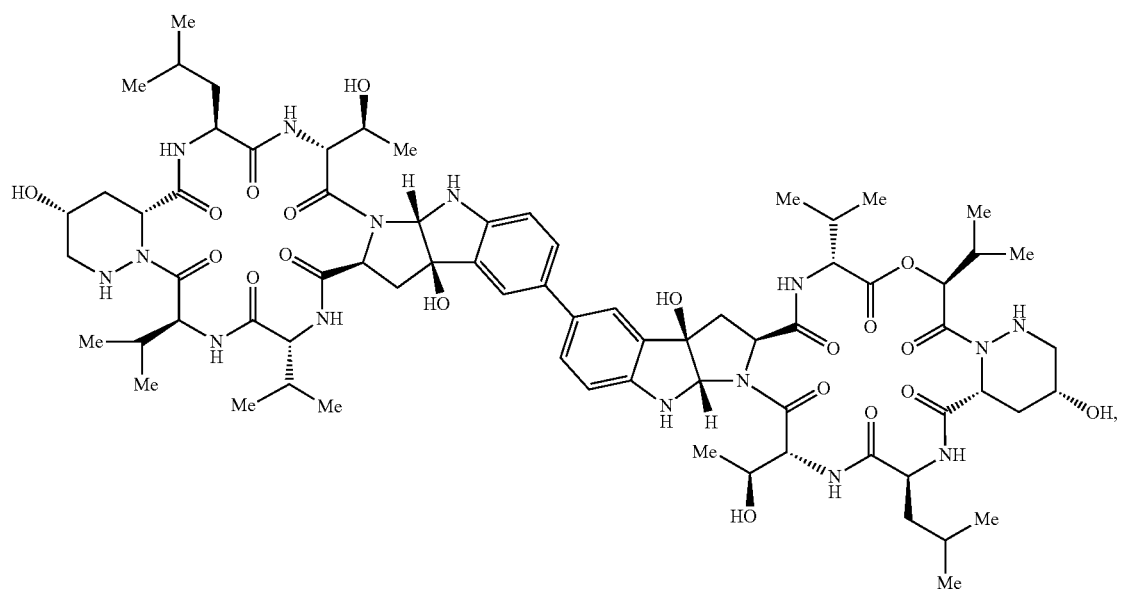
((−)-26)

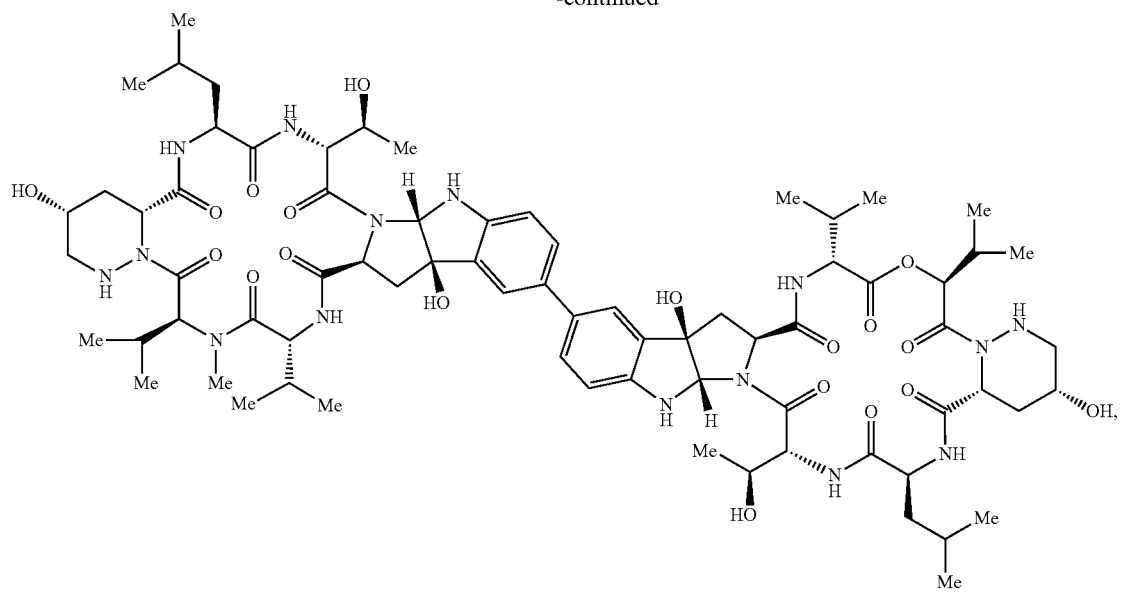
((-)-28)
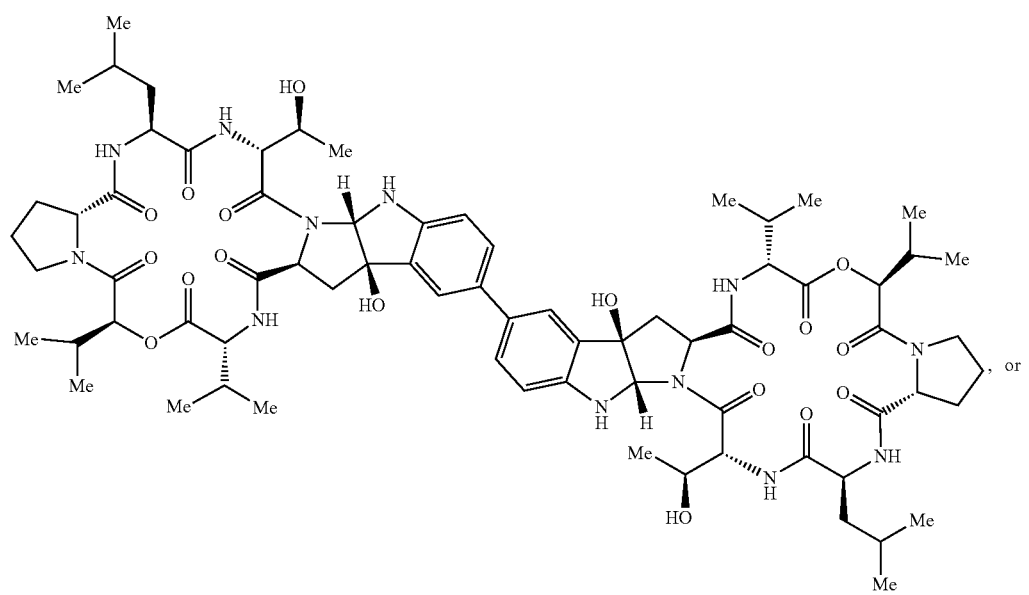
((-)-30)

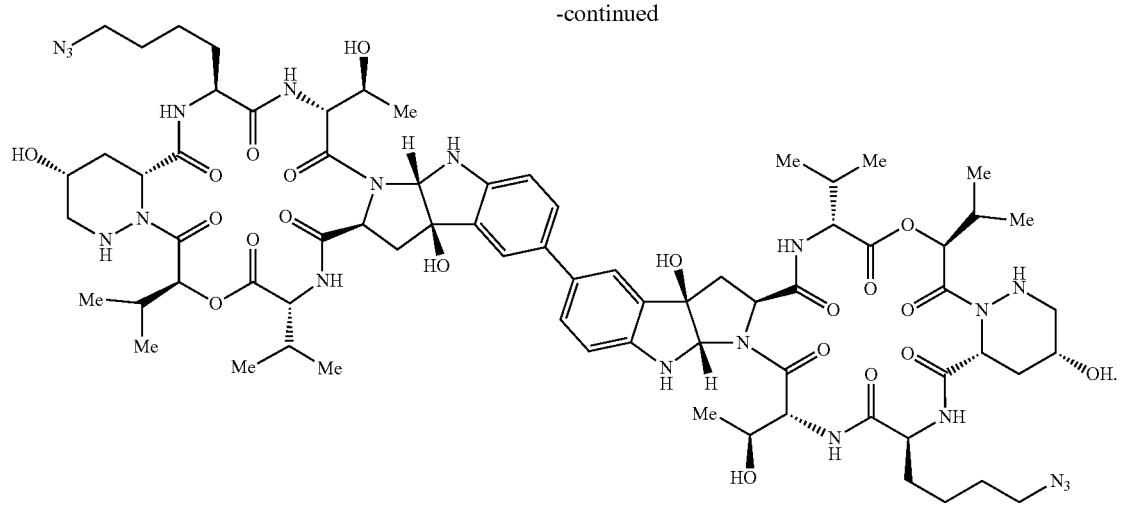
((-)-32)
In certain embodiments, the compound is racemic himastatin.
In certain embodiments, the compound is of the formula:
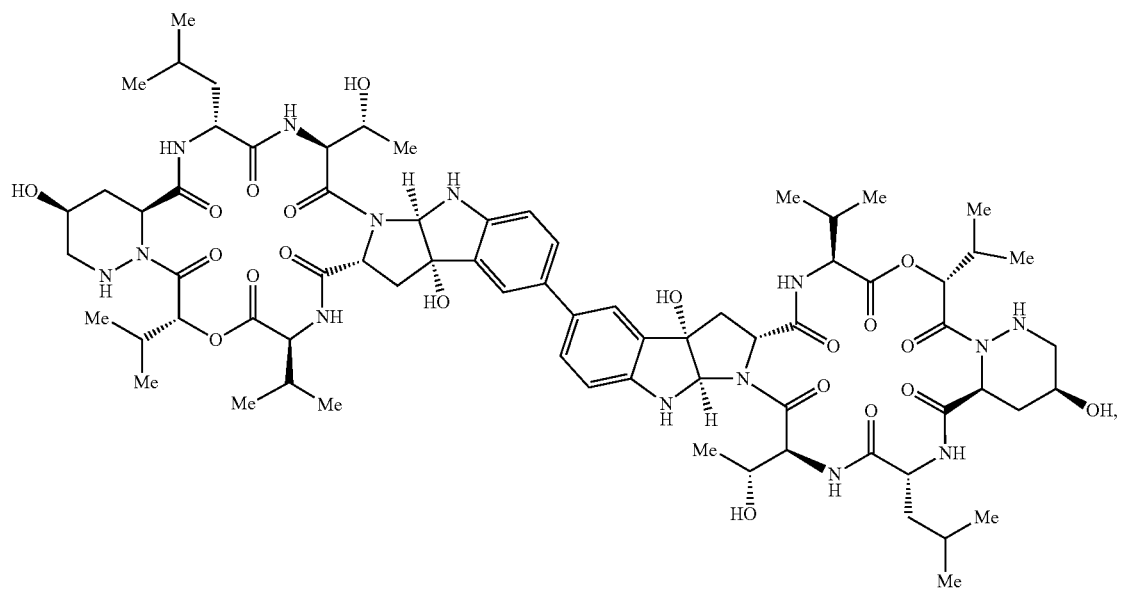
((+)-ent-himastatin)
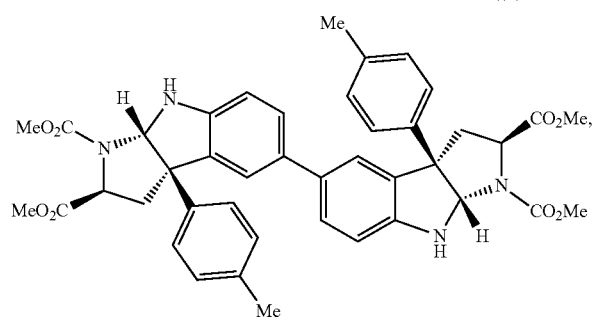
((-)-11a)
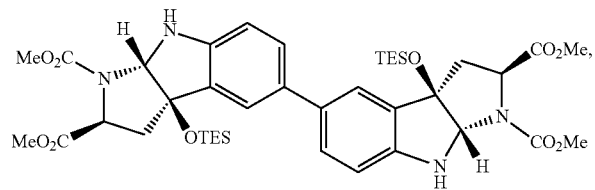
((-)-11b)

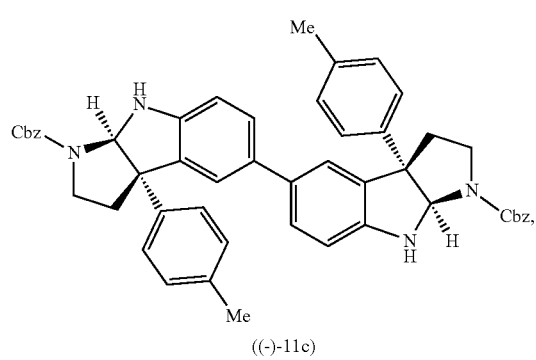
((-)-11c)
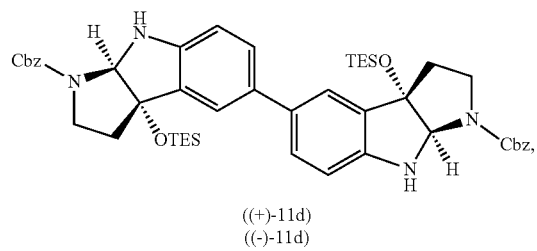
((+)-11d)
((-)-11d)
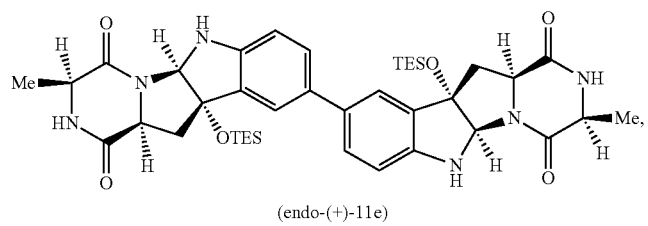
(endo-(+)-11e)
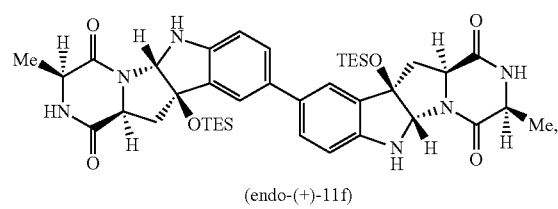
(endo-(+)-11f)
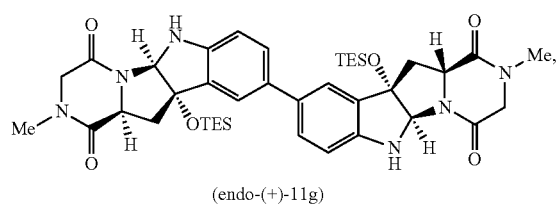
(endo-(+)-11g)
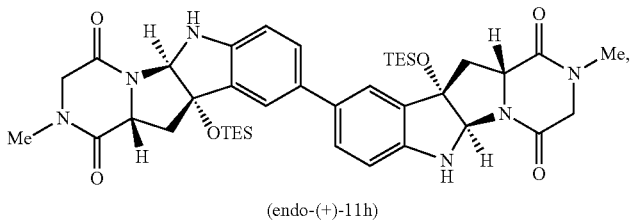
(endo-(+)-11h)
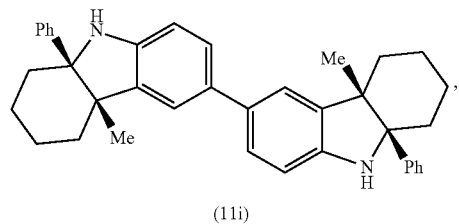
(11i)
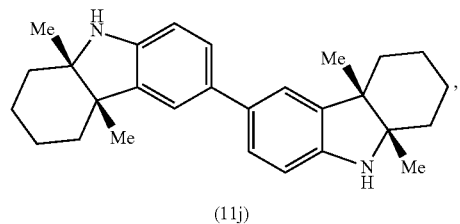
(11j)
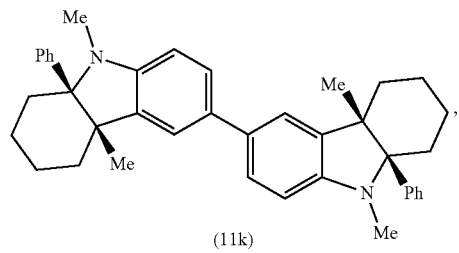
(11k)
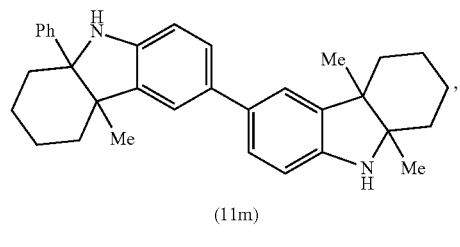
(11m)
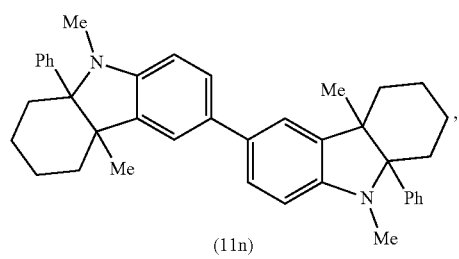
(11n)

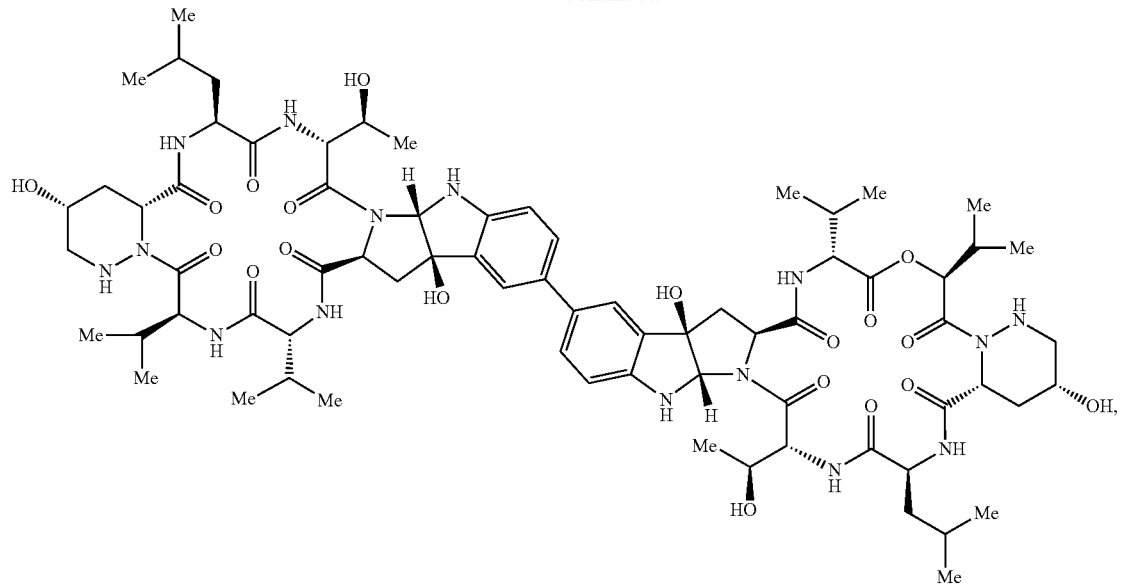
((-)-26)
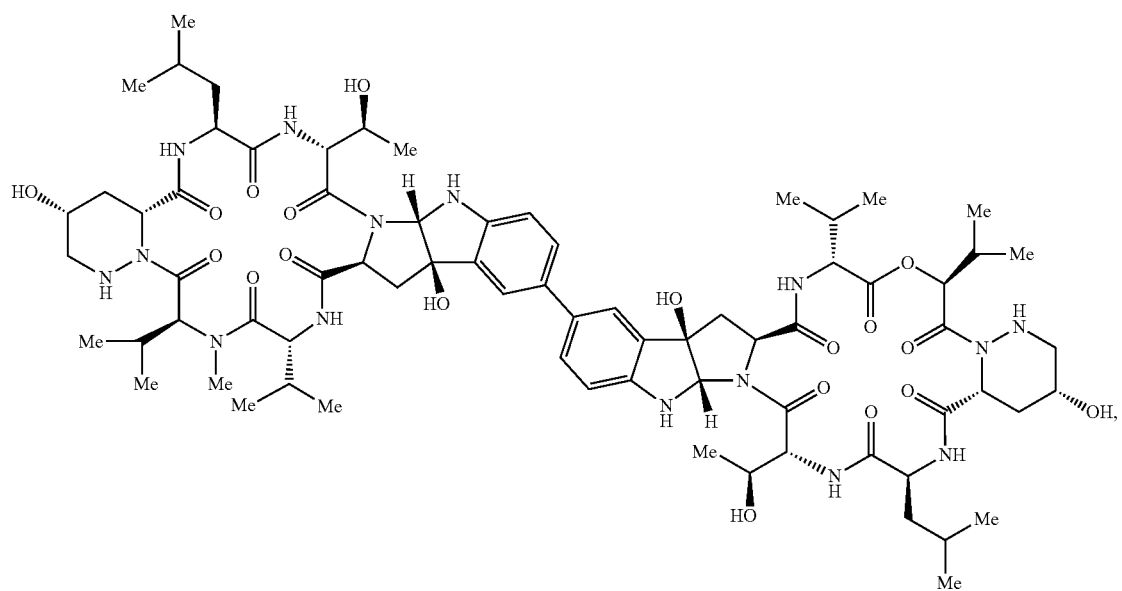
((-)-28)

-continued
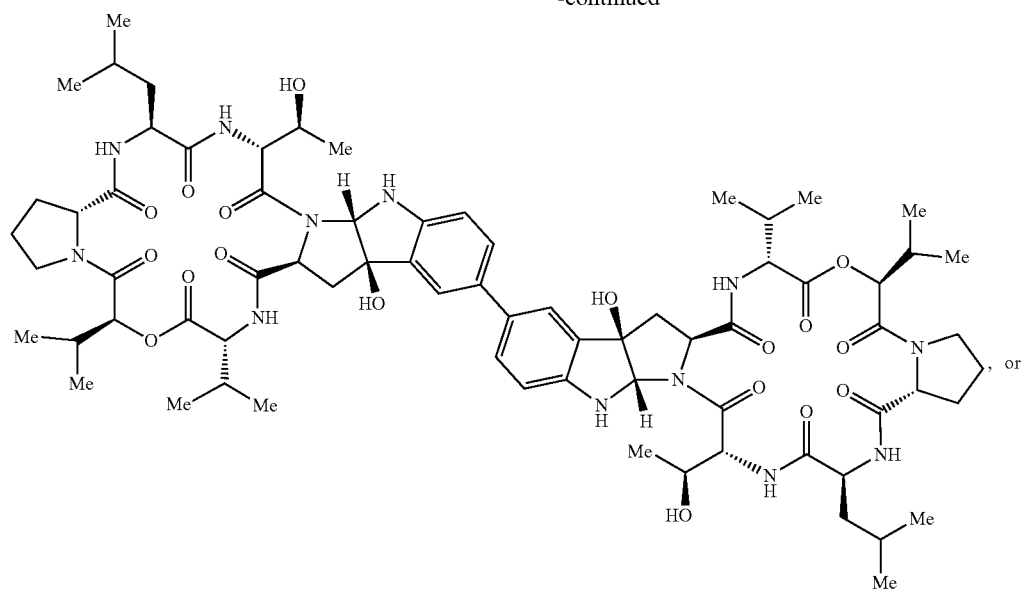
((-)-30)
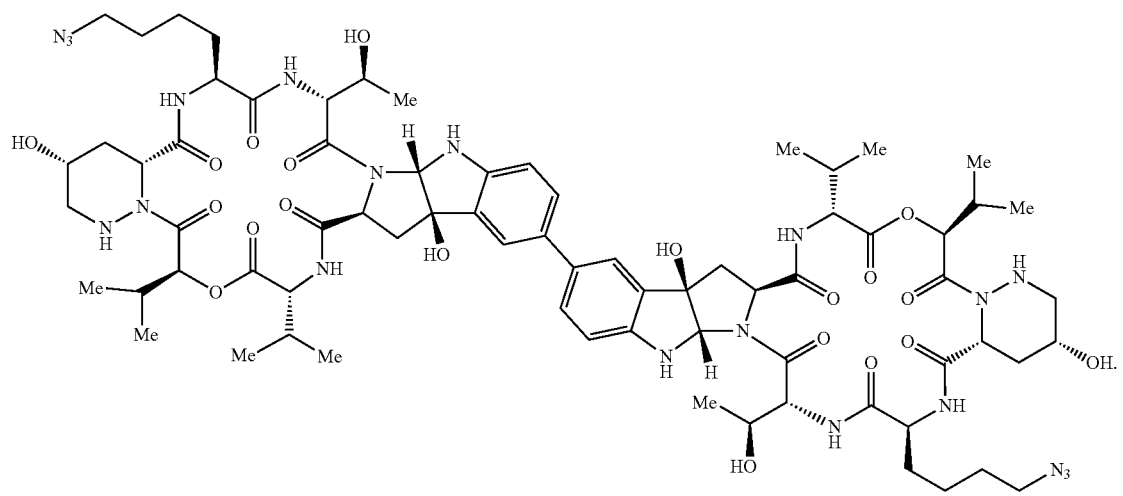
((-)-32)

In certain embodiments, the compound is of the formula:
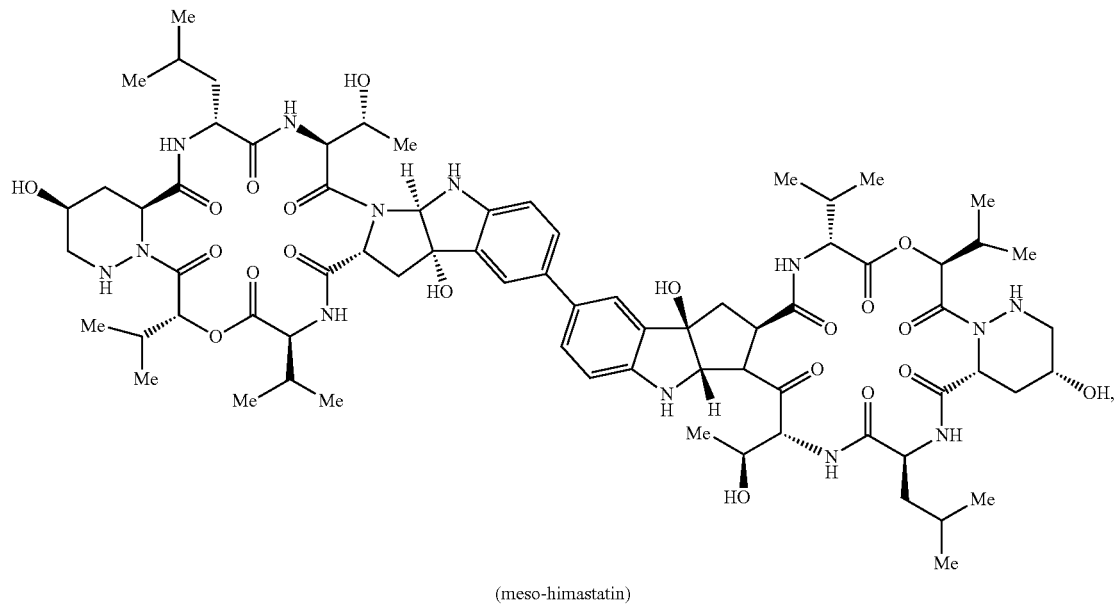
(meso-himastatin)
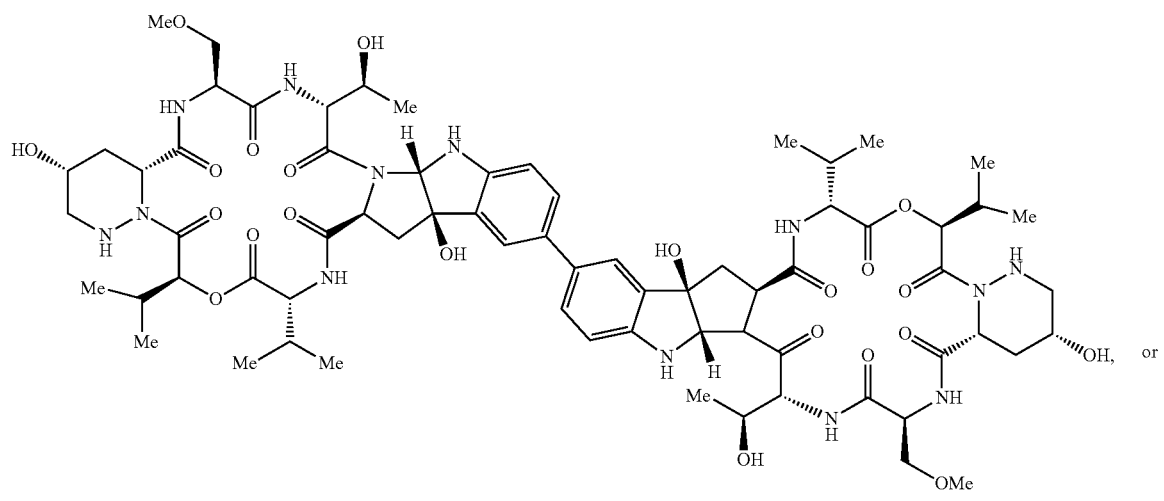
((-)-21)

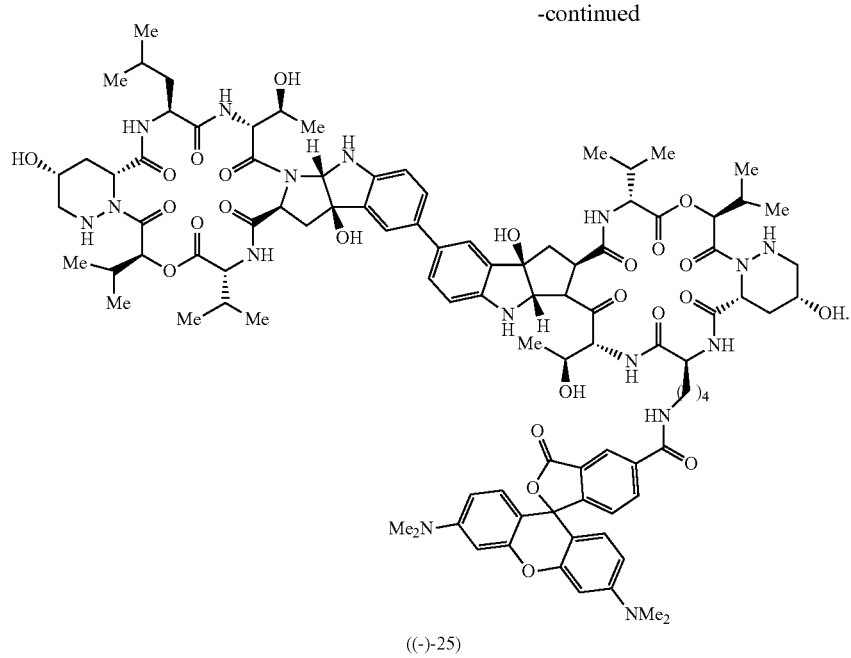
((-)-25)
In certain embodiments, the compound is of the formula:
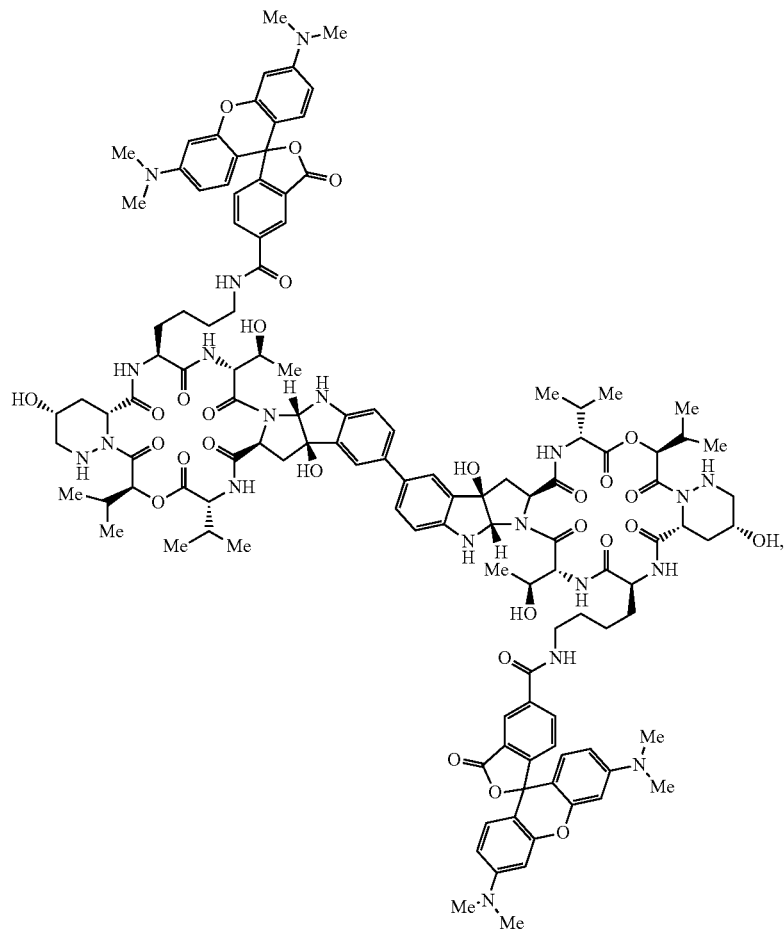
((-)-S17)

(41)
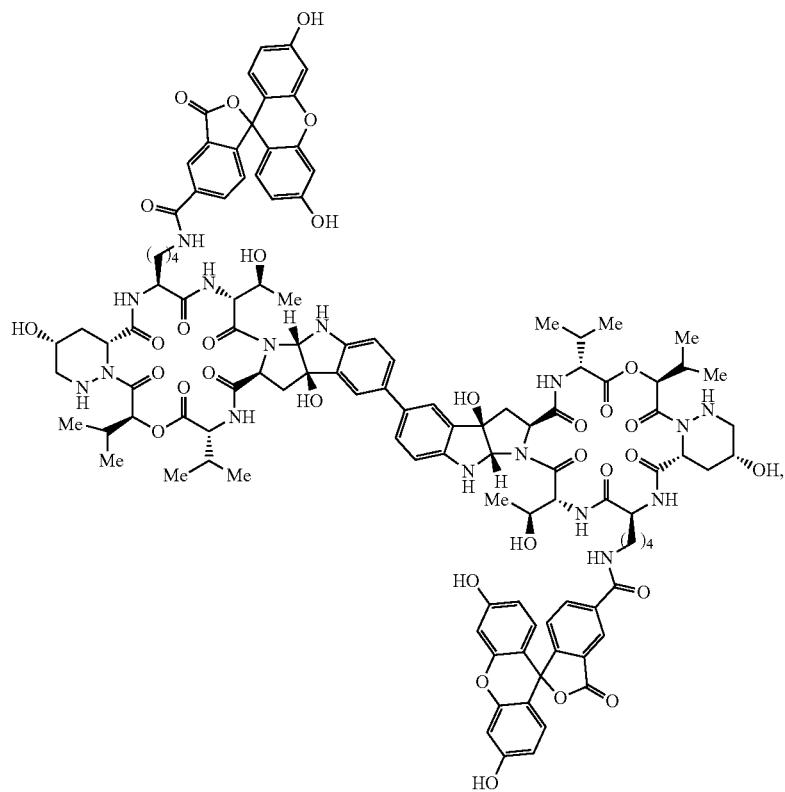
(42)
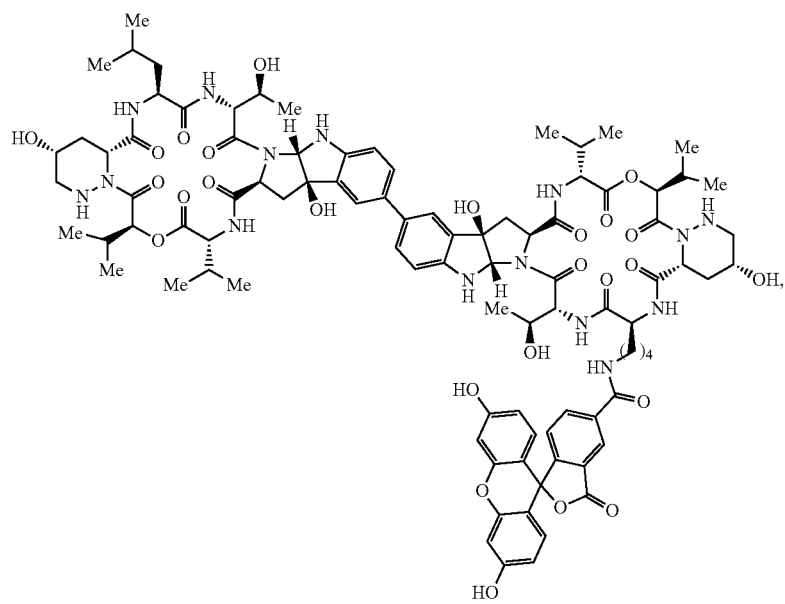

(43)
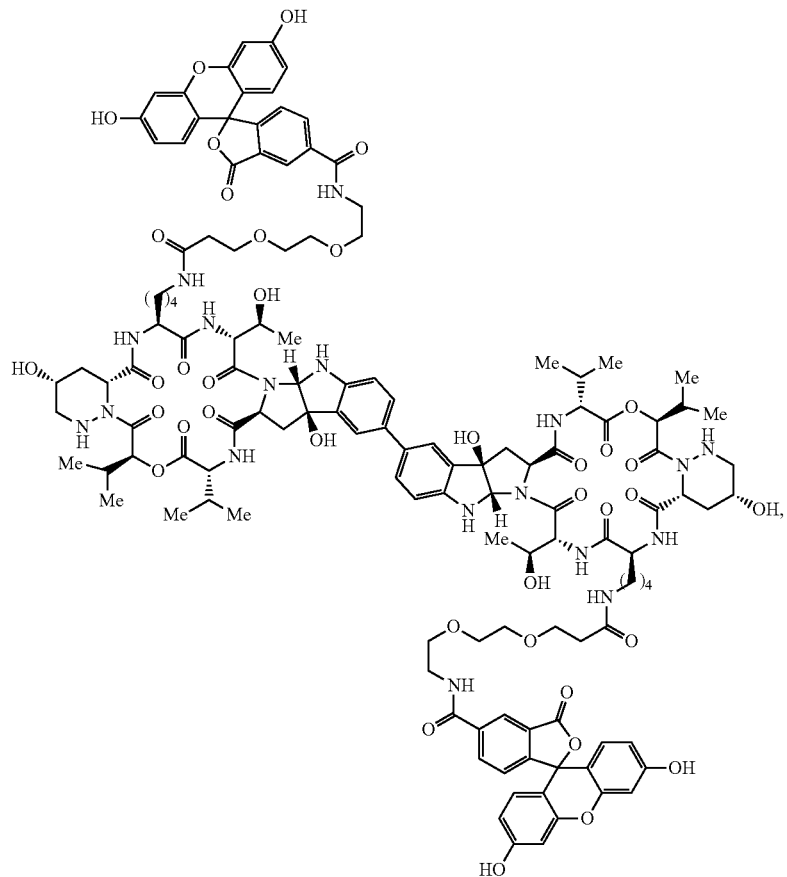
(44)
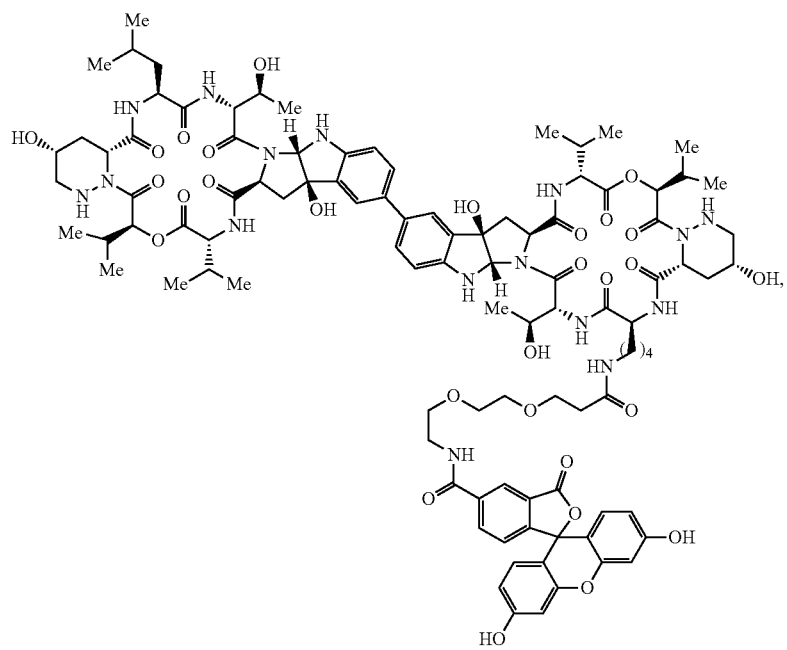

(45)

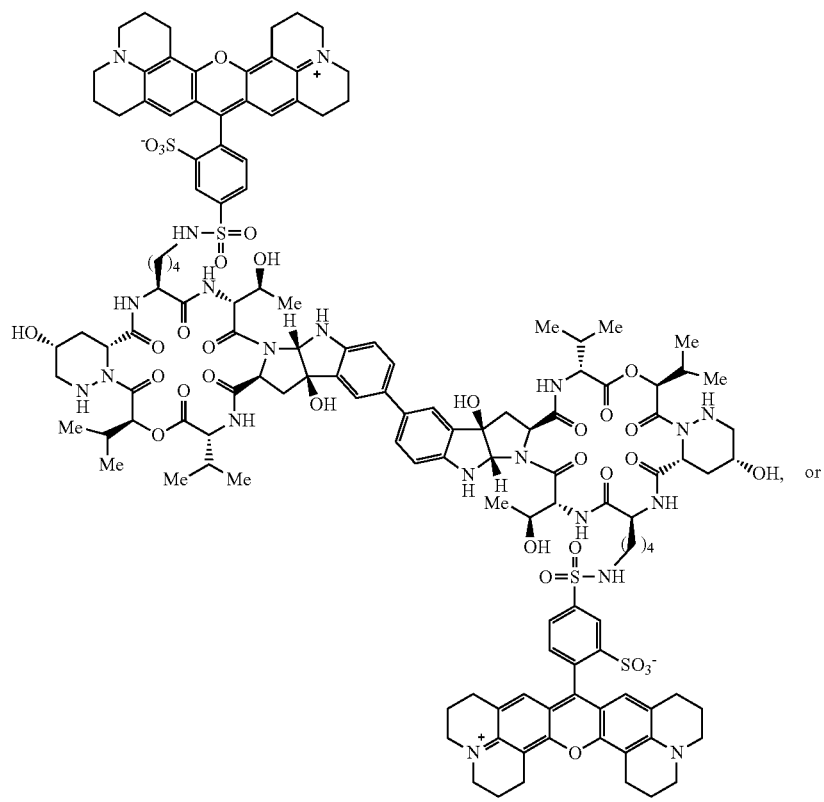

or (46)

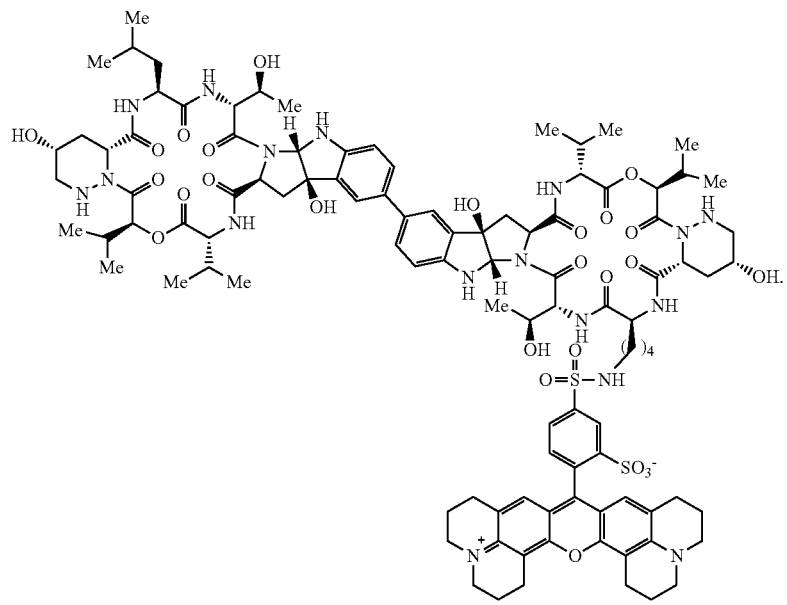

In certain embodiments, the single-electron oxidant is an inorganic single-electron oxidant. In certain embodiments, the single-electron oxidant comprises silver(I). In certain embodiments, the single-electron oxidant is $AgSbF_6$. In certain embodiments, the single-electron oxidant is AgOTf, $AgClO_4$, AgO, or $AgF_2$. In certain embodiments, the single-electron oxidant comprises copper(II), iron(III), or ruthenium(III). In certain embodiments, the single-electron oxidant is $Cu(SbF_6)_2$ or $Cu(OTf)_2$. In certain embodiments, the single-electron oxidant comprises Au(I) or Au(III). In certain embodiments, the single-electron oxidant is $Fe(bpy)_3(PF_6)_3$. In certain embodiments, the single-electron oxidant is an organic single-electron oxidant. In certain embodiments, the single-electron oxidant is of the formula:

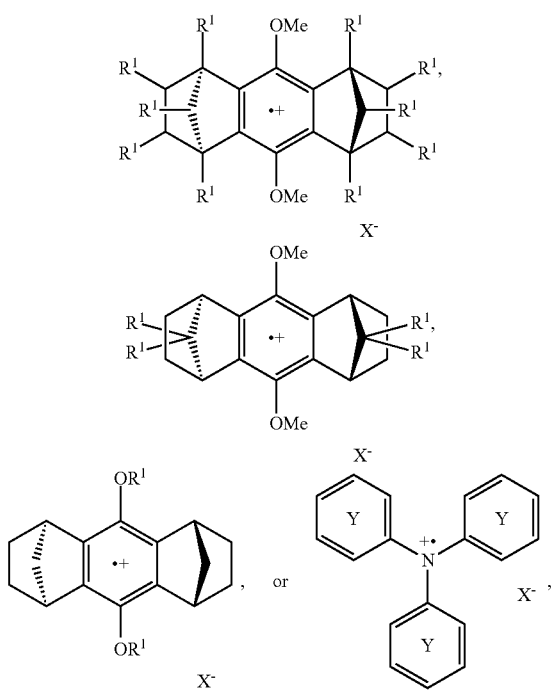

wherein:
X⁻ is $BF_4^-$, $SbF_6^-$, $OTf^-$, $PF_6^-$, or $ClO_4^-$;
each $R^1$ is independently substituted or unsubstituted alkyl, substituted or unsubstituted aryl, or halogen; and
each Ring Y is independently substituted or unsubstituted.

In certain embodiments, the base is of the formula:

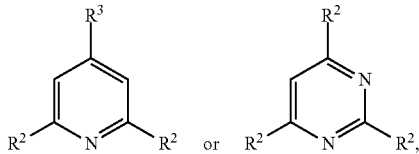

wherein:
each $R^2$ is independently substituted or unsubstituted, $C_{3-6}$ alkyl or —Si(substituted or unsubstituted alkyl)₃; and
each $R^3$ is independently hydrogen, substituted or unsubstituted alkyl, substituted or unsubstituted aryl, or halogen.

In certain embodiments, the base is an organic base, e.g., 2,4,6-tri-tert-butylpyrimidine or 2,6-di-tert-butyl-4-methylpyridine.

In certain embodiments, the base is an inorganic base, e.g., $Ag_2CO_3$, $Ag_3PO_4$, or $Ag_2O$.

In certain embodiments, the solvent is an organic solvent, e.g., 1,2-dichloroethane, dichloromethane, nitroethane, nitromethane, hexane, heptane, pentane, or α,α,α-trifluorotoluene.

In certain embodiments, the step of reacting further comprises an inert atmosphere (e.g., substantially nitrogen or substantially argon).

In certain embodiments, "substantially" refers to between 90% and 95%, between 95% and 98%, between 98% and 99%, between 99% and 99.9%, or between 99.9% and 99.99%, inclusive.

In certain embodiments, the step of reacting is substantially free of dioxygen.

In certain embodiments, the step of reacting is substantially free of water (including heavy water).

In certain embodiments, the step of reacting further comprises a temperature, and the temperature is between 10 and 40° C., inclusive. In certain embodiments, the temperature is between −20 and 0, between 0 and 20, between 20 and 25, between 25 and 36, between 36 and 38, between 38 and 50, or between 50 and 70° C., inclusive.

In certain embodiments, the step of reacting further comprises a pressure, and the pressure is between 0.5 and 1.5 atm, inclusive. In certain embodiments, the pressure is between 0.1 and 0.5, between 1.5 and 3, between 3 and 10 atm, inclusive.

In certain embodiments, the step of reacting further comprises a time duration, and the time duration is between 1 and 96 hours, inclusive. In certain embodiments, the time duration is between 10 and 60 minutes, between 1 and 8 hours, between 8 and 24 hours, between 1 and 3 days, or between 3 and 7 days, inclusive.

The present disclosure also provides processes of preparing the compounds described herein.

The present disclosure also provides compositions (e.g., pharmaceutical compositions) comprising a compound of the disclosure (e.g., a compound of Formula (I), or pharmaceutically acceptable salts thereof), and optionally an excipient (e.g., pharmaceutically acceptable excipient).

The present disclosure also provides compositions (e.g., pharmaceutical compositions) comprising a compound of the disclosure (e.g., a compound of Formula (I), or pharmaceutically acceptable salts thereof), and optionally an excipient (e.g., pharmaceutically acceptable excipient).

In certain embodiments, a composition of the disclosure is useful for disinfecting a surface. In certain embodiments, the compound of the disclosure is provided in an effective amount in the composition. In certain embodiments, the amount of the compound included in the composition is effective for killing at least 80%, at least 90%, at least 95%, at least 99%, at least 99.9%, or at least 99.99% of the microorganisms on the surface. In certain embodiments, the amount of the compound included in the composition is effective for killing at most 90%, at most 95%, at most 99%, at most 99.9%, at most 99.99%, or at most 99.999% of the microorganisms on the surface. A composition of the disclosure may include one or more excipients (e.g., water, detergent, bleach, surfactant) (e.g., pharmaceutically acceptable excipients).

In certain embodiments, a composition of the disclosure is a pharmaceutical composition comprising a compound of the disclosure and optionally a pharmaceutically acceptable excipient. In certain embodiments, the compound of the disclosure is provided in an effective amount in the pharmaceutical composition. In certain embodiments, the effective amount of the compound is a therapeutically effective amount. In certain embodiments, the effective amount of the compound is a prophylactically effective amount. The pharmaceutical compositions of the disclosure may be useful in the described methods. In certain embodiments, the pharmaceutical compositions are useful in treating a microbial infection (e.g., a bacterial infection). In certain embodiments, the pharmaceutical compositions are useful in preventing a microbial infection (e.g., a bacterial infection). In certain embodiments, the pharmaceutical compositions are useful in inhibiting the growth of a microorganism (e.g., a microorganism described herein). In certain embodiments, the pharmaceutical compositions are useful in inhibiting the reproduction of a microorganism. In certain embodiments, the pharmaceutical compositions are useful in killing a microorganism. In certain embodiments, the pharmaceutical compositions are useful in inhibiting the formation and/or growth of a biofilm. In certain embodiments, the pharmaceutical compositions are useful in reducing or removing a biofilm. In certain embodiments, the pharmaceutical compositions are useful in disinfecting a surface. In certain embodiments, the pharmaceutical compositions are useful in cleaning a surface.

Pharmaceutical compositions described herein can be prepared by any method known in the art of pharmacology. In general, such preparatory methods include the steps of bringing the compound of the disclosure (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™) polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the disclosure are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a microbial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this disclosure with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this disclosure may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the disclosure can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the disclosure formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the disclosure. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the disclosure can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the disclosure can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present disclosure will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is about 70 kg.

It will be also appreciated that a compound or composition, as described herein, can be administered in combination with one or more additional pharmaceutical agents. In certain embodiments, the additional pharmaceutical agent is different from a compound of the disclosure, or a pharmaceutically acceptable salt, solvate, hydrate, polymorph, co-crystal, tautomer, stereoisomer, isotopically labeled derivative, or prodrug thereof. The compounds or compositions can be administered in combination with additional pharmaceutical agents to improve their potency, efficacy, and/or bioavailability, reduce and/or modify their metabolism, inhibit their excretion, and/or modify their distribution within the body. It will also be appreciated that the therapy employed may achieve a desired effect for the same disorder, and/or it may achieve different effects. In certain embodiments, the combination of a compound of the disclosure and an additional pharmaceutical agent shows a synergistic effect.

The compound or composition can be administered concurrently with, prior to, or subsequent to, one or more additional pharmaceutical agents, which are different from the compound or composition and may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the described compound with the additional pharmaceutical agents and/or the desired therapeutic and/or prophylactic effect to be achieved. In general, it is expected that the additional pharmaceutical agents in combination be utilized at levels that do not exceed the levels at which they are utilized individually. In some embodiments, the levels utilized in combination will be lower than those utilized individually.

Exemplary additional pharmaceutical agents include, but are not limited to, antibiotics (e.g., antibacterial agents, antiviral agents, anti-fungal agents), anti-inflammatory agents, anti-pyretic agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is an antibiotic. In certain embodiments, the additional pharmaceutical agent is an antibiotic effective against a microorganism described herein. In certain embodiments, the additional pharmaceutical agent is an antibiotic effective against a bacterium. In certain embodiments, the additional pharmaceutical agent is an antibiotic effective against a Gram-positive bacterium (e.g., a *Staphylococcus* species or *Enterococcus* species). In certain embodiments, the additional pharmaceutical agent is an antibiotic effective against a Gram-negative bacterium (e.g., an *Acinetobacter* species). In certain embodiments, the additional pharmaceutical agent is an antibiotic effective against a multidrug-resistant bacterium. In certain embodiments, the additional pharmaceutical agent is a β-lactam antibiotic. In certain embodiments, the additional pharmaceutical agent is a penicillin (i.e., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g., pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin), a penem (e.g., faropenem), a carbapenem (e.g., biapenem, ertapenem, an antipseudomonal (e.g., doripenem, imipenem, meropenem), panipenem), a cephalosporin (i.e., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin), a monobactam (e.g., aztreonam, tigemonam, carumonam, nocardicin A), an aminoglycoside (e.g., amikacin, gentamicin, kanamycin, neomycin, netilmicin, tobramycin, paromomycin, spectinomycin), an ansamycin (e.g., geldanamycin, herbimycin, rifaximin), a glycopeptide (e.g., teicoplanin, vancomycin, telavancin), a lincosamide (e.g., clindamycin, lincomycin), a lipopeptide (e.g., daptomycin), a macrolide (e.g., azithromycin, clarithromycin, dirithromycin, erythromycin, roxithromycin, troleandomycin, telithromycin, spiramycin), a nitrofuran (e.g., furazolidone, nitrofurantoin), an oxazolidonone (e.g., linezolid, posizolid, radezolid, torezolid), a polypeptide (e.g., bacitracin, colistin, polymyxin B), a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine), a tetracycline (e.g., demeclocycline, doxycycline, minocycline, oxytetracycline, tetracycline), clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the additional pharmaceutical agent is an antiviral agent. In certain embodiments, the additional pharmaceutical agent is (−)-Oseltamivir, β-D-ribofuranose, 1-acetate 2,3,5-tribenzoate, 1-Docosanol, 2-Amino-6-chloropurine, 5-Iodo-2'-deoxyuridine, 6-Chloropurine, Abacavir sulfate, Abacavir-epivir mixt., Acyclovir, Acyclovir sodium, Adefovir dipivoxil, Amantadine (e.g., Amantadine hydrochloride), Amantadine hydrochloride, anti-HIV agent (e.g., Abacavir, Amprenavir, Atazanavir, Azidothymidine, Bryostatin (e.g., Bryostatin 1, Bryostatin 10, Bryostatin 11, Bryostatin 12, Bryostatin 13, Bryostatin 14, Bryostatin 15, Bryostatin 16, Bryostatin 17, Bryostatin 18, Bryostatin 19, Bryostatin 2, Bryostatin 20, Bryostatin 3, Bryostatin 4, Bryostatin 5, Bryostatin 6, Bryostatin 7, Bryostatin 8, Bryostatin 9), Dideoxycytidine, Dideoxyinosine, Efavirenz, Indinavir, Lamivudine, Lopinavir, Nevirapine, Ritonavir, Saquinavir, Stavudine, Tenofovir), Azauridine, ombivir, Deoxynojirimycin, Docosanol, Fomivirsen sodium, Foscarnet, Ganciclovir, Integrase inhibitors (e.g., 5CITEP, Chloropeptin I, Complestatin, Dolutegravir, Elvitegravir, L 708906, L 731988, MK 2048, Raltegravir, Raltegravir potassium), MK 5172, MK 8742, Palivizumab, Pegylated interferon alfa-2b, Phosphonoacetic acid, Ribavirin, Simeprevir, Sofosbuvir, Tubercidin, Vidarabine, or virus entry inhibitor (e.g., Enfuvirtide, Maraviroc). In certain embodiments, the additional pharmaceutical agent is a fungicide. In certain embodiments, the additional pharmaceutical agent is (−)-Fumagillin, (−)-Metalaxyl, 1,2,5-Fluorocytosine, Acrisorcin, Anilazine, Antifouling agent, Azoxystrobin, Benomyl, Bordeaux mixture, Captan, Carbendazim, Caspofungin acetate, Chlorothalonil, Clotrimazole, Dichlofluanid, Dinocap, Dodine, Fenhexamid, Fenpropimorph, Ferbam, Fluconazole, Fosetyl A1, Griseofulvin, Guanidine (e.g., Agmatine, Amiloride hydrochloride, Biguanide (e.g., Imidodicarbonimidic diamide, N,N-dimethyl-,hydrochloride (1:1) (e.g., Metformin hydrochloride), Metformin), Cimetidine, Guanethidine, Guanfacine, Guanidine, Guanidinium, Methylguanidine, Sulfaguanidine), Iprobenfos, Iprodione, Isoprothiolane, Itraconazole, Ketoconazole, Mancozeb, Metalaxyl, Metiram, Miconazole, Natamycin, Nystatin, Oxycarboxine, Pentachloronitrobenzene, Prochloraz, Procymidone, Propiconazole, Pyrazophos, Reduced viscotoxin A3, Salicylanilide, Tebuconazole, Terbinafine, Thiabendazole, Thiophanate, Thiophanate methyl, Triadimefon, Vinclozolin, or Voriconazole. In certain embodiments, the additional pharmaceutical agent is a protozoacide. In certain embodiments, the additional pharmaceutical agent is Amebicide, Antimalarial (e.g., Artemisinin, Chloroquine (e.g., Chloroquine phosphate), Mefloquine, Sulfadoxine), Coccidiostat, Leishmanicide, Trichomonacide, or Trypanosomicide (e.g., Eflornithine). In certain embodiments, the additional pharmaceutical agent is a parasiticide. In certain embodiments, the additional pharmaceutical agent is antihelmintic (e.g., Abamectin, Dimethylformocarbothialdine, Niclosamide, Schistosomicide), protozoacide (e.g., Amebicide, antimalarial (e.g., Artemisinin, chloroquine (e.g., chloroquine phosphate), Mefloquine, Sulfadoxine), coccidiostat, leishmanicide, trichomonacide, or trypanosomicide (e.g., Eflornithine)). In certain embodiments, the additional pharmaceutical agent is an iron chelator (e.g., iorn(II) chelator, iron(III) chelator). In certain embodiments, the additional pharmaceutical agent is 2,2'-bipyridyl, deferoxamine, deferiprone, or deferasirox. In certain embodiments, the additional pharmaceutical agent is a combination of two or more additional pharmaceutical agents described herein (e.g., a combination of an antibiotic and an iron chelator). In certain embodiments, the additional pharmaceutical agent is commercially available.

Also encompassed by the disclosure are kits (e.g., pharmaceutical packs). The kits provided may comprise a compound or composition (e.g., pharmaceutical composition) of the disclosure and a container (e.g., a vial, ampule, bottle, syringe, dispenser package, tube, inhaler, and/or other suitable container). In some embodiments, a kit of the disclosure further includes a second container comprising an excipient (e.g., pharmaceutically acceptable excipient) for dilution or suspension of an described compound or composition. In some embodiments, the compound or composition of the disclosure provided in a first container and a second container are combined to form one unit dosage form.

In one aspect, the present disclosure provides kits including a first container comprising a compound or composition of the disclosure. In certain embodiments, a kit of the disclosure includes a first container comprising a compound of Formula (I), or a pharmaceutically acceptable salt thereof, or a composition thereof. In certain embodiments, a kit of the disclosure includes a first container comprising a compound of Formula (I), or a pharmaceutically acceptable salt thereof, or a composition thereof.

In certain embodiments, the kits are useful in treating a microbial infection in a subject in need thereof. In certain embodiments, the kits are useful in preventing a microbial infection in a subject in need thereof. In certain embodiments, the microbial infection is a bacterial infection. In certain embodiments, the bacterial infection is an infection caused by a Gram-positive bacterium. In certain embodiments, the bacterial infection is an infection caused by a Gram-negative bacterium. In certain embodiments, the kits are useful in inhibiting the growth of a microorganism. In certain embodiments, the kits are useful in inhibiting the reproduction of a microorganism. In certain embodiments, the kits are useful in killing a microorganism. In certain embodiments, the kits are useful in inhibiting the formation and/or growth of a biofilm. In certain embodiments, the kits are useful in reducing or removing a biofilm. In certain embodiments, the kits are useful in disinfecting a surface. In certain embodiments, the kits are useful for screening a library of compounds to identify a compound that is useful in the methods of the disclosure. In certain embodiments, the kit further includes instructions for using the compound or pharmaceutical composition included in the kit (e.g., for administering to a subject in need of treatment of a microbial infection a compound or pharmaceutical composition of the disclosure, for contacting a microorganism with a compound or pharmaceutical composition of the disclosure, or for contacting a biofilm with a compound or pharmaceutical composition of the disclosure). The kits may also include information as required by a regulatory agency such as the U.S. Food and Drug Administration (FDA). In certain embodiments, the information included in the kits is prescribing information. In certain embodiments, the kits and instructions provide for treating a microbial infection in a subject in need thereof. In certain embodiments, the kits and instructions provide for preventing a microbial infection in a subject in need thereof. In certain embodiments, the kits and instructions provide for inhibiting the growth of a microorganism. In certain embodiments, the kits and instructions provide for inhibiting the reproduction of a microorganism. In certain embodiments, the kits and instructions provide for killing a microorganism. In certain embodiments, the kits and instructions provide for inhibiting the formation and/or growth of a biofilm. In certain embodiments, the kits and instructions provide for reducing or removing a biofilm. In certain embodiments, the kits and instructions provide for disinfecting a surface. In certain embodiments, the kits and instructions provide for screening a library of compounds to identify a compound that is useful in the methods of the disclosure. The kit of the disclosure may include one or more additional agents described herein (e.g., additional pharmaceutical agents) as a separate composition.

The present disclosure also provides methods for treating a microbial infection (e.g., bacterial infection) in a subject in need thereof. In certain embodiments, the microbial infection is treated by the described methods. In certain embodiments, the present disclosure further provides methods for preventing a microbial infection (e.g., bacterial infection) in a subject in need thereof. In certain embodiments, the microbial infection is prevented by the described methods.

In certain embodiments, the subject described herein is an animal. In certain embodiments, the subject is a non-human animal. In certain embodiments, the subject is a mammal. In certain embodiments, the subject is a human. In certain embodiments, the subject is a human with cystic fibrosis. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate. In certain embodiments, the subject is a non-human transgenic animal, such as a transgenic mouse or transgenic pig.

In certain embodiments, the methods of the disclosure include administering to a subject in need thereof an effective amount of a compound or pharmaceutical composition of the disclosure. In certain embodiments, the methods of the disclosure include administering to a subject in need thereof an effective amount of a compound of Formula (I), or a pharmaceutically acceptable salt thereof, or a pharmaceutical composition thereof. In certain embodiments, the methods of the disclosure include administering to a subject in need thereof an effective amount of a compound of Formula (I), or a pharmaceutically acceptable salt thereof, or a pharmaceutical composition thereof. In certain embodiments, the methods of the disclosure include administering to a subject in need thereof a therapeutically effective amount of a compound of the disclosure, or a pharmaceutical composition thereof. In certain embodiments, the methods of the disclosure include administering to a subject in need thereof a prophylactically effective amount of a compound of the disclosure, or a pharmaceutical composition thereof.

In certain embodiments, the microbial infection that is treated and/or prevented by the described methods or using the described compounds or pharmaceutical compositions thereof is caused by a multidrug-resistant microorganism and/or a microorganism resistant to methicillin, penicillin, ciprofloxacin, rifampin, vancomycin, daptomycin, linezolid, an antibiotic described herein, or a combination thereof. In certain embodiments, the microbial infection is a microbial respiratory tract infection. In certain embodiments, the microbial infection is microbial pneumonia. In certain embodiments, the microbial infection is microbial sinusitis. In certain embodiments, the microbial infection is tuberculosis (TB). In certain embodiments, the microbial infection is microbial Crohn's disease, paratuberculosis, Buruli ulcer, leprosy, or aquarium granuloma. In certain embodiments, the microbial infection is a microbial gastrointestinal tract infection. In certain embodiments, the microbial infection is microbial diarrhea. In certain embodiments, the microbial infection is a microbial urogenital tract infection. In certain embodiments, the microbial infection is a microbial bloodstream infection. In certain embodiments, the microbial infection is microbial hemolytic uremic syndrome. In certain embodiments, the microbial infection is microbial endocarditis. In certain embodiments, the microbial infection is a microbial ear infection. In certain embodiments, the microbial infection is a microbial skin infection (e.g., microbial acne vulgaris). In certain embodiments, the microbial infection is a microbial oral infection. In certain embodiments, the microbial infection is a microbial dental infection. In certain embodiments, the microbial infection is gingivitis. In certain embodiments, the microbial infection is dental plaque caused by a microorganism. In certain embodiments, the microbial infection is microbial meningitis. In certain embodiments, the microbial infection is a microbial wound or surgical site infection. In certain embodiments, the microbial infection is a microbial burn wound infection. In certain embodiments, the microbial infection is a microbial infection associated with cystic fibrosis. In certain embodiments, the microbial infection is a microbial infection associated with an implanted device. In certain embodiments, the microbial infection is a microbial infection associated with a dental implant. In certain embodiments, the microbial infection is a microbial infection associated with a catheter. In certain embodiments, the microbial infection is a microbial infection associated with a heart valve. In certain embodiments, the microbial infection is a microbial infection associated with an intrauterine device. In certain embodiments, the microbial infection is a microbial infection associated with a joint prosthesis. In certain embodiments, the microbial infection is a bacterial infection. In certain embodiments, the bacterial infection is caused by a Gram-positive bacterium (e.g., a Gram-positive bacterium described herein). In certain embodiments, the bacterial infection is caused by a Gram-negative bacterium (e.g., a Gram-negative bacterium described herein). In certain embodiments, the bacterial infection is caused by a multidrug-resistant bacterium. In certain embodiments, the bacterial infection is caused by a strain of *Staphylococcus aureus*. In certain embodiments, the bacterial infection is a methicillin-resistant *Staphylococcus aureus* (MRSA)-related infection. In certain embodiments, the bacterial infection is caused by a strain of *Staphylococcus epidermidis*. In certain embodiments, the bacterial infection is caused by a strain of *Enterococcus faecium*. In certain embodiments, the bacterial infection is caused by *Acinetobacter baumannii*. In certain embodiments, the microbial infection is caused by a mycobacterium (e.g., a strain of *Mycobacterium tuberculosis*). In certain embodiments, the microbial infection is caused by an archaeon. In certain embodiments, the microbial infection is caused by a protist. In certain embodiments, the microbial infection is caused by a protozoon. In certain embodiments, the microbial infection is caused by an alga. In certain embodiments, the microbial infection is caused by a fungus. In certain embodiments, the microbial infection is caused by yeast. In certain embodiments, the microbial infection is caused by a mold. In certain embodiments, the microbial infection is caused by a parasite. In certain embodiments, the microbial infection is a microbial infection associated with a biofilm.

Another aspect of the present disclosure relates to methods of inhibiting the growth of a microorganism using a compound of the disclosure, or a pharmaceutical composition thereof. In certain embodiments, an described method selectively inhibits the growth of a first microorganism (e.g., a microorganism described herein), compared to the inhibition of the growth of a host cell or a second microorganism. In certain embodiments, the growth of a microorganism is inhibited by the described methods. In certain embodiments, the growth of a first microorganism is selectively inhibited by the described methods, compared to the inhibition of the growth of a host cell or a second microorganism.

Another aspect of the present disclosure relates to methods of inhibiting the reproduction of a microorganism using a compound of the disclosure, or a pharmaceutical composition thereof. In certain embodiments, an described method selectively inhibits the reproduction of a first microorganism (e.g., a microorganism described herein), compared to the inhibition of the reproduction of a host cell or a second microorganism. In certain embodiments, the reproduction of a microorganism is inhibited by the described methods. In certain embodiments, the reproduction of a first microorganism is selectively inhibited by the described methods, compared to the inhibition of the reproduction of a host cell or a second microorganism.

Another aspect of the present disclosure relates to methods of inhibiting the viability of a microorganism using a compound of the disclosure, or a pharmaceutical composition thereof. In certain embodiments, an described method selectively inhibits the viability of a first microorganism (e.g., a microorganism described herein), compared to the inhibition of the viability of a host cell or a second microorganism. In certain embodiments, the viability of a microorganism is inhibited by the described methods. In certain embodiments, the viability of a first microorganism is selectively inhibited by the described methods, compared to the inhibition of the viability of a host cell or a second microorganism.

Another aspect of the present disclosure relates to methods of killing a microorganism using a compound of the disclosure, or a pharmaceutical composition thereof. In certain embodiments, an described method selectively kills a first microorganism (e.g., a microorganism described herein), compared to the killing of a host cell or a second microorganism. In certain embodiments, a microorganism is killed by the described methods. In certain embodiments, a first microorganism is selectively killed by the described methods, compared to the killing of a host cell or a second microorganism.

In certain embodiments, the methods of the disclosure include contacting a microorganism with an effective amount of a compound or pharmaceutical composition of the disclosure. In certain embodiments, the methods of the disclosure include contacting a microorganism with an effective amount of a compound of Formula (I), or a pharmaceutically acceptable salt thereof, or a pharmaceutical composition thereof. In certain embodiments, the methods of the disclosure include contacting a microorganism with an effective amount of a compound of Formula (I), or a pharmaceutically acceptable salt thereof, or a pharmaceutical composition thereof. In certain embodiments, the methods of the disclosure include contacting a microorganism with a therapeutically effective amount of a compound of the disclosure, or a pharmaceutical composition thereof. In certain embodiments, the methods of the disclosure include contacting a microorganism with a prophylactically effective amount of a compound of the disclosure, or a pharmaceutical composition thereof.

In a growth process of a microorganism (e.g., a bacterium), the microorganism may secrete viscous substances to form a biofilm. A biofilm is typically formed on a living or non-living, solid or liquid surface. In certain embodiments, a biofilm is formed on the surface of a biological sample (e.g., a tooth, oral soft tissue, middle ear, gastrointestinal tract, urogenital tract, respiratory tract, or eye). In certain embodiments, a biofilm is formed on the surface of an implanted device (e.g., a dental implant, catheter, heart valve, intrauterine device, or joint prosthesis). In certain embodiments, the biofilm is in vitro. In certain embodiments, the biofilm is in vivo. In certain embodiments, the biofilm described herein comprises a microorganism. In certain embodiments, the biofilm comprises a microorganism (e.g., bacterium). In certain embodiments, the biofilm comprises a strain of *Staphylococcus aureus* (e.g., a methicillin-resistant strain of *Staphylococcus aureus*). In certain embodiments, the biofilm comprises a strain of *Staphylococcus epidermidis* (e.g., a methicillin-resistant strain of *Staphylococcus epidermidis*). In certain embodiments, the biofilm comprises a strain of *Enterococcus faecium* (e.g., a vancomycin-resistant strain of *Enterococcus faecium*). Free-floating microorganisms may accumulate on a surface, and the resulting biofilm may grow. In a biofilm, the concentration of microorganisms may be high and/or the resistance of the microorganisms in the biofilm to antimicrobial agents may be high. Antimicrobials may be inactivated or fail to penetrate into the biofilm. Therefore, microbial infections associated with a biofilm (e.g., microbial infections caused by a biofilm) are typically more difficult to treat than microbial infections not associated with a biofilm.

Another aspect of the present disclosure relates to methods of inhibiting the formation of a biofilm using a compound of the disclosure, or a pharmaceutical composition thereof. In certain embodiments, the formation of a biofilm is inhibited by the described methods.

Another aspect of the present disclosure relates to methods of inhibiting the growth of a biofilm using a compound of the disclosure, or a pharmaceutical composition thereof. In certain embodiments, the growth of a biofilm is inhibited by the described methods.

Another aspect of the present disclosure relates to methods of reducing a biofilm using a compound of the disclosure, or a pharmaceutical composition thereof. In certain embodiments, a biofilm is reduced by the described methods, e.g., reduced by at least 10%, at least 20%, at least 30%, at least 50%, at least 70%, at least 90%, at least 99%, at least 99.9%, or at least 99.99%, in terms of the volume of the biofilm. In certain embodiments, a biofilm is reduced by the described methods by not more than 10%, not more than 20%, not more than 30%, not more than 50%, not more than 70%, not more than 90%, not more than 99%, not more than 99.9%, or not more than 99.99%, in terms of the volume of the biofilm. In certain embodiments, a biofilm is reduced by the described methods by at least 10%, at least 20%, at least 30%, at least 50%, at least 70%, at least 90%, at least 99%, at least 99.9%, or at least 99.99%, in terms of the number of microorganisms (e.g., bacteria) in the biofilm. In certain embodiments, a biofilm is reduced by the described methods by not more than 10%, not more than 20%, not more than 30%, not more than 50%, not more than 70%, not more than 90%, not more than 99%, not more than 99.9%, or not more than 99.99%, in terms of the number of microorganisms (e.g., bacteria) in the biofilm.

Another aspect of the present disclosure relates to methods of removing a biofilm (e.g., eradicating a biofilm (e.g., reducing the volume of the biofilm by at least 99% and/or killing essentially all (e.g., at least 99%) of the microorganisms (e.g., bacteria) in the biofilm)) using a compound of the disclosure, or a pharmaceutical composition thereof. In certain embodiments, a biofilm is removed by the described methods. In certain embodiments, a biofilm reduced or removed by a method of the disclosure does not regrow one day, two days, four days, one week, two weeks, three weeks, or one month subsequent to the biofilm being subject to the method.

In certain embodiments, the methods of the disclosure include contacting a biofilm with an effective amount of a compound or pharmaceutical composition of the disclosure. In certain embodiments, the methods of the disclosure include contacting a biofilm with an effective amount of a compound of Formula (I), or a pharmaceutically acceptable salt thereof, or a pharmaceutical composition thereof. In certain embodiments, the methods of the disclosure include contacting a biofilm with an effective amount of a compound of Formula (I), or a pharmaceutically acceptable salt thereof, or a pharmaceutical composition thereof. In certain embodiments, the methods of the disclosure include contacting a biofilm with a therapeutically effective amount of a compound of the disclosure, or a pharmaceutical composition thereof. In certain embodiments, the methods of the disclosure include contacting a biofilm with a prophylactically effective amount of a compound of the disclosure, or a pharmaceutical composition thereof.

Another aspect of the present disclosure relates to methods of disinfecting a surface, the methods including contacting the surface with an effective amount of a compound or composition (e.g., pharmaceutical composition) of the disclosure. In certain embodiments, the number of viable microorganisms on the surface is reduced after the surface is contacted with the compound or composition. In certain embodiments, the surface is a biological surface, such as skin (e.g., skin of: the hands, feet, arms, legs, face, neck, torso, or cavity (e.g., oral cavity)) of a subject. In certain embodiments, the surface is a non-biological surface (e.g., a surface in a household, industrial, or medical setting, such as a surface of: a kitchen, bathroom, table top, floor, wall, window, utensil, cutlery, crockery, or medical device). A non-biological surface may be a surface of a solid material, such as plastic, wood, bamboo, metal, ceramic, glass, concrete, stone, paper, fabric, or a combination thereof. A non-biological surface may be painted or non-painted, or coated or non-coated. In certain embodiments, the amount of the compound or composition is effective for killing at least 80%, at least 90%, at least 95%, at least 99%, at least 99.9%, or at least 99.99% of the microorganisms on the surface.

In certain embodiments, the microorganism described herein is a bacterium. In certain embodiments, the microorganism is multidrug-resistant. In certain embodiments, the microorganism is resistant to methicillin, penicillin, ciprofloxacin, rifampin, vancomycin, daptomycin, linezolid, or a combination thereof. In certain embodiments, the microorganism is associated with a biofilm (e.g., present in and/or on a biofilm, able to form a biofilm, and/or able to increase the size of a biofilm). In certain embodiments, the bacterium is a Gram-positive bacterium. In certain embodiments, the bacterium is a multidrug-resistant bacterium. In certain embodiments, the bacterium is a *Staphylococcus* species. In certain embodiments, the bacterium is a *Staphylococcus aureus* (*S. aureus*) strain (e.g., ATCC 25923). In certain embodiments, the bacterium is methicillin-resistant *Staphylococcus aureus* (MRSA). In certain embodiments, the bacterium is the methicillin-resistant *Staphylococcus aureus* clinical isolate (MRSA-2, a clinical isolate from a patient treated at Shands Hospital; obtained from the Emerging Pathogens Institute at the University of Florida), such as the methicillin-resistant *Staphylococcus aureus* clinical isolate reported in Abouelhassan et al., *Bioorg. Med. Chem. Lett.*, 2014, 24, 5076. In certain embodiments, the bacterium is a *Staphylococcus epidermidis* (*S. epidermidis*) strain (e.g., ATCC 12228 or ATCC 35984). In certain embodiments, the bacterium is a *Staphylococcus auricularis, Staphylococcus carnosus, Staphylococcus condimenti, Staphylococcus massiliensis, Staphylococcus piscifermentans, Staphylococcus simulans, Staphylococcus capitis, Staphylococcus caprae, Staphylococcus saccharolyticus, Staphylococcus devriesei, Staphylococcus haemolyticus, Staphylococcus hominis, Staphylococcus chromogenes, Staphylococcus felis, Staphylococcus delphini, Staphylococcus hyicus, Staphylococcus intermedius, Staphylococcus lutrae, Staphylococcus microti, Staphylococcus muscae, Staphylococcus pseudintermedius, Staphylococcus rostri, Staphylococcus schleiferi, Staphylococcus lugdunensis, Staphylococcus arlettae, Staphylococcus cohnii, Staphylococcus equorum, Staphylococcus gallinarum, Staphylococcus kloosii, Staphylococcus leei, Staphylococcus nepalensis, Staphylococcus saprophyticus, Staphylococcus succinus, Staphylococcus xylosus, Staphylococcus fleurettii, Staphylococcus lentus, Staphylococcus sciuri, Staphylococcus stepanovicii, Staphylococcus vitulinus, Staphylococcus simulans, Staphylococcus pasteuri*, or *Staphylococcus warneri* strain. In certain embodiments, the bacterium is a *Streptococcus* species. In certain embodiments, the bacterium is a *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans*, or *Streptococcus zooepidemicus* strain. In certain embodiments, the bacterium is an *Enterococcus* species. In certain embodiments, the bacterium is an *Enterococcus avium, Enterococcus durans, Enterococcus faecalis, Enterococcus faecium, Enterococcus gallinarum, Enterococcus hirae*, or *Enterococcus solitarius* strain. In certain embodiments, the bacterium is an *Enterococcus faecium* strain (e.g., a vancomycin-resistant strain of *Enterococcus faecium* (VRE); ATCC 700221). In certain embodiments, the bacterium is a *Listeria* species. In certain embodiments, the bacterium is a *Listeria fleischmannii, Listeria grayi, Listeria innocua, Listeria ivanovii, Listeria marthii, Listeria monocytogenes, Listeria rocourtiae, Listeria seeligeri, Listeria weihenstephanensis*, or *Listeria welshimeri* strain. In certain embodiments, the bacterium is a *Clostridium* species. In certain embodiments, the bacterium is a *Clostridium acetobutylicum, Clostridium argentinense, Clostridium aerotolerans, Clostridium baratii, Clostridium beijerinckii, Clostridium bifermentans, Clostridium botulinum, Clostridium butyricum, Clostridium cadaveris, Clostridium cellulolyticum, Clostridium chauvoei, Clostridium clostridioforme, Clostridium colicanis, Clostridium difficile, Clostridium estertheticum, Clostridium fallax, Clostridium feseri, Clostridium formicaceticum,*

*Clostridium histolyticum, Clostridium innocuum, Clostridium kluyveri, Clostridium ljungdahlii, Clostridium lavalense, Clostridium leptum, Clostridium novyi, Clostridium oedematiens, Clostridium paraputrificum, Clostridium perfringens* (Alias:, *Clostridium welchii*), *Clostridium phytofermentans, Clostridium pilforme, Clostridium ragsdalei, Clostridium ramosum, Clostridium scatologenes, Clostridium septicum, Clostridium sordellii, Clostridium sporogenes, Clostridium sticklandii, Clostridium tertium, Clostridium tetani, Clostridium thermocellum, Clostridium thermosaccharolyticum,* or *Clostridium tyrobutyricum* strain. In certain embodiments, the microbial infection is caused by *Bacillus, Staphylococcus,* or *Enterococcus*. In certain embodiments, the microbial infection is caused by *Bacillus subtilis*, methicillin-resistant *Staphylococcus aureus*, methicillin-sensitive *Staphylococcus aureus*, vancomycin-resistant *Enterococcusfaecalis*, or vancomycin-sensitive *Enterococcus faecalis*.

In certain embodiments, the bacterium is a Gram-negative bacterium. In certain embodiments, the Gram-negative bacterium is an *Escherichia* species. In certain embodiments, the Gram-negative bacterium is an *Escherichia coli* (*E. coli*) strain (e.g., ATCC 33475, K-12, CFT073, ATCC 43895). In certain embodiments, the Gram-negative bacterium is an *Escherichia albertii* strain, *Escherichia blattae* strain, *Escherichia fergusonii* strain, *Escherichia hermannii* strain, or *Escherichia vulneris* strain. In certain embodiments, the Gram-negative bacterium is a *Pseudomonas* species. In certain embodiments, the Gram-negative bacterium is a *Pseudomonas aeruginosa* strain. In certain embodiments, the Gram-negative bacterium is a *Pseudomonas alcaligenes* strain, *Pseudomonas anguilliseptica* strain, *Pseudomonas argentinensis* strain, *Pseudomonas borbori* strain, *Pseudomonas citronellolis* strain, *Pseudomonas flavescens* strain, *Pseudomonas mendocina* strain, *Pseudomonas nitroreducens* strain, *Pseudomonas oleovorans* strain, *Pseudomonas pseudoalcaligenes* strain, *Pseudomonas resinovorans* strain, *Pseudomonas straminea* strain, *Pseudomonas chlororaphis* strain, *Pseudomonas fluorescens* strain, *Pseudomonas pertucinogena* strain, *Pseudomonas putida* strain, *Pseudomonas stutzeri* strain, or *Pseudomonas syringae* strain. In certain embodiments, the Gram-negative bacterium is a *Klebsiella* species. In certain embodiments, the Gram-negative bacterium is a *Klebsiella granulomatis* strain, *Klebsiella oxytoca* strain, *Klebsiella pneumoniae* strain, *Klebsiella terrigena* strain, or *Klebsiella planticola* strain. In certain embodiments, the Gram-negative bacterium is a *Salmonella* species. In certain embodiments, the Gram-negative bacterium is a *Salmonella bongori* strain or *Salmonella enterica* strain, e.g., *Salmonella typhi*. In certain embodiments, the Gram-negative bacterium is an *Acinetobacter* species. In certain embodiments, the Gram-negative bacterium is an *Acinetobacter baumannii* strain. In certain embodiments, the Gram-negative bacterium is an *Acinetobacter baylyi* strain, *Acinetobacter bouvetii* strain, *Acinetobacter calcoaceticus* strain, *Acinetobacter gerneri* strain, *Acinetobacter grimontii* strain, *Acinetobacter haemolyticus* strain, *Acinetobacter johnsonii* strain, *Acinetobacter junii* strain, *Acinetobacter lwoffii* strain, *Acinetobacter parvus* strain, *Acinetobacter pittii* strain, *Acinetobacter radioresistens* strain, *Acinetobacter schindleri* strain, *Acinetobacter tandoii* strain, *Acinetobacter tjernbergiae* strain, *Acinetobacter towneri* strain, *Acinetobacter ursingii* strain, or *Acinetobacter gyllenbergii* strain. In certain embodiments, the microorganism is a mycobacterium. In certain embodiments, the microorganism is a strain of *Mycobacterium tuberculosis*.

In certain embodiments, the microorganism is a strain of: *Mycobacterium bovis, Mycobacterium bovis* BCG, *Mycobacterium africanum, Mycobacterium canetti, Mycobacterium caprae, Mycobacterium microti, Mycobacterium Pinnipedii, Mycobacterium avium, Mycobacterium avium paratuberculosis, Mycobacterium avium silvaticum, Mycobacterium avium hominissuis, Mycobacterium colombiense, Mycobacterium indicus pranii, Mycobacterium gastri, Mycobacterium kansasii, Mycobacterium hiberniae, Mycobacterium nonchromogenicum, Mycobacterium terrae, Mycobacterium triviale, Mycobacterium ulcerans, Mycobacterium pseudoshottsii, Mycobacterium shottsii, Mycobacterium triplex, Mycobacterium genavense, Mycobacterium florentinum, Mycobacterium lentiflavum, Mycobacterium palustre, Mycobacterium kubicae, Mycobacterium parascrofulaceum, Mycobacterium heidelbergense, Mycobacterium interjectum, Mycobacterium simiae, Mycobacterium bohemicum, Mycobacterium botniense, Mycobacterium branderi, Mycobacterium celatum, Mycobacterium chimaera, Mycobacterium conspicuum, Mycobacterium cookii, Mycobacterium doricum, Mycobacterium farcinogenes, Mycobacterium haemophilum, Mycobacterium heckeshornense, Mycobacterium intracellulare, Mycobacterium lacus, Mycobacterium leprae, Mycobacterium lepraemurium, Mycobacterium lepromatosis, Mycobacterium malmoense, Mycobacterium marinum, Mycobacterium monacense, Mycobacterium montefiorense, Mycobacterium murale, Mycobacterium nebraskense, Mycobacterium saskatchewanense, Mycobacterium scrofulaceum, Mycobacterium shimoidei, Mycobacterium szulgai, Mycobacterium tusciae, Mycobacterium xenopi, Mycobacterium yongonense, Mycobacterium intermedium, Mycobacterium abscessus, Mycobacterium chelonae, Mycobacterium bolletii, Mycobacterium fortuitum, Mycobacterium fortuitum* subsp. *acetamidolyticum, Mycobacterium boenickei, Mycobacterium peregrinum, Mycobacterium porcinum, Mycobacterium senegalense, Mycobacterium septicum, Mycobacterium neworleansense, Mycobacterium houstonense, Mycobacterium mucogenicum, Mycobacterium mageritense, Mycobacterium brisbanense, Mycobacterium cosmeticum, Mycobacterium parafortuitum, Mycobacterium austroafricanum, Mycobacterium diernhoferi, Mycobacterium hodleri, Mycobacterium neoaurum, Mycobacterium frederiksbergense, Mycobacterium aurum, Mycobacterium vaccae, Mycobacterium chitae, Mycobacterium fallax, Mycobacterium confluentis, Mycobacterium flavescens, Mycobacterium madagascariense, Mycobacterium phlei, Mycobacterium smegmatis Mycobacterium goodii, Mycobacterium wolinskyi, Mycobacterium thermoresistibile, Mycobacterium gadium, Mycobacterium komossense, Mycobacterium obuense, Mycobacterium sphagni, Mycobacterium agri, Mycobacterium aichiense, Mycobacterium alvei, Mycobacterium arupense, Mycobacterium brumae, Mycobacterium canariasense, Mycobacterium chubuense, Mycobacterium conceptionense, Mycobacterium duvalii, Mycobacterium elephantis, Mycobacterium gilvum, Mycobacterium hassiacum, Mycobacterium holsaticum, Mycobacterium immunogenum, Mycobacterium massiliense, Mycobacterium moriokaense, Mycobacterium psychrotolerans, Mycobacterium pyrenivorans, Mycobacterium vanbaalenii, Mycobacterium pulveris, Mycobacterium arosiense, Mycobacterium aubagnense, Mycobacterium caprae, Mycobacterium chlorophenolicum, Mycobacterium fluoroanthenivorans, Mycobacterium kumamotonense, Mycobacterium novocastrense, Mycobacterium parmense,*

*Mycobacterium phocaicum, Mycobacterium poriferae, Mycobacterium rhodesiae, Mycobacterium seoulense*, or *Mycobacterium tokaiense*.

In certain embodiments, the microorganism described herein is an archaeon. In certain embodiments, the microorganism is a protist. In certain embodiments, the microorganism is a protozoon. In certain embodiments, the microorganism is an alga. In certain embodiments, the microorganism is a fungus. In certain embodiments, the microorganism is yeast. In certain embodiments, the microorganism is a mold. In certain embodiments, the microorganism is a parasite.

In certain embodiments, the microorganism described herein is in vitro. In certain embodiments, the microorganism is in vivo.

In certain embodiments, a method of the disclosure is an in vitro method. In certain embodiments, a method of the disclosure is an in vivo method.

In another aspect, the present disclosure provides uses of the compounds, compositions, and pharmaceutical compositions of the disclosure for manufacturing a medicament for treating a microbial infection (e.g., bacterial infection).

In another aspect, the present disclosure provides uses of the compounds, compositions, and pharmaceutical compositions of the disclosure for manufacturing a medicament for preventing a microbial infection (e.g., bacterial infection).

In another aspect, the present disclosure provides the compounds, compositions, and pharmaceutical compositions of the disclosure for use in treating a microbial infection (e.g., bacterial infection).

In another aspect, the present disclosure provides the compounds, compositions, and pharmaceutical compositions of the disclosure for use in preventing a microbial infection (e.g., bacterial infection).

EXAMPLES

Example 1

Herein we disclose a radical-based methodology for the synthesis of $C_{sp2}$-$C_{sp2}$-linked cyclotryptophan, cyclotryptamine, and indoline dimers, and its application to the total synthesis of (−)-himastatin (1). A suite of derivatives produced by combining our dimerization methodology with a modular approach to peptide synthesis allowed us to deduce structural features important to the bioactivity of (−)-himastatin (1). Furthermore, biological studies demonstrated that this unique antibiotic targets the membrane, and that its mirror image form evades the innate resistance of the producing organism.

Figure 2:
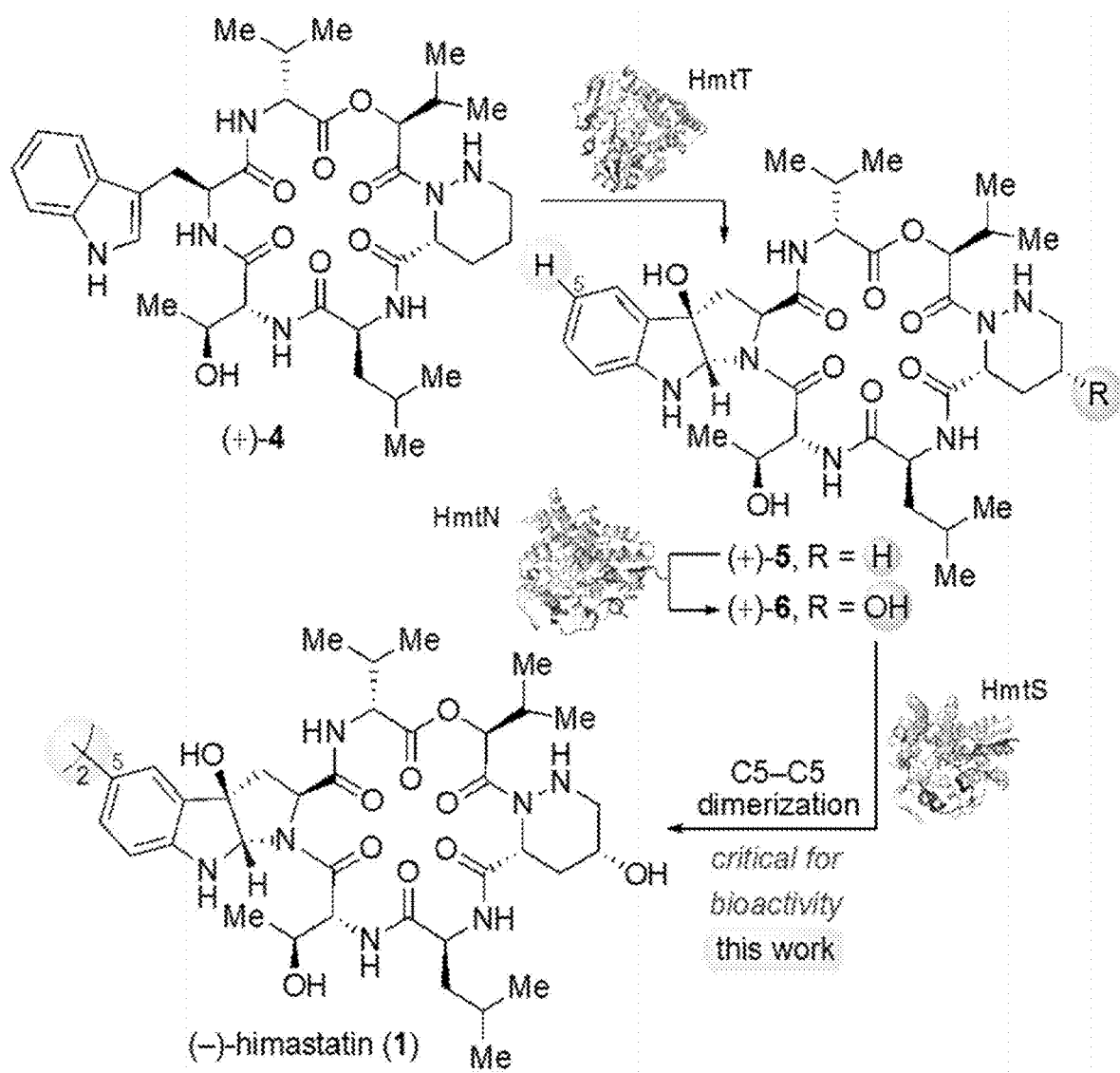
FIG. 2 shows the Oxidative Tailoring Steps in the Biogenesis of (−)-Himastatin (1)

A key challenge posed by the dimeric structure of (−)-himastatin (1), and the absence of an elegant means to address it, necessitated the development of new synthetic methodology. As part of our group's long-standing interest in natural product synthesis with an emphasis on complex fragment assembly, we have reported radical-based strategies for the formation of challenging C—C linkages. Specifically, our syntheses of cyclotryptamine,[xvii,xviii,xix] diketopiperazine,[xx] and epipolythiodiketopiperazine alkaloids[xxi,xxii] were predicated on Co(I)-mediated reductive radical homodimerization to secure $C_{sp3}$-$C_{sp3}$ linkages, and diazene-directed fragment assembly[xxiii] to secure $C_{sp3}$-$C_{sp3}$ and $C_{sp3}$-$C_{sp2}$ linkages between dissimilar fragments. Scheme 1 shows a concise approach to the central $C_{sp2}$-$C_{sp2}$ bond of (−)-himastatin (1). In particular, Ju and coworkers identified three sequential oxidative tailoring steps of cyclic peptide (+)-4, each catalyzed by cytochrome p450 enzymes, that culminate in oxidative dimerization of (+)-himastatin monomer (6) to afford dimeric (−)-himastatin (1).[xxiv] On the basis of computational and structural studies of related CYP450 enzymes,[xxv,xxvi] we hypothesized the key C5-C5' bond is formed by HmtS through radical-radical coupling (FIG. 2) of two activated monomers 6.

Our retrosynthetic analysis of (−)-himastatin (1) began with a $C_{sp2}$-$C_{sp2}$ radical-radical coupling of two cyclotryptophan radicals 7 generated by one-electron oxidation of (+)-himastatin monomer (6) (Scheme 2). With the goal of accessing derivatives in mind, and unconstrained by reliance on bidirectional elaboration, we considered that our synthesis of (+)-himastatin monomer (6) could take advantage of solid-phase peptide synthesis (SPPS) to aid its assembly. This would offer several practical advantages, such as fewer required purifications and a straightforward means of introducing single-residue substitutions. The required 3a-hydroxycyclotryptophan precursor 8 would then be accessed via oxidative cyclization of readily-available tryptophan 9.

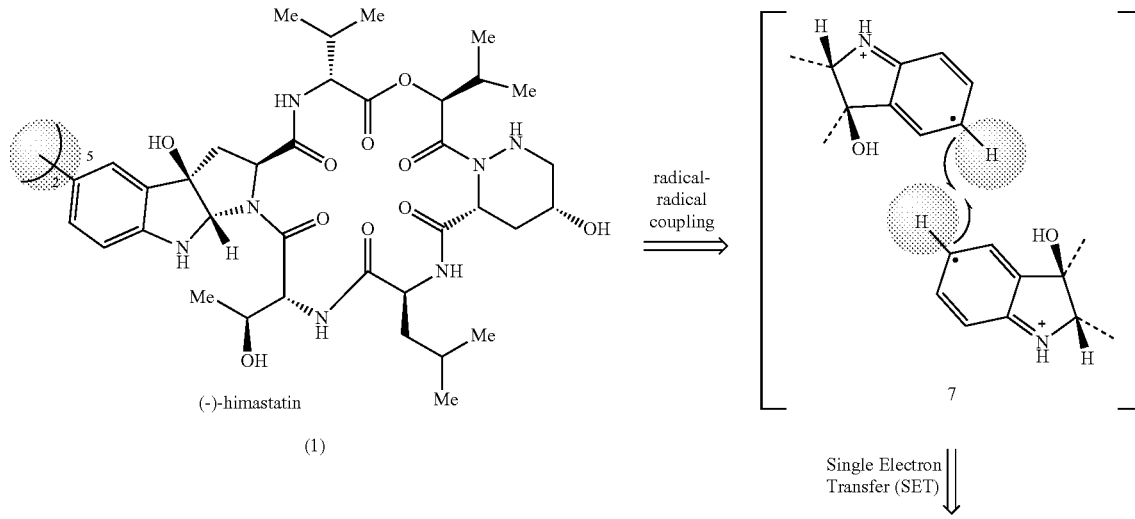

Scheme 2. Retrosynthetic Analysis of (−)-Himastatin (1)

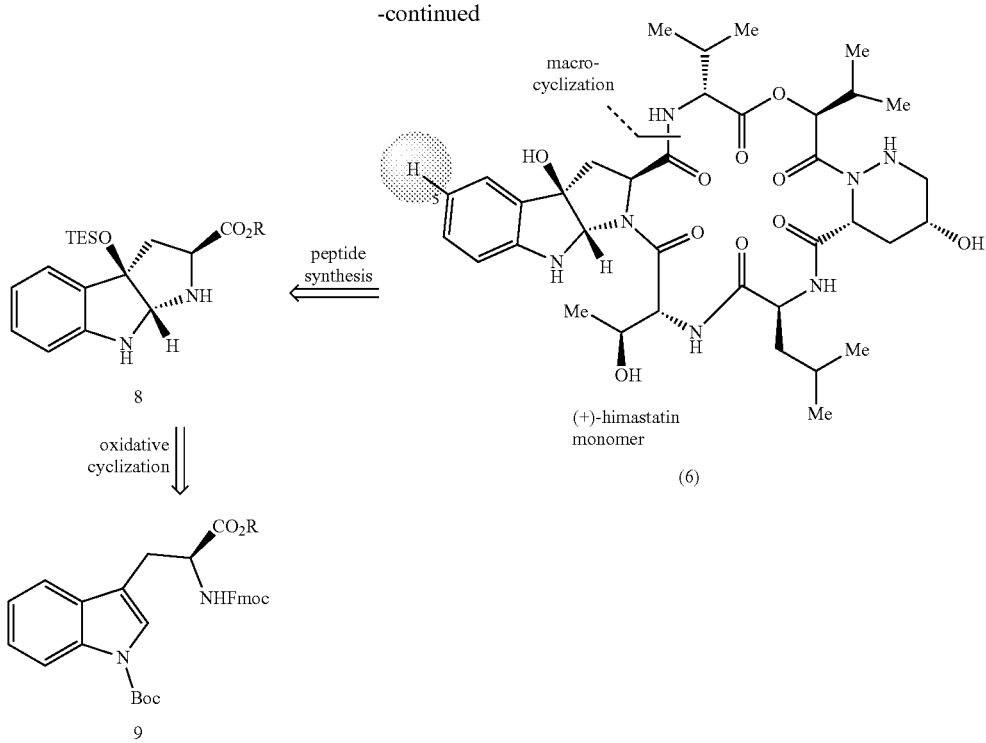

Our synthetic studies began with the development of a strategy for the direct C5-C5' dimerization of cyclotryptophan derivatives. We envisioned a strategy wherein one-election oxidation would generate an open-shell radical species, such as a neutral radical or radical cation, that would be subject to rapid combination as in our diazene-directed and reductive dimerization strategies. In contrast to earlier syntheses,[viii,xiv,xvi] this strategy would not require prior C5 functionalization to guide the union of monomers. This strategy may be useful for solving regioselectivity concerns associated with combination of relatively delocalized radicals.[xxvii] In certain embodiments, the single-electron oxidant is a chemoselective single-electron oxidant.

Figure 3:
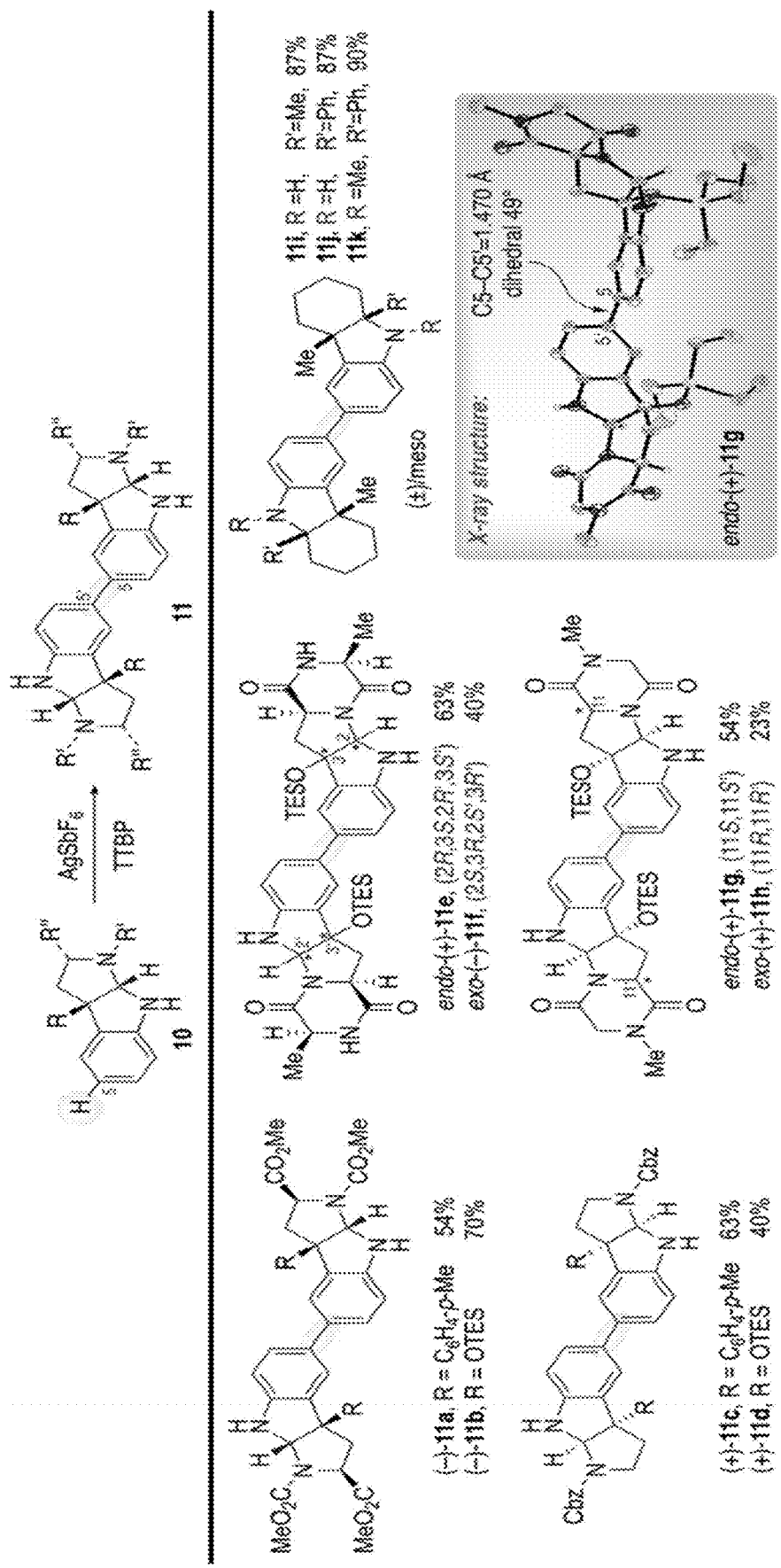
FIG. 3 shows the Oxidative Dimerization of Cyclotryptophan, Cyclotryptamine, and Indolines[a]. [a]Reagents and conditions: $AgSbF_6$, TTBP, $ClCH_2CH_2Cl$, 23° C. TTBP=2,4,6-tri-tert-butylpyrimidine.

We identified silver (I) salts, in combination with a non-nucleophilic pyrimidine base[xxviii] in non-polar solvents, as efficient one-electron oxidants[xxix] to effect C5-C5' dimerization of cyclotryptophan, cyclotryptamine, and indoline derivatives (FIG. 3). In each case, a single regioisomer was isolated whose $^1$H and $^{13}$C NMR spectra were consistent with a symmetric C5-C5' linked homodimer. The use of an aqueous reductive workup with sodium thiosulfate and sodium bicarbonate improved overall mass balance, as the dimeric products are subject to further reversible oxidation by silver(I) under the reaction conditions.[xxx] Notably, we observed an enhanced rate of oxidation of endo-configured diketopiperazines 6f, exo-configured 10h compared to exo-derivatives 6e, endo-derivatives 10g. These results correlate with increased accessibility of the N1 locus in exo-diketopiperazines, a feature we previously exploited in our total synthesis of C3-N1' linked natural products (+)-asperazine A and (+)-pestalazine B.[xxxi] We therefore hypothesize that the indoline nitrogen is the site of initial single-electron oxidation (SET).[xxxii] Substitution of the indoline nitrogen with a methyl group in the case of indoline 10k did not inhibit the dimerization, consistent with the intermediacy of a radical cation as opposed to a closed-shell arenium cation.[xxxiii,xxxiv] Single crystal X-ray diffraction of dimeric exo-diketopiperazine dimer (+)-7g verified the expected connectivity.

$^a$Reagents and conditions: AgSbF$_6$, TTBP, ClCH$_2$CH$_2$Cl, 23° C. TTBP=2,4,6-tri-tert-butylpyrimidine. In the ORTEP representation of dimeric exo-diketopiperazine dimer (+)-7g, the thermal ellipsoids are drawn at 30% probability and only selected hydrogen atoms are shown.

To investigate whether C—C bond formation takes place via radical-radical coupling upon one-electron oxidation, rather than a nucleophilic mechanism, we devised a series of experiments with mixtures of indoline substrates. When an equal mixture of C2-methyl and C2-phenyl indolines 6j and 6k was subjected to our dimerization conditions, we observed a statistical mixture of homo- and heterodimers (eq. 1), as expected for such similar substrates.

Statistical Heterodimerization with Similar Substrates:

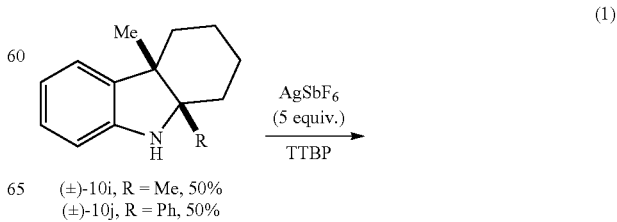

(±)-10i, R = Me, 50%
(±)-10j, R = Ph, 50%

(1)

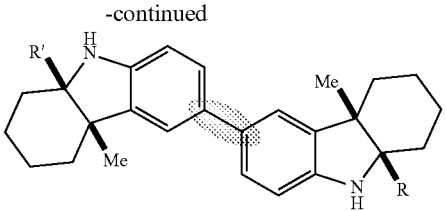

11i, R = Me, R' = Me, 24%
11j, R = Ph, R' = Ph, 22%
11m, R = Me, R' = Me, 50%

Subjecting a mixture of indolines 6k and 10k with differential N-substitution to identical conditions gave predominant homodimer formation, along with heterodimer 7n in trace quantities (eq. 2). Our suspicion that the indoline substrates were reacting sequentially owing to variation near the locus of initial SET oxidation was confirmed when a limiting quantity of oxidant was used, resulting in full consumption of N-methyl indoline 10k to homodimer 7k but near complete recovery of unsubstituted 6k (eq. 3).

Predominant Homodimerization with N-Substitution:

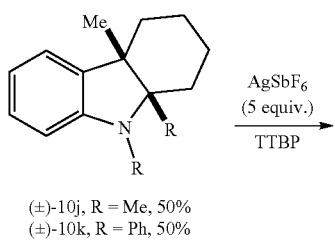

(±)-10j, R = Me, 50%
(±)-10k, R = Ph, 50%

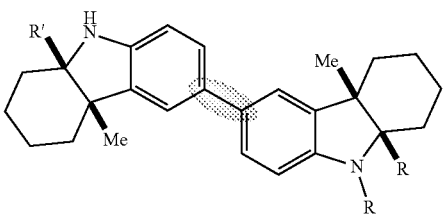

11j, R = Me, R' = H, 47%
11k, R = Ph, R' = Me, 43%
11n, R = Me, R' = Me, 4%

Competition Confirms Sequential Reactivity:

(3)

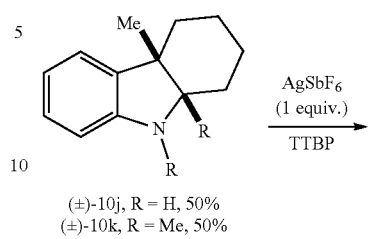

(±)-10j, R = H, 50%
(±)-10k, R = Me, 50%

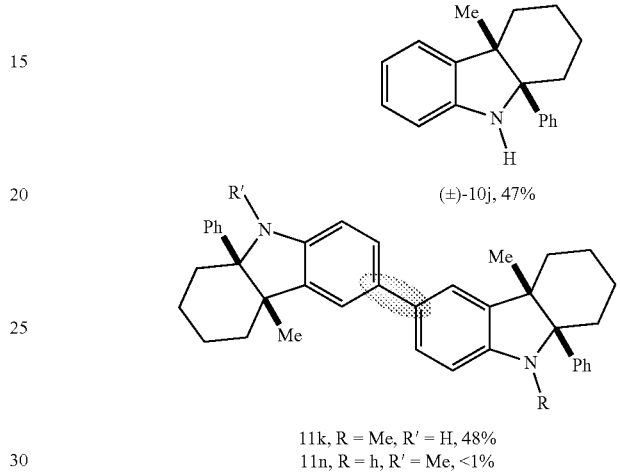

(±)-10j, 47%

11k, R = Me, R' = H, 48%
11n, R = h, R' = Me, <1%

As N-methyl indoline 10k reacts in the presence of an otherwise competent substrate (unsubstituted 6k) without appreciable formation of heterodimer 7n, we conclude that nucleophilic capture is not part of the operative dimerization mechanism.[xxxv] This conclusion is reinforced by our inability to divert the reaction course with nucleophilic additives.[xxxvi] Rather, our findings are consistent with rapid radical-radical coupling of two open-shell precursors, which is supported by independent kinetic studies that measured a rate constant of ~$10^7$ $M^{-1} \cdot s^{-1}$ for the dimerization of N,N-dimethylaniline radical cation.[xxxvii,xxxviii]

Having identified an oxidative dimerization method that might be suitable for the total synthesis of (−)-himastatin (1), we turned our attention to the synthesis of (+)-himastatin monomer (6). Rather than a typical linear approach,[viii] we favored convergent assembly of individual amino acid precursors, ultimately culminating in macrocyclization. While other amino acid fragments could be accessed according to known synthetic procedures, we required an efficient synthesis of protected 3a-hydroxycyclotryptophan (−)-17. To this end, commercially available tryptophan derivative (+)-12 (Scheme 3) was identified as a readily available starting material which could be subject to exo-selective oxidative cyclization. In practice, esterification of (+)-12 with allyl alcohol to give ester (+)-S4, followed by diastereoselective bromocyclization with N-bromosuccinimide in conjunction with a Brønsted acid gave bromocyclotryptophan (−)-S5.[xxxix,xl] Silver (I)-promoted hydrolysis afforded C3a-alcohol (−)-S6,[xli] which was subject to concomitant C3-O-silylation and Boc deprotection by triethylsilyl trifluoromethanesulfonate to afford Fmoc-cyclotryptophan (−)-S7.[xlii] Removal of the Fmoc group with piperidine under standard conditions afforded the desired protected cyclotryptophan (−)-12 in gram quantities.

Amino acid fragments in hand, we utilized a hybrid of solution and solid phase peptide synthesis to complete the assembly of linear hexadepsipeptide (−)-24 en route to (−)-himastatin (1) (Scheme 4). 2-Chlorotrityl-polystyrene resin-bound D-Thr 21 was elaborated with L-Leu 22 and depsitripeptide fragment (+)-20, prepared in one step from a depsipeptide block[xliii] and known Nε,O-protected D-5-hydroxypiperazic acid,[viii,xliv] by iterative HATU coupling followed by deprotection with piperidine. Acidic cleavage afforded pentadepsipeptide (+)-23 in excellent purity, taking care to avoid side-chain deprotection by minimizing resin exposure time and quenching the residual trifluoroacetic acid. Finally, the crude pentadepsipeptide acid (+)-23 was coupled with cyclotryptophan (−)-12 under weakly basic conditions to minimize epimerization, affording fully assembled linear hexadepsipeptide (−)-24 in 55% yield from starting resin 21. Overall, our efficient hybrid synthetic strategy facilitates a rapid and convergent approach with a single final purification.

Scheme 3. Synthesis of Cylcotryptophan(-)-12

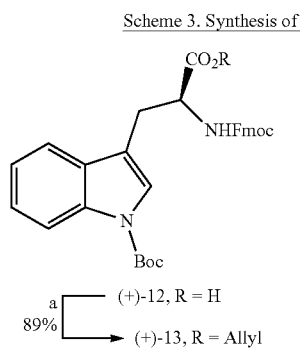

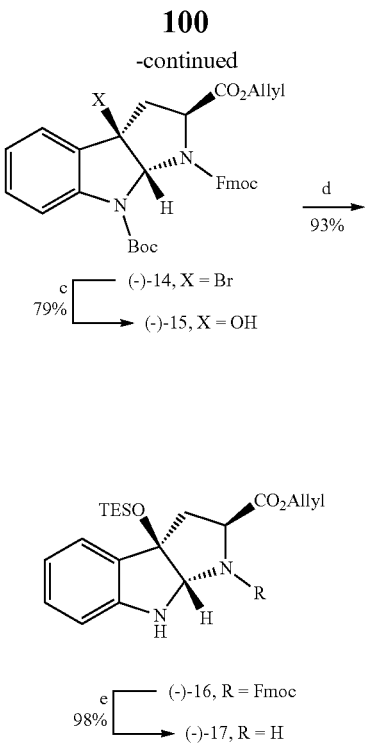

"Reagents and conditions:
(a) H2C = CH2OH, T3P, pyridine, 0 → 23° C.;
(b) NBS, PPTS, CH2Cl2;
(c) AgSbF6, H2O, DTBMP, MeNO2, 23° C.;
(d) TESOTf, i-Pr2NEt, CH2Cl2, 0 → 23° C.;
(e) piperidine, MeCN, 23° C. = 2,6-di-tert-butyl-4-methylpyridine.

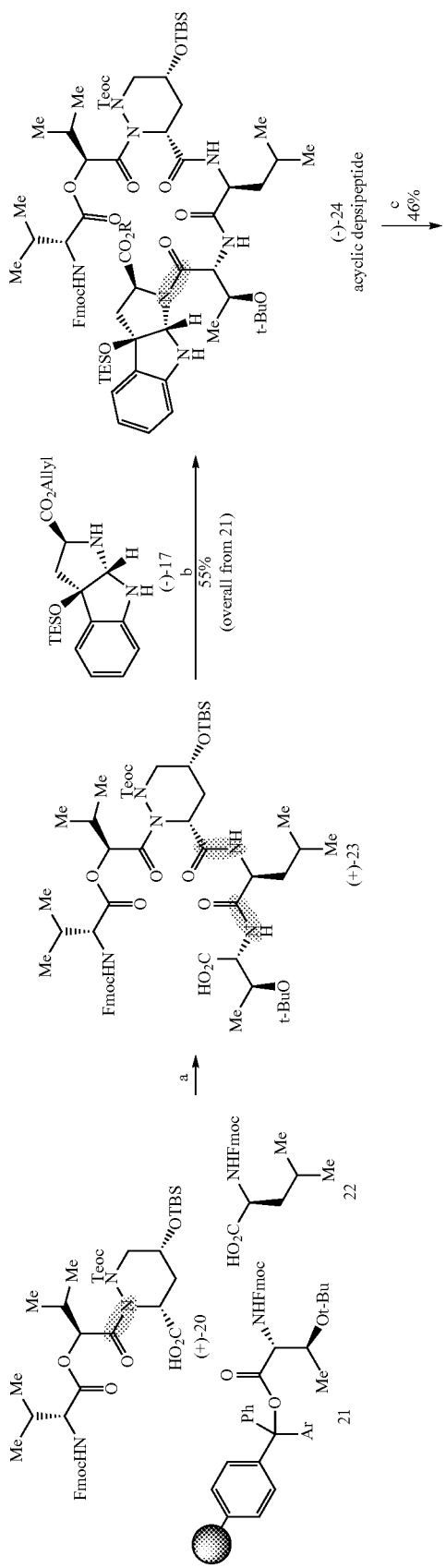
Scheme 4. Total Synthesis of (−)-Himastatin (1)[a]

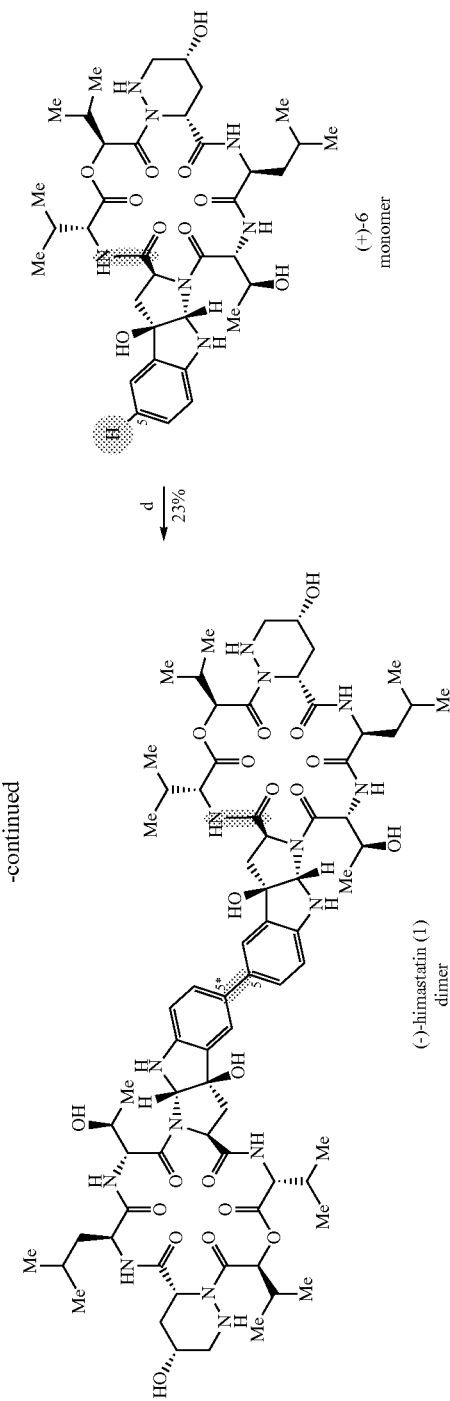

"Reagents and conditions:
(a) (i) piperidine, DMF, 23° C.,
(ii) Fmoc-L-Leu-OH, HATU, i-Pr₂NEt, DMF, 23° C.,
(iii) piperidine, DMF, 23° C.
(iv) (+)-20, HATU, i-Pr₂NEt, DMF, 23° C.,
(v) TFA, CH₂Cl₂, 23° C.;
(b) (–)-12, HATU, HOAt, s-collidine, CH₂Cl₂, 0 → 23° C.;
(c) (i) Pd(PPh₃)₄, N-methylaniline, THF, 23° C.,
(ii) i-Pr₂NH, MeCN, 23° C.,
(iii) HATU, HOAt, i-Pr₂NEt, CH₂Cl₂, 23° C.,
(iv) TFA, H₂O, anisole; Et₃N, MeOH, 23° C.;
(d) AgSbF₆, DTBMP, ClCH₂CH₂Cl, 23° C.
Ar = 2-chlorophenyl;
HATU = 1-[bis(dimethylamino)methylene]-1H-1,2,3-triazolo[4,5-b]pyridinium 3-oxide hexafluorophosphate.

Elaboration of linear peptide (−)-24 to (+)-himastatin monomer (6) was initiated by deprotection of the terminal protecting groups. Removal of the C-terminal allyl group was accomplished with Pd(PPh$_3$)$_4$ (0.2 mol %) in conjunction with N-methylaniline, followed by N-terminal deprotection with N,N-diisopropylamine in acetonitrile. The crude linear amino acid was then subjected to macrocyclization with HATU, HOAt, and N,N-diisopropylethylamine in dichloromethane (2.5 mM). Finally, global deprotection of side-chain protecting groups with trifluoroacetic acid afforded (+)-himastatin monomer (6) in 46% overall yield from linear precursor (−)-24. All $^1$H and $^{13}$C NMR data as well as optical rotation (observed $[\alpha]_D^{23}$=+34 (c=0.13, CHCl$_3$); lit: $[\alpha]_D^{25}$=+37.5 (c=0.7, CHCl$_3$),$^{viii}$ $[\alpha]_D^{25}$=+64 (c=1.87, CHCl$_3$)) for synthetic monomer (+)-6 were consistent with literature values from Ju's biosynthesis study, which isolated monomer (+)-6 from an ΔHmntS mutant (Scheme 1), as well as Danishefsky's total synthesis report.$^{viii}$ Having accessed the immediate biosynthetic precursor to (−)-himastatin (1), we focused on biomimetic final-stage application of our oxidative dimerization methodology to complete the total synthesis. Initial application of the conditions from FIG. 3 to the dimerization of underivatized (+)-himastatin monomer (6) led to only trace formation of (−)-himastatin (1) with near complete recovery of starting material. Evaluation of other silver (I) sources, as well as solvents and various additives did not improve the reaction outcome. We suspected that gradual inactivation of the silver (I) hexafluoroantimonate may be responsible for the low conversion. Fortunately, the use of a stronger base, 2,6-di-tert-butyl-4-methylpyridine, along with additional equivalents of silver (I) hexafluoroantimonate added in portions ultimately gave (−)-himastatin (1) in 24% yield, with the majority of the mass balance consisting of recovered (+)-himastatin monomer (6) (50%). All $^1$H and $^{13}$C NMR data, FTIR data, as well as optical rotation (observed $[\alpha]_D^{23}$=−36 (c=0.040, MeOH); lit: $[\alpha]_D^{25}$=−34 (c=0.35, MeOH)$^{vi, viii}$) for synthetic (−)-himastatin (1) were consistent with literature values.

Having achieved a concise, total synthesis of (−)-himastatin (1), we sought to take full advantage of our convergent and modular hybrid approach to access novel derivatives. We selected several single-residue substitutions that might provide insight into structural characteristics that are important for himastatin's antibiotic activity. In particular, we evaluated substitutions of the depsipeptide linkage, D-hydroxypiperazic acid residue, and L-leucine residue. In all cases, our modular peptide synthesis approach was quickly adapted to introduce a substituted residue without significant impact on overall efficiency.$^{xliv}$ Once prepared, each monomer was subjected to oxidative dimerization using conditions developed for the synthesis of (−)-himastatin (1) (FIG. 4) to yield a suite of novel dimeric derivatives.

To complement our series of derivatives, we also sought to probe the influence of absolute stereochemistry on the antibiotic activity of (−)-himastatin (1). The alternating sequence of D,L amino acids that comprise the macrocyclic rings of (−)-himastatin (1) is a structural feature of cyclic peptides that self-assemble into bacterial membrane-disrupting nanotubes.$^{xlv,xlvi}$ As self-association via non-covalent interactions is independent of absolute chirality, and the lipid chains of the membrane bilayer where (−)-himastatin (1) may associate comprise an essentially achiral environment,$^{xlvii,xlviii}$ we hypothesized that ent-(+)-himastatin (1) may exhibit similar if not identical activity to the natural enantiomer. To evaluate our hypothesis, we prepared ent-(+)-himastatin (1) via our concise route from amino acid precursors of opposite chirality. All $^1$H and $^{13}$C NMR data for ent-(+)-himastatin (1) were consistent with those of (−)-himastatin (1), with the exception of the recorded optical rotation which was of opposite sign ($[\alpha]_D^{23}$=+33 (c=0.071, MeOH)).

With (−)-himastatin (1) and a set of novel derivatives in hand, we proceeded to evaluate the antibiotic activity of our synthetic compounds. All monomers and dimers, including (−)-himastatin (1) as well as its enantiomer, were assayed against Gram-positive bacteria using the broth microdilution method (Table 2). As expected, synthetic (−)-himastatin (1) showed potent antibiotic activity against several Gram-positive species, including antibiotic-resistant strains, while the corresponding monomer (+)-6 was inactive.$^{iv,viii}$ The results underscore that dimerization is critical for bioactivity; indeed all monomeric derivatives were found to be inactive.

A structural feature unique to (−)-himastatin (1) as compared to related *Streptomyces* 3a-hydroxycyclotryptophan antibiotics is the presence of a depsipeptide linkage (FIG. 1). To evaluate the importance of this ester linkage, we compared dimeric derivatives (−)-26 and (−)-28 where the depsipeptide linkage was replaced a secondary and N-methyl tertiary amide respectively. In the case of secondary amide (−)-26, we observed a modest reduction in antibiotic activity. These results underscore that with respect to antibiotic activity, the depsipeptide linkage is an important, though not essential feature of (−)-himastatin (1). As esters are more prone to enzymatic hydrolysis compared to amides, a property that bacteria often exploit in the development of resistance,$^{xlix,l}$ amide derivative (−)-26 may be able to avoid inactivation via this pathway while still retaining antibiotic activity.

TABLE 2

Assessment of (−)-Himastatin (1) and Derivatives for Antibiotic Activity Against Gram-Positive Bacteria.$^a$

| Derivative | Compound (monomer, dimer) | MIC (µg/mL) | | | | | |
|---|---|---|---|---|---|---|---|
| | | B. subtilis | MRSA | MSSA | VRE faecalis | VSE faecalis | S. himastatinicus |
| himastatin | (+)-6 | >64 | >64 | >64 | >64 | >64 | >64 |
| | (−)-1 | 1 | 2 | 2 | 2 | 1 | 8 |
| L-Val | (+)-25 | >64 | >64 | >64 | >64 | >64 | >64 |
| | (−)-26 | 8 | 32 | 16 | 32 | 16 | >64 |
| L-$^{Me}$Val | (+)-27 | >64 | >64 | >64 | >64 | >64 | >64 |
| | (−)-28 | >64 | >64 | >64 | >64 | >64 | >64 |
| D-Pro | (+)-29 | >64 | >64 | >64 | >64 | >64 | >64 |
| | (−)-30 | >64 | >64 | >64 | >64 | >64 | >64 |

TABLE 2-continued

Assessment of (−)-Himastatin (1) and Derivatives for Antibiotic Activity Against Gram-Positive Bacteria.[a]

| Derivative | Compound (monomer, dimer) | MIC (μg/mL) | | | | | |
|---|---|---|---|---|---|---|---|
| | | B. subtilis | MRSA | MSSA | VRE faecalis | VSE faecalis | S. himastatinicus |
| L-Lys(N$_3$) | (+)-31 | >64 | >64 | >64 | >64 | >64 | >64 |
| | (−)-32 | 2 | 2 | 1 | 1 | 0.5 | 8 |
| ent- | (−)-6 | >64 | >64 | >64 | >64 | >64 | 8 |
| himastatin | (+)-1 | 0.5 | 4 | 2 | 2 | 1 | 0.5 |

[a]Minimum inhibitory concentration (MIC) values as determined by the broth microdilution method, in which inoculum is incubated with decreasing concentrations of compound and growth inhibition is determined by eye. Replicate assays (n ≥ 2) confirmed the observed MIC values. Bacterial Strains: *Bacillus subtilis* (ATCC 6633); MRSA = Methicillin-Resistant *Staphylococcus aureus*; MSSA = Methicillin-Sensitive *S. aureus* (Newman); VRE = Vancomycin-Resistant *Enterococcus faecalis* (V583); VRE = Vancomycin-Sensitive *E. faecalis* (T7); *Streptomyces himastatinicus* (ATCC 53653).

Another common feature among related natural products is the presence of one more piperazic acid residues, which enforce a strong conformational preference conducive to the formation of peptide turns per Ciufolini's seminal studies.[li,lii] Proline residues are also known to induce turn formation, especially when the adjacent amino acid is of opposite α-stereochemistry, but do not exhibit a rigidifying effect as pronounced as that seen in N-acyl piperazic acid derivatives. In evaluating dimeric derivative (−)-30, we found that replacement of the 5-hydroxypiperazic acid with a proline residue of identical configuration led to complete abolishment of antibiotic activity. Consistent with the predicted loss of rigidity upon proline substitution, NMR spectra of (−)-30 and monomer (+)-29 in various solvents at 23° C. revealed the presence of minor conformers not observed in the spectra of (−)-himastatin (1) or derivatives thereof. Taken together, these results provide evidence that himastatin's rigid structure is enforced by the presence of a piperazic acid residue, and is important to its mode of action.

The relative lack of a convenient functional handle in (−)-himastatin (1) to facilitate derivatization prompted our replacement of the L-Leu residue, a site of natural variation among related antibiotics, with the azide-containing amino acid L-azidolysine (L-Lys(N$_3$)). We were fortunate to find that this substitution had essentially no impact on the antibiotic activity of the resulting dimeric derivative (−)-32, providing a useful means of preparing unnatural derivatives by subsequent conjugation.

Our hypothesis that the absolute stereochemistry of (−)-himastatin (1) may have minimal impact on its antibiotic activity was confirmed upon evaluation of ent-(+)-himastatin (1). The pair of enantiomers was found to have nearly MIC values, a finding that is reflected in other membrane-targeting cyclic peptides with alternating stereochemistry.[xlv] Importantly, this finding also disagrees with an alternative mechanism of action involving diastereomeric chiral interactions (e.g. receptor-ligand) that would lead to differential activity of each enantiomer.[xlvii,xlviii] Furthermore, in comparing the activities of enantiomers of himastatin (1) against *Streptomyces himastatinicus*, which produces natural himastatin, we uncovered a remarkable ability of ent-(+)-himastatin (1) to completely evade its own resistance mechanism and inhibit its growth. This suggests that ent-(+)-himastatin (1) may show promise as an alternative means of avoiding typical defenses utilized by bacteria against membrane-active antibiotics, such as enzyme-mediated degradation.[1]

Having established that (−)-himastatin's (1) antibiotic activity is independent of its absolute chirality, we were prompted to initiate an orthogonal investigation of the possibility that it targets the bacterial membrane. Live-cell microscopy of membrane-disrupting antibiotics has been previously utilized to characterize their mechanism of action.[liii,liv] We therefore proceeded to image *B. subtilis* bacteria by fluorescence microscopy before and after treatment with varying concentrations of himastatin.

Figures 5A, 5B, 5C:
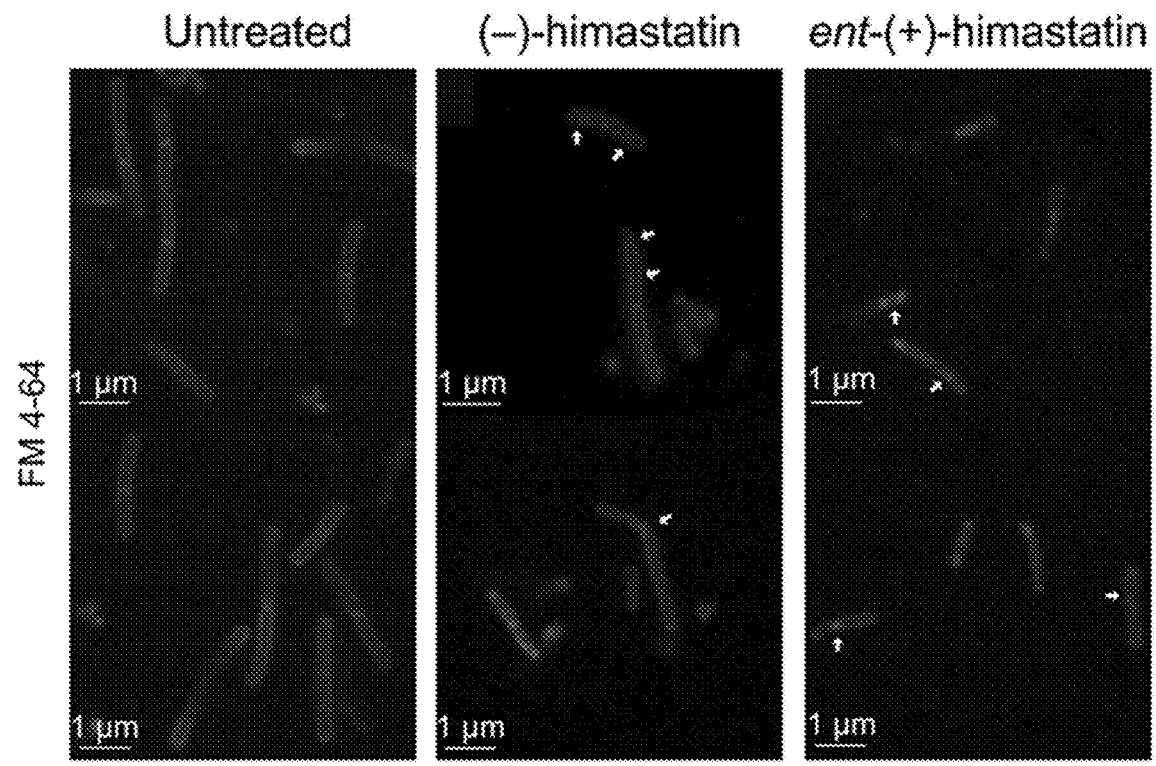
FIGS. 5A-5F shows the evaluation of the biological effects of himastatin by fluorescence microscopy.
Figures 5D, 5E, 5F:
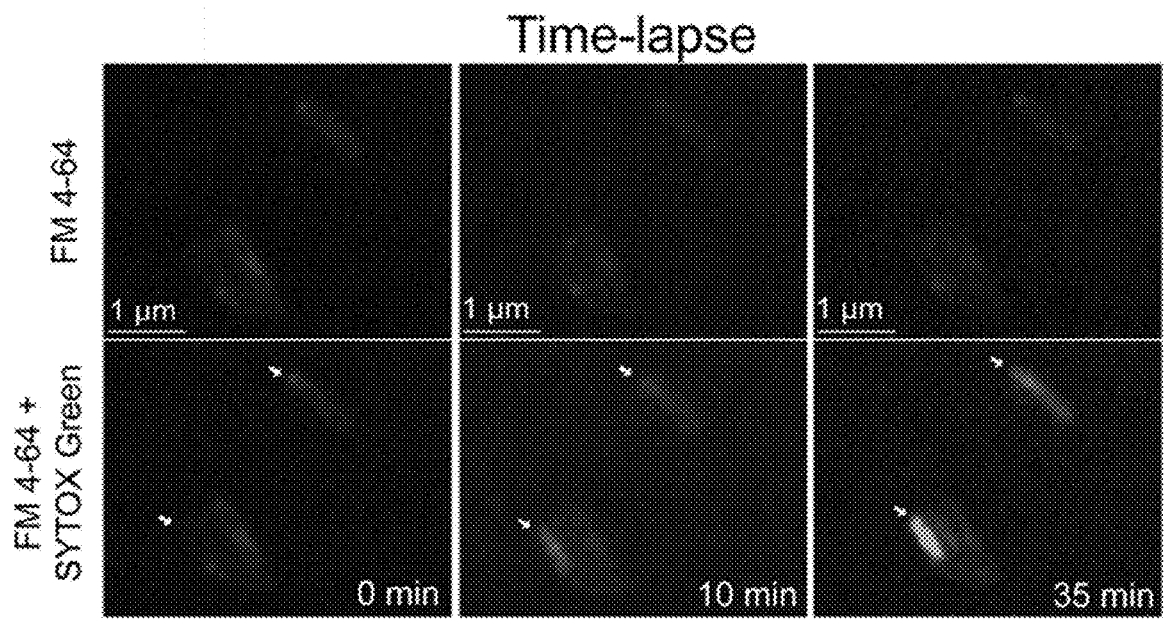
Figure 6:
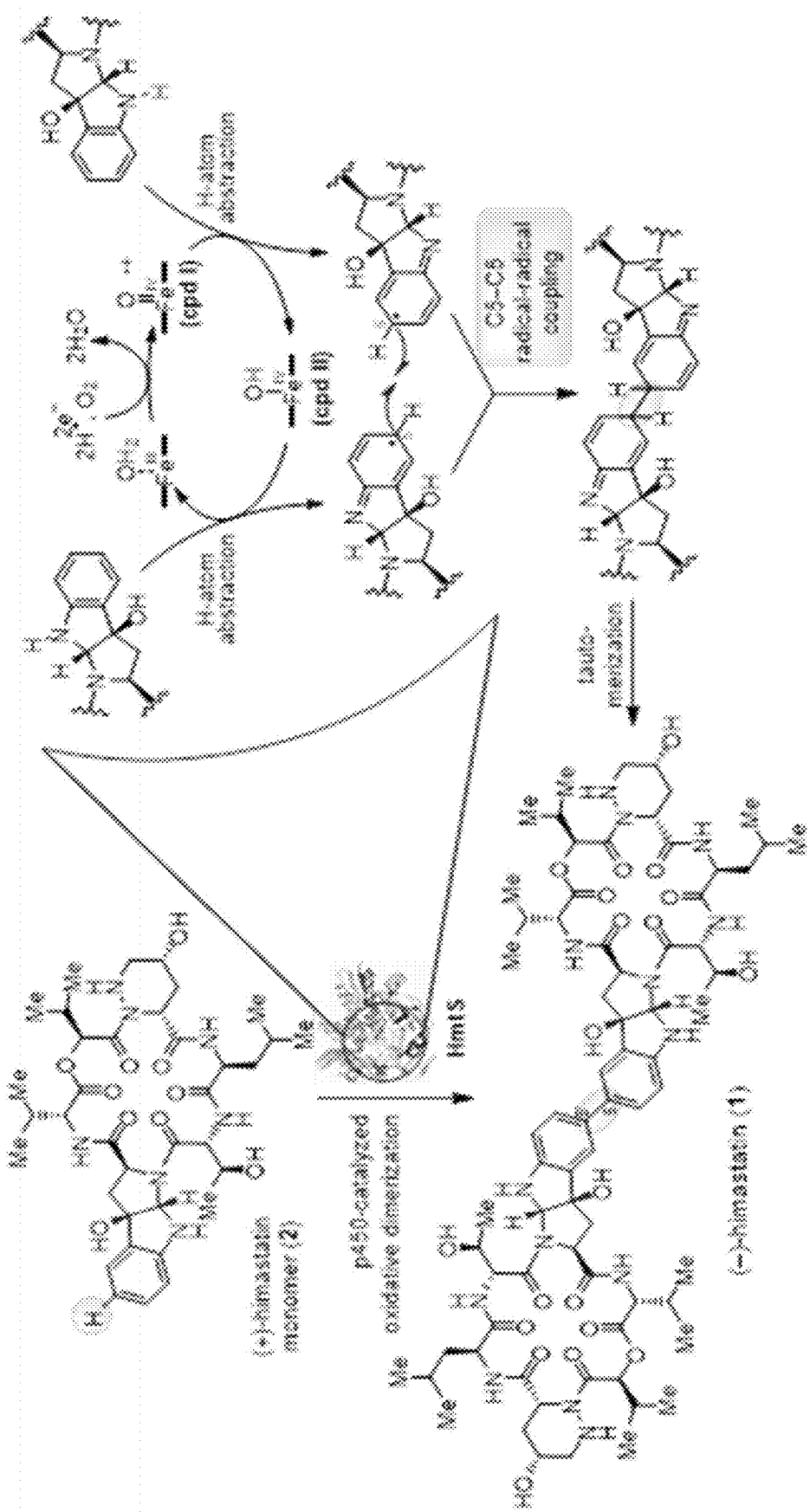
FIG. 6 shows the radical-radical coupling forms the central C5-C5' bond of himastatin in our proposed mechanism for the biosynthetic dimerization catalyzed by HmtS.

While untreated cells have smooth membranes and central division sites, cells treated with a sub-lethal concentration (0.25 μg/mL, one-fourth MIC) of either enantiomer of himastatin display striking membrane defects, including blebs and kinks, in addition to irregular division initiation sites (FIG. 5, A-C). The morphology of cells treated with (+)-ent-himastatin was identical, consistent with its similar activity and putative mechanism of action as its natural enantiomer. At lethal concentrations (2 μg/mL, twice MIC), (−)-himastatin (1) induced cell membrane permeabilization and cell death within 35 minutes (FIG. 5, D-F), as determined by viability staining with cell-impermeant SYTOX Green. The short timescale of himastatin's bactericidal activity is entirely consistent with a mechanism of action involving direct physical perturbations rather than disruption of biochemical pathways, a key signature of membrane-targeting antibiotics.[liii,lv,lvi]

Taken together, our results show that himastatin targets and disrupts bacterial membranes as part of its mechanism of action. With the alarming rise in multidrug resistant pathogens, membrane-targeting antibiotics, such as the first-in-class FDA approved macrocyclic peptide daptomycin, have attracted growing attention for targeting an essential bacterial organelle that is difficult to alter without fitness cost.[lvii] Our findings, leveraging live-cell microscopy in conjunction with an orthogonal synthetic probe, (+)-ent-himastatin, firmly place (−)-himastatin (1) as a unique member among the membrane-targeting class of antibiotics.

In summary, we report a concise total synthesis of (−)-himastatin (1) via final-stage dimerization. Our synthesis relies on a novel dimerization methodology to secure the biaryl linkage critical for potent antibiotic activity. We developed and demonstrated the application of a novel methodology for the direct and practical dimerization of cyclotryptophans, cyclotryptamines, and indolines to access C5-C5' linked dimers without prior functionalization. Mechanistic studies indicated that C—C bond formation occurs via rapid radical-radical coupling, a feature that mirrors the hypothesized biogenesis of (−)-himastatin (1). Final-stage application of the methodology to the biomimetic dimerization of underivatized (+)-himastatin monomer (6) then completed the total synthesis of (−)-himastatin (1).

The modular and efficient strategy developed to access (+)-himastatin monomer (6), leveraging the practical advantages inherent to solid-phase peptide synthesis, facilitated rapid preparation of novel himastatin derivatives after oxidative dimerization. Biological evaluation of these derivatives formed the basis of an initial survey of important structural features for the antibiotic activity of (−)-himastatin (1). We additionally report that the enantiomer of (−)-himastatin, ent-(+)-himastatin (1), shows identical bioactivity, a feature consistent with our ancillary finding that both enantiomers lead to visible membrane disruption in treated bacteria. Along with a short timescale of bactericidal action, we conclude that the primary biological target of (−)-himastatin (1) is the bacterial membrane. These findings, in conjunction with the enabling synthetic strategies we have developed, form the basis of our ongoing efforts to gain further insights into the molecular mechanism of (−)-himastatin.

REFERENCES

[i] Boucher, H. W.; Talbot, G. H.; Bradley, J. S.; Edwards, J. E.; Gilbert, D.; Rice, L. B.; Scheld, M.; Spellberg, B.; Bartlett, J. Bad Bugs, No Drugs: No ESKAPE! An Update from the Infectious Diseases Society of America. *Clin. Infect. Dis.* 2009, 48, 1-12.

[ii] Ventola, C. L. The Antibiotic Resistance Crisis: Part 1: Causes and Threats. *Pharm. Ther.* 2015, 40, 277-283.

[iii] Wright, G. D. Something Old, Something New: Revisiting Natural Products in Antibiotic Drug Discovery. *Can. J. Microbiol.* 2014, 60, 147-154.

[iv] Lam, K. S.; Hesler, G. A.; Mattei, J. M.; Mamber, S. W.; Forenza, S.; Tomita, K. Himastatin, a New Antitumor Antibiotic from *Streptomyces Hygroscopicus*. I. Taxonomy of Producing Organism, Fermentation and Biological Activity. *J. Antibiot.* 1990, 43, 956-960.

[v] Leet, J. E.; Schroeder, D. R.; Krishnan, B. S.; Matson, J. A. Himastatin, a New Antitumor Antibiotic from *Streptomyces Hygroscopicus*. II. Isolation and Characterization. *J. Antibiot.* 1990, 43, 961-966.

[vi] Leet, J. E.; Schroeder, D. R.; Golik, J.; Matson, J. A.; Doyle, T. W.; Lam, K. S.; Hill, S. E.; Lee, M. S.; Whitney, J. L.; Krishnan, B. S. Himastatin, a New Antitumor Antibiotic from *Streptomyces Hygroscopicus*. III. Structural Elucidation. *J. Antibiot.* 1996, 49, 299-311.

[vii] Umezawa, K.; Ikeda, Y; Uchihata, Y; Naganawa, H.; Kondo, S. Chloptosin, an Apoptosis-Inducing Dimeric Cyclohexapeptide Produced by *Streptomyces*. *J. Org. Chem.* 2000, 65, 459-463.

[viii] Kamenecka, T. M.; Danishefsky, S. J. Discovery through Total Synthesis: A Retrospective on the Himastatin Problem. *Chem. Eur. J.* 2001, 7, 41-63.

[ix] Guo, Z.; Shen, L.; Ji, Z.; Zhang, J.; Huang, L.; Wu, W. NW-G01, a Novel Cyclic Hexadepsipeptide Antibiotic, Produced by *Streptomyces Alboflavus* 313: I. Taxonomy, Fermentation, Isolation, Physicochemical Properties and Antibacterial Activities. *J. Antibiot.* 2009, 62, 201-205.

[x] Guo, Z.; Ji, Z.; Zhang, J.; Deng, J.; Shen, L.; Liu, W.; Wu, W. NW-G01, a Novel Cyclic Hexapeptide Antibiotic, Produced by *Streptomyces Alboflavus* 313: II. Structural Elucidation. *J. Antibiot.* 2010, 63, 231-235.

[xi] Guo, Z.; Li, P.; Chen, G.; Li, C.; Cao, Z.; Zhang, Y; Ren, J.; Xiang, H.; Lin, S.; Ju, J.; Chen, Y. Design and Biosynthesis of Dimeric Alboflavusins with Biaryl Linkages via Regiospecific C—C Bond Coupling. *J. Am. Chem. Soc.* 2018, 140, 18009-18015.

[xii] Kamenecka, T. M.; Danishefsky, S. J. Studies in the Total Synthesis of Himastatin: A Revision of the Stereochemical Assignment. *Angew. Chem. Int. Ed.* 1998, 37, 2993-2995.

[xiii] Hong, W.-X.; Chen, L.-J.; Zhong, C.-L.; Yao, Z.-J. Bidirectional Synthesis of the Central Amino Acid of Chloptosin. *Org. Lett.* 2006, 8, 4919-4922.

[xiv] Yu, S.-M.; Hong, W.-X.; Wu, Y; Zhong, C.-L.; Yao, Z.-J. Total Synthesis of Chloptosin, a Potent Apoptosis-Inducing Cyclopeptide. *Org. Lett.* 2010, 12, 1124-1127.

[xv] Oelke, A. J.; France, D. J.; Hofmann, T.; Wuitschik, G.; Ley, S. V. Total Synthesis of Chloptosin. *Angew. Chem. Int. Ed* 2010, 49, 6139-6142.

[xvi] Oelke, A. J.; Antonietti, F.; Bertone, L.; Cranwell, P. B.; France, D. J.; Goss, R. J. M.; Hofmann, T.; Knauer, S.; Moss, S. J.; Skelton, P. C.; Turner, R. M.; Wuitschik, G.; Ley, S. V. Total Synthesis of Chloptosin: A Dimeric Cyclohexapeptide. *Chem. Eur. J.* 2011, 17, 4183-4194.

[xviii] Movassaghi, M.; Schmidt, M. A. Concise Total Synthesis of (−)-Calycanthine, (+)-Chimonanthine, and (+)-Folicanthine. *Angew. Chem. Int. Ed* 2007, 46, 3725-3728.

[xviii] Lathrop, S. P.; Pompeo, M.; Chang, W.-T. T.; Movassaghi, M. Convergent and Biomimetic Enantioselective Total Synthesis of (−)-Communesin F. *J. Am. Chem. Soc.* 2016, 138, 7763-7769.

[xix] Pompeo, M. M.; Cheah, J. H.; Movassaghi, M. Total Synthesis and Anti-Cancer Activity of All Known Communesin Alkaloids and Related Derivatives. *J. Am. Chem. Soc.* 2019, 141, 14411-14420.

[xx] Movassaghi, M.; Schmidt, M. A.; Ashenhurst, J. A. Concise Total Synthesis of (+)-WIN 64821 and (−)-Ditryptophenaline. *Angew. Chem. Int. Ed* 2008, 47, 1485-1487.

[xxi] Kim, J.; Ashenhurst, J. A.; Movassaghi, M. Total Synthesis of (+)-11,11′-Dideoxyverticillin A. *Science* 2009, 324, 238-241.

[xxii] Kim, J.; Movassaghi, M. General Approach to Epipolythiodiketopiperazine Alkaloids: Total Synthesis of (+)-Chaetocins A and C and (+)-12,12′-Dideoxychetracin A. *J. Am. Chem. Soc.* 2010, 132, 14376-14378.

[xxiii] Movassaghi, M.; Ahmad, O. K.; Lathrop, S. P. Directed Heterodimerization: Stereocontrolled Assembly via Solvent-Caged Unsymmetrical Diazene Fragmentation. *J. Am. Chem. Soc.* 2011, 133, 13002-13005.

[xxiv] Ma, J.; Wang, Z.; Huang, H.; Luo, M.; Zuo, D.; Wang, B.; Sun, A.; Cheng, Y.-Q.; Zhang, C.; Ju, J. Biosynthesis of Himastatin: Assembly Line and Characterization of Three Cytochrome P450 Enzymes Involved in the Post-Tailoring Oxidative Steps. *Angew. Chem. Int. Ed* 2011, 50, 7797-7802.

[xxv] Grandner, J. M.; Cacho, R. A.; Tang, Y; Houk, K. N. Mechanism of the P450-Catalyzed Oxidative Cyclization in the Biosynthesis of Griseofulvin. *ACS Catal.* 2016, 6, 4506-4511.

[xxvi] Takahashi, R. H.; Grandner, J. M.; Bobba, S.; Liu, Y; Beroza, P.; Zhang, D.; Ma, S. Novel Homodimer Metabolites of GDC-0994 via Cytochrome P450-Catalyzed Radical Coupling. *Drug. Metab. Dispos.* 2020, 48, 521-527.

[xxvii] DFT calculations (B3LYP/cc-pVTZ) of cyclotryptophan radical cations showed that spin density was approximately equally partitioned between the N1 nitrogen and arene ring of cyclotryptophan radical cations. Amongst arene carbons, C5 had the highest spin density.

[xxviii] Crich, D.; Smith, M.; Yao, Q.; Picione, J. 2,4,6-Tri-Tert-Butylpyrimidine (TTBP): A Cost Effective, Readily Available Alternative to the Hindered Base 2,6-Di-Tert- Butylpyridine and Its 4-Substituted Derivatives in Glycosylation and Other Reactions. *Synthesis* 2001, No. 02, 323-326.

[xxix] Connelly, N. G.; Geiger, W. E. Chemical Redox Agents for Organometallic Chemistry. *Chem. Rev.* 1996, 96, 877-910.

[xxx] Ivashenko, O.; Herpt, J. T. van; Rudolf, P.; Feringa, B. L.; Browne, W. R. Oxidative Electrochemical Aryl C-C Coupling of Spiropyrans. *Chem. Commun.* 2013, 49, 6737-6739.

[xxxi] Nelson, B. M.; Loach, R. P.; Schiesser, S.; Movassaghi, M. Concise Total Synthesis of (+)-Asperazine A and (+)-Pestalazine B. *Org. Biomol. Chem.* 2018, 16, 202-207.

[xxxii] Inaccessibility of the nitrogen locus also appears to inhibit oligomerization that results from formation of alternative linkages (e.g. C—N1'). The lower yields of C5-C5' linked exo-configured DKP dimers 11f and 11h relative to their endo-configured counterparts can be attributed to this, see Hand, R. L.; Nelson, R. F. Anodic Oxidation Pathways of N-Alkylanilines. *J. Am. Chem. Soc.* 1974, 96, 850-860.

[xxxiii] Gassman, P. G.; Campbell, G. A.; Frederick, R. C. *J. Am. Chem. Soc.* Chemistry of Nitrenium Ions. XXI. Nucleophilic Aromatic Substitution of Anilines via Aryl Nitrenium Ions (Anilenium Ions). 1972, 94, 3884-3891.

[xxxiv] Palmisano, G.; Danieli, B.; Lesma, G.; Santagostino, M.; Fiori, G.; Toma, L. Aspidosperma Alkaloids. A New Didehydrodimerization Mode of β-Anilinoacrylic Alkaloids by Anodic Oxidation. *Helv. Chim. Acta* 1992, 75, 813-824.

[xxxv] In a separate competition experiment, N-methyl indoline 10k was slightly more nucleophilic than unsubstituted indoline 10j, as measured by their rates of bromination with N-bromosuccinimide ($k_{rel}$=2).

[xxxvi] Kirchgessner, M.; Sreenath, K.; Gopidas, K. R. Understanding Reactivity Patterns of the Dialkylaniline Radical Cation. *J. Org. Chem.* 2006, 71, 9849-9852.

[xxxvii] Larumbe, D.; Gallardo, I.; Andrieux, C. P. Anodic Oxidation of Some Tertiary Amines. *J. Electroanal. Chem.* 1991, 304, 241-247.

[xxxviii] Yang, H.; Wipf, D. O.; Bard, A. J. Application of Rapid Scan Cyclic Voltammetry to a Study of the Oxidation and Dimerization of N,N-Dimethylaniline in Acetonitrile. *J. Electroanal. Chem.* 1992, 331, 913-924.

[xxxix] López, C. S.; Pérez-Balado, C.; Rodríguez-Graña, P.; de Lera, Á. R. Mechanistic Insights into the Stereocontrolled Synthesis of Hexahydropyrrolo[2,3-b]Indoles by Electrophilic Activation of Tryptophan Derivatives. *Org. Lett.* 2008, 10, 77-80.

[xl] Ruiz-Sanchis, P.; Savina, S. A.; Acosta, G. A.; Albericio, F.; Álvarez, M. Orthogonal Protecting Groups in the Synthesis of Tryptophanyl-Hexahydropyrroloindoles. *Eur. J. Org. Chem.* 2012, 67-73.

[xli] Loach, R. P.; Fenton, O. S.; Movassaghi, M. Concise Total Synthesis of (+)-Asperazine, (+)-Pestalazine A, and (+)—Iso-Pestalazine A. Structure Revision of (+)-Pestalazine A. *J. Am. Chem. Soc.* 2016, 138, 1057-1064

[xlii] Sakaitani, M.; Ohfune, Y Syntheses and Reactions of Silyl Carbamates. 1. Chemoselective Transformation of Amino Protecting Groups via Tert-Butyldimethylsilyl Carbamates. *J. Org. Chem.* 1990, 55, 870-876.

[xliii] Nguyen, M. M.; Ong, N.; Suggs, L. A General Solid Phase Method for the Synthesis of Depsipeptides. *Org. Biomol. Chem.* 2013, 11, 1167-1170.

[xliv] See the supporting information for details.

[xlv] Fernandez-Lopez, S.; Kim, H.-S.; Choi, E. C.; Delgado, M.; Granja, J. R.; Khasanov, A.; Kraehenbuehl, K.; Long, G.; Weinberger, D. A.; Wilcoxen, K. M.; Ghadiri, M. R. Antibacterial Agents Based on the Cyclic D,L-α-Peptide Architecture. *Nature* 2001, 412, 452-455.

[xlvi] Rodríguez-Vázquez, N.; Ozores, H. L.; Guerra, A.; González-Freire, E.; Fuertes, A.; Panciera, M.; Priegue, J. M.; Outeiral, J.; Montenegro, J.; Garcia-Fandiño, R.; Amorín, M.; Granja, J. R. Membrane-Targeted Self-Assembling Cyclic Peptide Nanotubes. *Curr. Top. Med. Chem.* 2014, 14, 2647-2661.

[xlvii] Wade, D.; Boman, A.; Wåhlin, B.; Drain, C. M.; Andreu, D.; Boman, H. G.; Merrifield, R. B. All-D Amino Acid-Containing Channel-Forming Antibiotic Peptides. *Proc. Natl. Acad. Sci. U.S.A.* 1990, 87, 4761-4765.

[xlviii] Wang, C. K.; King, G. J.; Conibear, A. C.; Ramos, M. C.; Chaousis, S.; Henriques, S. T.; Craik, D. J. Mirror Images of Antimicrobial Peptides Provide Reflections on Their Functions and Amyloidogenic Properties. *J. Am. Chem. Soc.* 2016, 138, 5706-5713.

[xlix] Wright, G. D. Bacterial Resistance to Antibiotics: Enzymatic Degradation and Modification. *Adv. Drug. Deliv. Rev.* 2005, 57, 1451-1470.

[l] D'Costa, V. M.; Mukhtar, T. A.; Patel, T.; Koteva, K.; Waglechner, N.; Hughes, D. W.; Wright, G. D.; Pascale, G. D. Inactivation of the Lipopeptide Antibiotic Daptomycin by Hydrolytic Mechanisms. *Antimicrob. Agents Chemother.* 2012, 56, 757-764.

[li] Xi, N.; Alemany, L. B.; Ciufolini, M. A. Elevated Conformational Rigidity in Dipeptides Incorporating Piperazic Acid Derivatives. *J. Am. Chem. Soc.* 1998, 120, 80-86.

[lii] Ciufolini, M. A.; Xi, N. Synthesis, Chemistry and Conformational Properties of Piperazic Acids. *Chem. Soc. Rev.* 1998, 27, 437.

[liii] Pogliano, J.; Pogliano, N.; Silverman, J. A. Daptomycin-Mediated Reorganization of Membrane Architecture Causes Mislocalization of Essential Cell Division Proteins. *J. Bacteriol.* 2012, 194, 4494-4504.

[liv] Choi, H.; Rangarajan, N.; Weisshaar, J. C. Lights, Camera, Action! Antimicrobial Peptide Mechanisms Imaged in Space and Time. *Trends in Microbiol.* 2016, 24, 111-122.

[lv] Ooi, N.; Miller, K.; Hobbs, J.; Rhys-Williams, W.; Love, W.; Chopra, I. XF-73, a Novel Antistaphylococcal Membrane-Active Agent with Rapid Bactericidal Activity. *J. Antimicrob. Chemother.* 2009, 64, 735-740.

[lvi] Yasir, M.; Dutta, D.; Willcox, M. D. P. Mode of Action of the Antimicrobial Peptide Mel4 Is Independent of *Staphylococcus Aureus* Cell Membrane Permeability. *PLoS ONE* 2019, 14, e0215703.

[lvii] Steinbuch, K. B.; Fridman, M. Mechanisms of Resistance to Membrane-Disrupting Antibiotics in Gram-Positive and Gram-Negative Bacteria. *Med. Chem. Commun.* 2016, 7, 86-102.

Example 2

General Procedures.

All reactions were performed in oven-dried or flame-dried round-bottomed flasks fitted with rubber septa and were conducted under positive argon pressure using standard Schlenk techniques, unless noted otherwise. Cannulae or gas-tight syringes with stainless steel needles were used to transfer air- or moisture-sensitive liquids. Where necessary (so noted), solutions were degassed by sparging with argon for a minimum of 10 min. Flash column chromatography was performed as described by Still et al. using granular silica gel (60-Å pore size, 40-63 µm, 4-6% $H_2O$ content, Zeochem). Analytical thin layer chromatography (TLC) was performed using glass plates pre-coated with 0.25 mm 230-400 mesh silica gel impregnated with a fluorescent indicator (254 nm). TLC plates were visualized by exposure to short wave ultraviolet light (254 nm) and irreversibly stained by treatment with an aqueous solution of ceric ammonium molybdate (CAM) followed by heating (~1 min) on a hot plate (~250° C.). Organic solutions were concentrated at 30-35° C. on rotary evaporators capable of achieving a minimum pressure of ~10 Torr.

Materials.

Commercial reagents and solvents were used as received with the following exceptions: acetonitrile, dichloromethane, pyridine, and tetrahydrofuran were purchased from EMD Millipore (ReCycler™) or Sigma-Aldrich (PurePac™) and were purified by the method of Grubbs et al. under positive argon pressure. Benzene, 1,2-dichloroethane, and N,N-diisopropylethylamine were dried by distillation over calcium hydride under an inert dinitrogen atmosphere. Deuterated solvents used for nuclear magnetic resonance (NMR) spectroscopy were purchased from Cambridge Isotope Laboratories, Inc. and were used as received with the exception of chloroform-d, which was stored granular anhydrous potassium carbonate. Silver(I) hexafluoroantimonate was purchased from Strem Chemicals; 2,6-di-tert-butyl-4-methylpyridine was purchased from Matrix Scientific and was further purified by flash column chromatography on silica gel (eluent: hexanes); N-bromosuccinimide was purchased from Alfa Aesar and further purified by recrystallization from water; 2-chlorotrityl chloride polystyrene resin (200-400 mesh) was purchased from Chem-Impex and reactivated with thionyl chloride; copper(II) hexafluoroantimonate was prepared according to a literature procedure and was obtained as an off-white solid upon concentration of the resulting dichloromethane solution.[3] All other solvents and chemicals were purchased from Sigma-Aldrich, Alfa Aesar, Strem Chemicals, Chem-Impex International, ChemPep, CreoSalus, Ambeed, and BaChem Americas.

Instrumentation.

Nuclear magnetic resonance ($^1$H and $^{13}$C NMR) spectra were recorded with Bruker AVANCE NEO 600 or Bruker AVANCE NEO 500 spectrometers and are reported in parts per million on the δ scale. Proton NMR spectra are referenced from the residual protium in the NMR solvent (CHCl$_3$: δ 7.26, CD$_2$HCN: δ 1.94, DMSO-d$_5$: 2.50, C$_6$D$_5$H: δ 7.16).[4] Carbon-13 NMR spectra are referenced from the carbon resonances of the deuterated solvent (CDCl$_3$: δ 77.16, CD$_3$CN: δ 118.26, DMSO-d$_6$: 39.52, C$_6$D$_6$: δ 128.06). Data are reported as follows: chemical shift (multiplicity [s=singlet, d=doublet, t=triplet, q=quartet, p=pentet, sept=septet, m=multiplet, br=broad, app=apparent], coupling constant(s) in Hertz, integration, assignment). Fourier-Transform Infrared spectroscopic data were obtained with a Bruker ALPHA II FTIR spectrometer equipped with a diamond ATR sampling module and are reported as follows: frequency of absorption (cm$^{-1}$) [intensity of absorption (s=strong, m=medium, w=weak, br=broad)]. Optical rotations were measured on a Jasco P-1010 polarimeter with a sodium lamp and are reported as follows: $[\alpha]_\lambda^{T^\circ C.}$ (c=g/100 mL, solvent). Chiral HPLC analysis was performed on an Agilent Technologies 1100 Series instrument equipped with a diode array detector and columns with a chiral stationary phase from Daicel Chemical Industries (CHIRALPAK® IA 4.6 mm×250 mm, Lot #IAOOCE-PD046). UV spectroscopy was performed on a Hewlett-Packard 8452A diode array spectrophotometer. LC-MS analysis and mass-directed semi-preparative HPLC were performed on an Agilent Technologies 1260 Infinity II series instrument equipped with an Agilent 6125B single quadrupole MSD, a diode array detector, and a multicolumn compartment thermostatted to 35° C. Optical density measurements were performed on a Tecan Spark multimode microplate reader. Single crystal X-ray diffraction was carried out at the X-ray crystallography laboratory of the Department of Chemistry, Massachusetts Institute of Technology, with the assistance of Dr. Charlene Tsay, and Dr. Peter Müller. High-resolution mass spectra (HRMS) were recorded on an Agilent 6510 QToF with a Jet Steam ESI ionization source.

Positional Numbering System.

In assigning the $^1$H and $^{13}$C NMR data of all intermediates en route to (−)-himastatin (1) and its derivatives, we have employed a uniform numbering system illustrated below.

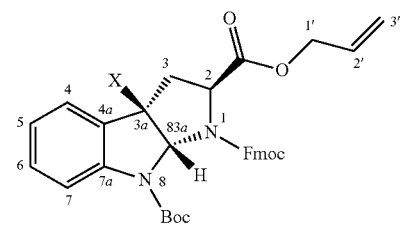

This document

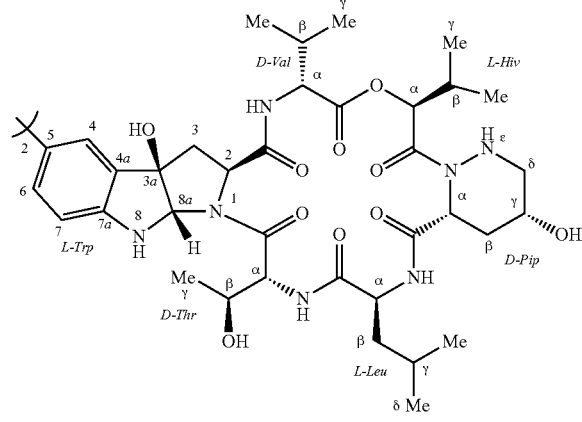

(−)-himastatin (1)

For dimeric diketopiperazines, a separate numbering scheme adapted from Barrow for (+)-WIN-64821 was used as illustrated below.[5]

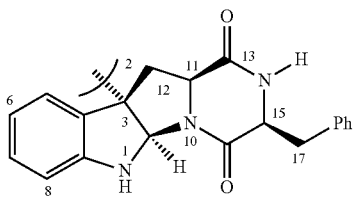

(+)-WIN-64821
Barrow's numbering for
dimeric diketopiperazines

-continued

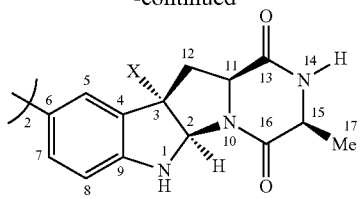

This document

Bacterial Strains.

Bacillus subtilis subsp. spizizenii (ATCC 6633) and Streptomyces himastatinicus (ATCC 53653) were obtained from the American Type Culture Collection (ATCC). Methicillin-resistant and methicillin-susceptible Staphylococcus aureus (Newman), and vancomycin-resistant (V583) and vancomycin-susceptible (T7) Enterococcus faecalis were obtained from the lab of Dr. Roby P. Bhattacharyya (Massachusetts General Hospital).[6] B. subtilis was grown in brain-heart infusion (BHI) medium at 37° C., S. himastatinicus was grown in tryptone-yeast extract broth (ISP medium 2) at 28° C., E. faecalis was grown in Todd-Hewitt broth, and all other organisms were grown in lysogeny broth (LB) medium at 37° C.

Broth Microdilution Susceptibility Assays.

Minimum inhibitory concentration (MIC) was determined using the broth microdilution method. 20-fold stocks of compound in DMSO were diluted 10-fold in MHB medium and 100 µL of each were added to the first well of a 96-well plate. 50 µL of the first well was then serially diluted through 50 µL MHB medium in wells 2-11. To prepare the bacterial culture, an overnight culture was diluted in MHB until the turbidity matched that of McFarland standard 0.5. Then, the culture was diluted 1:100 and added to wells 1-11, resulting in 2-fold dilutions of antibiotic beginning at 64 µg/mL and a final inoculum of 5×10[5] cfu/mL. 100 µL of MHB medium was added to well 12 as a sterility control, and a row containing no antibiotic was used as a growth control. The plate was incubated at the organism's respective growth temperature overnight (B. subtilis) or 72 h (S. himastatinicus) and the MIC was determined using OD600.

Broth Microdilution Susceptibility Assays.

Minimum inhibitory concentration (MIC) was determined using the broth microdilution method.[7] 20-fold (1.28 mg/mL) stocks of compound in dimethylsulfoxide, stored as frozen (−80° C.) 30-µL aliquots, were diluted 10-fold in Mueller Hinton broth (MHB) and a 100-µL sample of each was added to the first well of a 96-well plate. A 50-µL sample of the first well was then serially diluted two-fold through 50-µL NMB medium in wells 2-11. A bacterial culture was prepared from a frozen (−80° C.) stock in the organism's respective growth medium and grown overnight. The culture was then diluted in MHB until the turbidity matched that of McFarland standard 0.5 by measuring the optical density at 600 nm (1×10[8] cfu/mL). Then, the culture was diluted 1:100 and a 50-µL aliquot was added to wells 1-11, resulting in 2-fold dilutions of antibiotic from 64 µg/mL down to 0.0625 µg/mL and a final inoculum of 5×10[5] cfu/mL. A 100-µL aliquot of MHB medium was added to well 12 as a sterility control, and a row containing no antibiotic was used as a growth control. The plate was incubated at the organism's respective growth temperature overnight or 72 h (S. himastatinicus). The MIC was determined by observing the well density by eye and, with the exception of S. himastatinicus which grows in solid colonies in media, was confirmed by measuring the optical density of each well at 600 nm. At least two assays were conducted for each organism on identical lots of compound. No degradation of compound stocks in dimethylsulfoxide was observed by LC-MS analysis after being subjected to multiple freeze-thaw cycles. Dimethylsulfoxide alone (vehicle) did not affect bacterial growth at the range of concentrations tested.

Microscopy.

B. subtilis (ATCC 6633) was used for all microscopy experiments. For time-course studies at lethal concentration, culture containing 1 µg/mL FM 4-64 was combined with medium containing himastatin before being immediately added to a 1% agarose pad containing 0.5 µg/mL sytox green (Invitrogen). One section of the agarose pad was then imaged every 5 minutes to monitor cell death. For studies of morphological changes in sub-lethal concentrations, culture was incubated with 0.25 µg/mL (−) or (+)-himastatin for 3 h at 37 C, before being combined with FM 4-64 and added to an agarose pad containing sytox green. Images were collected on a Zeiss AxioPlan2 upright microscope using phase-contrast and equipped with a Hamamatsu Orca-ER cooled CCD camera using standard filter sets for GFP (to visualize SYTOX green; excitation 470/40 nm and emission 525/50 nm), TxRED (to visualize FM 4-64; excitation 565/40 and emission 620/60 nm), and DIC (for phase-contrast). Additional imaged were collected with an RPI Spinning Disk Confocal microscope equipped with a Hamamatsu Orca-ER cooled CCD camera using standard filter sets for GFP (488 nm laser, emission 525/50 nm), RFP (561 nm laser, emission 605/70 nm), and brightfield.

Confocal Microscopy.

B. subtilis (ATCC 6633) in Mueller Hinton broth (NMB) was used for all microscopy experiments. For time-course studies with natural himastatin at lethal concentration, a bacterial culture matching the optical density of McFarland standard 0.5 (1×10[8] cfu/mL) was supplemented with 1 µg/mL FM 4-64 before being combined with medium containing (−)- or (+)-himastatin (1) (2 µg/mL) immediately before imaging on a 1% agarose pad containing 0.5 µg/mL SYTOX Green (Invitrogen). One section of the agarose pad was then imaged every 5 min to monitor cell death. For studies of morphological changes in bacteria treated with sub-lethal concentrations, culture was incubated with 0.25 µg/mL (−)- or (+)-himastatin (1) for 3 h at 37° C., before being supplemented with 1 µg/mL FM 4-64 and added immediately to an agarose pad. For studies using TAMRA-himastatin (−)-25, growing cultures (1×10[8] cfu/mL) were incubated with 8 or 16 µg/mL TAMRA-himastatin (−)-25 for 30 min before being transferred to an agarose pad and imaged. Images were collected on a Zeiss AxioPlan2 upright microscope equipped with a Hamamatsu Orca-ER cooled CCD camera using standard filter sets for GFP (to visualize SYTOX Green; excitation 470/40 nm and emission 525/50 nm), TxRED (to visualize FM 4-64 or TAMRA; excitation 565/40 and emission 620/60 nm), and phase-contrast (tungsten halogen lamp); or on an RPI Spinning Disk Confocal microscope equipped with a Hamamatsu Orca-ER cooled CCD camera using standard filter sets for GFP (to visualize SYTOX Green; 488 nm laser, emission 525/50 nm), RFP (to visualize FM 4-64; 561 nm laser, emission 605/70 nm).

Biogenetic Hypothesis.

Our proposed dimerization mechanism for the cytochrome P450 enzyme HmtS is shown in Scheme S1.[8] We propose that two monomers, likely held simultaneously within the enzyme active site, undergo successive hydrogen-atom abstractions by high-valent iron-oxo and iron-hydroxo porphyrin species, followed by C5-C5 radical-radical coupling to give (−)-himastatin (1). Our proposal is supported by multiple structural and computational studies of related P450-mediated C—C coupling reactions. Specifically, several structural studies of cytochrome P450 enzymes with functions similar to that of HmtS have demonstrated that the enzyme active site can accommodate simultaneous binding of individual fragments and may guide the regio- and stereochemical course of their union.[9] Furthermore, recent theoretical calculations have shown that radical-radical coupling is strongly preferred ($\Delta\Delta G^{\ddagger}=>25$ kcal/mol) over other potential pathways for C—C bond formation (in particular, radical addition to a neutral monomer).[10] The favorability of the radical-radical coupling pathway is additionally supported by the finding that the generation of a second monomer radical through a subsequent N—H or O—H hydrogen-atom abstraction by iron(IV)-hydroxo compound II is nearly barrierless ($\Delta G^{\ddagger}=<1$ kcal/mol).[b,c] We propose that two monomers (+)-2 undergo indoline N—H hydrogen-atom abstractions in rapid succession by high-valent iron-oxo and iron-hydroxo porphyrin species, followed by C5-C5 radical-radical coupling to give (−)-himastatin (1). In support of this proposal, theoretical calculations) have established that C—C bond formation via radical-radical coupling is strongly preferred over radical addition to a neutral monomer, and that N—H or O—H hydrogen-atom abstraction by iron(IV)-hydroxo cpd II to generate a second monomer radical is virtually barrierless. cpd=cytochrome p450 compound.

P450 compound I and P450 compound II are denoted as cpd I and cpd II, respectively.

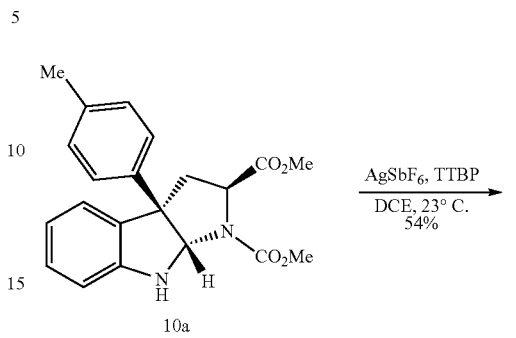

Scheme S1. Proposed mechanism for the dimerization reaction catalyzed by HmtS

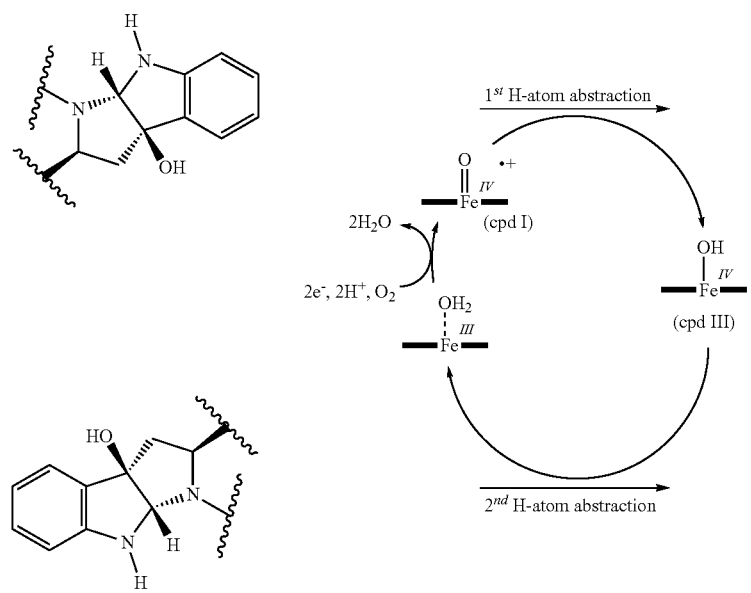

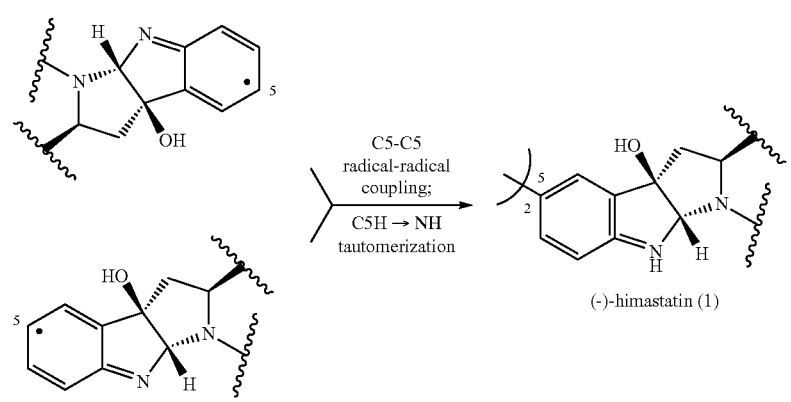

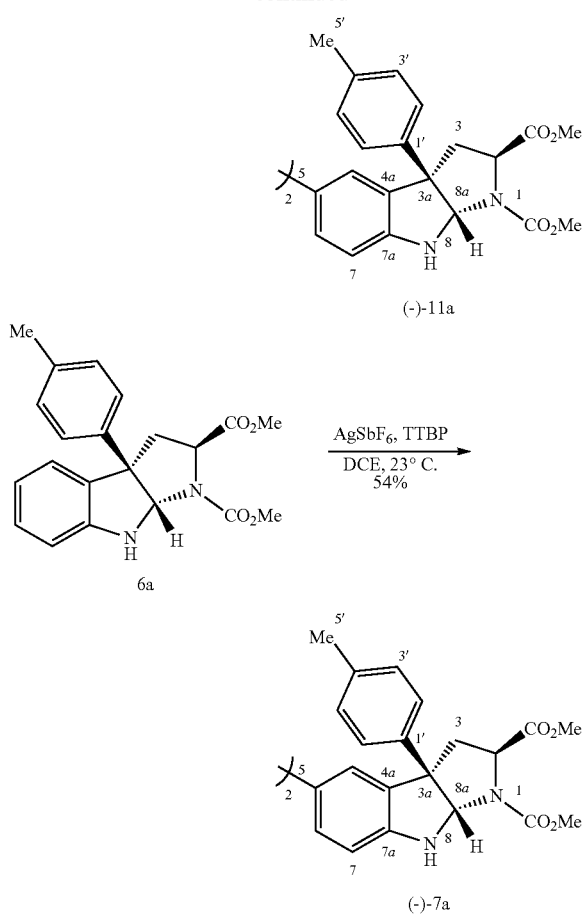

p-Tolyl Cyclotryptophan Dimer (−)-7a:

A sample of silver(I) hexafluoroantimonate (86.0 mg, 0.250 mmol, 5.00 equiv) was added to a solution of p-tolyl cyclotryptophan 6a (18.3 mg, 50.0 μmol, si 1 equiv) and 2,4,6-tri-tert-butyl-4-methylpyrimidine (TTBP, 31.1 mg, 0.125 mmol, 2.50 equiv) in 1,2-dichloethane (500 μL) at 23° C. After 40 min, the heterogeneous solution was diluted with dichloromethane (10 mL), a saturated aqueous sodium thiosulfate solution (5 mL), a saturated aqueous sodium hydrogen carbonate solution (5 mL), and deionized water (10 mL) and was stirred vigorously for 1 h. The layers were separated and the aqueous layer was extracted with dichloromethane (10 mL). The combined organic extracts were washed with a saturated aqueous sodium chloride solution (10 mL), were dried over anhydrous sodium sulfate, were filtered, and were concentrated under reduced pressure. The resulting residue was purified by flash column chromatography on silica gel (eluent: 40%→60% ethyl acetate in hexanes) to afford p-tolyl cyclotryptophan dimer (−)-7a (9.8 mg, 54%) as an off-white solid. Structural assignments were made using additional information from gCOSY, gHSQC, and gHMBC experiments.

Cu(II)-Catalyzed Dimerization:

Replacing silver(I) hexafluoroantimonate and 2,4,6-tri-tert-butyl-4-methylpyrimidine (TTBP) in the above procedure with copper(II) trifluoromethanesulfonate (1.45 mg, 4.00 μmol, 0.200 equiv) and silver(I) carbonate (13.8 mg, 50.0 μmol, 2.50 equiv) and increasing the reaction time to 30 h afforded p-tolyl cyclotryptophan dimer (−)-7a (2.5 mg, 34%) and recovered p-tolyl cyclotryptophan 6a (1.3 mg, 18%). No reaction was observed with silver(I) carbonate alone. $^1$H NMR (500 MHz, CDCl$_3$, 25° C., 1.6:1 mixture of atropisomers, * denotes minor atropisomer):

δ 7.29-7.21 (m, 12H, C3'H, C3'H*, C6H, C6H*), 7.19 (d, J=1.4 Hz, 2H, C4H), 7.17 (d, J=1.4 Hz, 2H, C4H*), 7.10 (d, J=8.0 Hz, 8H, C2'H, C2'H*), 6.71 (d, J=8.1 Hz, 2H, C7H), 6.69 (d, J=8.1 Hz, 2H, C7H*), 5.64 (s, 2H, C8aH), 5.57 (s, 2H, C8aH*), 5.54 (br-s, 2H, N8H), 5.00 (br-s, 2H, N8H*), 4.22-4.15 (m, 4H, C2H, C2H*), 3.81 (s, 6H, N1CO$_2$CH$_3$*), 3.76 (s, 6H, C2CO$_2$CH$_3$*), 3.74 (s, 6H, C2CO$_2$CH$_3$), 3.66 (s, 6H, N1CO$_2$CH$_3$), 3.05 (dd, J=12.8, 7.2 Hz, 2H, C3H$_a$), 2.97 (dd, J=12.6, 6.6 Hz, 2H, C3H$_a$*), 2.81 (d, J=12.3 Hz, 2H, C3H$_b$*), 2.75 (dd, J=12.8, 9.5 Hz, 2H, C3H$_b$), 2.29 (s, 12H, C5'H$_3$, C5'H$_3$*).

$^{13}$C NMR (125.8 MHz, CDCl$_3$, 25° C., 1.6:1 mixture of atropisomers, * denotes minor atropisomer):

δ 173.0 (C2CO$_2$), 172.6 (C2CO$_2$*), 154.9 (N1CO$_2$), 154.5 (N1CO$_2$*), 147.4 (C7a), 147.0 (C7a*), 139.4 (C1'*), 139.3 (C1'), 137.1 (2C, C4', C4'*) 133.6 (C5*), 133.4 (C5), 132.8 (C4a), 132.6 (C4a*), 129.6 (2C, C3', C3'*), 127.5 (2C, C6, C6*), 125.9 (2C, C2', C2'*), 122.3 (2C, C4, C4*), 110.8 (C7), 110.4 (C7*), 84.7 (C8a), 83.9 (C8a*), 60.4 (C3a*), 60.3 (C2*), 59.8 (C2), 59.3 (C3a), 53.2 (N1CO$_2$CH$_3$*), 52.7 (N1CO$_2$CH$_3$), 52.6 (C2CO$_2$CH$_3$*), 52.5 (C2CO$_2$CH$_3$), 41.0 (C3), 40.7 (C3*), 21.1 (2C, C5, C5').

FTIR (thin film) cm$^{-1}$:3385 (br-m), 3021 (m), 2953 (m), 1747 (s), 1700 (s), 1480 (m), 1449 (s), 1200 (m), 1045 (m), 884 (m), 753 (s).

HRMS (ESI) (m/z): calc'd for C$_{42}$H$_{43}$N$_4$O$_8$ [M+H]$^+$: 731.0375, found: 731.3074.

$[α]_D^{23}$: −323 (c=0.46, CHCl$_3$).

TLC (60% ethyl acetate in hexanes), Rf: 0.34 (UV, CAM).

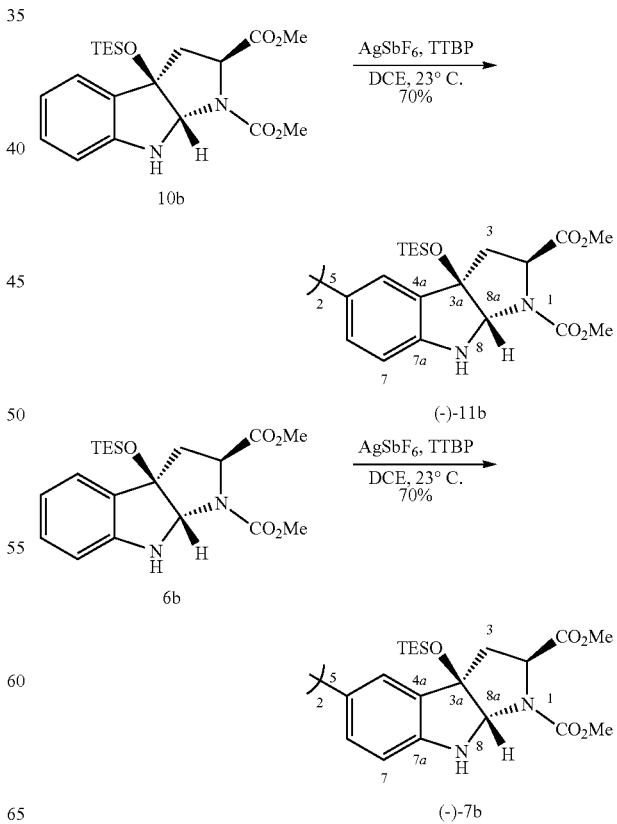

Triethylsiloxy Cyclotryptophan Dimer (−)-7b:

Prepared according to the procedure described previously for p-tolyl cyclotryptophan dimer (−)-7a from triethylsiloxy cyclotryptophan 6b (20.1 mg, 49.4 μmol, 1 equiv.) after a reaction time of 2.5 h. Triethylsilyloxy cyclotryptophan dimer (−)-7b was obtained by flash column chromatography on silica gel (eluent: 30%→50% ethyl acetate in hexanes) as a colorless film (14.1 mg, 70.3%). Structural assignments were made using additional information from gCOSY, gHSQC, and gHMBC experiments.

$^1$H NMR (500 MHz, CDCl$_3$, 25° C., 1.6:1 mixture of atropisomers, * denotes minor atropisomer): δ 7.35-7.33 (m, 4H, C6H, C6H*), 7.31 (d, J=1.9 Hz, 2H, C4H), 7.29 (d, J=1.9 Hz, 2H, C4H*), 6.66 (d, J=8.2 Hz, 2H, C7H), 6.65 (d, J=8.1 Hz, 2H, C7H*), 5.40 (d, J=1.8 Hz, 2H, C8aH), 5.34 (s, 2H, C8aH*), 5.31 (br-s, 2H, N8H), 4.92 (br-s, 2H, N8H*), 4.28-4.21 (m, 4H, C2H, C2H*), 3.81 (s, 6H, N1CO$_2$CH$_3$*), 3.76 (s, 6H, C2CO$_2$CH$_3$*), 3.75 (s, 6H, C2CO$_2$CH$_3$), 3.68 (s, 6H, N1CO$_2$CH$_3$), 2.72-2.56 (m, 8H, C3H$_2$, C3H$_2$*), 0.87-0.82 (m, 36H, Si(CH$_2$CH$_3$)$_3$, Si(CH$_2$CH$_3$)$_3$*), 0.52-0.36 (m, 24H, Si(CH$_2$CH$_3$)$_3$, Si(CH$_2$CH$_3$)$_3$*).

$^{13}$C NMR (125.8 MHz, CDCl$_3$, 25° C., 1.6:1 mixture of atropisomers, * denotes minor atropisomer): δ 172.4 (C2CO$_2$), 172.0 (C2CO$_2$*), 155.5 (N1CO$_2$), 155.1 (N1CO$_2$*), 147.8 (C7a), 147.4 (C7a*), 133.2 (C5*), 132.9 (C5), 130.3 (C4a), 130.1 (C4a*), 128.9 (C4*), 128.8 (C4), 122.4 (2C, C6, C6*), 110.8 (C7), 110.6 (C7*), 88.8 (C3a*), 87.7 (C3a), 83.6 (C8a), 82.8 (C8a*), 59.6 (C2*), 59.2 (C2), 53.2 (N1CO$_2$CH$_3$*), 52.8 (N1CO$_2$CH$_3$), 52.5 (2C, C2CO$_2$CH$_3$, C2CO$_2$CH$_3$*), 43.7 (C3), 43.1 (C3*), 6.9 (2C, Si(CH$_2$CH$_3$)$_3$, Si(CH$_2$CH$_3$)$_3$*), 5.9 (Si(CH$_2$CH$_3$)$_3$*), 5.8 (Si(CH$_2$CH$_3$)$_3$).

FTIR (thin film) cm$^{-1}$:3377 (br-m), 2953 (m), 2876 (m), 1753 (s), 1703 (s), 1620 (m), 1482 (m), 1450 (s), 1260 (m), 1108 (m), 743 (s).

HRMS (ESI) (m/z): calc'd for C$_{40}$H$_{59}$N$_4$O$_{10}$Si$_2$ [M+H]$^+$: 811.3764, found: 811.3745.

[α]$_D^{23}$: −241 (c=0.69, CHCl$_3$).

TLC (50% ethyl acetate in hexanes), Rf: 0.37 (UV, CAM).

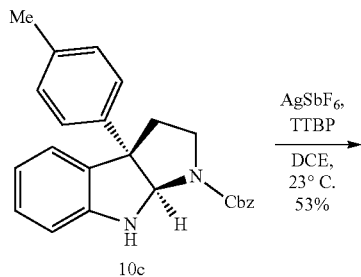

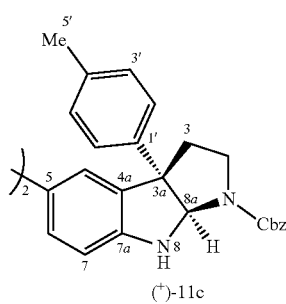

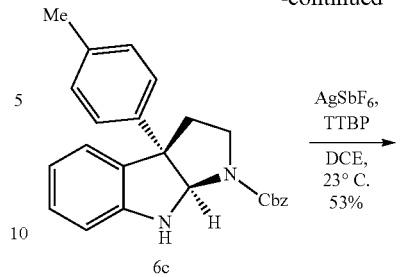

p-Tolyl Cyclotryptamine Dimer (+)-7c:

Prepared according to f the procedure described previously for p-tolyl cyclotryptophan dimer (−)-7a from p-tolyl cyclotryptamine 6c (19.0 mg, 50.0 μmol, 1 equiv) after a reaction time of 15 min. p-Tolyl cyclotryptamine dimer (+)-7c was obtained by flash column chromatography on silica gel (eluent: 20%→35% ethyl acetate in hexanes) as a colorless film (10.1 mg, 53%). Structural assignments were made using additional information from gCOSY, gHSQC, and gHMBC experiments.

$^1$H NMR (500 MHz, CDCl$_3$, 25° C., 1.4:1 mixture of atropisomers, * denotes minor atropisomer): δ 7.41-7.30 (m, 20H, Ar$_{Cbz}$H, Ar$_{Cbz}$H*), 7.29-7.21 (m, 12H, C3'H, C3'H*, C6H, C6H*), 7.16 (d, J=1.8 Hz, 2H, C4H), 7.13 (d, J=2.2 Hz, 2H, C4H*), 7.10 (d, J=7.9 Hz, 8H, C2'H, C2'H*), 6.68 (d, J=8.1 Hz, 2H, C7H), 6.61 (d, J=8.1 Hz, 2H, C7H*), 5.50 (s, 2H, C8aH), 5.43 (s, 2H, C8aH*), 5.27-5.21 (m, 4H, N8H, N1CO$_2$CH$_a$*), 5.18 (d, J=11.2 Hz, 4H, N1CO$_2$CH$_a$, N1CO$_2$CH$_a$*), 5.09 (d, J=12.4 Hz, 2H, N1CO$_2$CH$_b$), 4.68 (br-s, 2H, N8H*), 3.96-3.88 (m, 2H, C2H$_a$*), 3.88-3.80 (m, 2H, C2H$_a$), 3.25-3.18 (m, 4H, C2H$_b$, C2H$_b$*), 2.74-2.55 (m, 8H, C3H$_2$, C3H$_2$*), 2.29 (s, 12H, C5'H$_3$, C5'H$_3$*).

$^{13}$C NMR (125.8 MHz, CDCl$_3$, 25° C., 1.4:1 mixture of atropisomers, * denotes minor atropisomer):

δ 154.9 (N1CO$_2$), 154.0 (N1CO$_2$*), 147.9 (C7a), 147.6 (C7a*), 140.7 (C1'*), 140.6 (C1'), 136.9 (C4'*), 136.8 (C4'), 136.6 (2C, Ar$_{Cbz}$-ipso-C, Ar$_{Cbz}$-ipso-C*), 133.5 (C5*), 133.2 (C5), 133.1 (2C, C4a, C4a*), 129.5 (2C, C3', C3'*), 128.8 (Ar$_{Cbz}$), 128.6 (Ar$_{Cbz}$), 128.4 (Ar$_{Cbz}$*), 128.2 (2C, Ar$_{Cbz}$*), 128.0 (Ar$_{Cbz}$), 127.1 (2C, C6, C6*), 125.9 (2C, C2', C2'*), 122.1 (2C, C4, C4*), 110.3 (C7), 110.0 (C7*), 83.7 (C8a), 83.2 (C8a*), 67.3 (N1CO$_2$CH$_2$*), 67.0 (N1CO$_2$CH$_2$), 61.3 (C3a*), 60.2 (C3a), 46.6 (C2*), 46.3 (C2), 36.3 (C3), 35.9 (C3*), 21.1 (2C, C5, C5').

FTIR (thin film) cm$^{-1}$:3373 (br-m), 3027 (m), 2952 (m), 1691 (s), 1513 (m), 1353 (m), 1479 (m), 1415 (s), 1194 (m), 1112 (m), 752 (m).

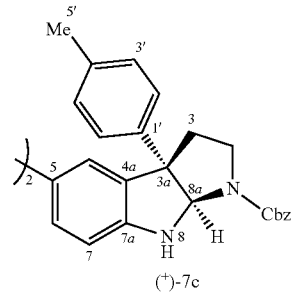

HRMS (ESI) (m/z): calc'd for $C_{50}H_{47}N_4O_4$ $[M+H]^+$: 767.3592, found: 767.3586.

$[\alpha]_D^{23}$: +336 (c=0.46, $CHCl_3$).

TLC (30% ethyl acetate in hexanes), Rf: 0.30 (UV, CAM).

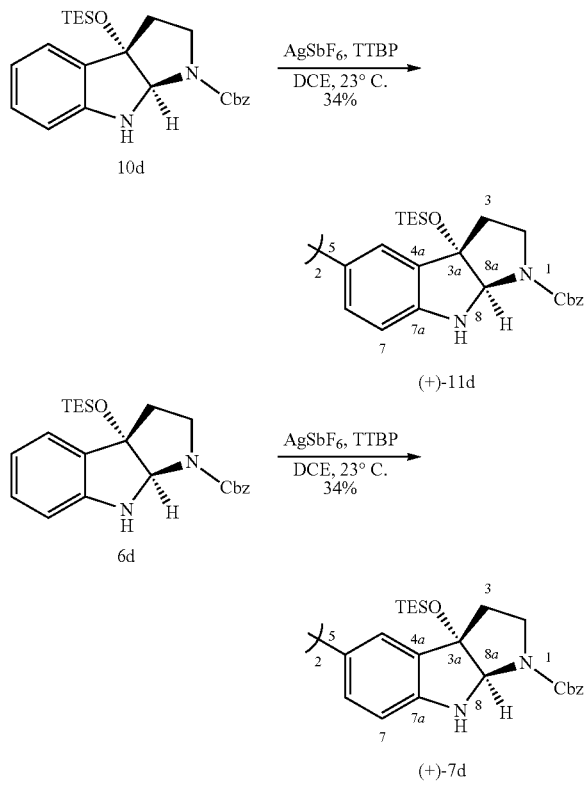

Triethylsiloxy Cyclotryptamine Dimer (+)-7d:

Prepared according to the procedure described previously for p-tolyl cyclotryptophan dimer (−)-7a from triethylsilyloxy cyclotryptamine 6d (21.2 mg, 50.0 μmol, 1 equiv) after a reaction time of 20 min. Triethylsilyloxy cyclotryptamine dimer (+)-7d was obtained by flash column chromatography on silica gel (eluent: 20%→30% ethyl acetate in hexanes) as a colorless film (7.1 mg, 34%). Structural assignments were made using additional information from gCOSY, gHSQC, and gHMBC experiments.

$^1$H NMR (500 MHz, $CDCl_3$, 25° C., 1.5:1 mixture of atropisomers, * denotes minor atropisomer): δ 7.43-7.40 (m, 8H, $Ar_{Cbz}$H, $Ar_{Cbz}$H*), 7.38-7.36 (m, 4H, C4H, C4H*), 7.35-7.27 (m, 16H, C6H, C6H*, $Ar_{Cbz}$H, $Ar_{Cbz}$H*), 6.66 (d, J=8.1 Hz, 2H, C7H), 6.59 (d, J=8.2 Hz, 2H, C7H*), 5.26-5.15 (m, 12H, C8aH, C8aH*, N8H, N1CO$_2$CH$_a$, N1CO$_2$CH$_2$*), 5.08 (d, J=12.4 Hz, 2H, N1CO$_2$CH$_b$), 4.67 (br-s, 2H, N8H*), 3.80 (ddd, J=10.7, 6.9, 3.6 Hz, 2H, C2H$_a$*), 3.72 (ddd, J=10.6, 7.8, 2.6 Hz, 2H, C2H$_a$), 3.17-3.06 (m, 4H, C2H$_b$, C2H$_b$*), 2.54-2.38 (m, 8H, C3H$_2$, C3H$_2$*), 0.85 (t, J=7.9 Hz, 36H, Si(CH$_2$CH$_3$)$_3$, Si(CH$_2$CH$_3$)$_3$*), 0.52-0.37 (m, 24H, Si(CH$_2$CH$_3$)$_3$, Si(CH$_2$CH$_3$)$_3$*).

$^{13}$C NMR (125.8 MHz, $CDCl_3$, 25° C., 1.5:1 mixture of atropisomers, * denotes minor atropisomer):
δ 155.2 (N1CO$_2$), 154.4 (N1CO$_2$*), 148.8 (C7a), 148.4 (C7a*), 136.8 ($Ar_{Cbz}$-ipso-C*), 136.6 ($Ar_{Cbz}$-ipso-C), 133.1 (C5*), 132.8 (C5), 130.2 (C4a), 130.1 (C4a*), 128.8 (3C, C6, C6*, $Ar_{Cbz}$*), 128.7 ($Ar_{Cbz}$), 128.4 (2C, $Ar_{Cbz}$*), 128.2 (2C, $Ar_{Cbz}$, $Ar_{Cbz}$*), 128.0 ($Ar_{Cbz}$), 122.6 (2C, C4, C4*), 110.4 (C7), 110.3 (C7*), 89.7 (C3a*), 88.6 (C3a), 82.0 (C8a), 81.8 (C8a*), 67.3 (N1CO$_2$CH$_2$*), 67.0 (N1CO$_2$CH$_2$), 45.9 (C2*), 45.5 (C2), 38.6 (C3), 38.4 (C3*), 7.0 (2C, Si(CH$_2$CH$_3$)$_3$, Si(CH$_2$CH$_3$)$_3$*), 5.9 (Si(CH$_2$CH$_3$)$_3$*), 5.8 (Si(CH$_2$CH$_3$)$_3$).

FTIR (thin film) cm$^{-1}$: 3361 (br-m), 2953 (m), 2875 (m), 1699 (s), 1481 (m), 1455 (s), 1194 (m), 1101 (m), 743 (s).

HRMS (ESI) (m/z): calc'd for $C_{48}H_{63}N_4O_6Si_2$ $[M+H]^+$: 847.4281, found: 847.4282.

$[\alpha]_D^{23}$: +284 (c=0.17, $CHCl_3$).

TLC (20% ethyl acetate in hexanes), Rf: 0.29 (UV, CAM).

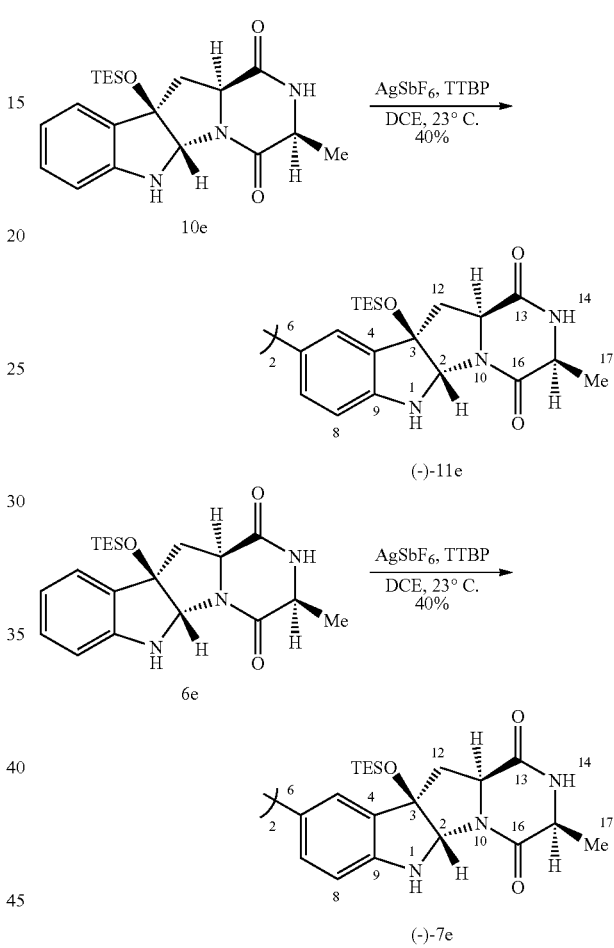

Alanine Exo-Diketopiperazine Dimer (−)-7e:

Prepared according to the procedure described previously for p-tolyl cyclotryptophan dimer (−)-7a from alanine exo-diketopiperazine 6e (16.7 mg, 43.1 μmol, 1 equiv.) after a reaction time of 20 min. Alanine exo-diketopiperazine dimer (−)-7e was obtained by flash column chromatography on silica gel (eluent: 20%→50% acetone in dichloromethane) as a white solid (6.6 mg, 40%). Structural assignments were made using additional information from gCOSY, gHSQC, and gHMBC experiments.

$^1$H NMR (500 MHz, $CDCl_3$, 25° C.): δ 7.40 (d, J=1.9 Hz, 2H, C5H), 7.32 (dd, J=8.1, 1.8 Hz, 2H, C7H), 6.68 (d, J=8.1 Hz, 2H, C8H), 5.99 (s, 2H, N14H), 5.34 (s, 2H, C2H), 5.19 (br-s, 2H, N1H), 4.09-3.99 (m, 4H, C11H, C15H), 2.94 (dd, J=12.7, 6.1 Hz, 2H, C12H$_a$), 2.68 (app-t, J=12.2 Hz, 2H, C12H$_b$), 1.47 (s, 6H, C17H$_3$), 0.85 (t, J=7.9 Hz, 18H, Si(CH$_2$CH$_3$)$_3$), 0.50-0.36 (m, 12H, Si(CH$_2$CH$_3$)$_3$).

$^{13}$C NMR (125.8 MHz, $CDCl_3$, 25° C.): δ 169.1 (C13), 167.3 (C16), 148.9 (C9), 133.2 (C6), 129.4 (C7), 129.1 (C4), 123.0 (C5), 110.6 (C8), 86.8 (C3), 80.9 (C2), 58.9 (C11), 51.2 (C15), 41.8 (C12), 16.5 (C17), 6.9 (Si(CH$_2$CH$_3$)$_3$), 5.7 (Si(CH$_2$CH$_3$)$_3$).

FTIR (thin film) cm$^{-1}$: 3257 (br-m), 2955 (m), 2876 (m), 1675 (s), 1420 (m), 1307 (w), 1211 (w), 1107 (m), 7n44 (m).

HRMS (ESI) (m/z): calc'd for C$_{40}$H$_{57}$N$_6$O$_6$Si$_2$ [M+H]$^+$: 773.3873, found: 773.3864.

[α]$_D^{23}$: −440 (c=0.16, MeOH).

TLC (40% acetone in dichloromethane), Rf: 0.22 (UV, CAM).

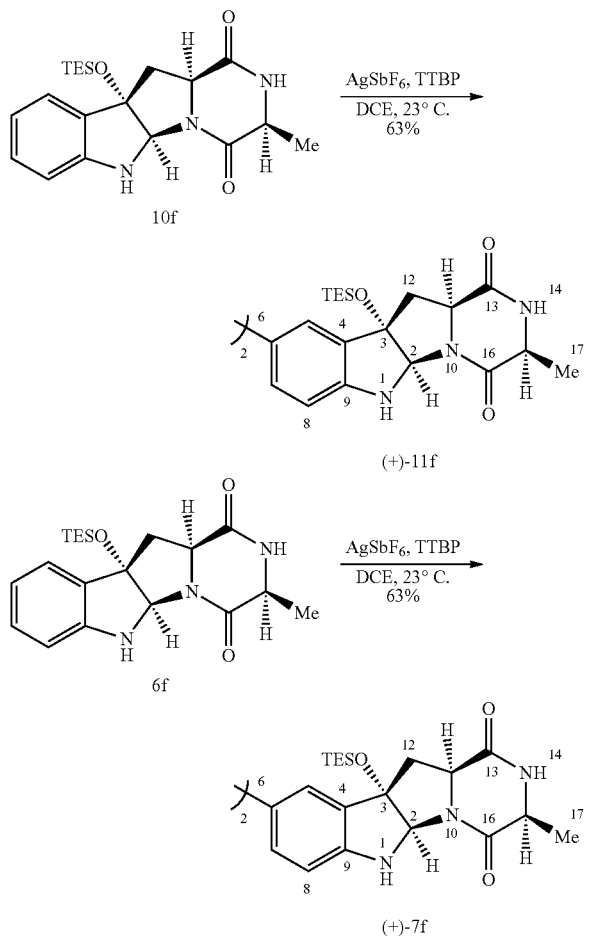

Alanine Endo-Diketopiperazine Dimer (+)-7f:

Prepared according to the procedure described previously for p-tolyl cyclotryptophan dimer (−)-7a from alanine endo-diketopiperazine 6f (19.0 mg, 49.0 µmol, 1 equiv) after a reaction time of 30 min. Alanine endo-diketopiperazine dimer (+)-7f was obtained by flash column chromatography on silica gel (eluent: 20%→60% acetone in dichloromethane) as a white solid (11.9 mg, 63%). Structural assignments were made using additional information from gCOSY, gHSQC, and gHMBC experiments.

$^1$H NMR (500 MHz, CDCl$_3$, 25° C.): δ 7.37 (d, J=1.9 Hz, 2H, C5H), 7.29 (dd, J=8.2, 1.9 Hz, 2H, C7H), 6.63 (d, J=8.2 Hz, 2H, C8H), 6.53 (s, 2H, N14H), 5.51 (s, 2H, C2H), 5.29 (br-s, 2H, N1H), 4.58 (ddd, J=10.7, 6.9, 1.5 Hz, 2H, C11H), 4.17 (qd, J=6.8, 1.5 Hz, 2H, C15H), 2.77 (dd, J=13.3, 6.7 Hz, 2H, C12H$_a$), 2.39 (dd, J=13.3, 10.7 Hz, 2H, C12H$_b$), 1.47 (d, J=6.8 Hz, 6H, C17H$_3$), 0.87 (t, J=7.9 Hz, 18H, Si(CH$_2$CH$_3$)$_3$), 0.57-0.44 (m, 12H, Si(CH$_2$CH$_3$)$_3$).

$^{13}$C NMR (125.8 MHz, CDCl$_3$, 25° C.): δ 169.9 (C13), 168.1 (C16), 146.2 (C9), 133.0 (C6), 130.3 (C4), 128.4 (C7), 121.7 (C5), 110.6 (C8), 88.6 (C3), 84.7 (C2), 59.0 (C11), 51.3 (C15), 43.6 (C12), 16.3 (C17), 6.9 (Si(CH$_2$CH$_3$)$_3$), 6.2 (Si(CH$_2$CH$_3$)$_3$).

FTIR (thin film) cm$^{-1}$: 3349 (br-m), 3269 (br-m), 2953 (m), 2874 (m), 1672 (s), 1414 (m), 1301 (m), 1190 (m), 1114 (m), 1004 (m), 728 (s).

HRMS (ESI) (m/z): calc'd for C$_{40}$H$_{57}$N$_6$O$_6$Si$_2$ [M+H]$^+$: 773.3873, found: 773.3872.

[α]$_D^{23}$: +217 (c=0.52, CHCl$_3$).

TLC (40% acetone in dichloromethane), Rf: 0.35 (UV, CAM).

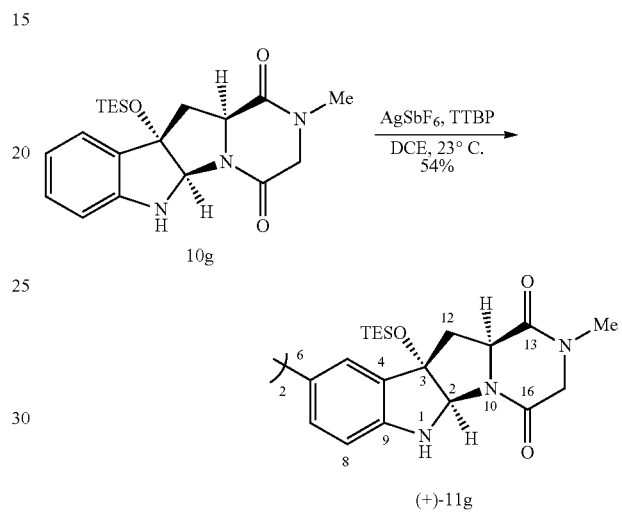

Glycine Endo-Diketopiperazine Dimer (+)-11g:

Prepared according to the procedure described previously for p-tolyl cyclotryptophan dimer (−)-11a from glycine endo-diketopiperazine 10g (19.7 mg, 49.1 µmol, 1 equiv.) after a reaction time of 20 min. Glycine endo-diketopiperazine dimer (+)-11g was obtained by flash column chromatography on silica gel (eluent: 20%→40% acetone in dichloromethane) as a white solid (10.7 mg, 54.4%). Crystals suitable for X-ray diffraction were obtained by layer diffusion of n-heptane into a solution of (+)-11g in dichloromethane at 2° C. Crystallographic data tables and a thermal ellipsoid projection of (+)-11g are provided later in this document. Structural assignments were made using additional information from gCOSY, gHSQC, and gHMBC experiments.

$^1$H NMR (500 MHz, CDCl$_3$, 25° C.): δ 7.38 (d, J=1.9 Hz, 2H, C5H), 7.30 (dd, J=8.2, 1.9 Hz, 2H, C7H), 6.64 (d, J=8.2 Hz, 2H, C8H), 5.52 (d, J=3.8 Hz, 2H, C2H), 5.18 (d, J=3.9 Hz, 2H, N1H), 4.56 (ddd, J=11.5, 6.2, 1.7 Hz, 2H, C11H), 4.21 (dd, J=17.2, 1.9 Hz, 2H, C15H$_a$), 3.86 (d, J=17.2 Hz, 2H, C15H$_b$), 2.97 (s, 6H, N14CH$_3$), 2.85 (dd, J=13.3, 6.4 Hz, 2H, C12H$_a$), 2.32 (dd, J=13.3, 11.3 Hz, 2H, C12H$_b$), 0.87 (t, J=7.9 Hz, 18H, Si(CH$_2$CH$_3$)$_3$), 0.57-0.44 (m, 12H, Si(CH$_2$CH$_3$)$_3$).

$^{13}$C NMR (125.8 MHz, CDCl$_3$, 25° C.): δ 166.8 (C13), 164.4 (C16), 146.2 (C9), 133.1 (C6), 130.4 (C4), 128.4 (C7), 121.7 (C5), 110.6 (C8), 88.7 (C3), 84.8 (C2), 58.4 (C11), 53.6 (C15), 44.7 (C12), 33.7 (N14CH$_3$), 6.9 (Si(CH$_2$CH$_3$)$_3$), 6.2 (Si(CH$_2$CH$_3$)$_3$).

FTIR (thin film) cm$^{-1}$: 3322 (br-m), 2952 (m), 2874 (m), 1667 (s), 1455 (m), 1190 (m), 1117 (m), 1012 (m), 741 (m).

HRMS (ESI) (m/z): calc'd for $C_{40}H_{57}N_6O_6Si_2$ [M+H]$^+$: 773.3873, found: 773.3863.

$[\alpha]_D^{23}$: +193 (c=0.43, CHCl$_3$).

TLC (40% acetone in dichloromethane), Rf: 0.38 (UV, CAM).

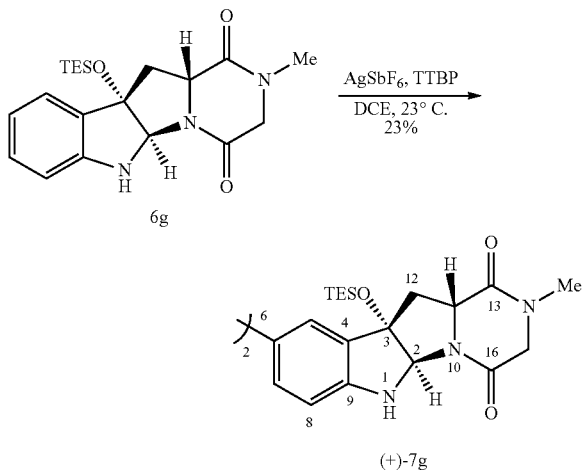

6g

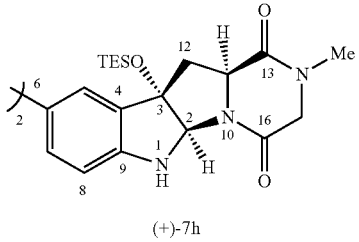

(+)-7h

Glycine Endo-Diketopiperazine Dimer (+)-7h:

Prepared according to the procedure described previously for p-tolyl cyclotryptophan dimer (−)-7a from glycine endo-diketopiperazine 6h (19.7 mg, 49.1 µmol, 1 equiv) after a reaction time of 20 min. Glycine endo-diketopiperazine dimer (+)-7g was obtained by flash column chromatography on silica gel (eluent: 20%→40% acetone in dichloromethane) as a white solid (10.7 mg, 54%). Crystals suitable for X-ray diffraction were obtained by layer diffusion of n-heptane into a solution of dimer (+)-7g in dichloromethane at 2° C. Crystallographic data tables and a thermal ellipsoid projection of dimer (+)-7g are provided later in this document. Structural assignments were made using additional information from gCOSY, gHSQC, and gHMBC experiments.

$^1$H NMR (500 MHz, CDCl$_3$, 25° C.): δ 7.38 (d, J=1.9 Hz, 2H, C5H), 7.30 (dd, J=8.2, 1.9 Hz, 2H, C7H), 6.64 (d, J=8.2 Hz, 2H, C8H), 5.52 (d, J=3.8 Hz, 2H, C2H), 5.18 (d, J=3.9 Hz, 2H, N1H), 4.56 (ddd, J=11.5, 6.2, 1.7 Hz, 2H, C11H), 4.21 (dd, J=17.2, 1.9 Hz, 2H, C15H$_a$), 3.86 (d, J=17.2 Hz, 2H, C15H$_b$), 2.97 (s, 6H, N14CH$_3$), 2.85 (dd, J=13.3, 6.4 Hz, 2H, C12H$_a$), 2.32 (dd, J=13.3, 11.3 Hz, 2H, C12H$_b$), 0.87 (t, J=7.9 Hz, 18H, Si(CH$_2$CH$_3$)$_3$), 0.57-0.44 (m, 12H, Si(CH$_2$CH$_3$)$_3$).

$^{13}$C NMR (125.8 MHz, CDCl$_3$, 25° C.): δ 166.8 (C13), 164.4 (C16), 146.2 (C9), 133.1 (C6), 130.4 (C4), 128.4 (C7), 121.8 (C5), 110.6 (C8), 88.7 (C3), 84.8 (C2), 58.4 (C11), 53.6 (C15), 44.7 (C12), 33.7 (N14CH$_3$), 6.9 (Si(CH$_2$CH$_3$)$_3$), 6.2 (Si(CH$_2$CH$_3$)$_3$).

FTIR (thin film) cm$^{-1}$: 3322 (br-m), 2952 (m), 2874 (m), 1667 (s), 1455 (m), 1190 (m), 1117 (m), 1012 (m), 741 (m).

HRMS (ESI) (m/z): calc'd for $C_{40}H_{57}N_6O_6Si_2$ [M+H]$^+$: 773.3873, found: 773.3863.

$[\alpha]_D^{23}$: +193 (c=0.43, CHCl$_3$).

TLC (40% acetone in dichloromethane), Rf: 0.38 (UV, CAM).

(+)-7g

Glycine Exo-Diketopiperazine Dimer (+)-7g:

Prepared according to the procedure described previously for p-tolyl cyclotryptophan dimer (−)-6a from glycine exo-diketopiperazine 7g (19.0 mg, 49.0 µmol, 1 equiv) after a reaction time of 15 min. Glycine exo-diketopiperazine dimer (+)-7g was obtained by flash column chromatography on silica gel (eluent: 20%→50% acetone in dichloromethane) as a white solid (4.2 mg, 23%). Structural assignments were made using additional information from gCOSY, gHSQC, and gHMBC experiments.

$^1$H NMR (500 MHz, CDCl$_3$, 25° C.): δ 7.40 (d, J=1.9 Hz, 2H, C5H), 7.32 (dd, J=8.2, 1.8 Hz, 2H, C7H), 6.68 (d, J=8.1 Hz, 2H, C8H), 5.38 (s, 2H, C2H), 5.07 (br-s, 2H, N1H), 4.10 (dd, J=17.2, 1.9 Hz, 2H, C15H$_a$), 3.99 (ddd, J=12.2, 6.1, 2.2 Hz, 2H, C11H), 3.82 (d, J=17.2 Hz, 2H, C15H$_b$), 3.01-2.95 (m, 8H, C12H$_a$, N14CH$_3$), 2.64 (app-t, J=12.3 Hz, 2H, C12H$_b$), 0.84 (t, J=7.9 Hz, 18H, Si(CH$_2$CH$_3$)$_3$), 0.51-0.36 (m, 12H, Si(CH$_2$CH$_3$)$_3$).

$^{13}$C NMR (125.8 MHz, CDCl$_3$, 25° C.): δ 166.3 (C13), 163.8 (C16), 148.9 (C9), 133.2 (C6), 129.4 (C7), 129.0 (C4), 123.1 (C5), 110.5 (C8), 87.1 (C3), 80.9 (C2), 58.3 (C11), 53.3 (C15), 42.8 (C12), 33.8 (N14CH$_3$), 6.9 (Si(CH$_2$CH$_3$)$_3$), 5.7 (Si(CH$_2$CH$_3$)$_3$).

FTIR (thin film) cm$^{-1}$: 3342 (br-m), 2955 (m), 2876 (m), 1666 (s), 1458 (m), 1245 (m), 1148 (m), 745 (m).

HRMS (ESI) (m/z): calc'd for $C_{40}H_{57}N_6O_6Si_2$ [M+H]$^+$: 773.3873, found: 773.3870.

$[\alpha]_D^{23}$: +434 (c=0.15, CHCl$_3$).

TLC (40% acetone in dichloromethane), Rf: 0.28 (UV, CAM).

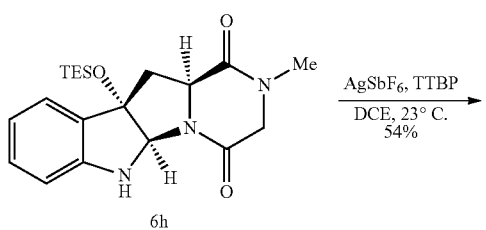

6h

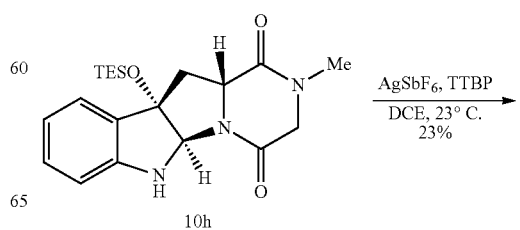

10h

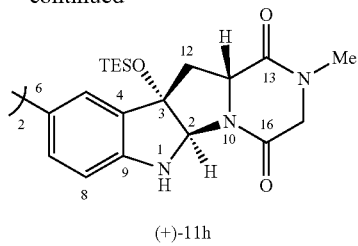

(+)-11h

Glycine Exo-Diketopiperazine Dimer (+)-11h:

Prepared according to a scale-down of the procedure described previously for p-tolyl cyclotryptophan dimer (−)-11a from glycine exo-diketopiperazine 10h (19.0 mg, 49.0 μmol, 1 equiv.) after a reaction time of 15 min. Glycine exo-diketopiperazine dimer (+)-11h was obtained by flash column chromatography on silica gel (eluent: 20%→50% acetone in dichloromethane) as a white solid (4.2 mg, 23%). Structural assignments were made using additional information from gCOSY, gHSQC, and gHMBC experiments.

$^1$H NMR (500 MHz, CDCl$_3$, 25° C.): δ 7.40 (d, J=1.9 Hz, 2H, C5H), 7.32 (dd, J=8.2, 1.8 Hz, 2H, C7H), 6.68 (d, J=8.1 Hz, 2H, C8H), 5.38 (s, 2H, C2H), 5.07 (br-s, 2H, N1H), 4.10 (dd, J=17.2, 1.9 Hz, 2H, C15H$_a$), 3.99 (ddd, J=12.2, 6.1, 2.2 Hz, 2H, C11H), 3.82 (d, J=17.2 Hz, 2H, C15H$_b$), 3.01-2.95 (m, 8H, C12H$_a$, N14CH$_3$), 2.64 (app-t, J=12.3 Hz, 2H, C12H$_b$), 0.84 (t, J=7.9 Hz, 18H, Si(CH$_2$CH$_3$)$_3$), 0.51-0.36 (m, 12H, Si(CH$_2$CH$_3$)$_3$).

$^{13}$C NMR (125.8 MHz, CDCl$_3$, 25° C.): δ 166.3 (C13), 163.8 (C16), 148.9 (C9), 133.2 (C6), 129.4 (C7), 129.0 (C4), 123.1 (C5), 110.5 (C8), 87.1 (C3), 80.9 (C2), 58.3 (C11), 53.3 (C15), 42.8 (C12), 33.8 (N14CH$_3$), 6.9 (Si(CH$_2$CH$_3$)$_3$), 5.7 (Si(CH$_2$CH$_3$)$_3$).

FTIR (thin film) cm$^{-1}$: 3342 (br-m), 2955 (m), 2876 (m), 1666 (s), 1458 (m), 1245 (m), 1148 (m), 745 (m).

HRMS (ESI) (m/z): calc'd for C$_{40}$H$_{57}$N$_6$O$_6$Si$_2$ [M+H]$^+$: 773.3873, found: 773.3870.

$[\alpha]_D^{23}$: +434 (c=0.15, CHCl$_3$).

TLC (40% acetone in dichloromethane), Rf: 0.28 (UV, CAM).

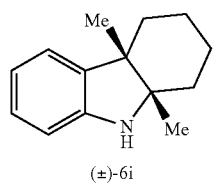

(±)-6i

AgSbF$_6$, TTBP
DCE, 23° C.
87%

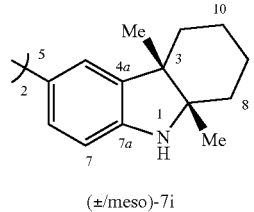

(±/meso)-7i

C2-Methyl Indoline Dimer 7i:

Prepared according to the procedure described previously for p-tolyl cyclotryptophan dimer (−)-7a from C2-methyl indoline (±)-6i (12.1 mg, 60.1 μmol, 1 equiv) after a reaction time of 5 min. C2-Methyl indoline dimer 7i was obtained as a diastereomeric mixture by flash column chromatography on silica gel (eluent: 5%→15% ethyl acetate in hexanes) as a colorless film (10.5 mg, 87%). Structural assignments were made using additional information from gCOSY, gHSQC, and gHMBC experiments.

$^1$H NMR (600 MHz, CDCl$_3$, 25° C., 1:1, mixture of diastereomers): δ 7.21 (dd, J=7.9, 1.9 Hz, 2H, C6H), 7.17 (d, J=1.9 Hz, 2H, C4H), 6.66 (d, J=7.9 Hz, 2H, C7H), 3.39 (br-s, 2H, N1H), 1.91 (ddd, J=14.1, 6.8, 3.1 Hz, 2H, C11H$_a$), 1.64-1.55 (m, 4H, C8H$_a$, C9H$_a$), 1.51-1.32 (m, 10H, C8H$_b$, C9H$_b$, C10CH$_2$, C11H$_b$), 1.19 (s, 6H, C2CH$_3$), 1.16 (s, 3H, C3CH$_3$), 1.15 (s, 3H, C3CH$_3$).

$^{13}$C NMR (150.9 MHz, CDCl$_3$, 25° C., 1:1 mixture of diastereomers): δ 147.4 (C7a), 139.1 (C4a), 133.4 (C5), 125.4 (C6), 120.4 (C4), 110.6 (C7), 66.4 (C2), 46.4 (C3), 36.9 (C8), 35.1 (C11), 22.9 (2C, C9, C3 CH$_3$), 22.5 (C10), 22.4 (C2CH$_3$).

FTIR (thin film) cm$^{-1}$: 3347 (br-m), 3015 (m), 2925 (m), 2854 (m), 1614 (m), 1475 (s), 1376 (m), 1251 (m), 1196 (m), 809 (m).

HRMS (ESI) (m/z): calc'd for C$_{28}$H$_{37}$N$_2$[M+H]$^+$: 401.2951, found: 401.2949.

TLC (15% ethyl acetate in hexanes), Rf: 0.29 (UV, CAM).

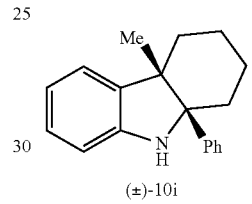

(±)-10i

AgSbF$_6$, TTBP
DCE, 23° C.
87%

(±/meso)-11i

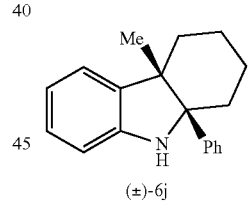

(±)-6j

AgSbF$_6$, TTBP
DCE, 23° C.
87%

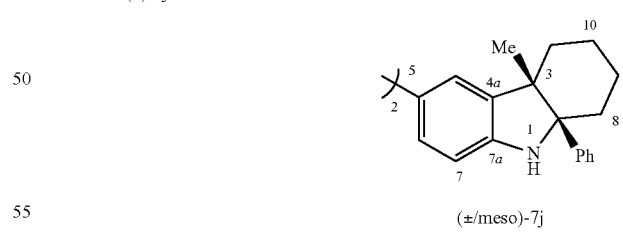

(±/meso)-7j

C2-Phenyl Indoline Dimer 7j:

Prepared according to the procedure described previously for p-tolyl cyclotryptophan dimer (−)-7a from C2-phenyl indoline (±)-6j (15.9 mg, 60.4 μmol, 1 equiv after a reaction time of 7 min. C2-phenyl indoline dimer 7j was obtained as a diastereomeric mixture by flash column chromatography on silica gel (eluent: 0%→10% ethyl acetate in hexanes) as a colorless film (13.8 mg, 87%). Structural assignments were made using additional information from gCOSY, gHSQC, and gHMBC experiments.

$^1$H NMR (600 MHz, CDCl$_3$, 25° C., 1:1, mixture of diastereomers): δ 7.71-7.68 (m, 4H, Ar$_{Ph}$-o-H), 7.37-7.31 (m, 4H, Ar$_{Ph}$-m-H), 7.30-7.24 (m, 4H, C6H, Ar$_{Ph}$-p-H), 7.17-7.16 (m, 2H, C4H), 6.77 (d, J=7.9 Hz, 2H, C7H), 3.90 (br-s, 2H, N1H), 2.12 (app-dt, J=14.4, 4.2 Hz, 2H, C11H$_a$), 2.08-2.04 (m, 2H, C8H$_a$), 1.85-1.75 (m, 6H, C8H$_b$, C9H$_a$, C11H$_b$), 1.73-1.66 (m, 4H, C9H$_b$, C10H$_a$), 1.59-1.52 (m, 2H, C10H$_b$), 0.80 (s, 3H, C3CH$_3$), 0.80 (s, 3H, C3CH$_3$).

$^{13}$C NMR (150.9 MHz, CDCl$_3$, 25° C., 1:1 mixture of diastereomers): δ 147.2 (C7a), 145.7 (Ar$_{Ph}$-ipso-C), 137.4 (C4a), 133.4 (C5), 128.0 (Ar$_{Ph}$-m-C), 126.9 (Ar$_{Ph}$-o-C), 126.6 (Ar$_{Ph}$-p-C), 125.8 (C6), 120.8 (C4), 110.0 (C7), 71.6 (C2), 47.9 (C3), 37.8 (C8), 34.0 (C11), 26.7 (C3CH$_3$), 22.7 (C9), 21.7 (C10).

FTIR (thin film) cm$^{-1}$: 3340 (br-m), 3020 (w), 2924 (m), 2859 (m), 1612 (m), 1478 (m), 1442 (m), 1248 (m), 1044 (m), 811 (m), 760 (m), 700 (m).

HRMS (ESI) (m/z): calc'd for C$_{38}$H$_{41}$N$_2$[M+H]$^+$: 525.3264, found: 525.3259.

TLC (10% ethyl acetate in hexanes), Rf: 0.28 (UV, CAM).

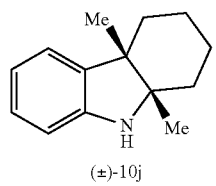

(±)-10j

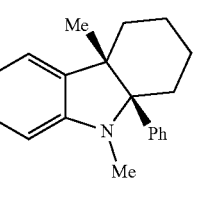

(±)-10k

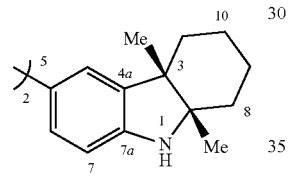

(±/meso)-11j

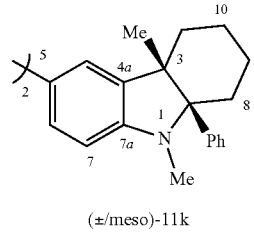

(±/meso)-11k

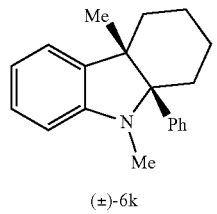

(±)-6k

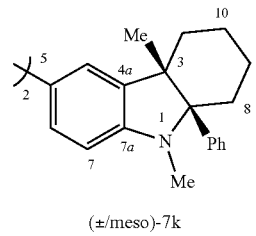

(±/meso)-7k

N-Methyl Indoline Dimer 7k:

Prepared according to a scale-up of the procedure described previously for p-tolyl cyclotryptophan dimer (−)-7a from C2-methyl indoline (±)-6k (12.1 mg, 60.1 μmol, 1 equiv.) after a reaction time of 5 min. C2-methyl indoline dimer 11j was obtained as a diastereomeric mixture by flash column chromatography on silica gel (eluent: 5%→15% ethyl acetate in hexanes) as a colorless film (10.5 mg, 87.2%). Structural assignments were made using additional information from gCOSY, gHSQC, and gHMBC experiments.

$^1$H NMR (600 MHz, CDCl$_3$, 25° C., 1:1, mixture of diastereomers): δ 7.21 (dd, J=7.9, 1.9 Hz, 2H, C6H), 7.17 (d, J=1.9 Hz, 2H, C4H), 6.66 (d, J=7.9 Hz, 2H, C7H), 3.39 (br-s, 2H, N1H), 1.91 (ddd, J=14.1, 6.8, 3.1 Hz, 2H, C11H$_a$), 1.64-1.55 (m, 4H, C8H$_a$, C9H$_a$), 1.51-1.32 (m, 10H, C8H$_b$, C9H$_b$, C10CH$_2$, C11H$_b$), 1.19 (s, 6H, C2CH$_3$), 1.16 (s, 3H, C3CH$_3$), 1.15 (s, 3H, C3CH$_3$).

$^{13}$C NMR (150.9 MHz, CDCl$_3$, 25° C., 1:1 mixture of diastereomers): δ 147.4 (C7a), 139.1 (C4a), 133.4 (C5), 125.4 (C6), 120.4 (C4), 110.6 (C7), 66.4 (C2), 46.4 (C3), 36.9 (C8), 35.1 (C11), 22.9 (2C, C9, C3 CH$_3$), 22.5 (C10), 22.4 (C2CH$_3$).

FTIR (thin film) cm$^{-1}$: 3347 (br-m), 3015 (m), 2925 (m), 2854 (m), 1614 (m), 1475 (s), 1376 (m), 1251 (m), 1196 (m), 809 (m).

HRMS (ESI) (m/z): calc'd for C$_{28}$H$_{37}$N$_2$[M+H]$^+$: 401.2951, found: 401.2949.

TLC (15% ethyl acetate in hexanes), Rf: 0.29 (UV, CAM).

N-Methyl Indoline Dimer 11k:

Prepared according to a scale-up of the procedure described previously for p-tolyl cyclotryptophan dimer (−)-11a from N-methyl indoline (±)-10k (16.8 mg, 60.6 μmol, 1 equiv.) after a reaction time of 5 min. N-methyl indoline dimer 7k was obtained as a diastereomeric mixture by flash column chromatography on silica gel (eluent: 0%→5% ethyl acetate in hexanes) as a yellow film (15.0 mg, 90%). Structural assignments were made using additional information from gCOSY, gHSQC, and gHMBC experiments.

$^1$H NMR (500 MHz, CDCl$_3$, 25° C., 1:1, mixture of diastereomers): δ 7.54-7.49 (m, 4H, Ar$_{Ph}$-o-H), 7.37-7.29 (m, 6H, C6H, Ar$_{Ph}$-m-H), 7.28-7.23 (m, 2H, Ar$_{Ph}$-p-H), 7.14-7.11 (m, 2H, C4H), 6.49 (d, J=8.0 Hz, 2H, C7H), 2.64 (s, 6H, N1CH$_3$), 2.21 (app-dt, J=13.1, 4.1 Hz, 2H, C8H$_a$), 1.97-1.88 (m, 2H, C11H$_a$), 1.85-1.67 (m, 6H, C8H$_b$, C9H$_2$), 1.66-1.55 (m, 4H, C11H$_b$, C10H$_a$), 1.53-1.45 (m, 2H, C10H$_b$), 0.75 (s, 3H, C3CH$_3$), 0.74 (s, 3H, C3CH$_3$).

$^{13}$C NMR (125.8 MHz, CDCl$_3$, 25° C., 1:1 mixture of diastereomers): δ 149.7 (C7a), 143.2 (Ar$_{Ph}$-ipso-C), 137.0 (C4a), 131.8 (C5), 128.0 (Ar$_{Ph}$-m-C), 127.9 (Ar$_{Ph}$-o-C), 126.7 (Ar$_{Ph}$-p-C), 125.6 (C6), 120.3 (C4), 106.2 (C7), 75.9 (C2), 48.2 (C3), 34.5 (C11), 30.1 (C8), 29.7 (N1CH$_3$), 27.2 (C3CH$_3$), 23.1 (C9), 21.2 (C10).

FTIR (thin film) cm$^{-1}$: 3347 (br-m), 3015 (m), 2925 (m), 2854 (m), 1614 (m), 1475 (s), 1376 (m), 1251 (m), 1196 (m), 809 (m).

HRMS (ESI) (m/z): calc'd for $C_{40}H_{45}N_2[M+H]^+$: 553.3577, found: 553.3563.

TLC (5% ethyl acetate in hexanes), Rf: 0.43 (UV, CAM).

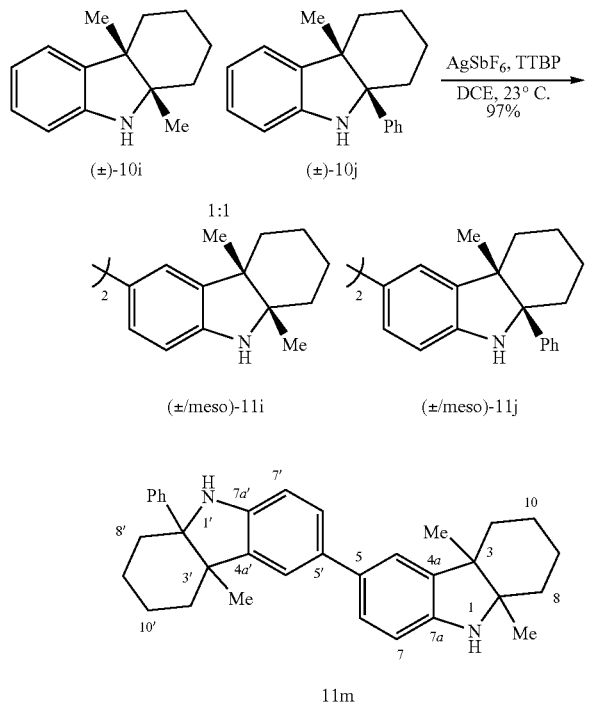

Figure 7:
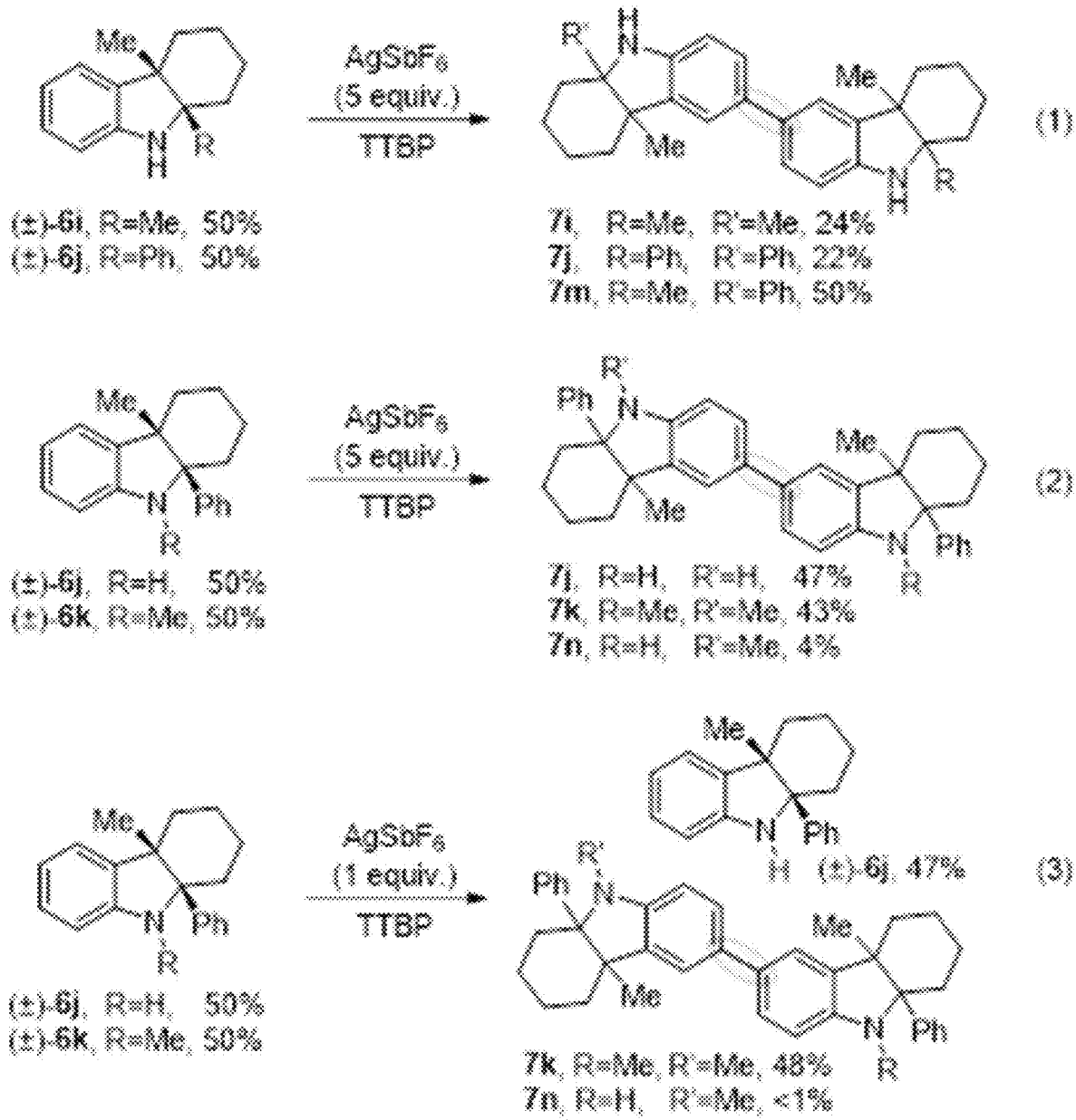
FIG. 7 shows the detailed summary of mechanistic experiments. Equimolar mixtures of indolines with similar rates of one-electron oxidation give rise to a statistical mixture of homo-/heterodimers upon dimerization (eq. 1). Homodimer formation predominates, however, when N-substitution is introduced (eq. 2). A competition experiment reveals that N-methyl indoline dimerizes much faster due to its increased rate of one-electron oxidation, with NH indoline 6j effectively acting as a spectator (eq. 3). A separate competition experiment revealed that despite the faster rate of oxidation, N-methyl indoline 6 k is only moderately more nucleophilic than NH indoline 6j, as determined by their rates of aromatic bromination with N-bromosuccinimide in chloroform-d ($k_{rel}$=2). Reagents and conditions: $AgSbF_6$, TTBP, $ClCH_2CH_2Cl$, 23° C. TTBP=2,4,6-tri-tert-butylpyrimidine.
Figure 8:
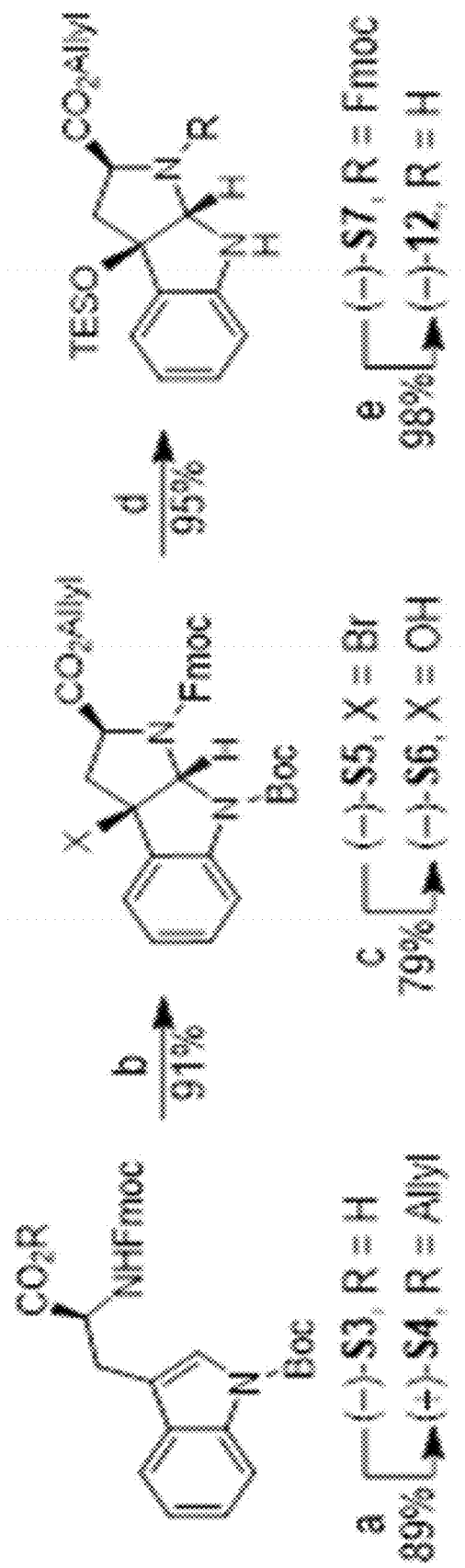
FIG. 8 shows the synthesis of cyclotryptophan (−)-12. Diastereoselective bromocyclization secures efficient gram-scale access to (−)-12 from commercially available tryptophan precursor (+)-S3. Reagents and conditions: (a) $H_2C=CHCH_2OH$, T3P, pyridine, 0→23° C.; (b) NBS, PPTS, $CH_2Cl_2$, 23° C.; (c) $AgSbF_6$, $H_2O$, DTBMP, $MeNO_2$, 23° C.; (d) TESOTf, i-$Pr_2NEt$, $CH_2Cl_2$, 0→23° C.; (e) piperidine, MeCN, 23° C. Boc=tert-butyloxycarbonyl; DTBMP=2,6-di-tert-butyl-4-methylpyridine; Fmoc=9-fluorenylmethoxycarbonyl; NBS=N-bromosuccinimide; PPTS=pyridinium para-toluenesulfonate; T3P=propanephosphonic acid anhydride; TES=triethylsilyl.
Figure 9:
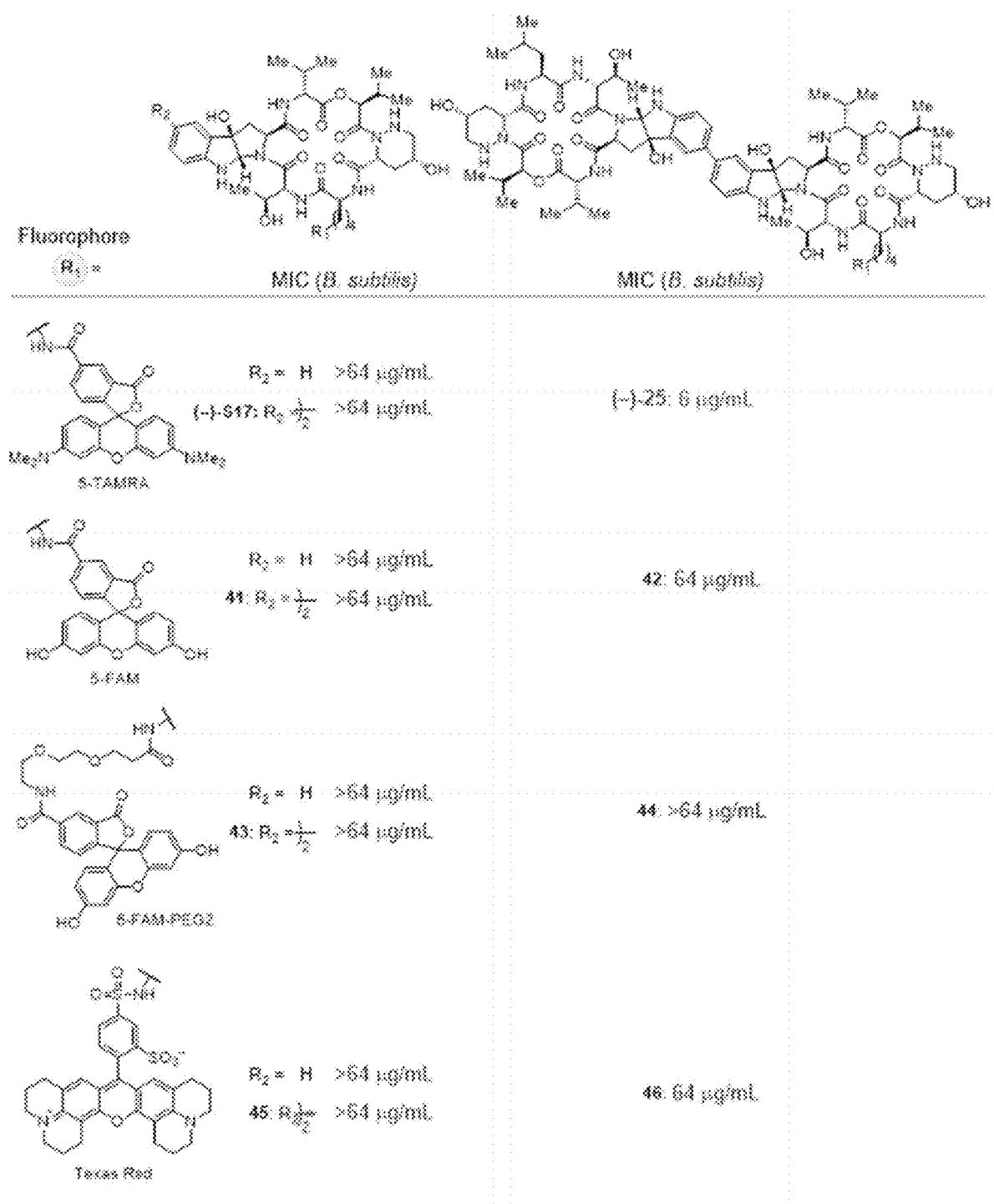
FIG. 9 shows the antibiotic activity of monomeric, homodimeric, and heterodimeric himastatin fluorescent derivatives against *Bacillus subtilis*.
Figures 10A, 10B:
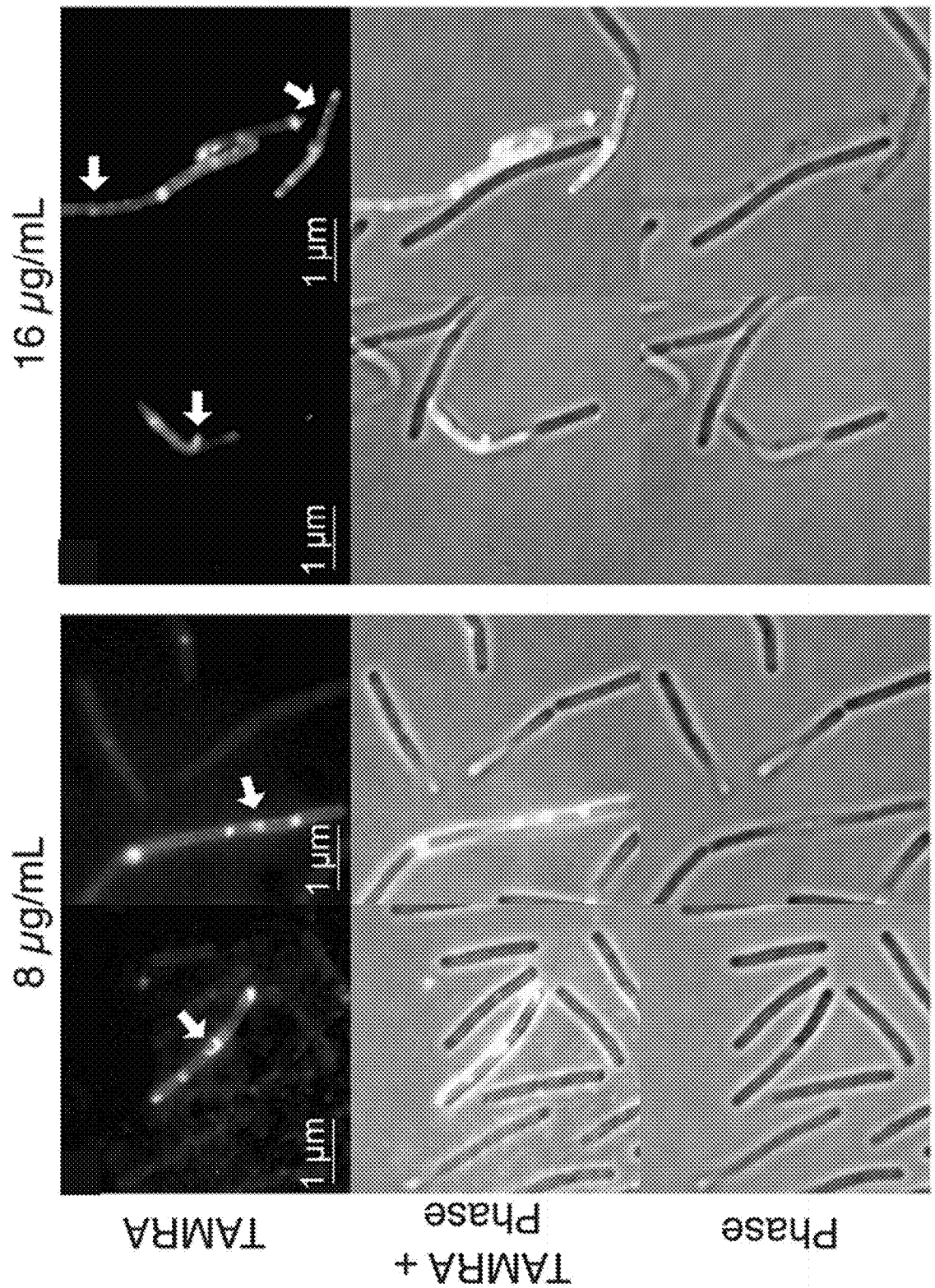
FIGS. 10A-10B show the heterodimeric fluorescent himastatin probe enables direct visualization of its interaction with bacteria. Confocal fluorescence and phase-contrast micrographs showing (−)-TAMRA-himastatin (25, orange) staining of *B. subtilis* during growth. Cells were labeled with (FIG. 10A) 8 μg/mL or (FIG. 10B) 16 μg/mL of TAMRA-himastatin. Cells incubated at 8 μg/mL (near the MIC) show intense septal staining (white arrows). At 16 μg/mL, fluorescence also accumulates at discrete foci along bacterial sidewalls and sites of membrane extrusion (white arrows). The middle row of frames correspond to overlaid fluorescence (top row) and phase-contrast (bottom row) images.
Figures 11A, 11B, 11C:
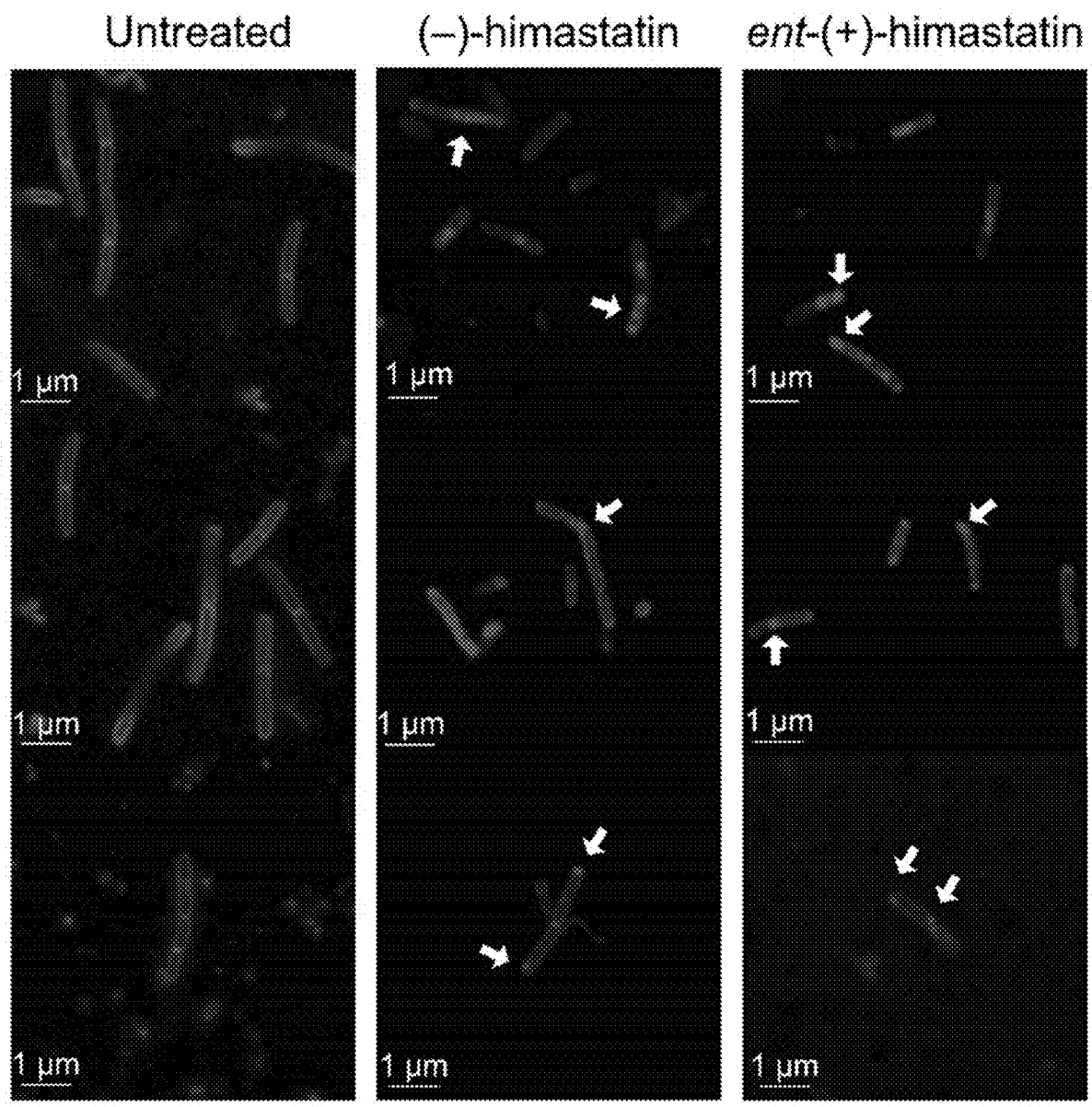
FIGS. 11A-11C shows that himastatin leads to visual membrane defects following sublethal treatment in bacteria. Confocal micrographs showing (FIG. 11A) untreated *B. subtilis*, or *B. subtilis* incubated with a sublethal concentration (0.25 μg/mL) of either (FIG. 11B) (−)-himastatin (1) or (FIG. 11C) ent-(+)-himastatin (1), stained with FM 4-64 (membrane, red). White arrows highlight regions of abnormal membrane thickening.
Figure 13:
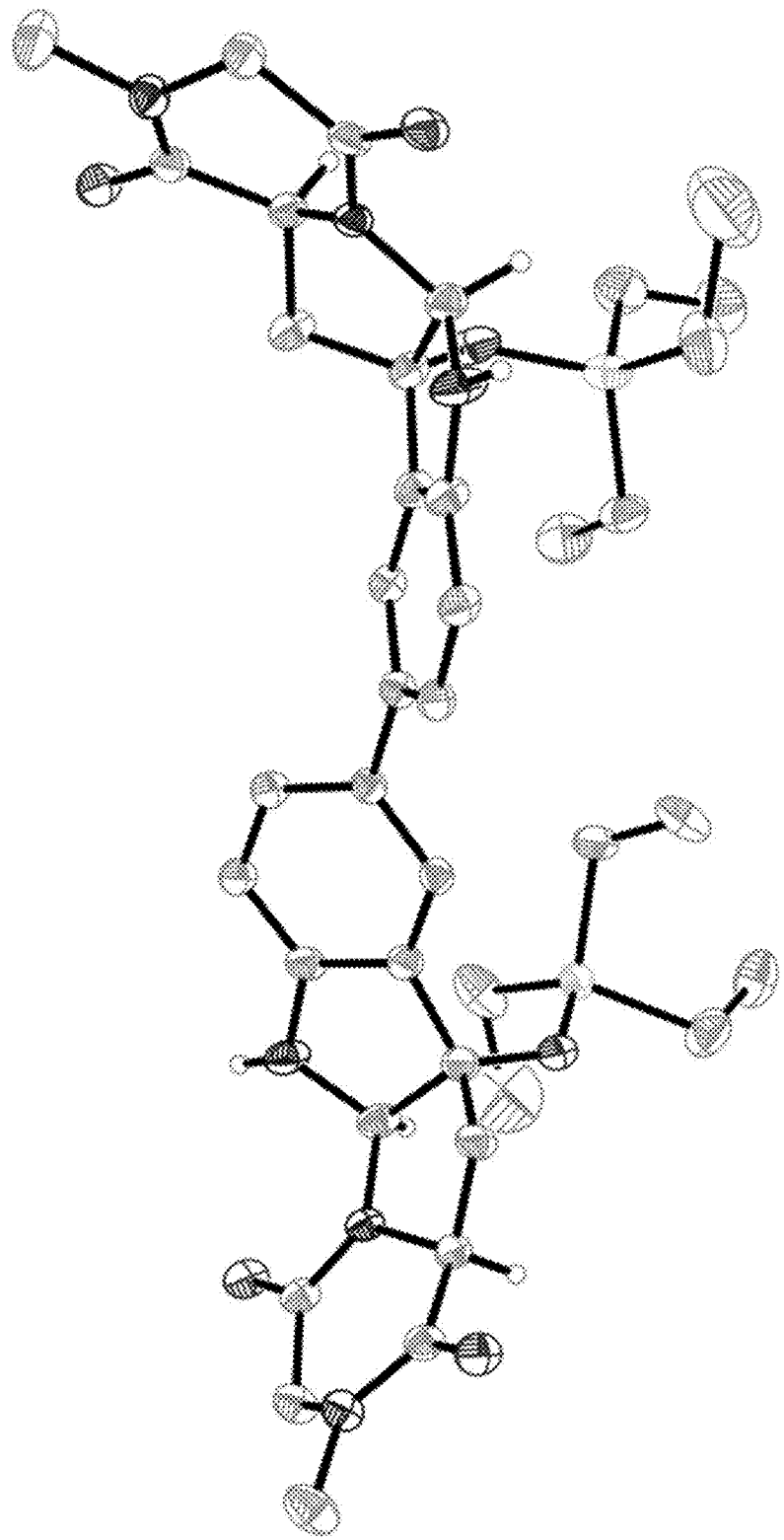
FIG. 13 shows the crystal structure of glycine endo-diketopiperazine dimer (+)-7h
Figure 14:
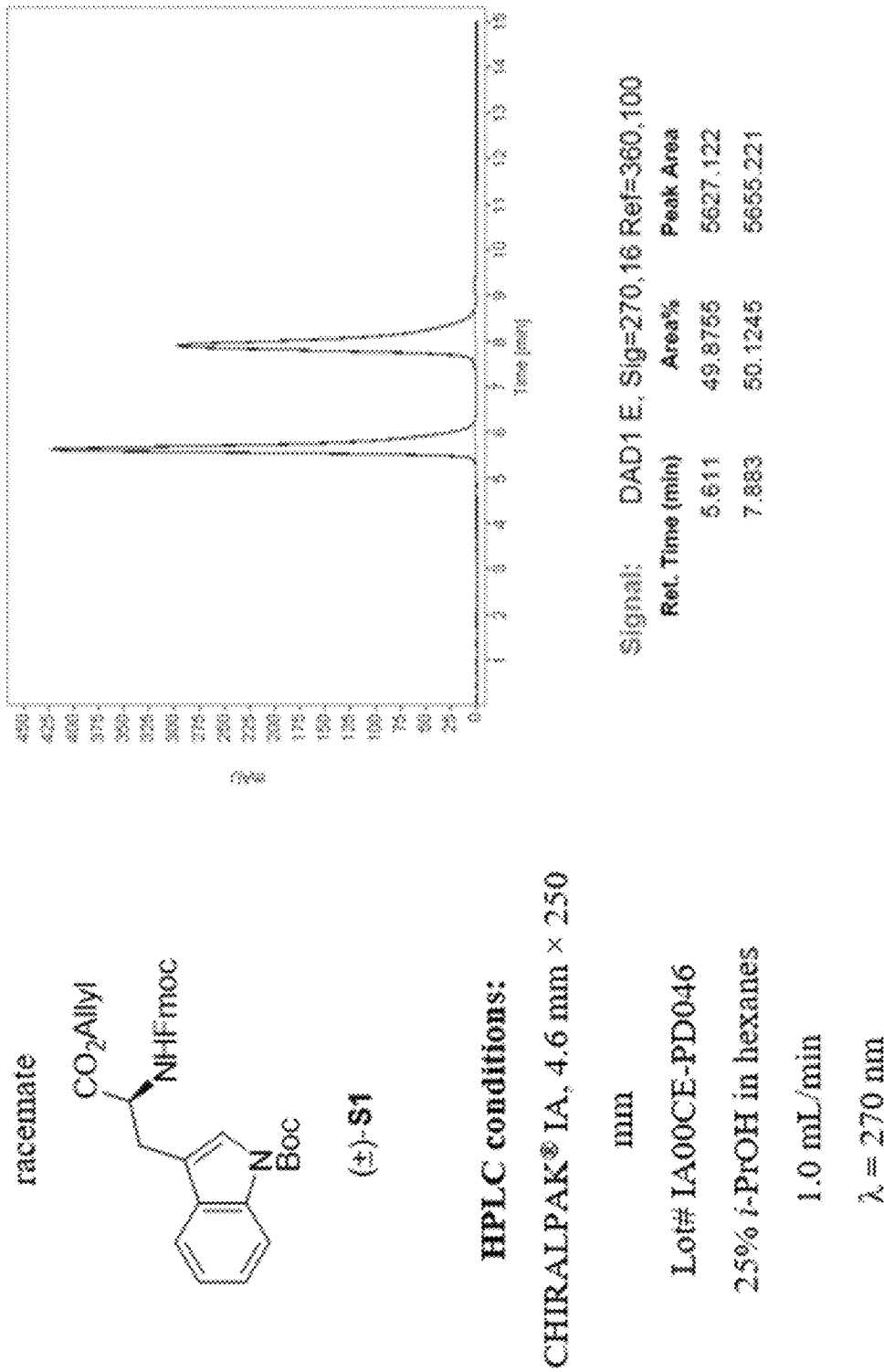
FIG. 14 shows an HPLC chromatogram.
Figure 16A:
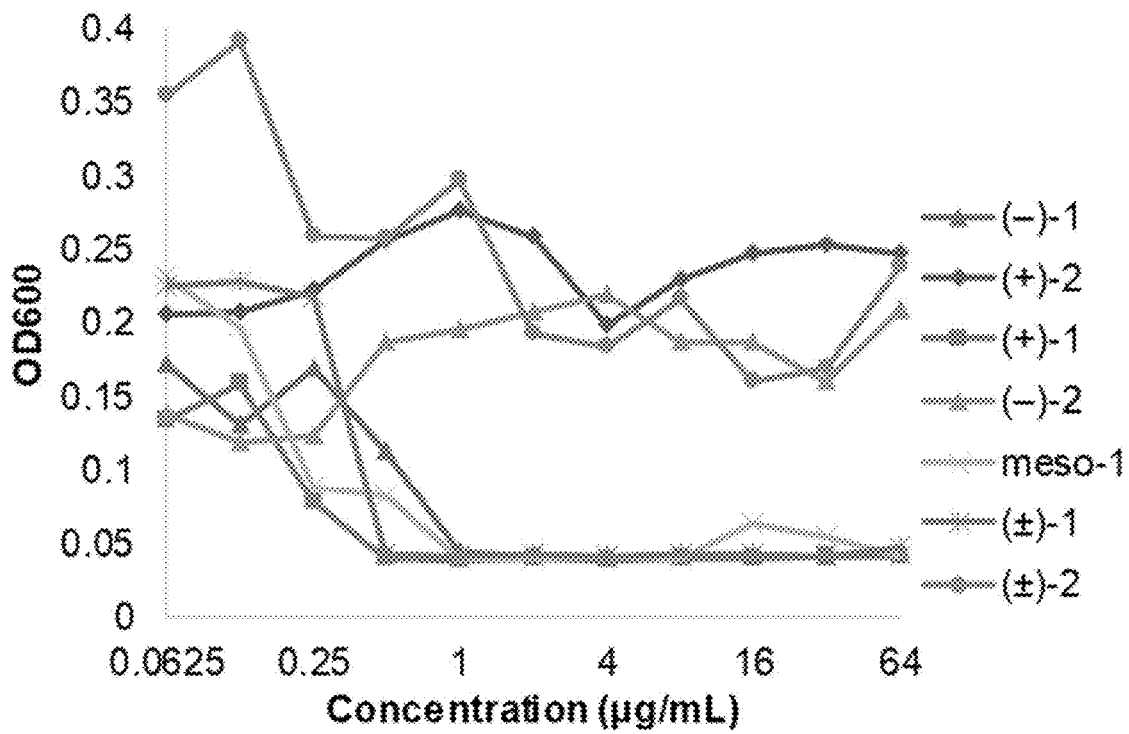
FIGS. 16A-16D show the concentration-response (OD600) curves of representative broth microdilution assays of *B. subtilis*.
Figure 16B:
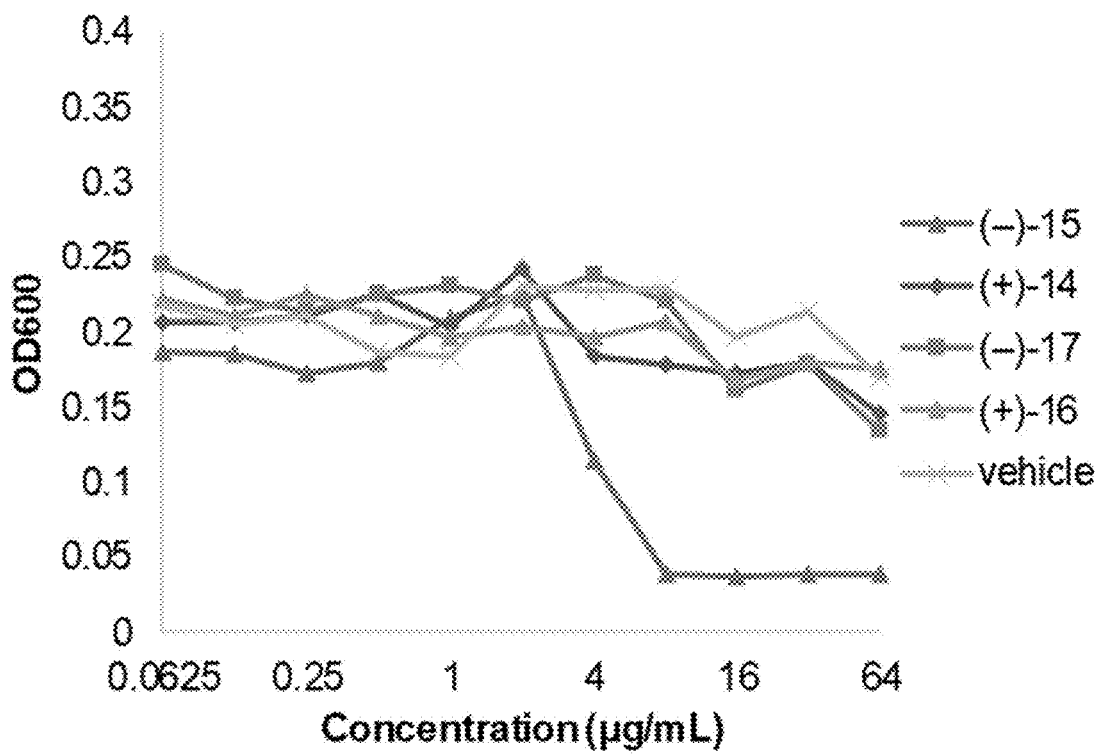
Figure 16C:
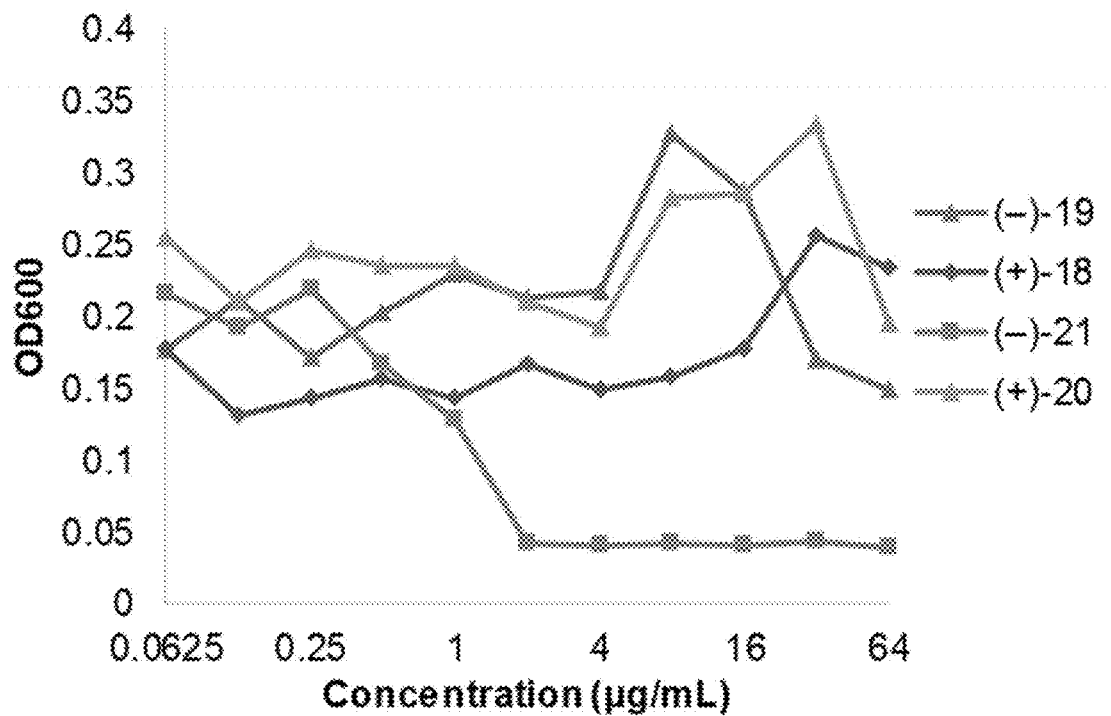
Figure 16D:
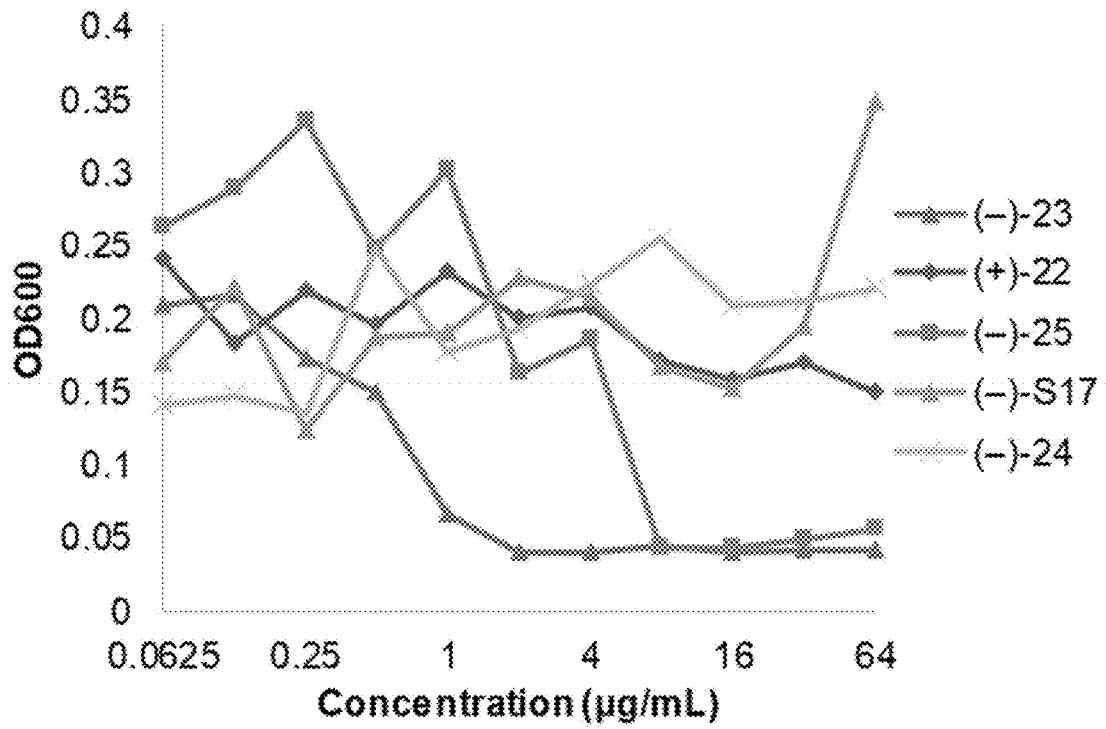
Figure 17A:
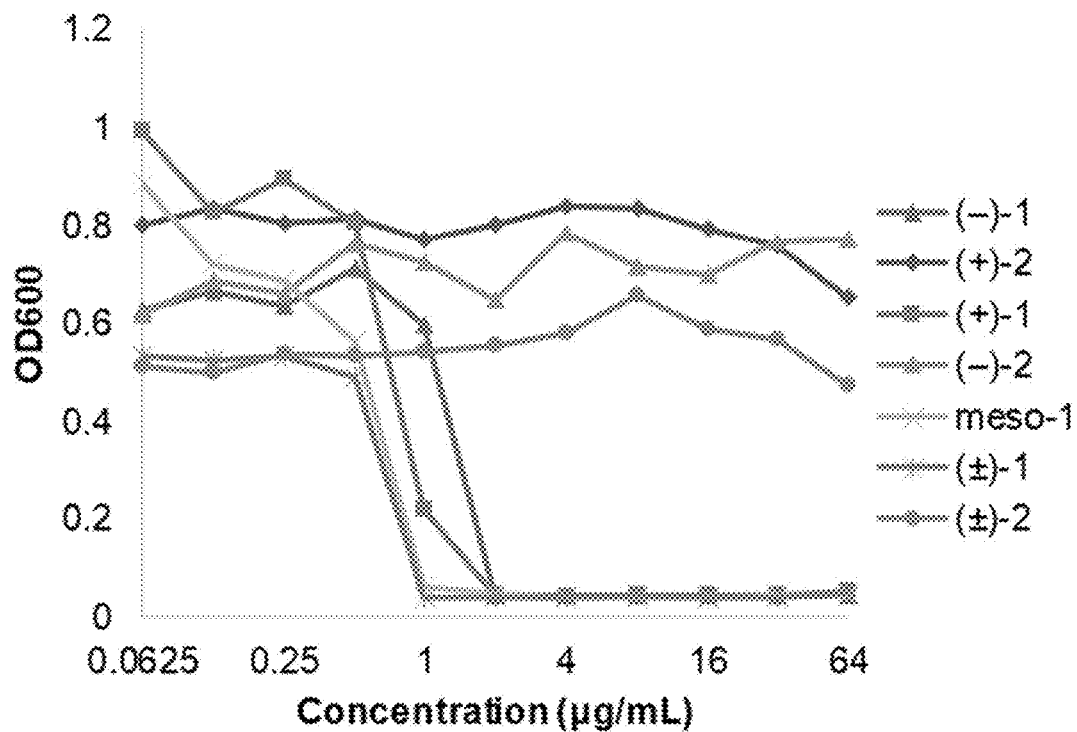
FIGS. 17A-17D show the concentration-response (OD600) curves of representative broth microdilution assays of methicillin-resistant *S. aureus* (MRSA).
Figure 17B:
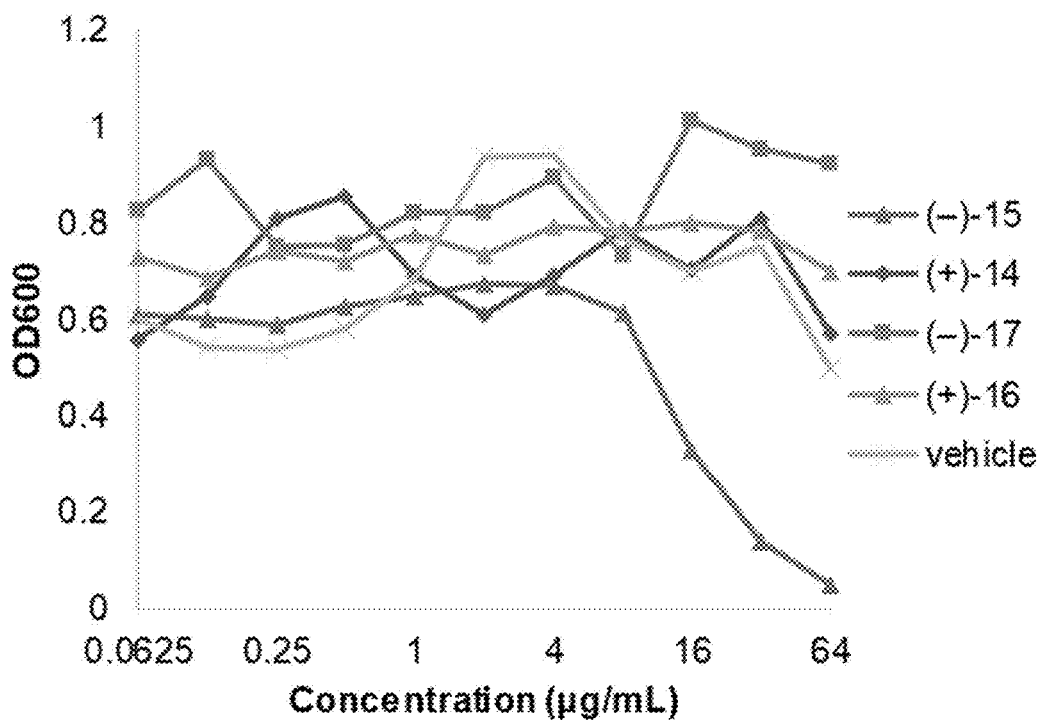
Figure 17C:
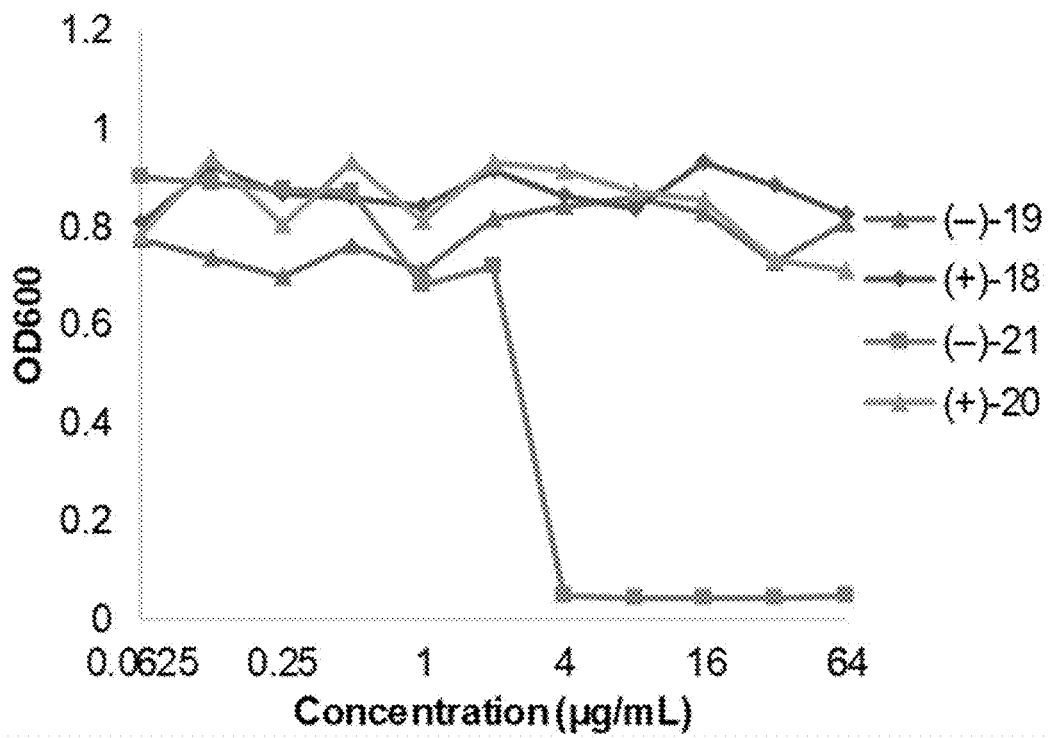
Figure 17D:
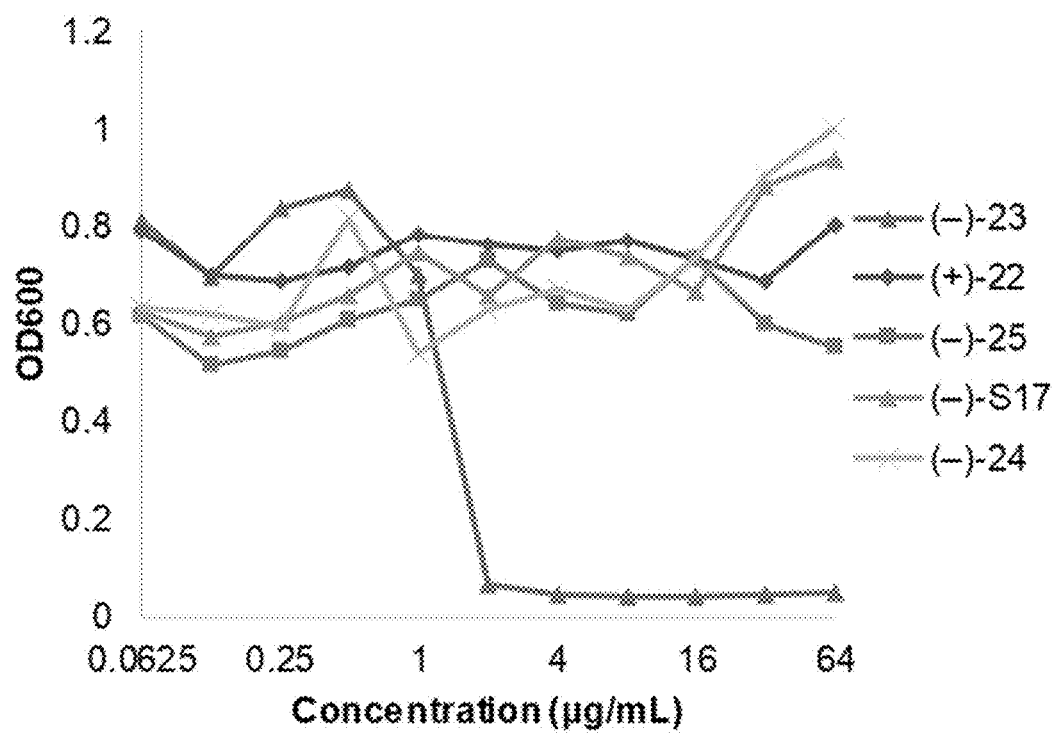
Figure 18A:
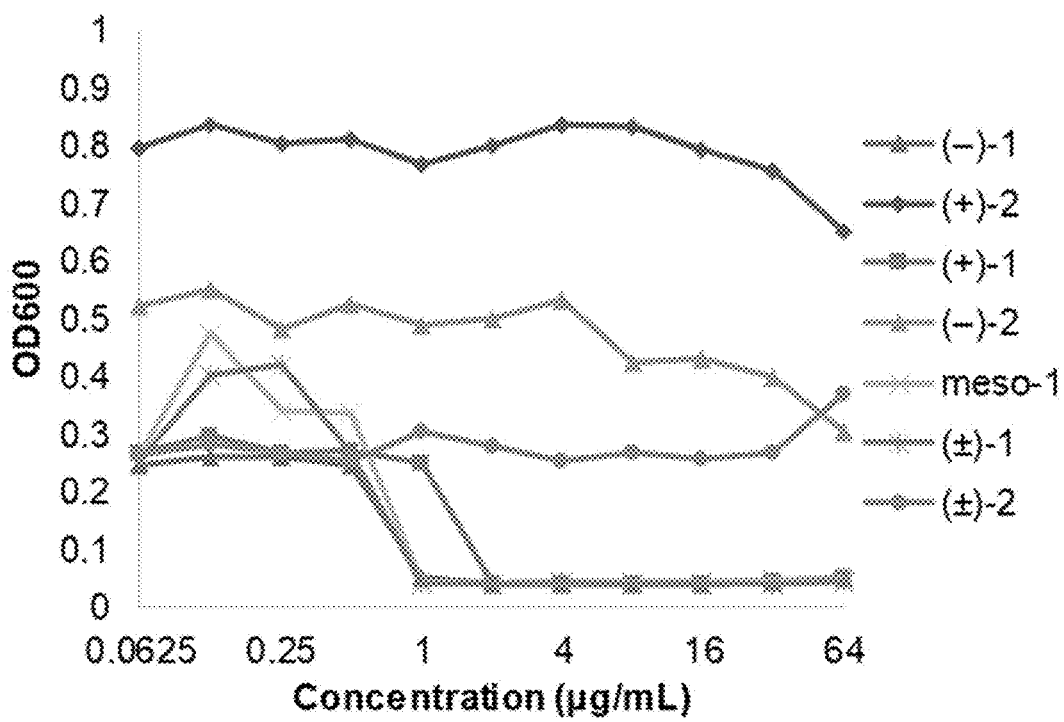
FIGS. 18A-18D show the concentration-response (OD600) curves of representative broth microdilution assays of methicillin-sensitive *S. aureus* (MSSA).
Figure 18B:
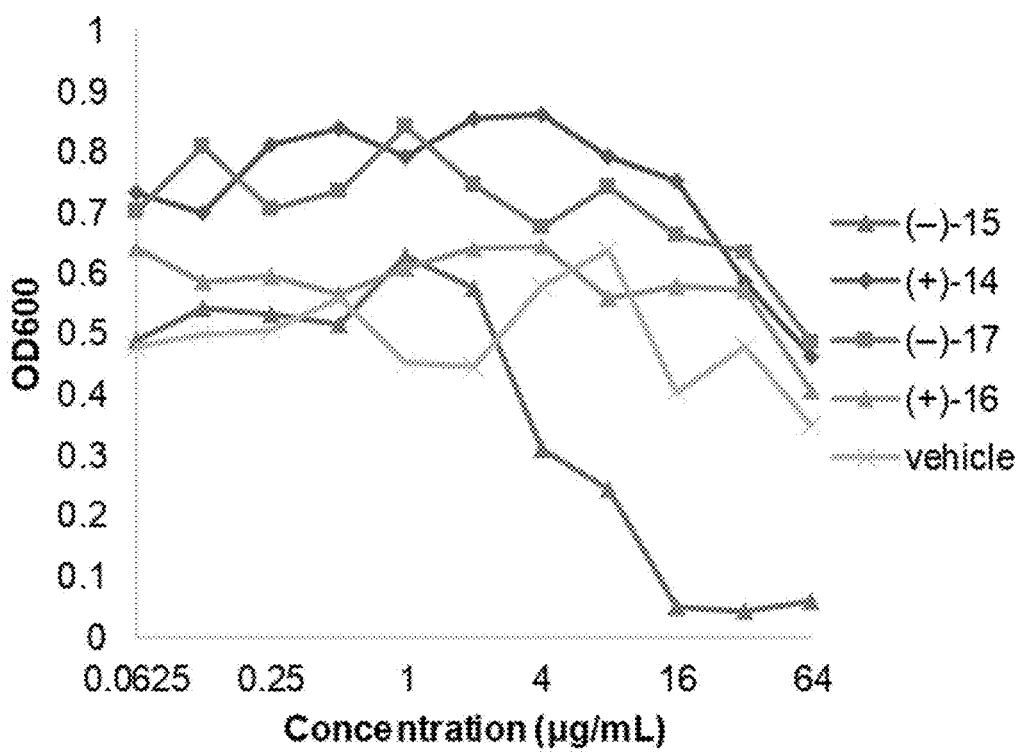
Figure 18C:
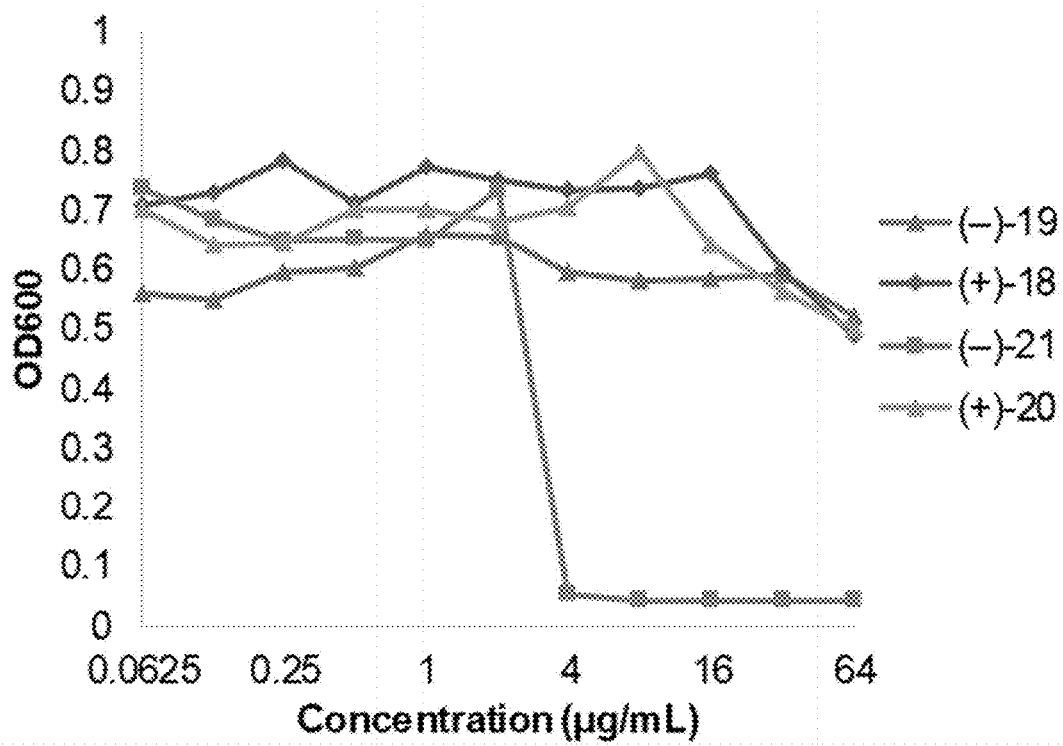
Figure 18D:
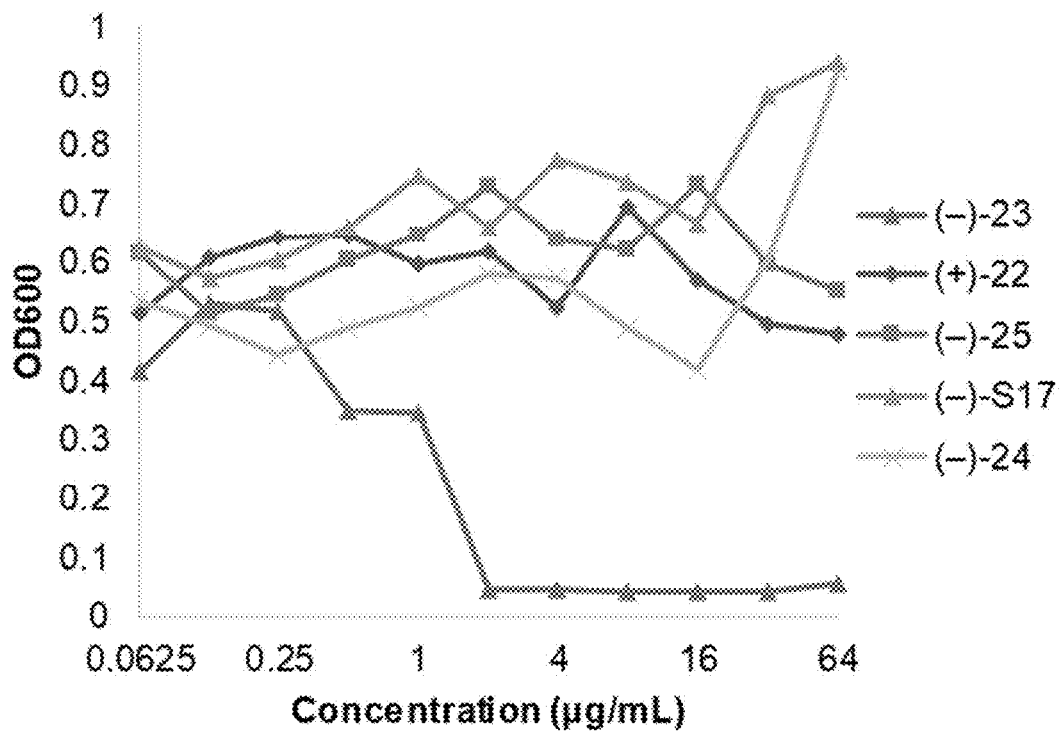
Figure 19A:
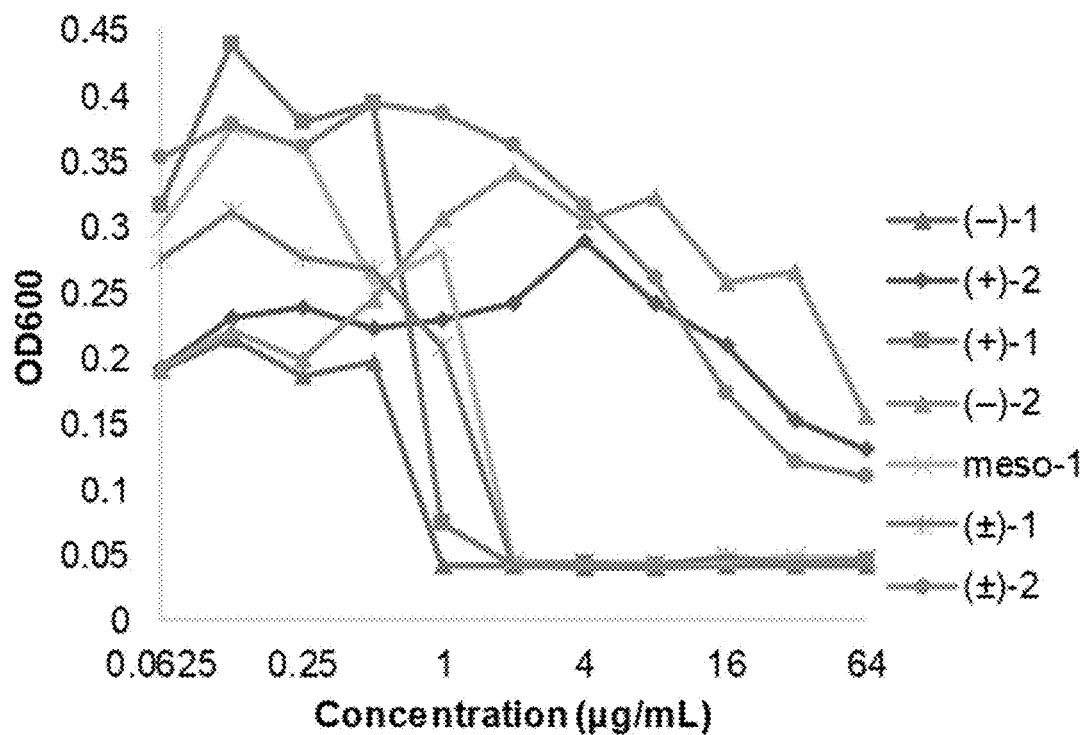
FIGS. 19A-19D Show the concentration-response (OD600) curves of representative broth microdilution assays of vancomycin-resistant *E. faecalis* (VRE).
Figure 19B:
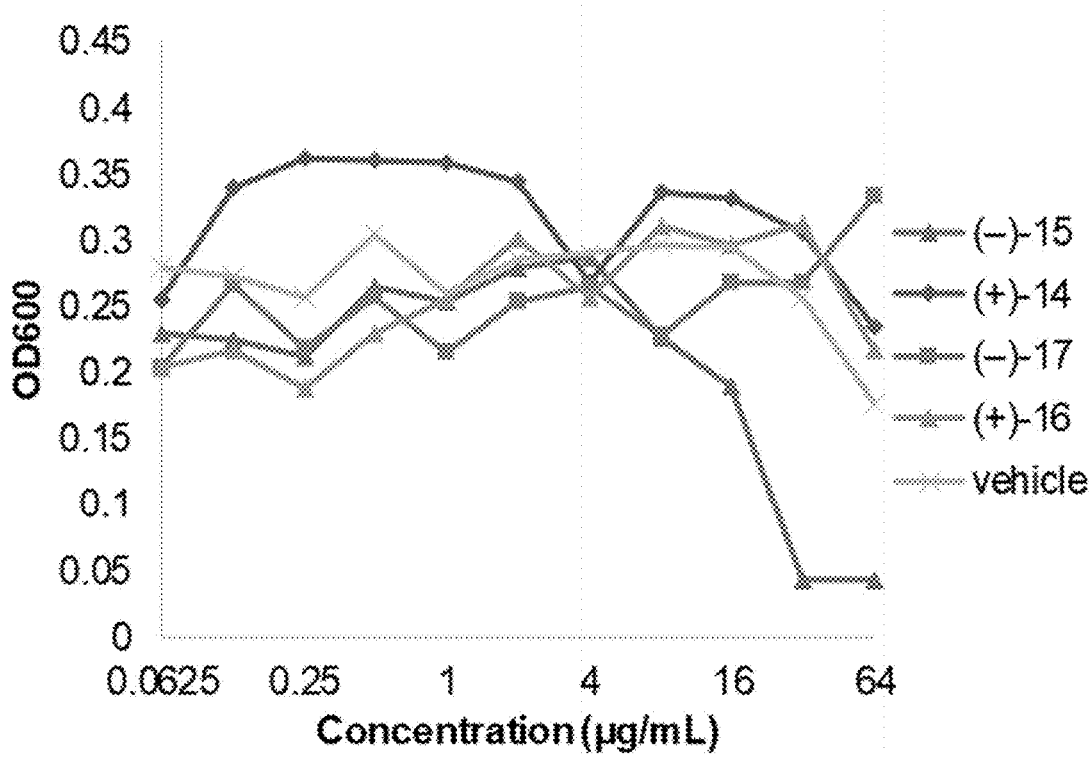
Figure 19C:
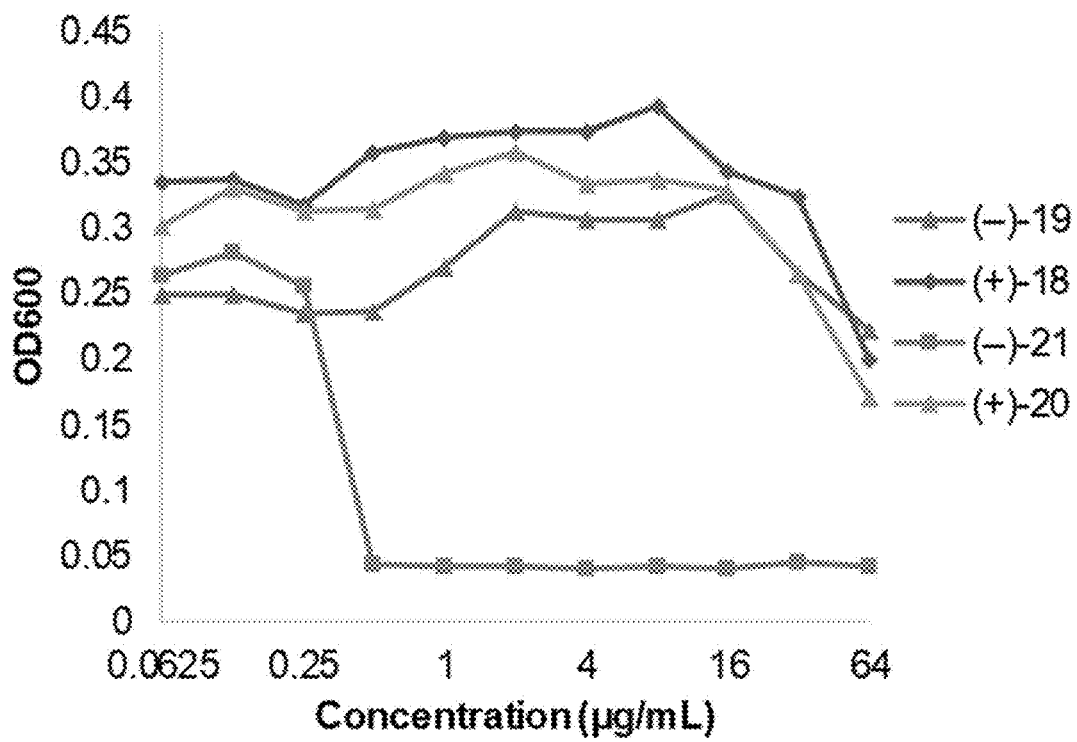
Figure 19D:
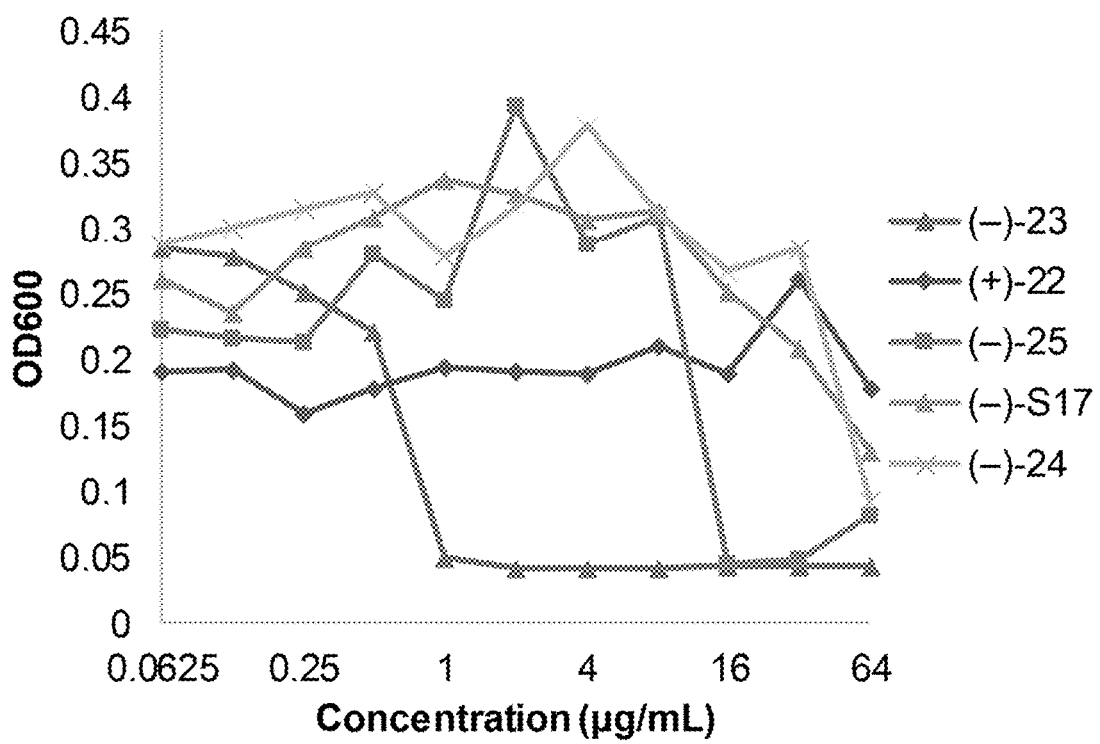
Figure 20A:
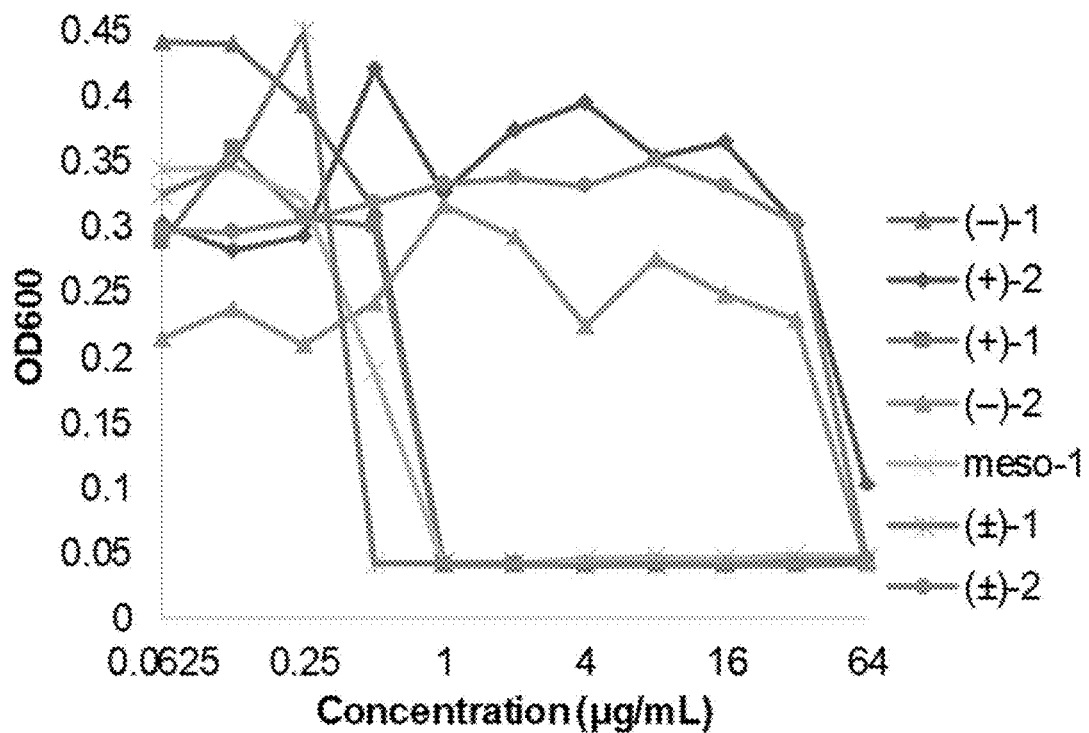
FIGS. 20A-20D show the concentration-response (OD600) curves of representative broth microdilution assays of vancomycin-sensitive *E. faecalis* (VSE).
Figure 20B:
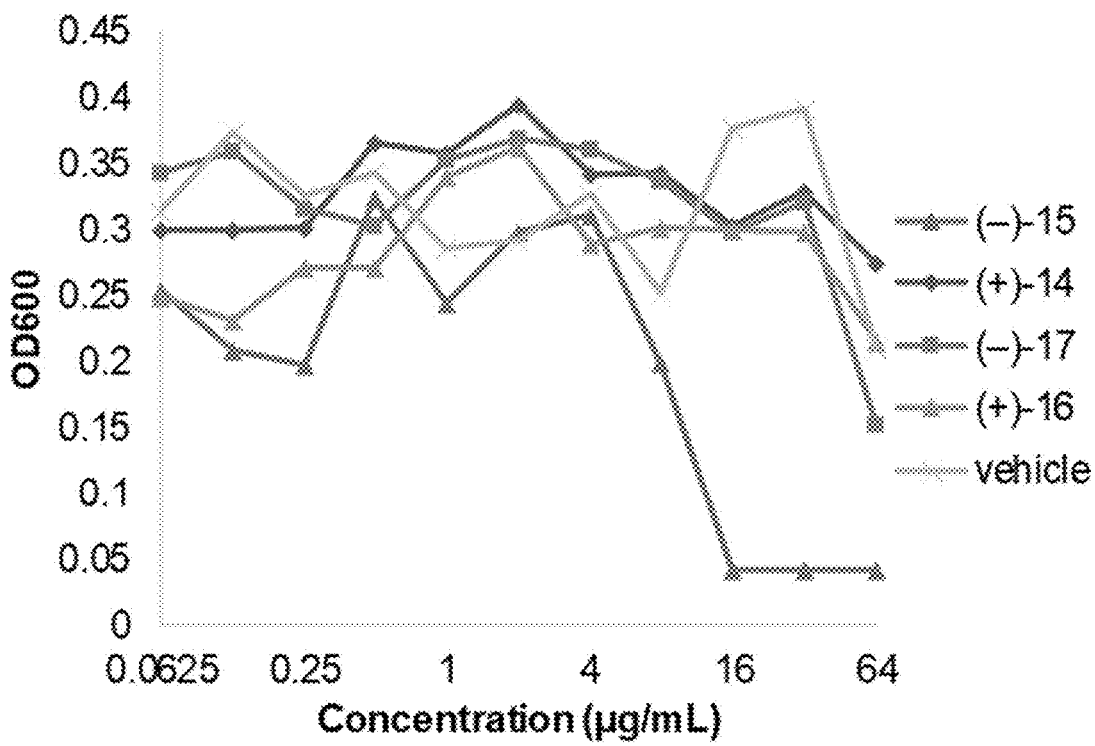
Figure 20C:
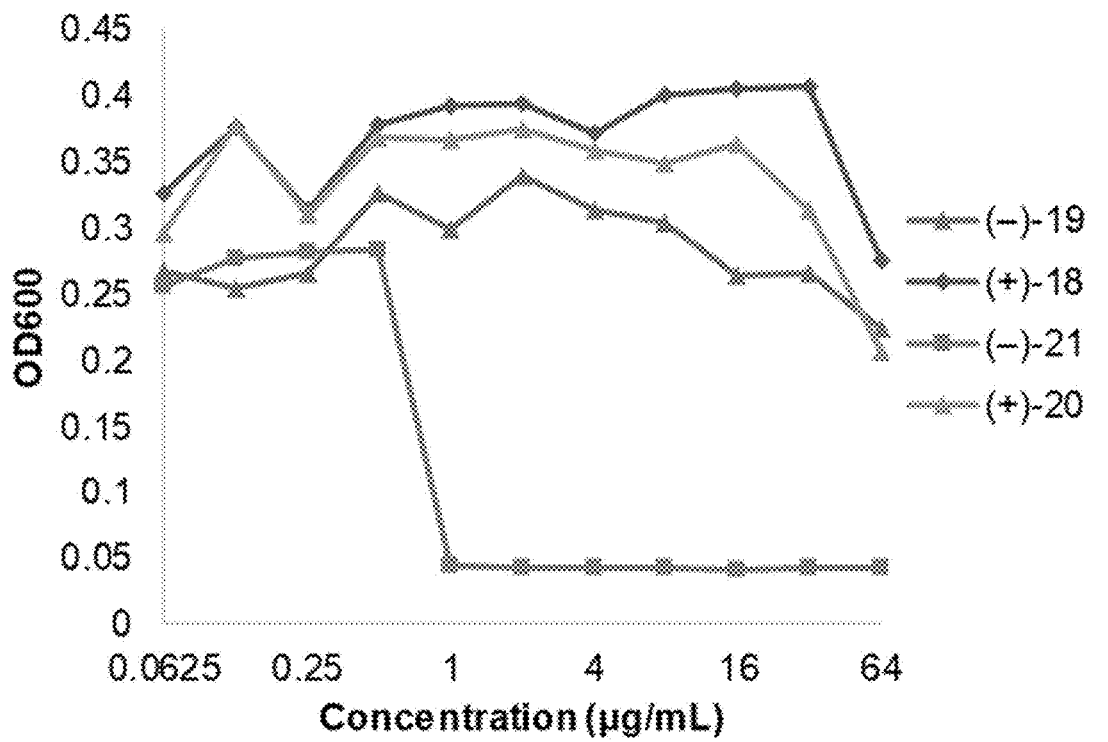
Figure 20D:
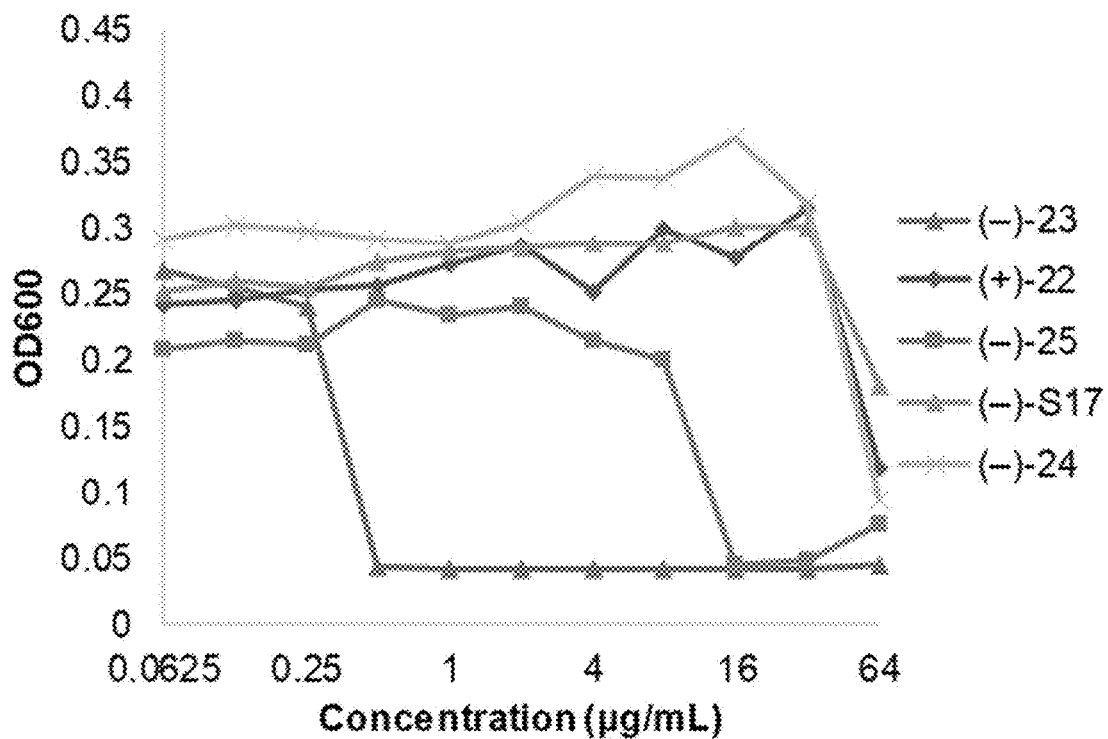
Figure 22:
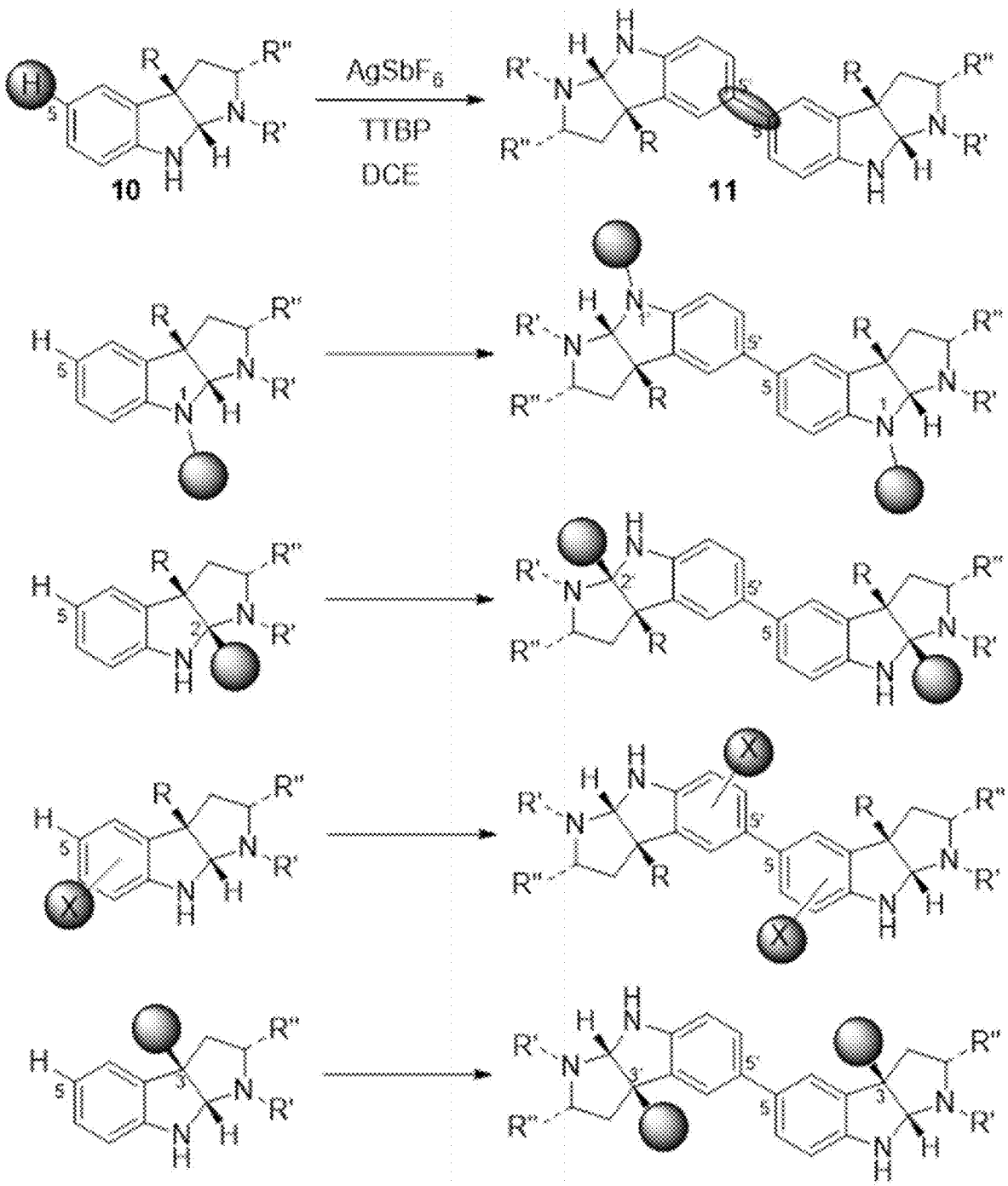
FIG. 22 shows exemplary compound scaffolds.
Figure 24:
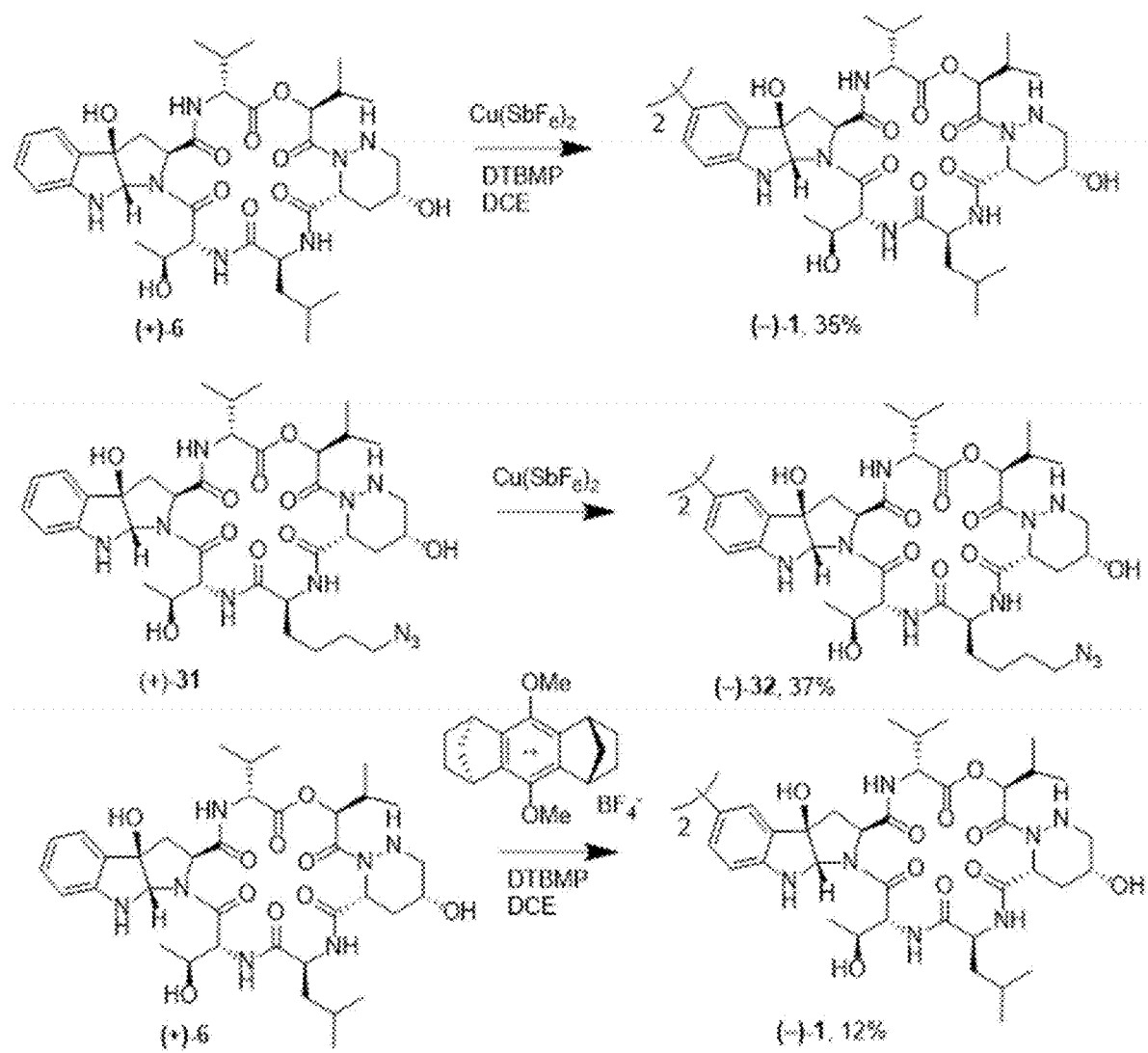
FIG. 24 shows exemplary single-electron oxidations.
Figure 25:
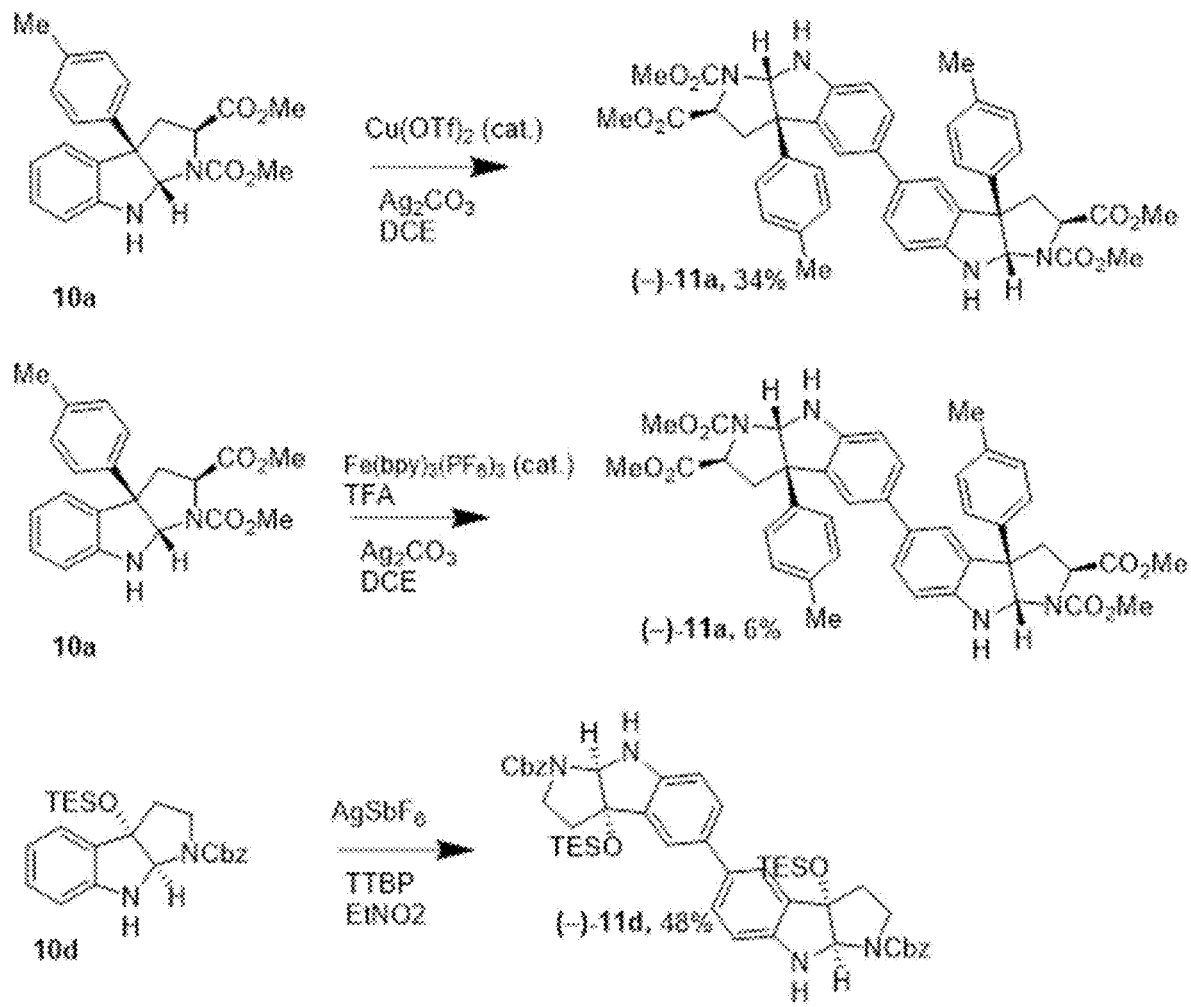
FIG. 25 shows exemplary single-electron oxidations.
Figure 26:
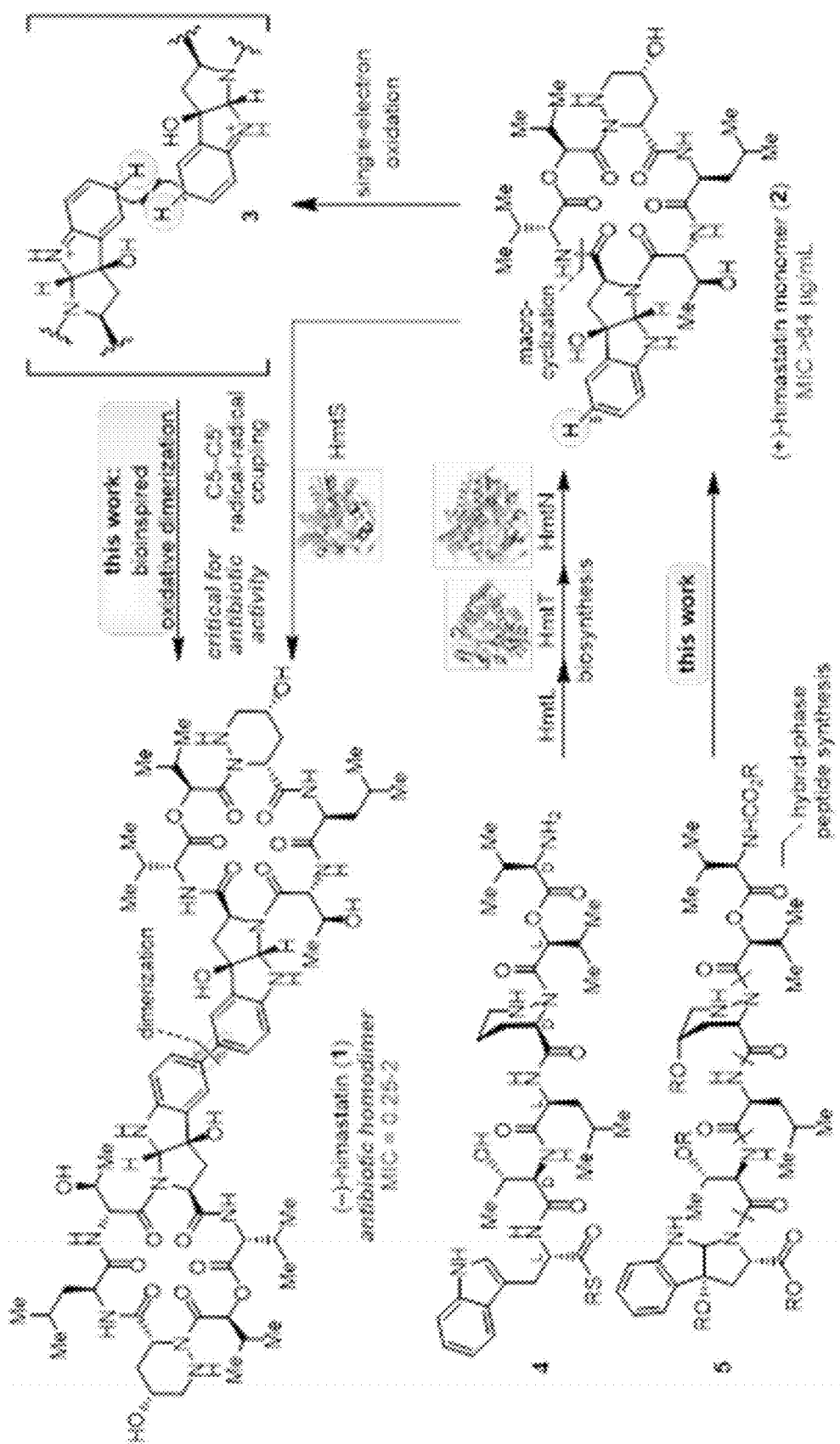
FIG. 26 shows the comparison of the biogenesis of himastatin and our bioinspired synthetic strategy. MIC values for (−)-himastatin (1) are taken from ref. 4 against Gram-positive bacteria. MIC=minimum inhibitory concentration.
Figure 27A:
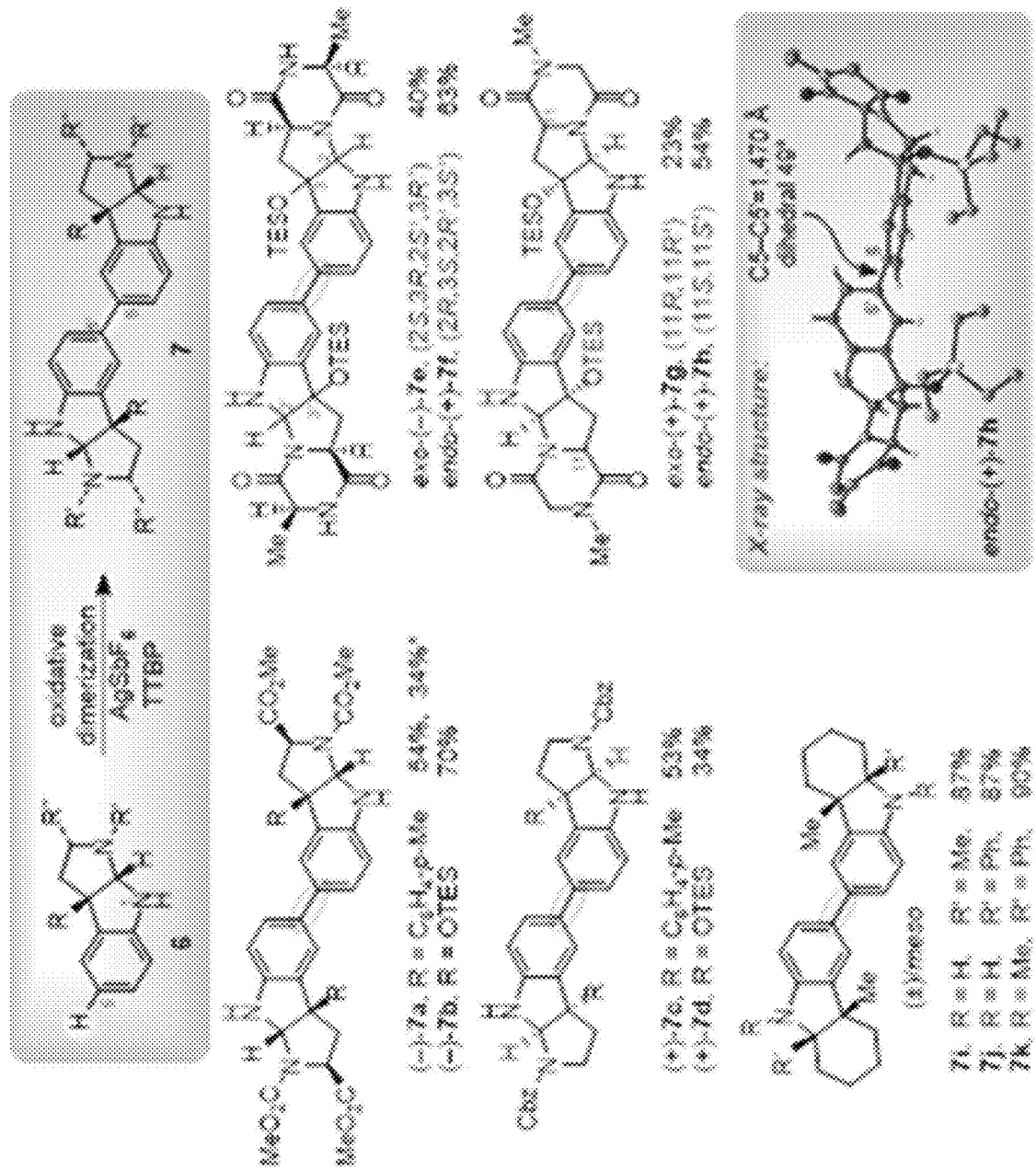
FIGS. 27A-27B show the oxidative dimerization of Cyclotryptophan, Cyclotryptamine, and Indolines.
Figure 27B:
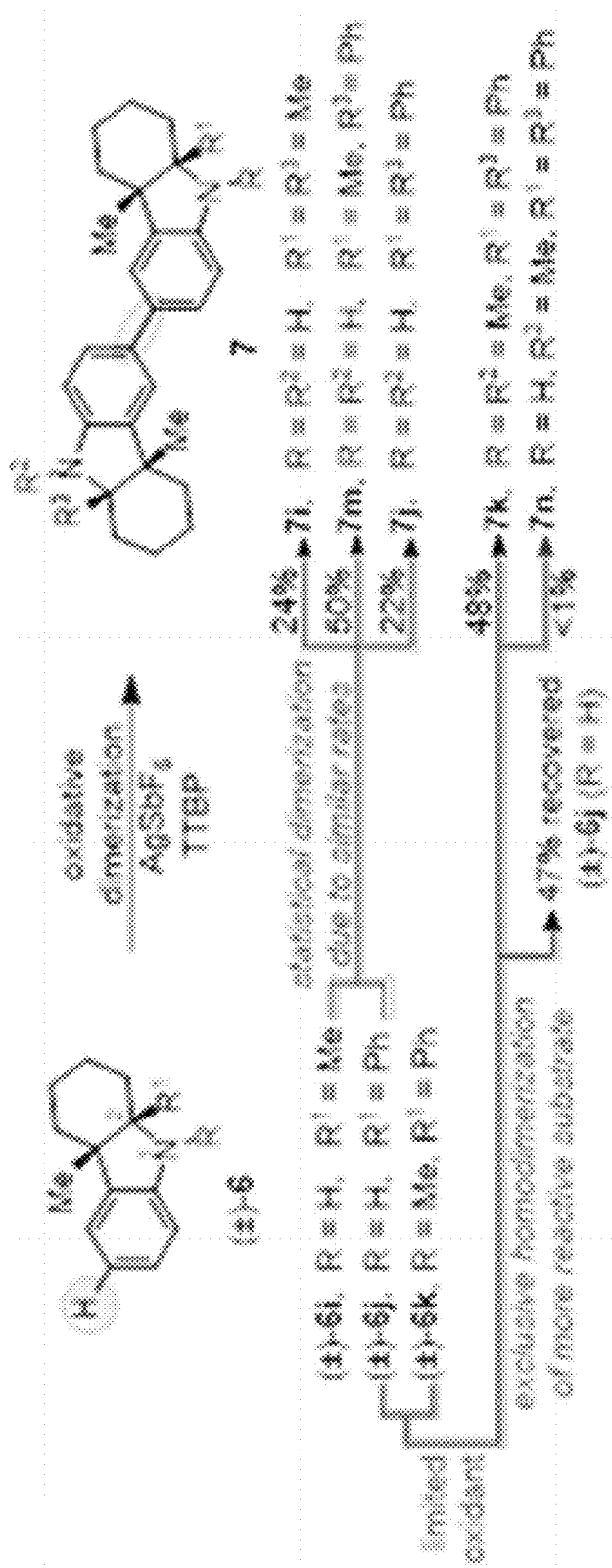
Figure 28:
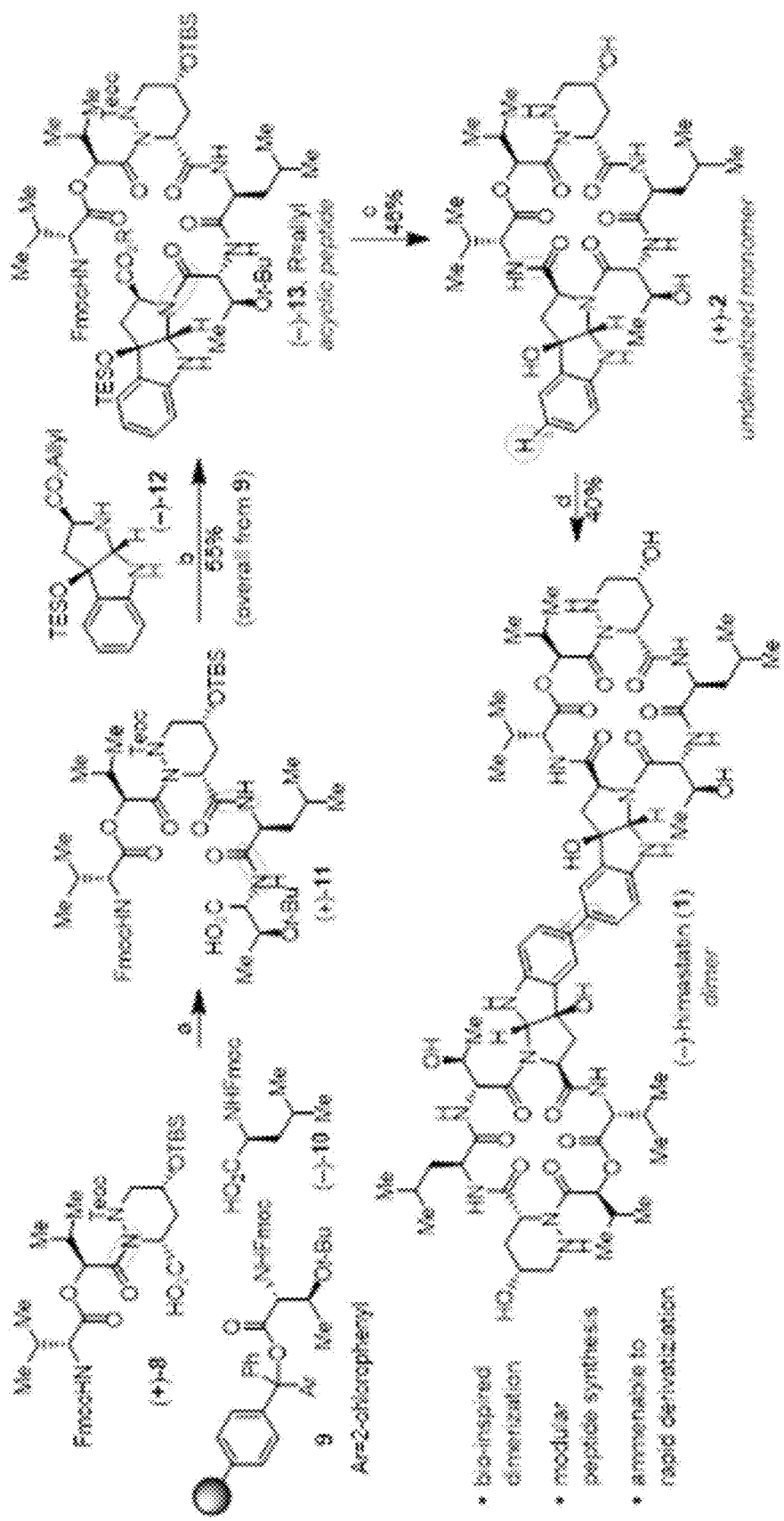
FIG. 28 shows the concise total synthesis of (−)-himastatin (1). Reagents and conditions: (a) (i) piperidine, DMF, 23° C., (ii) (−)-10, HATU, i-Pr$_2$NEt, DMF, 23° C., (iii) piperidine, DMF, 23° C., (iv) (+)-8, HATU, i-Pr$_2$NEt, DMF, 23° C., (v) TFA, CH$_2$Cl$_2$, 23° C.; (b) (−)-12, HATU, HOAt, 2,4,6-collidine, CH$_2$Cl$_2$, 0→23° C.; (c) (i) Pd(PPh$_3$)$_4$, N-methylaniline, THF, 23° C., (ii) i-Pr$_2$NH, MeCN, 23° C., (iii) HATU, HOAt, i-Pr$_2$NEt, CH$_2$Cl$_2$, 23° C., (iv) TFA, H$_2$O, anisole; Et$_3$N, MeOH, 23° C.; (d) Cu(SbF$_6$)$_2$, DTBMP, ClCH$_2$CH$_2$Cl, 23° C. Ar=2-chlorophenyl; DMF=N,N-dimethylformamide; DTBMP=2,6-di-tert-butyl-4-methylpyridine; Fmoc=9-fluorenylmethoxycarbonyl; HATU=hexafluorophosphate azabenzotriazole tetramethyl uronium; HOAt=1-hydroxy-7-azabenzotriazole; Leu=Leucine; TBS=tert-butyldimethylsilyl; Teoc=2-trimethylsilylethyloxycarbonyl; TFA=trifluoroacetic acid; THF=tetrahydrofuran.
Figure 29A:
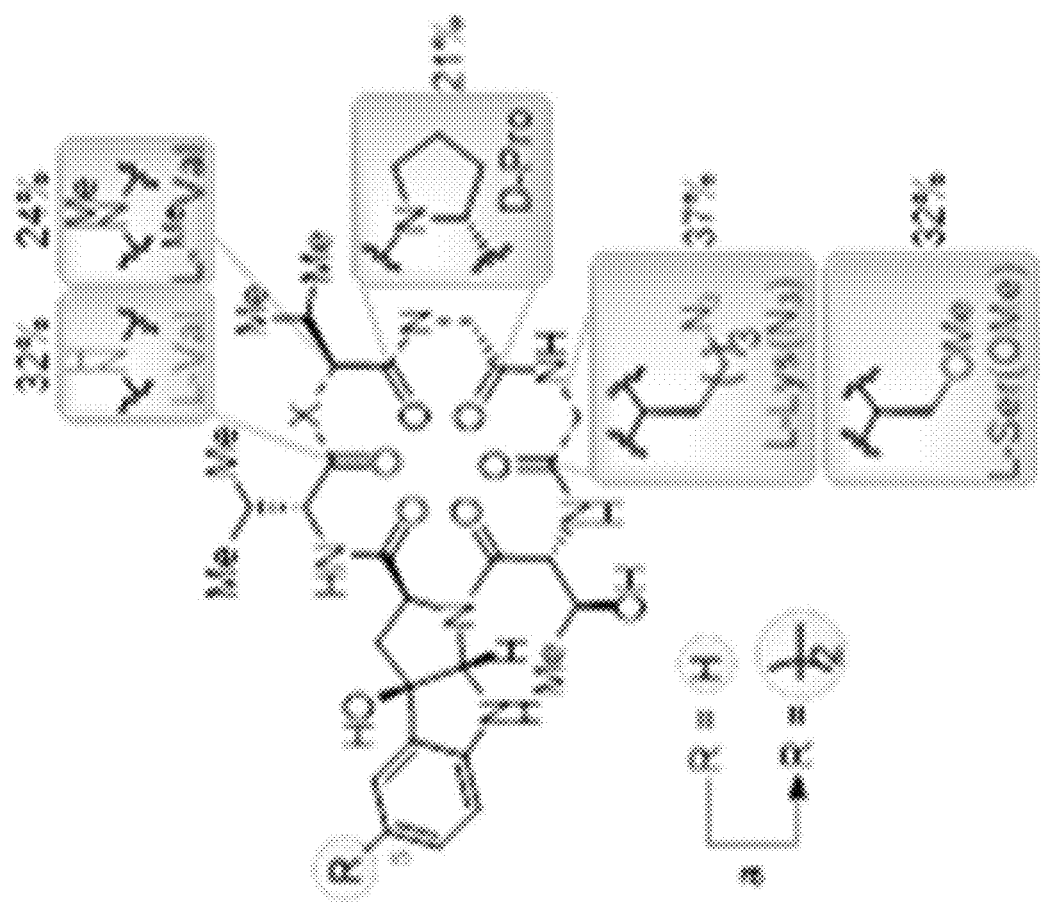
Figure 29B:
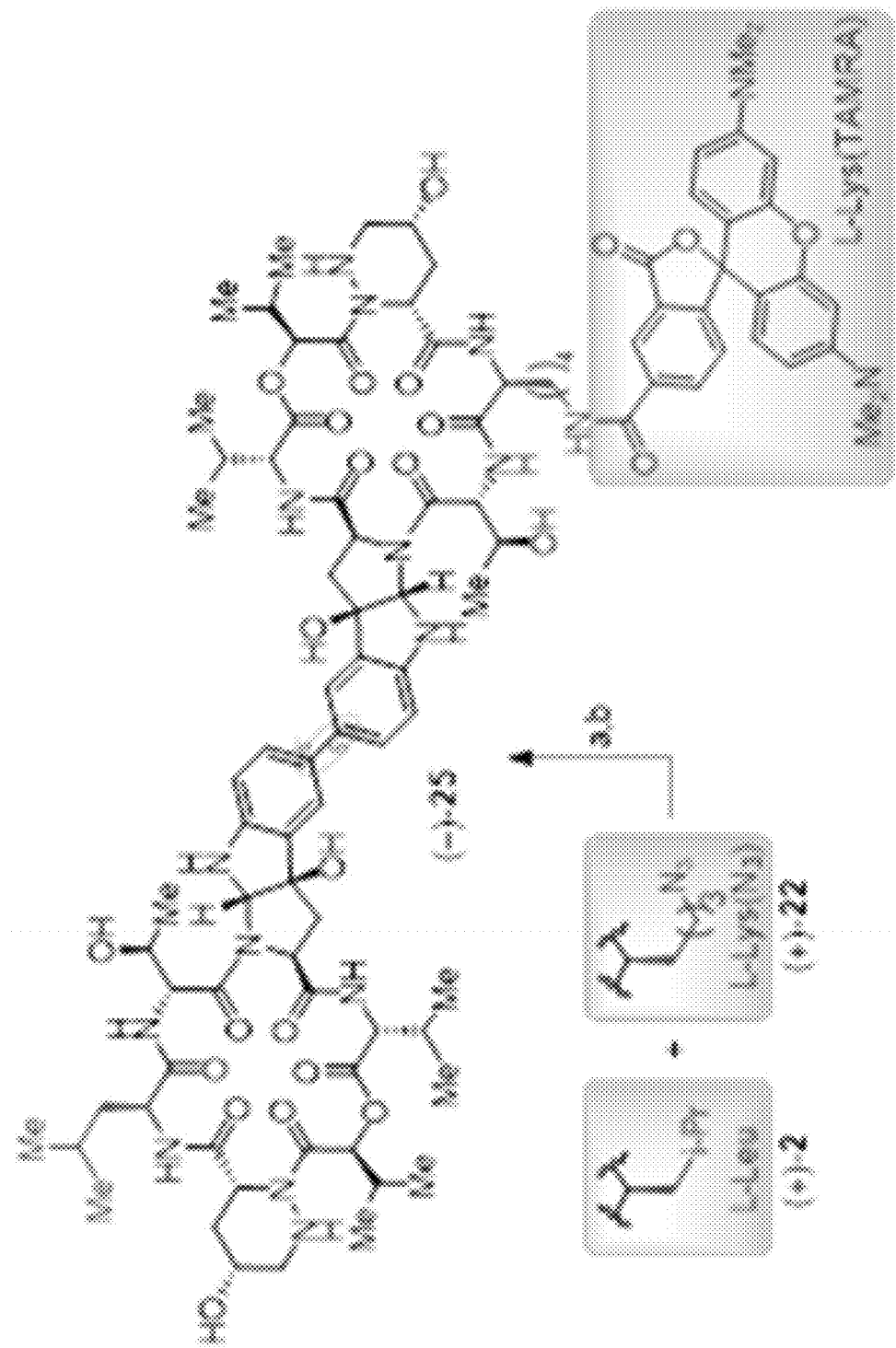

Mechanistic Experiment 1 (FIG. 7, eq. 1)

A sample of silver(I) hexafluoroantimonate (103.1 mg, 0.300 mmol, 5.00 equiv.) was added to a solution of C2-methyl indoline (±)-6i (6.04 mg, 30.0 μmol, 0.500 equiv), C2-phenyl indoline (±)-6j (7.90 mg, 30.0 μmol, 0.500 equiv), and 2,4,6-tri-tert-butyl-4-methylpyrimidine (TTBP, 37.3 mg, 0.150 mmol, 2.50 equiv) in 1,2-dichloethane (600 μL) at 23° C. After 5 min, the heterogeneous solution was diluted with dichloromethane (10 mL), a saturated aqueous sodium thiosulfate solution (5 mL), a saturated aqueous sodium hydrogen carbonate solution (5 mL), and deionized water (10 mL) and was stirred vigorously for 1 h. The layers were separated and the aqueous layer was extracted with dichloromethane (10 mL). The combined organic extracts were washed with a saturated aqueous sodium chloride solution (10 mL), were dried over anhydrous sodium sulfate, were filtered, and were concentrated under reduced pressure. The resulting residue was purified by flash column chromatography on silica gel (eluent: 0%→100% ethyl acetate in hexanes) to afford a diastereomeric mixture of homo- and heterodimers as a colorless film (13.5 mg, 97% of theory).

The distribution of products was determined by HPLC analysis (Zorbax® StableBond 80 Å CN, 4.6 mm×250 mm, 40%→95% acetonitrile in water, 0.1% formic acid, 10 min, 1.5 mL/min, 270 nm, $t_R$ (7i)=3.03 min, $t_R$ (7j)=7.09 min, $t_R$ (7m)=4.83 min) to be 25.1% 7i, 23.0% 7j, and 51.9% 7m after adjusting for relative UV response factors. Coelution of the stereoisomers of each dimer was verified by LC-MS analysis.

For structural characterization and construction of calibration curves, a pure sample of heterodimer 11m was obtained by semi-preparative HPLC (Zorbax® StableBond 80 Å CN, 9.4 mm×250 mm, 60%→95% acetonitrile in water, 16 min, 5.0 mL/min, 270 nm, $t_R$ (7m)=8.21 min). Structural assignments were made using additional information from gCOSY, gHSQC, and gHMBC experiments.

Heterodimer 7m $^1$H NMR (600 MHz, CDCl$_3$, 25° C., mixture of diastereomers): δ 7.72-7.68 (m, 2H, Ar$_{Ph}$-o-H), 7.36-7.32 (m, 2H, Ar$_{Ph}$-m-H), 7.30-7.24 (m, 2H, C6'H, Ar$_{Ph}$-p-H), 7.24-7.21 (m, 1H, C6H), 7.19-7.18 (m, 1H, C4H), 7.18-7.16 (m, 1H, C4'H), 6.77 (d, J=7.9 Hz, 1H, C7'H), 6.67 (d, J=8.0 Hz, 1H, C7H), 3.87 (br-s, 1H, N1'H), 3.45 (br-s, 1H, N1H), 2.15-2.09 (m, 1H, C11'H$_a$), 2.08-2.04 (m, 1H, C8'H$_a$), 1.94-1.89 (m, 1H, C11H$_a$), 1.86-1.76 (m, 3H, C8'H$_b$, C9'H$_a$, C11'H$_b$), 1.73-1.66 (m, 2H, C9'H$_b$, C10'H$_a$), 1.66-1.52 (m, 3H, C8H$_a$, C9H$_a$, C10'H$_b$), 1.52-1.32 (m, 5H, C8H$_b$, C9H$_b$, C10H$_2$, C11H$_b$), 1.21-1.20 (m, 3H, C2CH$_3$), 1.17-1.15 (m, 3H, C3CH$_3$), 0.81-0.79 (m, 3H, C3'CH$_3$).

$^{13}$C NMR (150.9 MHz, CDCl$_3$, 25° C., mixture of diastereomers): δ 147.4 (C7a), 147.2 (C7a'), 145.7 (Ar$_{Ph}$-ipso-C), 139.1 (C4a), 137.4 (C4a'), 133.5 (C5a'), 133.3 (C5a), 128.0 (Ar$_{Ph}$-m-C), 126.9 (Ar$_{Ph}$-o-C), 126.6 (Ar$_{Ph}$-p-C), 125.8 (C6'), 125.4 (C6), 120.8 (C4'), 120.3 (C4), 110.6 (C7), 110.0 (C7'), 71.6 (C2'), 66.4 (C2), 47.9 (C3'), 46.4 (C3), 37.8 (C8'), 36.9 (C8), 35.1 (C11), 34.0 (C11'), 26.7 (C3'CH$_3$), 22.9 (2C, C9, C3CH$_3$), 22.7 (C9'), 22.5 (C10), 22.4 (C2CH$_3$), 21.7 (C10').

FTIR (thin film) cm$^{-1}$: 3346 (br-w), 3019 (m), 2927 (m), 2856 (m), 1613 (m), 1477 (s), 1376 (w), 1251 (m), 1043 (w), 908 (m), 730 (m).

HRMS (ESI) (m/z): calc'd for $C_{33}H_{39}N_2[M+H]^+$: 463.3108, found: 463.3105.

TLC (15% ethyl acetate in hexanes), Rf: 0.33 (UV, CAM).

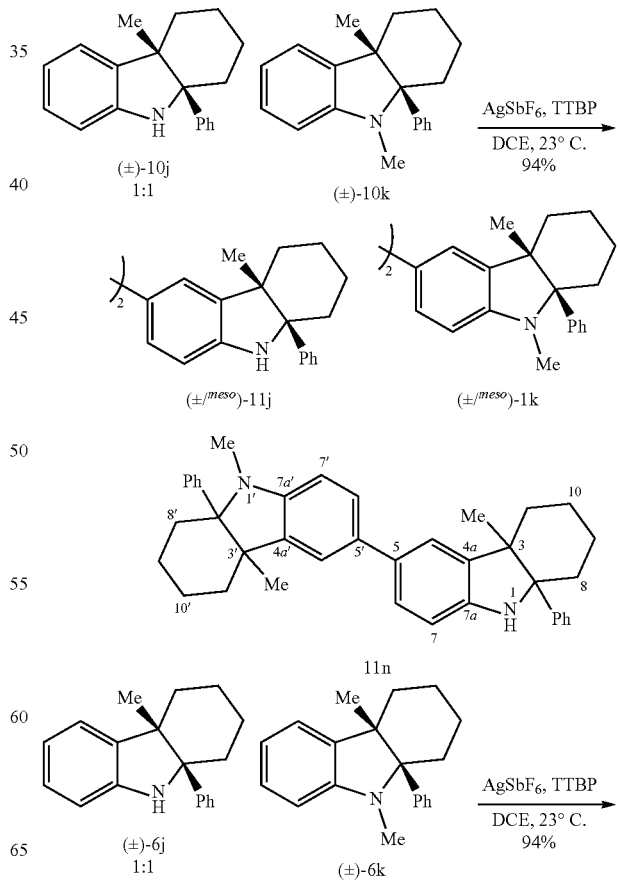

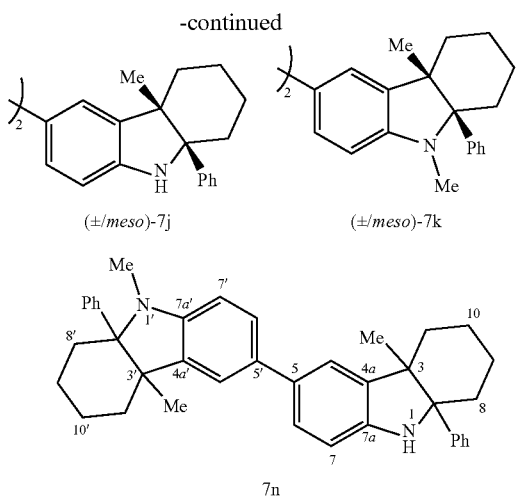

(±/meso)-7j    (±/meso)-7k

7n

Mechanistic Experiments 2 and 3 (FIG. 7, Eqs. 2,3)

A sample of silver(I) hexafluoroantimonate (26.9 mg, 78.2 µmol, 5.00 equiv.) was added to a solution of C2-phenyl indoline (±)-1.45 (2.06 mg, 7.82 µmol, 0.500 equiv), N-methyl indoline (±)-10k (2.17 mg, 7.82 µmol, 0.500 equiv), and 2,4,6-tri-tert-butyl-4-methylpyrimidine (TTBP, 9.7 mg, 39 µmol, 2.5 equiv) in 1,2-dichloethane (156 µL) at 23° C. After 4 min, the heterogeneous solution was diluted with dichloromethane (10 mL), a saturated aqueous sodium thiosulfate solution (5 mL), a saturated aqueous sodium hydrogen carbonate solution (5 mL), and deionized water (10 mL) and was stirred vigorously for 1 h. The layers were separated and the aqueous layer was extracted with dichloromethane (10 mL). The combined organic extracts were washed with a saturated aqueous sodium chloride solution (10 mL), were dried over anhydrous sodium sulfate, were filtered, and were concentrated under reduced pressure. The resulting residue was purified by flash column chromatography on silica gel (eluent: 0%→25% ethyl acetate in hexanes) to afford a diastereomeric mixture of homo- and heterodimers as a yellow film (3.96 mg, 94% of theory).

The distribution of products was determined by HPLC analysis (Zorbax® StableBond 80 Å CN, 4.6 mm×250 mm, 40%→95% acetonitrile in water, 0.1% formic acid, 10 min, 1.5 mL/min, 270 nm, $t_R$ (7j)=7.09 min, $t_R$ (7k)=7.73 min, $t_R$ (7n)=7.42 min) to be 49.7% 7j, 45.7% 7k, and 4.6% 7n after adjusting for relative UV response factors. Coelution of the stereoisomers of each dimer was verified by LC-MS analysis.

When the quantities of silver(I) hexafluoroantimonate and 2,4,6-tri-tert-butyl-4-methylpyrimidine were reduced to 1.00 equiv and 0.50 equiv respectively, N-methyl homodimer 7k was formed nearly quantitatively as the sole major product (48%), with unreacted (±)-7j ($t_R$=5.69 min) and heterodimer 7n comprising 47% and <1% respectively of the remaining mass balance.

For structural characterization and construction of calibration curves, a pure sample of heterodimer 11n was obtained by semi-preparative HPLC (Zorbax® StableBond 80 Å CN, 9.4 mm×250 mm, 65%→95% acetonitrile in water, 16 min, 5.0 mL/min, 270 nm, $t_R$ (tin)=8.67 min). Structural assignments were made using additional information from gCOSY, gHSQC, and gHMBC experiments.

Heterodimer 7n $^1$H NMR (600 MHz, CDCl$_3$, 25° C., mixture of diastereomers): δ 7.72-7.68 (m, 2H, C2$_{Ph}$-o-H), 7.53-7.48 (m, 2H, C2'$_{Ph}$-o-H), 7.36-7.27 (m, 6H, C2$_{Ph}$-m-H, C2'$_{Ph}$-m-H, C6H, C6'H), 7.27-7.23 (m, 2H, C2$_{Ph}$-m-H, C2'$_{Ph}$-p-H), 7.18-7.17 (m, 1H, C4H), 7.12-7.11 (m, 1H, C4'H), 6.77 (d, J=7.9 Hz, 1H, C7H), 6.49 (d, J=7.6 Hz, 1H, C7'H), 3.90 (br-s, 1H, N1H), 2.64 (s, 3H, N1'CH$_3$), 2.24-2.18 (m, 1H, C8'H$_a$), 2.15-2.10 (m, 1H, C11H$_a$), 2.07-2.03 (m, 1H, C8H$_a$), 1.94-1.89 (m, 1H, C11'H$_a$), 1.86-1.66 (m, 8H, C8H$_b$, C8'H$_b$, C9H$_2$, C9'H$_2$, C10H$_a$, C11H$_b$), 1.64-1.51 (m, 3H, C10'H$_a$, C10H$_b$, C11'H$_b$), 1.50-1.43 (m, 1H, C10'H$_b$), 0.81-0.80 (m, 3H, C3CH$_3$), 0.75-0.73 (m, 3H, C3'CH$_3$).

$^{13}$C NMR (150.9 MHz, CDCl$_3$, 25° C., mixture of diastereomers): δ 149.9 (C7a'), 147.0 (C7a), 145.7 (C2$_{Ph}$-ipso-C), 143.1 (C2'$_{Ph}$-ipso-C), 137.4 (C4a), 137.0 (C4a'), 133.6 (C5), 131.6 (C5'), 128.0 (2C, C2$_{Ph}$-m-C, C2'$_{Ph}$-o-C) 127.9 (C2'$_{Ph}$-m-C), 126.9 (C2$_{Ph}$-o-C), 126.8 (C2'$_{Ph}$-p-C), 126.6 (C2$_{Ph}$-p-C), 125.8 (C6), 125.6 (C6'), 120.6 (C4), 120.4 (C4'), 110.1 (C7), 106.1 (C7'), 76.0 (C2'), 71.6 (C2), 48.2 (C3'), 47.9 (C3), 37.8 (C8), 34.5 (C11'), 34.0 (C11), 30.1 (C8'), 29.7 (N1'CH$_3$), 27.2 (C3'CH$_3$), 26.7 (C3CH$_3$), 23.1 (C9'), 22.7 (C9), 21.7 (C10), 21.2 (C10').

FTIR (thin film) cm$^{-1}$: 3343 (br-m), 3020 (w), 2928 (m), 2862 (m), 1613 (m), 1481 (s), 1253 (m), 908 (m), 731 (m), 701 (m).

HRMS (ESI) (m/z): calc'd for $C_{39}H_{43}N_2[M+H]^+$: 539.3421, found: 539.3410.

TLC (10% ethyl acetate in hexanes), Rf: 0.37 (UV, CAM).

Heterodimer 7n $^1$H NMR (600 MHz, CDCl$_3$, 25° C., mixture of diastereomers): δ 7.72-7.68 (m, 2H, C2$_{Ph}$-o-H), 7.53-7.48 (m, 2H, C2'$_{Ph}$-o-H), 7.36-7.27 (m, 6H, C2$_{Ph}$-m-H, C2'$_{Ph}$-m-H, C6H, C6'H), 7.27-7.23 (m, 2H, C2$_{Ph}$-m-H, C2'$_{Ph}$-p-H), 7.18-7.17 (m, 1H, C4H), 7.12-7.11 (m, 1H, C4'H), 6.77 (d, J=7.9 Hz, 1H, C7H), 6.49 (d, J=7.6 Hz, 1H, C7'H), 3.90 (br-s, 1H, N1H), 2.64 (s, 3H, N1'CH$_3$), 2.24-2.18 (m, 1H, C8'H$_a$), 2.15-2.10 (m, 1H, C11H$_a$), 2.07-2.03 (m, 1H, C8H$_a$), 1.94-1.89 (m, 1H, C11'H$_a$), 1.86-1.66 (m, 8H, C8H$_b$, C8'H$_b$, C9H$_2$, C9'H$_2$, C10H$_a$, C11H$_b$), 1.64-1.51 (m, 3H, C10'H$_a$, C10H$_b$, C11'H$_b$), 1.50-1.43 (m, 1H, C10'H$_b$), 0.81-0.80 (m, 3H, C3CH$_3$), 0.75-0.73 (m, 3H, C3'CH$_3$).

$^{13}$C NMR (150.9 MHz, CDCl$_3$, 25° C., mixture of diastereomers): δ 149.9 (C7a'), 147.0 (C7a), 145.7 (C2$_{Ph}$-ipso-C), 143.1 (C2'$_{Ph}$-ipso-C), 137.4 (C4a), 137.0 (C4a'), 133.6 (C5), 131.6 (C5'), 128.0 (2C, C2$_{Ph}$-m-C, C2'$_{Ph}$-o-C) 127.9 (C2'$_{Ph}$-m-C), 126.9 (C2$_{Ph}$-o-C), 126.8 (C2'$_{Ph}$-p-C), 126.6 (C2$_{Ph}$-p-C), 125.8 (C6), 125.6 (C6'), 120.6 (C4), 120.4 (C4'), 110.1 (C7), 106.1 (C7'), 76.0 (C2'), 71.6 (C2), 48.2 (C3'), 47.9 (C3), 37.8 (C8), 34.5 (C11'), 34.0 (C11), 30.1 (C8'), 29.7 (N1'CH$_3$), 27.2 (C3'CH$_3$), 26.7 (C3CH$_3$), 23.1 (C9'), 22.7 (C9), 21.7 (C10), 21.2 (C10').

FTIR (thin film) cm$^{-1}$: 3343 (br-m), 3020 (w), 2928 (m), 2862 (m), 1613 (m), 1481 (s), 1253 (m), 908 (m), 731 (m), 701 (m).

HRMS (ESI) (m/z): calc'd for $C_{39}H_{43}N_2[M+H]^+$: 539.3421, found: 539.3410.

TLC (10% ethyl acetate in hexanes), Rf: 0.37 (UV, CAM).

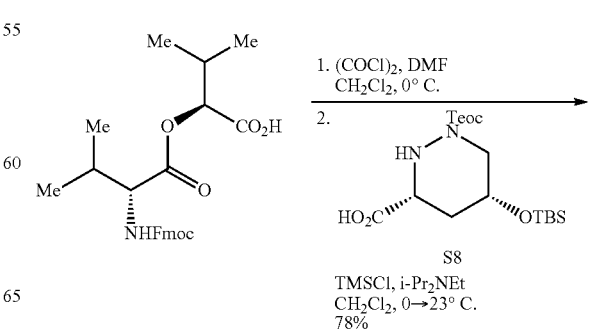

S8

TMSCl, i-Pr$_2$NEt
CH$_2$Cl$_2$, 0→23° C.
78%

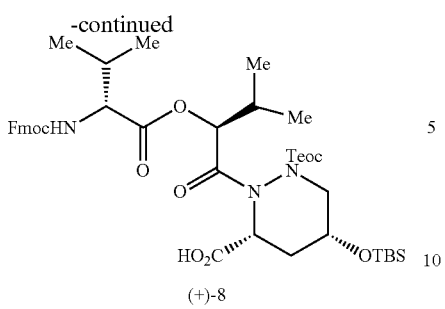

(+)-8

Depsitripeptide (+)-8:

Oxalyl chloride (720 μL, 8.40 mmol, 2.40 equiv) was added dropwise via syringe over 5 min to a solution of Fmoc-D-Val-L-Hiv-OH[49] (1.85 g, 4.20 mmol, 1.20 equiv) and N,N-dimethylformamide (32 μL, 0.42 mmol, 0.12 equiv) in dichloromethane (6.0 mL) at 0° C. After 30 min, the yellow solution was concentrated under reduced pressure (~1 Torr) at 0° C. The resulting residue was dissolved in dichloromethane (6 mL) and transferred by cannula over 2 min to a solution of piperazic acid S8[9] (1.42 g, 3.50 mmol, 1 equiv), N,N-diisopropylethylamine (1.28 mL, 7.35 mmol, 2.10 equiv), and chlorotrimethylsilane (886 μL, 7.00 mmol, 2.00 equiv) in dichloromethane (8 mL) at 0° C. The transfer was quantitated with additional dichloromethane (2×2 mL). After 30 min, the cold bath was removed and the yellow solution was allowed to stir at 23° C. After 1 h, the reaction mixture was diluted with an aqueous hydrogen chloride solution (1 M, 100 mL) and stirred vigorously for 5 min. The mixture was extracted with dichloromethane (3×50 mL) and the combined organic extracts were washed with an aqueous saturated sodium chloride solution (100 mL), were dried over anhydrous sodium sulfate, were filtered, and were concentrated under reduced pressure. The resulting residue was purified by flash column chromatography on silica gel (eluent: 1% acetic acid, 40% ethyl acetate in hexanes) to afford depsitripeptide (+)-8 (2.63 g, 78%) as a white foam. The reported $^1$H NMR integrals are an approximation due to the presence of multiple conformers and significant atropisomerism. The $^{13}$C data are listed as observed with more than the expected number of $^{13}$C resonances due to atropisomerism.

$^1$H NMR (600 MHz, CD$_3$CN, 25° C.): δ 11.34 (br-s, 1H), 7.84 (d, J=7.7 Hz, 2H), 7.70 (app-t, J=6.4 Hz, 2H), 7.44-7.40 (m, 2H), 7.34 (app-t, J=7.4 Hz, 2H), 6.04 (d, J=9.1 Hz, 1H), 5.19-5.03 (m, 2H), 4.43 (br-s, 1H), 4.32 (br-s, 2H), 4.24 (app-t, J=7.3 Hz, 1H), 4.19 (br-s, 2H), 4.06 (br-s, 2H), 3.70 (d, J=12.2 Hz, 0.1H), 3.21 (d, J=13.7 Hz, 0.7H), 3.04 (d, J=13.5 Hz, 0.2H), 2.38 (d, J=14.1 Hz, 1H), 2.24-1.96 (m, 7H), 1.01-0.93 (m, 8H), 0.92-0.88 (m, 2H), 0.84 (s, 9H), 0.08-0.00 (m, 15H).

$^{13}$C NMR (125.8 MHz, CD$_3$CN, 25° C.): δ 172.9, 172.8, 172.5, 171.9, 171.3, 171.2, 170.9, 170.3, 168.4, 167.1, 164.5, 163.0, 161.9, 161.5, 159.2, 157.9, 157.4, 156.7, 145.1 (2C), 145.0, 142.1 (2C), 129.9, 129.2, 128.7, 128.2, 128.1, 126.3, 121.0 (2C), 77.8, 76.5, 76.1, 68.8, 68.5, 67.8, 67.5, 67.0, 66.5, 63.6, 63.4 (2C), 63.3, 60.8, 58.1, 56.3, 53.7, 53.1, 52.8, 52.2, 50.9, 50.8, 48.0, 34.9, 33.4, 33.2, 32.9, 32.7, 31.4 (2C), 30.8, 30.2, 30.0, 26.2, 26.0, 19.9, 19.7, 19.5 (3C), 19.1, 18.7, 18.6, 18.5, 18.3, 18.2, 18.1 (2C), 18.0, 17.7, 17.4, 16.9, 16.1, −1.4, −4.5, −4.6, −5.0, −5.1.

FTIR (thin film) cm$^{-1}$: 3331 (br-w), 2958 (m), 2858 (w), 1746 (s), 1701 (s), 1405 (m), 1250 (m), 1120 (m), 837 (m), 758 (m), 741 (m).

HRMS (ESI) (m/z): calc'd for C$_{42}$H$_{63}$N$_3$NaO$_{10}$Si$_2$ [M+Na]$^+$: 848.3944, found: 848.3961.

$[\alpha]_D^{23}$: +67 (c=0.07, CHCl$_3$).

TLC (1% acetic acid, 40% ethyl acetate in hexanes), Rf: 0.34 (UV, CAM).

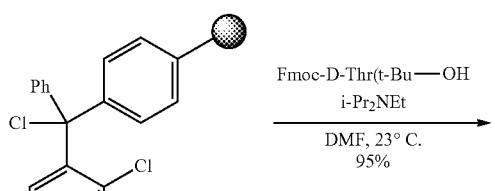

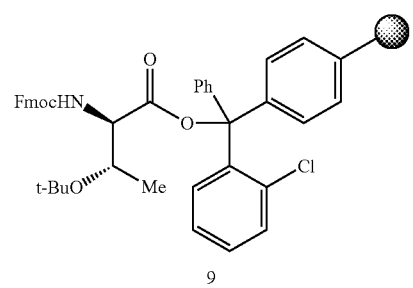

9

Fmoc-D-Thr(t-Bu)-2-Chlorotrityl Polystyrene Resin 9

A solution of Fmoc-D-Thr(t-Bu)-OH (3.97 g, 10.0 mmol, 4.00 equiv) and N,N-diisopropylethylamine (5.00 mL, 28.7 mmol, 11.5 equiv) in N,N-dimethylformamide (15 mL) was added to 2-chlorotrityl chloride polystyrene resin (2.19 g, 1.14 mmol/g on 200-400 mesh resin, 2.50 mmol, 1 equiv) in a fritted syringe at 23° C. After 1.5 h, the liquid phase was drained and the resin was washed with N,N-dimethylformamide (3×20 mL) and dichloromethane (3×20 mL) and was dried under reduced pressure to yield Fmoc-D-Thr(t-Bu)-2-chlorotrityl polystyrene resin 9 (2.96 g, 0.802 mmol/g, 95%) as yellow beads.

The loading was determined by treatment of two samples of the resulting resin with 20% piperidine-DMF and quantitation of 1-((9H-fluoren-9-yl)methyl)piperidine by UV spectroscopy in triplicate (289.8 nm, ε=6089 M$^{-1}$ cm$^{-1}$) according to a literature procedure.[50]

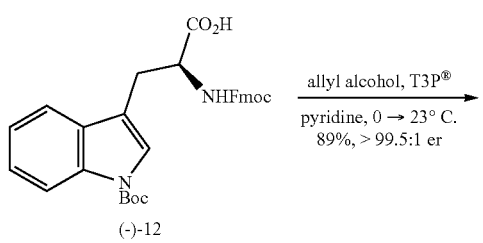

(-)-12

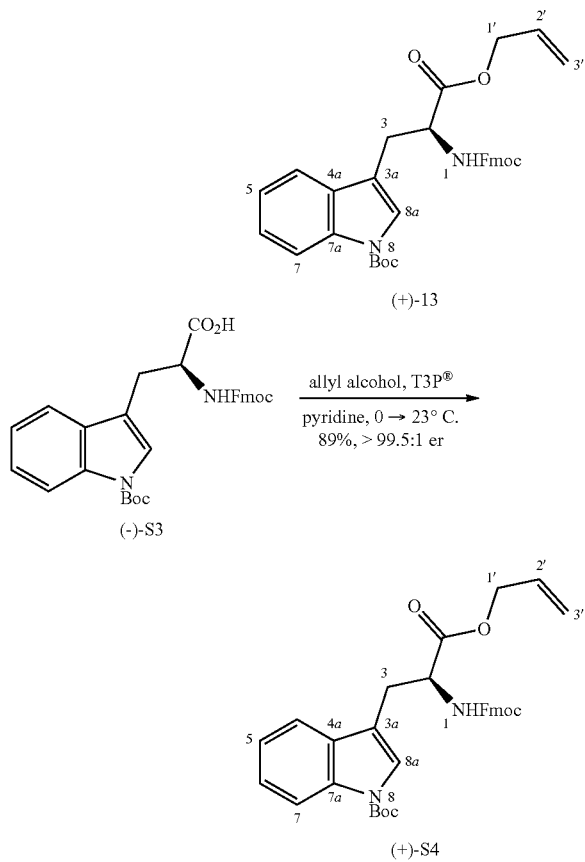

Allyl Tryptophan (+)-S4:

T3P® (50 wt. % in ethyl acetate, 25.0 mL, 42.0 mmol, 3.00 equiv) was added to a solution of tryptophan (−)-S3 (7.37 g, 14.0 mmol, 1 equiv) and allyl alcohol (1.90 mL, 28.0 mmol, 2.00 equiv) in pyridine (25 mL) at 0° C. After 30 min, the cold bath was removed and the yellow solution was allowed to stir at 23° C. After 12 h, the mixture was concentrated under reduced pressure. The resulting residue was dissolved in ethyl acetate (200 mL) and washed with an aqueous potassium hydrogen sulfate solution (1 M, 2×125 mL), a saturated aqueous sodium hydrogen carbonate solution (2×125 mL), and a saturated aqueous sodium chloride solution (125 mL), dried over anhydrous sodium sulfate, filtered, and concentrated under reduced pressure. The resulting residue was purified by flash column chromatography on silica gel (eluent: 20%→30% ethyl acetate in hexanes) to afford allyl tryptophan (+)-S4 (7.06 g, 89%, >99.5:1 er) as a white foam. The enantiomeric ratio was determined by chiral HPLC analysis (CHIRALPAK® IA 4.6 mm×250 mm, Lot #IAOOCE-PD046, 25% i-PrOH in hexanes, 1.0 mL/min, 270 nm, $t_R$=7.88 min); the D enantiomer ($t_R$=5.61 min) was not detected and its retention time was independently determined by chiral HPLC analysis of a racemic sample of allyl tryptophan S4. Structural assignments were made using additional information from gCOSY, gHSQC, and gHMBC experiments.

$^1$H NMR (500 MHz, CDCl$_3$, 25° C.): δ 8.15 (d, J=7.7 Hz, 1H, C7H), 7.77 (d, J=7.6 Hz, 2H, Ar$_{Fmoc}$H), 7.62-7.51 (m, 3H, C4H, Ar$_{Fmoc}$H), 7.46 (s, 1H, C8aH), 7.44-7.37 (m, 2H, Ar$_{Fmoc}$H), 7.36-7.27 (m, 3H, C6H, Ar$_{Fmoc}$H), 7.25 (app-t, J=7.8 Hz, 1H, C5H), 5.87 (app-ddt, J=16.5, 11.2, 5.9 Hz, 1H, C2'H), 5.48 (d, J=8.2 Hz, 1H, N1H), 5.32 (d, J=17.2 Hz, 1H, C3'H$_a$), 5.26 (d, J=10.3 Hz, 1H, C3'H$_b$), 4.82 (app-dt, J=8.3, 5.6 Hz, 1H, C2H), 4.69-4.55 (m, 2H, C1'H$_2$), 4.45-4.34 (m, 2H, N1CO$_2$CH$_2$), 4.23 (app-t, J=7.3 Hz, 1H, N1CO$_2$CH$_2$H), 3.36-3.24 (m, 2H, C3H$_2$), 1.67 (s, 9H, N8CO$_2$C(CH$_3$)$_3$).

$^{13}$C NMR (125.8 MHz, CDCl$_3$, 25° C.): δ 171.4 (C2CO$_2$), 155.8 (N1CO$_2$), 149.6 (N8CO$_2$), 143.9 (Ar$_{Fmoc}$), 143.8 (Ar$_{Fmoc}$), 141.4 (2C, Ar$_{Fmoc}$), 135.5 (C7a), 131.4 (C2'), 130.6 (C4a), 127.8 (2C, Ar$_{Fmoc}$), 127.2 (2C, Ar$_{Fmoc}$), 125.2 (2C, Ar$_{Fmoc}$), 124.7 (C6), 124.4 (C8a), 122.8 (C5), 120.1 (2C, Ar$_{Fmoc}$), 119.3 (C3'), 119.0 (C4), 115.4 (C7), 114.9 (C3a), 83.8 (N8CO$_2$C(CH$_3$)$_3$), 67.3 (N1CO$_2$CH$_2$), 66.3 (C1'), 54.3 (C2), 47.2 (N1CO$_2$CH$_2$CH), 28.3 (N8CO$_2$C(CH$_3$)$_3$), 28.0 (C3).

FTIR (thin film) cm$^{-1}$: 3345 (br-w), 3066 (w), 2978 (w), 2939 (w), 1724 (s), 1609 (m), 1510 (m), 1451 (m), 1369 (m), 1254 (m), 1154 (m), 1086 (m), 738 (m).

HRMS (ESI) (m/z): calc'd for C$_{34}$H$_{34}$N$_2$NaO$_6$ [M+Na]$^+$: 589.2309, found: 589.2326.

$[α]_D^{23}$: +12 (c=0.55, CH$_2$Cl$_2$).

TLC (25% ethyl acetate in hexanes), Rf: 0.32 (UV, CAM).

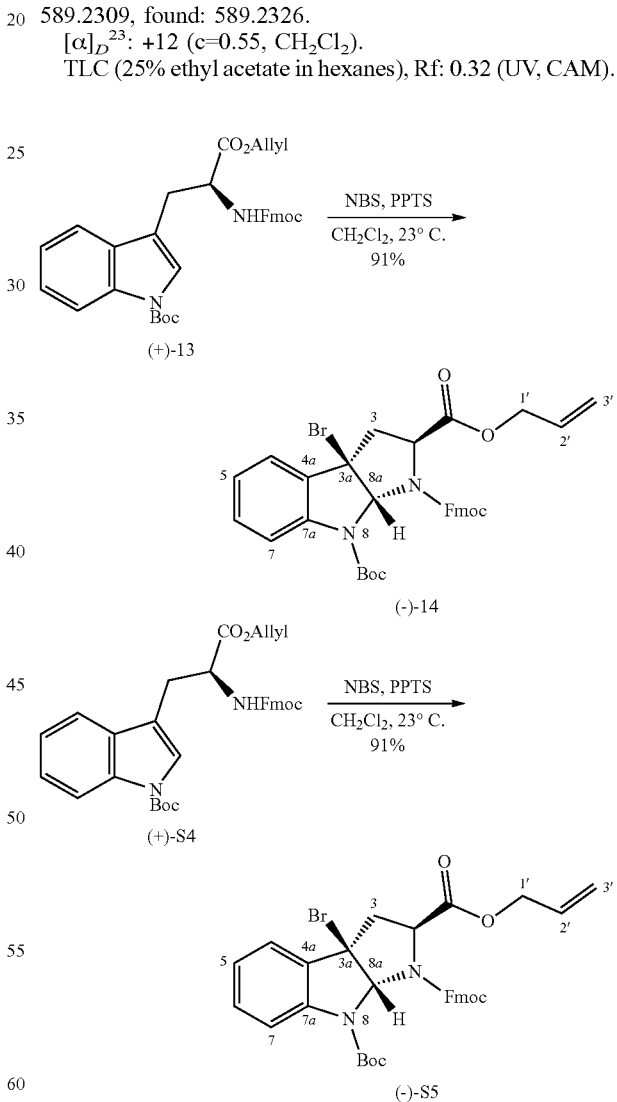

Bromocyclotryptophan (−)-S5

A sample of N-bromosuccinimide (2.45 g, 13.7 mmol, 1.10 equiv) was added to a solution of allyl tryptophan (+)-S4 (7.08 g, 12.5 mmol, 1 equiv) and pyridinium p-toluenesulfonate (3.48 g, 13.7 mmol, 1.10 equiv) in dichloromethane (125 mL) at 23° C. After 1.5 h, the yellow solution was diluted with a saturated aqueous sodium hydrogen carbonate solution (125 mL). The layers were separated and the organic layer was washed with a saturated aqueous sodium chloride solution (125 mL), was dried over anhydrous sodium sulfate, was filtered, and was concentrated under reduced pressure. The resulting residue was purified by flash column chromatography on silica gel (eluent: 20%→25% ethyl acetate in hexanes) to afford bromocyclotryptophan (−)-S5 (7.33 g, 91%) as an off-white foam. As a result of the slow conformational equilibration at ambient temperature, NMR spectra were collected at elevated temperature. Structural assignments were made using additional information from gCOSY, gHSQC, and gHMBC experiments. Acquisition of NMR spectra in $CD_3CN$ at 60° C. resulted in simplification of the spectra by convergence of the signals derived from various conformational isomers, though we observed gradual sample decomposition during extended acquisition time.

$^1H$ NMR (500 MHz, $CD_3CN$, 60° C.): δ 7.81-7.77 (m, 2H, $Ar_{Fmoc}H$), 7.65 (dd, J=8.2, 0.8 Hz, 1H, C7H), 7.58-7.52 (m, 2H, $Ar_{Fmoc}H$, C4H), 7.49 (d, J=7.6 Hz, 1H, $Ar_{Fmoc}H$), 7.47-7.34 (m, 3H, $Ar_{Fmoc}H$, C6H), 7.30 (app-t, J=7.3 Hz, 1H, $Ar_{Fmoc}H$), 7.26-7.20 (m, 2H, C5H, $Ar_{Fmoc}H$), 6.40 (s, 1H, C8aH), 5.90 (app-ddt, J=17.2, 10.5, 5.6 Hz, 1H, C2'H), 5.31 (app-dq, J=17.3, 1.6 Hz, 1H, $C3'H_a$), 5.21 (app-dq, J=10.5, 1.3 Hz, 1H, $C3'H_b$), 4.59 (app-ddt, J=13.4, 5.6, 1.5 Hz, 1H, $C1'H_a$), 4.53 (app-ddt, J=13.3, 5.9, 1.4 Hz, 1H, $C1'H_b$), 4.36-4.29 (m, 2H, $N1CO_2CH_2$), 4.27-4.20 (m, 1H, $N1CO_2CH_2CH$), 4.02 (dd, J=9.2, 7.3 Hz, 1H, C2H), 3.49 (dd, J=13.3, 7.3 Hz, 1H, $C3H_a$), 2.84 (dd, J=13.3, 9.2 Hz, 1H, $C3H_b$), 1.52 (s, 9H, $N8CO_2C(CH_3)_3$).

$^{13}C$ NMR (125.8 MHz, $CD_3CN$, 60° C.): δ 171.6 ($C2CO_2$), 154.2 ($N8CO_2$), 153.2 ($N1CO_2$), 145.3 ($Ar_{Fmoc}$), 144.8 ($Ar_{Fmoc}$), 142.4 ($Ar_{Fmoc}$), 142.3 ($Ar_{Fmoc}$), 142.2 (C7a), 134.4 (C4a), 133.3 (C2'), 132.0 (C6), 129.0 ($Ar_{Fmoc}$), 128.9 ($Ar_{Fmoc}$), 128.4 ($Ar_{Fmoc}$), 128.3 ($Ar_{Fmoc}$), 126.3 ($Ar_{Fmoc}$), 126.2 ($Ar_{Fmoc}$), 125.9 (C5), 125.2 (C4), 121.1 (2C, $Ar_{Fmoc}$), 119.2 (C7), 119.0 (C3'), 85.6 (C8a), 83.5 ($N8CO_2C(CH_3)_3$), 68.8 ($N1CO_2CH_2$), 66.9 (C1'), 61.6 (C3a), 60.6 (C2), 48.1 ($N1CO_2CH_2CH$), 42.2 (C3), 28.6 ($N8CO_2C(CH)$).

FTIR (thin film) $cm^{-1}$: 3067 (w), 2979 (w), 2949 (w), 1747 (s), 1716 (s), 1412 (m), 1333 (m), 1155 (s), 754 (m).

HRMS (ESI) (m/z): calc'd for $C_{34}H_{33}BrN_2NaO_6$ $[M+Na]^+$: 667.1414, found: 667.1424.

$[α]_D^{23}$: −143 (c=0.46, $CHCl_3$).

TLC (25% ethyl acetate in hexanes), Rf: 0.38 (UV, CAM).

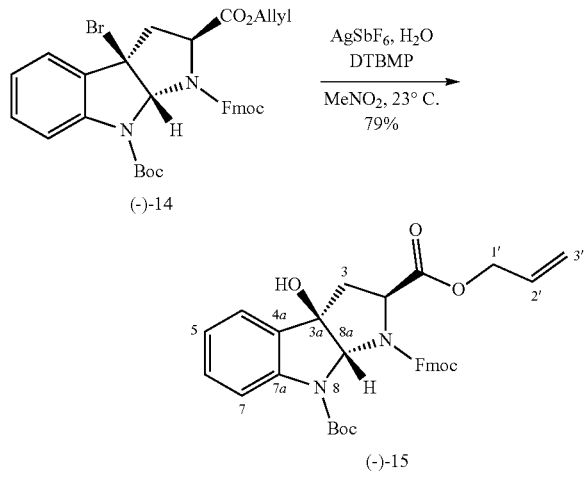

(−)-14

(−)-15

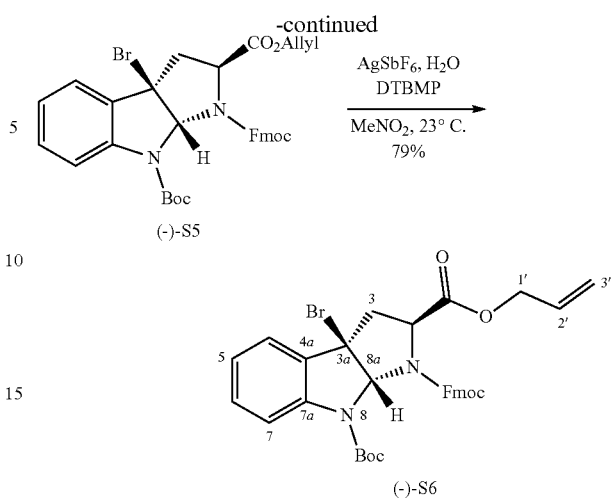

(−)-S5

(−)-S6

Hydroxycyclotryptophan (−)-S6:

A sample of silver(I) hexafluoroantimonate (5.83 g, 17.0 mmol, 1.50 equiv) was added to a solution of bromocyclotryptophan (−)-S5 (7.30 g, 11.3 mmol, 1 equiv), 2,6-di-tert-butyl-4-methylpyridine (DTBMP, 4.65 g, 22.6 mmol, 2.00 equiv), and water (2.04 mL, 113 mmol, 10.0 equiv.) in nitromethane (113 mL) at 23° C. in the dark. After 1.5 h, the heterogeneous solution was diluted with dichloromethane (200 mL), a saturated aqueous sodium thiosulfate solution (75 mL), a saturated aqueous sodium hydrogen carbonate solution (75 mL), and deionized water (150 mL). The layers were separated and the aqueous layer was extracted with dichloromethane (200 mL). The combined organic extracts were washed with a saturated aqueous sodium chloride solution (200 mL), were dried over anhydrous sodium sulfate, were filtered, and were concentrated under reduced pressure. The resulting residue was purified by flash column chromatography on silica gel (eluent: 25%→40% ethyl acetate in hexanes) to afford hydroxycyclotryptophan (−)-S6 (5.21 g, 79.1%) as a white solid. As a result of the slow conformational equilibration at ambient temperature, NMR spectra were collected at elevated temperature. Structural assignments were made using additional information from gCOSY, gHSQC, and gHMBC experiments.

$^1H$ NMR (500 MHz, $CD_3CN$, 70° C.): δ 7.81-7.77 (m, 2H, $Ar_{Fmoc}H$), 7.69 (dd, J=8.1, 0.8 Hz, 1H, C7H), 7.57 (d, J=7.5 Hz, 1H, $Ar_{Fmoc}H$), 7.51 (d, J=7.6 Hz, 1H, $Ar_{Fmoc}H$), 7.47 (dd, J=7.5, 1.3 Hz, 1H, C4H), 7.44-7.35 (m, 3H, C6H, $Ar_{Fmoc}H$), 7.31 (app-td, J=7.5, 1.2 Hz, 1H, $Ar_{Fmoc}H$), 7.25 (app-td, J=7.5, 1.1 Hz, 1H, $Ar_{Fmoc}H$), 7.18 (app-td, J=7.5, 1.0 Hz, 1H, C5H), 5.99 (s, 1H, C8aH), 5.90 (app-ddt, J=17.4, 10.7, 5.6 Hz, 1H, C2'H), 5.32 (app-dq, J=17.3, 1.6 Hz, 1H, $C3'H_a$), 5.20 (app-dq, J=10.6, 1.4 Hz, 1H, $C3'H_b$), 4.60 (app-ddt, J=13.4, 5.6, 1.5 Hz, 1H, $C1'H_a$), 4.53 (app-ddt, J=13.4, 5.6, 1.4 Hz, 1H, $C1'H_b$), 4.36-4.22 (m, 3H, $N1CO_2CH_2CH$, $N1CO_2CH_2$), 4.01 (dd, J=9.3, 7.7 Hz, 1H, C2H), 3.95 (br-s, 1H, C3aOH), 2.97 (dd, J=13.0, 7.7 Hz, 1H, $C3H_a$), 2.41 (dd, J=13.0, 9.3 Hz, 1H, $C3H_b$), 1.51 (s, 9H, $N8CO_2C(CH_3)_3$).

$^{13}C$ NMR (125.8 MHz, $CD_3CN$, 70° C.): δ 172.7 ($C2CO_2$), 154.9 ($N8CO_2$), 153.7 ($N1CO_2$), 145.4 ($Ar_{Fmoc}$), 145.0 ($Ar_{Fmoc}$), 143.8 (C7a), 142.4 ($Ar_{Fmoc}$), 142.3 ($Ar_{Fmoc}$), 134.5 (C4a), 133.5 (C2'), 131.5 (C6'), 129.0 ($Ar_{Fmoc}$), 128.9 ($Ar_{Fmoc}$), 128.4 ($Ar_{Fmoc}$), 128.3 ($Ar_{Fmoc}$), 126.4 ($Ar_{Fmoc}$), 126.3 ($Ar_{Fmoc}$), 125.1 (C5), 125.0 (C4), 121.2 (2C, $Ar_{Fmoc}$), 118.9 (C3'), 118.8 (C7), 84.7 (C3a), 82.9

(C8a), 82.8 (N8CO$_2$C(CH$_3$)$_3$), 68.6 (N1CO$_2$CH$_2$), 66.7 (C1'), 60.3 (C2), 48.2 (N1CO$_2$CH$_2$CH), 38.8 (C3), 28.8 (N8CO$_2$C(CH$_3$)$_3$).

FTIR (thin film) cm$^{-1}$: 3428 (br-m), 3016 (w), 2979 (w), 2946 (w), 1713 (s), 1479 (m), 1334 (m), 1154 (s), 754 (m).

HRMS (ESI) (m/z): calc'd for C$_{34}$H$_{34}$N$_2$NaO$_7$ [M+Na]$^+$: 605.2258, found: 605.2271.

[α]$_D^{23}$: −72 (c=0.36, CHCl$_3$).

TLC (40% ethyl acetate in hexanes), Rf: 0.44 (UV, CAM).

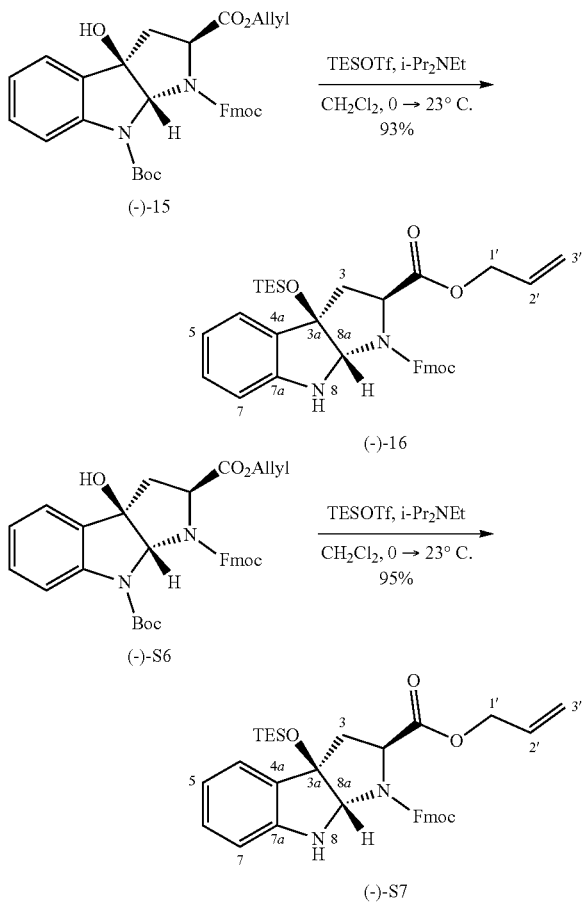

Fmoc-Cyclotryptophan Triethylsilyl Ether (−)-S7:

Triethylsilyl trifluoromethanesulfonate (5.16 mL, 22.8 mmol, 4.00 equiv) was added to a solution of hydroxycyclotryptophan (−)-S6 (3.32 g, 5.70 mmol, 1 equiv) and N,N-diisopropylethylamine (5.96 mL, 34.2 mmol, 6.00 equiv) in dichloromethane (40 mL) at 0° C. After 30 min, the cold bath was removed and the colorless solution was allowed to stir at 23° C. After 2.5 h, the reaction mixture was diluted with a saturated aqueous sodium hydrogen carbonate solution (100 mL) and stirred vigorously for 15 min. Ethyl acetate (100 mL) was added and the layers were separated. The organic layer was washed sequentially with an aqueous hydrogen chloride solution (1 M, 2×50 mL), a saturated aqueous sodium hydrogen carbonate solution (2×100 mL), and a saturated aqueous sodium chloride solution (100 mL), was dried over anhydrous sodium sulfate, was filtered, and was concentrated under reduced pressure. The resulting residue was purified by flash column chromatography on silica gel (eluent: 15%→25% ethyl acetate in hexanes) to afford Fmoc-cyclotryptophan triethylsilyl ether (−)-s7 (3.25 g, 95%) as a colorless oil. Structural assignments were made using additional information from gCOSY, gHSQC, and gHMBC experiments.

$^1$H NMR (500 MHz, CDCl$_3$, 25° C., 1.9:1 mixture of atropisomers, * denotes minor atropisomer):

δ 7.83 (d, J=7.6 Hz, 1H, Ar$_{Fmoc}$H), 7.77 (d, J=7.4 Hz, 1H, Ar$_{Fmoc}$H), 7.75-7.71 (m, 2H, Ar$_{Fmoc}$H*), 7.64 (d, J=7.4 Hz, 1H, Ar$_{Fmoc}$H), 7.61 (d, J=7.4 Hz, 1H, Ar$_{Fmoc}$H), 7.55-7.48 (m, 3H, Ar$_{Fmoc}$H, Ar$_{Fmoc}$H*), 7.45 (app-t, J=7.5 Hz, 1H, Ar$_{Fmoc}$H), 7.43-7.35 (m, 4H, Ar$_{Fmoc}$H, Ar$_{Fmoc}$H*), 7.27 (app-t, J=7.1 Hz, 2H, Ar$_{Fmoc}$H*), 7.24 (d, J=8.0 Hz, 1H, C4H*), 7.17 (app-t, J=7.7 Hz, 1H, C6H*), 7.11-7.05 (m, 2H, C4H, C6H), 6.80 (app-t, J=7.4 Hz, 1H, C5H*), 6.68 (app-t, J=7.4 Hz, 1H, C5H), 6.62 (d, J=7.9 Hz, 1H, C7H*), 6.26 (d, J=8.0 Hz, 1H, C7H), 5.93-5.81 (m, 2H, C2'H, C2'H*), 5.43 (d, J=2.0 Hz, 1H, C8aH*), 5.33-5.26 (m, 3H, C3'H$_a$, C3'H$_a$*, N1H*), 5.23-5.19 (m, 2H, C3'H$_b$, C3'H$_b$*), 4.76-4.73 (m, 2H, N1CO$_2$CH$_2$), 4.72 (d, J=2.2 Hz, 1H, C8aH), 4.67-4.60 (m, 2H, C1'H$_a$, C1'H$_a$*), 4.56 (dd, J=13.3, 5.7 Hz, 1H, C1'H$_b$), 4.50 (dd, J=13.2, 5.7 Hz, 1H, C1'H$_b$*), 4.42 (dd, J=10.6, 6.6 Hz, 1H, N1CO$_2$CH$_a$), 4.36-4.29 (m, 3H, C2H*, N1CO$_2$CH$_2$CH, N1CO$_2$CH$_b$*), 4.14 (app-t, J=7.0 Hz, 1H, N1CO$_2$CH$_2$CH*), 4.11 (app-t, J=7.1 Hz, 1H, C2H), 3.50 (d, J=2.5 Hz, 1H, N1H), 2.71 (dd, J=13.1, 8.3 Hz, 1H, C3H$_a$*), 2.64 (dd, J=13.1, 5.8 Hz, 1H, C3H$_b$*), 2.48-2.41 (m, 2H, C3H$_2$), 0.82 (t, J=7.9 Hz, 9H, Si(CH$_2$CH$_3$)$_3$*), 0.73 (t, J=7.9 Hz, 9H, Si(CH$_2$CH$_3$)$_3$), 0.48-0.33 (m, 6H, Si(CH$_2$CH$_3$)$_3$*), 0.31-0.16 (m, 6H, Si(CH$_2$CH$_3$)$_3$).

$^{13}$C NMR (125.8 MHz, CDCl$_3$, 25° C., 1.9:1 mixture of atropisomers, * denotes minor atropisomer):

δ 171.5 (C2CO$_2$*), 170.9 (C2CO$_2$), 155.1 (N1CO$_2$*), 154.2 (N1CO$_2$), 148.8 (C7a*), 148.3 (C7a), 144.2 (Ar$_{Fmoc}$), 144.1 (2C, Ar$_{Fmoc}$, Ar$_{Fmoc}$*), 143.6 (Ar$_{Fmoc}$*), 141.9 (Ar$_{Fmoc}$), 141.4 (2C, Ar$_{Fmoc}$*), 141.3 (Ar$_{Fmoc}$), 132.0 (C2'), 131.8 (C2'*), 130.4 (C6*), 130.2 (C6), 129.7 (C4a*), 129.3 (C4a'), 128.1 (Ar$_{Fmoc}$), 127.9 (2C, Ar$_{Fmoc}$, Ar$_{Fmoc}$*), 127.8 (Ar$_{Fmoc}$), 127.7 (Ar$_{Fmoc}$), 127.5 (Ar$_{Fmoc}$), 127.2 (2C, Ar$_{Fmoc}$*), 125.2 (Ar$_{Fmoc}$*), 125.1 (Ar$_{Fmoc}$*), 124.8 (Ar$_{Fmoc}$), 124.6 (Ar$_{Fmoc}$), 124.0 (C4*), 123.8 (C4), 120.2 (Ar$_{Fmoc}$), 120.1 (2C, Ar$_{Fmoc}$, Ar$_{Fmoc}$*), 119.2 (C5*), 118.9 (C3'*), 118.8 (C5), 118.4 (C3'), 110.6 (C7*), 109.7 (C7), 88.3 (C3a), 87.8 (C3a*), 83.7 (C8a*), 82.7 (C8a), 67.9 (N1CO$_2$CH$_2$*), 66.4 (N1CO$_2$CH$_2$), 66.1 (C1'*), 65.9 (C1'), 59.3 (C2H*), 59.1 (C2H), 47.3 (2C, N1CO$_2$CH$_2$CH, N1CO$_2$CH$_2$CH*), 44.0 (C3*), 43.4 (C3), 6.9 (Si(CH$_2$CH$_3$)$_3$*), 6.8 (Si(CH$_2$CH$_3$)$_3$), 5.8 (Si(CH$_2$CH$_3$)$_3$*), 5.6 (Si(CH$_2$CH$_3$)$_3$).

FTIR (thin film) cm$^{-1}$: 3382 (br-w), 3064 (w), 2953 (m), 2875 (w), 1752 (s), 1712 (s), 1420 (m), 1189 (m), 1106 (m), 741 (s).

HRMS (ESI) (m/z): calc'd for C$_{35}$H$_{41}$N$_2$O$_5$Si[M+H]$^+$: 597.2779, found: 597.2789.

[α]$_D^{23}$: −200 (c=0.22, CHCl$_3$).

TLC (25% ethyl acetate in hexanes), Rf: 0.42 (UV, CAM).

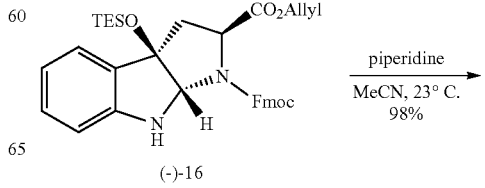

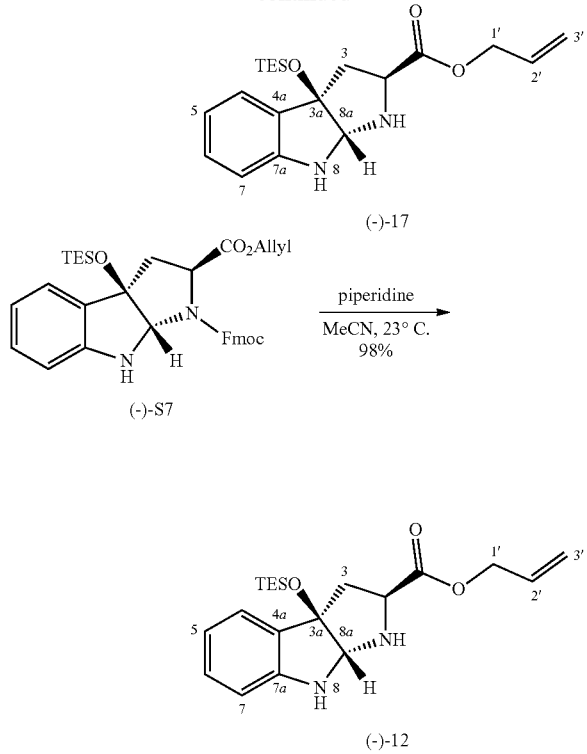

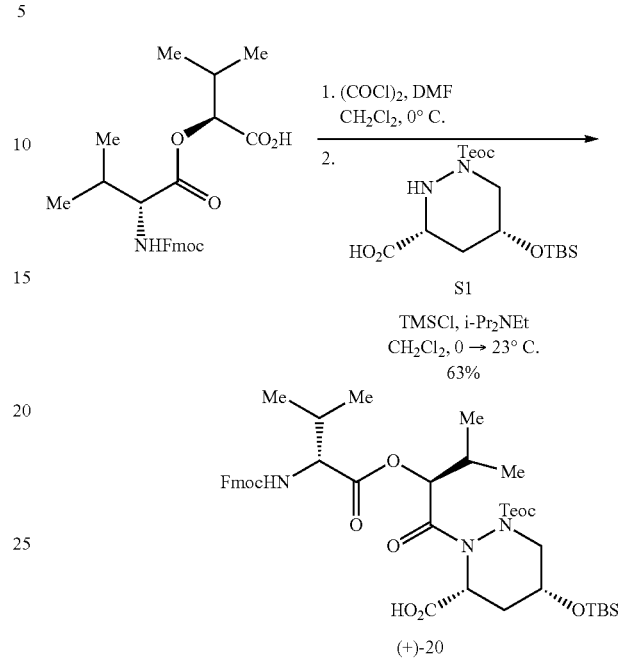

Depsitripeptide (+)-20:

Cyclotryptophan Triethylsilyl Ether (−)-12:

Piperidine (2.10 mL, 21.3 mmol, 4.00 equiv) was added to a solution of Fmoc-cyclotryptophan triethylsilyl ether (−)-S7 (3.19 g, 5.33 mmol. 1 equiv) in acetonitrile (53 mL) at 23° C. After 2 h, the heterogeneous solution was concentrated under reduced pressure. The resulting residue was purified by flash column chromatography on silica gel (eluent: 20%→45% ethyl acetate in hexanes) to afford cyclotryptophan triethylsilyl ether (−)-12 (96 g, 98%) as a light yellow oil. Spectral data and optical rotation (lit. $[\alpha]_D^{25}=−98.2$ (c=1.00, CHCl$_3$)) were in agreement with those previously reported in the literature.[11] Structural assignments were made using additional information from gCOSY, gHSQC, and gHMBC experiments.

$^1$H NMR (600 MHz, CDCl$_3$, 25° C.): δ 7.22 (dd, J=7.7, 1.2 Hz, 1H, C4H), 7.12 (app-td, J=7.6, 1.3 Hz, 1H, C6H), 6.76 (app-td, J=7.4, 1.0 Hz, 1H, C5H), 6.58 (dd, J=8.0, 1.0 Hz, 1H, C7H), 5.89 (app-ddt, J=17.2, 10.4, 5.8 Hz, 1H, C2'H), 5.30 (app-dq, J=17.2, 1.5 Hz, 1H, C3'H$_a$), 5.23 (app-dq, J=10.4, 1.3 Hz, 1H, C3'H$_b$), 4.98 (s, 1H, C8aH), 4.65-4.57 (m, 2H, C1'H$_2$), 4.25 (br-s, 1H, N8H), 3.71 (dd, J=9.5, 6.1 Hz, 1H, C2H), 2.92 (br-s, 1H, N1H), 2.59 (dd, J=12.2, 6.1 Hz, 1H, C3H$_a$), 2.43 (dd, J=12.2, 9.6 Hz, 1H, C3H$_b$), 0.82 (t, J=7.9 Hz, 9H, Si(CH$_2$CH$_3$)$_3$), 0.46-0.34 (m, 6H, Si(CH$_2$CH$_3$)$_3$).

$^{13}$C NMR (150.9 MHz, CDCl$_3$, 25° C.): δ 173.3 (C2CO$_2$), 150.1 (C7a), 131.9 (C2'), 130.6 (C4a), 130.1 (C6), 124.8 (C4), 119.0 (C5), 118.7 (C3'), 110.1 (C7), 91.3 (C3a), 84.4 (C8a), 65.7 (C1'), 59.4 (C2), 47.1 (C3), 6.9 (Si(CH$_2$CH$_3$)$_3$), 5.8 (Si(CH$_2$CH$_3$)$_3$).

FTIR (thin film) cm$^{-1}$: 3348 (br-m), 3053 (w), 2953 (m), 2912 (w), 2879 (m), 1737 (s), 1611 (m), 1469 (m), 1131 (s), 741 (s).

HRMS (ESI) (m/z): calc'd for C$_{20}$H$_{31}$N$_2$O$_3$Si[M+H]$^+$: 375.2098, found: 375.2104.

$[\alpha]_D^{23}$: −96 (c=1.00, CHCl$_3$).[12]

TLC (40% ethyl acetate in hexanes), Rf: 0.37 (UV, CAM).

Depsitripeptide (+)-20:

Oxalyl chloride (515 μL, 6.00 mmol, 2.40 equiv.) was added dropwise via syringe over 2 minutes to a solution of Fmoc-D-Val-L-Hiv-OH[13] (1.32 g, 3.00 mmol, 1.20 equiv.) and N,N-dimethylformamide (23 μL, 0.30 mmol, 0.12 equiv) in dichloromethane (4.0 mL) at 0° C. After 1 h, the yellow solution was concentrated under reduced pressure (~1 torr) at 0° C. The resulting residue was dissolved in dichloromethane (5 mL) and transferred by cannula over 2 min to a solution of piperazic acid S[14] (1.01 g, 2.50 mmol, 1 equiv.), N,N-diisopropylethylamine (914 μL, 5.25 mmol, 2.10 equiv.), and chlorotrimethylsilane (635 μL, 5.00 mmol, 2.00 equiv.) in dichloromethane (6 mL) at 0° C. The transfer was quantitated with additional dichloromethane (2×1.5 mL). After 30 min, the cold bath was removed and the yellow solution was allowed to stir at 23° C. After 1 h, the reaction mixture was diluted with an aqueous hydrogen chloride solution (1 M, 50 mL) and stirred vigorously for 5 min. The mixture was extracted with ethyl acetate (3×50 mL) and the combined organic extracts were washed with an aqueous saturated sodium chloride solution (100 mL), were dried over anhydrous sodium sulfate, were filtered, and were concentrated under reduced pressure. The resulting residue was purified by flash column chromatography on silica gel (eluent: 1% acetic acid, 20%→50% ethyl acetate in hexanes), including a second chromatographic purification of mixed fractions of (+)-20 and Fmoc-D-Val-L-Hiv-OH on silica gel (eluent: 1% acetic acid, 30%→50% ethyl acetate in hexanes), to afford depsitripeptide (+)-20 (1.30 g, 62.7%) as a white foam.

$^1$H NMR (600 MHz, CD$_3$CN, 25° C.): δ 11.34 (br-s, 1H), 7.84 (d, J=7.7 Hz, 2H), 7.70 (app-t, J=6.4 Hz, 2H), 7.44-7.40 (m, 2H), 7.34 (app-t, J=7.4 Hz, 2H), 6.04 (d, J=9.1 Hz, 1H), 5.19-5.03 (m, 2H), 4.43 (br-s, 1H), 4.32 (br-s, 2H), 4.24 (app-t, J=7.3 Hz, 1H), 4.19 (br-s, 2H), 4.06 (br-s, 2H), 3.70 (d, J=12.2 Hz, 0.1H), 3.21 (d, J=13.7 Hz, 0.7H), 3.04 (d, J=13.5 Hz, 0.2H), 2.38 (d, J=14.1 Hz, 1H), 2.24-1.96 (m, 7H), 1.01-0.93 (m, 8H), 0.92-0.88 (m, 2H), 0.84 (s, 9H), 0.08-0.00 (m, 15H).

$^{13}$C NMR (125.8 MHz, CD$_3$CN, 25° C.): δ 172.9, 172.8, 172.5, 171.9, 171.3, 171.2, 170.9, 170.3, 168.4, 167.1, 164.5, 163.0, 161.9, 161.5, 159.2, 157.9, 157.4, 156.7, 145.1 (2C), 145.0, 142.1 (2C), 129.9, 129.2, 128.7, 128.2, 128.1, 126.3, 121.0 (2C), 77.8, 76.5, 76.1, 68.8, 68.5, 67.8, 67.5, 67.0, 66.5, 63.6, 63.4 (2C), 63.3, 60.8, 58.1, 56.3, 53.7, 53.1, 52.8, 52.2, 50.9, 50.8, 48.0, 34.9, 33.4, 33.2, 32.9, 32.7, 31.4 (2C), 30.8, 30.2, 30.0, 26.2, 26.0, 19.9, 19.7, 19.5 (3C), 19.1, 18.7, 18.6, 18.5, 18.3, 18.2, 18.1 (2C), 18.0, 17.7, 17.4, 16.9, 16.1, −1.4, −4.5, −4.6, −5.0, −5.1.

FTIR (thin film) cm$^{-1}$: 3331 (br-w), 2958 (m), 2858 (w), 1746 (s), 1701 (s), 1405 (m), 1250 (m), 1120 (m), 837 (m), 758 (m), 741 (m).

HRMS (ESI) (m/z): calc'd for C$_{42}$H$_{63}$N$_3$NaO$_{10}$Si$_2$ [M+Na]$^+$: 848.3944, found: 848.3961.

[α]$_D^{23}$: +67 (c=0.07, CHCl$_3$).

TLC (1% acetic acid, 40% ethyl acetate in hexanes), Rf: 0.34 (UV, CAM).

Depsihexapeptide (−)-13:

A sample of Fmoc-D-Thr(t-Bu)-2-chlorotrityl polystyrene resin 9 (499 mg, 0.802 mmol/g, 0.400 mmol, 1 equiv) in a fritted syringe connected to a vacuum manifold was treated twice with piperidine (20% in N,N-dimethylformamide, 2×10 mL) at 23° C. for 5 min. The liquid phase was drained and the resin was washed with N,N-dimethylformamide (3×10 mL).

A solution of Fmoc-L-Leu-OH (565.5 mg, 1.60 mmol, 4 equiv), 1-[bis(dimethylamino)methylene]-1H-1,2,3-triazolo [4,5-b]pyridinium 3-oxide hexafluorophosphate (HATU, 578 mg, 1.52 mmol, 3.80 equiv), and N,N-diisopropylethylamine (800 μL, 4.59 mmol, 11.5 equiv) in N,N-dimethylformamide (4.0 mL) was added to the resulting resin at 23° C. After 1 h, the liquid phase was drained and the resin was washed with N,N-dimethylformamide (3×10 mL) and was treated twice with piperidine (20% in N,N-dimethylforma-

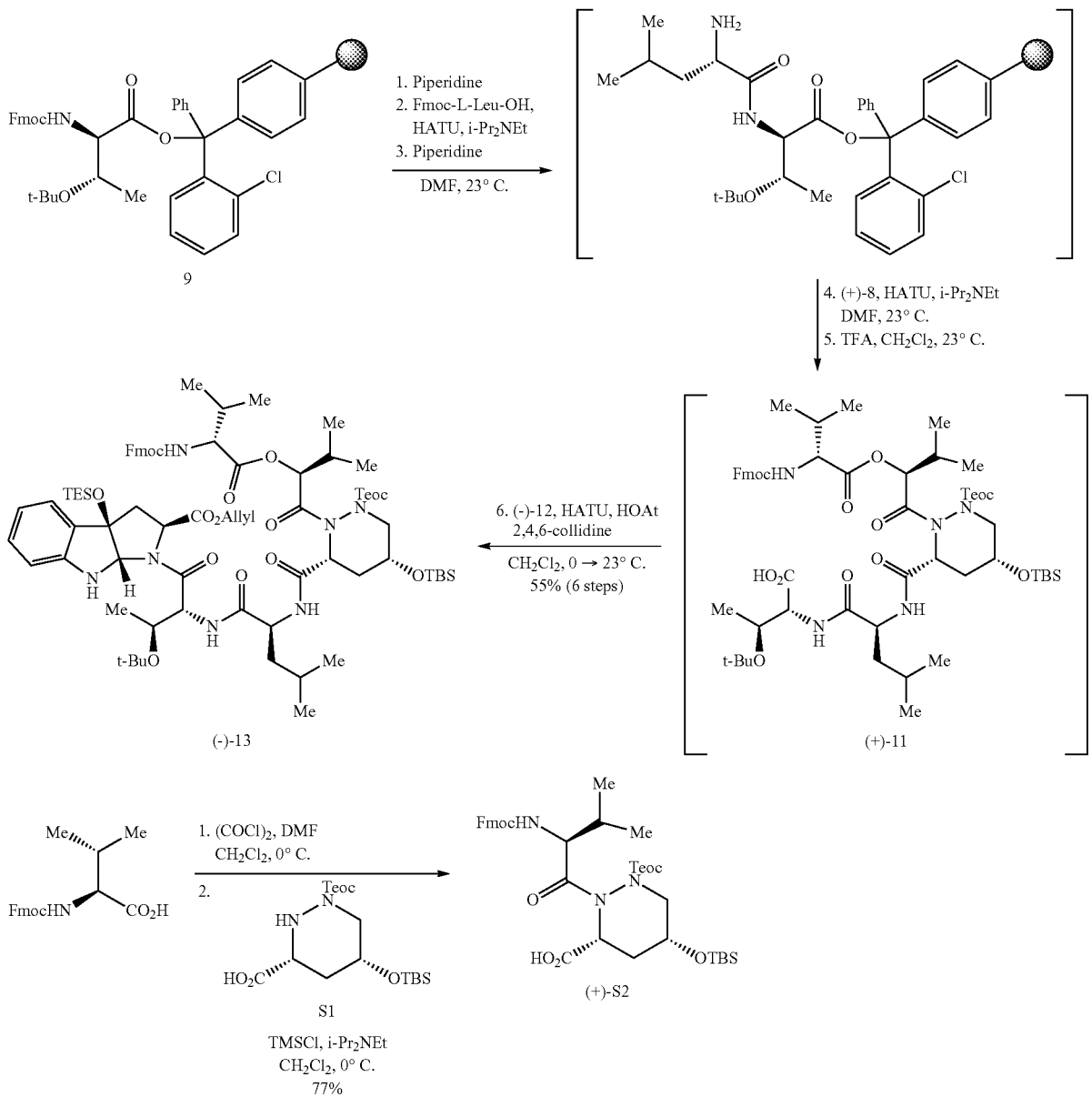

mide, 2×10 mL) at 23° C. for 5 min. The liquid phase was drained and the resin was washed with N,N-dimethylformamide (3×10 mL).

A solution of depsitripeptide (+)-8 (427 mg, 0.520 mmol, 1.30 equiv), HATU (198 mg, 0.520 mmol, 1.30 equiv), and N,N-diisopropylethylamine (154 µL, 0.884 mmol, 2.21 equiv) in N,N-dimethylformamide (2.3 mL) was added to the resulting resin at 23° C. After 20 h, the liquid phase was drained and the resin was washed with N,N-dimethylformamide (3×10 mL) and dichloromethane (3×10 mL).

The resulting resin was treated twice with trifluoroacetic acid (1% in dichloromethane, 2×15 mL) at 23° C. for 2 min. The liquid phases were separated into a vessel containing pyridine (1.0 mL). The resin was washed with dichloromethane (3×5 mL) and the liquid phases were separated into the same vessel. The combined liquid phases were diluted with an aqueous hydrogen chloride solution (1 M, 100 mL) and extracted with dichloromethane (3×50 mL). The combined organic extracts were washed with a saturated aqueous sodium chloride solution (100 mL), were dried over anhydrous sodium sulfate, were filtered, and were concentrated under reduced pressure to provide the crude depsipentapeptide acid (+)-11 as an off-white foam, which was used in the next step without further purification.

A sample of HATU (304 mg, 0.800 mmol, 2.00 equiv) was added to a solution of the crude depsipentapeptide acid, cyclotryptophan triethylsilyl ether (−)-12 (180 mg, 0.480 mmol, 1.20 equiv), 1-hydroxy-7-azabenzotriazole (HOAt, 381 mg, 2.80 mmol, 7.00 equiv), and 2,4,6-collidine (423 µL, 3.20 mmol, 8.00 equiv) in dichloromethane (8 mL) at 0° C. After 1 h, the cold bath was removed and the cloudy solution was allowed to stir at 23° C. After 5 h, the reaction mixture was diluted with ethyl acetate-hexanes (4:1, 100 mL) and washed with an aqueous potassium hydrogen sulfate solution (1 M, 60 mL), a saturated aqueous sodium hydrogen carbonate solution (60 mL), and a saturated aqueous sodium chloride solution (60 mL). The organic layer was dried over anhydrous sodium sulfate, was filtered, and was concentrated under reduced pressure. The resulting residue was purified by flash column chromatography on silica gel (eluent: 30%→40% ethyl acetate in hexanes) to afford depsihexapeptide (−)-13 (321 mg, 55%) as a white foam. The reported $^1$H NMR integrals are an approximation due to the presence of multiple conformers and significant atropisomerism. The $^{13}$C data are listed as observed with more than the expected number of $^{13}$C resonances due to atropisomerism.

$^1$H NMR (500 MHz, DMSO-d$_6$, 100° C.): δ 7.85 (d, J=7.6 Hz, 2H), 7.79 (br-s, 1.5H), 7.69 (d, J=7.5 Hz, 2H), 7.40 (app-t, J=7.5 Hz, 2H), 7.31 (app-t, J=7.5 Hz, 2H), 7.24 (br-s, 0.5H), 7.14 (br-s, 2.5H), 6.76 (br-s, 1H), 6.67 (br-s, 2H), 6.10 (br-s, 0.5H), 5.92 (br-s, 1.5H), 5.49 (br-s, 1H), 5.33 (br-s, 1H), 5.21 (br-d, J=6.1 Hz, 1H), 5.08 (br-s, 1H), 4.89 (br-s, 0.5H), 4.77 (br-s, 1H), 4.62 (br-s, 2.5H), 4.39-4.19 (m, 6H), 4.03 (br-s, 3.5H), 3.73 (br-d, J=12.3 Hz, 1H), 3.51 (br-s, 1H), 2.64 (br-s, 1H), 2.38 (br-s, 1H), 2.24-2.02 (m, 3H), 1.93-1.35 (m, 4H), 1.17-1.08 (m, 12H), 1.08-1.01 (m, 3H), 0.99-0.90 (m, 12H), 0.89-0.82 (m, 14H), 0.80 (t, J=7.9 Hz, 9H), 0.49-0.33 (m, 6H), 0.09-0.00 (m, 15H).

$^{13}$C NMR (125.8 MHz, DMSO-d$_6$, 25° C.): 172.0, 171.8, 171.6, 171.2, 171.1, 171.0, 170.6, 170.5, 170.3, 170.0, 169.9, 169.6, 168.8, 168.1, 156.4, 155.5, 154.2, 149.2, 148.4, 143.7, 140.7, 132.4, 132.2, 132.0, 130.5, 130.3, 129.4, 129.1, 129.1, 128.9, 127.6, 127.3, 127.0, 125.3, 124.0, 123.7, 122.3, 121.4, 120.1, 117.7, 117.6, 117.5, 117.3, 117.2, 110.0, 109.7, 88.0, 87.9, 85.5, 82.8, 82.2, 74.9, 74.5, 74.4, 74.1, 73.7, 73.4, 73.2, 68.7, 68.0, 66.9, 66.4, 66.2, 65.9, 65.2, 64.7, 64.1, 63.1, 60.0, 59.1, 58.6, 58.5, 57.4, 54.9, 54.7, 54.4, 51.6, 51.2, 50.5, 50.3, 46.6, 45.5, 42.9, 41.2, 30.1, 29.8, 28.7, 28.6, 28.0, 28.0, 25.6, 25.4, 24.2, 23.4, 23.3, 23.1, 21.2, 20.9, 19.9, 19.7, 19.6, 19.4, 19.1 (2C), 18.9, 18.2, 17.9, 17.6, 17.5, 17.2, 17.0, 16.8, 16.7, 6.6, 6.4, 5.4, 5.2, −1.5, −1.7, −5.1 (2C), −5.2, −5.3 (2C), −5.4.

FTIR (thin film) cm$^{-1}$: 3367 (br-m), 3306 (br-m), 2956 (m), 2877 (w), 1708 (s), 1661 (s), 1408 (w), 1249 (m), 1116 (m), 1017 (m), 837 (m), 741 (m).

HRMS (ESI) (m/z): calc'd for C$_{76}$H$_{118}$N$_7$O$_{15}$Si$_3$ [M+H]$^+$: 1452.7988, found: 1452.7987.

$[\alpha]_D^{23}$: −43 (c=0.27, CHCl$_3$).

TLC (35% ethyl acetate in hexanes), Rf: 0.41 (UV, CAM).

Depsipentapeptide Acid (+)-11

For structural characterization, a sample of the crude depsipentapeptide acid (+)-11 was purified by flash column chromatography on silica gel (eluent: 0.5%→10% methanol in dichloromethane).

$^1$H NMR (500 MHz, C6D$_6$, 70° C.): δ 8.61 (br-s, 1H), 7.59 (d, J=7.3 Hz, 2H), 7.53 (d, J=7.0 Hz, 2H), 7.26-7.18 (m, 5H), 6.21 (br-s, 0.2H), 5.42 (d, J=3.3 Hz, 0.2H), 5.21 (br, 1.2H), 4.97 (app-t, J=7.4 Hz, 1H), 4.88 (dd, J=7.8, 4.0 Hz, 0.2H), 4.78 (s, 1H), 4.72 (br-s, 0.2H) 4.59 (dd, J=6.2, 3.9 Hz, 1.2H), 4.53-4.33 (m, 5.4H), 4.27 (app-q, J=7.8 Hz, 0.4H), 4.13 (app-t, J=6.8 Hz, 1H), 4.04 (br-s, 0.8H), 3.80 (s, 1H), 3.48 (d, J=12.0 Hz, 0.4H), 3.32 (br-s, 0.6H), 2.58-2.08 (m, 4H), 2.08-1.75 (m, 3H), 1.67 (ddd, J=14.5, 9.1, 5.9 Hz, 0.2H), 1.10 (d, J=6.4 Hz, 3H), 1.05 (s, 9H), 1.03-0.98 (m, 9H), 0.96 (d, J=6.3 Hz, 4.5H), 0.93 (s, 9H), 0.92 (d, J=6.5 Hz, 3H), 0.89 (s, 1.5H), 0.84 (d, J=6.2 Hz, 3H), 0.06 (d, J=12.9 Hz, 6H), 0.00 (br, 7.5H), −0.07 (s, 1.5H).

$^{13}$C NMR (125.8 MHz, C6D$_6$, 70° C.): δ 172.3, 171.7, 171.0, 170.7, 170.2, 156.4, 144.7, 144.6, 142.0 (2C), 128.3, 128.0, 127.4 (2C), 125.5, 125.4, 120.3 (2C), 76.2, 75.9, 67.4, 67.3, 66.9, 64.9, 60.2, 58.1, 57.9, 53.2, 48.0, 41.4, 31.4, 28.2, 28.1, 26.1, 26.0, 25.3, 23.1, 22.2, 19.5, 19.3, 19.2, 18.4, 18.3, 18.2, 18.1, 17.7, 17.4, −1.5, −1.7, −4.3, −4.5, −4.7, −4.9.

FTIR (thin film) cm$^{-1}$: 3367 (br-m), 2958 (m), 2936 (m), 2896 (w), 1715 (s), 1702 (s), 1510 (m), 1393 (m) 1250 (m), 1126 (w), 838 (m).

HRMS (ESI) (m/z): calc'd for C$_{56}$H$_{90}$N$_5$O$_{13}$Si$_2$ [M+H]$^+$: 1096.6068, found: 1096.6062.

$[\alpha]_D^{23}$: +5.9 (c=0.27, CHCl$_3$).

TLC (10% methanol in dichloromethane), Rf: 0.55 (UV, CAM).

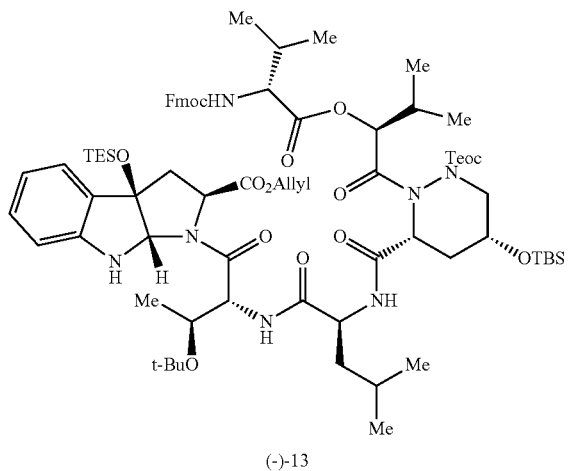

1. Pd(PPh₃)₄, N-methylaniline
   THF, 23° C.
2. i-Pr₂NH, MeCN, 23° C.
3. HATU, HOAt, i-Pr₂NEt
   CH₂Cl₂, 23° C.
4. TFA, H₂O, anisole
   CH₂Cl₂, 23° C.;
   Et₃N, MeOH, 23° C.

49% (4 steps)

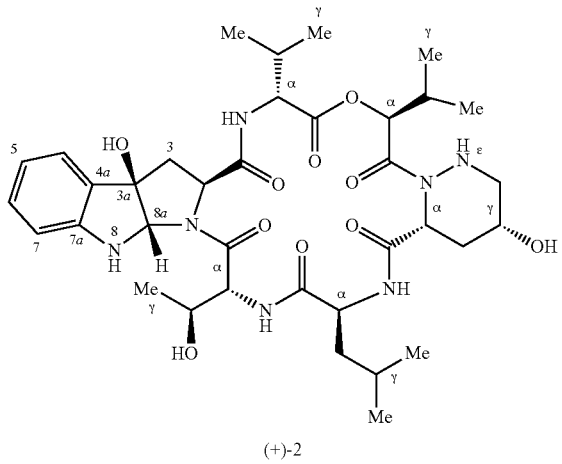

Himastatin Monomer (+)-2:

A solution of tetrakis(triphenylphosphine)palladium(0) (10 mM in degassed tetrahydrofuran, 110 µL, 1.1 µmol, 5.0×10⁻³ equiv) was added solution of depsihexapeptide (−)-13 (320.6 mg, 0.221 mmol, 1 equiv) and N-methylaniline (120 µL, 1.10 mmol, 5.00 equiv) in degassed tetrahydrofuran (2.21 mL) at 23° C. After 1 h, the yellow solution was diluted with ethyl acetate (25 mL) and washed with an aqueous hydrogen chloride solution (1 M, 2×20 mL) and a saturated aqueous sodium chloride solution (20 mL). The organic layer was dried over anhydrous sodium sulfate, was filtered, and was concentrated under reduced pressure to provide the crude carboxylic acid, which was used in the next step without further purification.

Diisopropyl amine (5 mL) was added to a solution of the crude carboxylic acid in acetonitrile (5 mL) at 23° C. After 16 h, the reaction mixture was concentrated under reduced pressure to provide the crude amino acid, which was used in the next step without further purification.

N,N-Diisopropylethylamine (384 µL, 2.21 mmol, 10.0 equiv) was added to a suspension of the crude amino acid, HATU (503 mg, 1.32 mmol, 6.00 equiv), and HOAt (180 mg, 1.32 mmol, 6.00 equiv) in dichloromethane (88 mL) at 23° C. After 2 days, the yellow heterogeneous solution was filtered through a pad of Celite. The filter cake washed with dichloromethane (50 mL) and the filtrate was concentrated under reduced pressure. The resulting residue was loaded onto a pad of silica gel with dichloromethane and was washed with 5% ethyl acetate in hexanes (200 mL). The crude protected macrocycle was obtained by eluting with 30% ethyl acetate in hexanes (200 mL), and was used in the next step without further purification.

Trifluoroacetic acid (2.0 mL) was added to a solution of the crude protected macrocycle, deionized water (80 µL, 4.4 mmol, 20 equiv), and anisole (200 µL, 1.84 mmol, 8.34 equiv) in dichloromethane (2.0 mL) at 23° C. After 2.5 h, the reaction mixture was diluted with toluene (2.5 ml) and concentrated under reduced pressure. The resulting residue was azeotropically dried by concentration from toluene (3×2.5 mL) under reduced pressure and was dissolved in methanol (2.0 mL) and triethylamine (400 µL, 2.87 mmol, 13.0 equiv). After 2.5 h, the colorless solution was concentrated under reduced pressure and the resulting residue was purified by flash column chromatography on silica gel (eluent: 0.9% methanol, 0.1% ammonium hydroxide→3.6% methanol, 0.4% ammonium hydroxide in chloroform) to afford himastatin monomer (+)-2 (79.7 mg, 49%) as an off-white solid. Spectral data and optical rotation (lit. $[\alpha]_D^{25}$=+37.5 (c=0.7, CHCl₃),[12] lit. $[\alpha]_D^{25}$=+64 (c=1.87, CHCl₃)[15]) were in agreement with those previously reported in the literature (see Table S1 and Table S2 for details). Structural assignments were made using additional information from gCOSY, gHSQC, and gHMBC experiments.

¹H NMR (600 MHz, CDCl₃, 25° C.): δ 7.41 (d, J=5.1 Hz, 1H, Leu-NH), 7.35 (dd, J=7.4, 1.0 Hz, 1H, Trp-C4H), 7.30 (d, J=10.0 Hz, 1H, Val-NH), 7.20 (app-td, J=7.9, 1.1 Hz, 1H, Trp-C6H), 7.11 (d, J=10.5 Hz, 1H, Thr-NH), 6.91 (app-td, J=7.4, 0.9 Hz, 1H, Trp-C5H), 6.77 (dd, J=8.0, 0.9 Hz, 1H, Trp-C7H), 5.85 (br-s, 1H, Trp-C3aOH), 5.80 (d, J=6.3 Hz, 1H, Trp-N8H), 5.64 (d, J=8.6 Hz, 1H, Hiv-CαH), 5.42 (dd, J=12.9, 2.0 Hz, 1H, Pip-NεH), 5.21-5.19 (m, 2H, Trp-C2H, Pip-CγOH), 5.12 (dd, J=7.1, 1.7 Hz, 2H, Pip-CαH), 5.11 (d, J=6.4 Hz, 1H, Trp-C8aH) 4.97 (d, J=10.5 Hz, 1H, Thr-CαH), 4.89 (dd, J=10.0, 3.2 Hz, 1H, Val-CαH), 4.44 (qd, J=6.4, 1.4 Hz, 1H, Thr-CβH), 4.24 (ddd, J=10.8, 5.1, 3.6 Hz, 1H, Leu-CαH), 3.82 (app-sept, J=2.6 Hz, 1H, Pip-CγH), 3.61 (d, J=1.4 Hz, 1H, Thr-CβOH), 3.07 (app-dq, J=14.2, 2.3 Hz, 1H, Pip-CδH$_b$), 2.84 (app-t, J=13.5 Hz, 1H, Pip-CδH$_b$), 2.75 (d, J=14.4 Hz, 1H, Trp-C3H$_a$), 2.56 (septd, J=6.9, 3.2 Hz, 1H, Val-CβH), 2.49 (app-dp, J=15.1, 2.3 Hz, 1H, Pip-CβH$_a$), 2.21-2.12 (m, 2H, Trp-C3H$_b$, Hiv-CβH), 1.95 (ddd, J=15.1, 7.1, 3.4 Hz, 1H, Pip-CβH$_b$), 1.71-1.64 (m, 2H, Leu-CβH$_a$, Leu-CγH), 1.39 (dd, J=10.7, 8.7 Hz, 1H, Leu-CβH$_b$), 1.16 (d, J=6.6 Hz, 3H, Thr-CγH$_3$), 1.12 (d, J=6.6 Hz, 3H, Hiv-CγH$_3$), 1.00 (d, J=6.9 Hz, 6H, Hiv-CγH$_3$, Val-CγH$_3$), 0.93 (d, J=6.0 Hz, 3H, Leu-CδH$_3$), 0.87 (d, J=6.9 Hz, 3H, Val-CγH$_3$), 0.86 (d, J=5.7 Hz, 3H, Leu-CδH$_3$).

$^{13}$C NMR (150.9 MHz, CDCl$_3$, 25° C.): δ 174.2 (Hiv-CO), 174.1 (Leu-CO), 173.6 (Val-CO), 173.4 (Pip-CO), 173.2 (Trp-CO), 172.5 (Thr-CO), 147.9 (Trp-C7a), 131.9 (Trp-C4a), 130.0 (Trp-C6), 123.4 (Trp-C4), 121.2 (Trp-C5), 112.5 (Trp-C7), 91.0 (Trp-C3a), 86.1 (Trp-C8a), 77.5 (Hiv-Cα), 66.8 (Thr-Cβ), 60.9 (Trp-C2), 58.8 (Pip-Cγ), 57.3 (Val-Cα), 54.4 (Leu-Cα), 53.9 (Thr-Cα), 52.8 (Pip-Cδ), 50.1 (Pip-Cα), 41.1 (Leu-Cβ), 39.6 (Trp-C3), 30.1 (2C, Hiv-Cβ, Val-Cβ) 28.8 (Pip-Cβ), 25.4 (Leu-Cγ), 23.1 (Leu-Cδ), 21.1 (Leu-Cδ), 19.5 (Val-Cγ), 19.1 (Hiv-Cγ), 18.4 (Hiv-Cγ), 17.5 (Thr-Cγ), 16.6 (Val-Cγ).

FTIR (thin film) cm$^{-1}$: 3391 (m), 3326 (br-r), 3252 (w), 2964 (m), 2932 (m), 2876 (w), 1725 (s), 1671 (s), 1522 (m), 1228 (m), 1152 (m), 751 (s).

HRMS (ESI) (m/z): calc'd for C$_{36}$H$_{53}$N$_7$NaO$_{10}$ [M+Na]$^+$: 766.3746, found: 766.3741.

[α]$_D^{23}$: +34 (c=0.13, CHCl$_3$).

TLC (9% methanol, 1% ammonium hydroxide in chloroform), Rf: 0.40 (UV, CAM).

TABLE S1

Comparison of our $^1$H NMR data for (+)-Himastatin Monomer (2) with literature data (CDCl$_3$):

| Assignment | Ju's Biosynthesis Report[8] (+)-Himastatin Monomer (2) $^1$H NMR, 500 MHz, CDCl$_3$ $^a$ | Danishefsky's Report[9] (+)-Himastatin Monomer (2) $^1$H NMR, 500 MHz, CDCl$_3$ $^a$ | This Work (+)-Himastatin Monomer (2) $^1$H NMR, 600 MHz, CDCl$_3$ |
|---|---|---|---|
| Trp | | | |
| C$_2$H | 5.20 (d, J = 8.0 Hz, 1H) | 5.20-5.18 (m, 2H) | 5.21-5.19 (m, 2H) |
| C$_3$H$_2$ | 2.75 (d, J = 14.5 Hz, 1H) | 2.74 (d, J = 14.3 Hz, 1H) | 2.75 (d, J = 14.4 Hz, 1H) |
| | 2.16 (m, 1H) | 2.25-2.10 (m, 2H) | 2.21-2.12 (m, 2H) |
| C$_{3a}$OH | 5.89 (br-s, 1H) | 5.85 (s, 1H) | 5.85 (br-s, 1H) |
| C$_4$H | 7.34 (d, J = 7.0 Hz, 1H) | 7.33 (d, J = 7.4 Hz, 1H) | 7.35 (dd, J = 7.4, 1.0 Hz, 1H) |
| C$_5$H | 6.90 (t, J = 7.0 Hz, 1H) | 6.89 (t, J = 7.4 Hz, 1H) | 6.90 (app-td, J = 7.5, 0.9 Hz, 1H) |
| C$_6$H | 7.19 (d, J = 8.0 Hz, 1H) | 7.19 (t, J = 7.6 Hz, 1H) | 7.20 (app-td, J = 7.9, 1.1 Hz, 1H) |
| C$_7$H | 6.77 (d, J = 8.0 Hz, 1H) | 6.76 (d, J = 7.9 Hz, 1H) | 6.77 (dd, J = 8.0, 0.9 Hz, 1H) |
| N$_8$H | 5.79 (d, J = 6.5 Hz, 1H) | 5.80 (br-s, 1H) | 5.80 (d, J = 6.3 Hz, 1H) |
| C$_{8a}$H | 5.11 (d, J = 6.5 Hz, 1H) | 5.13-5.10 (m, 2H) | 5.11 (d, J = 6.4 Hz, 1H) |
| Thr | | | |
| NH | 7.11 (d, J = 10.5 Hz, 1H) | 7.10 (d, J = 10.4 Hz, 1H) | 7.11 (d, J = 10.5 Hz, 1H) |
| C$_α$H | 4.97 (d, J= 10.5 Hz, 1H) | 4.96 (d, J = 10.5 Hz, 1H) | 4.97 (d, J = 10.5 Hz, 1H) |
| C$_β$H | 4.43 (q, J = 6.4 Hz, 1H) | 4.45-4.40 (m, 1H) | 4.44 (qd, J = 6.4, 1.4 Hz, 1H) |
| C$_β$OH | 3.61 (br-s, 1H) | 3.61 (s, 1H) | 3.61 (d, J = 1.4 Hz, 1H) |
| C$_γ$H$_3$ | 1.15 (d, J = 6.4, 3H) | 1.15 (d, J = 6.5, 3H) | 1.16 (d, J = 6.6 Hz, 3H) |
| Leu | | | |
| NH | 7.41 (d, J = 5.0 Hz, 1H) | 7.41 (d, J = 4.8 Hz, 1H) | 7.41 (d, J = 5.1 Hz, 1H) |
| C$_α$H | 4.23 (m 1H) | 4.28-4.23 (m, 1H) | 4.24 (ddd, J = 10.8, 5.1, 3.6 Hz, 1H) |
| C$_β$H$_2$ | 1.68 (m, 1H) | 1.80-1.62 (m, 2H) | 1.71-1.64 (m, 2H) |
| | 1.38 (dd, J = 10.5, 9.0 Hz, 1H) | 1.42-1.35 (m, 1H) | 1.39 (dd, J = 10.7, 8.7 Hz, 1H) |
| C$_γ$H | 1.68 (m, 1H) | 1.80-1.62 (m, 2H) | 1.71-1.64 (m, 2H) |
| C$_δ$H$_3$ | 0.92 (d, J = 6.0 Hz, 3H) | 0.91 (d, J = 5.6 Hz, 3H) | 0.93 (d, J = 6.0 Hz, 3H) |
| | 0.86 (d, J = 5.6 Hz, 3H) | 0.85 (d, J = 6.5 Hz, 3H) | 0.86 (d, J = 5.7 Hz, 3H) |
| Pip | | | |
| C$_α$H | 5.12 (d, J = 8.5 Hz, 1H) | 5.13-5.10 (m, 2H) | 5.12 (dd, J = 7.1, 1.7 Hz, 1H) |
| C$_β$H$_2$ | 2.49 (d, J = 15.0 Hz, 1H) | 2.48 (d, J = 15.1 Hz, 1H) | 2.49 (app-dp, J = 15.1, 2.3 Hz, 1H) |
| | 1.95 (ddd, J = 15.0, 7.0, 3.0 Hz, 1H) | 2.00-1.88 (m, 1H) | 1.95 (ddd, J = 15.1, 7.1, 3.4 Hz, 1H) |
| C$_γ$H | 3.81 (br-s, 1H) | 3.81 (s, 1H) | 3.82 (app-sept, J = 2.6 Hz, 1H) |
| C$_γ$OH | 5.20 (d, J = 5.0 Hz, 1H) | 5.20-5.18 (m, 2H) | 5.21-5.19 (m, 2H) |
| C$_δ$H$_2$ | 3.07 (d, J = 14.5 Hz, 1H) | 3.06 (d, J = 14.0 Hz, 1H) | 3.07 (app-dq, J = 14.2, 2.3 Hz, 1H) |
| | 2.83 (t, J = 13.5 Hz, 1H) | 2.83 (t, J = 13.2 Hz, 1H) | 2.84 (app-t, J = 13.5 Hz, 1H) |
| N$_ε$H | 5.42 (d, J = 11.5 Hz, 1H) | 5.41 (d, J = 12.6 Hz, 1H) | 5.42 (dd, J = 12.9, 2.0 Hz, 1H) |
| Hiv | | | |
| C$_α$H | 5.64 (d, J = 8.5 Hz, 1H) | 5.63 (d, J = 8.6 Hz, 1H) | 5.64 (d, J = 8.6 Hz, 1H) |
| C$_β$H | 2.16 (m, 1H) | 2.25-2.10 (m, 2H) | 2.21-2.12 (m, 2H) |
| C$_γ$H$_3$ | 1.12 (d, J = 6.6 Hz, 3H) | 1.11 (d, J = 6.6 Hz, 3H) | 1.12 (d, J = 6.6 Hz, 3H) |
| | 1.00 (d, J = 6.8 Hz, 6H) | 1.00 (d, J = 6.8 Hz, 6H) | 1.00 (d, J = 6.9 Hz, 6H) |

TABLE S1-continued

Comparison of our $^1$H NMR data for (+)-Himastatin Monomer (2) with literature data (CDCl$_3$):

| Assignment | Ju's Biosynthesis Report[8] (+)-Himastatin Monomer (2) $^1$H NMR, 500 MHz, CDCl$_3$ [a] | Danishefsky's Report[9] (+)-Himastatin Monomer (2) $^1$H NMR, 500 MHz, CDCl$_3$ [a] | This Work (+)-Himastatin Monomer (2) $^1$H NMR, 600 MHz, CDCl$_3$ |
|---|---|---|---|
| | | Val | |
| NH | 7.30 (d, J = 10.0 Hz, 1H) | 7.29 (d, J = 10.0 Hz, 1H) | 7.30 (d, J = 10.0 Hz, 1H) |
| C$_\alpha$H | 4.89 (dd, J = 10.0, 3.0 Hz, 1H) | 4.89 (dd, J = 9.9, 2.9 Hz, 1H) | 4.89 (dd, J = 10.0, 3.2 Hz, 1H) |
| C$_\beta$H | 2.56 (m, 1H) | 2.60-2.50 (m, 1H) | 2.56 (septd, J = 6.9, 3.2 Hz, 1H) |
| C$_\gamma$H$_3$ | 1.00 (d, J = 6.8 Hz, 6H) | 1.00 (d, J = 6.8 Hz, 6H) | 1.00 (d, J = 6.9 Hz, 6H) |
| | 0.87 (d, J = 6.8 Hz, 3H) | 0.86 (d, J = 6.5 Hz, 3H) | 0.87 (d, J = 6.9 Hz, 3H) |

[a] The chemical shift reference for $^1$H NMR spectra was not given. Our data are referenced to δ 7.26 (CHCl$_3$).

TABLE S2

Comparison of our $^{13}$C NMR data for (+)-Himastatin Monomer (2) with literature data (CDCl$_3$):

| Assignment | Ju's Biosynthesis Report[8] (+)-Himastatin Monomer (2) $^{13}$C NMR, 125 MHz, CDCl$_3$ [a] | Danishefsky's Report[9] (+)-Himastatin Monomer (2) $^{13}$C NMR, 125 MHz, CDCl$_3$ [a] | This Work (+)-Himastatin Monomer (2) $^{13}$C NMR, 150.9 MHz, CDCl$_3$ | Chemical Shift Difference Δδ = δ (this work) − δ (Ju's report) |
|---|---|---|---|---|
| | | Trp | | |
| CO | 173.0 | 173.0 | 173.2 | 0.2 |
| C$_2$ | 60.8 | 60.7 | 60.9 | 0.1 |
| C$_3$ | 39.4 | 39.4 | 39.6 | 0.2 |
| C$_{3a}$ | 90.8 | 90.8 | 91.0 | 0.2 |
| C$_{4a}$ | 131.7 | 131.7 | 131.9 | 0.2 |
| C$_4$ | 123.2 | 123.2 | 123.4 | 0.2 |
| C$_5$ | 121.0 | 121.0 | 121.2 | 0.2 |
| C$_6$ | 129.9 | 129.8 | 130.0 | 0.1 |
| C$_7$ | 112.4 | 112.3 | 112.5 | 0.1 |
| C$_{7a}$ | 147.8 | 147.7 | 147.9 | 0.1 |
| C$_{8a}$ | 86.0 | 85.9 | 86.1 | 0.1 |
| | | Thr | | |
| CO | 172.4 | 172.3 | 172.5 | 0.1 |
| C$_\alpha$ | 53.8 | 53.8 | 53.9 | 0.1 |
| C$_\beta$ | 66.7 | 66.6 | 66.8 | 0.1 |
| C$_\gamma$ | 17.4 | 17.3 | 17.5 | 0.1 |
| | | Leu | | |
| CO | 173.9 | 173.9 | 174.1 | 0.2 |
| C$_\alpha$ | 54.3 | 54.2 | 54.4 | 0.1 |
| C$_\beta$ | 40.9 | 40.9 | 41.1 | 0.2 |
| C$_\gamma$ | 25.3 | 25.2 | 25.4 | 0.1 |
| C$_\delta$ | 23.0 | 22.9 | 23.1 | 0.1 |
| | 21.0 | 20.9 | 21.1 | 0.1 |
| | | Pip | | |
| CO | 173.3 | 173.2 | 173.4 | 0.1 |
| C$_\alpha$ | 49.9 | 49.9 | 50.1 | 0.2 |
| C$_\beta$ | 28.6 | 28.6 | 28.8 | 0.2 |
| C$_\gamma$ | 58.7 | 58.6 | 58.8 | 0.1 |
| C$_\delta$ | 52.6 | 52.6 | 52.8 | 0.2 |
| | | Hiv | | |
| CO | 174.1 | 174.1 | 174.2 | 0.1 |
| C$_\alpha$ | 77.2 | — | 77.5 | 0.3 |
| C$_\beta$ | 29.9 | 29.9 | 30.1 | 0.2 |
| C$_\gamma$ | 18.9 | 18.9 | 19.1 | 0.2 |
| | 18.3 | 18.2 | 18.4 | 0.1 |
| | | Val | | |
| CO | 173.5 | 173.4 | 173.6 | 0.1 |
| C$_\alpha$ | 57.2 | 57.2 | 57.3 | 0.1 |
| C$_\beta$ | 30.0 | 30.0 | 30.1 | 0.1 |
| C$_\gamma$ | 19.4 | 19.3 | 19.5 | 0.1 |
| | 16.4 | 16.4 | 16.6 | 0.2 |

[a] The chemical shift reference for $^{13}$C NMR spectra was not given. Our data are referenced to δ 77.16 (CDCl$_3$).

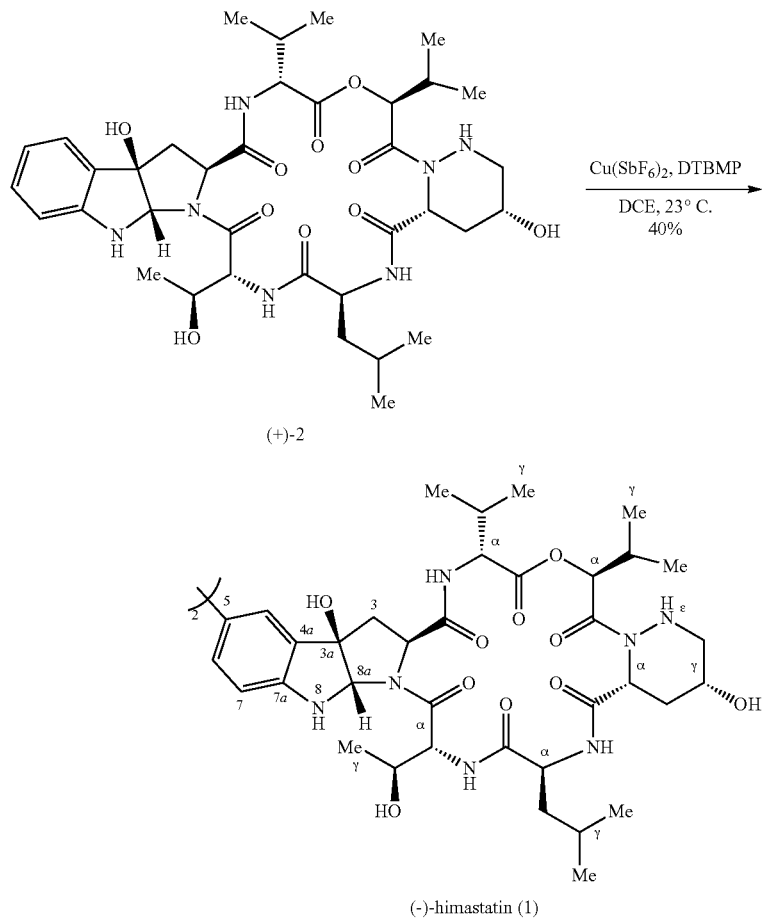

(−)-Himastatin (1):

A sample of copper(II) hexafluoroantimonate (107 mg, 200 μmol, 20.0 equiv) was added to a solution of himastatin monomer (+)-2 (7.44 mg, 10.0 μmol, 1 equiv) and 2,6-di-tert-butyl-4-methylpyridine (DTBMP, 8.21 mg, 40.0 μmol, 4.00 equiv) in 1,2-dichloroethane (500 μL) at 23° C. After 18 h, the heterogeneous solution was diluted with dichloromethane (20 mL), a saturated aqueous sodium thiosulfate solution (5 mL), a saturated aqueous sodium hydrogen carbonate solution (5 mL), and deionized water (10 mL) and was stirred vigorously for 1 h. The layers were separated and the aqueous layer was extracted with dichloromethane (10 mL). The combined organic extracts were washed with a saturated aqueous sodium chloride solution (20 mL), were dried over anhydrous sodium sulfate, were filtered, and were concentrated under reduced pressure. The resulting residue was purified by flash column chromatography on silica gel (eluent: 2.7% methanol, 0.3% ammonium hydroxide→4.5% methanol, 0.5% ammonium hydroxide in chloroform) to afford (−)-himastatin (1, 2.96 mg, 40%) as an off-white solid. Spectral data and optical rotation (lit. $[\alpha]_D^{25}$=−33.8 (c=0.35, MeOH),[12] lit. $[\alpha]_D$=−34 (c=0.35, MeOH)[16]) were in agreement with those previously reported in the literature (see Table S3 and Table S4 for details). Structural assignments were made using additional information from gCOSY, gHSQC, and gHMBC experiments.

$^1$H NMR (600 MHz, CDCl$_3$, 25° C.): δ 7.59 (d, J=2.0 Hz, 2H, Trp-C4H), 7.44-7.40 (m, 4H, Trp-C6H, Leu-NH), 7.29 (d, J=10.0 Hz, 2H, Val-NH), 7.12 (d, J=10.5 Hz, 2H, Thr-NH), 6.80 (d, J=8.3 Hz, 2H, Trp-C7H), 5.91 (s, 2H, Trp-C3αOH), 5.81 (d, J=6.3 Hz, 2H, Trp-N8H), 5.64 (d, J=8.6 Hz, 2H, Hiv-CαH), 5.43 (dd, J=12.8, 2.0 Hz, 2H, Pip-NεH), 5.21 (d, J=8.0 Hz, 2H, Trp-C2H), 5.20 (d, J=5.3 Hz, 2H, Pip-CγOH), 5.14 (d, J=6.3 Hz, 2H, Trp-C8aH), 5.13 (d, J=7.1 Hz, 2H, Pip-CαH), 4.99 (d, J=10.5 Hz, 2H, Thr-CαH), 4.90 (dd, J=10.0, 3.2 Hz, 2H, Val-CαH), 4.45 (qd, J=6.7, 2.0 Hz, 2H, Thr-CβH), 4.24 (ddd, J=10.7, 5.4, 3.5 Hz, 2H, Leu-CαH), 3.82 (app-sept, J=2.5 Hz, 2H, Pip-CγH), 3.61 (br-s, 2H, Thr-CβOH), 3.07 (app-dq, J=14.5, 2.3 Hz, 2H, Pip-CδH$_a$), 2.84 (app-t, J=13.5 Hz, 2H, Pip-CδH$_b$), 2.77 (d, J=14.3 Hz, 2H, Trp-C3H$_a$), 2.57 (septd, J=6.9, 3.2 Hz, 2H, Val-CβH), 2.49 (app-dp, J=14.7, 2.3 Hz, 2H, Pip-CβH$_a$), 2.20 (dd, J=14.4, 8.1 Hz, 2H, Trp-C3H$_b$), 2.20-2.12 (m, 2H, Hiv-CβH), 1.95 (ddd, J=15.0, 7.2, 3.4 Hz, 2H, Pip-CβH$_b$), 1.73-1.65 (m, 4H, Leu-CβH$_a$, Leu-CγH), 1.41-1.36 (m, 2H, Leu-CβH$_b$), 1.16 (d, J=6.5 Hz, 6H, Thr-CγH$_3$), 1.13 (d, J=6.6 Hz, 6H, Hiv-CγH$_3$), 1.01 (d, J=6.9 Hz, 6H, Hiv-CγH$_3$), 1.01 (d, J=6.8 Hz, 6H, Val-CγH$_3$), 0.93 (d, J=6.1 Hz, 6H, Leu-CδH$_3$), 0.87 (d, J=6.9 Hz, 6H, Val-CγH$_3$), 0.87 (d, J=6.0 Hz, 6H, Leu-CδH$_3$).

$^{13}$C NMR (150.9 MHz, CDCl$_3$, 25° C.): 174.3 (Hiv-CO), 174.1 (Leu-CO), 173.6 (Val-CO), 173.4 (Pip-CO), 173.2 (Trp-CO), 172.5 (Thr-CO), 146.8 (Trp-C7a), 134.5 (Trp-C5), 132.4 (Trp-C4a), 128.5 (Trp-C6), 121.5 (Trp-C4), 112.8 (Trp-C7), 91.0 (Trp-C3a), 86.3 (Trp-C8a), 77.5 (Hiv-Cα), 66.8 (Thr-Cβ), 60.9 (Trp-C2), 58.8 (Pip-Cγ), 57.3 (Val-Cα), 54.4 (Leu-Cα), 53.9 (Thr-Cα), 52.8 (Pip-Cδ), 50.1 (Pip-Cα), 41.1 (Leu-Cβ), 39.6 (Trp-C3), 30.1 (2C, Hiv-Cβ, Val-Cβ), 28.8 (Pip-Cβ), 25.5 (Leu-Cγ), 23.1 (Leu-Cδ), 21.1 (Leu-Cδ), 19.5 (Val-Cγ), 19.1 (Hiv-Cγ), 18.4 (Hiv-Cγ), 17.5 (Thr-Cγ), 16.6 (Val-Cγ).

FTIR (thin film) cm$^{-1}$: 3391 (m), 3329 (br-s), 2962 (m), 2930 (m), 2875 (w), 1725 (s), 1672 (m), 1624 (m), 1534 (m), 1417 (m), 1246 (m), 1153 (w), 916 (w), 755 (w).

HRMS (ESI) (m/z): calc'd for $C_{72}H_{104}N_{14}NaO_2O$ [M+Na]$^+$: 1507.7444, found: 1507.7445.
$[\alpha]_D^{23}$: −36 (c=0.040, MeOH).
TLC (9% methanol, 1% ammonium hydroxide in chloroform), Rf: 0.27 (UV, CAM).

TABLE S3

Comparison of our $^1$H NMR data for (−)-Himastatin (1) with literature data (CDCl$_3$):

| Assignment | Leet's Isolation Report[5] (−)-Himastatin (1) $^1$H NMR, 360 MHz, CDCl$_3$ $^a$ | Danishefsky's Report[9] (−)-Himastatin (1) $^1$H NMR, 500 MHz, CDCl$_3$ $^b$ | This Work (−)-Himastatin (1) $^1$H NMR, 600 MHz, CDCl$_3$ |
|---|---|---|---|
| Trp | | | |
| C$_2$H | 5.16 (d, J = 8.0 Hz, 2H) | 5.30-5.20 (m, 4H) | 5.21 (d, J = 8.0 Hz, 2H) |
| C$_3$H$_2$ | 2.70 (d, J = 14.5 Hz, 2H) | 2.76 (d, J = 14.3 Hz, 2H) | 2.77 (d, J = 14.3 Hz, 2H) |
| | 2.16 (dd, J = 14.3, 8.0 Hz, 2H) | 2.25-2.10 (m, 4H) | 2.20 (dd, J = 14.4, 8.1 Hz, 2H) |
| C$_{3a}$OH | 5.89 (s, 2H) | 5.91 (s, 2H) | 5.91 (s, 2H) |
| C$_4$H | 7.52 (d, J = 1.8 Hz, 2H) | 7.58 (s, 2H) | 7.59 (d, J = 2.0 Hz, 2H) |
| C$_6$H | 7.31 (dd, J = 8.3, 1.8 Hz, 2H) | 7.43-7.41 (m, 4H) | 7.44-7.40 (m, 4H) |
| C$_7$H | 6.74 (d, J = 8.3 Hz, 2H) | 6.79 (d, J = 8.3 Hz, 2H) | 6.80 (d, J = 8.3 Hz, 2H) |
| N$_8$H | 5.78 (d, J = 5.8 Hz, 2H) | 5.81 (br-s, 2H) | 5.81 (d, J = 6.3 Hz, 2H) |
| C$_{8a}$H | 5.11 (m, 2H) | 5.14-5.12 (m, 4H) | 5.14 (d, J = 6.3 Hz, 2H) |
| Thr | | | |
| NH | 7.08 (d, J = 10.5 Hz, 2H) | 7.11 (d, J = 10.4 Hz, 2H) | 7.12 (d, J = 10.5 Hz, 2H) |
| C$_\alpha$H | 4.94 (d, J = 10.5 Hz, 2H) | 4.98 (d, J = 10.5 Hz, 2H) | 4.99 (d, J = 10.5 Hz, 2H) |
| C$_\beta$H | 4.40 (q, J = 6.6 Hz, 2H) | 4.50-4.44 (m, 2H) | 4.45 (qd, J = 6.7, 2.0 Hz, 2H |
| C$_\beta$OH | 3.59 (s, 2H) | 3.62 (s, 2H) | 3.61 (br-s, 2H) |
| C$_\gamma$H$_3$ | 1.11 (d, J = 6.6 Hz, 6H) | 1.15 (d, J = 6.5, 6H) | 1.16 (d, J = 6.5 Hz, 6H) |
| Leu | | | |
| NH | 7.38 (d, J = 3.9 Hz, 2H) | 7.43-7.41 (m, 4H) | 7.44-7.40 (m, 4H) |
| C$_\alpha$H | 4.18 (m, 2H) | 4.25-4.21 (m, 2H) | 4.24 (ddd, J = 10.7, 5.4, 3.5 Hz, 2H) |
| C$_\beta$H$_2$ | 1.64 (m, 2H) | 1.72-1.65 (m, 6H) | 1.73-1.64 (m, 4H) |
| | 1.35 (dd, J = 10.5, 8.8 Hz, 2H) | 1.41-1.35 (m, 2H) | 1.41-1.36 (m, 2H) |
| C$_\gamma$H | 1.64 (m, 2H) | 1.72-1.65 (m, 6H) | 1.73-1.64 (m, 4H) |
| C$_\delta$H$_3$ | 0.88 (d, J = 6.0 Hz, 6H) | 0.92 (d, J = 5.7 Hz, 6H) | 0.93 (d, J = 6.1 Hz, 6H) |
| | 0.83 (d, J = 6.0 Hz, 12H) | 0.85 (d, J = 6.5 Hz, 12H) | 0.87 (d, J = 6.0 Hz, 6H) |
| Pip | | | |
| C$_\alpha$H | 5.08 (d, J = 7.1 Hz, 2H) | 5.14-5.12 (m, 4H) | 5.13 (d, J = 7.1 Hz, 2H) |
| C$_\beta$H$_2$ | 2.44 (d, J = 14.9 Hz, 2H) | 2.48 (d, J = 14.8 Hz, 2H) | 2.49 (app-dp, J = 14.7, 2.3 Hz, 2H) |
| | 1.92 (ddd, J = 14.9, 7.1, 3.3 Hz, 2H) | 1.98-1.90 (m, 2H) | 1.95 (ddd, J = 15.0, 7.2, 3.4 Hz,2H) |
| C$_\gamma$H | 3.77 (br-s, 2H) | 3.82 (s, 2H) | 3.82 (app-sept, J = 2.5 Hz, 2H) |
| C$_\gamma$OH | 5.17 (d, J = 4.5 Hz, 2H) | 5.30-5.20 (m, 4H) | 5.20 (d, J = 5.3 Hz, 2H) |
| C$_\delta$H$_2$ | 3.02 (d, J = 12.6 Hz, 2H) | 3.06 (d, J= 13.1 Hz, 2H) | 3.07 (app-dq, J = 14.5, 2.3 Hz, 2H) |
| | 2.79 (t, J = 13.6 Hz, 2H) | 2.85 (t, J = 13.5 Hz, 2H) | 2.84 (app-t, J = 13.5 Hz, 2H) |
| N$_\varepsilon$H | 5.37 (d, J = 12.1 Hz, 2H) | 5.42 (d, J = 12.3 Hz, 2H) | 5.43 (dd, J = 12.8, 2.0 Hz, 2H) |
| Hiv | | | |
| C$_\alpha$H | 5.62 (d, J = 8.6 Hz, 2H) | 5.63 (d, J = 8.6 Hz, 2H) | 5.64 (d, J = 8.6 Hz, 2H) |
| C$_\beta$H | 2.16 (sept, J = 6.7 Hz, 2H) | 2.25-2.10 (m, 4H) | 2.20-2.12 (m, 2H) |
| C$_\gamma$H$_3$ | 1.08 (d, J = 6.7 Hz, 6H) | 1.11 (d, J = 6.6 Hz, 6H) | 1.13 (d, J = 6.6 Hz, 6H) |
| | 0.96 (d, J = 6.7 Hz, 12H) | 1.02 (d, J = 6.5 Hz, 6H) | 1.01 (d, J = 6.9 Hz, 6H) |
| Val | | | |
| NH | 7.25 (d, J = 10.0 Hz, 2H) | 7.28 (d, J = 10.0 Hz, 2H) | 7.29 (d, J = 10.0 Hz, 2H) |
| CαH | 4.84 (dd, J = 10.0, 3.3 Hz, 2H) | 4.89 (dd, J = 9.9, 3.0 Hz, 2H) | 4.90 (dd, J = 10.3, 3.2 Hz, 2H) |
| C$_\beta$H | 2.52 (dd, J = 6.8, 3.3 Hz, 2H) | 2.60-2.50 (m, 2H) | 2.57 (septd, J = 6.9, 3.2 Hz, 2H) |
| C$_\gamma$H$_3$ | 0.96 (d, J = 6.8 Hz, 12H) | 1.00 (d, J = 6.6 Hz, 12H) | 1.01 (d, J = 6.8 Hz, 6H) |
| | 0.83 (d, J = 6.8 Hz, 12H) | 0.87 (d, J = 6.7 Hz, 6H) | 0.87 (d, J = 6.9 Hz, 6H) |
| Pip | | | |
| C$_\alpha$H | 5.08 (d, J = 7.1 Hz, 2H) | 5.14-5.12 (m, 4H) | 5.13 (d, J = 7.1 Hz, 2H) |
| C$_\beta$H$_2$ | 2.44 (d, J = 14.9 Hz, 2H) | 2.48 (d, J = 14.8 Hz, 2H) | 2.49 (app-dp, J = 14.7, 2.3 Hz, 2H) |
| | 1.92 (ddd, J = 14.9, 7.1, 3.3 Hz, 2H) | 1.98-1.90 (m, 2H) | 1.95 (ddd, J = 15.0, 7.2, 3.4 Hz,2H) |
| C$_\gamma$H | 3.77 (br-s, 2H) | 3.82 (s, 2H) | 3.82 (app-sept, J = 2.5 Hz, 2H) |
| C$_\gamma$OH | 5.17 (d, J = 4.5 Hz, 2H) | 5.30-5.20 (m, 4H) | 5.20 (d, J = 5.3 Hz, 2H) |
| C$_\delta$H$_2$ | 3.02 (d, J = 12.6 Hz, 2H) | 3.06 (d, J = 13.1 Hz, 2H) | 3.07 (app-dq, J = 14.5, 2.3 Hz, 2H) |
| | 2.79 (t, J = 13.6 Hz, 2H) | 2.85 (t, J = 13.5 Hz, 2H) | 2.84 (app-t, J = 13.5 Hz, 2H) |
| N$_\varepsilon$H | 5.37 (d, J = 12.1 Hz, 2H) | 5.42 (d, J = 12.3 Hz, 2H) | 5.43 (dd, J= 12.8,2.0 Hz, 2H) |
| Hiv | | | |
| C$_\alpha$H | 5.62 (d, J = 8.6 Hz, 2H) | 5.63 (d, J = 8.6 Hz, 2H) | 5.64 (d, J = 8.6 Hz, 2H) |
| C$_\beta$H | 2.16 (sept, J = 6.7 Hz, 2H) | 2.25-2.10 (m, 4H) | 2.20-2.12 (m, 2H) |
| C$_\gamma$H$_3$ | 1.08 (d, J = 6.7 Hz, 6H) | 1.11 (d, J = 6.6 Hz, 6H) | 1.13 (d, J = 6.6 Hz, 6H) |
| | 0.96 (d, J = 6.7 Hz, 12H) | 1.02 (d, J = 6.5 Hz, 6H) | 1.01 (d, J = 6.9 Hz, 6H) |

TABLE S3-continued

Comparison of our $^1$H NMR data for (−)-Himastatin (1) with literature data (CDCl$_3$):

| Assignment | Leet's Isolation Report[5]<br>(−)-Himastatin (1)<br>$^1$H NMR, 360 MHz,<br>CDCl$_3$ [a] | Danishefsky's Report[9]<br>(−)-Himastatin (1)<br>$^1$H NMR, 500 MHz,<br>CDCl$_3$ [b] | This Work<br>(−)-Himastatin (1)<br>$^1$H NMR, 600 MHz,<br>CDCl$_3$ |
|---|---|---|---|
| | | Val | |
| NH | 7.25 (d, J = 10.0 Hz, 2H) | 7.28 (d, J = 10.0 Hz, 2H) | 7.29 (d, J = 10.0 Hz, 2H) |
| C$_\alpha$H | 4.84 (dd, J = 10.0, 3.3 Hz, 2H) | 4.89 (dd, J = 9.9, 3.0 Hz, 2H) | 4.90 (dd, J = 10.3, 3.2 Hz, 2H) |
| C$_\beta$H | 2.52 (dd, J = 6.8, 3.3 Hz, 2H) | 2.60-2.50 (m, 2H) | 2.57 (septd, J = 6.9, 3.2 Hz, 2H) |
| C$_\gamma$H$_3$ | 0.96 (d, J = 6.8 Hz, 12H) | 1.00 (d, J = 6.6 Hz, 12H) | 1.01 (d, J = 6.8 Hz, 6H) |
| | 0.83 (d, J = 6.8 Hz, 12H) | 0.87 (d, J = 6.7 Hz, 12H) | 0.87 (d, J = 6.9 Hz, 6H) |

[a] For $^1$H NMR, the chemical shift reference used for the residual protium in the NMR solvent (CHCl$_3$) was δ 7.24. Our data are referenced to δ 7.26 (CHCl$_3$).
[b] The chemical shift reference for $^1$H NMR spectra was not given.

TABLE S4

Comparison of our $^{13}$C NMR data for (−)-Himastatin (1) with literature data (CDCl$_3$):

| Assignment | Leet's Isolation Report[5]<br>(−)-Himastatin (1)<br>$^{13}$C NMR, 90.7 MHz, CDCl$_3$ [a] | Danishefsky's Report[9]<br>(−)-Himastatin (1)<br>$^{13}$C NMR, 125 MHz, CDCl$_3$ [b] | This Work<br>(−)-Himastatin (1)<br>$^{13}$C NMR, 150.9 MHz, CDCl$_3$ | Chemical Shift Difference<br>Δδ = δ (this work) − δ (Leet's report) | Chemical Shift Difference<br>Δδ = δ (this work) − δ (Danishefsky's report) |
|---|---|---|---|---|---|
| | | | Trp | | |
| CO | 172.79 | 173.0 | 173.16 | 0.37 | 0.2 |
| C$_2$ | 60.62 | 60.8 | 60.95 | 0.33 | 0.2 |
| C$_3$ | 39.30 | 39.4 | 39.61 | 0.31 | 0.2 |
| C$_{3a}$ | 90.61 | 90.8 | 91.00 | 0.39 | 0.2 |
| C$_{4a}$ | 132.08 | 132.2 | 132.44 | 0.36 | 0.2 |
| C$_4$ | 121.18 | 121.3 | 121.53 | 0.35 | 0.2 |
| C$_5$ | 134.21 | 134.3 | 134.53 | 0.32 | 0.2 |
| C$_6$ | 128.21 | 128.4 | 128.54 | 0.33 | 0.1 |
| C$_7$ | 112.30 | 112.6 | 112.77 | 0.47 | 0.2 |
| C$_{7a}$ | 146.41 | 146.6 | 146.80 | 0.39 | 0.2 |
| C$_{8a}$ | 85.98 | 86.2 | 86.34 | 0.36 | 0.1 |
| | | | Thr | | |
| CO | 172.17 | 172.3 | 172.47 | 0.30 | 0.2 |
| C$_\alpha$ | 53.63 | 53.8 | 53.95 | 0.32 | 0.2 |
| C$_\beta$ | 66.47 | 66.7 | 66.83 | 0.36 | 0.1 |
| C$_\gamma$ | 17.17 | 17.3 | 17.50 | 0.33 | 0.2 |
| | | | Leu | | |
| CO | 173.67 | 173.9 | 174.06 | 0.39 | 0.2 |
| C$_\alpha$ | 54.10 | 54.3 | 54.43 | 0.33 | 0.1 |
| C$_\beta$ | 40.77 | 40.9 | 41.08 | 0.31 | 0.2 |
| C$_\gamma$ | 25.09 | 25.3 | 25.45 | 0.36 | 0.1 |
| C$_\delta$ | 22.75 | 23.0 | 23.14 | 0.39 | 0.1 |
| | 20.81 | 21.0 | 21.13 | 0.32 | 0.1 |
| | | | Pip | | |
| CO | 173.02 | 173.2 | 173.40 | 0.38 | 0.2 |
| C$_\alpha$ | 49.72 | 49.9 | 50.07 | 0.35 | 0.2 |
| C$_\beta$ | 28.44 | 28.6 | 28.77 | 0.33 | 0.2 |
| C$_\gamma$ | 58.50 | 58.7 | 58.82 | 0.32 | 0.1 |
| C$_\delta$ | 52.44 | 52.6 | 52.78 | 0.34 | 0.2 |
| | | | Hiv | | |
| CO | 173.84 | 174.1 | 174.25 | 0.41 | 0.2 |
| C$_\alpha$ | 77.08 | — | 77.47 | 0.39 | — |
| C$_\beta$ | 29.78 | 30.0 | 30.14 | 0.36 | 0.1 |
| C$_\gamma$ | 18.64 | 18.9 | 19.08 | 0.44 | 0.2 |
| | 18.09 | 18.3 | 18.44 | 0.35 | 0.1 |

TABLE S4-continued

Comparison of our $^{13}$C NMR data for (−)-Himastatin (1) with literature data (CDCl$_3$):

| Assignment | Leet's Isolation Report[5] (−)-Himastatin (1) $^{13}$C NMR, 90.7 MHz, CDCl$_3$ [a] | Danishefsky's Report[9] (−)-Himastatin (1) $^{13}$C NMR, 125 MHz, CDCl$_3$ [b] | This Work (−)-Himastatin (1) $^{13}$C NMR, 150.9 MHz, CDCl$_3$ | Chemical Shift Difference $\Delta\delta = \delta$ (this work) − $\delta$ (Leet's report) | Chemical Shift Difference $\Delta\delta = \delta$ (this work) − $\delta$ (Danishefsky's report) |
|---|---|---|---|---|---|
| | | | Val | | |
| CO | 173.20 | 173.4 | 173.61 | 0.41 | 0.2 |
| C$_\alpha$ | 57.02 | 57.1 | 57.34 | 0.32 | 0.2 |
| C$_\beta$ | 29.66 | 29.8 | 30.06 | 0.40 | 0.3 |
| C$_\gamma$ | 19.14 | 19.3 | 19.52 | 0.38 | 0.2 |
| | 16.27 | 16.4 | 16.57 | 0.30 | 0.2 |

[a] For $^{13}$C NMR, the chemical shift reference used for the $^{13}$C resonances of the deuterated NMR solvent (CDCl$_3$) was δ 77.0. Our data are referenced to δ 77.16 (CDCl$_3$).
[b] The chemical shift reference for $^{13}$C NMR spectra was not given.

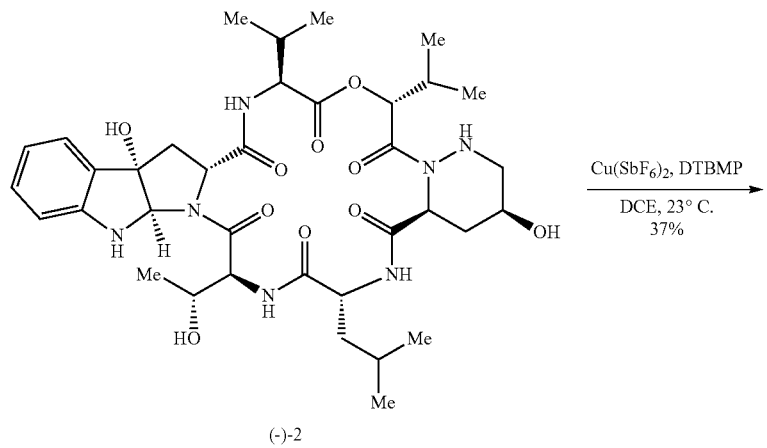

(−)-2

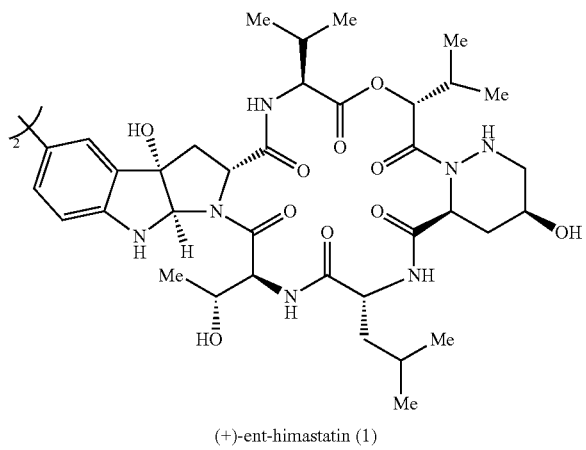

(+)-ent-himastatin (1)

(+)-Ent-Himastatin (1):

Prepared according to the procedure described previously for (−)-himastatin (1) from ent-himastatin monomer (−)-2 (9.82 mg, 13.2 μmol, 1 equiv). Flash column chromatography on silica gel (eluent: 2.7% o methanol, 0.3% ammonium hydroxide→4.5% methanol, 0.5% ammonium hydroxide in chloroform) to afforded (+)-ent-himastatin (1, 3.60 mg, 370%) as an off-white solid. Spectral data of (+)-ent-himastatin (1) were in agreement with those previously reported in this document for (−)-himastatin (1).

$[\alpha]_D^{24}$: +33 (c=0.071, MeOH).

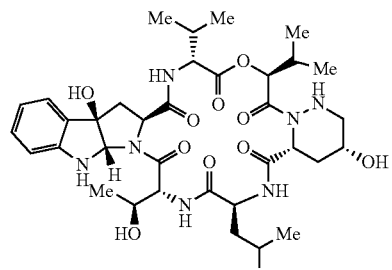
(+)-2
Cu(SbF$_6$)$_2$, DTBMP
DCE, 23° C.
32%
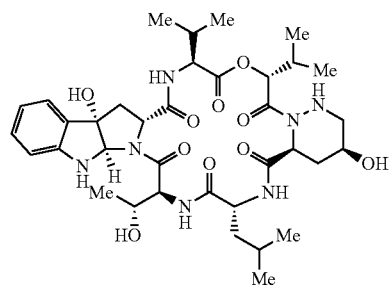
(−)-2
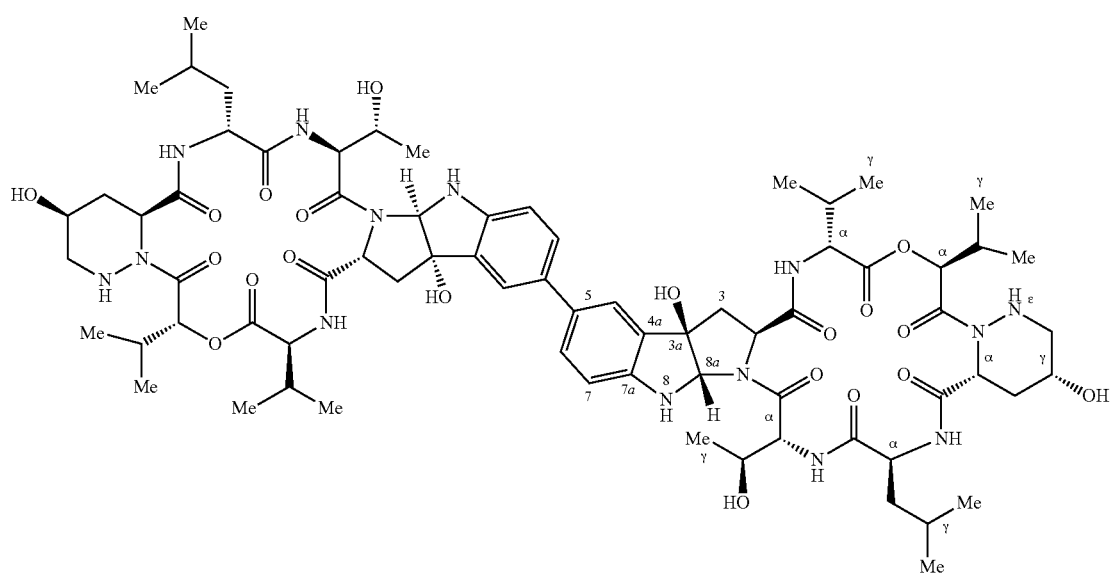
meso-himastatin (1)
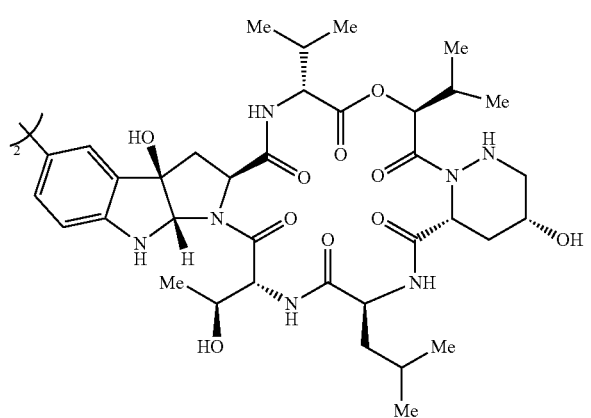
(−)-himastatin (1)

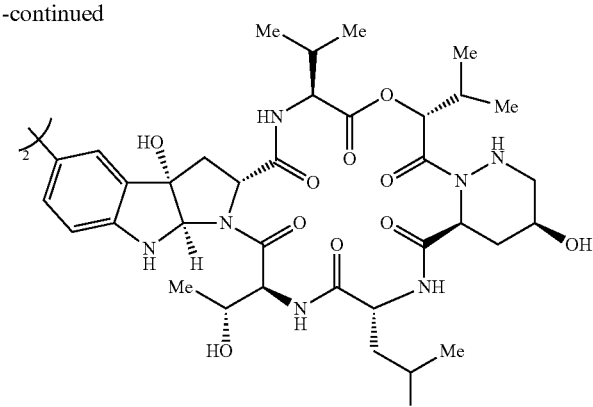

(+)-ent-himastatin (1)

Meso-Himastatin (1):

Prepared according to the procedure described previously for (−)-himastatin (1) from himastatin monomer (+)-2 (3.72 mg 5.00 μmol 0.500 equiv) and ent-himastatin monomer (−)-2 (3.72 mg, 5.00 μmol, 0.500 equiv). Flash column chromatography on silica gel (eluent: 2.7% methanol, 0.3% ammonium hydroxide→4.5% methanol, 0.5% ammonium hydroxide in chloroform) afforded a stereoisomeric mixture of himastatin (2.35 mg, 32%) as an off-white solid. The stereoisomers of himastatin were separated by chiral HPLC (CHIRALPAK® IA 4.6 mm×250 mm, Lot #IA00CE-PD046, 60% i-PrOH in hexanes, 1.0 mL/min, 270 nm, $t_R$ ((−)-1) 8.32 min, $t_R$ (meso-1)=15.1 min, $t_R$ ((+)-1)=22.35 min) to afford (−)-himastatin (1, 0.62 mg, 8%), meso-himastatin (1, 0.47 mg, 6%), and (+)-ent-himastatin (1, 0.35 mg, 5%). Spectral data of (−)-himastatin (1) and of (+)-ent-himastatin (1) were in agreement with those previously reported in this document. Structural assignments of meso-himastatin (1) shown below were made using additional information from gCOSY, gHSQC, and gHMBC experiments.

$^1$H NMR (600 MHz, CDCl$_3$, 25° C.): δ 7.53 (d, J=1.9 Hz, 2H, Trp-C4H), 7.44-7.39 (m, 4H, Trp-C6H, Leu-NH), 7.29 (d, J=10.0 Hz, 2H, Val-NH), 7.12 (d, J=10.5 Hz, 2H, Thr-NH), 6.80 (d, J=8.3 Hz, 2H, Trp-C7H), 5.87 (s, 2H, Trp-C3aOH), 5.82 (d, J=6.3 Hz, 2H, Trp-N8H), 5.64 (d, J=8.7 Hz, 2H, Hiv-CαH), 5.43 (d, J=13.1 Hz, 2H, Pip-NεH), 5.22 (d, J=8.0 Hz, 2H, Trp-C2H), 5.20 (d, J=5.3 Hz, 2H, Trp-C2H), 5.14 (d, J=5.9 Hz, 2H, Trp-C8aH), 5.13 (d, J=6.5 Hz, 2H, Pip-CαH), 4.99 (d, J=10.5 Hz, 2H, Thr-CαH), 4.90 (dd, J=10.0, 3.2 Hz, 2H, Val-CαH), 4.45 (qd, J=6.7, 2.0 Hz, 2H, Thr-CβH), 4.24 (ddd, J=10.8, 5.4, 3.6 Hz, 2H, Leu-CαH), 3.82 (s, 2H, app-br-s, Pip-CγH), 3.61 (s, 2H, Thr-CβOH), 3.07 (d, J=14.0 Hz, 2H, Pip-CδH$_a$), 2.84 (app-t, J=13.4 Hz, 2H, Pip-CδH$_b$), 2.78 (d, J=14.3 Hz, 2H, Trp-C3H$_a$), 2.57 (septd, J=6.8, 3.1 Hz, 2H, Val-CβH), 2.49 (d, J=15.0 Hz, 2H, Pip-CβH$_a$), 2.21 (dd, J=14.3, 8.0 Hz, 2H, Trp-C3H$_b$), 2.20-2.12 (m, 2H, Hiv-CβH), 1.95 (ddd, J=15.0, 7.1, 3.4 Hz, 2H, Pip-CβH$_b$), 1.73-1.65 (m, 4H, Leu-CβH$_a$, Leu-CγH), 1.42-1.37 (m, 2H, Leu-CβH$_b$), 1.16 (d, J=6.5 Hz, 6H, Thr-CγH$_3$), 1.13 (d, J=6.7 Hz, 6H, Hiv-CγH$_3$), 1.01 (d, J=6.9 Hz, 6H, Hiv-CγH$_3$), 1.01 (d, J=6.8 Hz, 6H, Val-CγH$_3$), 0.93, (d, J=6.1 Hz, 6H, Leu-CδH$_3$), 0.87 (d, J=6.9 Hz, 6H, Val-CγH$_3$), 0.87 (d, J=6.0 Hz, 6H, Leu-CδH$_3$).

$^{13}$C NMR (150.9 MHz, CDCl$_3$, 25° C.): 174.3 (Hiv-CO), 174.1 (Leu-CO), 173.6 (Val-CO), 173.4 (Pip-CO), 173.2 (Trp-CO), 172.5 (Thr-CO), 146.8 (Trp-C7a), 134.9 (Trp-C5), 132.4 (Trp-C4a), 128.8 (Trp-C6), 121.8 (Trp-C4), 112.7 (Trp-C7), 91.0 (Trp-C3a), 86.4 (Trp-C8a), 77.5 (Hiv-Cα), 66.8 (Thr-Cβ), 61.0 (Trp-C2), 58.8 (Pip-Cγ), 57.3 Val-Cα), 54.4 (Leu-Cα), 53.9 (Thr-Cα), 52.8 (Pip-Cδ), 50.1 (Pip-Cα), 41.1 (Leu-Cβ), 39.6 (Trp-C3), 30.1 (2C, Hiv-Cβ, Val-Cβ), 28.8 (Pip-Cβ), 25.5 (Leu-Cγ), 23.1 (Leu-Cδ), 21.1 (Leu-Cδ), 19.5 (Val-Cγ), 19.1 (Hiv-Cγ), 18.4 (Hiv-Cγ), 17.5 (Thr-Cγ), 16.6 (Val-Cγ).

FTIR (thin film) cm$^{-1}$: 3394 (m), 3324 (br-s), 2963 (m), 2931 (m), 2874 (w), 1726 (s), 1673 (m), 1625 (m), 1535 (m), 1416 (m), 1249 (m), 1156 (w), 916 (w), 772 (w).

HRMS (ESI) (m/z): calc'd for C$_{72}$H$_{104}$N$_{14}$NaO$_{20}$ [M+Na]$^+$: 1507.7444, found: 1507.7436.

TLC (9% methanol, 1% ammonium hydroxide in chloroform), Rf: 0.28 (UV, CAM).

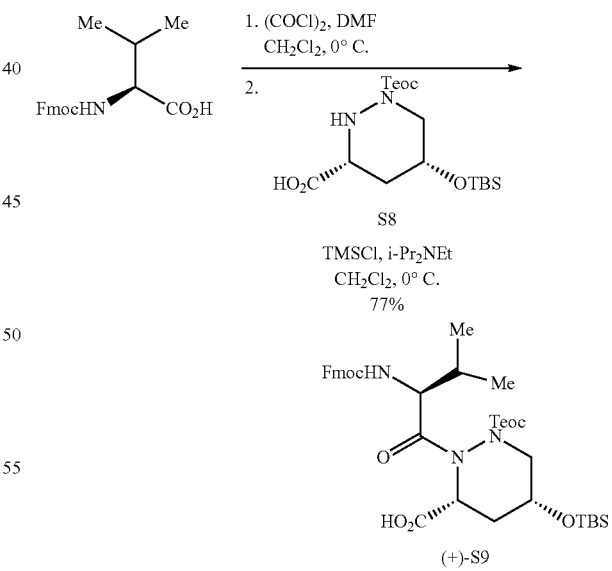

(+)-S9

Dipeptide (+)-S9:

Oxalyl chloride (77.3 μL, 0.900 mmol, 2.40 equiv) was added dropwise via syringe over 2 minutes to a solution of Fmoc-L-Val-OH (153 mg, 0.450 mmol, 1.20 equiv) and N,N-dimethylformamide (3.5 μL, 0.045 mmol, 0.12 equiv) in dichloromethane (1.5 mL) at 0° C. After 1 h, the yellow solution was concentrated under reduced pressure (~1 torr)

at 0° C. The resulting residue was dissolved in dichloromethane (1.5 mL) and transferred by cannula over 2 min to a solution of piperazic acid S8[13] (152 mg, 0.375 mmol, 1 equiv), N,N-diisopropylethylamine (137 μL, 0.778 mmol, 2.10 equiv), and chlorotrimethylsilane (95.3 μL, 0.750 mmol, 2.00 equiv) in dichloromethane (1 mL) at 0° C. The transfer was quantitated with additional dichloromethane (0.5 mL). After 1 h, the reaction mixture was diluted with an aqueous hydrogen chloride solution (1 M, 20 mL) and stirred vigorously for 5 min. The mixture was extracted with ethyl acetate (3×15 mL) and the combined organic extracts were washed with an aqueous saturated sodium chloride solution (30 mL), were dried over anhydrous sodium sulfate, were filtered, and were concentrated under reduced pressure. The resulting residue was purified by flash column chromatography on silica gel (eluent: 1% acetic acid, 25%→40% ethyl acetate in hexanes)[17] to afford dipeptide (+)-S9 (208 mg, 77%) as a white foam. The reported $^1$H NMR integrals are an approximation due to the presence of multiple conformers and significant atropisomerism. The $^{13}$C data are listed as observed with more than the expected number of $^{13}$C resonances due to atropisomerism.

$^1$H NMR (600 MHz, CD$_3$CN, 25° C.): δ 11.26 (br-s, 1H), 7.83 (d, J=7.6 Hz, 2H), 7.67 (app-t, J=7.6 Hz, 2H), 7.42 (app-t, J=7.4 Hz, 2H), 7.33 (app-t, J=7.2 Hz, 2H), 5.96 (d, J=9.8 Hz, 1H), 5.12 (d, J=7.8 Hz, 1H), 4.46 (app-t, J=8.3 Hz, 1H), 4.40-4.20 (m, 4H), 4.14 (app-td, J=11.4, 5.3 Hz, 1H), 4.08 (d, J=17.4 Hz, 1H), 3.24 (d, J=13.5 Hz, 1H), 2.39 (app-d, J=15.0 Hz, 0.7H), 2.33 (app-d, J=15.1 Hz, 0.3H), 2.27-2.05 (m, 1H), 2.00 (app-ddd, J=20.3, 13.8, 7.3 Hz, 2H), 1.16-1.09 (m, 1H), 1.08-0.99 (m, 1H), 0.98-0.86 (m, 6H), 0.83 (s, 9H), 0.06 (s, 3H), 0.05 (s, 3H), −0.01 (s, 9H).

$^{13}$C NMR (150.9 MHz, CD$_3$CN, 25° C.): δ 175.0, 172.0, 162.1, 157.1, 145.2, 144.9, 142.1, 128.7, 128.1, 126.3, 121.0, 68.5, 67.5, 63.4, 56.4, 53.4, 51.1, 48.0, 33.0, 31.9, 26.0, 19.9, 18.6, 18.0, 17.9, −1.5, −5.1, −5.2.

FTIR (thin film) cm$^{-1}$: 3323 (br-w), 3067 (w), 2955 (m), 2930 (m), 2858 (w), 1752 (s), 1726 (s), 1690 (s), 1405 (m), 1345 (m), 1249 (m), 1120 (m), 837 (m), 757 (m), 741 (m).

HRMS (ESI) (m/z): calc'd for C$_{37}$H$_{55}$N$_3$NaO$_8$Si$_2$ [M+Na]$^+$: 748.3420, found: 748.3419.

[α]$_D^{23}$: +36 (c=0.58, CHCl$_3$).

TLC (1% acetic acid, 50% ethyl acetate in hexanes), Rf: 0.42 (UV, CAM).

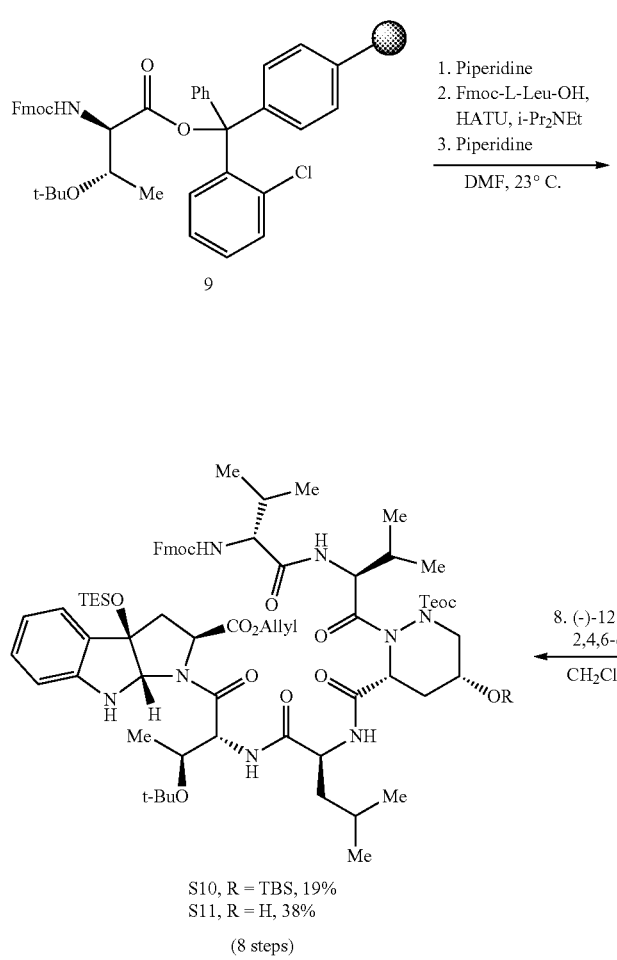

S10, R = TBS, 19%
S11, R = H, 38%
(8 steps)

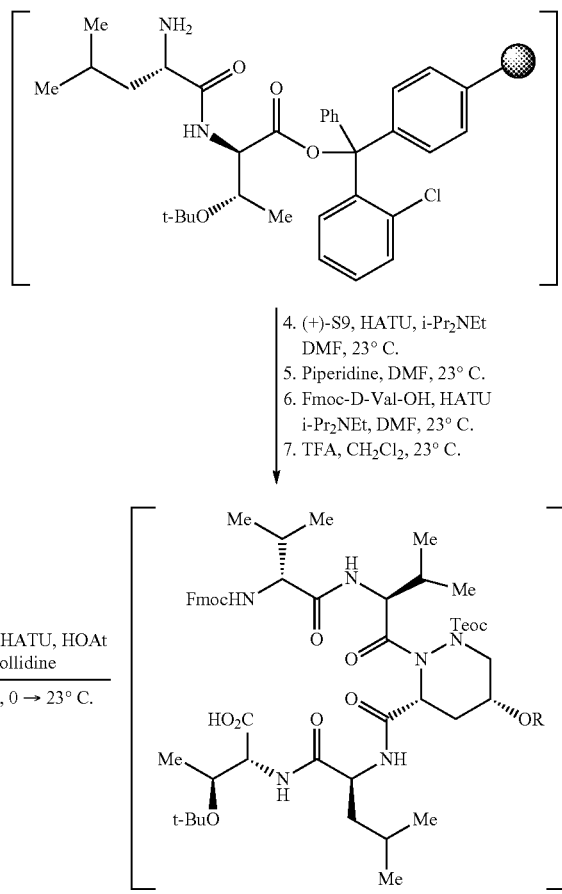

Hexapeptide Tert-Butyldimethylsilyl Ether S10 and Hexapeptide S11:

A sample of Fmoc-D-Thr(t-Bu)-2-chlorotrityl polystyrene resin 9 (263 mg, 0.712 mmol/g, 0.187 mmol, 1 equiv) in a fritted syringe connected to a vacuum manifold was treated twice with piperidine (20% in N,N-dimethylformamide, 2×10 mL) at 23° C. for 5 min. The liquid phase was drained and the resin was washed with N,N-dimethylformamide (3×10 mL).

A solution of Fmoc-L-Leu-OH (265 mg, 0.750 mmol, 4 equiv), HATU (271 mg, 0.712 mmol, 3.80 equiv), and N,N-diisopropylethylamine (375 μL, 2.15 mmol, 11.5 equiv) in N,N-dimethylformamide (1.9 mL) was added to the resulting resin at 23° C. After 1 h, the liquid phase was drained and the resin was washed with N,N-dimethylformamide (3×10 mL) and was treated twice with piperidine (20% in N,N-dimethylformamide, 2×10 mL) at 23° C. for 5 min. The liquid phase was drained and the resin was washed with N,N-dimethylformamide (3×10 mL).

A solution of dipeptide (+)-S9 (177 mg, 0.244 mmol, 1.30 equiv), HATU (92.8 mg, 0.244 mmol, 1.30 equiv), and N,N-diisopropylethylamine (72.1 μL, 0.414 mmol, 2.21 equiv) in N,N-dimethylformamide (1.0 mL) was added to the resulting resin at 23° C. After 22 h, the liquid phase was drained and the resin was washed with N,N-dimethylformamide (3×10 mL) and was treated twice with piperidine (20% in N,N-dimethylformamide, 2×10 mL) at 23° C. for 5 min. The liquid phase was drained and the resin was washed with N,N-dimethylformamide (3×10 mL).

A solution of Fmoc-D-Val-OH (255 mg, 0.750 mmol, 4 equiv), (HATU, 271 mg, 0.712 mmol, 3.80 equiv), and N,N-diisopropylethylamine (375 μL, 2.15 mmol, 11.5 equiv) in N,N-dimethylformamide (1.9 mL) was added to the resulting resin at 23° C. After 4 h, the liquid phase was drained and the resin was washed with N,N-dimethylformamide (3×10 mL) and dichloromethane (3×10 mL).

The resulting resin was treated twice with trifluoroacetic acid (1% in dichloromethane, 2×10 mL) at 23° C. for 2 min. The liquid phases were separated into a vessel containing pyridine (0.75 mL). The resin was washed with dichloromethane (3×5 mL) and the liquid phases were separated into the same vessel. The combined liquid phases were diluted with an aqueous hydrogen chloride solution (1 M, 75 mL) and extracted with dichloromethane (3×50 mL). The combined organic extracts were washed with a saturated aqueous sodium chloride solution (100 mL), were dried over anhydrous sodium sulfate, were filtered, and were concentrated under reduced pressure to provide the crude pentapeptide acid as an off-white foam, which was used in the next step without further purification.

A sample of HATU (143 mg, 0.375 mmol, 2.00 equiv) was added to a solution of the crude pentapeptide acid, cyclotryptophan triethylsilyl ether (−)-12 (84.3 mg, 0.225 mmol, 1.20 equiv), 1-hydroxy-7-azabenzotriazole (HOAt, 179 mg, 1.31 mmol, 7.00 equiv), and 2,4,6-collidine (198 μL, 1.50 mmol, 8.00 equiv) in dichloromethane (4 mL) at 0° C. After 1 h, the cold bath was removed and the cloudy solution was allowed to stir at 23° C. After 4 h, the reaction mixture was diluted with ethyl acetate-hexanes (4:1, 100 mL) and washed with an aqueous potassium hydrogen sulfate solution (1 M, 60 mL), a saturated aqueous sodium hydrogen carbonate solution (60 mL), and a saturated aqueous sodium chloride solution (60 mL). The organic layer was dried over anhydrous sodium sulfate, was filtered, and was concentrated under reduced pressure. The resulting residue was purified by flash column chromatography on silica gel (eluent: 25%→80% ethyl acetate in hexanes), including a second chromatographic purification of mixed fractions of hexapeptide tert-butyldimethylsilyl ether S10 and cyclotryptophan triethylsilyl ether (−)-12 on silica gel (eluent: 45% ethyl acetate in hexanes), to afford hexapeptide tert-butyldimethylsilyl ether S10 (50.4 mg, 19%) and hexapeptide S11 (94.4 mg, 38%) as white foams. The reported $^1$H NMR integrals are an approximation due to the presence of multiple conformers and significant atropisomerism. The $^{13}$C data are listed as observed with more than the expected number of $^{13}$C resonances due to atropisomerism.

Hexapeptide Tert-Butyldimethylsilyl Ether S10

$^1$H NMR (600 MHz, CD$_3$CN, 25° C.): δ 8.49 (d, J=7.1 Hz, 0.2H), 8.45 (br-s, 0.2H), 8.36 (br-s, 0.1H), 8.26 (d, J=7.5 Hz, 0.1H), 7.84-7.81 (m, 2H), 7.70-7.64 (m, 2H), 7.41 (app-td, J=7.5, 3.2 Hz, 2H), 7.36-7.31 (m, 2H), 7.26 (d, J=7.4 Hz, 0.4H), 7.20-7.14 (m, 1H), 7.08 (app-t, J=7.6 Hz, 0.6H), 7.00 (br-s, 0.3H), 6.91 (d, J=9.3 Hz, 0.4H), 6.83 (app-t, J=7.4 Hz, 0.5H), 6.79-6.65 (m, 2H), 6.58 (d, J=8.1 Hz, 0.2H), 6.03 (d, J=4.2 Hz, 0.2H), 5.97 (ddd, J=17.2, 10.7, 5.4 Hz, 0.8H), 5.93-5.82 (m, 1.2H), 5.59 (br-s, 0.2H), 5.55 (d, J=4.0 Hz, 0.2H), 5.48 (d, J=3.7 Hz, 0.7H), 5.39 (dd, J=17.2, 1.6 Hz, 0.5H), 5.35-5.28 (m, 0.5H), 5.26 (dd, J=10.5, 1.4 Hz, 0.6H), 5.19 (d, J=11.2 Hz, 0.6H), 4.90 (d, J=8.3 Hz, 0.5H), 4.84 (br-s, 0.2H), 4.76-4.59 (m, 2.5H), 4.57-3.88 (m, 12.5H), 3.74-3.53 (m, 1H), 2.69 (d, J=13.1 Hz, 0.5H), 2.55 (dd, J=13.3, 8.6 Hz, 0.3H), 2.43 (dd, J=13.4, 5.4 Hz, 0.4H), 2.33 (dd, J=13.3, 8.9 Hz, 0.4H), 2.27 (br-s, 0.2H), 2.15 (br-s, 0.5H), 2.09 (br-s, 1.5H), 1.98 (app-dt, J=13.1, 6.6 Hz, 1.5H), 1.79 (br-s, 0.3H), 1.71-1.40 (m, 3.2H), 1.20-1.13 (m, 6H), 1.13-1.07 (m, 6H), 0.96-0.76 (m, 40H), 0.46-0.33 (m, 6H), 0.08-0.00 (m, 12.5H), −0.05 (br-s, 1H), −0.14 (br-s, 1.5H).

$^{13}$C NMR (150.9 MHz, CD$_3$CN, 25° C.): δ 174.4, 172.9, 172.4, 172.3, 172.2, 171.8, 171.6 (2C), 171.2 (2C), 171.0, 170.8, 159.6, 157.1, 149.5, 148.9, 145.2, 145.0, 142.1, 133.5, 133.2, 132.1, 131.2, 130.6, 128.7, 128.2, 128.1, 126.2, 124.7, 124.0, 121.0, 120.7, 119.1, 118.9, 118.7, 118.5, 112.4, 110.9, 91.2, 89.0, 87.0, 86.7, 84.7, 84.2, 75.6, 74.8, 69.6, 69.3, 68.1, 67.7, 67.4, 67.4, 66.8, 66.1, 65.7, 65.4, 64.5, 61.2, 61.1, 60.8, 60.7, 60.5, 58.1, 57.5, 57.2, 57.1, 56.9, 56.7, 56.3, 55.3, 55.0, 54.6, 53.6, 53.1, 52.3, 48.1, 47.2, 46.7, 43.1, 41.6, 40.5, 33.0, 32.8, 32.3, 32.1, 31.9, 31.7, 29.3, 29.0, 28.9, 28.6, 28.5, 25.5 (2C), 23.5, 22.2, 22.0, 21.9, 21.5, 20.4, 20.3, 20.1, 19.9, 18.7 (2C), 18.2, 18.1, 17.8, 17.7, 17.6, 7.2, 7.1, 6.6, 6.5, −1.2, −1.3, −1.5, −1.6, −4.7 (2C), −4.8.

FTIR (thin film) cm$^{-1}$: 3312 (br-s), 2956 (m), 2876 (w), 1710 (s), 1663 (s), 1413 (m), 1249 (m), 1173 (m), 1123 (m), 837 (m), 740 (m).

HRMS (ESI) (m/z): calc'd for C$_{76}$H$_{119}$N$_8$O$_{14}$Si$_3$ [M+H]$^+$: 1451.8148, found: 1451.8152.

TLC (45% ethyl acetate in hexanes), Rf: 0.53 (UV, CAM).

Hexapeptide S11

$^1$H NMR (600 MHz, CD$_3$CN, 25° C.): δ 8.53 (d, J=6.6 Hz, 0.1H), 8.40 (d, J=7.2 Hz, 0.2H), 8.16 (d, J=6.8 Hz, 0.1H), 8.11 (d, J=7.1 Hz, 0.1H), 7.87-7.81 (m, 2H), 7.70-7.65 (m, 2H), 7.46-7.38 (m, 2H), 7.37-7.30 (m, 2H), 7.29-7.13 (m, 2.5H), 7.13-7.01 (m, 0.5H), 7.01-6.90 (m, 0.5H), 6.87-6.56 (m, 2.5H), 6.08 (d, J=3.3 Hz, 0.2H), 6.04-5.87 (m, 2H), 5.83 (d, J=4.5 Hz, 0.2H), 5.77 (d, J=4.7 Hz, 0.1H), 5.59-5.44 (m, 1H), 5.39 (d, J=17.3 Hz, 0.5H), 5.35-5.29 (m, 0.4H), 5.26 (d, J=10.5 Hz, 0.6H), 5.20 (dd, J=10.6, 1.5 Hz, 0.5H), 5.12 (d, J=6.9 Hz, 0.2H), 5.08 (d, J=6.3 Hz, 0.2H), 4.92-4.76 (m, 1.6H), 4.73-4.66 (m, 0.8H), 4.68-4.57 (m, 1.4H), 4.55-4.39 (m, 1.6H), 4.37-3.87 (m, 10H), 3.83 (s, 0.4H), 3.77 (s, 0.5H), 3.56 (s, 0.1H), 3.40 (d, J=13.2 Hz, 0.1H), 3.25 (d, J=14.1 Hz, 0.2H), 3.14-3.04 (m, 0.3H), 3.02 (dd, J=12.9, 7.5 Hz, 0.1H), 2.96 (d, J=14.0 Hz, 0.1H), 2.85 (d, J=17.5 Hz, 0.2H), 2.81-2.74 (m, 0.2H), 2.70 (dd, J=13.5, 10.3 Hz, 0.7H), 2.62-2.23 (m, 2.4H), 2.13 (s, 0.6H), 2.09-1.96 (m, 1.4H), 1.92-1.79 (m, 1H), 1.67-1.58 (m, 1.2H), 1.58-1.42 (m, 1.1H), 1.40-1.32 (m, 0.5H), 1.20 (s, 1H), 1.17

(s, 4.5H), 1.14 (d, J=5.7 Hz, 2.6H), 1.11 (d, J=9.4 Hz, 4H), 1.03-0.68 (m, 30H), 0.50-0.34 (m, 6H), 0.08-0.00 (m, 7.5H), −0.18 (s, 1.5H).

$^{13}$C NMR (150.9 MHz, CD$_3$CN, 25° C.): δ 174.4, 172.8, 172.5, 172.3, 172.2, 172.1, 172.0, 171.9, 171.7, 171.5, 171.2, 170.7, 157.2, 149.5, 148.4, 148.2, 145.2, 145.0, 142.1, 133.4, 133.1, 131.6, 131.2, 130.8, 130.7, 128.7, 128.1, 128.1, 126.2 (2C), 124.7, 124.2, 121.0 (2C), 120.8, 120.5, 118.8 (2c), 112.5, 112.1, 110.7, 110.5, 91.3, 91.1, 89.2, 89.0, 86.6, 86.4, 84.7, 84.4, 76.1, 75.2, 74.9, 69.9, 69.7, 68.8, 68.2, 67.4, 66.9 (2C), 66.5, 66.4, 66.2 (2C), 66.1, 62.9, 62.2, 61.9, 61.7, 61.4, 60.8, 60.7, 60.6 (2C), 57.2, 57.0, 56.7, 56.3, 56.1, 55.5, 54.3, 54.2, 53.8, 53.6, 53.4, 53.0, 52.9, 52.8, 52.7, 52.5, 51.2, 50.3, 48.0 (2C), 46.8, 46.4, 46.2, 43.0, 42.7, 40.8, 40.2, 39.6, 39.4, 33.6, 32.9, 32.5, 31.9, 31.8 (2C), 31.5, 28.9, 28.8, 28.5, 28.4, 28.3, 26.1, 25.7, 25.4, 25.4, 25.3, 23.6, 23.5, 23.3, 22.0, 21.7, 21.6, 21.3, 21.3, 20.7, 20.2, 20.1, 19.7, 19.5, 18.9, 18.4, 18.2, 18.1, 18.0, 17.9, 17.8, 17.6, 7.1 (3C), 7.0 (2C), 6.5, 6.4, 6.3, 6.1, −1.2, −1.3, −1.3, −1.4, −1.9.

FTIR (thin film) cm$^{-1}$: 3294 (br-s), 2957 (m), 2875 (w), 1707 (s), 1660 (s), 1531 (m), 1414 (m), 1241 (m), 1184 (m), 1119 (m), 838 (m), 741 (m).

HRMS (ESI) (m/z): calc'd for C$_{70}$H$_{105}$N$_8$O$_{14}$Si$_2$ [M+H]$^+$: 1337.7283, found: 1337.7278.

TLC (45% ethyl acetate in hexanes), Rf: 0.27 (UV, CAM).

Cyclic Hexapeptide (+)-14:

Prepared according to the procedure described previously for himastatin monomer (+)-2 from hexapeptide tert-butyldimethylsilyl ether S10 (47.0 mg, 32.4 μmol, 0.329 equiv) and hexapeptide S11 (88.2 mg, 65.9 μmol, 0.671 equiv). Cyclic hexapeptide (+)-14 was obtained by flash column chromatography on silica gel (eluent: 2.7% methanol, 0.3% ammonium hydroxide→4.5% methanol, 0.5% ammonium hydroxide in chloroform) as an off-white solid (21.4 mg, 29%). Structural assignments were made using additional information from gCOSY, gHSQC, and gHMBC experiments.

$^1$H NMR (600 MHz, CDCl$_3$, 25° C.): δ 7.67 (d, J=9.1 Hz, 1H, D-Val-NH), 7.37 (d, J=5.9 Hz, 1H, Leu-NH), 7.33 (dd, J=7.5, 1.3 Hz, 1H, Trp-C4H), 7.18 (app-td, J=7.7, 1.3 Hz, 1H, Trp-C6H), 6.88 (app-td, J=7.4, 0.9 Hz, 1H, Trp-C5H), 6.74 (dd, J=7.9, 0.9 Hz, 1H, Trp-C7H), 6.73 (d, J=10.3 Hz, 1H, Thr-NH), 6.17 (d, J=7.6 Hz, 1H, L-Val-NH), 5.98 (br-s, 1H, Trp-C3aOH), 5.83 (d, J=6.2 Hz, 1H, Trp-N8H), 5.50 (app-t, J=7.4 Hz, 1H, L-ValCαH), 5.39 (dd, J=12.9, 2.1 Hz, 1H, Pip-NεH), 5.35 (d, J=5.7 Hz, 1H, Pip-CγOH), 5.19 (d, J=8.2 Hz, 1H, Trp-C2H), 5.15 (d, J=6.1 Hz, 1H, Trp-C8aH), 5.11 (d, J=7.1 Hz, 1H, Pip-CαH), 4.82 (d, J=10.3 Hz, 1H, Thr-CαH), 4.53 (qd, J=6.6, 2.4 Hz, 1H, Thr-CβH), 4.41 (dd, J=9.1, 5.5 Hz, 1H, D-Val-CαH), 4.30 (ddd, J=10.4, 5.9, 3.9

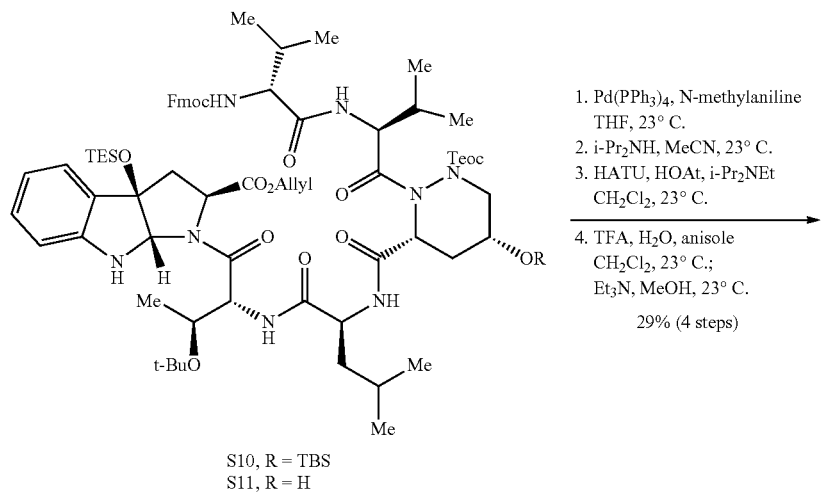

1. Pd(PPh$_3$)$_4$, N-methylaniline THF, 23° C.
2. i-Pr$_2$NH, MeCN, 23° C.
3. HATU, HOAt, i-Pr$_2$NEt CH$_2$Cl$_2$, 23° C.
4. TFA, H$_2$O, anisole CH$_2$Cl$_2$, 23° C.; Et$_3$N, MeOH, 23° C.

29% (4 steps)

S10, R = TBS
S11, R = H

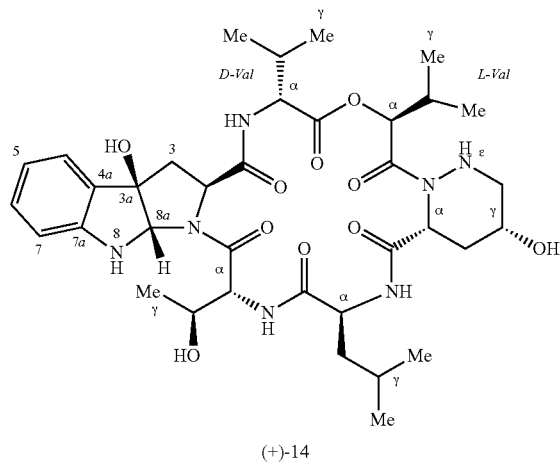

(+)-14

Hz, 1H, Leu-CαH), 3.82-3.78 (m, 1H, Pip-CγH), 3.72 (d, J=2.4 Hz, 1H, Thr-CβOH), 3.09 (app-dq, J=14.2, 2.4 Hz, 1H, Pip-CδH$_a$), 2.85 (app-td, J=13.5, 1.5 Hz, 1H, Pip-CδH$_b$), 2.71 (d, J=14.3 Hz, 1H, Trp-C3H$_a$), 2.45-2.40 (m, 1H, Pip-CβH$_a$), 2.14 (dd, J=14.3, 8.3 Hz, 1H, Trp-C3H$_b$), 2.11-2.04 (m, 1H, D-Val-CβH), 2.02-1.94 (m, 2H, Pip-CβH$_b$, L-Val-CβH), 1.74-1.63 (m, 2H, Leu-CβH$_a$, Leu-CγH), 1.44 (ddd, J=13.1, 10.6, 4.5 Hz, 1H, Leu-CβH$_b$), 1.11 (d, J=6.5 Hz, 3H, Thr-CγH$_3$), 1.02 (d, J=6.7 Hz, 3H, D-Val-CγH$_3$), 1.00 (d, J=6.8 Hz, 6H, L-Val-CγH$_3$), 0.94 (d, J=6.8 Hz, 3H, D-Val-CγH$_3$), 0.93 (d, J=6.3 Hz, 3H, Leu-CδH$_3$), 0.86 (d, J=6.3 Hz, 3H, Leu-CδH$_3$).

$^{13}$C NMR (150.9 MHz, CDCl$_3$, 25° C.): δ 176.3 (L-Val-CO), 174.4 (Leu-CO), 173.2 (Pip-CO), 172.8 (Trp-CO), 171.6 (Thr-CO), 171.1 (D-Val-CO), 147.8 (Trp-C7a), 131.6 (Trp-C4a), 129.9 (Trp-C6), 123.2 (Trp-C4), 120.9 (Trp-C5), 112.3 (Trp-C7), 91.0 (Trp-C3a), 86.2 (Trp-C8a), 66.4 (Thr-Cβ), 61.5 (Trp-C2), 58.9 (D-Val-Cα), 58.6 (Pip-Cγ), 54.7 (Thr-Cα), 54.1 (2C, Leu-Cα, L-Val-Cα), 52.7 (Pip-Cδ), 50.1 (Pip-Cα), 40.9 (Leu-Cβ), 39.5 (Trp-C3), 32.2 (D-Val-Cβ), 30.8 (L-Val-Cβ), 28.9 (Pip-Cβ), 25.5 (Leu-Cγ), 23.1 (Leu-Cδ), 21.2 (Leu-Cδ), 19.8 (L-Val-Cγ), 19.6 (D-Val-Cγ), 18.6 (L-Val-Cγ), 17.4 (2C, Thr-Cγ, D-Val-Cγ).

FTIR (thin film) cm$^{-1}$: 3296 (br-s), 2962 (m), 2873 (m), 1647 (s), 1529 (m), 1250 (m), 752 (m).

HRMS (ESI) (m/z): calc'd for C$_{36}$H$_{54}$N$_8$NaO$_9$ [M+Na]$^+$: 765.3906, found: 765.3904.

[α]$_D^{23}$: +46 (c=0.10, CHCl$_3$)

TLC (9% methanol, 1% ammonium hydroxide in chloroform), Rf: 0.31 (UV, CAM).

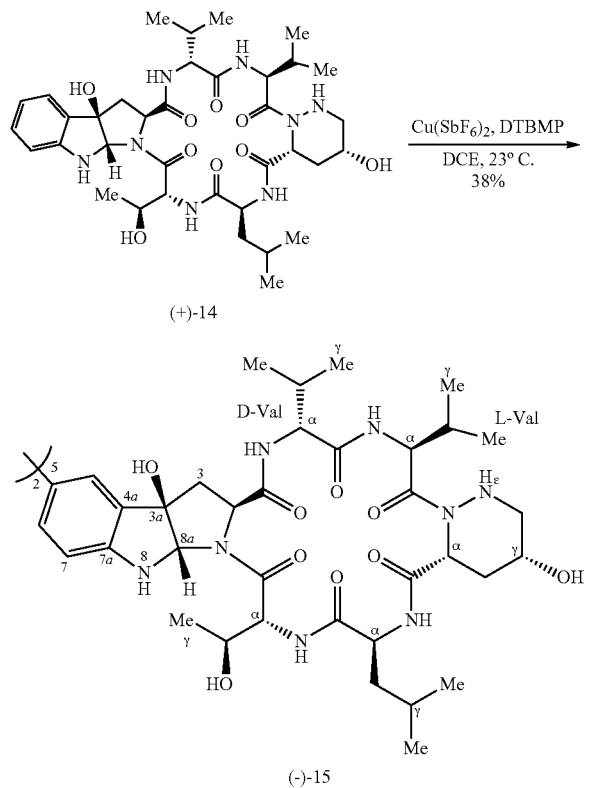

Himastatin Lactam Derivative (−)-15:

Prepared according to the procedure described previously for (−)-himastatin (1) from cyclic hexapeptide (+)-14 (5.29 mg, 7.12 μmol, 1 equiv). Flash column chromatography on silica gel (eluent: 2.7% methanol, 0.3% ammonium hydroxide→7.2% methanol, 0.8% ammonium hydroxide in chloroform) to afforded Himastatin lactam derivative (−)-15 (2.03 mg, 38%) as an off-white solid. Structural assignments were made using additional information from gCOSY, gHSQC, and gHMBC experiments.

$^1$H NMR (600 MHz, CDCl$_3$, 25° C.): δ 7.66 (d, J=9.1 Hz, 2H, D-Val-NH), 7.57 (d, J=1.9 Hz, 2H, Trp-C4H), 7.42 (dd, J=8.3, 1.9 Hz, 2H, Trp-C6H), 7.37 (d, J=5.9 Hz, 2H, Leu-NH), 6.77 (d, J=8.3 Hz, 2H, Trp-C7H), 6.74 (d, J=10.3 Hz, 2H, Thr-NH), 6.09 (d, J=7.6 Hz, 2H, L-Val-NH), 6.02 (s, 2H, Trp-C3aOH), 5.85 (d, J=6.2 Hz, 2H, Trp-N8H), 5.51 (app-t, J=7.4 Hz, 2H, L-ValCαH), 5.41 (dd, J=13.0, 2.0 Hz, 2H, Pip-NεH), 5.33 (d, J=5.6 Hz, 2H, Pip-CγOH), 5.21 (d, J=8.2 Hz, 2H, Trp-C2H), 5.17 (d, J=6.2 Hz, 2H, Trp-C8aH), 5.12 (d, J=7.2 Hz, 2H, Pip-CαH), 4.84 (d, J=10.3 Hz, 2H, Thr-CαH), 4.54 (qd, J=6.6, 2.3 Hz, 2H, Thr-CβH), 4.42 (dd, J=9.1, 5.3 Hz, 2H, D-Val-CαH), 4.30 (ddd, J=10.4, 5.9, 3.9 Hz, 2H, Leu-CαH), 3.83-3.78 (m, 2H, Pip-CγH), 3.71 (br-s, 2H, Thr-CβOH), 3.09 (app-dq, J=14.3, 1.8 Hz, 2H, Pip-CδH$_a$), 2.85 (app-t, J=13.4 Hz, 2H, Pip-CδH$_b$), 2.73 (d, J=14.3 Hz, 2H, Trp-C3H$_a$), 2.45-2.40 (m, 2H, Pip-CβOH$_a$), 2.17 (dd, J=14.3, 8.2 Hz, 2H, Trp-C3H$_b$), 2.12-2.04 (m, 2H, D-Val-CβH), 2.02-1.95 (m, 4H, Pip-CβH$_b$, L-Val-CβH), 1.76-1.63 (m, 4H, Leu-CβH$_a$, Leu-CγH), 1.45 (ddd, J=13.4, 10.5, 4.5 Hz, 2H, Leu-CβH$_b$), 1.12 (d, J=6.5 Hz, 6H, Thr-CγH$_3$), 1.03 (d, J=6.7 Hz, 6H, D-Val-CγH$_3$), 1.01 (d, J=6.8 Hz, 12H, L-Val-CγH$_3$), 0.95 (d, J=6.5 Hz, 6H, D-Val-CγH$_3$), 0.93 (d, J=6.2 Hz, 6H, Leu-CδH$_3$), 0.87 (d, J=6.3 Hz, 6H, Leu-CδH$_3$).

$^{13}$C NMR (150.9 MHz, CDCl$_3$, 25° C.): δ 176.3 (L-Val-CO), 174.4 (Leu-CO), 173.2 (Pip-CO), 172.8 (Trp-CO), 171.5 (Thr-CO), 171.1 (D-Val-CO), 147.8 (Trp-C7a), 134.3 (Trp-C5), 132.2 (Trp-C4a), 128.5 (Trp-C6), 121.4 (Trp-C4), 112.5 (Trp-C7), 91.1 (Trp-C3a), 86.5 (Trp-C8a), 66.4 (Thr-Cβ), 61.5 (Trp-C2), 58.9 (D-Val-Cα), 58.6 (Pip-Cγ), 54.7 (Thr-Cα), 54.2 (Leu-Cα), 54.1 (L-Val-Cα), 52.7 (Pip-Cδ), 50.1 (Pip-Cα), 41.0 (Leu-Cβ), 39.6 (Trp-C3), 32.3 (D-Val-Cβ), 30.9 (L-Val-Cβ), 28.9 (Pip-Cβ), 25.5 (Leu-Cγ), 23.1 (Leu-Cδ), 21.2 (Leu-Cδ), 19.8 (L-Val-Cγ), 19.6 (D-Val-Cγ), 18.7 (L-Val-Cγ), 17.4 (2C, Thr-Cγ, D-Val-Cγ).

FTIR (thin film) cm$^{-1}$: 3307 (br-s), 2967 (m), 2929 (m), 2873 (w), 1647 (s), 1530 (m), 1372 (m), 1228 (w), 1102 (m).

HRMS (ESI) (m/z): calc'd for C$_{72}$H$_{106}$N$_{16}$NaO$_{18}$ [M+Na]$^+$: 1505.7763, found: 1505.7756.

[α]$_D^{24}$: −52 (c=0.053, MeOH).

TLC (9% methanol, 1% ammonium hydroxide in chloroform), Rf: 0.20 (UV, CAM).

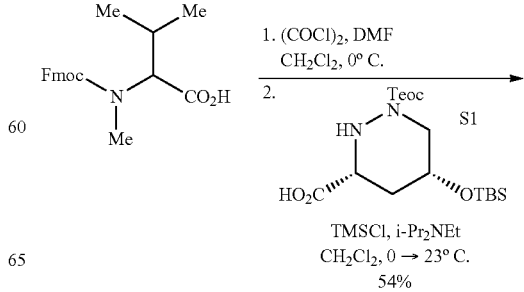

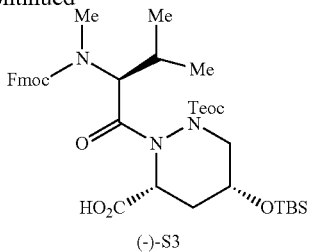

(-)-S3

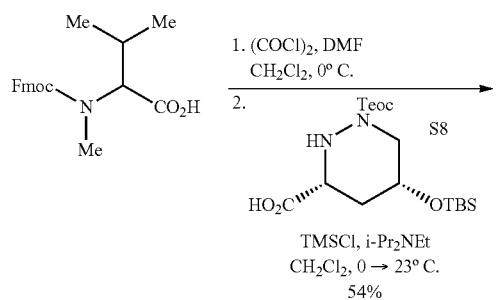

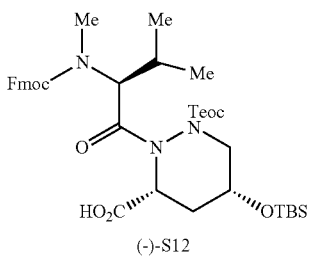

(-)-S12

N-Methyl Dipeptide (−)-S12:

Oxalyl chloride (77.3 μL, 0.900 mmol, 2.40 equiv) was added dropwise via syringe over 2 minutes to a solution of Fmoc-L-Val-OH (153 mg, 0.450 mmol, 1.20 equiv) and N,N-dimethylformamide (3.5 μL, 0.045 mmol, 0.12 equiv) in dichloromethane (1 mL) at 0° C. After 1 h, the yellow solution was concentrated under reduced pressure (~1 torr) at 0° C. The resulting residue was dissolved in dichloromethane (1.5 mL) and transferred by cannula over 2 min to a solution of piperazic acid S8[13] (152 mg, 0.375 mmol, 1 equiv), N,N-diisopropylethylamine (137 μL, 0.778 mmol, 2.10 equiv.), and chlorotrimethylsilane (95.3 μL, 0.750 mmol, 2.00 equiv) in dichloromethane (1 mL) at 0° C. The transfer was quantitated with additional dichloromethane (0.5 mL). After 30 min, the cold bath was removed and the yellow solution was allowed to stir at 23° C. After 10 h, the reaction mixture was diluted with an aqueous hydrogen chloride solution (1 M, 15 mL) and stirred vigorously for 5 min. The mixture was extracted with ethyl acetate (3×15 mL) and the combined organic extracts were washed with an aqueous saturated sodium chloride solution (30 mL), were dried over anhydrous sodium sulfate, were filtered, and were concentrated under reduced pressure. The resulting residue was purified by flash column chromatography on silica gel (eluent: 1% acetic acid, 20%→40% ethyl acetate in hexanes)[17] to afford N-methyl dipeptide (−)-S12 (148 mg, 54%) as a white foam. The reported $^1$H NMR integrals are an approximation due to the presence of multiple conformers and significant atropisomerism. The $^{13}$C data are listed as observed with more than the expected number of $^{13}$C resonances due to atropisomerism.

$^1$H NMR (600 MHz, CD$_3$CN, 25° C.): δ 11.48 (br-s, 1H), 7.85-7.80 (m, 2H), 7.68 (d, J=7.4 Hz, 0.3H), 7.66-7.59 (m, 1.7H), 7.44-7.30 (m, 4H), 5.22 (dd, J=7.8, 2.0 Hz, 0.7H), 5.03 (dd, J=7.8, 2.2 Hz, 0.3H), 4.88 (d, J=11.0 Hz, 1H), 4.51 (dd, J=10.3, 6.6 Hz, 0.7H), 4.38 (dd, J=10.8, 4.2 Hz, 0.3H), 4.31-4.27 (m, 1.3H), 4.24 (dd, J=10.3, 6.8 Hz, 0.7H), 4.17 (ddd, J=12.3, 10.5, 6.1 Hz, 0.7H), 4.12-4.03 (m, 2.7H), 3.88 (s, 0.3H), 3.80 (d, J=10.7 Hz, 0.3H), 3.40 (app-dt, J=14.2, 2.6 Hz, 0.3H), 3.18 (d, J=12.6 Hz, 0.7H), 2.76 (s, 2.2H), 2.50 (s, 0.8H), 2.46-2.42 (m, 0.3H), 2.36 (app-ddt, J=14.2, 4.1, 2.1 Hz, 0.7H), 2.27-2.09 (m, 2.5H), 2.08-2.01 (m, 0.5H), 1.98 (ddd, J=14.1, 7.8, 2.2 Hz, 0.7H), 1.85 (ddd, J=14.0, 7.7, 2.1 Hz, 0.3H), 1.10-0.95 (m, 2H), 0.85-0.81 (m, 9H), 0.75 (d, J=6.7 Hz, 2H), 0.56 (d, J=6.5 Hz, 0.3H), 0.48 (d, J=6.4 Hz, 0.7H), 0.19 (d, J=7.0 Hz, 1H), 0.05-0.03 (m, 9H), −0.09 (s, 6H).

$^{13}$C NMR (150.9 MHz, CD$_3$CN, 25° C.): δ 173.8, 173.0, 172.0, 162.2, 161.9, 157.4, 156.1, 145.3, 145.1, 145.0, 142.2 (2C), 128.7, 128.6, 128.3, 128.1, 126.2, 126.1, 125.9, 125.7, 121.1, 121.0 (2C), 120.9, 68.5, 68.2, 67.3, 63.4, 63.3, 61.8, 58.8, 53.6, 53.2, 52.0, 51.0, 48.1, 33.0, 32.9, 30.0, 29.1, 28.2, 27.4, 26.1, 26.0, 20.1, 19.6, 18.7, 18.6, 18.4, 18.1, 17.8, 17.0, −1.6, −4.9, −5.1 (2C), −5.2.

FTIR (thin film) cm$^{-1}$: 3067 (w), 2955 (m), 2857 (w), 1753 (s), 1688 (s), 1409 (m), 1250 (m), 1117 (m), 837 (m), 757 (m), 740 (m).

HRMS (ESI) (m/z): calc'd for C$_{38}$H$_{57}$N$_3$NaO$_8$Si$_2$ [M+Na]$^+$: 762.3576, found: 762.3574.

[α]$_D^{23}$: −29 (c=0.42, CHCl$_3$).

TLC (1% acetic acid, 50% ethyl acetate in hexanes), Rf: 0.49 (UV, CAM).

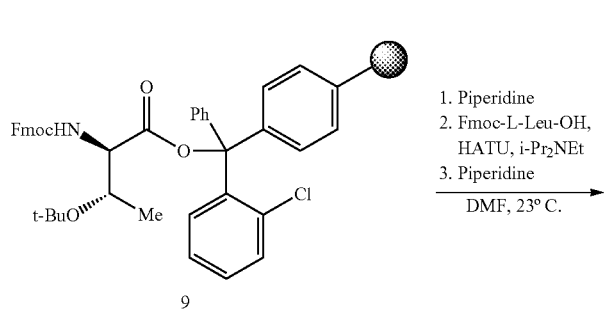
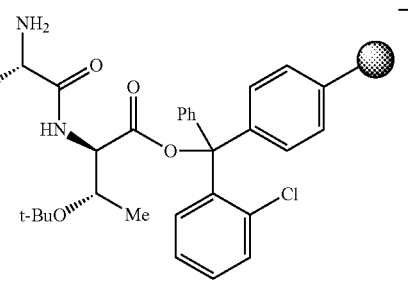
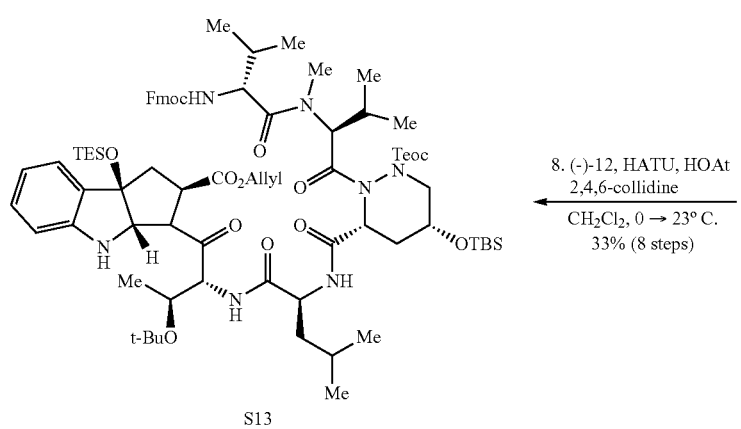
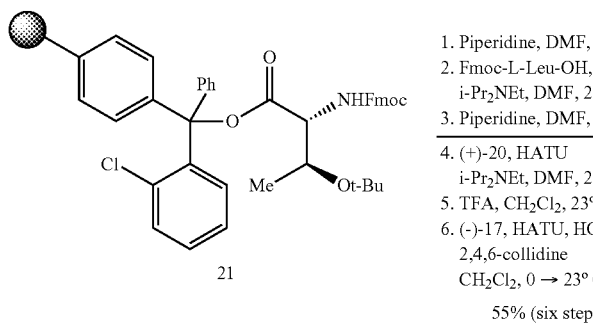
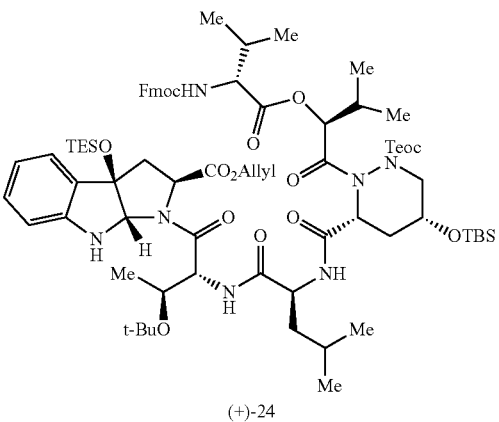

Depsihexapeptide (+)-24:

A sample of Fmoc-D-Thr(t-Bu)-2-chlorotrityl polystyrene resin 21 (499 mg, 0.802 mmol/g, 0.400 mmol, 1 equiv.) in a fritted syringe connected to a vacuum manifold was treated twice with piperidine (20% in N,N-dimethylformamide, 2×10 mL) at 23° C. for 5 minutes. The liquid phase was drained and the resin was washed with N,N-dimethylformamide (3×10 mL).

A solution of Fmoc-L-Leu-OH (565.5 mg, 1.60 mmol, 4 equiv.), 1-[bis(dimethylamino)methylene]-1H-1,2,3-triazolo[4,5-b]pyridinium 3-oxide hexafluorophosphate (HATU, 578 mg, 1.52 mmol, 3.80 equiv.), and N,N-diisopropylethylamine (800 μL, 4.59 mmol, 11.5 equiv.) in N,N-dimethylformamide (4.0 mL) was added to the resulting resin at 23° C. After 1 h, the liquid phase was drained and the resin was washed with N,N-dimethylformamide (3×10 mL) and was treated twice with piperidine (20% in N,N-dimethylformamide, 2×10 mL) at 23° C. for 5 minutes. The liquid phase was drained and the resin was washed with N,N-dimethylformamide (3×10 mL).

A solution of depsitripeptide (+)-20 (427 mg, 0.520 mmol, 1.30 equiv.), HATU (198 mg, 0.520 mmol, 1.30 equiv.), and N,N-diisopropylethylamine (154 μL, 0.884 mmol, 2.21 equiv.) in N,N-dimethylformamide (2.3 mL) was added to the resulting resin at 23° C. After 20 h, the liquid phase was drained and the resin was washed with N,N-dimethylformamide (3×10 mL) and dichloromethane (3×10 mL).

The resulting resin was treated twice with trifluoroacetic acid (1% in dichloromethane, 2×15 mL) at 23° C. for 2 minutes. The liquid phases were separated into a vessel containing pyridine (1.0 mL). The resin was washed with dichloromethane (3×5 mL) and the liquid phases were separated into the same vessel. The combined liquid phases were diluted with an aqueous hydrogen chloride solution (1 M, 100 mL) and extracted with dichloromethane (3×50 mL). The combined organic extracts were washed with a saturated aqueous sodium chloride solution (100 mL), were dried over anhydrous sodium sulfate, were filtered, and were concentrated under reduced pressure to provide the crude pentadepsipeptide acid as an off-white foam, which was used in the next step without further purification.

A sample of HATU (304 mg, 0.800 mmol, 2.00 equiv.) was added to a solution of the crude pentadepsipeptide acid, cyclotryptophan triethylsilyl ether (−)-17 (180 mg, 0.480 mmol, 1.20 equiv), 1-hydroxy-7-azabenzotriazole (HOAt, 381 mg, 2.80 mmol, 7.00 equiv.), and 2,4,6-collidine (423 μL, 3.20 mmol, 8.00 equiv.) in dichloromethane (8 mL) at 0° C. After 1 h, the cold bath was removed and the cloudy solution was allowed to stir at 23° C. After 5 h, the reaction mixture was diluted with ethyl acetate-hexanes (4:1, 100 mL) and washed with an aqueous potassium hydrogen sulfate solution (1 M, 60 mL), a saturated aqueous sodium hydrogen carbonate solution (60 mL), and a saturated aqueous sodium chloride solution (60 mL). The organic layer was dried over anhydrous sodium sulfate, was filtered, and was concentrated under reduced pressure. The resulting residue was purified by flash column chromatography on silica gel (eluent: 30%→40% ethyl acetate in hexanes) to afford depsihexapeptide (−)-S10 (321 mg, 55.2%) as a white foam.

$^1$H NMR (500 MHz, DMSO-$d_6$, 100° C.): δ 7.85 (d, J=7.6 Hz, 2H), 7.79 (br-s, 1.5H), 7.69 (d, J=7.5 Hz, 2H), 7.40 (app-t, J=7.5 Hz, 2H), 7.31 (app-t, J=7.5 Hz, 2H), 7.24 (br-s, 0.5H), 7.14 (br-s, 2.5H), 6.76 (br-s, 1H), 6.67 (br-s, 2H), 6.10 (br-s, 0.5H), 5.92 (br-s, 1.5H), 5.49 (br-s, 1H), 5.33 (br-s, 1H), 5.21 (br-d, J=6.1 Hz, 1H), 5.08 (br-s, 1H), 4.89 (br-s, 0.5H), 4.77 (br-s, 1H), 4.62 (br-s, 2.5H), 4.39-4.19 (m, 6H), 4.03 (br-s, 3.5H), 3.73 (br-d, J=12.3 Hz, 1H), 3.51 (br-s, 1H), 2.64 (br-s, 1H), 2.38 (br-s, 1H), 2.24-2.02 (m, 3H), 1.93-1.35 (m, 4H), 1.17-1.08 (m, 12H), 1.08-1.01 (m, 3H), 0.99-0.90 (m, 12H), 0.89-0.82 (m, 14H), 0.80 (t, J=7.9 Hz, 9H), 0.49-0.33 (m, 6H), 0.09-0.00 (m, 15H).

$^{13}$C NMR (125.8 MHz, DMSO-$d_6$, 25° C.): δ 172.4, 172.3, 172.0, 171.7, 171.6, 171.5, 171.1, 171.0, 170.7, 170.5, 170.3, 170.1, 169.3, 168.6, 156.8, 156.0, 154.6, 149.7, 148.8, 144.2, 141.2, 132.9, 132.6, 132.5, 130.9, 130.7, 129.9, 129.6, 129.5, 129.4, 128.1, 127.7, 127.5, 125.8, 124.5, 124.1, 122.7, 121.8, 120.6, 118.2, 118.1, 117.9, 117.8, 117.7, 110.4, 110.2, 88.5, 88.4, 85.9, 83.3, 82.6, 75.4, 75.0, 74.8, 74.6, 74.1, 73.8, 73.7, 69.1, 68.4, 67.3, 66.9, 66.7, 66.4, 65.6, 65.1, 64.6, 63.5, 60.5, 59.5, 59.1, 59.0, 57.9, 55.4, 55.1, 54.9, 52.1, 51.6, 51.0, 50.8, 47.1, 45.9, 43.4, 41.7, 30.5, 30.2, 29.1, 29.0, 28.5, 28.4, 26.0, 25.9, 24.7, 23.9, 23.7, 23.6, 21.7, 21.4, 20.4, 20.2, 20.1, 19.8, 19.6, 19.5, 19.4, 18.7, 18.4, 18.0 (2C), 17.7, 17.5, 17.3, 17.1, 7.1, 6.9, 5.8, 5.6, −1.1, −1.3, −4.6, −4.7, (2C), −4.8, −4.9 (2C).

FTIR (thin film) cm$^{-1}$: 3367 (br-m), 3306 (br-m), 2956 (m), 2877 (w), 1708 (s), 1661 (s), 1408 (w), 1249 (m), 1116 (m), 1017 (m), 837 (m), 741 (m).

HRMS (ESI) (m/z): calc'd for $C_{76}H_{118}N_7O_{15}Si_3$ [M+H]$^+$: 1452.7988, found: 1452.7987.

[α]$_D^{23}$: −43 (c=0.27, CHCl$_3$).

TLC (35% ethyl acetate in hexanes), Rf: 0.41 (UV, CAM).

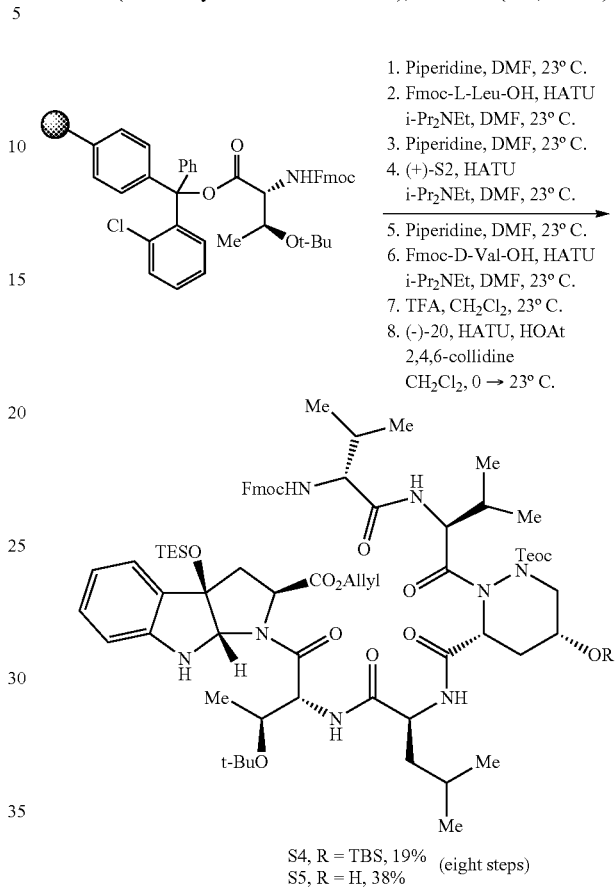

S4, R = TBS, 19%
S5, R = H, 38%  (eight steps)

Hexapeptide Tert-Butyldimethylsilyl Ether S4 and Hexapeptide S5:

A sample of Fmoc-D-Thr(t-Bu)-2-chlorotrityl polystyrene resin 21 (263 mg, 0.712 mmol/g, 0.187 mmol, 1 equiv.) in a fritted syringe connected to a vacuum manifold was treated twice with piperidine (20% in N,N-dimethylformamide, 2×10 mL) at 23° C. for 5 minutes. The liquid phase was drained and the resin was washed with N,N-dimethylformamide (3×10 mL).

A solution of Fmoc-L-Leu-OH (265 mg, 0.750 mmol, 4 equiv.), HATU (271 mg, 0.712 mmol, 3.80 equiv.), and N,N-diisopropylethylamine (375 μL, 2.15 mmol, 11.5 equiv.) in N,N-dimethylformamide (1.9 mL) was added to the resulting resin at 23° C. After 1 h, the liquid phase was drained and the resin was washed with N,N-dimethylformamide (3×10 mL) and was treated twice with piperidine (20% in N,N-dimethylformamide, 2×10 mL) at 23° C. for 5 minutes. The liquid phase was drained and the resin was washed with N,N-dimethylformamide (3×10 mL).

A solution of dipeptide (+)-S2 (177 mg, 0.244 mmol, 1.30 equiv.), HATU (92.8 mg, 0.244 mmol, 1.30 equiv.), and N,N-diisopropylethylamine (72.1 μL, 0.414 mmol, 2.21 equiv.) in N,N-dimethylformamide (1.0 mL) was added to the resulting resin at 23° C. After 22 h, the liquid phase was drained and the resin was washed with N,N-dimethylformamide (3×10 mL) and was treated twice with piperidine (20% in N,N-dimethylformamide, 2×10 mL) at 23° C. for 5 minutes. The liquid phase was drained and the resin was washed with N,N-dimethylformamide (3×10 mL).

A solution of Fmoc-D-Val-OH (255 mg, 0.750 mmol, 4 equiv.), (HATU, 271 mg, 0.712 mmol, 3.80 equiv.), and N,N-diisopropylethylamine (375 μL, 2.15 mmol, 11.5 equiv.) in N,N-dimethylformamide (1.9 mL) was added to the resulting resin at 23° C. After 4 h, the liquid phase was drained and the resin was washed with N,N-dimethylformamide (3×10 mL) and dichloromethane (3×10 mL).

The resulting resin was treated twice with trifluoroacetic acid (1% in dichloromethane, 2×10 mL) at 23° C. for 2 minutes. The liquid phases were separated into a vessel containing pyridine (0.75 mL). The resin was washed with dichloromethane (3×5 mL) and the liquid phases were separated into the same vessel. The combined liquid phases were diluted with an aqueous hydrogen chloride solution (1 M, 75 mL) and extracted with dichloromethane (3×50 mL). The combined organic extracts were washed with a saturated aqueous sodium chloride solution (100 mL), were dried over anhydrous sodium sulfate, were filtered, and were concentrated under reduced pressure to provide the crude pentapeptide acid as an off-white foam, which was used in the next step without further purification.

A sample of HATU (143 mg, 0.375 mmol, 2.00 equiv.) was added to a solution of the crude pentapeptide acid, cyclotryptophan triethylsilyl ether (−)-17 (84.3 mg, 0.225 mmol, 1.20 equiv), 1-hydroxy-7-azabenzotriazole (HOAt, 179 mg, 1.31 mmol, 7.00 equiv.), and 2,4,6-collidine (198 μL, 1.50 mmol, 8.00 equiv.) in dichloromethane (4 mL) at 0° C. After 1 h, the cold bath was removed and the cloudy solution was allowed to stir at 23° C. After 4 h, the reaction mixture was diluted with ethyl acetate-hexanes (4:1, 100 mL) and washed with an aqueous potassium hydrogen sulfate solution (1 M, 60 mL), a saturated aqueous sodium hydrogen carbonate solution (60 mL), and a saturated aqueous sodium chloride solution (60 mL). The organic layer was dried over anhydrous sodium sulfate, was filtered, and was concentrated under reduced pressure. The resulting residue was purified by flash column chromatography on silica gel (eluent: 25%→80% ethyl acetate in hexanes), including a second chromatographic purification of mixed fractions of S5 and cyclotryptophan triethylsilyl ether (−)-17 on silica gel (eluent: 45% ethyl acetate in hexanes), to afford hexapeptide tert-butyldimethylsilyl ether S4 (50.4 mg, 18.5%) and hexapeptide S5 (94.4 mg, 37.6%) as white foams.

Hexapeptide Tert-Butyldimethylsilyl Ether S4

$^1$H NMR (600 MHz, CD$_3$CN, 25° C.): δ 8.49 (d, J=7.1 Hz, 0.2H), 8.45 (br-s, 0.2H), 8.36 (br-s, 0.1H), 8.26 (d, J=7.5 Hz, 0.1H), 7.84-7.81 (m, 2H), 7.70-7.64 (m, 2H), 7.41 (app-td, J=7.5, 3.2 Hz, 2H), 7.36-7.31 (m, 2H), 7.26 (d, J=7.4 Hz, 0.4H), 7.20-7.14 (m, 1H), 7.08 (app-t, J=7.6 Hz, 0.6H), 7.00 (br-s, 0.3H), 6.91 (d, J=9.3 Hz, 0.4H), 6.83 (app-t, J=7.4 Hz, 0.5H), 6.79-6.65 (m, 2H), 6.58 (d, J=8.1 Hz, 0.2H), 6.03 (d, J=4.2 Hz, 0.2H), 5.97 (ddd, J=17.2, 10.7, 5.4 Hz, 0.8H), 5.93-5.82 (m, 1.2H), 5.59 (br-s, 0.2H), 5.55 (d, J=4.0 Hz, 0.2H), 5.48 (d, J=3.7 Hz, 0.7H), 5.39 (dd, J=17.2, 1.6 Hz, 0.5H), 5.35-5.28 (m, 0.5H), 5.26 (dd, J=10.5, 1.4 Hz, 0.6H), 5.19 (d, J=11.2 Hz, 0.6H), 4.90 (d, J=8.3 Hz, 0.5H), 4.84 (br-s, 0.2H), 4.76-4.59 (m, 2.5H), 4.57-3.88 (m, 12.5H), 3.74-3.53 (m, 1H), 2.69 (d, J=13.1 Hz, 0.5H), 2.55 (dd, J=13.3, 8.6 Hz, 0.3H), 2.43 (dd, J=13.4, 5.4 Hz, 0.4H), 2.33 (dd, J=13.3, 8.9 Hz, 0.4H), 2.27 (br-s, 0.2H), 2.15 (br-s, 0.5H), 2.09 (br-s, 1.5H), 1.98 (app-dt, J=13.1, 6.6 Hz, 1.5H), 1.79 (br-s, 0.3H), 1.71-1.40 (m, 3.2H), 1.20-1.13 (m, 6H), 1.13-1.07 (m, 6H), 0.96-0.76 (m, 40H), 0.46-0.33 (m, 6H), 0.08-0.00 (m, 12.5H), −0.05 (br-s, 1H), −0.14 (br-s, 1.5H).

$^{13}$C NMR (150.9 MHz, CD$_3$CN, 25° C.): δ 174.4, 172.9, 172.4, 172.3, 172.2, 171.8, 171.6 (2C), 171.2 (2C), 171.0, 170.8, 159.6, 157.1, 149.5, 148.9, 145.2, 145.0, 142.1, 133.5, 133.2, 132.1, 131.2, 130.6, 128.7, 128.2, 128.1, 126.2, 124.7, 124.0, 121.0, 120.7, 119.1, 118.9, 118.7, 118.5, 112.4, 110.9, 91.2, 89.0, 87.0, 86.7, 84.7, 84.2, 75.6, 74.8, 69.6, 69.3, 68.1, 67.7, 67.4, 67.4, 66.8, 66.1, 65.7, 65.4, 64.5, 61.2, 61.1, 60.8, 60.7, 60.5, 58.1, 57.5, 57.2, 57.1, 56.9, 56.7, 56.3, 55.3, 55.0, 54.6, 53.6, 53.1, 52.3, 48.1, 47.2, 46.7, 43.1, 41.6, 40.5, 33.0, 32.8, 32.3, 32.1, 31.9, 31.7, 29.3, 29.0, 28.9, 28.6, 28.5, 25.5 (2C), 23.5, 22.2, 22.0, 21.9, 21.5, 20.4, 20.3, 20.1, 19.9, 18.7 (2C), 18.2, 18.1, 17.8, 17.7, 17.6, 7.2, 7.1, 6.6, 6.5, −1.2, −1.3, −1.5, −1.6, −4.7 (2C), −4.8.

FTIR (thin film) cm$^{-1}$: 3312 (br-s), 2956 (m), 2876 (w), 1710 (s), 1663 (s), 1413 (m), 1249 (m), 1173 (m), 1123 (m), 837 (m), 740 (m).

HRMS (ESI) (m/z): calc'd for C$_{76}$H$_{119}$N$_8$O$_{14}$Si$_3$ [M+H]$^+$: 1451.8148, found: 1451.8152.

TLC (45% ethyl acetate in hexanes), Rf: 0.53 (UV, CAM).

Hexapeptide S5

$^1$H NMR (600 MHz, CD$_3$CN, 25° C.): δ 8.53 (d, J=6.6 Hz, 0.1H), 8.40 (d, J=7.2 Hz, 0.2H), 8.16 (d, J=6.8 Hz, 0.1H), 8.11 (d, J=7.1 Hz, 0.1H), 7.87-7.81 (m, 2H), 7.70-7.65 (m, 2H), 7.46-7.38 (m, 2H), 7.37-7.30 (m, 2H), 7.29-7.13 (m, 2.5H), 7.13-7.01 (m, 0.5H), 7.01-6.90 (m, 0.5H), 6.87-6.56 (m, 2.5H), 6.08 (d, J=3.3 Hz, 0.2H), 6.04-5.87 (m, 2H), 5.83 (d, J=4.5 Hz, 0.2H), 5.77 (d, J=4.7 Hz, 0.1H), 5.59-5.44 (m, 1H), 5.39 (d, J=17.3 Hz, 0.5H), 5.35-5.29 (m, 0.4H), 5.26 (d, J=10.5 Hz, 0.6H), 5.20 (dd, J=10.6, 1.5 Hz, 0.5H), 5.12 (d, J=6.9 Hz, 0.2H), 5.08 (d, J=6.3 Hz, 0.2H), 4.92-4.76 (m, 1.6H), 4.73-4.66 (m, 0.8H), 4.68-4.57 (m, 1.4H), 4.55-4.39 (m, 1.6H), 4.37-3.87 (m, 10H), 3.83 (s, 0.4H), 3.77 (s, 0.5H), 3.56 (s, 0.1H), 3.40 (d, J=13.2 Hz, 0.1H), 3.25 (d, J=14.1 Hz, 0.2H), 3.14-3.04 (m, 0.3H), 3.02 (dd, J=12.9, 7.5 Hz, 0.1H), 2.96 (d, J=14.0 Hz, 0.1H), 2.85 (d, J=17.5 Hz, 0.2H), 2.81-2.74 (m, 0.2H), 2.70 (dd, J=13.5, 10.3 Hz, 0.7H), 2.62-2.23 (m, 2.4H), 2.13 (s, 0.6H), 2.09-1.96 (m, 1.4H), 1.92-1.79 (m, 1H), 1.67-1.58 (m, 1.2H), 1.58-1.42 (m, 1.1H), 1.40-1.32 (m, 0.5H), 1.20 (s, 1H), 1.17 (s, 4.5H), 1.14 (d, J=5.7 Hz, 2.6H), 1.11 (d, J=9.4 Hz, 4H), 1.03-0.68 (m, 30H), 0.50-0.34 (m, 6H), 0.08-0.00 (m, 7.5H), −0.18 (s, 1.5H).

$^{13}$C NMR (150.9 MHz, CD$_3$CN, 25° C.): δ 174.4, 172.8, 172.5, 172.3, 172.2, 172.1, 172.0, 171.9, 171.7, 171.5, 171.2, 170.7, 157.2, 149.5, 148.4, 145.2, 145.0, 142.1, 133.4, 133.1, 131.6, 131.2, 130.8, 130.7, 128.7, 128.1, 128.1, 126.2 (2C), 124.7, 124.2, 121.0 (2C), 120.8, 120.5, 118.8 (2c), 112.5, 112.1, 110.7, 110.5, 91.3, 91.1, 89.2, 89.0, 86.6, 86.4, 84.7, 84.4, 76.1, 75.2, 74.9, 69.9, 69.7, 68.8, 68.2, 67.4, 66.9 (2C), 66.5, 66.4, 66.2 (2C), 66.1, 62.9, 62.2, 61.9, 61.7, 61.4, 60.8, 60.7, 60.6 (2C), 57.2, 57.0, 56.7, 56.3, 56.1, 55.5, 54.3, 54.2, 53.8, 53.6, 53.4, 53.0, 52.9, 52.8, 52.7, 52.5, 51.2, 50.3, 48.0, 46.8, 46.4, 46.2, 43.0, 42.7, 40.8, 40.2, 39.6, 39.4, 33.6, 32.9, 32.5, 31.9, 31.8 (2C), 31.5, 28.9, 28.8, 28.5, 28.4, 28.3, 26.1, 25.7, 25.4, 25.4, 25.3, 23.6, 23.5, 23.3, 22.0, 21.7, 21.6, 21.3, 21.3, 20.7, 20.2, 20.1, 19.7, 19.5, 18.9, 18.4, 18.2, 18.1, 18.0, 17.9, 17.8, 17.6, 7.1 (3C), 7.0 (2C), 6.5, 6.4, 6.3, 6.1, −1.2, −1.3, −1.3, −1.4, −1.9.

FTIR (thin film) cm$^{-1}$: 3294 (br-s), 2957 (m), 2875 (w), 1707 (s), 1660 (s), 1531 (m), 1414 (m), 1241 (m), 1184 (m), 1119 (m), 838 (m), 741 (m).

HRMS (ESI) (m/z): calc'd for $C_{70}H_{105}N_8O_{14}Si_2$ [M+H]$^+$: 1337.7283, found: 1337.7278.

TLC (45% ethyl acetate in hexanes), Rf: 0.27 (UV, CAM).

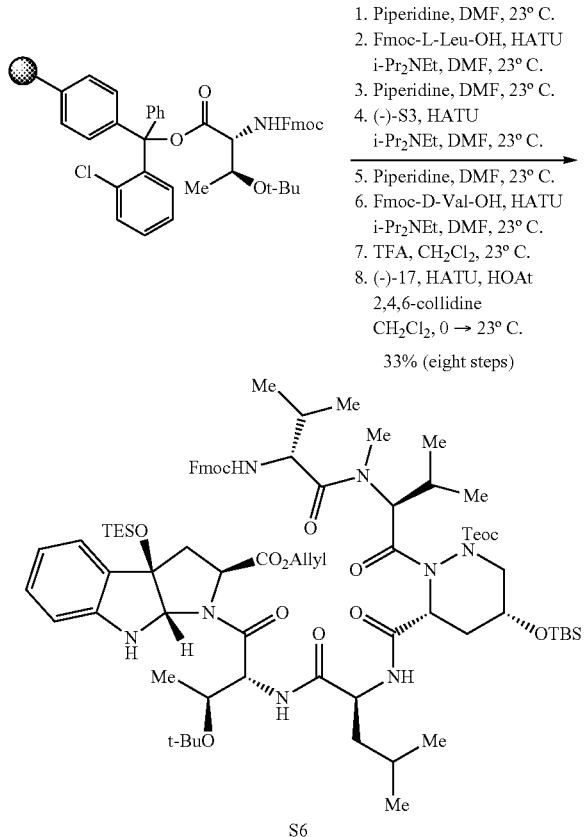

1. Piperidine, DMF, 23° C.
2. Fmoc-L-Leu-OH, HATU i-Pr$_2$NEt, DMF, 23° C.
3. Piperidine, DMF, 23° C.
4. (−)-S3, HATU i-Pr$_2$NEt, DMF, 23° C.
5. Piperidine, DMF, 23° C.
6. Fmoc-D-Val-OH, HATU i-Pr$_2$NEt, DMF, 23° C.
7. TFA, CH$_2$Cl$_2$, 23° C.
8. (−)-17, HATU, HOAt 2,4,6-collidine CH$_2$Cl$_2$, 0 → 23° C.

33% (eight steps)

S6

N-Methyl Hexapeptide S13

Prepared according to a scale-down of the procedure described previously for hexapeptides S10 and S1t from Fmoc-D-Thr(t-Bu)-2-chlorotrityl polystyrene resin 19 (176 mg, 0.712 mmol/g, 0.125 mmol, 1 equiv) and N-methyl dipeptide (−)-S12 (120 mg, 0.162 mmol, 1.30 equiv). The coupling of Fmoc-D-Val-OH (step 6) was repeated six times and the cleaved crude N-methyl pentapeptide acid was purified by flash column chromatography on silica gel (eluent: 1%→10% methanol in dichloromethane). N-Methyl hexapeptide S13 was obtained by flash column chromatography on silica gel (eluent: 35%→50% ethyl acetate in hexanes) as an off-white foam (60.6 mg, 33%). The reported $^1$H NMR integrals are an approximation due to the presence of multiple conformers and significant atropisomerism. The $^{13}$C data are listed as observed with more than the expected number of $^{13}$C resonances due to atropisomerism.

$^1$H NMR (600 MHz, CD$_3$CN, 25° C.): δ 8.58 (d, J=7.1 Hz, 0.2H), 8.45 (d, J=7.7 Hz, 0.3H), 8.36-8.31 (m, 0.1H), 8.24 (d, J=7.9 Hz, 0.1H), 7.85-7.78 (m, 2H), 7.73-7.52 (m, 2.1H), 7.44-7.38 (m, 2H), 7.36-7.29 (m, 2.2H), 7.26 (dd, J=7.5, 1.2 Hz, 0.4H), 7.18 (app-t, J=7.7 Hz, 0.5H), 7.14 (d, J=7.5 Hz, 0.5H), 7.09-7.03 (m, 0.5H), 6.98 (dd, J=12.8, 8.4 Hz, 0.2H), 6.86 (d, J=9.5 Hz, 0.3H), 6.83 (app-td, J=7.4, 0.9 Hz, 0.4H), 6.79 (d, J=8.9 Hz, 0.3H), 6.71 (d, J=7.9 Hz, 0.3H), 6.68 (app-t, J=7.4 Hz, 0.7H), 6.66-6.56 (m, 0.4H), 6.54 (d, J=7.9 Hz, 0.3H), 6.06-5.80 (m, 1.6H), 5.70 (dd, J=13.1, 8.9 Hz, 0.5H), 5.60 (d, J=3.9 Hz, 0.3H), 5.54 (d, J=4.1 Hz, 0.3H), 5.46 (d, J=4.1 Hz, 0.6H), 5.38 (app-t, J=16.5 Hz, 0.5H), 5.33-5.19 (m, 1.8H), 5.16 (dd, J=10.6, 1.5 Hz, 0.3H), 5.11 (br-s, 0.2H), 5.07 (br-s, 0.1H), 5.02 (d, J=10.7 Hz, 0.1H), 4.93 (d, J=8.9 Hz, 0.3H), 4.93-4.80 (m, 0.8H), 4.72 (app-td, J=8.9, 8.3, 2.5 Hz, 0.4H), 4.66 (dd, J=14.2, 4.8 Hz, 0.6H), 4.63-4.53 (m, 1.5H), 4.53-4.43 (m, 2H), 4.42 (app-dt, J=5.5, 1.5 Hz, 0.2H), 4.39 (app-dt, J=5.6, 1.5 Hz, 0.2H), 4.34 (app-qd, J=10.6, 5.7 Hz, 0.8H), 4.30-4.20 (m, 3.5H), 4.20-4.09 (m, 2.2H), 4.02 (app-t, J=6.0 Hz, 0.8H), 3.98-3.87 (m, 1.5H), 3.75-3.62 (m, 1.3H), 3.14 (s, 0.3H), 3.11-3.05 (m, 0.7H), 2.97 (s, 1H), 2.95 (s, 1H), 2.71 (dd, J=13.5, 5.8 Hz, 0.3H), 2.66 (d, J=13.3 Hz, 0.4H), 2.53 (dd, J=13.3, 8.7 Hz, 0.3H), 2.49 (br-s, 0.3H), 2.44-2.38 (m, 0.7H), 2.35 (br-s, 0.3H), 2.29-2.20 (m, 1.5H), 2.13 (app-t, J=3.1 Hz, 0.3H), 2.02 (br-s, 1.2H), 1.88-1.79 (m, 0.4H), 1.74-1.65 (m, 0.6H), 1.64-1.41 (m, 3.5H), 1.21-1.15 (m, 3H), 1.13 (s, 3H), 1.07 (s, 6H), 1.02-0.88 (m, 10H), 0.87 (s, 8H), 0.85-0.73 (m, 19H), 0.65 (s, 0.5H), 0.58 (s, 0.5H), 0.49-0.31 (m, 6H), 0.06 (s, 4H), 0.05-0.04 (m, 1H), 0.04-0.02 (m, 2H), 0.02 (s, 3H), 0.00 (s, 3H), −0.04 (s, 0.6H), −0.06 (s, 0.2H), −0.07 (s, 0.2H), −0.10 (s, 0.2H), −0.12 (s, 0.2H), −0.17 (s, 0.6H).

13C NMR (150.9 MHz, CD$_3$CN, 25° C.): δ 173.8, 173.8, 172.7, 172.4, 172.3, 172.2 (2C), 172.1, 171.8, 171.6, 171.3, 171.2 (2C), 171.1, 159.3 (2C), 157.0, 156.8, 149.4, 148.8, 145.3, 145.2, 144.9, 144.8, 142.1 (3C), 133.5, 133.4, 133.2, 133.1, 132.3, 131.3, 131.1, 130.6, 130.5 (2C), 128.7 (2C), 128.6, 128.2, 128.1, 126.3, 126.2 (2C), 126.1, 124.7, 123.9, 121.0 (4C), 120.9, 120.8, 119.1, 118.7, 112.5, 111.0, 91.3, 89.0, 86.8, 84.7, 75.5, 74.7, 69.3, 67.9, 67.4, 67.3, 67.2 (2C), 66.8, 66.1, 66.0 (2C), 65.9, 64.4, 64.3, 60.9, 60.7, 60.5, 59.1, 58.5, 57.5, 57.3, 57.1 (2C), 56.7, 56.6, 56.2, 55.5, 55.3, 53.6, 53.5, 52.9, 52.2, 52.0, 51.9, 48.1 (2C), 46.6, 43.1, 41.1, 40.7, 33.2 (2C), 31.6 (2C), 30.3, 29.1, 28.8, 28.5 (2C), 27.9, 27.8, 26.2, 26.1 (2C), 26.0, 25.6, 25.5, 23.5, 23.4, 21.6, 21.5, (2C), 20.5, 20.4 (2C), 19.7 (2C), 18.6, 18.4 (2C), 17.8 (2C), 16.8, 16.7, 7.2 (2C), 7.1 (2C), 7.0, 6.6, 6.5, −1.1, −1.2, −1.3, −1.4, −1.5, −1.6, −4.7 (2C), −4.8 (2C).

FTIR (thin film) cm$^{-1}$: 3293 (br-m), 2956 (m), 2876 (w), 1650 (s), 1410 (m), 1249 (m), 1173 (m), 1112 (m), 837 (m), 739 (m).

HRMS (ESI) (m/z): calc'd for $C_{77}H_{121}N_8O_{14}Si_3$ [M+H]$^+$: 1465.8305, found: 1465.8302.

TLC (40% ethyl acetate in hexanes), Rf: 0.50 (UV, CAM).

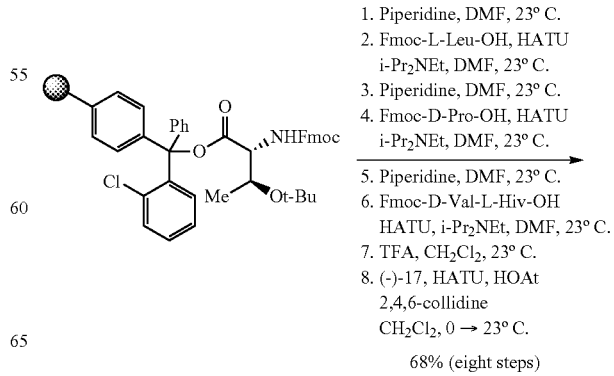

1. Piperidine, DMF, 23° C.
2. Fmoc-L-Leu-OH, HATU i-Pr$_2$NEt, DMF, 23° C.
3. Piperidine, DMF, 23° C.
4. Fmoc-D-Pro-OH, HATU i-Pr$_2$NEt, DMF, 23° C.
5. Piperidine, DMF, 23° C.
6. Fmoc-D-Val-L-Hiv-OH HATU, i-Pr$_2$NEt, DMF, 23° C.
7. TFA, CH$_2$Cl$_2$, 23° C.
8. (−)-17, HATU, HOAt 2,4,6-collidine CH$_2$Cl$_2$, 0 → 23° C.

68% (eight steps)

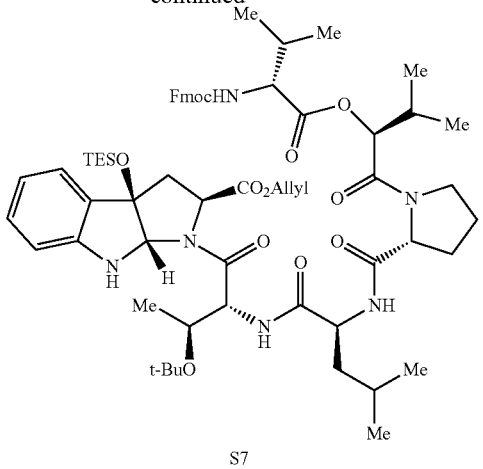

S7

Proline Hexadepsipeptide S7

Prepared according to a scale-up of the procedure described previously for hexapeptides S4/S5 from Fmoc-D-Thr(t-Bu)-2-chlorotrityl polystyrene resin 21 (351 mg, 0.712 mmol/g, 0.250 mmol, 1 equiv.), Fmoc-D-Pro-OH (337 mg, 1.00 mmol, 4.00 equiv.), and Fmoc-D-Val-L-Hiv-OH (264 mg, 0.600 mmol, 2.40 equiv.). Proline depsihexapeptide S7 was obtained by flash column chromatography on silica gel (eluent: 30%→80% ethyl acetate in hexanes) as an off-white foam (200 mg, 67.9%).

$^1$H NMR (600 MHz, CD$_3$CN, 25° C.): δ 7.86-7.78 (m, 2H), 7.72-7.63 (m, 2H), 7.44-7.37 (m, 2H), 7.35-7.30 (m, 2H), 7.25 (app-td, J=7.8, 1.2 Hz, 0.5H), 7.21-7.15 (m, 0.8H), 7.16-7.04 (m, 1.5H), 7.02 (d, J=7.6 Hz, 0.2H), 6.92 (d, J=8.1 Hz, 0.4H), 6.86-6.71 (m, 1.4H), 6.68 (app-td, J=7.4, 1.0 Hz, 0.4H), 6.60 (d, J=7.9 Hz, 0.3H), 6.52 (app-t, J=8.3 Hz, 0.5H), 6.33 (d, J=9.2 Hz, 0.1H), 6.21 (d, J=8.9 Hz, 0.3H), 6.08 (d, J=8.9 Hz, 0.2H), 6.06 (d, J=4.3 Hz, 0.2H), 6.02-5.85 (m, 1.2H), 5.64 (d, J=3.9 Hz, 0.2H), 5.60 (d, J=4.2 Hz, 0.2H), 5.55 (d, J=1.1 Hz, 0.2H), 5.52-5.44 (m, 0.5H), 5.38 (d, J=15.7 Hz, 0.2H), 5.34 (dd, J=17.3, 1.7 Hz, 0.3H), 5.30 (app-dq, J=17.3, 1.7 Hz, 0.4H), 5.26-5.21 (m, 0.5H), 5.21-5.17 (m, 0.5H), 5.03 (d, J=8.9 Hz, 0.2H), 4.91 (dd, J=9.3, 1.7 Hz, 0.3H), 4.88-4.83 (m, 0.5H), 4.80 (dd, J=10.3, 6.5 Hz, 0.5H), 4.74-4.11 (m, 9.5H), 4.11-4.01 (m, 0.5H), 3.99-3.91 (m, 0.4H), 3.91-3.78 (m, 1H), 3.70-3.63 (m, 0.1H), 3.59-3.34 (m, 1H), 2.73-2.64 (m, 0.8H), 2.56 (dd, J=13.4, 8.7 Hz, 0.2H), 2.48-2.39 (m, 0.8H), 2.38 (s, 0.6H), 2.26-2.07 (m, 4.5H), 2.04-1.96 (m, 1.1H), 1.90 (d, J=35.2 Hz, 1.5H), 1.77 (br-s, 0.5H), 1.66-1.50 (m, 2H), 1.50-1.35 (m, 1H), 1.26 (br-s, 1H), 1.20 (s, 2H), 1.19-0.93 (m, 20H), 0.88-0.74 (m, 15H), 0.51-0.30 (m, 6H).

$^{13}$C NMR (150.9 MHz, CD$_3$CN, 25° C.): δ 174.2, 173.8 (2C), 173.7, 173.4 (2C), 172.8, 172.4, 172.3, 172.2, 171.8, 171.1, 170.8, 169.7, 169.6, 169.5, 169.4, 158.2, 157.4 (2C), 157.3 (2C), 150.7, 149.5, 149.3, 148.8, 148.5, 145.2, 145.1, 145.0 (3C), 144.9, 142.1, 136.4, 133.5, 133.4 (2C), 133.2 (2C), 131.5, 131.1, 130.7, 130.5, 129.7, 128.7 (2C), 128.2, 128.1 (3C), 128.1, 126.6, 126.3 (2C), 125.1, 124.7, 124.3, 124.1, 121.8, 121.0, 120.9, 120.8 (2C), 119.6, 119.1, 118.9, 118.8, 118.7, 118.5, 112.4, 110.7, 91.2, 90.1, 89.3, 89.1, 86.8, 86.6, 86.5, 84.8, 83.2, 79.4, 78.9 (2C), 78.6, 77.7, 75.5, 75.2, 74.8, 74.7, 71.3, 69.5, 68.6, 68.1, 67.7 (2C), 67.6 (2C), 67.5, 67.1, 66.8, 66.2, 66.1, 61.7 (2C), 61.5, 60.9, 60.8, 60.8, 60.7 (2C), 60.6 (2C), 60.3, 57.2, 57.1, 56.6, 56.1, 53.1 (2C), 52.8 (2C), 48.0 (2C), 47.9 (2C), 47.8 (2C), 46.7, 46.5, 43.6, 43.0, 41.5, 41.2, 41.1, 32.3, 32.1, 31.7, 30.4, 30.3, 30.1, 30.0, 29.6, 29.2, 29.1, 29.0, 28.9, 28.7, 28.5, 25.4 (2C), 25.3, 25.2, 25.0 (2C), 24.9, 24.3, 23.4 (2C), 23.3, 23.2, 22.1, 22.1, 22.0, 21.8 (2C), 21.5, 21.2, 20.8, 20.5, 19.9, 19.7 (2C), 19.6, 19.5, 18.8, 18.7, 18.3, 18.1, 18.0 (2C), 17.9 (3C), 7.1 (2C), 7.0, 6.5 (2C), 6.4, 6.3.

FTIR (thin film) cm$^{-1}$: 3313 (br-m), 2958 (m), 2924 (m), 2875 (w), 1721 (s), 1654 (s), 1518 (m), 1468 (m), 1245 (m), 1188 (m), 1110 (m), 1005 (w), 740 (s).

HRMS (ESI) (m/z): calc'd for $C_{64}H_{91}N_6O_{12}Si[M+H]^+$: 1163.6459, found: 1163.6462.

TLC (60% ethyl acetate in hexanes), Rf: 0.36 (UV, CAM).

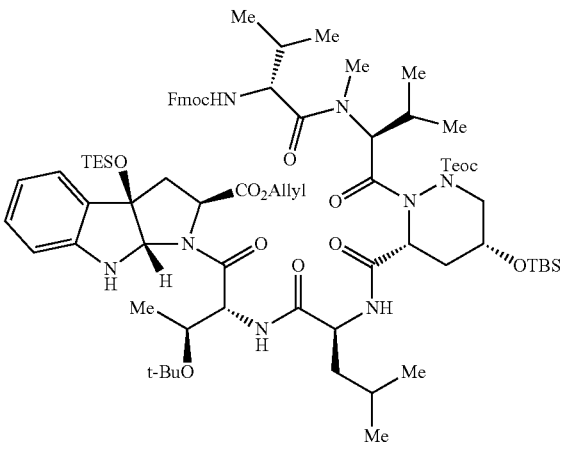

1. Pd(PPh$_3$)$_4$, N-methylaniline
2. i-Pr$_2$NH, MeCN, 23° C.
3. HATU, HOAt, i-Pr$_2$NEt CH$_2$Cl$_2$, 23° C.
4. TFA, H$_2$O, anisole CH$_2$Cl$_2$, 23° C; Et$_3$N, MeOH, 23° C.

26% (4-steps)

S13

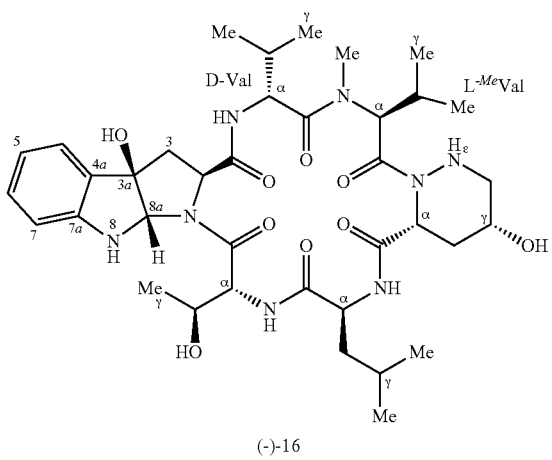

(−)-16

N-Methyl Cyclic Hexapeptide (+)-16:

Prepared according to the procedure described previously for himastatin monomer (+)-2 from N-methyl cyclic hexapeptide S13 (57.0 mg, 38.9 μmol, 1 equiv). N-Methyl cyclic hexapeptide (+)-16 was obtained by flash column chromatography on silica gel (eluent: 2.7% methanol, 0.3% ammonium hydroxide→4.5% methanol, 0.5% ammonium hydroxide in chloroform) as an off-white solid (7.7 mg, 26%). Structural assignments were made using additional information from gCOSY, gHSQC, and gHMBC experiments.

$^1$H NMR (600 MHz, CDCl$_3$, 25° C.): δ 7.99 (d, J=9.1 Hz, 1H, D-Val-NH), 7.34 (dd, J=7.5, 1.3 Hz, 1H, Trp-C4H), 7.25 (d, J=5.1 Hz, 1H, Leu-NH), 7.19 (ddd, J=8.0, 7.4, 1.3 Hz, 1H, Trp-C6H), 6.89 (app-td, J=7.4, 0.9 Hz, 1H, Trp-C5H), 6.75 (dd, J=8.0, 0.8 Hz, 1H, Trp-C7H), 6.61 (d, J=10.2 Hz, 1H, Thr-NH), 5.89 (d, J=6.3 Hz, 1H, Trp-N8H), 5.82 (s, 1H, Trp-C3aOH), 5.77 (d, J=11.2 Hz, 1H, L-$^{Me}$Val-CαH), 5.75 (dd, J=12.7, 2.1 Hz, 1H, Pip-NεH), 5.30 (d, J=8.1 Hz, 1H, Trp-C2H), 5.20 (dd, J=13.1, 1.5 Hz, 1H, Pip-CαH), 5.13 (d, J=6.2 Hz, 1H, Trp-C8aH), 4.96 (dd, J=9.2, 3.2 Hz, 1H, D-Val-CαH), 4.94 (d, J=5.2 Hz, 1H, Pip-CγOH), 4.85 (d, J=10.2 Hz, 1H, Thr-CαH), 4.55 (qd, J=6.6, 1.9 Hz, 1H, Thr-CβH), 4.27 (ddd, J=9.1, 5.0, 3.7 Hz, 1H, Leu-CαH), 4.02 (s, 1H, Thr-CβOH), 3.80 (app-sept, J=2.6 Hz, 1H, Pip-CγH), 3.28 (s, 3H, L-$^{Me}$Val-NCH$_3$), 3.09 (app-dq, J=14.3, 2.4 Hz, 1H, Pip-CδH$_a$), 2.87 (dd, J=7.2, 1.4 Hz, 1H, Pip-CδH$_b$), 2.80 (d, J=14.3 Hz, 1H, Trp-C3H$_a$), 2.51-2.46 (m, 1H, Pip-CβH$_a$), 2.24-2.16 (m, 1H, L-$^{Me}$Val-CβH), 2.12 (dd, J=14.2, 8.0 Hz, 1H, Trp-C3H$_b$), 2.11-2.05 (m, 1H, D-Val-CβH), 1.93 (ddd, J=15.1, 7.3, 3.4 Hz, 1H, Pip-CβH$_b$), 1.70-1.63 (m, 2H, Leu-CβH$_a$, Leu-CγH), 1.50-1.43 (m, 1H, Leu-CβH$_b$), 1.14 (dd, J=6.6, 0.9 Hz, 3H, Thr-CγH$_3$), 1.04 (d, J=6.7 Hz, 3H, L-$^{Me}$Val-CγH$_3$), 1.01 (d, J=6.8 Hz, 3H, D-Val-CγH$_3$), 0.98 (d, J=6.5 Hz, 3H, L-$^{Me}$Val-CγH$_3$), 0.91 (d, J=6.0 Hz, 3H, Leu-CδH$_3$), 0.86 (d, J=6.0 Hz, 3H, Leu-CδH$_3$), 0.82 (d, J=6.8 Hz, 3H, D-Val-CδH$_3$).

$^{13}$C NMR (150.9 MHz, CDCl$_3$, 25° C.): δ 177.0 (L-$^{Me}$Val-CO), 174.2 (Pip-CO), 174.1 (Leu-CO), 173.4 (D-Val-CO), 172.8 (Trp-CO), 171.7 (Thr-CO), 147.9 (Trp-C7a), 131.7 (Trp-C4a), 130.0 (Trp-C6), 123.3 (Trp-C4), 121.0 (Trp-C5), 112.4 (Trp-C7), 91.2 (Trp-C3a), 85.9 (Trp-C8a), 66.4 (Thr-Cβ), 60.9 (Trp-C2), 58.9 (Pip-Cγ), 57.9 (L-$^{Me}$Val-Cα), 55.5 (D-Val-Cα), 54.5 (Thr-Cα), 54.3 (Leu-Cα), 52.5 (Pip-Cδ), 49.3 (Pip-Cα), 40.8 (Leu-Cβ), 39.3 (Trp-C3), 31.9 (L-$^{Me}$Val NCH$_3$), 30.8 (D-Val-Cβ), 28.7 (Pip-Cβ), 28.0 (L-$^{Me}$Val-Cβ), 25.6 (Leu-Cγ), 23.2 (Leu-Cδ), 21.5 (Leu-Cδ), 20.6 (L-$^{Me}$Val-Cγ), 20.1 (D-Val-Cγ), 19.6 (L-$^{Me}$Val-Cγ), 17.3 (Thr-Cγ), 16.0 (D-Val-Cγ).

FTIR (thin film) cm$^{-1}$: 3406 (br-m), 3330 (br-s), 3285 (br-s), 2961 (m), 2930 (m), 2873 (w), 1660 (s), 1633 (s), 1470 (w), 1260 (m), 1101 (m), 750 (m).

HRMS (ESI) (m/z): calc'd for C$_{37}$H$_{56}$N$_8$NaO$_9$ [M+Na]$^+$: 779.4062, found: 779.4059.

[α]$_D$$^{23}$: +32 (c=0.10, CHCl$_3$)

TLC (9% methanol, 1% ammonium hydroxide in chloroform), Rf: 0.36 (UV, CAM).

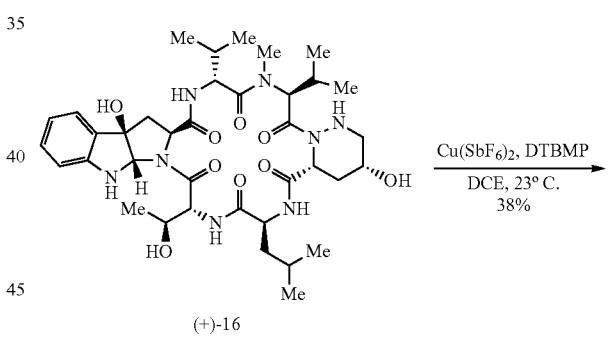

(+)-16

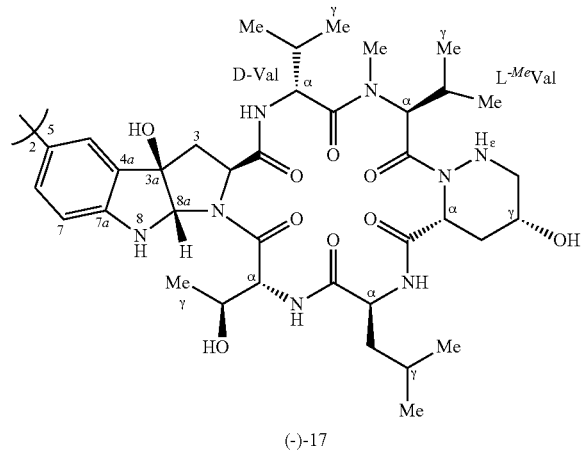

(−)-17

Himastatin N-Methyl Lactam Derivative (−)-17:

A sample of copper(II) hexafluoroantimonate (39.3 mg, 73.5 μmol, 20.0 equiv) was added to a solution of N-methyl cyclic hexapeptide (+)-16 (2.78 mg, 3.67 μmol, 1 equiv) and 2,6-di-tert-butyl-4-methylpyridine (DTBMP, 3.02 mg, 14.7 μmol, 4.00 equiv) in 1,2-dichloroethane (300 μL) at 23° C. After 18 h, a second portion of copper(II) hexafluoroantimonate (39.3.7 mg, 73.5 μmol, 20.0 equiv) was added. After 18 h a final portion of copper(II) hexafluoroantimonate (39.3.7 mg, 73.5 μmol, 20.0 equiv) were added. After 18 h, the heterogeneous solution was diluted with dichloromethane (20 mL), a saturated aqueous sodium thiosulfate solution (5 mL), a saturated aqueous sodium hydrogen carbonate solution (5 mL), and deionized water (10 mL) and was stirred vigorously for 1 h. The layers were separated and the aqueous layer was extracted with dichloromethane (10 mL). The combined organic extracts were washed with a saturated aqueous sodium chloride solution (20 mL), were dried over anhydrous sodium sulfate, were filtered, and were concentrated under reduced pressure. The resulting residue was purified by flash column chromatography on silica gel (eluent: 2.7% methanol, 0.3% ammonium hydroxide→5.4% methanol, 0.6% ammonium hydroxide in chloroform) to afford himastatin N-methyl lactam derivative (−)-17 (0.65 mg, 24%) and recovered N-methyl cyclic hexapeptide (+)-16 (0.93 mg, 34%) as off-white solids. Structural assignments were made using additional information from gCOSY, gHSQC, and gHMBC experiments.

$^1$H NMR (600 MHz, CDCl$_3$, 25° C.): δ 7.99 (d, J=9.2 Hz, 2H, D-Val-NH), 7.58 (d, J=2.0 Hz, 2H, Trp-C4H), 7.42 (dd, J=8.3, 2.0 Hz, 2H, Trp-C6H), 7.25 (d, J=5.1 Hz, 2H, Leu-NH), 6.79 (d, J=8.3 Hz, 2H, Trp-C5H), 6.62 (d, J=10.2 Hz, 2H, Thr-NH), 5.90 (d, J=6.3 Hz, 2H, Trp-N8H), 5.87 (s, 2H, Trp-C3aOH), 5.80-5.75 (m, 4H, Pip-NεH, L-$^{Me}$Val-CαH), 5.32 (d, J=8.0 Hz, 2H, Trp-C2H), 5.21 (dd, J=7.4, 1.2 Hz, 2H, Pip-CαH), 5.16 (d, J=6.3 Hz, 2H, Trp-C8aH), 4.97 (dd, J=9.2, 3.2 Hz, 2H, D-Val-CαH), 4.92 (d, J=5.2 Hz, 2H, Pip-CγOH), 4.86 (d, J=10.3 Hz, 2H, Thr-CαH), 4.56 (qd, J=6.5, 1.1 Hz, 2H, Thr-CβH), 4.28 (ddd, J=9.2, 5.0, 3.6 Hz, 2H, Leu-CαH), 4.02 (s, 2H, Thr-CβOH), 3.80 (app-sept, J=2.4 Hz, 2H, Pip-CγH), 3.28 (s, 6H, L-$^{Me}$Val-NCH$_3$), 3.09 (app-dq, J=14.6, 2.0 Hz, 2H, Pip-CδH$_a$), 2.87 (app-t, J=13.4 Hz, 2H, Pip-CδH$_b$), 2.81 (d, J=14.3 Hz, 2H, Trp-C3H$_a$), 2.51-2.46 (m, 2H, Pip-CβHa), 2.25-2.17 (m, 2H, L-$^{Me}$Val-CβH), 2.15 (dd, J=14.3, 8.1 Hz, 2H, Trp-C3H$_b$), 2.08 (septd, J=6.8, 3.2 Hz, 2H, D-Val-CβH), 1.93 (ddd, J=14.8, 7.1, 3.4 Hz, 2H, Pip-CβH$_b$), 1.71-1.64 (m, 4H, Leu-CβH$_a$, Leu-CγH), 1.50-1.44 (m, 2H, Leu-CβH$_b$), 1.14 (d, J=6.6 Hz, 6H, Thr-CγH$_3$), 1.04 (d, J=6.7 Hz, 6H, L-$^{Me}$Val-CγH$_3$), 1.02 (d, J=6.8 Hz, 6H, D-Val-CγH$_3$), 0.98 (d, J=6.5 Hz, 6H, L-$^{Me}$Val-CγH$_3$), 0.92 (d, J=6.1 Hz, 6H, Leu-CδH$_3$), 0.87 (d, J=6.0 Hz, 6H, Leu-CδH$_3$), 0.82 (d, J=6.8 Hz, 6H, D-Val-CγH$_3$)

$^{13}$C NMR (150.9 MHz, CDCl$_3$, 25° C.): δ 177.0 (L-$^{Me}$Val-CO), 174.2 (2C, Pip-CO, Leu-CO), 173.5 (D-Val-CO), 172.8 (Trp-CO), 171.7 (Thr-CO), 146.8 (Trp-C7a), 134.4 (Trp-C5), 132.3 (Trp-C4a), 128.8 (Trp-C6), 121.5 (Trp-C4), 112.6 (Trp-C7), 91.2 (Trp-C3a), 86.2 (Trp-C8a), 66.4 (Thr-Cβ), 60.9 (Trp-C2), 58.9 (Pip-Cγ), 57.9 (L-$^{Me}$Val-Cα), 55.5 (D-Val-Cα), 54.6 (Thr-Cα), 54.3 (Leu-Cα), 52.5 (Pip-Cδ), 49.3 (Pip-Cα), 40.8 (Leu-Cβ), 39.4 (Trp-C3), 31.9 (L-$^{Me}$Val NCH$_3$), 30.8 (D-Val-Cβ), 28.7 (Pip-Cβ), 28.0 (L-$^{Me}$Val-Cβ), 25.6 (Leu-Cγ), 23.2 (Leu-Cδ), 21.5 (Leu-Cδ), 20.6 (L-$^{Me}$Val-Cγ), 20.1 (D-Val-Cγ), 19.7 (L-$^{Me}$Val-Cγ), 17.3 (Thr-Cγ), 16.0 (D-Val-Cγ).

FTIR (thin film) cm$^{-1}$: 3322 (br-s), 2963 (m), 2929 (m), 2874 (w), 1635 (s), 1529 (m), 1254 (w), 1101 (m).

HRMS (ESI) (m/z): calc'd for C$_{74}$H$_{110}$N$_{16}$NaO$_{18}$ [M+Na]$^+$: 1533.8076, found: 1533.8059.

$[α]_D^{24}$: −78 (c=0.057, MeOH).

TLC (9% methanol, 1% ammonium hydroxide in chloroform), Rf: 0.29 (UV, CAM).

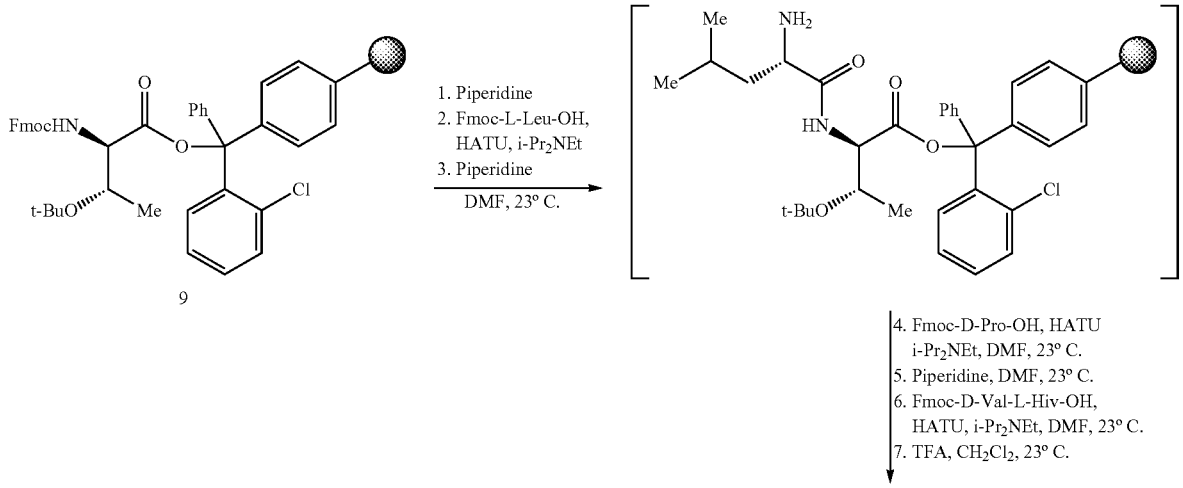

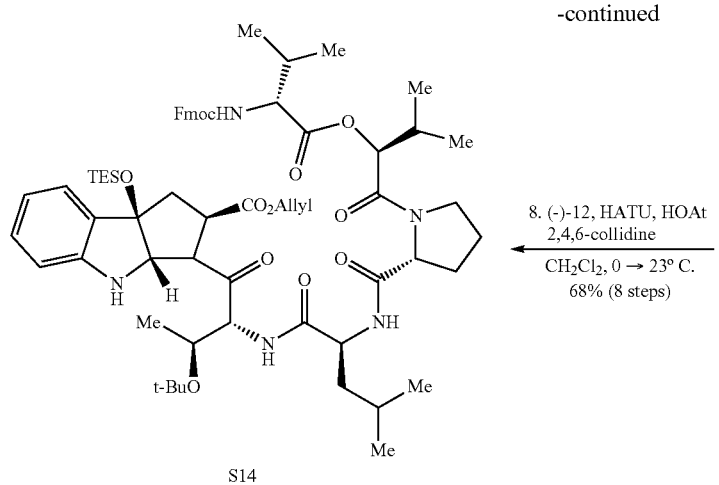
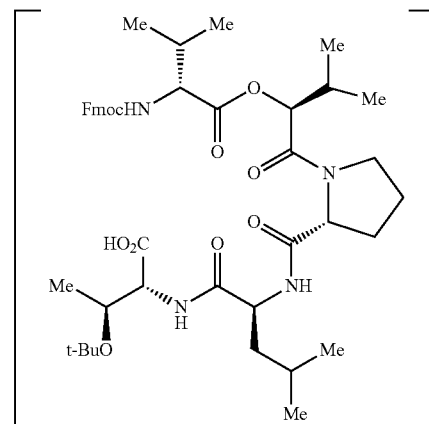

Proline Depsihexapeptide S14:

Prepared according to the procedure described previously for hexapeptides S10 and S11 from Fmoc-D-Thr(t-Bu)-2-chlorotrityl polystyrene resin 9 (351 mg, 0.712 mmol/g, 0.250 mmol, 1 equiv), Fmoc-D-Pro-OH (337 mg, 1.00 mmol, 4.00 equiv), and Fmoc-D-Val-L-Hiv-OH[49] (264 mg, 0.600 mmol, 2.40 equiv). Proline depsihexapeptide S14 was obtained by flash column chromatography on silica gel (eluent: 30%→80% ethyl acetate in hexanes) as an off-white foam (200 mg, 68%). The reported $^1$H NMR integrals are an approximation due to the presence of multiple conformers and significant atropisomerism. The $^{13}$C data are listed as observed with more than the expected number of $^{13}$C resonances due to atropisomerism.

$^1$H NMR (600 MHz, CD$_3$CN, 25° C.): δ 7.86-7.78 (m, 2H), 7.72-7.63 (m, 2H), 7.44-7.37 (m, 2H), 7.35-7.30 (m, 2H), 7.25 (app-td, J=7.8, 1.2 Hz, 0.5H), 7.21-7.15 (m, 0.8H), 7.16-7.04 (m, 1.5H), 7.02 (d, J=7.6 Hz, 0.2H), 6.92 (d, J=8.1 Hz, 0.4H), 6.86-6.71 (m, 1.4H), 6.68 (app-td, J=7.4, 1.0 Hz, 0.4H), 6.60 (d, J=7.9 Hz, 0.3H), 6.52 (app-t, J=8.3 Hz, 0.5H), 6.33 (d, J=9.2 Hz, 0.1H), 6.21 (d, J=8.9 Hz, 0.3H), 6.08 (d, J=8.9 Hz, 0.2H), 6.06 (d, J=4.3 Hz, 0.2H), 6.02-5.85 (m, 1.2H), 5.64 (d, J=3.9 Hz, 0.2H), 5.60 (d, J=4.2 Hz, 0.2H), 5.55 (d, J=1.1 Hz, 0.2H), 5.52-5.44 (m, 0.5H), 5.38 (d, J=15.7 Hz, 0.2H), 5.34 (dd, J=17.3, 1.7 Hz, 0.3H), 5.30 (app-dq, J=17.3, 1.7 Hz, 0.4H), 5.26-5.21 (m, 0.5H), 5.21-5.17 (m, 0.5H), 5.03 (d, J=8.9 Hz, 0.2H), 4.91 (dd, J=9.3, 1.7 Hz, 0.3H), 4.88-4.83 (m, 0.5H), 4.80 (dd, J=10.3, 6.5 Hz, 0.5H), 4.74-4.11 (m, 9.5H), 4.11-4.01 (m, 0.5H), 3.99-3.91 (m, 0.4H), 3.91-3.78 (m, 1H), 3.70-3.63 (m, 0.1H), 3.59-3.34 (m, 1H), 2.73-2.64 (m, 0.8H), 2.56 (dd, J=13.4, 8.7 Hz, 0.2H), 2.48-2.39 (m, 0.8H), 2.38 (s, 0.6H), 2.26-2.07 (m, 4.5H), 2.04-1.96 (m, 1.1H), 1.90 (d, J=35.2 Hz, 1.5H), 1.77 (br-s, 0.5H), 1.66-1.50 (m, 2H), 1.50-1.35 (m, 1H), 1.26 (br-s, 1H), 1.20 (s, 2H), 1.19-0.93 (m, 20H), 0.88-0.74 (m, 15H), 0.51-0.30 (m, 6H).

$^{13}$C NMR (150.9 MHz, CD$_3$CN, 25° C.): δ 174.2, 173.8 (2C), 173.7, 173.4 (2C), 172.8, 172.4, 172.3, 172.2, 171.8, 171.1, 170.8, 169.7, 169.6, 169.5, 169.4, 158.2, 157.4 (2C), 157.3 (2C), 150.7, 149.5, 149.3, 148.8, 148.5, 145.2, 145.1, 145.0 (3C), 144.9, 142.1, 136.4, 133.5, 133.4 (2C), 133.2 (2C), 131.5, 131.1, 130.7, 130.5, 129.7, 128.7 (2C), 128.2, 128.1 (3C), 128.1, 126.6, 126.3 (2C), 125.1, 124.7, 124.3, 124.1, 121.8, 121.0, 120.9, 120.8 (2C), 119.6, 119.1, 118.9, 118.8, 118.7, 118.5, 112.4, 110.7, 91.2, 90.1, 89.3, 89.1, 86.8, 86.6, 86.5, 84.8, 83.2, 79.4, 78.9 (2C), 78.6, 77.7, 75.5, 75.2, 74.8, 74.7, 71.3, 69.5, 68.6, 68.1, 67.7 (2C), 67.6 (2C), 67.5, 67.1, 66.8, 66.2, 66.1, 61.7 (2C), 61.5, 60.9, 60.8, 60.7 (2C), 60.6 (2C), 60.3, 57.2, 57.1, 56.6, 56.1, 53.1 (2C), 52.8 (2C), 48.0 (2C), 47.9 (2C), 47.8 (2C), 46.7, 46.5, 43.6, 43.0, 41.5, 41.2, 41.1, 33.2, 32.1, 31.7, 30.4, 30.3, 30.1, 30.0, 29.6, 29.2, 29.1, 29.0, 28.9, 28.7, 28.5, 25.4 (2C), 25.3, 25.2, 25.0 (2C), 24.9, 24.3, 23.4 (2C), 23.3, 23.2, 22.1, 22.1, 22.0, 21.8 (2C), 21.5, 21.2, 20.8, 20.5, 19.9, 19.7 (2C), 19.6, 19.5, 18.8, 18.7, 18.3, 18.1, 18.0 (2C), 17.9 (3C), 7.1 (2C), 7.0, 6.5 (2C), 6.4, 6.3.

FTIR (thin film) cm$^{-1}$: 3313 (br-m), 2958 (m), 2924 (m), 2875 (w), 1721 (s), 1654 (s), 1518 (m), 1468 (m), 1245 (m), 1188 (m), 1110 (m), 1005 (w), 740 (s).

HRMS (ESI) (m/z): calc'd for C$_{64}$H$_{91}$N$_6$O$_{12}$Si[M+H]$^+$: 1163.6459, found: 1163.6462.

TLC (60% ethyl acetate in hexanes), Rf: 0.36 (UV, CAM).

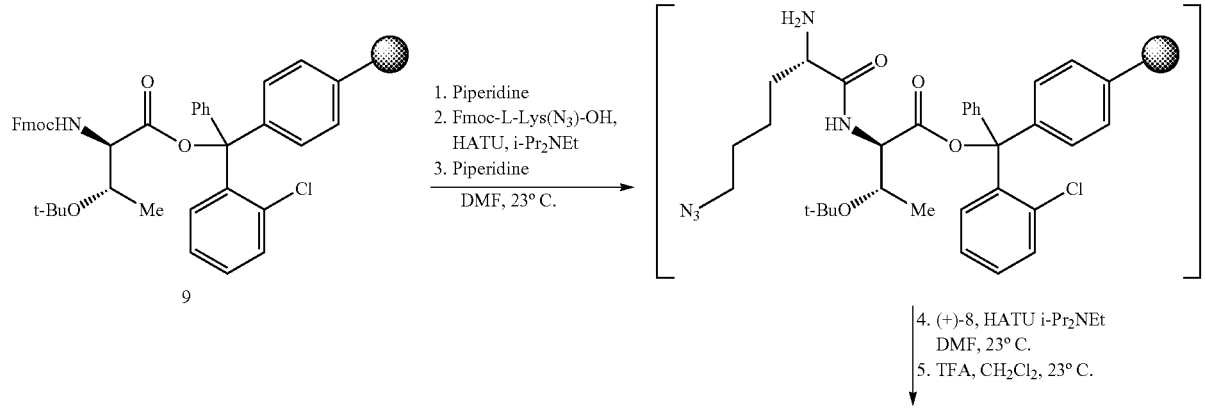

195

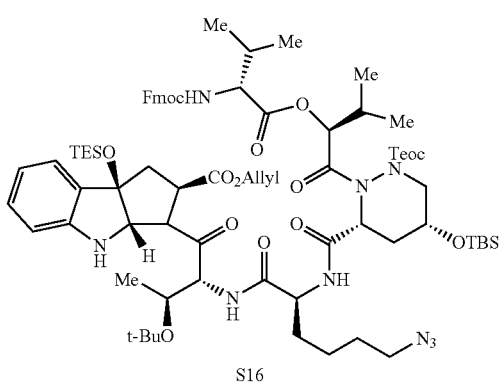

S16

6. (-)-12, HATU, HOAt
2,4,6-collidine
CH₂Cl₂, 0 → 23° C.
54% (6 steps)

-continued

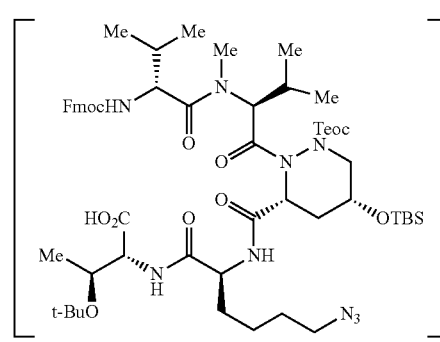

Azido Depsihexapeptide S16:

Prepared according to the procedure described previously for depsihexapeptide (−)-13 from Fmoc-D-Thr(t-Bu)-2-chlorotrityl polystyrene resin 9 (499 mg, 0.802 mmol/g, 0.400 mmol, 1 equiv) and Fmoc-L-Lys(N₃)—OH (379 mg, 0.960 mmol, 2.40 equiv). Azido depsihexapeptide S16 was obtained by flash column chromatography on silica gel (eluent: 45%→50% ethyl acetate in hexanes) as a white foam (324 mg, 54%). The reported $^1$H NMR integrals are an approximation due to the presence of multiple conformers and significant atropisomerism. The $^{13}$C data are listed as observed with more than the expected number of $^{13}$C resonances due to atropisomerism.

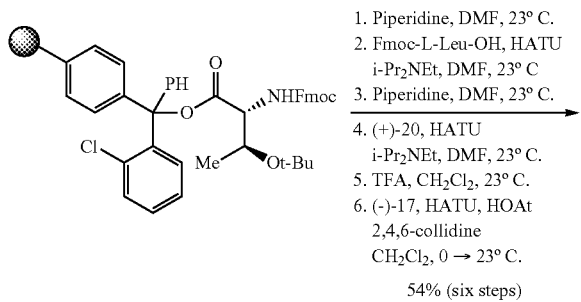

1. Piperidine, DMF, 23° C.
2. Fmoc-L-Leu-OH, HATU
   i-Pr₂NEt, DMF, 23° C
3. Piperidine, DMF, 23° C.
4. (+)-20, HATU
   i-Pr₂NEt, DMF, 23° C.
5. TFA, CH₂Cl₂, 23° C.
6. (−)-17, HATU, HOAt
   2,4,6-collidine
   CH₂Cl₂, 0 → 23° C.

54% (six steps)

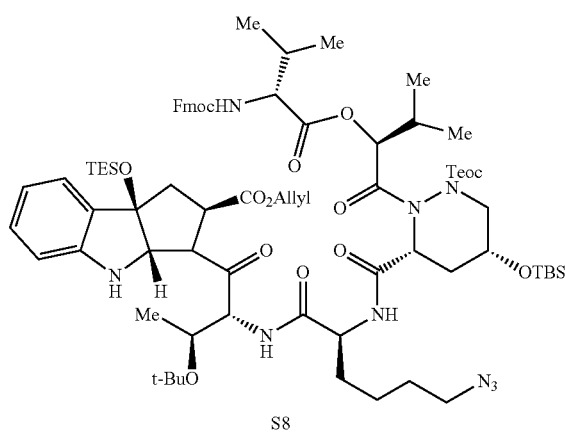

S8

196

Azido Depsihexapeptide S8

Prepared according to the procedure described previously for depsihexapeptide (−)-24 from Fmoc-D-Thr(t-Bu)-2-chlorotrityl polystyrene resin 21 (499 mg, 0.802 mmol/g, 0.400 mmol, 1 equiv.) and Fmoc-L-Lys(N₃)—OH (379 mg, 0.960 mmol, 2.40 equiv.). Azido depsihexapeptide S8 was obtained by flash column chromatography on silica gel (eluent: 45%→50% ethyl acetate in hexanes) as a white foam (324 mg, 54.3%).

$^1$H NMR (600 MHz, CD₃CN, 25° C.): δ 8.47 (d, J=7.1 Hz, 0.2H), 8.42 (s, 0.3H), 8.20 (s, 0.2H), 7.86-7.79 (m, 2.1H), 7.73-7.65 (m, 2H), 7.61 (br-s, 0.3H), 7.41 (app-td, J=7.6, 3.6 Hz, 2.1H), 7.36-7.30 (m, 2.1H), 7.27 (d, J=7.3 Hz, 0.5H), 7.21-7.15 (m, 1H), 7.09 (app-t, J=7.7 Hz, 0.5H), 6.87 (d, J=7.8 Hz, 0.3H), 6.86-6.76 (m, 1H), 6.74-6.66 (m, 1H), 6.62-6.56 (m, 0.4H), 6.12-5.86 (m, 2H), 5.56 (s, 0.5H), 5.48 (d, J=3.8 Hz, 0.5H), 5.39 (dd, J=17.3, 1.6 Hz, 0.5H), 5.32 (app-dq, J=17.3, 1.6 Hz, 0.5H), 5.26 (dd, J=10.5, 1.4 Hz, 0.5H), 5.23-5.18 (m, 0.5H), 5.11-5.03 (m, 0.8H), 4.97-4.82 (m, 0.8H), 4.78 (d, J=6.4 Hz, 0.6H), 4.70 (dd, J=5.5, 1.5 Hz, 0.4H), 4.67 (app-dt, J=5.5, 1.6 Hz, 0.4H), 4.65 (d, J=5.6 Hz, 0.4H), 4.63-4.61 (m, 0.4H), 4.57-4.08 (m, 10H), 4.04 (br-s, 1.7H), 3.94 (br-s, 0.7H), 3.33-3.10 (m, 2.3H), 2.70 (d, J=13.2 Hz, 0.5H), 2.56 (dd, J=13.3, 8.6 Hz, 0.4H), 2.43 (dd, J=13.3, 5.5 Hz, 0.6H), 2.33 (dd, J=13.1, 9.2 Hz, 0.5H), 2.21 (br-s, 1.5H), 2.11 (d, J=17.6 Hz, 2H), 1.84 (br-s, 0.6H), 1.74 (br-s, 1H), 1.68-1.29 (m, 5.4H), 1.23-0.73 (m, 45H), 0.49-0.31 (m, 6H), 0.08-0.00 (m, 12.5H), −0.01 (s, 1.5H), −0.15 (s, 1H).

$^{13}$C NMR (150.9 MHz, CD₃CN, 25° C.): δ 172.4, 172.0, 171.7, 171.2, 171.1, 170.7, 159.0, 157.3, 149.4, 148.8, 145.1, 145.0, 142.1, 133.5, 133.2, 132.1, 131.3, 131.1, 130.6, 128.7 (2C), 128.1 (2C), 126.2, 124.7, 124.0, 121.0 (2C), 120.7, 120.4, 119.1, 118.8, 118.5, 112.2, 111.6, 110.9, 91.1, 86.7, 84.7, 76.8, 76.1, 75.7, 74.8, 70.1, 69.8, 69.4, 68.3, 68.0, 67.7, 67.5, 66.8, 66.1, 65.6, 65.5, 64.2, 60.9, 60.7, 60.6, 60.5, 57.7, 57.1, 56.9, 56.7, 56.2, 56.0, 55.7, 54.7, 53.4, 51.9, 48.0, 46.6, 43.1, 43.0, 32.7, 32.6, 32.3, 31.6, 31.3, 30.2, 29.6, 29.3, 29.2, 29.0, 28.9, 28.6, 28.4, 26.1, 26.0, 23.4, 23.2, 23.1, 21.5, 20.3, 19.8, 19.6, 19.4, 18.6, 18.3, 18.0, 17.7, 17.6, 16.9, 16.8, 7.2, 7.0, 6.5, 6.5, −1.3 (2C), −1.5, −1.6, −4.7 (2C), −4.8.

FTIR (thin film) cm$^{-1}$: 3310 (br-m), 2955 (m), 2877 (w), 2095 (m), 1714 (s), 1653 (s), 1470 (m), 1248 (m), 1185 (m), 1120 (m), 1017 (m), 837 (m), 740 (m).

HRMS (ESI) (m/z): calc'd for $C_{76}H_{117}N_{10}O_{15}Si_3$ [M+H]⁺: 1493.8002, found: 1493.7994.

TLC (40% ethyl acetate in hexanes), Rf: 0.35 (UV, CAM).

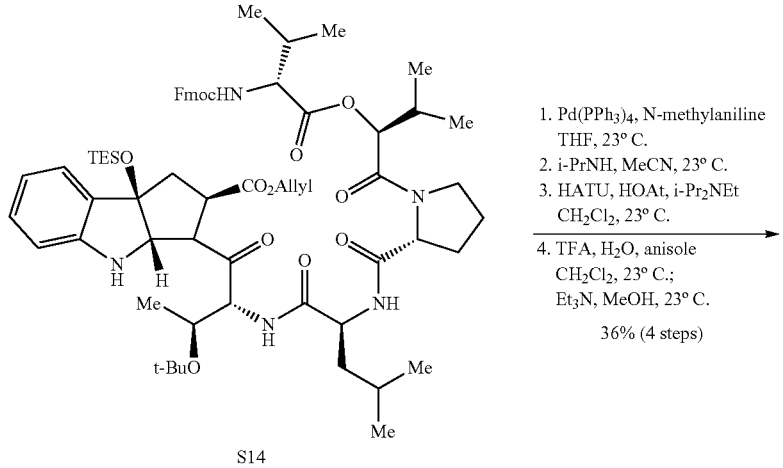

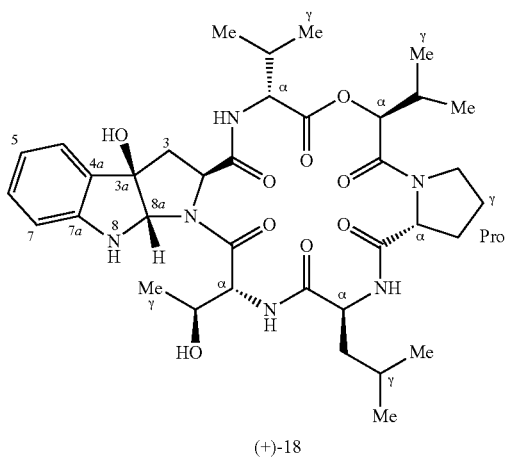

Proline Cyclic Depsihexapeptide (+)-18:

Prepared according to the procedure described previously for himastatin monomer (+)-2 from S14 (194.9 mg, 0.168 mmol, 1 equiv). Proline cyclic depsihexapeptide (+)-18 was obtained by flash column chromatography on silica gel (eluent: 3.6% methanol, 0.4% ammonium hydroxide→5.4% methanol, 0.6% ammonium hydroxide in chloroform) as an off-white solid (42.9 mg, 36%). Structural assignments were made using additional information from gCOSY, gHSQC, and gHMBC experiments. Sample purity (≥97%) was confirmed by LC-MS analysis (Zorbax® StableBond 80 Å CN, 4.6 mm×250 mm, 40%→95% acetonitrile in water, 0.1% formic acid, 16 min, 1.5 mL/min, 254 nm, $t_R$ ((+)-29)=5.87 min).

¹H NMR (600 MHz, CDCl₃, 25° C., 7.5:1 mixture of conformers, * denotes minor conformer): δ 7.91 (d, J=9.2 Hz, 1H, Leu-NH), 7.73 (br-s, 1H, Thr-NH*), 7.30 (dd, J=7.5, 1.3 Hz, 1H, Trp-C4H), 7.27 (dd, J=7.0, 1.2 Hz, 1H, Trp-C4H*), 7.17 (app-td, J=7.7, 1.3 Hz, 1H, Trp-C6H*), 7.13 (app-td, J=7.7, 1.3 Hz, 1H, Trp-C6H), 6.88 (d, J=7.8 Hz, 1H, Val-NH), 6.84 (d, J=8.5 Hz, 1H, Thr-NH), 6.81 (app-td, J=7.4, 0.9 Hz, 1H, Trp-C5H, Trp-C5H*), 6.71-6.65 (m, 2H, Trp-C7H*, Val-NH), 6.57 (dd, J=7.9, 0.9 Hz, 1H, Trp-C7H), 5.90 (br-s, 1H, Leu-NH*), 5.82 (br-s, 1H, Trp-N8H*), 5.76 (d, J=4.7 Hz, 2H, Trp-C8aH, Trp-C8aH*), 5.57 (br-s, 1H, Trp-N8H), 5.47 (s, 1H, Trp-C3aOH), 5.24 (br-s, 1H, Trp-C3aOH*), 5.10 (d, J=9.9 Hz, 1H, Hiv-CαH), 4.95 (dd, J=8.1, 3.2 Hz, 1H, Val-CαH), 4.90 (d, J=8.9 Hz, 1H, Trp-C2H), 4.77 (d, J=7.6 Hz, 1H, Pro-CαH), 4.75 (d, J=10.5 Hz, 1H, Hiv-CαH*), 4.62 (app-t, J=8.4 Hz, 1H, Thr-CαH), 4.49 (dd, J=8.6, 6.3 Hz, 1H, Thr-CαH*), 4.46 (dd, J=8.7, 7.6 Hz, 1H, Val-CαH*), 4.35 (ddd, J=10.1, 7.9, 4.4 Hz, 1H, Leu-CαH*), 4.25 (app-td, J=9.6, 5.4 Hz, 2H, Leu-CαH, Trp-C2H*), 4.22-4.18 (m, 1H, Pro-CδH$_a$*), 4.16 (dd, J=7.1, 2.9 Hz, 1H, Pro-CαH*), 4.06-3.99 (m, 2H, Thr-CβH, Thr-CβH*), 3.93 (app-td, J=9.5, 2.1 Hz, 1H, Pro-CδH$_a$), 3.69 (br-s, 2H, Thr-CβOH, Thr-CβOH*), 3.49 (app-td, J=10.0, 7.4 Hz, 2H, Pro-CδH$_b$, Pro-CδH$_b$*), 2.72 (dd, J=12.9, 7.4 Hz, 1H, Trp-C3H$_a$*), 2.52 (app-dd, J=14.1, 9.1 Hz, 2H, Trp-C3aH$_a$, Trp-C3aH$_b$*), 2.51-2.44 (m, 1H, Pro-CβH$_a$), 2.45-2.39 (m, 3H, Hiv-CβH, Val-CβH, Pro-CβH$_a$*), 2.37 (d, J=14.1 Hz, 1H, Trp-C3H$_b$*), 2.25-2.18 (m, 1H, Hiv-CβH*), 2.14-2.02 (m, 3H, Pro-CγH$_a$, Pro-CγH$_a$*, Pro-CβH$_b$*), 2.02-1.96 (m, 2H, Pro-CγH$_b$, Pro-CγH$_b$*), 1.95-1.88 (m, 1H, Val-CβH*), 1.85 (ddd, J=13.9, 8.9, 4.5 Hz, 1H, Leu-CβH$_a$*), 1.74-1.65 (m, 2H, Pro-CβH$_b$, Leu-CγH*), 1.65-1.58 (m, 1H, Leu-CγH), 1.55 (ddd, J=13.9, 9.9, 5.4 Hz, 1H, Leu-CβH$_a$), 1.51-1.45 (m, 1H, Leu-CβH$_b$*), 1.41 (ddd, J=14.0, 8.7, 5.4 Hz, 1H, Leu-CβH$_b$), 1.30 (d, J=6.4 Hz, 3H, Thr-CγH₃*), 1.22 (d, J=6.2 Hz, 3H, Thr-CγH₃), 1.06 (d, J=6.6 Hz, 3H, Hiv-CγH₃*), 1.05 (d, J=6.6 Hz, 3H, Hiv-CγH₃), 1.03 (d, J=6.9 Hz, 3H, Val-CγH₃), 0.95 (d, J=6.9 Hz, 6H, Hiv-CγH₃, Leu-CδH₃*), 0.94 (d, J=6.7 Hz, 6H, Hiv- CγH₃*, Val-CγH₃*), 0.92 (d, J=6.4 Hz, 6H, Leu-CδH₃*, Val-CγH₃*), 0.89 (d, J=6.6 Hz, 3H, Leu-CδH₃), 0.87 (d, J=6.9 Hz, 3H, Val-CγH₃), 0.84 (d, J=6.5 Hz, 3H, Leu-CδH₃).

¹³C NMR (150.9 MHz, CDCl₃, 25° C., major conformer): δ 173.4 (Trp-CO), 172.8 (Thr-CO), 171.9 (Hiv-CO), 171.3 (Leu-CO), 170.9 (Pro-CO), 169.6 (Val-CO), 147.3 (Trp-C7a), 130.8 (Trp-C4a), 129.8 (Trp-C6), 123.1 (Trp-C4), 120.0 (Trp-C5), 110.9 (Trp-C7), 87.8 (Trp-C8a), 86.5 (Trp-C3a), 77.2 (Hiv-Cα), 69.3 (Thr-Cβ), 62.4 (Trp-C2), 58.9 (Pro-Cα), 57.5 (Val-Cα), 55.4 (Thr-Cα), 52.3 (Leu-Cα), 47.1 (Pro-Cδ), 44.3 (Trp-C3), 40.1 (Leu-Cβ), 31.8 (Val-Cβ), 30.0 (Hiv-Cβ), 25.9 (Pro-Cβ), 24.9 (Leu-Cγ), 24.8 (Pro-Cγ), 23.2 (Leu-Cδ), 22.0 (Leu-Cδ), 19.9 (Thr-Cγ), 19.8 (Val-Cγ), 18.7 (Hiv-Cγ), 17.9 (Hiv-Cγ), 16.8 (Val-Cγ).

FTIR (thin film) cm⁻¹: 3296 (br-s), 2962 (m), 2932 (m), 2874 (w), 1741 (m), 1673 (s), 1637 (s), 1537 (m), 1438 (m), 1182 (m), 747 (m).

HRMS (ESI) (m/z): calc'd for $C_{36}H_{52}N_6NaO_9$ [M+Na]⁺: 735.3688, found: 735.3685.

[α]$_D^{23}$: +5.4 (c=0.11, CHCl₃)

TLC (9% methanol, 1% ammonium hydroxide in chloroform), Rf: 0.37 (UV, CAM).

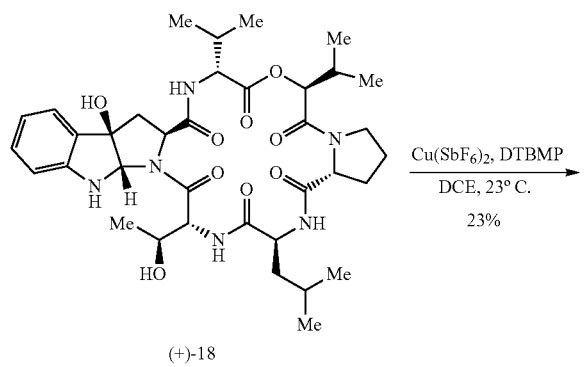

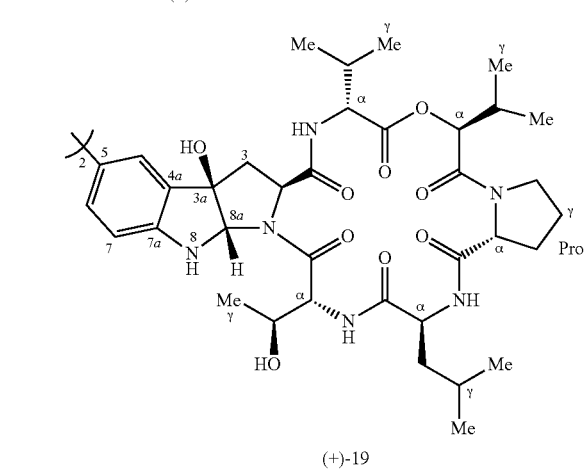

Himastatin Proline Derivative (−)-19:

Prepared according to the procedure described previously for (−)-himastatin (1) from proline cyclic depsihexapeptide (+)-18 (5.88 mg, 8.25 μmol, 1 equiv). Flash column chromatography on silica gel (eluent: 2%→10% methanol in dichloromethane), followed by semi-preparative HPLC purification of mixed fractions of dimer (−)-19 (Zorbax® StableBond 80 Å CN, 9.4 mm×250 mm, 40%→95% acetonitrile in water, 16 min, 5.0 mL/min, 270 nm, t$_R$ ((−)-19)=7.88 min) afforded himastatin proline derivative (−)-19 (1.35 mg, 23%) as a white foam. Structural assignments were made using additional information from gCOSY, gHSQC, and gHMBC experiments. Chemical exchange between conformers was observed and verified by exchange (EXSY) spectroscopy (τ$_m$=400 μs).

¹H NMR (600 MHz, DMSO-d₆, 25° C., 6.0:1 mixture of conformers, * denotes minor conformer): δ 8.66 (d, J=7.6 Hz, 2H, Leu-NH*), 8.57 (d, J=9.5 Hz, 2H, Val-NH), 8.35 (d, J=9.6 Hz, 2H, Val-NH*), 8.05 (d, J=8.4 Hz, 2H, Thr-NH), 7.52 (d, J=9.4 Hz, 2H, Leu-NH), 7.48 (d, J=8.9 Hz, 2H, Thr-NH*), 7.44 (d, J=1.9 Hz, 2H, Trp-C4H*), 7.40 (d, J=2.0 Hz, 2H, Trp-C4H), 7.34 (dd, J=8.2, 1.8 Hz, 2H, Trp-C6H*), 7.25 (dd, J=8.2, 1.9 Hz, 2H, Trp-C6H), 6.63 (d, J=8.2 Hz, 2H, Trp-C7H*), 6.59 (d, J=8.2 Hz, 2H, Trp-C7H), 6.30 (d, J=2.2 Hz, 2H, Trp-N8H*), 6.28 (d, J=2.3 Hz, 2H, Trp-N8H), 5.99 (s, 2H, Trp-C3aOH*), 5.84 (s, 2H, Trp-C3aOH), 5.39 (s, 2H, Trp-C8aH*), 5.33 (d, J=2.2 Hz, 2H, Trp-C8aH), 5.14 (d, J=9.1 Hz, 2H, Hiv-CαH), 4.91 (d, J=8.3 Hz, 2H, Hiv-CαH*), 4.77 (dd, J=8.1, 5.1 Hz, 2H, Trp-C2H), 4.72 (s, 2H, Thr-CβOH*), 4.67 (s, 2H, Thr-CβOH), 4.65 (dd, J=9.5, 3.5 Hz, 2H, Val-CαH), 4.63 (d, J=7.2 Hz, 2H, Pro-CαH), 4.44 (app-t, J=8.0 Hz, 2H, Thr-CαH*), 4.32-4.23 (m, 6H, Thr-CαH, Leu-CαH, Pro-CαH*), 4.17 (app-t, J=9.4 Hz, 2H, Val-CαH*), 4.04 (dd, J=10.6, 6.2 Hz, 2H, Trp-C2H*), 3.99 (ddd, J=11.4, 7.7, 3.4 Hz, 2H, Leu-CαH*), 3.91 (app-q, J=6.1 Hz, 2H, Thr-CβH*), 3.87 (app-t, 2H, J=8.5 Hz, Pro-CδH$_a$*), 3.74-3.64 (m, 4H, Thr-CβH, Pro-CδH$_a$), 3.55 (app-q, J=9.2 Hz, 4H, Pro-CδH$_b$, Pro-CδH$_b$*), 2.64-2.58 (m, 2H, Trp-C3H$_a$*), 2.53 (dd, J=13.2, 7.9 Hz, 2H, Trp-C3H$_a$), 2.41-2.34 (m, 2H, Trp-C3H$_b$*), 2.31 (dd, J=13.2, 4.7 Hz, 2H, Trp-C3H$_b$), 2.24-2.12 (m, 8H, Pro-CβH$_a$, Val-CβH, Hiv-CβH, Pro-CγH$_a$*), 2.07-2.00 (m, 2H, Hiv-CβH*), 1.98-1.91 (m, 2H, Pro-CβH$_a$*), 1.91-1.84 (m, 4H, Pro-CγH$_a$, Pro-CγH$_b$*), 1.79 (heptd, J=6.8, 3.7 Hz, 2H, Val-CβH*), 1.74-1.67 (m, 4H, Pro-CγH$_b$, Pro-CβH$_b$*), 1.67-1.51 (m, 8H, Leu-CγH, Pro-CβH$_b$, Leu-CβH$_a$*, Leu-CγH*), 1.33-1.19 (m, 6H, Leu-CβH$_a$, Leu-CβH$_b$, Leu-CβH$_b$*), 1.13 (d, J=6.2 Hz, 6H, Thr-CγH₃*), 0.95 (d, J=6.2 Hz, 6H, Thr-CγH₃), 0.94 (d, J=6.6 Hz, 12H, Hiv-CγH₃, Hiv-CγH₃*), 0.90 (d, J=6.7 Hz, 12H, Leu-CδH₃, Leu-CδH₃*), 0.89-0.87 (m, 24H, Leu-CδH₃, Hiv-CγH₃, Val-CγH₃, Hiv-CγH₃*), 0.86 (d, J=6.8 Hz, 6H, Leu-CδH₃*), 0.84 (d, J=6.8 Hz, 6H, Val-CγH₃*), 0.83 (d, J=6.5 Hz, 6H, Val-CγH₃*), 0.81 (d, J=6.8 Hz, 6H, Val-CγH₃).

¹³C NMR (150.9 MHz, DMSO-d₆, 25° C., major conformer): δ 171.9 (2C, Trp-CO, Thr-CO), 170.7 (Leu-CO), 170.6 (Pro-CO), 170.2 (Hiv-CO), 168.6 (Val-CO), 147.9 (Trp-C7a), 131.6 (Trp-C4a), 130.8 (Trp-C5), 126.9 (Trp-C6), 120.6 (Trp-C4), 109.9 (Trp-C7), 84.9 (Trp-C3a), 84.5 (Trp-C8a), 75.1 (Hiv-Cα), 68.0 (Thr-Cβ), 60.3 (Trp-C2), 58.5 (Pro-Cα), 55.5 (Val-Cα), 55.4 (Thr-Cα), 51.0 (Leu-Cα), 46.2 (Pro-Cδ), 43.9 (Trp-C3), 41.1 (Leu-Cβ), 31.0 (Val-Cβ), 29.3 (Hiv-Cδ), 25.5 (Pro-Cβ), 24.4 (Leu-Cγ), 23.9 (Pro-Cγ), 23.3 (Leu-Cδ), 21.7 (Leu-Cδ), 19.6 (Thr-Cγ), 19.2 (Val-Cγ), 17.8 (Hiv-Cγ), 17.4 (Hiv-Cγ), 16.5 (Val-Cγ).

FTIR (thin film) cm⁻¹: 3312 (br-s), 2964 (m), 2931 (m), 2875 (w), 1744 (m), 1666 (s), 1650 (s), 1537 (m), 1442 (m), 1182 (m).

HRMS (ESI) (m/z): calc'd for $C_{72}H_{103}N_{12}O_{18}$ [M+H]⁺: 1423.7508, found: 1423.7465.

[α]$_D^{24}$: −139 (c=0.091, MeOH).

TLC (10% methanol in dichloromethane), Rf: 0.17 (UV, CAM).

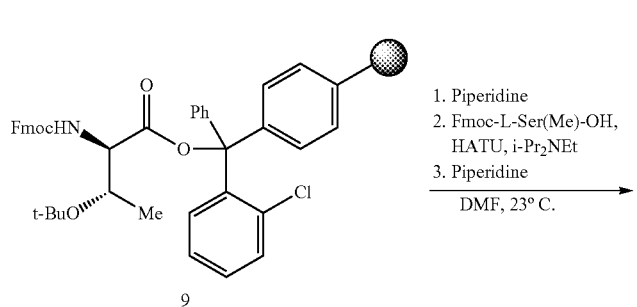
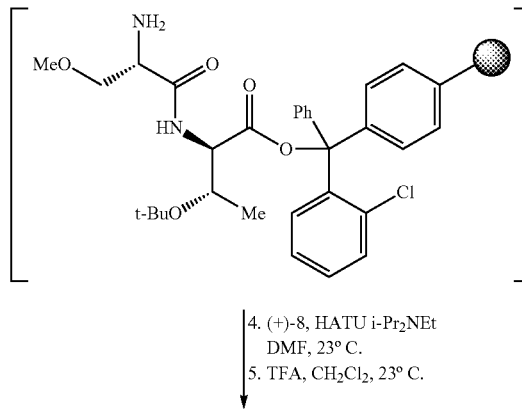
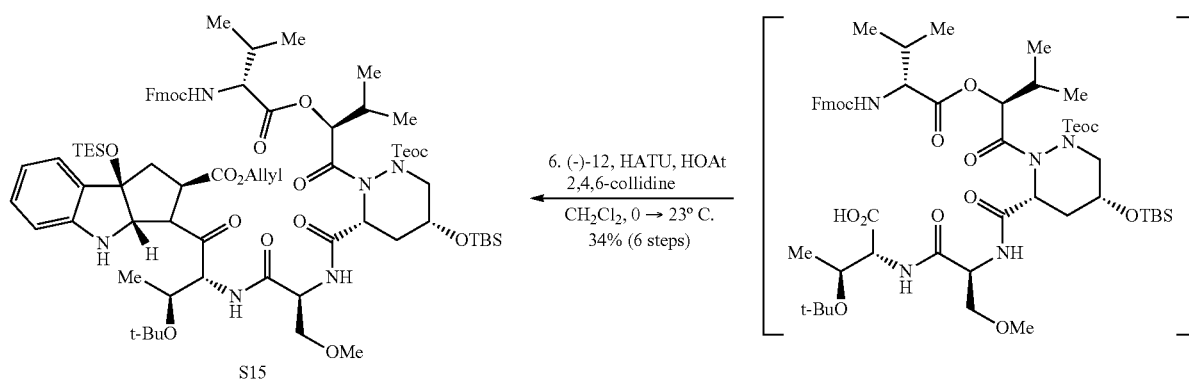

Serine Depsihexapeptide S15:

Prepared according to the procedure described previously for depsihexapeptide (−)-13 from Fmoc-D-Thr(t-Bu)-2-chlorotrityl polystyrene resin 9 (154.5 mg, 0.712 mmol/g, 0.110 mmol, 1 equiv) and Fmoc-L-Ser(Me)-OH (150 mg, 0.440 mmol, 4.00 equiv). Serine depsihexapeptide S15 was obtained by flash column chromatography on silica gel (eluent: 35%→50% ethyl acetate in hexanes) as a white foam (54.3 mg, 34%). The reported $^1$H NMR integrals are an approximation due to the presence of multiple conformers and significant atropisomerism. The $^{13}$C data are listed as observed with more than the expected number of $^{13}$C resonances due to atropisomerism.

$^1$H NMR (600 MHz, CD$_3$CN, 25° C.): δ 8.50 (s, 0.2H), 8.30-8.17 (m, 0.2H), 7.90-7.74 (m, 2.6H), 7.75-7.64 (m, 1.6H), 7.64-7.51 (m, 0.5H), 7.47-7.22 (m, 5H), 7.21-7.04 (m, 1.5H), 7.04-6.93 (m, 0.5H), 6.86-6.77 (m, 0.5H), 6.74-6.63 (m, 1H), 6.63-6.53 (m, 0.5H), 6.35-6.22 (m, 0.2H), 6.11-5.87 (m, 2H), 5.55 (s, 0.4H), 5.48 (s, 0.4H), 5.46-5.35 (m, 0.8H), 5.35-5.24 (m, 1.2H), 5.24-5.17 (m, 0.5H), 5.16-4.73 (m, 2.5H), 4.73-4.45 (m, 3.5H), 3.87-3.36 (m, 9H), 3.87-3.36 (m, 3H), 3.36-3.17 (m, 2.8H), 3.09 (s, 0.4H), 3.06 (s, 0.2H), 2.72 (app-td, J=14.3, 4.3 Hz, 0.6H), 2.64-2.45 (m, 0.6H), 2.42 (dd, J=13.2, 5.9 Hz, 0.4H), 2.35-2.04 (m, 4H), 1.35 (d, J=5.7 Hz, 0.4H), 1.23-1.07 (m, 12H), 1.07-0.76 (m, 29H), 0.76-0.63 (m, 2.5H), 0.48-0.32 (m, 6H), 0.11 (s, 1.5H), 0.08--0.16 (m, 15H).

$^{13}$C NMR (150.9 MHz, CD$_3$CN, 25° C.): δ 174.7, 173.0, 172.4, 172.2, 172.0, 171.3, 166.1, 157.4, 157.1, 148.9, 148.6, 145.1, 145.0, 144.8, 144.3, 142.1, 133.5, 133.2 (2C), 131.3, 131.2, 130.8, 130.6, 130.2, 128.9, 128.8, 128.7, 128.2, 128.1 (2C), 126.3, 126.2 (2C), 124.7, 124.2, 124.1, 121.0 (3C), 112.2, 110.2, 89.5, 87.2, 86.9, 84.8, 84.6, 84.3, 84.1, 76.8, 76.1, 76.0, 75.7, 74.9, 74.7, 74.1, 73.4, 72.9, 69.8, 69.6, 69.3, 69.2, 68.1 (2C), 67.5, 66.9, 66.8, 66.1, 64.2, 64.1, 61.6, 60.9, 60.7, 60.5, 60.4, 59.7, 59.5, 59.3, 57.2, 57.0, 56.9, 56.8, 56.5, 54.3, 53.5, 48.0, 47.7, 47.3 (2C), 46.5, 46.4, 43.0, 42.9, 31.7, 31.4, 29.3, 29.2, 29.0, 28.8, 28.6, 28.5, 26.2, 26.1 (2C), 22.0, 21.3, 20.9, 20.2, 20.1, 20.0 (2C), 19.6, 19.4, 19.3, 18.8, 18.7, 18.6, 18.3, 18.2, 18.1, 17.7, 16.9, 16.7, 16.1, 7.2, 7.1, 6.8, 6.5 (2C), 6.4, −1.3, −1.4, −1.5, −1.6, −4.5, −4.7, −4.8.

FTIR (thin film) cm$^{-1}$: 3344 (br-m), 2956 (m), 2877 (w), 1723 (s), 1648 (s), 1522 (m), 1414 (m), 1301 (s), 1108 (s), 837 (s), 740 (s).

HRMS (ESI) (m/z): calc'd for C$_{74}$H$_{114}$N$_7$O$_{16}$Si$_3$ [M+H]$^+$: 1440.7624, found: 1440.7620.

TLC (45% ethyl acetate in hexanes), Rf: 0.48 (UV, CAM).

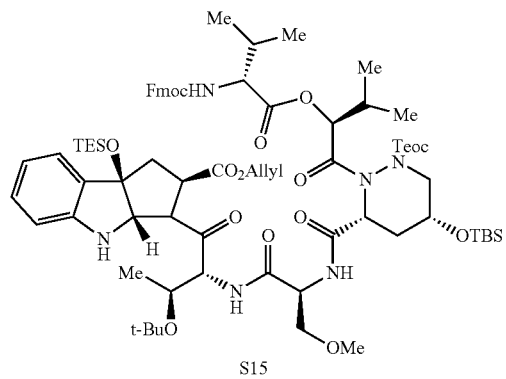

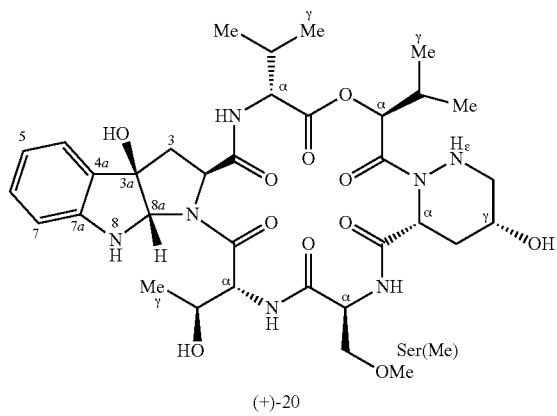

Serine Cyclic Depsihexapeptide (+)-20:

Prepared according to the procedure described previously for himastatin monomer (+)-2 from serine depsihexapeptide S15 (51.2 mg, 35.5 μmol, 1 equiv). Serine cyclic depsihexapeptide (+)-20 was obtained by flash column chromatography on silica gel (eluent: 2.7% methanol, 0.3% ammonium hydroxide→4.5% methanol, 0.5% ammonium hydroxide in chloroform) as an off-white solid (13.3 mg, 51%). Structural assignments were made using additional information from gCOSY, gHSQC, and gHMBC experiments.

$^1$H NMR (600 MHz, CDCl$_3$, 25° C.): δ 7.83 (d, J=5.8 Hz, 1H, Ser-NH), 7.43 (d, J=9.6 Hz, 1H, Val-NH), 7.34 (dd, J=7.5, 1.3 Hz, 1H, Trp-C4H), 7.19 (app-td, J=7.7, 1.3 Hz, 1H, Trp-C6H), 7.01 (d, J=10.6 Hz, 1H, Thr-NH), 6.89 (app-td, J=7.5, 0.9 Hz, 1H, Trp-C5H), 6.77 (d, J=7.9 Hz, 1H, Trp-C7H), 6.05 (d, J=6.3 Hz, 1H, Trp-N8H), 5.86 (s, 1H, Trp-C3aOH), 5.64 (d, J=8.9 Hz, 1H, Hiv-CαH), 5.40 (dd, J=12.8, 2.0 Hz, 1H, Pip-NεH), 5.25 (d, J=7.9 Hz, 1H, Trp-C2H), 5.21-5.19 (m, 2H, Trp-C8aH, Pip-CγOH), 5.15 (d, J=7.0 Hz, 1H, Pip-CαH), 5.08 (d, J=10.6 Hz, 1H, Thr-CαH), 4.83 (dd, J=9.7, 3.1 Hz, 1H, Val-CαH), 4.44 (qd, J=6.6, 1.8 Hz, 1H, Thr-CβH), 4.31 (ddd, J=5.5, 3.1, 2.1 Hz, 1H, Ser-CαH), 3.82 (app-sept, J=2.3 Hz, 1H, Pip-CγH), 3.79 (dd, J=9.5, 2.1 Hz, 1H, Ser-CβH$_a$), 3.64 (s, 1H, Thr-CβOH), 3.43 (dd, J=9.6, 3.2 Hz, 1H, Ser-CβH$_b$), 3.29 (s, 3H, Ser-OCH$_3$), 3.07 (app-dq, J=14.2, 2.3 Hz, 1H, Pip-CδH$_a$), 2.84 (app-t, J=13.4 Hz, 1H, Pip-CδH$_b$), 2.78 (d, J=14.3 Hz, 1H, Trp-C3H$_a$), 2.56 (septd, J=6.8, 3.2 Hz, 1H, Val-CβH), 2.49 (app-dp, J=15.1, 2.3 Hz, 1H, Pip-CβH$_a$), 2.21-2.12 (m, 2H, Trp-C3H$_b$, Hiv-CβH), 1.94 (ddd, J=15.0, 7.2, 3.5 Hz, 1H, Pip-CβH$_b$), 1.16 (d, J=6.3 Hz, 3H, Thr-CγH$_3$), 1.12 (d, J=6.6 Hz, 3H, Hiv-CγH$_3$), 1.00 (d, J=6.9 Hz, 6H, Hiv-CγH$_3$, Val-CγH$_3$), 0.85 (d, J=6.9 Hz, 3H, Val-CγH$_3$).

$^{13}$C NMR (150.9 MHz, CDCl$_3$, 25° C.): δ 174.0 (Hiv-CO), 173.5 (Val-CO), 173.3 (Pip-CO), 173.1 (Trp-CO), 172.0 (Thr-CO), 171.7 (Ser-CO), 148.2 (Trp-C7a), 131.9 (Trp-C4a), 130.0 (Trp-C6), 123.4 (Trp-C4), 121.0 (Trp-C5), 112.4 (Trp-C7), 91.2 (Trp-C3a), 85.8 (Trp-C8a), 77.3 (Hiv-Cα), 71.0 (Ser-Cβ), 66.8 (Thr-Cβ), 60.6 (Trp-C2), 59.8 (Ser-OCH$_3$), 58.9 (Pip-Cγ), 57.3 (Val-Cα), 56.3 (Ser-Cα), 54.2 (Thr-Cα), 52.8 (Pip-Cδ), 49.9 (Pip-Cα), 39.6 (Trp-C3), 30.4 (Val-Cβ), 30.0 (Hiv-Cβ), 28.8 (Pip-Cβ), 19.5 (Val-Cγ), 19.1 (Hiv-Cγ), 18.5 (Hiv-Cγ), 17.5 (Thr-Cγ), 16.5 (Val-Cγ).

FTIR (thin film) cm$^{-1}$: 3395 (m), 3322 (br-s), 3252 (m), 2965 (m), 2930 (m), 2875 (w), 1726 (m), 1669 (s), 1613 (m), 1524 (m), 1307 (m), 750 (m).

HRMS (ESI) (m/z): calc'd for C$_{34}$H$_{49}$N$_7$NaO$_{11}$ [M+Na]$^+$: 754.3382, found: 754.3380.

$[α]_D^{23}$: +16 (c=0.10, CHCl$_3$)

TLC (9% methanol, 1% ammonium hydroxide in chloroform), Rf: 0.42 (UV, CAM).

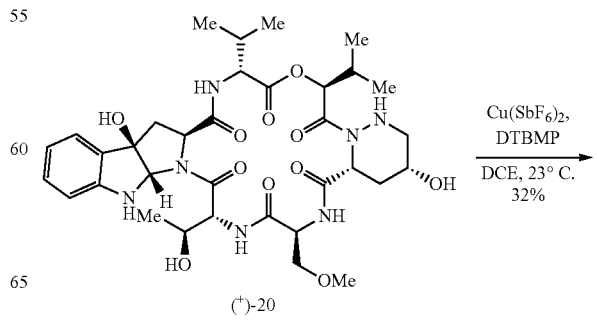

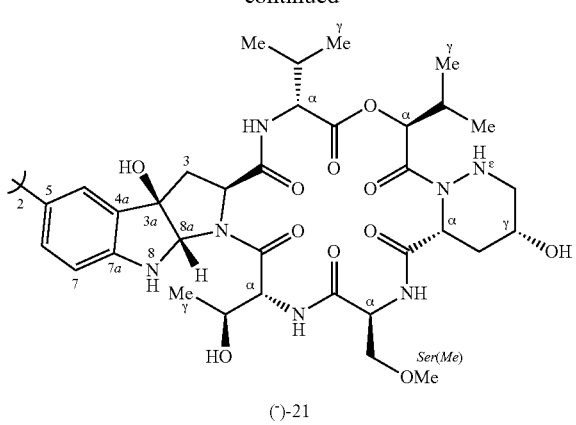

(−)-21

Himastatin Serine Derivative (−)-21:

Prepared according to the procedure described previously for (−)-himastatin (1) from serine cyclic depsihexapeptide (+)-20 (8.56 mg, 11.7 µmol, 1 equiv). Flash column chromatography on silica gel (eluent: 1.8% methanol, 0.2% ammonium hydroxide→3.6% methanol, 0.4% ammonium hydroxide in chloroform) afforded himastatin serine derivative (−)-21 (2.72 mg, 32%) as an off-white solid. Structural assignments were made using additional information from gCOSY, gHSQC, and gHMBC experiments.

$^1$H NMR (600 MHz, CDCl$_3$, 25° C.): δ 7.83 (d, J=5.7 Hz, 2H, Ser-NH), 7.59 (d, J=1.9 Hz, 2H, Trp-C4H), 7.44-7.41 (m, 4H, Val-NH, Trp-C6H), 7.02 (d, J=10.6 Hz, 2H, Thr-NH), 6.80 (d, J=8.3 Hz, 2H, Trp-C7H), 6.06 (d, J=6.1 Hz, 2H, Trp-N8H), 5.92 (s, 2H, Trp-C3aOH), 5.64 (d, J=8.9 Hz, 2H, Hiv-CαH), 5.41 (dd, J=12.9, 2.0 Hz, 2H, Pip-NεH), 5.26 (d, J=7.9 Hz, 2H, Trp-C2H), 5.23 (d, J=4.7 Hz, 2H, Trp-C8aH), 5.20 (d, J=5.2 Hz, 2H, Pip-CγOH), 5.15 (d, J=7.0 Hz, 2H, Pip-CαH), 5.09 (d, J=10.7 Hz, 2H, Thr-CαH), 4.83 (dd, J=9.7, 3.1 Hz, 2H, Val-CαH), 4.45 (q, J=6.5 Hz, 2H, Thr-CβH), 4.32 (app-dt, J=5.5, 2.7 Hz, 2H, Ser-CαH), 3.83-3.79 (m, 4H, Pip-CγH, Ser-CβH$_a$), 3.63 (br-s, 2H, Thr-CβOH), 3.44 (dd, J=9.6, 3.2 Hz, 2H, Ser-CβH$_b$), 3.31 (s, 6H, Ser-OCH$_3$), 3.06 (dd, J=14.3, 2.4 Hz, 2H, Pip-CδH$_a$), 2.84 (app-td, J=13.5, 1.4 Hz, 2H, Pip-CδH$_b$), 2.79 (d, J=14.3 Hz, 2H, Trp-C3H), 2.57 (septd, J=6.8, 3.1 Hz, 2H, Val-CβH), 2.49 (app-dp, J=14.3, 2.4 Hz, 2H, Pip-CβH$_a$), 2.21-2.14 (m, 4H, Trp-C3H$_b$, Hiv-CβH), 1.94 (ddd, J=15.0, 7.2, 3.4 Hz, 2H, Pip-CβH$_b$), 1.16 (d, J=6.5 Hz, 6H, Thr-CγH$_3$), 1.12 (d, J=6.6 Hz, 6H, Hiv-CγH$_3$), 1.00 (d, J=6.9 Hz, 12H, Hiv-CγH$_3$, Val-CγH$_3$), 0.85 (d, J=6.8 Hz, 6H, Val-CδH$_3$).

$^{13}$C NMR (150.9 MHz, CDCl$_3$, 25° C.): δ 174.1 (Hiv-CO), 173.5 (Val-CO), 173.3 (Pip-CO), 173.1 (Trp-CO), 172.0 (Thr-CO), 171.7 (Ser-CO), 147.0 (Trp-C7a), 134.4 (Trp-C5), 132.4 (Trp-C4a), 128.6 (Trp-C6), 121.5 (Trp-C4), 112.7 (Trp-C7), 91.2 (Trp-C3a), 86.0 (Trp-C8a), 77.3 (Hiv-Cα), 71.0 (Ser-Cβ), 66.8 (Thr-Cβ), 60.6 (Trp-C2), 59.8 (Ser-OCH$_3$), 58.9 (Pip-Cγ), 57.2 (Val-Cα), 56.3 (Ser-Cα), 54.2 (Thr-Cα), 52.8 (Pip-Cδ), 49.9 (Pip-Cα), 39.6 (Trp-C3), 30.4 (Val-Cβ), 30.0 (Hiv-Cβ), 28.8 (Pip-Cβ), 19.5 (Val-Cγ), 19.2 (Hiv-Cγ), 18.5 (Hiv-Cγ), 17.5 (Thr-Cγ), 16.5 (Val-Cγ).

FTIR (thin film) cm$^{-1}$: 3393 (m), 3316 (br-s), 2963 (m), 2930 (m), 2877 (w), 1727 (m), 1672 (s), 1620 (m), 1525 (m), 1307 (m), 1119 (w).

HRMS (ESI) (m/z): calc'd for C$_{68}$H$_{96}$N$_{14}$NaO$_{22}$ [M+Na]$^+$: 1483.6716, found: 1483.6715.

[α]$_D^{24}$: −37 (c=0.11, MeOH).

TLC (9% methanol, 1% ammonium hydroxide in chloroform), Rf: 0.33 (UV, CAM).

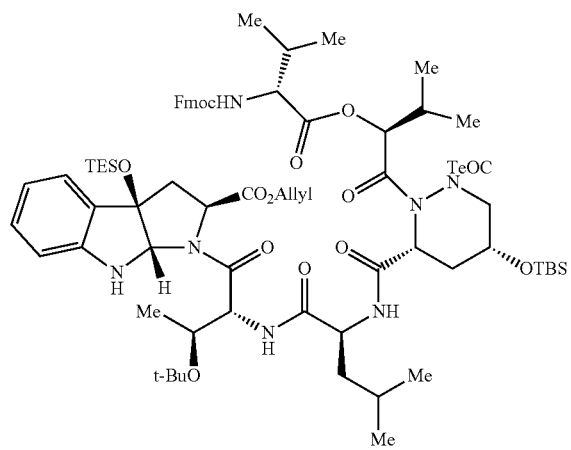

(−)-24

1. Pd(PPh$_3$)$_4$ N-methylaniline THF, 23° C.
2. i-Pr$_2$NH, MeCN, 23° C.
3. HATU, HOAt, i-Pr$_2$NEt CH$_2$Cl$_2$, 23° C.
4. TFA, H$_2$O, anisole CH$_2$Cl$_2$, 23° C.; Et$_3$N, MeOH, 23° C. 49% (four steps)

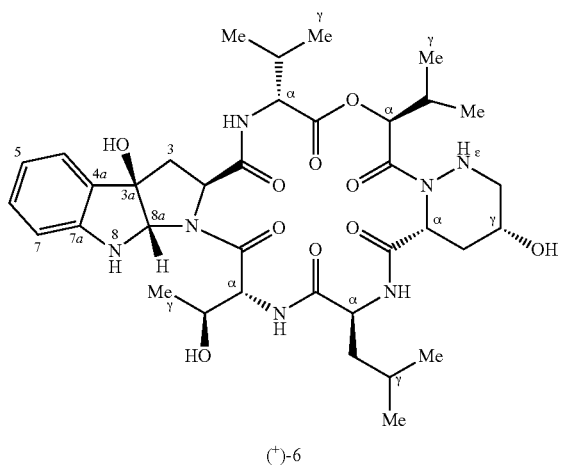

(+)-6

Himastatin Monomer (+)-6:

A solution of tetrakis(triphenylphosphine)palladium(0) (10 mM in degassed tetrahydrofuran, 110 μL, 1.1 μmol, $5.0\times10_{-3}$ equiv.) was added solution of hexadepsipeptide (−)-24 (320.6 mg, 0.221 mmol, 1 equiv.) and N-methylaniline (120 μL, 1.10 mmol, 5.00 equiv.) in degassed tetrahydrofuran (2.21 mL) at 23° C. After 1 h, the yellow solution was diluted with ethyl acetate (25 mL) and washed with an aqueous hydrogen chloride solution (1 M, 2×20 mL) and a saturated aqueous sodium chloride solution (20 mL). The organic layer was dried over anhydrous sodium sulfate, was filtered, and was concentrated under reduced pressure to provide the crude carboxylic acid, which was used in the next step without further purification.

Diisopropyl amine (5 mL) was added to a solution of the crude carboxylic acid in acetonitrile (5 mL) at 23° C. After 16 h, the reaction mixture was concentrated under reduced pressure to provide the crude amino acid, which was used in the next step without further purification.

N,N-Diisopropylethylamine (384 μL, 2.21 mmol, 10.0 equiv.) was added to a suspension of the crude amino acid, HATU (503 mg, 1.32 mmol, 6.00 equiv.), and HOAt (180 mg, 1.32 mmol, 6.00 equiv.) in dichloromethane (88 mL) at 23° C. After 2 days, the yellow heterogeneous solution was filtered through a pad of Celite. The filter cake washed with dichloromethane (50 mL) and the filtrate was concentrated under reduced pressure. The resulting residue was loaded onto a pad of silica gel with dichloromethane and was washed with 5% ethyl acetate in hexanes (200 mL). The crude protected macrocycle was obtained by eluting with 30% ethyl acetate in hexanes (200 mL), and was used in the next step without further purification.

Trifluoroacetic acid (2.0 mL) was added to a solution of the crude protected macrocycle, deionized water (80 μL, 4.4 mmol, 20 equiv.), and anisole (200 μL, 1.84 mmol, 8.34 equiv.) in dichloromethane (2.0 mL) at 23° C. After 2.5 h, the reaction mixture was diluted with toluene (2.5 ml) and concentrated under reduced pressure. The resulting residue was azeotropically dried by concentration from toluene (3×2.5 mL) under reduced pressure and was dissolved in methanol (2.0 mL) and triethylamine (400 μL, 2.87 mmol, 13.0 equiv.). After 2.5 h, the colorless solution was concentrated under reduced pressure and the resulting residue was purified by flash column chromatography on silica gel (eluent: 0.9% methanol, 0.1% ammonium hydroxide→3.6% methanol, 0.4% ammonium hydroxide in chloroform) to afford himastatin monomer (+)-6 (79.7 mg, 48.6%) as an off-white solid. Structural assignments were made using additional information from gCOSY, gHSQC, and gHMBC experiments.

$^1$H NMR (600 MHz, CDCl$_3$, 25° C.): δ 7.41 (d, J=5.1 Hz, 1H, Leu-NH), 7.35 (dd, J=7.4, 1.0 Hz, 1H, Trp-C4H), 7.30 (d, J=10.0 Hz, 1H, Val-NH), 7.20 (app-td, J=7.9, 1.1 Hz, 1H, Trp-C6H), 7.11 (d, J=10.5 Hz, 1H, Thr-NH), 6.91 (app-td, J=7.4, 0.9 Hz, 1H, Trp-C5H), 6.77 (dd, J=8.0, 0.9 Hz, 1H, Trp-C7H), 5.85 (br-s, 1H, Trp-C3aOH), 5.80 (d, J=6.3 Hz, 1H, Trp-N8H), 5.64 (d, J=8.6 Hz, 1H, Hiv-CαH), 5.42 (dd, J=12.9, 2.0 Hz, 1H, Pip-NεH), 5.21-5.19 (m, 2H, Trp-C2H, Pip-CγOH), 5.12 (dd, J=7.1, 1.7 Hz, 2H. Pip-CαH), 5.11 (d, J=6.4 Hz, 1H, Trp-C8aH) 4.97 (d, J=10.5 Hz, 1H, Thr-CαH), 4.89 (dd, J=10.0, 3.2 Hz, 1H, Val-CαH), 4.44 (qd, J=6.4, 1.4 Hz, 1H, Thr-CβH), 4.24 (ddd, J=10.8, 5.1, 3.6 Hz, 1H, Leu-CαH), 3.82 (app-sept, J=2.6 Hz, 1H, Pip-CγH), 3.61 (d, J=1.4 Hz, 1H, Thr-CβOH), 3.07 (app-dq, J=14.2, 2.3 Hz, 1H, Pip-CδH$_a$), 2.84 (app-t, J=13.5 Hz, 1H, Pip-CδH$_b$), 2.75 (d, J=14.4 Hz, 1H, Trp-C3H$_a$), 2.56 (septd, J=6.9, 3.2 Hz, 1H, Val-CβH), 2.49 (app-dp, J=15.1, 2.3 Hz, 1H, Pip-CβH$_a$), 2.21-2.12 (m, 2H, Trp-C3H$_b$, Hiv-CβH), 1.95 (ddd, J=15.1, 7.1, 3.4 Hz, 1H, Pip-CβH$_b$), 1.71-1.64 (m, 2H, Leu-CβH$_a$, Leu-CγH), 1.39 (dd, J=10.7, 8.7 Hz, 1H, Leu-CβH$_b$), 1.16 (d, J=6.6 Hz, 3H, Thr-CγH$_3$), 1.12 (d, J=6.6 Hz, 3H, Hiv-CγH$_3$), 1.00 (d, J=6.9 Hz, 6H, Hiv-CγH$_3$, Val-CγH$_3$), 0.93 (d, J=6.0 Hz, 3H, Leu-CδH$_3$), 0.87 (d, J=6.9 Hz, 3H, Val-CγH$_3$), 0.86 (d, J=5.7 Hz, 3H, Leu-CδH$_3$).

$^{13}$C NMR (150.9 MHz, CDCl$_3$, 25° C.): δ 174.2 (Hiv-CO), 174.1 (Leu-CO), 173.6 (Val-CO), 173.4 (Pip-CO), 173.2 (Trp-CO), 172.5 (Thr-CO), 147.9 (Trp-C7a), 131.9 (Trp-C4a), 130.0 (Trp-C6), 123.4 (Trp-C4), 121.2 (Trp-C5), 112.5 (Trp-C7), 91.0 (Trp-C3a), 86.1 (Trp-C8a), 77.5 (Hiv-Cα), 66.8 (Thr-Cβ), 60.9 (Trp-C2), 58.8 (Pip-Cγ), 57.3 (Val-Cα), 54.4 (Leu-Cα), 53.9 (Thr-Cα), 52.8 (Pip-Cδ), 50.1 (Pip-Cα), 41.1 (Leu-Cβ), 39.6 (Trp-C3), 30.1 (2C, Hiv-Cβ, Val-Cβ) 28.8 (Pip-Cβ), 25.4 (Leu-Cγ), 23.1 (Leu-Cδ), 21.1 (Leu-Cδ), 19.5 (Val-Cγ), 19.1 (Hiv-Cγ), 18.4 (Hiv-Cγ), 17.5 (Thr-Cγ), 16.6 (Val-Cγ).

FTIR (thin film) cm$^{-1}$: 3391 (m), 3326 (br-m), 3252 (w), 2964 (m), 2932 (m), 2876 (w), 1725 (m), 1671 (s), 1522 (m), 1228 (m), 1152 (m), 751 (s).

HRMS (ESI) (m/z): calc'd for C$_{36}$H$_{53}$N$_7$NaO$_{10}$ [M+Na]$^+$: 766.3746, found: 766.3741.

$[α]_D^{23}$: +34 (c=0.13, CHCl$_3$).[18]

TLC (9% methanol, 1% ammonium hydroxide in chloroform), Rf: 0.40 (UV, CAM).

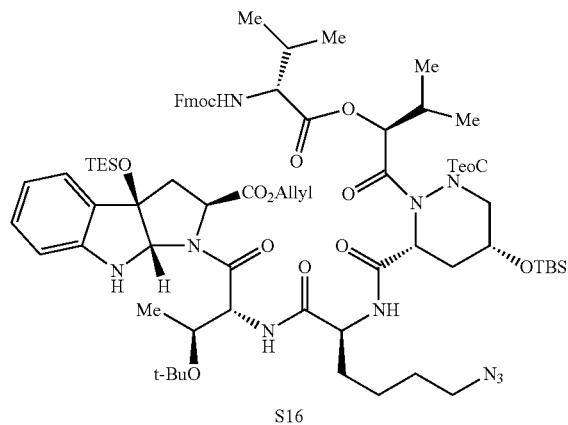

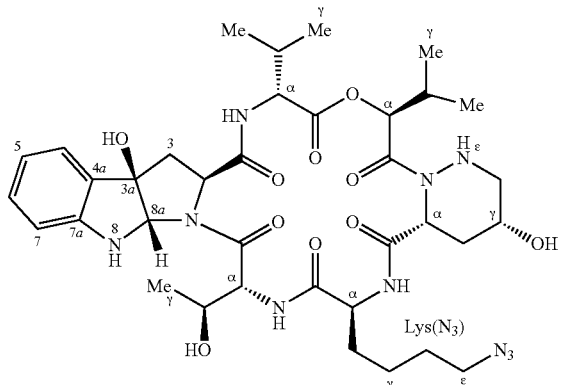

(+)-22

Azido Cyclic Depsihexapeptide (+)-22:

Prepared according to the procedure described previously for himastatin monomer (+)-2 from azido depsihexapeptide S16 (121.4 mg, 81.3 μmol, 1 equiv.). Azido cyclic depsihexapeptide (+)-22 was obtained by flash column chromatography on silica gel (eluent: 2.7% methanol, 0.3% ammonium hydroxide→4.5% methanol, 0.5% ammonium hydroxide in chloroform) as an off-white solid.

TABLE S1

| | Comparison of our $^1$H NMR data for (+)-Himastatin Monomer ((+)-6) with literature data (CDCl$_3$): | | |
|---|---|---|---|
| Assignment | Ju's Biosynthesis Report[15] (+)-Himastatin Monomer (6) $^1$H NMR, 500 MHz, CDCl$_3$ | Danishefsky's Report (+)-Himastatin Monomer (6) $^1$H NMR, 500 MHz, CDCl$_3$ | This Work (+)-Himastatin Monomer (6) $^1$H NMR, 600 MHz, CDCl$_3$ |
| | Trp | | |
| $C_2H$ | 5.20 (d, J = 8.0 Hz, 1H) | 5.20-5.18 (m, 2H) | 5.21-5.19 (m, 2H) |
| $C_3H_2$ | 2.75 (d, J = 14.5 Hz, 1H) 2.16 (m, 1H) | 2.74 (d, J = 14.3 Hz, 1H) 2.25-2.10 (m, 2H) | 2.75 (d, J = 14.4 Hz, 1H) 2.21-2.12 (m, 2H) |
| $C_{3a}OH$ | 5.89 (br-s, 1H) | 5.85 (s, 1H) | 5.85 (br-s, 1H) |
| $C_4H$ | 7.34 (d, J = 7.0 Hz, 1H) | 7.33 (d, J = 7.4 Hz, 1H) | 7.35 (dd, J = 7.4, 1.0 Hz, 1H) |
| $C_5H$ | 6.90 (t, J = 7.0 Hz, 1H) | 6.89 (t, J = 7.4 Hz, 1H) | 6.90 (app-td, J = 7.5, 0.9 Hz, 1H) |
| $C_6H$ | 7.19 (d, J = 8.0 Hz, 1H) | 7.19 (t, J = 7.6 Hz, 1H) | 7.20 (app-td, J = 7.9, 1.1 Hz, 1H) |
| $C_7H$ | 6.77 (d, J = 8.0 Hz, 1H) | 6.76 (d, J = 7.9 Hz, 1H) | 6.77 (dd, J = 8.0, 0.9 Hz, 1H) |
| $N_8H$ | 5.79 (d, J = 6.5 Hz, 1H) | 5.80 (br-s, 1H) | 5.80 (d, J = 6.3 Hz, 1H) |
| $C_{8a}H$ | 5.11 (d, J = 6.5 Hz, 1H) | 5.13-5.10 (m, 2H) | 5.11 (d, J = 6.4 Hz, 1H) |
| | Thr | | |
| NH | 7.11 (d, J = 10.5 Hz, 1H) | 7.10 (d, J = 10.4 Hz, 1H) | 7.11 (d, J = 10.5 Hz, 1H) |
| $C_\alpha H$ | 4.97 (d, J = 10.5 Hz, 1H) | 4.96 (d, J = 10.5 Hz, | 4.97 (d, J = 10.5 Hz, 1H) |
| $C_\beta H$ | 4.43 (q, J = 6.4 Hz, 1H) | 4.45-4.40 (m, 1H) | 4.44 (qd, J = 6.4, 1.4 Hz, 1H) |
| $C_\beta OH$ | 3.61 (br-s, 1H) | 3.61 (s, 1H) | 3.61 (d, J = 1.4 Hz, 1H) |
| $C_\gamma H_3$ | 1.15 (d, J = 6.4, 3H) | 1.15 (d, J = 6.5, 3H) | 1.16 (d, J = 6.6 Hz, 3H) |

TABLE S1-continued

Comparison of our $^1$H NMR data for (+)-Himastatin Monomer ((+)-6) with literature data (CDCl$_3$):

| Assignment | Ju's Biosynthesis Report[15] (+)-Himastatin Monomer (6) $^1$H NMR, 500 MHz, CDCl$_3$ | Danishefsky's Report (+)-Himastatin Monomer (6) $^1$H NMR, 500 MHz, CDCl$_3$ | This Work (+)-Himastatin Monomer (6) $^1$H NMR, 600 MHz, CDCl$_3$ |
|---|---|---|---|
| | Leu | | |
| NH | 7.41 (d, J = 5.0 Hz, 1H) | 7.41 (d, J = 4.8 Hz, 1H) | 7.41 (d, J = 5.1 Hz, 1H) |
| C$_\alpha$H | 4.23 (m 1H) | 4.28-4.23 (m, 1H) | 4.24 (ddd, J = 10.8, 5.1, 3.6 Hz, 1H) |
| C$_\beta$H$_2$ | 1.68 (m, 1H) | 1.80-1.62 (m, 2H) | 1.71-1.64 (m, 2H) |
| | 1.38 (dd, J = 10.5, 9.0 Hz, 1H) | 1.42-1.35 (m, 1H) | 1.39 (dd, J = 10.7, 8.7 Hz, 1H) |
| C$_\gamma$H | 1.68 (m, 1H) | 1.80-1.62 (m, 2H) | 1.71-1.64 (m, 2H) |
| C$_\delta$H$_3$ | 0.92 (d, J = 6.0 Hz, 3H) | 0.91 (d, J = 5.6 Hz, 3H) | 0.93 (d, J = 6.0 Hz, 3H) |
| | 0.86 (d, J = 5.6 Hz, 3H) | 0.85 (d, J = 6.5 Hz, 3H) | 0.86 (d, J = 5.7 Hz, 3H) |
| | Pip | | |
| C$_\alpha$H | 5.12 (d, J = 8.5 Hz, 1H) | 5.13-5.10 (m, 2H) | 5.12 (dd, J = 7.1, 1.7 Hz, 1H) |
| C$_\beta$H$_2$ | 2.49 (d, J = 15.0 Hz, 1H) | 2.48 (d, J = 15.1 Hz, 1H) | 2.49 (app-dp, J = 15.1, 2.3 Hz, 1H) |
| | 1.95 (ddd, J = 15.0, 7.0, 3.0 Hz, 1H) | 2.00-1.88 (m, 1H) | 1.95 (ddd, J = 15.1,7.1, 3.4 Hz, 1H) |
| C$_\gamma$H | 3.81 (br-s, 1H) | 3.81 (s, 1H) | 3.82 (app-sept, J = 2.6 Hz, 1H) |
| C$_\gamma$OH | 5.20 (d, J = 5.0 Hz, 1H) | 5.20-5.18 (m, 2H) | 5.21-5.19 (m, 2H) |
| C$_\delta$H$_2$ | 3.07 (d, J = 14.5 Hz, 1H) | 3.06 (d, J = 14.0 Hz, 1H) | 3.07 (app-dq, J = 14.2, 2.3 Hz, 1H) |
| | 2.83 (t, J = 13.5 Hz, 1H) | 2.83 (t, J = 13.2 Hz, 1H) | 2.84 (app-t, J = 13.5 Hz, 1H) |
| N$_\epsilon$H | 5.42 (d, J = 11.5 Hz, 1H) | 5.41 (d, J = 12.6 Hz, 1H) | 5.42 (dd, J = 12.9, 2.0 Hz, 1H) |
| | Hiv | | |
| C$_\alpha$H | 5.64 (d, J = 8.5 Hz, 1H) | 5.63 (d, J = 8.6 Hz, 1H) | 5.64 (d, J = 8.6 Hz, 1H) |
| C$_\beta$H | 2.16 (m, 1H) | 2.25-2.10 (m, 2H) | 2.21-2.12 (m, 2H) |
| C$_\gamma$H$_3$ | 1.12 (d, J = 6.6 Hz, 3H) | 1.11 (d, J = 6.6 Hz, 3H) | 1.12 (d, J = 6.6 Hz, 3H) |
| | 1.00 (d, J = 6.8 Hz, 6H) | 1.00 (d, J = 6.8 Hz, 6H) | 1.00 (d, J = 6.9 Hz, 6H) |
| | Val | | |
| NH | 7.30 (d, J = 10.0 Hz, 1H) | 7.29 (d, J= 10.0 Hz, 1H) | 7.30 (d, J = 10.0 Hz, 1H) |
| C$_\alpha$H | 4.89 (dd, J = 10.0, 3.0 Hz, 1H) | 4.89 (dd, J = 9.9, 2.9 Hz, 1H) | 4.89 (dd, J = 10.0, 3.2 Hz, 1H) |
| C$_\beta$H | 2.56 (m, 1H) | 2.60-2.50 (m, 1H) | 2.56 (septd, J = 6.9, 3.2 Hz, 1H) |
| C$_\gamma$H$_3$ | 1.00 (d, J = 6.8 Hz, 6H) | 1.00 (d, J = 6.8 Hz, 6H) | 1.00 (d, J = 6.9 Hz, 6H) |
| | 0.87 (d, J = 6.8 Hz, 3H) | 0.86 (d, J = 6.5 Hz, 3H) | 0.87 (d, J = 6.9 Hz, 3H) |

TABLE S2

Comparison of our $^{13}$C NMR data for (+)-Himastatin Monomer ((+)-6) with literature data (CDCl$_3$):

| Assignment | Ju's Biosynthesis Report (+)-Himastatin Monomer (6) $^{13}$C NMR, 125 MHz, CDCl$_3$ | Danishefsky's Report (+)-Himastatin Monomer (6) $^{13}$C NMR, 125 MHz, CDCl$_3$ | This Work (+)-Himastatin Monomer (6) $^{13}$C NMR, 150.9 MHz, CDCl$_3$ | Chemical Shift Difference $\Delta\delta = \delta$ (this work) − $\delta$ (Ju's report) |
|---|---|---|---|---|
| | Trp | | | |
| CO | 173.0 | 173.0 | 173.2 | 0.2 |
| C$_2$ | 60.8 | 60.7 | 60.9 | 0.1 |
| C$_3$ | 39.4 | 39.4 | 39.6 | 0.2 |
| C$_{3a}$ | 90.8 | 90.8 | 91.0 | 0.2 |
| C$_{4a}$ | 131.7 | 131.7 | 131.9 | 0.2 |
| C$_4$ | 123.2 | 123.2 | 123.4 | 0.2 |
| C$_5$ | 121.0 | 121.0 | 121.2 | 0.2 |
| C$_6$ | 129.9 | 129.8 | 130.0 | 0.1 |
| C$_7$ | 112.4 | 112.3 | 112.5 | 0.1 |
| C$_{7a}$ | 147.8 | 147.7 | 147.9 | 0.1 |
| C$_{8a}$ | 86.0 | 85.9 | 86.1 | 0.1 |
| | Thr | | | |
| CO | 172.4 | 172.3 | 172.5 | 0.1 |
| C$_\alpha$ | 53.8 | 53.8 | 53.9 | 0.1 |
| C$_\beta$ | 66.7 | 66.6 | 66.8 | 0.1 |
| C$_\gamma$ | 17.4 | 17.3 | 17.5 | 0.1 |

TABLE S2-continued

Comparison of our $^{13}$C NMR data for (+)-Himastatin
Monomer ((+)-6) with literature data (CDCl$_3$):

| Assignment | Ju's Biosynthesis Report (+)-Himastatin Monomer (6) $^{13}$C NMR, 125 MHz, CDCl$_3$ | Danishefsky's Report (+)-Himastatin Monomer (6) $^{13}$C NMR, 125 MHz, CDCl$_3$ | This Work (+)-Himastatin Monomer (6) $^{13}$C NMR, 150.9 MHz, CDCl$_3$ | Chemical Shift Difference $\Delta\delta = \delta$ (this work) − $\delta$ (Ju's report) |
|---|---|---|---|---|
| | | Leu | | |
| CO | 173.9 | 173.9 | 174.1 | 0.2 |
| $C_\alpha$ | 54.3 | 54.2 | 54.4 | 0.1 |
| $C_\beta$ | 40.9 | 40.9 | 41.1 | 0.2 |
| $C_\gamma$ | 25.3 | 25.2 | 25.4 | 0.1 |
| $C_\delta$ | 23.0 | 22.9 | 23.1 | 0.1 |
| | 21.0 | 20.9 | 21.1 | 0.1 |
| | | Pip | | |
| CO | 173.3 | 173.2 | 173.4 | 0.1 |
| $C_\alpha$ | 49.9 | 49.9 | 50.1 | 0.2 |
| $C_\beta$ | 28.6 | 28.6 | 28.8 | 0.2 |
| $C_\gamma$ | 58.7 | 58.6 | 58.8 | 0.1 |
| $C_\delta$ | 52.6 | 52.6 | 52.8 | 0.2 |
| | | Hiv | | |
| CO | 174.1 | 174.1 | 174.2 | 0.1 |
| $C_\alpha$ | 77.2 | — | 77.5 | 0.3 |
| $C_\beta$ | 29.9 | 29.9 | 30.1 | 0.2 |
| $C_\gamma$ | 18.9 | 18.9 | 19.1 | 0.2 |
| | 18.3 | 18.2 | 18.4 | 0.1 |
| | | Val | | |
| CO | 173.5 | 173.4 | 173.6 | 0.1 |
| $C_\alpha$ | 57.2 | 57.2 | 57.3 | 0.1 |
| $C_\beta$ | 30.0 | 30.0 | 30.1 | 0.1 |
| $C_\gamma$ | 19.4 | 19.3 | 19.5 | 0.1 |
| | 16.4 | 16.4 | 16.6 | 0.2 |

40

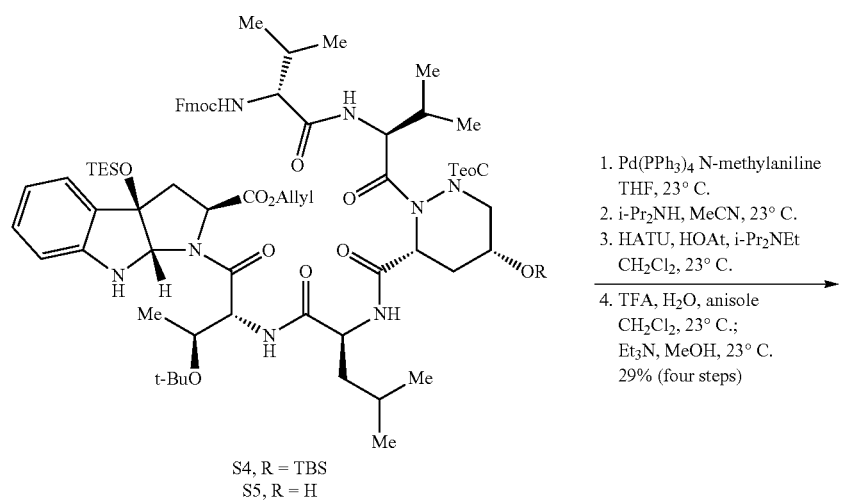

1. Pd(PPh$_3$)$_4$ N-methylaniline THF, 23° C.
2. i-Pr$_2$NH, MeCN, 23° C.
3. HATU, HOAt, i-Pr$_2$NEt CH$_2$Cl$_2$, 23° C.
4. TFA, H$_2$O, anisole CH$_2$Cl$_2$, 23° C.; Et$_3$N, MeOH, 23° C. 29% (four steps)

S4, R = TBS
S5, R = H

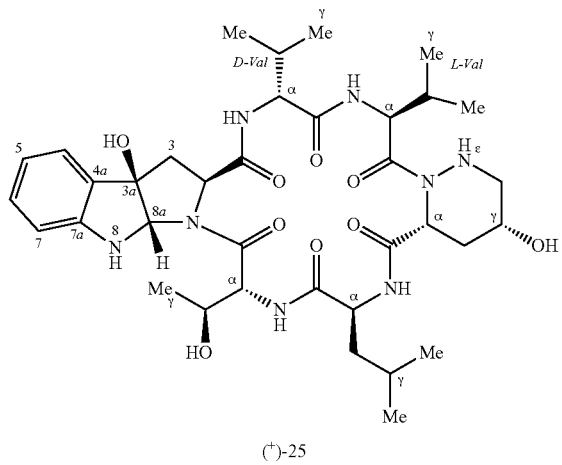

(+)-25

Cyclic Hexapeptide (+)-25:

Prepared according to a scale-down of the procedure described previously for himastatin monomer (+)-6 from hexapeptide tert-butyldimethylsilyl ether S4 (47.0 mg, 32.4 μmol, 0.329 equiv.) and hexapeptide S5 (88.2 mg, 65.9 μmol, 0.671 equiv.). Cyclic hexapeptide (+)-25 was obtained by flash column chromatography on silica gel (eluent: 2.7% methanol, 0.3% ammonium hydroxide→4.5% methanol, 0.5% ammonium hydroxide in chloroform) as an off-white solid (21.4 mg, 29.3%). Structural assignments were made using additional information from gCOSY, gHSQC, and gHMBC experiments.

$^1$H NMR (600 MHz, CDCl$_3$, 25° C.): δ 7.67 (d, J=9.1 Hz, 1H, D-Val-NH), 7.37 (d, J=5.9 Hz, 1H, Leu-NH), 7.33 (dd, J=7.5, 1.3 Hz, 1H, Trp-C4H), 7.18 (app-td, J=7.7, 1.3 Hz, 1H, Trp-C6H), 6.88 (app-td, J=7.4, 0.9 Hz, 1H, Trp-C5H), 6.74 (dd, J=7.9, 0.9 Hz, 1H, Trp-C7H), 6.73 (d, J=10.3 Hz, 1H, Thr-NH), 6.17 (d, J=7.6 Hz, 1H, L-Val-NH), 5.98 (br-s, 1H, Trp-C3aOH), 5.83 (d, J=6.2 Hz, 1H, Trp-N8H), 5.50 (app-t, J=7.4 Hz, 1H, L-ValCαH), 5.39 (dd, J=12.9, 2.1 Hz, 1H, Pip-NεH), 5.35 (d, J=5.7 Hz, 1H, Pip-CγOH), 5.19 (d, J=8.2 Hz, 1H, Trp-C2H), 5.15 (d, J=6.1 Hz, 1H, Trp-C8aH), 5.11 (d, J=7.1 Hz, 1H, Pip-CαH), 4.82 (d, J=10.3 Hz, 1H, Thr-CαH), 4.53 (qd, J=6.6, 2.4 Hz, 1H, Thr-CβH), 4.41 (dd, J=9.1, 5.5 Hz, 1H, D-Val-CαH), 4.30 (ddd, J=10.4, 5.9, 3.9 Hz, 1H, Leu-CαH), 3.82-3.78 (m, 1H, Pip-CγH), 3.72 (d, J=2.4 Hz, 1H, Thr-CβOH), 3.09 (app-dq, J=14.2, 2.4 Hz, 1H, Pip-CδH$_a$), 2.85 (app-td, J=13.5, 1.5 Hz, 1H, Pip-CδH$_b$), 2.71 (d, J=14.3 Hz, 1H, Trp-C3H$_a$), 2.45-2.40 (m, 1H, Pip-CβH$_a$), 2.14 (dd, J=14.3, 8.3 Hz, 1H, Trp-C3H$_b$), 2.11-2.04 (m, 1H, D-Val-CβH), 2.02-1.94 (m, 2H, Pip-CβH$_b$, L-Val-CβH), 1.74-1.63 (m, 2H, Leu-CβH$_a$, Leu-CγH), 1.44 (ddd, J=13.1, 10.6, 4.5 Hz, 1H, Leu-CβH$_b$), 1.11 (d, J=6.5 Hz, 3H, Thr-CγH$_3$), 1.02 (d, J=6.7 Hz, 3H, D-Val-CγH$_3$), 1.00 (d, J=6.8 Hz, 6H, L-Val-CγH$_3$), 0.94 (d, J=6.8 Hz, 3H, D-Val-CγH$_3$), 0.93 (d, J=6.3 Hz, 3H, Leu-CδH$_3$), 0.86 (d, J=6.3 Hz, 3H, Leu-CδH$_3$).

$^{13}$C NMR (150.9 MHz, CDCl$_3$, 25° C.): δ 176.3 (L-Val-CO), 174.4 (Leu-CO), 173.2 (Pip-CO), 172.8 (Trp-CO), 171.6 (Thr-CO), 171.1 (D-Val-CO), 147.8 (Trp-C7a), 131.6 (Trp-C4a), 129.9 (Trp-C6), 123.2 (Trp-C4), 120.9 (Trp-C5), 112.3 (Trp-C7), 91.0 (Trp-C3a), 86.2 (Trp-C8a), 66.4 (Thr-Cβ), 61.5 (Trp-C2), 58.9 (D-Val-Cα), 58.6 (Pip-Cγ), 54.7 (Thr-Cα), 54.1 (2C, Leu-Cα, L-Val-Cα), 52.7 (Pip-Cδ), 50.1 (Pip-Cα), 40.9 (Leu-Cβ), 39.5 (Trp-C3), 32.2 (D-Val-Cβ), 30.8 (L-Val-Cβ), 28.9 (Pip-Cβ), 25.5 (Leu-Cγ), 23.1 (Leu-Cδ), 21.2 (Leu-Cδ), 19.8 (L-Val-Cγ), 19.6 (D-Val-Cγ), 18.6 (L-Val-Cγ), 17.4 (2C, Thr-Cγ, D-Val-Cγ).

FTIR (thin film) cm$^{-1}$: 3296 (br-s), 2962 (m), 2873 (m), 1647 (s), 1529 (m), 1250 (m), 752 (m).

HRMS (ESI) (m/z): calc'd for C$_{36}$H$_{54}$N$_8$NaO$_9$ [M+Na]$^+$: 765.3906, found: 765.3904.

[α]$_D^{23}$: +46 (c=0.10, CHCl$_3$)

TLC (9% methanol, 1% ammonium hydroxide in chloroform), Rf: 0.31 (UV, CAM).

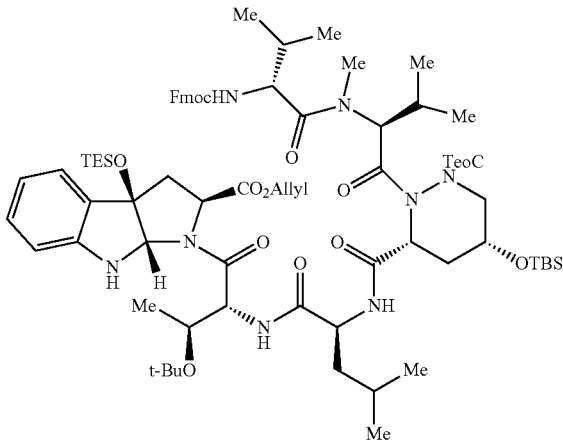

1. Pd(PPh$_3$)$_4$ N-methylaniline THF, 23° C.
2. i-Pr$_2$NH, MeCN, 23° C.
3. HATU, HOAt, i-Pr$_2$NEt CH$_2$Cl$_2$, 23° C.
4. TFA, H$_2$O, anisole CH$_2$Cl$_2$, 23° C.; Et$_3$N, MeOH, 23° C. 26% (four steps)

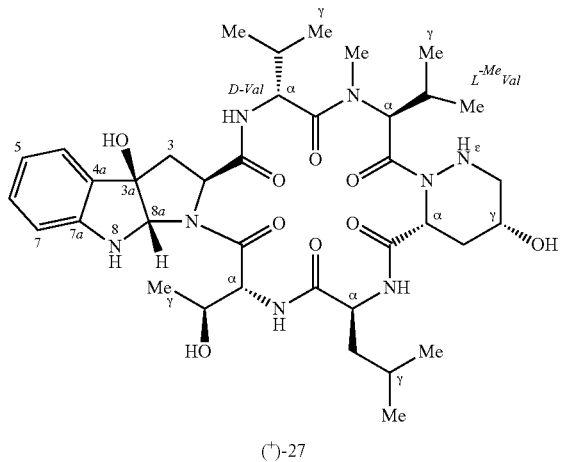

(+)-27

N-Methyl Cyclic Hexapeptide (+)-27:

Prepared according to a scale-down of the procedure described previously for himastatin monomer (+)-6 from N-methyl hexapeptide S6 (57.0 mg, 38.9 μmol, 1 equiv.). N-Methyl cyclic hexapeptide (+)-27 was obtained by flash column chromatography on silica gel (eluent: 2.7% methanol, 0.3% ammonium hydroxide→4.5% methanol, 0.5% ammonium hydroxide in chloroform) as an off-white solid (7.7 mg, 26%). Structural assignments were made using additional information from gCOSY, gHSQC, and gHMBC experiments.

$^1$H NMR (600 MHz, CDCl$_3$, 25° C.): δ 7.99 (d, J=9.1 Hz, 1H, D-Val-NH), 7.34 (dd, J=7.5, 1.3 Hz, 1H, Trp-C4H), 7.25 (d, J=5.1 Hz, 1H, Leu-NH), 7.19 (ddd, J=8.0, 7.4, 1.3 Hz, 1H, Trp-C6H), 6.89 (app-td, J=7.4, 0.9 Hz, 1H, Trp-C5H), 6.75 (dd, J=8.0, 0.8 Hz, 1H, Trp-C7H), 6.61 (d, J=10.2 Hz, 1H, Thr-NH), 5.89 (d, J=6.3 Hz, 1H, Trp-N8H), 5.82 (s, 1H, Trp-C3aOH), 5.77 (d, J=11.2 Hz, 1H, L-$^{Me}$Val-CαH), 5.75 (dd, J=12.7, 2.1 Hz, 1H, Pip-NεH), 5.30 (d, J=8.1 Hz, 1H, Trp-C2H), 5.20 (dd, J=13.1, 1.5 Hz, 1H, Pip-CαH), 5.13 (d, J=6.2 Hz, 1H, Trp-C8aH), 4.96 (dd, J=9.2, 3.2 Hz, 1H, D-Val-CαH), 4.94 (d, J=5.2 Hz, 1H, Pip-CγOH), 4.85 (d, J=10.2 Hz, 1H, Thr-CαH), 4.55 (qd, J=6.6, 1.9 Hz, 1H, Thr-CβH), 4.27 (ddd, J=9.1, 5.0, 3.7 Hz, 1H, Leu-CαH), 4.02 (s, 1H, Thr-CβOH), 3.80 (app-sept, J=2.6 Hz, 1H, Pip-CγH), 3.28 (s, 3H, L-$^{Me}$Val-NCH$_3$), 3.09 (app-dq, J=14.3, 2.4 Hz, 1H, Pip-CδH$_a$), 2.87 (dd, J=7.2, 1.4 Hz, 1H, Pip-CδH$_b$), 2.80 (d, J=14.3 Hz, 1H, Trp-C3H$_a$), 2.51-2.46 (m, 1H, Pip-CβH$_a$), 2.24-2.16 (m, 1H, L-$^{Me}$Val-CβH), 2.12 (dd, J=14.2, 8.0 Hz, 1H, Trp-C3H$_b$), 2.11-2.05 (m, 1H, D-Val-CβH), 1.93 (ddd, J=15.1, 7.3, 3.4 Hz, 1H, Pip-CβH$_b$), 1.70-1.63 (m, 2H, Leu-CβH$_a$, Leu-CγH), 1.50-1.43 (m, 1H, Leu-CβH$_b$), 1.14 (dd, J=6.6, 0.9 Hz, 3H, Thr-CγH$_3$), 1.04 (d, J=6.7 Hz, 3H, L-$^{Me}$Val-CγH$_3$), 1.01 (d, J=6.8 Hz, 3H, D-Val-CγH$_3$), 0.98 (d, J=6.5 Hz, 3H, L-$^{Me}$Val-CγH$_3$), 0.91 (d, J=6.0 Hz, 3H, Leu-CδH$_3$), 0.86 (d, J=6.0 Hz, 3H, Leu-CδH$_3$), 0.82 (d, J=6.8 Hz, 3H, D-Val-CγH$_3$).

$^{13}$C NMR (150.9 MHz, CDCl$_3$, 25° C.): δ 177.0 (L-$^{Me}$Val-CO), 174.2 (Pip-CO), 174.1 (Leu-CO), 173.4 (D-Val-CO), 172.8 (Trp-CO), 171.7 (Thr-CO), 147.9 (Trp-C7a), 131.7 (Trp-C4a), 130.0 (Trp-C6), 123.3 (Trp-C4), 121.0 (Trp-C5), 112.4 (Trp-C7), 91.2 (Trp-C3a), 85.9 (Trp-C8a), 66.4 (Thr-Cβ), 60.9 (Trp-C2), 58.9 (Pip-Cγ), 57.9 (L-$^{Me}$Val-Cα), 55.5 (D-Val-Cα), 54.5 (Thr-Cα), 54.3 (Leu-Cα), 52.5 (Pip-Cδ), 49.3 (Pip-Cα), 40.8 (Leu-Cβ), 39.3 (Trp-C3), 31.9 (L-$^{Me}$Val NCH$_3$), 30.8 (D-Val-Cβ), 28.7 (Pip-Cβ), 28.0 (L-$^{Me}$Val-Cβ), 25.6 (Leu-Cγ), 23.2 (Leu-Cδ), 21.5 (Leu-Cδ), 20.6 (L-$^{Me}$Val-Cγ), 20.1 (D-Val-Cγ), 19.6 (L-$^{Me}$Val-Cγ), 17.3 (Thr-Cγ), 16.0 (D-Val-Cγ).

FTIR (thin film) cm$^{-1}$: 3406 (br-m), 3330 (br-s), 3285 (br-s), 2961 (m), 2930 (m), 2873 (w), 1660 (s), 1633 (s), 1470 (w), 1260 (m), 1101 (m), 750 (m).

HRMS (ESI) (m/z): calc'd for C$_{37}$H$_{56}$N$_8$NaO$_9$ [M+Na]$^+$: 779.4062, found: 779.4059.

[α]$_D^{23}$: +32 (c=0.10, CHCl$_3$)

TLC (9% methanol, 1% ammonium hydroxide in chloroform), Rf: 0.36 (UV, CAM).

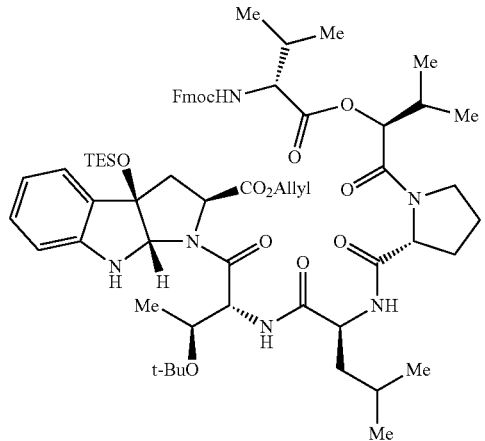

1. Pd(PPh$_3$)$_4$ N-methylaniline THF, 23° C.
2. i-Pr$_2$NH, MeCN, 23° C.
3. HATU, HOAt, i-Pr$_2$NEt CH$_2$Cl$_2$, 23° C.
4. TFA, H$_2$O, anisole CH$_2$Cl$_2$, 23° C.; Et$_3$N, MeOH, 23° C. 36% (four steps)

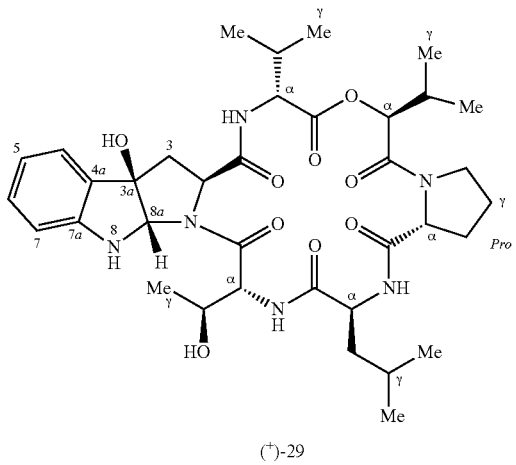

(+)-29

Proline Cyclic Depsihexapeptide (+)-29:

Prepared according to a scale-up of the procedure described previously for himastatin monomer (+)-6 from S7 (194.9 mg, 0.168 mmol, 1 equiv.). Proline cyclic depsihexapeptide (+)-29 was obtained by flash column chromatography on silica gel (eluent: 3.6% methanol, 0.4% ammonium hydroxide→5.4% methanol, 0.6% ammonium hydroxide in chloroform) as an off-white solid (42.9 mg, 35.9%). Structural assignments were made using additional information from gCOSY, gHSQC, and gHMBC experiments.

$^1$H NMR (600 MHz, CDCl$_3$, 25° C., 7.5:1 mixture of conformers, * denotes minor conformer): δ 7.91 (d, J=9.2 Hz, 1H, Leu-NH), 7.73 (br-s, 1H, Thr-NH*), 7.30 (dd, J=7.5, 1.3 Hz, 1H, Trp-C4H), 7.27 (dd, J=7.0, 1.2 Hz, 1H, Trp-C4H*), 7.17 (app-td, J=7.7, 1.3 Hz, 1H, Trp-C6H*), 7.13 (app-td, J=7.7, 1.3 Hz, 1H, Trp-C6H), 6.88 (d, J=7.8 Hz, 1H, Val-NH), 6.84 (d, J=8.5 Hz, 1H, Thr-NH), 6.81 (app-td, J=7.4, 0.9 Hz, 2H, Trp-C5H, Trp-C5H*), 6.71-6.65 (m, 2H, Trp-C7H*, Val-NH*), 6.57 (dd, J=7.9, 0.9 Hz, 1H, Trp-C7H), 5.90 (br-s, 1H, Leu-NH*), 5.82 (br-s, 1H, Trp-N8H*), 5.76 (d, J=4.7 Hz, 2H, Trp-C8aH, Trp-C8aH*), 5.57 (br-s, 1H, Trp-N8H), 5.47 (s, 1H, Trp-C3aOH), 5.24 (br-s, 1H, Trp-C3aOH*), 5.10 (d, J=9.9 Hz, 1H, Hiv-CαH), 4.95 (dd, J=8.1, 3.2 Hz, 1H, Val-CαH), 4.90 (d, J=8.9 Hz, 1H, Trp-C2H), 4.77 (d, J=7.6 Hz, 1H, Pro-CαH), 4.75 (d, J=10.5 Hz, 1H, Hiv-CαH*), 4.62 (app-t, J=8.4 Hz, 1H, Thr-CαH), 4.49 (dd, J=8.6, 6.3 Hz, 1H, Thr-CαH*), 4.46 (dd, J=8.7, 7.6 Hz, 1H, Val-CαH*), 4.35 (ddd, J=10.1, 7.9, 4.4 Hz, 1H, Leu-CαH*), 4.25 (app-td, J=9.6, 5.4 Hz, 2H, Leu-CαH, Trp-C2H*), 4.22-4.18 (m, 1H, Pro-CδH$_a$*), 4.16 (dd, J=7.1, 2.9 Hz, 1H, Pro-CαH*), 4.06-3.99 (m, 2H, Thr-CβH, Thr-CβH*), 3.93 (app-td, J=9.5, 2.1 Hz, 1H, Pro-CδH$_a$), 3.69 (br-s, 2H, Thr-CδOH, Thr-CδOH*), 3.49 (app-td, J=10.0, 7.4 Hz, 2H, Pro-CδH$_b$, Pro-CδH$_b$*), 2.72 (dd, J=12.9, 7.4 Hz, 1H, Trp-C3H$_a$*), 2.52 (app-dd, J=14.1, 9.1 Hz, 2H, Trp-C3H$_a$, Trp-C3H$_b$*), 2.51-2.44 (m, 1H, Pro-CβH$_a$), 2.45-2.39 (m, 3H, Hiv-COH, Val-CβH, Pro-CβH$_a$*), 2.37 (d, J=14.1 Hz, 1H, Trp-C3H$_b$*), 2.25-2.18 (m, 1H, Hiv-CβH*), 2.14-2.02 (m, 3H, Pro-CγH$_a$, Pro-CγH$_a$*, Pro-CβH$_b$*), 2.02-1.96 (m, 2H, Pro-CγH$_b$, Pro-CγH$_b$*), 1.95-1.88 (m, 1H, Val-CβOH*), 1.85 (ddd, J=13.9, 8.9, 4.5 Hz, 1H, Leu-CβH$_a$*), 1.74-1.65 (m, 2H, Pro-CβH$_b$, Leu-CγH*), 1.65-1.58 (m, 1H, Leu-CγH), 1.55 (ddd, J=13.9, 9.9, 5.4 Hz, 1H, Leu-CβH$_a$), 1.51-1.45 (m, 1H, Leu-CβH$_b$*), 1.41 (ddd, J=14.0, 8.7, 5.4 Hz, 1H, Leu-CβH$_b$), 1.30 (d, J=6.4 Hz, 3H, Thr-CγH$_3$*), 1.22 (d, J=6.2 Hz, 3H, Thr-CγH$_3$), 1.06 (d, J=6.6 Hz, 3H, Hiv-CγH$_3$*), 1.05 (d, J=6.6 Hz, 3H, Hiv-CγH$_3$), 1.03 (d, J=6.9 Hz, 3H, Val-CγH$_3$), 0.95 (d, J=6.9 Hz, 6H, Hiv-CγH$_3$, Leu-CδH$_3$*), 0.94 (d, J=6.7 Hz, 6H, Hiv-CγH$_3$*, Val-CγH$_3$*), 0.92 (d, J=6.4 Hz, 6H, Leu-CδH$_3$*, Val-CγH$_3$*), 0.89 (d, J=6.6 Hz, 3H, Leu-CδH$_3$), 0.87 (d, J=6.9 Hz, 3H, Val-CγH$_3$), 0.84 (d, J=6.5 Hz, 3H, Leu-CδH$_3$).

$^{13}$C NMR (150.9 MHz, CDCl$_3$, 25° C., major conformer): δ 173.4 (Trp-CO), 172.8 (Thr-CO), 171.9 (Hiv-CO), 171.3 (Leu-CO), 170.9 (Pro-CO), 169.6 (Val-CO), 147.3 (Trp-C7a), 130.8 (Trp-C4a), 129.8 (Trp-C6), 123.1 (Trp-C4), 120.0 (Trp-C5), 110.9 (Trp-C7), 87.8 (Trp-C8a), 86.5 (Trp-C3a), 77.2 (Hiv-Cα), 69.3 (Thr-Cβ), 62.4 (Trp-C2), 58.9 (Pro-Cα), 57.5 (Val-Cα), 55.4 (Thr-Cα), 52.3 (Leu-Cα), 47.1 (Pro-Cδ), 44.3 (Trp-C3), 40.1 (Leu-Cβ), 31.8 (Val-Cβ), 30.0 (Hiv-Cβ), 25.9 (Pro-Cβ), 24.9 (Leu-Cγ), 24.8 (Pro-Cγ), 23.2 (Leu-Cδ), 22.0 (Leu-Cδ), 19.9 (Thr-Cδ), 19.8 (Val-Cγ), 18.7 (Hiv-Cγ), 17.9 (Hiv-Cγ), 16.8 (Val-Cγ).

FTIR (thin film) cm$^{-1}$: 3296 (br-s), 2962 (m), 2932 (m), 2874 (w), 1741 (m), 1673 (s), 1637 (s), 1537 (m), 1438 (m), 1182 (m), 747 (m).

HRMS (ESI) (m/z): calc'd for C$_{36}$H$_{52}$N$_6$NaO$_9$ [M+Na]$^+$: 735.3688, found: 735.3685.

[α]$_D^{23}$: +5 (c=0.11, CHCl$_3$)

TLC (9% methanol, 1% ammonium hydroxide in chloroform), Rf: 0.37 (UV, CAM).

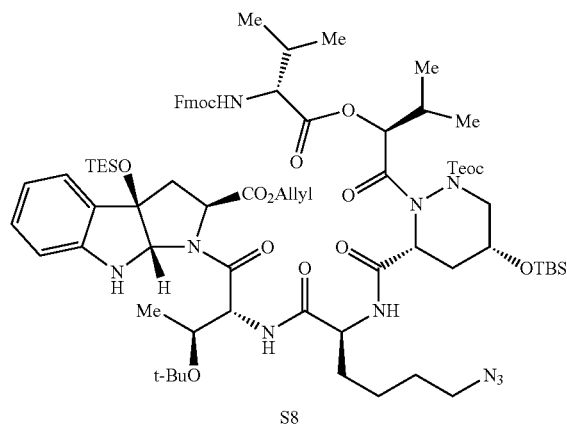

1. Pd(PPh₃)₄ N-methylaniline THF, 23° C.
2. i-Pr₂NH, MeCN, 23° C.
3. HATU, HOAt, i-Pr₂NEt CH₂Cl₂, 23° C.
4. TFA, H₂O, anisole CH₂Cl₂, 23° C.; Et₃N, MeOH, 23° C.
47% (four steps)

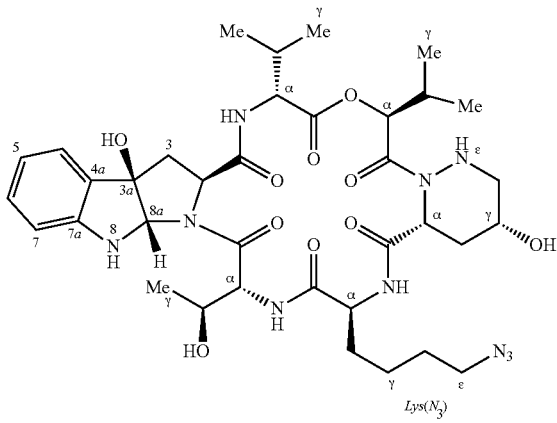

(+)-31

Azido Cyclic Depsihexapeptide (+)-31:

Prepared according to a scale-down of the procedure described previously for himastatin monomer (+)-6 from azido depsihexapeptide S8 (121.4 mg, 81.3 μmol, 1 equiv.). Azido cyclic depsihexapeptide (+)-31 was obtained by flash column chromatography on silica gel (eluent: 2.7% methanol, 0.3% ammonium hydroxide→4.5% methanol, 0.5% ammonium hydroxide in chloroform) as an off-white solid (29.8 mg, 46.7%). Structural assignments were made using additional information from gCOSY, gHSQC, and gHMBC experiments.

$^1$H NMR (600 MHz, CDCl₃, 25° C.): δ 7.56 (d, J=5.3 Hz, 1H, Lys(N₃)—NH), 7.36-7.32 (m, 2H, Val-NH, Trp-C4H), 7.20 (app-td, J=7.7, 1.3 Hz, 1H, Trp-C6H), 7.13 (d, J=10.5 Hz, 1H, Thr-NH), 6.91 (app-td, J=7.5, 0.9 Hz, 1H, Trp-C5H), 6.77 (d, J=7.9 Hz, 1H, Trp-C7H), 5.92 (s, 1H, Trp-C3aOH), 5.77 (d, J=6.4 Hz, 1H, Trp-N8H), 5.63 (d, J=8.5 Hz, 1H, Hiv-CαH), 5.41 (dd, J=12.8, 2.0 Hz, 1H, Pip-NεH), 5.21 (d, J=8.0 Hz, 1H, Trp-C2H), 5.16 (d, J=5.2 Hz, 1H, Pip-CγOH), 5.12 (d, J=6.8 Hz, 1H, Pip-CαH), 5.10 (d, J=6.4 Hz, 1H, Trp-C8aH), 4.95 (d, J=10.4 Hz, 1H, Thr-CαH), 4.88 (dd, J=9.9, 3.2 Hz, 1H, Val-CαH), 4.44 (qd, J=6.6, 1.8 Hz, 1H, Thr-CβH), 4.22 (app-dt, J=8.0, 5.0 Hz, 1H, Lys(N₃)—CαH), 3.84-3.80 (m, 1H, Pip-CγH), 3.62 (br-s, 1H, Thr-CβOH), 3.28-3.18 (m, 2H, Lys(N₃)—CεH), 3.06 (app-dq, J=14.2, 2.3 Hz, 1H, Pip-CδH$_a$), 2.84 (app-td, J=13.5, 2.0 Hz, 1H, Pip-CδH$_b$), 2.76 (d, J=14.4 Hz, 1H, Trp-C3H$_a$), 2.56 (septd, J=6.9, 3.3 Hz, 1H, Val-CβH), 2.50-2.45 (m, 1H, Pip-CβH$_a$), 2.21-2.13 (m, 2H, Hiv-CβH, Trp-C3H$_b$), 1.95 (ddd, J=15.0, 7.1, 3.4 Hz, 1H, Pip-CβH$_b$), 1.85-1.78 (m, 1H, Lys(N₃)—CβH$_a$), 1.67-1.59 (m, 1H, Lys(N₃)—CβH$_b$), 1.59-1.52 (m, 2H, Lys(N₃)—CδH), 1.32 (app-p, J=8.5 Hz, 2H, Lys(N₃)—CγH), 1.16 (dd, J=6.6, 0.9 Hz, 3H, Thr-CγH₃), 1.12 (d, J=6.6 Hz, 3H, Hiv-CγH₃), 1.00 (d, J=6.9 Hz, 6H, Hiv-CγH₃, Val-CγH₃), 0.87 (d, J=6.9 Hz, 3H, Val-CγH₃).

$^{13}$C NMR (150.9 MHz, CDCl₃, 25° C.): δ 174.2 (Hiv-CO), 173.6 (Val-CO), 173.5 (Pip-CO), 173.2 (2C, Trp-CO, Lys(N₃)—CO), 172.5 (Thr-CO), 147.9 (Trp-C7a), 131.7 (Trp-C4a), 130.1 (Trp-C6), 123.3 (Trp-C4), 121.2 (Trp-C5), 112.5 (Trp-C7), 90.9 (Trp-C3a), 86.2 (Trp-C8a), 77.5 (Hiv-Cα), 66.8 (Thr-Cβ), 61.0 (Trp-C2), 58.8 (Pip-CγH), 57.4 (Val-Cα), 55.6 (Lys(N₃)—Cα), 54.0 (Thr-Cα), 52.7 (Pip-Cδ), 50.9 (Lys(N₃)—Cε), 50.1 (Pip-Cα), 39.5 (Trp-C3), 31.4 (Lys(N₃)—Cβ), 30.1 (2C, Val-Cβ, Hiv-Cβ), 28.7 (Pip-Cβ), 28.3 (Lys(N₃)—Cδ), 22.9 (Lys(N₃)—Cγ), 19.5 (Val-Cγ), 19.1 (Hiv-Cγ), 18.4 (Hiv-Cγ), 17.5 (Thr-Cγ), 16.6 (Val-Cγ).

FTIR (thin film) cm$^{-1}$: 3390 (m), 3322 (br-s), 3252 (m), 2965 (m), 2933 (m), 2875 (w), 2096 (m), 1724 (m), 1669 (s), 1615 (m), 1526 (m), 1250 (m), 751 (m).

HRMS (ESI) (m/z): calc'd for $C_{36}H_{52}N_{10}NaO_{10}$ [M+Na]$^+$: 807.3760, found: 807.3757.

$[\alpha]_D^{23}$: +39 (c=0.11, CHCl₃)

TLC (9% methanol, 1% ammonium hydroxide in chloroform), Rf: 0.41 (UV, CAM).

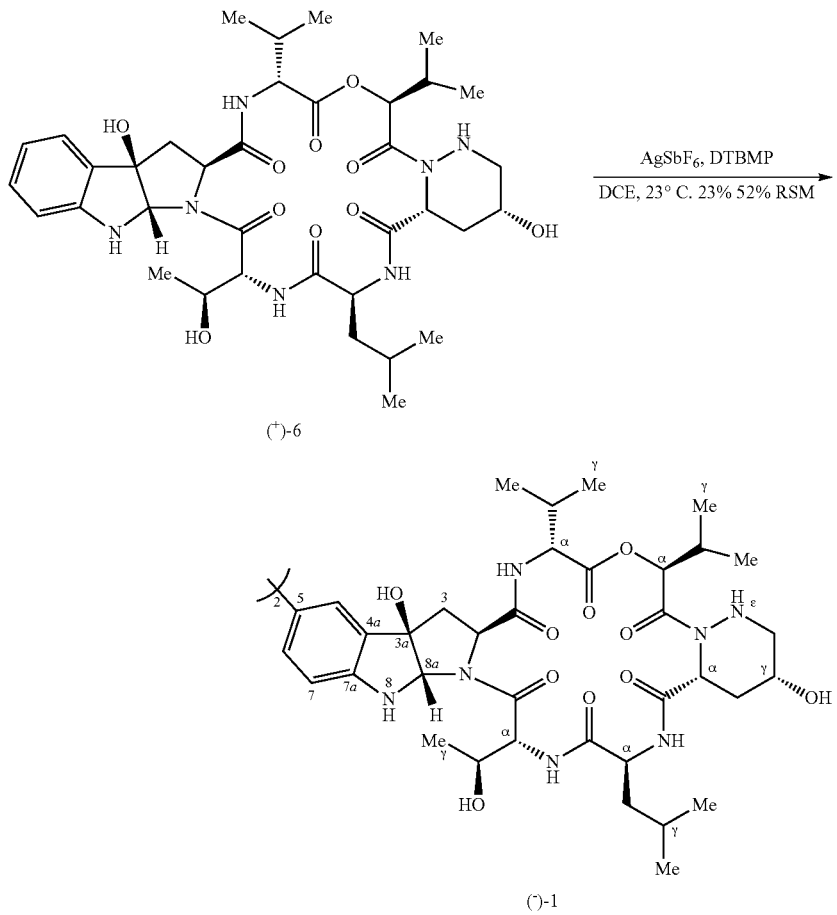

(+)-6

(−)-1

Himastatin (−)-1:

A sample of silver hexafluoroantimonate(V) (13.7 mg, 40.0 μmol, 4.00 equiv.) was added to a solution of himastatin monomer (+)-6 (7.44 mg, 10.0 μmol, 1 equiv.) and 2,6-di-tert-butyl-4-methylpyridine (DTBMP, 10.3 mg, 50.0 μmol, 5.00 equiv.) in 1,2-dichloroethane (200 μL) at 23° C. After 2 h, a second portion of silver hexafluoroantimonate(V) (13.7 mg, 40.0 μmol, 4.00 equiv.) was added. After 2 h, additional 1,2-dichloroethane (100 μL) and a final portion of silver hexafluoroantimonate(V) (13.7 mg, 40.0 μmol, 4.00 equiv.) were added. After 18 h, the heterogeneous solution was diluted with dichloromethane (20 mL), a saturated aqueous sodium thiosulfate solution (5 mL), a saturated aqueous sodium hydrogen carbonate solution (5 mL), and deionized water (10 mL) and was stirred vigorously for 1 h. The layers were separated and the aqueous layer was extracted with dichloromethane (10 mL). The combined organic extracts were washed with a saturated aqueous sodium chloride solution (20 mL), were dried over anhydrous sodium sulfate, were filtered, and were concentrated under reduced pressure. The resulting residue was purified by flash column chromatography on silica (eluent: 1.8% methanol, 0.2% ammonium hydroxide→7.2% methanol, 0.8% ammonium hydroxide in chloroform), followed by semi-preparative HPLC purification of mixed fractions of dimer (−)-6 and monomer (+)-1 (Zorbax® StableBond 80 Å CN, 9.4 mm×250 mm, 40%→95% acetonitrile in water, 16 min, 5.0 mL/min, 270 nm, $t_R$ ((−)-1)=8.52 min, $t_R$ ((+)-6) =6.89 min), to afford himastatin (−)-1 (1.71 mg, 23.0%) and recovered himastatin monomer (+)-6 (3.83 mg, 51.5%) as white foams. Structural assignments were made using additional information from gCOSY, gHSQC, and gHMBC experiments.

$^1$H NMR (600 MHz, CDCl$_3$, 25° C.): δ 7.59 (d, J=2.0 Hz, 2H, Trp-C4H), 7.44-7.40 (m, 4H, Trp-C6H, Leu-NH), 7.29 (d, J=10.0 Hz, 2H, Val-NH), 7.12 (d, J=10.5 Hz, 2H, Thr-NH), 6.80 (d, J=8.3 Hz, 2H, Trp-C7H), 5.91 (s, 2H, Trp-C3aOH), 5.81 (d, J=6.3 Hz, 2H, Trp-N8H), 5.64 (d, J=8.6 Hz, 2H, Hiv-CαH), 5.43 (dd, J=12.8, 2.0 Hz, 2H, Pip-NεH), 5.21 (d, J=8.0 Hz, 2H, Trp-C2H), 5.20 (d, J=5.3 Hz, 2H, Pip-CγOH), 5.14 (d, J=6.3 Hz, 2H, Trp-C8aH), 5.13 (d, J=7.1 Hz, 2H, Pip-CαH), 4.99 (d, J=10.5 Hz, 2H, Thr-CαH), 4.90 (dd, J=10.0, 3.2 Hz, 2H, Val-CαH), 4.45 (qd, J=6.7, 2.0 Hz, 2H, Thr-CβH), 4.24 (ddd, J=10.7, 5.4, 3.5 Hz, 2H, Leu-CαH), 3.82 (app-sept, J=2.5 Hz, 2H, Pip-CγH), 3.61 (br-s, 2H, Thr-CβOH), 3.07 (app-dq, J=14.5, 2.3 Hz, 2H, Pip-CδH$_a$), 2.84 (app-t, J=13.5 Hz, 2H, Pip-CδH$_b$), 2.77 (d, J=14.3 Hz, 2H, Trp-C3H$_a$), 2.57 (septd, J=6.9, 3.2 Hz, 2H, Val-CβH), 2.49 (app-dp, J=14.7, 2.3 Hz, 2H, Pip-CβH$_a$), 2.20 (dd, J=14.4, 8.1 Hz, 2H, Trp-C3H$_b$), 2.20-2.12 (m, 2H, Hiv-CβH), 1.95 (ddd, J=15.0, 7.2, 3.4 Hz, 2H, Pip-CβH$_b$), 1.73-1.65 (m, 4H, Leu-CβH$_a$, Leu-CγH), 1.44-1.36 (m, 2H, Leu-CβH$_b$), 1.16 (d, J=6.5 Hz, 6H, Thr-CγH$_3$), 1.13 (d, J=6.6 Hz, 6H, Hiv-CγH$_3$), 1.01 (d, J=6.9 Hz, 6H, Hiv-CγH$_3$), 1.01 (d, J=6.8 Hz, 6H, Val-CγH$_3$), 0.93 (d, J=6.1 Hz, 6H, Leu-CδH$_3$), 0.87 (d, J=6.9 Hz, 6H, Val-CγH$_3$), 0.87 (d, J=6.0 Hz, 6H, Leu-CδH$_3$).

$^{13}$C NMR (150.9 MHz, CDCl$_3$, 25° C.): 174.3 (Hiv-CO), 174.1 (Leu-CO), 173.6 (Val-CO), 173.4 (Pip-CO), 173.2

(Trp-CO), 172.5 (Thr-CO), 146.8 (Trp-C7a), 134.5 (Trp-C5), 132.4 (Trp-C4a), 128.5 (Trp-C6), 121.5 (Trp-C4), 112.8 (Trp-C7), 91.0 (Trp-C3a), 86.3 (Trp-C8a), 77.5 (Hiv-Cα), 66.8 (Thr-Cβ), 60.9 (Trp-C2), 58.8 (Pip-Cγ), 57.3 Val-Cα), 54.4 (Leu-Cα), 53.9 (Thr-Cα), 52.8 (Pip-Cδ), 50.1 (Pip-Cα), 41.1 (Leu-Cβ), 39.6 (Trp-C3), 30.1 (2C, Hiv-Cβ, Val-Cβ), 28.8 (Pip-Cβ), 25.5 (Leu-Cγ), 23.1 (Leu-Cδ), 21.1 (Leu-Cδ), 19.5 (Val-Cγ), 19.1 (Hiv-Cγ), 18.4 (Hiv-Cγ), 17.5 (Thr-Cγ), 16.6 (Val-Cγ).

FTIR (thin film) cm$^{-1}$: 3391 (m), 3329 (br-s), 2962 (m), 2930 (m), 2875 (w), 1725 (s), 1672 (m), 1624 (m), 1534 (m), 1417 (m), 1246 (m), 1153 (w), 916 (w), 755 (w).

HRMS (ESI) (m/z): calc'd for $C_{72}H_{104}N_{14}NaO_{20}$ [M+Na]$^+$: 1507.7444, found: 1507.7445.

$[\alpha]_D^{23}$: −36 (c=0.040, MeOH).[19]

TLC (9% methanol, 1% ammonium hydroxide in chloroform), Rf: 0.27 (UV, CAM).

TABLE S3

Comparison of our $^1$H NMR data for (−)-Himastatin ((−)-1) with literature data (CDCl$_3$):

| Assignment | Leet's Isolation Report[20] (−)-Himastatin (1) $^1$H NMR, 360 MHz, CDCl$_3$ | Danishefsky's Report (−)-Himastatin (1) $^1$H NMR, 500 MHz, CDCl$_3$ | This Work (−)-Himastatin (1) $^1$H NMR, 600 MHz, CDCl$_3$ |
|---|---|---|---|
| Trp | | | |
| C$_2$H | 5.16 (d, J = 8.0 Hz, 2H) | 5.30-5.20 (m, 4H) | 5.21 (d, J = 8.0 Hz, 2H) |
| C$_3$H$_2$ | 2.70 (d, J = 14.5 Hz, 2H) | 2.76 (d, J = 14.3 Hz, 2H) | 2.77 (d, J = 14.3 Hz, 2H) |
| | 2.16 (dd, J = 14.3, 8.0 Hz, 2H) | 2.25-2.10 (m, 4H) | 2.20 (dd, J = 14.4, 8.1 Hz, 2H) |
| C$_{3a}$OH | 5.89 (s, 2H) | 5.91 (s, 2H) | 5.91 (s, 2H) |
| C$_4$H | 7.52 (d, J = 1.8 Hz, 2H) | 7.58 (s, 2H) | 7.59 (d, J = 2.0 Hz, 2H) |
| C$_6$H | 7.31 (dd, J = 8.3, 1.8 Hz, 2H) | 7.43-7.41 (m, 4H) | 7.44-7.40 (m, 4H) |
| C$_7$H | 6.74 (d, J = 8.3 Hz, 2H) | 6.79 (d, J = 8.3 Hz, 2H) | 6.80 (d, J = 8.3 Hz, 2H) |
| N$_8$H | 5.78 (d, J = 5.8 Hz, 2H) | 5.81 (br-s, 2H) | 5.81 (d, J = 6.3 Hz, 2H) |
| C$_{8a}$H | 5.11 (m, 2H) | 5.14-5.12 (m, 4H) | 5.14 (d, J = 6.3 Hz, 2H) |
| Thr | | | |
| NH | 7.08 (d, J = 10.5 Hz, 2H) | 7.11 (d, J = 10.4 Hz, 2H) | 7.12 (d, J = 10.5 Hz, 2H) |
| C$_\alpha$H | 4.94 (d, J = 10.5 Hz, 2H) | 4.98 (d, J = 10.5 Hz, 2H) | 4.99 (d, J = 10.5 Hz, 2H) |
| C$_\beta$H | 4.40 (q, J = 6.6 Hz, 2H) | 4.50-4.44 (m, 2H) | 4.45 (qd, J = 6.7, 2.0 Hz, 2H |
| C$_\beta$OH | 3.59 (s, 2H) | 3.62 (s, 2H) | 3.61 (br-s, 2H) |
| C$_\gamma$H$_3$ | 1.11 (d, J = 6.6 Hz, 6H) | 1.15 (d, J = 6.5, 6H) | 1.16 (d, J = 6.5 Hz, 6H) |
| Leu | | | |
| NH | 7.38 (d, J = 3.9 Hz, 2H) | 7.43-7.41 (m, 4H) | 7.44-7.40 (m, 4H) |
| C$_\alpha$H | 4.18 (m, 2H) | 4.25-4.21 (m, 2H) | 4.24 (ddd, J = 10.7, 5.4, 3.5 Hz, 2H) |
| C$_\beta$H$_2$ | 1.64 (m, 2H) | 1.72-1.65 (m, 6H) | 1.73-1.64 (m, 4H) |
| | 1.35 (dd, J = 10.5, 8.8 Hz, 2H) | 1.41-1.35 (m, 2H) | 1.44-1.36 (m, 2H) |
| C$_\gamma$H | 1.64 (m, 2H) | 1.72-1.65 (m, 6H) | 1.73-1.64 (m, 4H) |
| C$_\delta$H$_3$ | 0.88 (d, J = 6.0 Hz, 6H) | 0.92 (d, J = 5.7 Hz, 6H) | 0.93 (d, J = 6.1 Hz, 6H) |
| | 0.83 (d, J = 6.0 Hz, 12H) | 0.85 (d, J = 6.5 Hz, 12H) | 0.87 (d, J = 6.0 Hz, 6H) |
| Pip | | | |
| C$_\alpha$H | 5.08 (d, J = 7.1 Hz, 2H) | 5.14-5.12 (m, 4H) | 5.13 (d, J = 7.1 Hz, 2H) |
| C$_\beta$H$_2$ | 2.44 (d, J = 14.9 Hz, 2H) | 2.48 (d, J = 14.8 Hz, 2H) | 2.49 (app-dp, J = 14.7, 2.3 Hz, 2H) |
| | 1.92 (ddd, J = 14.9, 7.1, 3.3 Hz, 2H) | 1.98-1.90 (m, 2H) | 1.95 (ddd, J = 15.0, 7.2, 3.4 Hz, 2H) |
| C$_\gamma$H | 3.77 (br-s, 2H) | 3.82 (s, 2H) | 3.82 (app-sept, J = 2.5 Hz, 2H) |
| C$_\gamma$OH | 5.17 (d, J = 4.5 Hz, 2H) | 5.30-5.20 (m, 4H) | 5.20 (d, J = 5.3 Hz, 2H) |
| C$_\delta$H$_2$ | 3.02 (d, J= 12.6 Hz, 2H) | 3.06 (d, J = 13.1 Hz, 2H) | 3.07 (app-dq, J = 14.5, 2.3 Hz, 2H) |
| | 2.79 (t, J= 13.6 Hz, 2H) | 2.85 (t, J = 13.5 Hz, 2H) | 2.84 (app-t, J = 13.5 Hz, 2H) |
| N$_\varepsilon$H | 5.37 (d, J = 12.1 Hz, 2H) | 5.42 (d, J = 12.3 Hz, 2H) | 5.43 (dd, J = 12.8, 2.0 Hz, 2H) |
| Hiv | | | |
| C$_\alpha$H | 5.62 (d, J = 8.6 Hz, 2H) | 5.63 (d, J = 8.6 Hz, 2H) | 5.64 (d, J = 8.6 Hz, 2H) |
| C$_\beta$H | 2.16 (sept, J = 6.7 Hz, 2H) | 2.25-2.10 (m, 4H) | 2.20-2.12 (m, 2H) |
| C$_\gamma$H$_3$ | 1.08 (d, J = 6.7 Hz, 6H) | 1.11 (d, J = 6.6 Hz, 6H) | 1.13 (d, J = 6.6 Hz, 6H) |
| | 0.96 (d, J = 6.7 Hz, 12H) | 1.02 (d, J = 6.5 Hz, 12H) | 1.01 (d, J = 6.9 Hz, 6H) |
| Val | | | |
| NH | 7.25 (d, J = 10.0 Hz, 2H) | 7.28 (d, J = 10.0 Hz, 2H) | 7.29 (d, J = 10.0 Hz, 2H) |
| C$_\alpha$H | 4.84 (dd, J = 10.0, 3.3 Hz, 2H) | 4.89 (dd, J = 9.9, 3.0 Hz, 2H) | 4.90 (dd, J = 10.3, 3.2 Hz, 2H) |
| C$_\beta$H | 2.52 (dd, J = 6.8, 3.3 Hz, 2H) | 2.60-2.50 (m, 2H) | 2.57 (septd, J = 6.9, 3.2 Hz, 2H) |
| C$_\gamma$H$_3$ | 0.96 (d, J = 6.8 Hz, 12H) | 1.00 (d, J = 6.6 Hz, 12H) | 1.01 (d, J = 6.8 Hz, 6H) |
| | 0.83 (d, J = 6.8 Hz, 12H) | 0.87 (d, J = 6.7 Hz, 6H) | 0.87 (d, J = 6.9 Hz, 6H) |

TABLE S4

Comparison of our $^{13}$C NMR data for (−)-Himastatin ((−)-1) with literature data (CDCl$_3$):

| Assignment | Leet's Isolation Report (−)-Himastatin (1) $^{13}$C NMR, 90.7 MHz, CDCl$_3$ | Danishefsky's Report (−)-Himastatin (1) $^{13}$C NMR, 125 MHz, CDCl$_3$ | This Work (−)-Himastatin (1) $^{13}$C NMR, 150.9 MHz, CDCl$_3$ | Chemical Shift Difference $\Delta\delta = \delta$ (this work) − $\delta$ (Leet's report) |
|---|---|---|---|---|
| Trp | | | | |
| CO | 172.79 | 173.0 | 173.16 | 0.37 |
| C$_2$ | 60.62 | 60.8 | 60.95 | 0.33 |
| C$_3$ | 39.30 | 39.4 | 39.61 | 0.31 |
| C$_{3a}$ | 90.61 | 90.8 | 91.00 | 0.39 |
| C$_{4a}$ | 132.08 | 132.2 | 132.44 | 0.36 |
| C$_4$ | 121.18 | 121.3 | 121.53 | 0.35 |
| C$_5$ | 134.21 | 134.3 | 134.53 | 0.32 |
| C$_6$ | 128.21 | 128.4 | 128.54 | 0.33 |
| C$_7$ | 112.30 | 112.6 | 112.77 | 0.47 |
| C$_{7a}$ | 146.41 | 146.6 | 146.80 | 0.39 |
| C$_{8a}$ | 85.98 | 86.2 | 86.34 | 0.36 |
| Thr | | | | |
| CO | 172.17 | 172.3 | 172.47 | 0.30 |
| C$_\alpha$ | 53.63 | 53.8 | 53.95 | 0.32 |
| C$_\beta$ | 66.47 | 66.7 | 66.83 | 0.36 |
| C$_\gamma$ | 17.17 | 17.3 | 17.50 | 0.33 |
| Leu | | | | |
| CO | 173.67 | 173.9 | 174.06 | 0.39 |
| C$_\alpha$ | 54.10 | 54.3 | 54.43 | 0.33 |
| C$_\beta$ | 40.77 | 40.9 | 41.08 | 0.31 |
| C$_\gamma$ | 25.09 | 25.3 | 25.45 | 0.36 |
| C$_\delta$ | 22.75 | 23.0 | 23.14 | 0.39 |
| | 20.81 | 21.0 | 21.13 | 0.32 |
| Pip | | | | |
| CO | 173.02 | 173.2 | 173.40 | 0.38 |
| C$_\alpha$ | 49.72 | 49.9 | 50.07 | 0.35 |
| C$_\beta$ | 28.44 | 28.6 | 28.77 | 0.33 |
| C$_\gamma$ | 58.50 | 58.7 | 58.82 | 0.32 |
| C$_\delta$ | 52.44 | 52.6 | 52.78 | 0.34 |
| Hiv | | | | |
| CO | 173.84 | 174.1 | 174.25 | 0.41 |
| C$_\alpha$ | 77.08 | — | 77.47 | 0.39 |
| C$_\beta$ | 29.78 | 30.0 | 30.14 | 0.36 |
| C$_\gamma$ | 18.64 | 18.9 | 19.08 | 0.44 |
| | 18.09 | 18.3 | 18.44 | 0.35 |
| Val | | | | |
| CO | 173.20 | 173.4 | 173.61 | 0.41 |
| C$_\alpha$ | 57.02 | 57.1 | 57.34 | 0.32 |
| C$_\beta$ | 29.66 | 29.8 | 30.06 | 0.40 |
| C$_\gamma$ | 19.14 | 19.3 | 19.52 | 0.38 |
| | 16.27 | 16.4 | 16.57 | 0.30 |

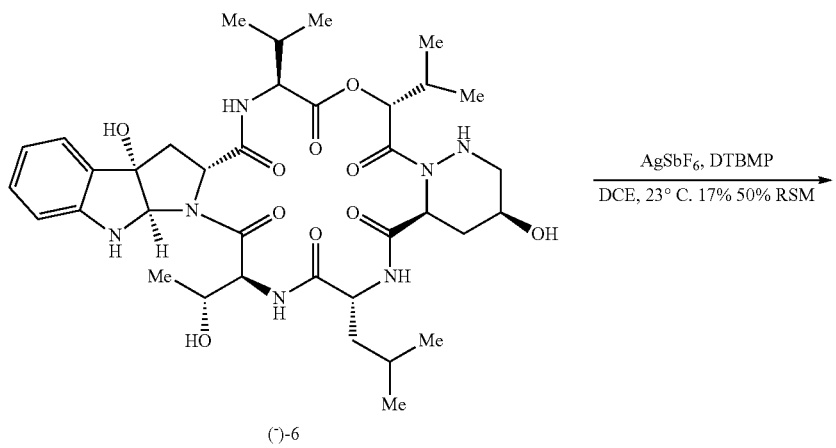

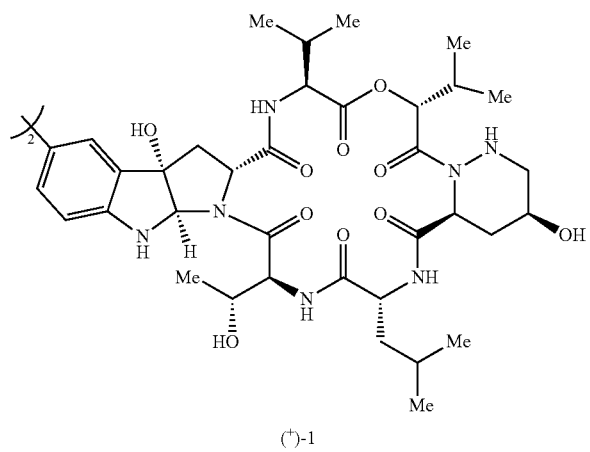

Ent-Himastatin (+)-1:

Prepared according to a scale-up of the procedure described previously for himastatin (−)-1 from ent-himastatin monomer (−)-6 (11.9 mg, 16.0 μmol, 1 equiv.). Flash column chromatography on silica (eluent: 1.8% methanol, 0.2% ammonium hydroxide→7.2% methanol, 0.8% ammonium hydroxide in chloroform), followed by semi-preparative HPLC purification of mixed fractions of dimer (+)-1 and monomer (−)-6 (Zorbax® StableBond 80 Å CN, 9.4 mm×250 mm, 40%→95% acetonitrile in water, 16 min, 5.0 mL/min, 270 nm, $t_R$ ((+)-1)=7.37 min, $t_R$ ((−)-6)=6.04 min) afforded ent-himastatin (+)-1 (2.01 mg, 16.9%) and recovered cyclic hexapeptide (−)-6 (5.96 mg, 50.1%) as white foams. Spectral data of ent-himastatin (+)-1 were in agreement with those previously reported in this document for himastatin (−)-1.

$[α]_D^{24}$: +33 (c=0.071, MeOH).

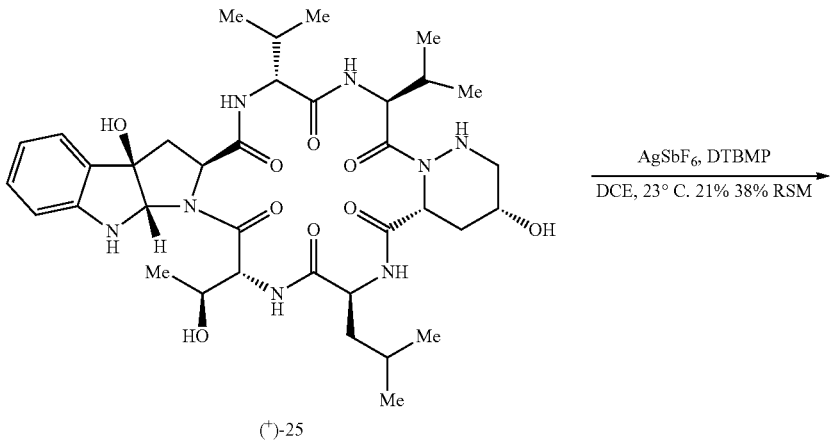

-continued

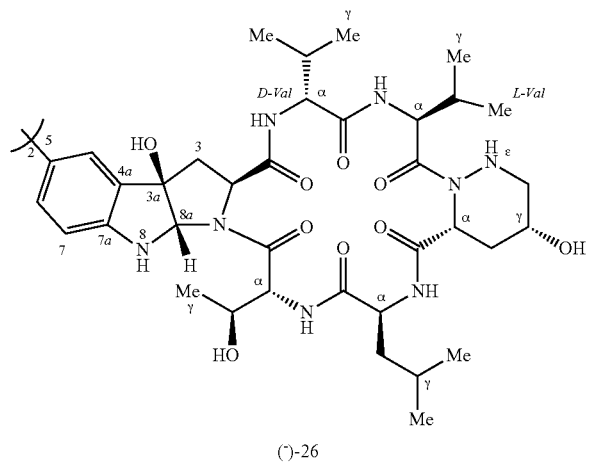

(−)-26

Himastatin Lactam Derivative (−)-26:

Prepared according to a scale-down of the procedure described previously for himastatin (−)-1 from cyclic hexapeptide (+)-25 (6.71 mg, 9.03 μmol, 1 equiv.). Flash column chromatography on silica (eluent: 1.8% methanol, 0.2% ammonium hydroxide→7.2% methanol, 0.8% ammonium hydroxide in chloroform), followed by semi-preparative HPLC purification of mixed fractions of dimer (−)-26 and monomer (+)-25 (Zorbax® StableBond 80 Å CN, 9.4 mm×250 mm, 40%→95% acetonitrile in water, 16 min, 5.0 mL/min, 270 nm, $t_R$ ((−)-26)=7.02 min, $t_R$ ((+)-25)=5.73 min) afforded himastatin lactam derivative (−)-26 (1.38 mg, 20.6%) and recovered cyclic hexapeptide (+)-25 (2.53 mg, 37.7%) as white foams. Structural assignments were made using additional information from gCOSY, gHSQC, and gHMBC experiments.

$^1$H NMR (600 MHz, CDCl$_3$, 25° C.): δ 7.66 (d, J=9.1 Hz, 2H, D-Val-NH), 7.57 (d, J=1.9 Hz, 2H, Trp-C4H), 7.42 (dd, J=8.3, 1.9 Hz, 2H, Trp-C6H), 7.37 (d, J=5.9 Hz, 2H, Leu-NH), 6.77 (d, J=8.3 Hz, 2H, Trp-C7H), 6.74 (d, J=10.3 Hz, 2H, Thr-NH), 6.09 (d, J=7.6 Hz, 2H, L-Val-NH), 6.02 (s, 2H, Trp-C3aOH), 5.85 (d, J=6.2 Hz, 2H, Trp-N8H), 5.51 (app-t, J=7.4 Hz, 2H, L-ValCαH), 5.41 (dd, J=13.0, 2.0 Hz, 2H, Pip-NεH), 5.33 (d, J=5.6 Hz, 2H, Pip-CγOH), 5.21 (d, J=8.2 Hz, 2H, Trp-C2H), 5.17 (d, J=6.2 Hz, 2H, Trp-C8aH), 5.12 (d, J=7.2 Hz, 2H, Pip-CαH), 4.84 (d, J=10.3 Hz, 2H, Thr-CαH), 4.54 (qd, J=6.6, 2.3 Hz, 2H, Thr-CβH), 4.42 (dd, J=9.1, 5.3 Hz, 2H, D-Val-CαH), 4.30 (ddd, J=10.4, 5.9, 3.9 Hz, 2H, Leu-CαH), 3.83-3.78 (m, 2H, Pip-CγH), 3.71 (br-s, 2H, Thr-CβOH), 3.09 (app-dq, J=14.3, 1.8 Hz, 2H, Pip-CδH$_a$), 2.85 (app-t, J=13.4 Hz, 2H, Pip-CδH$_b$), 2.73 (d, J=14.3 Hz, 2H, Trp-C3H$_a$), 2.45-2.40 (m, 2H, Pip-CβH$_a$), 2.17 (dd, J=14.3, 8.2 Hz, 2H, Trp-C3H$_b$), 2.12-2.04 (m, 2H, D-Val-CβH), 2.02-1.95 (m, 4H, Pip-CβH$_b$, L-Val-CβH), 1.76-1.63 (m, 4H, Leu-CβH$_a$, Leu-CγH), 1.45 (ddd, J=13.4, 10.5, 4.5 Hz, 2H, Leu-CβH$_b$), 1.12 (d, J=6.5 Hz, 6H, Thr-CγH$_3$), 1.03 (d, J=6.7 Hz, 6H, D-Val-CγH$_3$), 1.01 (d, J=6.8 Hz, 12H, L-Val-CγH$_3$), 0.95 (d, J=6.5 Hz, 6H, D-Val-CγH$_3$), 0.93 (d, J=6.2 Hz, 6H, Leu-CδH$_3$), 0.87 (d, J=6.3 Hz, 6H, Leu-CδH$_3$).

$^{13}$C NMR (150.9 MHz, CDCl$_3$, 25° C.): δ 176.3 (L-Val-CO), 174.4 (Leu-CO), 173.2 (Pip-CO), 172.8 (Trp-CO), 171.5 (Thr-CO), 171.1 (D-Val-CO), 147.8 (Trp-C7a), 134.3 (Trp-C5), 132.2 (Trp-C4a), 128.5 (Trp-C6), 121.4 (Trp-C4), 112.5 (Trp-C7), 91.1 (Trp-C3a), 86.5 (Trp-C8a), 66.4 (Thr-Cβ), 61.5 (Trp-C2), 58.9 (D-Val-Cα), 58.6 (Pip-Cγ), 54.7 (Thr-Cα), 54.2 (Leu-Cα), 54.1 (L-Val-Cα), 52.7 (Pip-Cδ), 50.1 (Pip-Cα), 41.0 (Leu-Cβ), 39.6 (Trp-C3), 32.3 (D-Val-Cβ), 30.9 (L-Val-Cβ), 28.9 (Pip-Cβ), 25.5 (Leu-Cγ), 23.1 (Leu-Cδ), 21.2 (Leu-Cδ), 19.8 (L-Val-Cγ), 19.6 (D-Val-Cγ), 18.7 (L-Val-Cγ), 17.4 (2C, Thr-Cγ, D-Val-Cγ).

FTIR (thin film) cm$^{-1}$: 3307 (br-s), 2967 (m), 2929 (m), 2873 (w), 1647 (s), 1530 (m), 1372 (m), 1228 (w), 1102 (m).

HRMS (ESI) (m/z): calc'd for $C_{72}H_{106}N_{16}NaO_{18}$ [M+Na]$^+$: 1505.7763, found: 1505.7756.

$[α]_D^{24}$: −52 (c=0.053, MeOH).

TLC (9% methanol, 1% ammonium hydroxide in chloroform), Rf: 0.20 (UV, CAM).

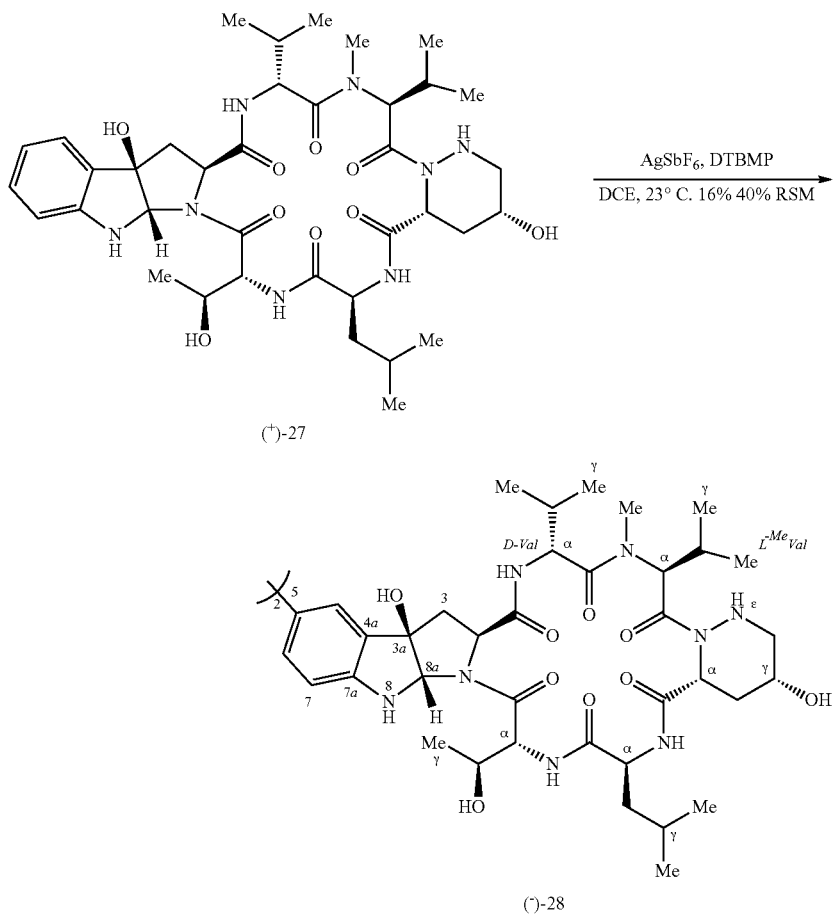

Himastatin N-Methyl Lactam Derivative (−)-28:

Prepared according to a scale-down of the procedure described previously for himastatin (−)-1 from cyclic N-methyl hexapeptide (+)-27 (5.95 mg, 7.86 μmol, 1 equiv.). Flash column chromatography on silica (eluent: 1.8% methanol, 0.2% ammonium hydroxide→7.2% methanol, 0.8% ammonium hydroxide in chloroform), followed by semi-preparative HPLC purification of mixed fractions of dimer (−)-28 and monomer (+)-27 (Zorbax® StableBond 80 Å CN, 9.4 mm×250 mm, 40%→95% acetonitrile in water, 16 min, 5.0 mL/min, 270 nm, $t_R$ ((−)-28)=7.36 min, $t_R$ ((+)-27)=6.00 min) afforded himastatin N-methyl lactam derivative (−)-28 (0.93 mg, 15.7%) and recovered cyclic hexapeptide (+)-27 (2.40 mg, 40.3%) as white foams. Structural assignments were made using additional information from gCOSY, gHSQC, and gHMBC experiments.

$^1$H NMR (600 MHz, CDCl$_3$, 25° C.): δ 7.99 (d, J=9.2 Hz, 2H, D-Val-NH), 7.58 (d, J=2.0 Hz, 2H, Trp-C4H), 7.42 (dd, J=8.3, 2.0 Hz, 2H, Trp-C6H), 7.25 (d, J=5.1 Hz, 2H, Leu-NH), 6.79 (d, J=8.3 Hz, 2H, Trp-C5H), 6.62 (d, J=10.2 Hz, 2H, Thr-NH), 5.90 (d, J=6.3 Hz, 2H, Trp-N8H), 5.87 (s, 2H, Trp-C3aOH), 5.80-5.75 (m, 4H, Pip-NεH, L-$^{Me}$Val-CαH), 5.32 (d, J=8.0 Hz, 2H, Trp-C2H), 5.21 (dd, J=7.4, 1.2 Hz, 2H, Pip-CαH), 5.16 (d, J=6.3 Hz, 2H, Trp-C8aH), 4.97 (dd, J=9.2, 3.2 Hz, 2H, D-Val-CαH), 4.92 (d, J=5.2 Hz, 2H, Pip-CγOH), 4.86 (d, J=10.3 Hz, 2H, Thr-CαH), 4.56 (qd, J=6.5, 1.1 Hz, 2H, Thr-CβH), 4.28 (ddd, J=9.2, 5.0, 3.6 Hz, 2H, Leu-CαH), 4.02 (s, 2H, Thr-CβOH), 3.80 (app-sept, J=2.4 Hz, 2H, Pip-CγH), 3.28 (s, 6H, L-$^{Me}$Val-NCH$_3$), 3.09 (app-dq, J=14.6, 2.0 Hz, 2H, Pip-CδH$_a$), 2.87 (app-t, J=13.4 Hz, 2H, Pip-CδH$_b$), 2.81 (d, J=14.3 Hz, 2H, Trp-C3H$_a$), 2.51-2.46 (m, 2H, Pip-CβH$_a$), 2.25-2.17 (m, 2H, L-$^{Me}$Val-CβH), 2.15 (dd, J=14.3, 8.1 Hz, 2H, Trp-C3H$_b$), 2.08 (septd, J=6.8, 3.2 Hz, 2H, D-Val-CβH), 1.93 (ddd, J=14.8, 7.1, 3.4 Hz, 2H, Pip-CβH$_b$), 1.71-1.64 (m, 4H, Leu-CβH$_a$, Leu-CγH), 1.50-1.44 (m, 2H, Leu-CβH$_b$), 1.14 (d, J=6.6 Hz, 6H, Thr-CγH$_3$), 1.04 (d, J=6.7 Hz, 6H, L-$^{Me}$Val-CγH$_3$), 1.02 (d, J=6.8 Hz, 6H, D-Val-CδH$_3$), 0.98 (d, J=6.5 Hz, 6H, L-$^{Me}$Val-CγH$_3$), 0.92 (d, J=6.1 Hz, 6H, Leu-CδH$_3$), 0.87 (d, J=6.0 Hz, 6H, Leu-CδH$_3$), 0.82 (d, J=6.8 Hz, 6H, D-Val-CγH$_3$)

$^{13}$C NMR (150.9 MHz, CDCl$_3$, 25° C.): δ 177.0 (L-$^{Me}$Val-CO), 174.2 (2C, Pip-CO, Leu-CO), 173.5 (D-Val-CO), 172.8 (Trp-CO), 171.7 (Thr-CO), 146.8 (Trp-C7a), 134.4 (Trp-C5), 132.3 (Trp-C4a), 128.8 (Trp-C6), 121.5 (Trp-C4), 112.6 (Trp-C7), 91.2 (Trp-C3a), 86.2 (Trp-C8a), 66.4 (Thr-Cβ), 60.9 (Trp-C2), 58.9 (Pip-Cγ), 57.9 (L-$^{Me}$Val-Cα), 55.5 (D-Val-Cα), 54.6 (Thr-Cα), 54.3 (Leu-Cα), 52.5 (Pip-Cδ), 49.3 (Pip-Cα), 40.8 (Leu-Cβ), 39.4 (Trp-C3), 31.9 (L-$^{Me}$Val NCH$_3$), 30.8 (D-Val-Cβ), 28.7 (Pip-Cβ), 28.0 (L-$^{Me}$Val-Cβ), 25.6 (Leu-Cγ), 23.2 (Leu-Cδ), 21.5 (Leu-Cδ), 20.6 (L-$^{Me}$Val-Cγ), 20.1 (D-Val-Cγ), 19.7 (L-$^{Me}$Val-Cγ), 17.3 (Thr-Cγ), 16.0 (D-Val-Cγ).

FTIR (thin film) cm$^{-1}$: 3322 (br-s), 2963 (m), 2929 (m), 2874 (w), 1635 (s), 1529 (m), 1254 (w), 1101 (m).

HRMS (ESI) (m/z): calc'd for C$_{74}$H$_{110}$N$_{16}$NaO$_{18}$ [M+Na]$^+$: 1533.8076, found: 1533.8059.

[α]$_D^{24}$: −78 (c=0.057, MeOH).

TLC (9% methanol, 1% ammonium hydroxide in chloroform), Rf: 0.29 (UV, CAM).

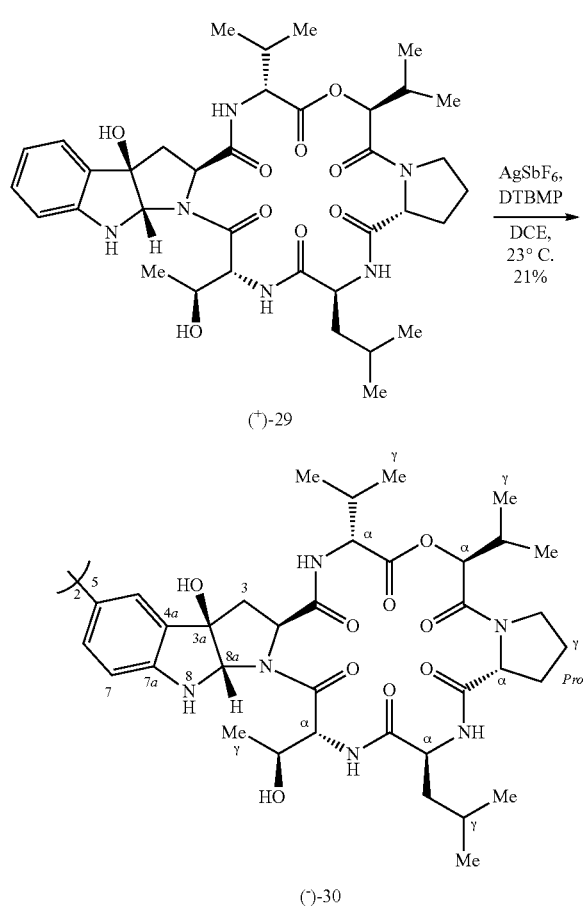

(+)-29

(−)-30

Himastatin Proline Derivative (−)-30:

Prepared according to the procedure described previously for himastatin monomer (−)-6 from proline cyclic hexadepsipeptide (+)-29 (7.13 mg, 10.0 μmol, 1 equiv.). Flash column chromatography on silica (eluent: 2%→10% methanol in dichloromethane), followed by semi-preparative HPLC purification of mixed fractions of dimer (−)-30 and monomer (+)-29 (Zorbax® StableBond 80 Å CN, 9.4 mm×250 mm, 40%→95% acetonitrile in water, 16 min, 5.0 mL/min, 270 nm, $t_R$ ((−)-30)=7.88 min) afforded himastatin proline derivative (−)-30 (1.50 mg, 21%) as a white foam. Structural assignments were made using additional information from gCOSY, gHSQC, and gHMBC experiments.

$^1$H NMR (600 MHz, DMSO-d$_6$, 25° C., 6.0:1 mixture of conformers, * denotes minor conformer): δ 8.66 (d, J=7.6 Hz, 2H, Leu-NH*), 8.57 (d, J=9.5 Hz, 2H, Val-NH), 8.35 (d, J=9.6 Hz, 2H, Val-NH*), 8.05 (d, J=8.4 Hz, 2H, Thr-NH), 7.52 (d, J=9.4 Hz, 2H, Leu-NH), 7.48 (d, J=8.9 Hz, 2H, Thr-NH*), 7.44 (d, J=1.9 Hz, 2H, Trp-C4H*), 7.40 (d, J=2.0 Hz, 2H, Trp-C4H), 7.34 (dd, J=8.2, 1.8 Hz, 2H, Trp-C6H*), 7.25 (dd, J=8.2, 1.9 Hz, 2H, Trp-C6H), 6.63 (d, J=8.2 Hz, 2H, Trp-C7H*), 6.59 (d, J=8.2 Hz, 2H, Trp-C7H), 6.30 (d, J=2.2 Hz, 2H, Trp-N8H*), 6.28 (d, J=2.3 Hz, 2H, Trp-N8H), 5.99 (s, 2H, Trp-C3aOH*), 5.84 (s, 2H, Trp-C3aOH), 5.39 (s, 2H, Trp-C8aH*), 5.33 (d, J=2.2 Hz, 2H, Trp-C8aH), 5.14 (d, J=9.1 Hz, 2H, Hiv-CαH), 4.91 (d, J=8.3 Hz, 2H, Hiv-CαH*), 4.77 (dd, J=8.1, 5.1 Hz, 2H, Trp-C2H), 4.72 (s, 2H, Thr-CβOH*), 4.67 (s, 2H, Thr-CβOH), 4.65 (dd, J=9.5, 3.5 Hz, 2H, Val-CαH), 4.63 (d, J=7.2 Hz, 2H, Pro-CαH), 4.44 (app-t, J=8.0 Hz, 2H, Thr-CαH*), 4.32-4.23 (m, 6H, Thr-CαH, Leu-CαH, Pro-CαH*), 4.17 (app-t, J=9.4 Hz, 2H, Val-CαH*), 4.04 (dd, J=10.6, 6.2 Hz, 2H, Trp-C2H*), 3.99 (ddd, J=11.4, 7.7, 3.4 Hz, 2H, Leu-CαH*), 3.91 (app-q, J=6.1 Hz, 2H, Thr-CβH*), 3.87 (app-t, 2H, J=8.5 Hz, Pro-CδH$_a$*), 3.74-3.64 (m, 4H, Thr-CβH, Pro-CH$_a$), 3.55 (app-q, J=9.2 Hz, 4H, Pro-CδH$_b$, Pro-CδH$_b$*), 2.64-2.58 (m, 2H, Trp-C3H$_a$*), 2.53 (dd, J=13.2, 7.9 Hz, 2H, Trp-C3H$_a$), 2.41-2.34 (m, 2H, Trp-C3H$_b$*), 2.31 (dd, J=13.2, 4.7 Hz, 2H, Trp-C3H$_b$), 2.24-2.12 (m, 8H, Pro-CβH$_a$, Val-CβH, Hiv-CβH, Pro-CγH$_a$*), 2.07-2.00 (m, 2H, Hiv-CβH*), 1.98-1.91 (m, 2H, Pro-CβH$_a$*), 1.91-1.84 (m, 4H, Pro-CγH$_a$, Pro-CγH$_b$*), 1.79 (heptd, J=6.8, 3.7 Hz, 2H, Val-CβH*), 1.74-1.67 (m, 4H, Pro-CγH$_b$, Pro-CβH$_b$*), 1.67-1.51 (m, 8H, Leu-CγH, Pro-CβH$_b$, Leu-CβH$_a$*, Leu-CγH*), 1.33-1.19 (m, 6H, Leu-CβH$_a$, Leu-CβH$_b$, Leu-CβH$_b$*), 1.13 (d, J=6.2 Hz, 6H, Thr-CγH$_3$*), 0.95 (d, J=6.2 Hz, 6H, Thr-CγH$_3$), 0.94 (d, J=6.6 Hz, 12H, Hiv-CγH$_3$, Hiv-CγH$_3$*), 0.90 (d, J=6.7 Hz, 12H, Leu-CδH$_3$, Leu-CδH$_3$*), 0.89-0.87 (m, 24H, Leu-CδH$_3$, Hiv-CγH$_3$, Val-CγH$_3$, Hiv-CγH$_3$*), 0.86 (d, J=6.8 Hz, 6H, Leu-CδH$_3$*), 0.84 (d, J=6.8 Hz, 6H, Val-CγH$_3$*), 0.83 (d, J=6.5 Hz, 6H, Val-CγH$_3$*), 0.81 (d, J=6.8 Hz, 6H, Val-CγH$_3$).

$^{13}$C NMR (150.9 MHz, DMSO-d$_6$, 25° C., major conformer): δ 171.9 (2C, Trp-CO, Thr-CO), 170.7 (Leu-CO), 170.6 (Pro-CO), 170.2 (Hiv-CO), 168.6 (Val-CO), 147.9 (Trp-C7a), 131.6 (Trp-C4a), 130.8 (Trp-C5), 126.9 (Trp-C6), 120.6 (Trp-C4), 109.9 (Trp-C7), 84.9 (Trp-C3a), 84.5 (Trp-C8a), 75.1 (Hiv-Cα), 68.0 (Thr-Cβ), 60.3 (Trp-C2), 58.5 (Pro-Cα), 55.5 (Val-Cα), 55.4 (Thr-Cα), 51.0 (Leu-Cα), 46.2 (Pro-Cδ), 43.9 (Trp-C3), 41.1 (Leu-Cβ), 31.0 (Val-Cβ), 29.3 (Hiv-Cδ), 25.5 (Pro-Cβ), 24.4 (Leu-Cγ), 23.9 (Pro-Cγ), 23.3 (Leu-Cδ), 21.7 (Leu-Cδ), 19.6 (Thr-Cγ), 19.2 (Val-Cγ), 17.8 (Hiv-Cγ), 17.4 (Hiv-Cγ), 16.5 (Val-Cγ).

FTIR (thin film) cm$^{-1}$: 3312 (br-s), 2964 (m), 2931 (m), 2875 (w), 1744 (m), 1666 (s), 1650 (s), 1537 (m), 1442 (m), 1182 (m).

HRMS (ESI) (m/z): calc'd for $C_{72}H_{103}N_{12}O_{18}$ [M+H]$^+$: 1423.7508, found: 1423.7465.

$[α]_D^{24}$: −139 (c=0.091, MeOH).

TLC (10% methanol in dichloromethane), Rf: 0.17 (UV, CAM).

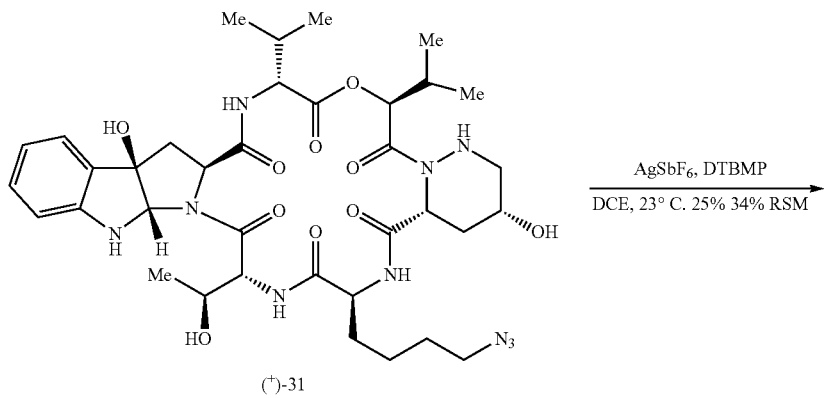

(+)-31

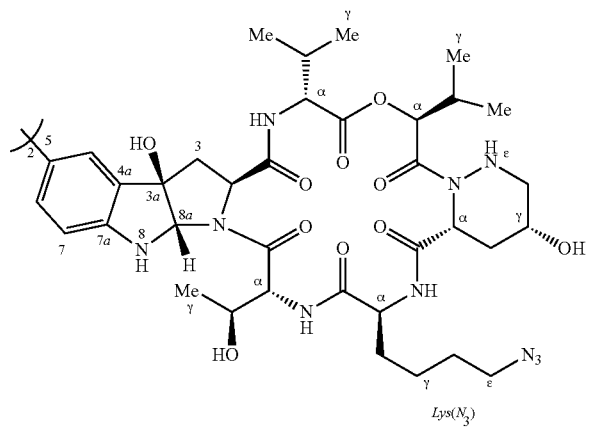

Lys(N₃)

(−)-32

Himastatin ε-Azidolysine Derivative (−)-32:

Prepared according to a scale-down of the procedure described previously for himastatin monomer (−)-1 from azido cyclic hexapeptide (+)-31 (7.05 mg, 8.98 μmol, 1 equiv.). Flash column chromatography on silica (eluent: 1.8% methanol, 0.2% ammonium hydroxide→7.2% methanol, 0.8% ammonium hydroxide in chloroform), followed by semi-preparative HPLC purification of mixed fractions of dimer (−)-32 and monomer (+)-31 (Zorbax® StableBond 80 Å CN, 9.4 mm×250 mm, 40%→95% acetonitrile in water, 16 min, 5.0 mL/min, 270 nm, $t_R$ ((−)-32)=8.77 min, $t_R$ ((+)-31)=7.19 min) afforded himastatin F-azidolysine derivative (−)-32 (1.77 mg, 25.1%) and recovered azido cyclic hexapeptide (+)-31 (2.40 mg, 34.0%) as white foams. Structural assignments were made using additional information from gCOSY, gHSQC, and gHMBC experiments.

Himastatin ε-Azidolysine Derivative (−)-23:

Prepared according to the procedure described previously for (−)-himastatin (1) from azido cyclic depsihexapeptide (+)-22 (5.10 mg, 6.50 μmol, 1 equiv). Flash column chromatography on silica gel (eluent: 1.8% methanol, 0.2% ammonium hydroxide→4.5% methanol, 0.5% ammonium hydroxide in chloroform) afforded himastatin F-azidolysine derivative (−)-23 (1.87 mg, 37%) as an off-white solid. Structural assignments were made using additional information from gCOSY, gHSQC, and gHMBC experiments.

$^1$H NMR (600 MHz, CDCl₃, 25° C.): δ 7.59-7.56 (m, 4H, Lys(N₃)—NH, Trp-C4H), 7.42 (dd, J=8.2, 1.9 Hz, 2H, Trp-C6H), 7.33 (d, J=9.9 Hz, 2H, Val-NH), 7.14 (d, J=10.4 Hz, 2H, Thr-NH), 6.80 (d, J=8.3, 2H, Trp-C7H), 5.98 (s, 2H, Trp-C3aOH), 5.79 (d, J=6.3 Hz, 2H, Trp-N8H), 5.64 (d, J=8.6 Hz, 2H, Hiv-CαH), 5.42 (dd, J=12.8, 1.8 Hz, 2H, Pip-NεH), 5.23 (d, J=8.0 Hz, 2H, Trp-C2H), 5.15 (d, J=5.2 Hz, 2H, Pip-CγOH), 5.14 (d, J=6.4 Hz, 2H, Trp-C8aH), 5.12 (d, J=7.0 Hz, 2H, Pip-CαH), 4.96 (d, J=10.5 Hz, 2H, Thr-CαH), 4.89 (dd, J=10.0, 3.2 Hz, 2H, Val-CαH), 4.45 (qd, J=6.9, 1.8 Hz, 2H, Thr-CβH), 4.23 (app-dt, J=8.0, 5.0 Hz, 2H, Lys(N₃)—CαH), 3.82 (app-sept, J=2.3 Hz, 2H, Pip-CγH), 3.61 (br-s, 2H, Thr-CβOH), 3.30-3.20 (m, 4H, Lys(N₃)—CεH), 3.09-3.04 (m, 2H, Pip-CδH$_a$), 2.84 (app-t, J=13.5 Hz, 2H, Pip-CδH$_b$), 2.77 (d, J=14.4 Hz, 2H, Trp-C3H$_a$), 2.57 (septd, J=6.7, 3.3 Hz, 2H, Val-CβH), 2.51-2.46 (m, 2H, Pip-CβH$_a$), 2.21 (dd, J=14.3, 8.0 Hz, 2H, Trp-C3H$_b$), 2.19-2.13 (m, 2H, Hiv-CβH), 1.95 (ddd, J=15.0, 7.2, 3.5 Hz, 2H, Pip-CβH$_b$), 1.87-1.80 (m, 2H, Lys(N₃)—CβH$_a$), 1.68-1.53 (m, 6H, Lys(N₃)—CβH$_b$, Lys(N₃)—CδH), 1.34 (app-p, J=7.9 Hz, 4H, Lys(N₃)—CγH), 1.16 (dd, J=6.5 Hz, 6H, Thr-CγH₃), 1.13 (d, J=6.6 Hz, 6H, Hiv-CγH₃), 1.02 (d, J=6.9 Hz, 6H, Hiv-CγH₃), 1.01 (d, J=6.9 Hz, 6H, Val-CγH₃) 0.87 (d, J=6.9 Hz, 6H, Val-CγH₃).

$^{13}$C NMR (150.9 MHz, CDCl₃, 25° C.): δ 174.3 (Hiv-CO), 173.6 (Val-CO), 173.5 (Pip-CO), 173.2 (2C, Trp-CO, Lys(N₃)—CO), 172.4 (Thr-CO), 146.8 (Trp-C7a), 134.6 (Trp-C5), 132.3 (Trp-C4a), 128.6 (Trp-C6), 121.5 (Trp-C4), 112.8 (Trp-C7), 91.0 (Trp-C3a), 86.4 (Trp-C8a), 77.5 (Hiv-Cα), 66.8 (Thr-Cβ), 61.0 (Trp-C2), 58.8 (Pip-CγH), 57.4 (Val-Cα), 55.6 (Lys(N₃)—Cα), 54.0 (Thr-Cα), 52.8 (Pip-Cδ), 50.9 (Lys(N₃)—Cε), 50.1 (Pip-Cα), 39.5 (Trp-C3), 31.4 (Lys(N₃)—Cβ), 30.1 (2C, Val-Cβ, Hiv-Cβ), 28.7 (Pip-Cβ), 28.3 (Lys(N₃)—Cδ), 22.9 (Lys(N₃)—Cγ), 19.5 (Val-Cγ), 19.1 (Hiv-Cγ), 18.4 (Hiv-Cγ), 17.5 (Thr-Cγ), 16.6 (Val-Cγ).

FTIR (thin film) cm$^{-1}$: 3307 (br-s), 2964 (m), 2932 (m), 2876 (w), 2094 (m), 1739 (m), 1670 (s), 1533 (m), 1420 (m), 1251 (m), 1110 (w).

HRMS (ESI) (m/z): calc'd for $C_{72}H_{102}N_{20}NaO_{20}$ [M+Na]$^+$: 1589.7471, found: 1589.7459.

$[\alpha]_D^{24}$: −29 (c=0.091, MeOH).

TLC (9% methanol, 1% ammonium hydroxide in chloroform), Rf: 0.28 (UV, CAM).

solution of the crude amine and N,N-diisopropylethylamine (9.1 µL, 52 mol, 20 equiv) in N,N-dimethylformamide (150 µL) at 23° C. After 17 h, the reaction mixture was concentrated under reduced pressure. The resulting residue was purified by semi-preparative HPLC purification (Zorbax® StableBond 80 Å CN, 9.4 mm×250 mm, 40%→95% acetonitrile, 0.1% formic acid in water, 16 min, 5.0 mL/min, 254 nm, $t_R$ ((−)-24)=7.53 min) to afford TAMRA himastatin

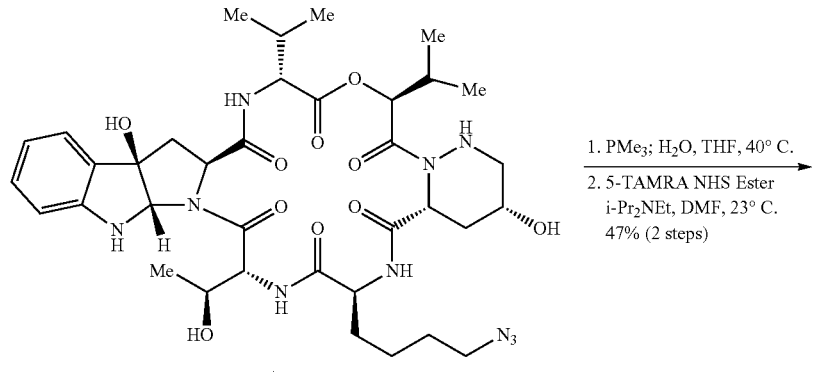

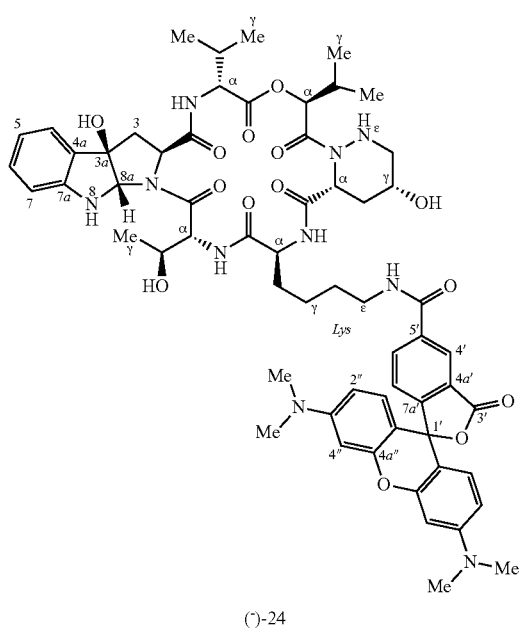

TAMRA Himastatin Monomer (−)-24:

A solution of trimethyl phosphine (1.0 M in tetrahydrofuran, 40 µL, 40 µmol, 15 equiv) was added to a pressure flask containing a solution of azido cyclic depsihexapeptide (+)-22 (2.05 mg, 2.61 µmol, 1 equiv) in tetrahydrofuran (150 µL) at 23° C. The reaction vessel was sealed with a Teflon screwcap under an argon atmosphere and was immersed in a preheated oil bath at 40° C. After 24 h, the reaction mixture was cooled to 23° C. and deionized water (5.0 µL) was added. The vessel was then resealed and reheated to 40° C. After 1 h, the reaction mixture was diluted with 10% methanol in dichloromethane and concentrated under reduced pressure to provide the crude amine as a thin film, which was used directly in the next step without further purification.

5-Carboxy-tetramethylrhodamine N-succinimidyl ester (6.89 mg, 13.1 µmol, 5.00 equiv) was added as a solid to a monomer (−)-24 (1.44 mg, 47%) as a pink foam. Structural assignments were made using additional information from gCOSY, gHSQC, and gHMBC experiments. Additional $^{13}$C signals were identified from gHSQC, and gHMBC spectra.

$^1$H NMR (600 MHz, CDCl$_3$, 25° C.): δ 8.40 (d, J=1.5 Hz, 1H, C4'H), 8.13 (dd, J=8.0, 1.6 Hz, 1H, C6'H), 7.64 (d, J=5.2 Hz, 1H, Lys-NaH), 7.36 (dd, J=7.6, 1.3 Hz, 1H, Trp-C4H), 7.32 (d, J=10.0 Hz, 1H, Val-NH), 7.21-7.14 (m, 3H, C7'H, Thr-NH, Trp-C6H), 7.03 (app-t, J=6.2 Hz, 1H, Lys-NH), 6.86 (app-td, J=7.4, 1.0 Hz, 1H, Trp-C5H), 6.73 (d, J=8.0 Hz, 1H, Trp-C7H), 6.61-6.56 (m, 2H, C2″H), 6.50 (d, J=2.6 Hz, 2H, C4″H), 6.42-6.38 (m, 2H, C1″H), 6.12 (br-s, 1H, Trp-C3aOH) 5.83 (br-s, 1H, Trp-N8H), 5.64 (d, J=8.6 Hz, 1H, Hiv-CαH), 5.41 (dd, J=13.0, 2.1 Hz, Pip-NεH), 5.23-5.17 (m, 4H, Trp-C8aH, Trp-C2H, Pip-CαH, Pip-CγOH), 4.97 (d, J=10.4 Hz, 1H, Thr-CαH), 4.88 (dd, J=10.0, 3.2 Hz, 1H, Val-CαH), 4.44 (q, J=6.5 Hz, 1H, Thr-CβH), 4.27 (app-q, J=5.9 Hz, 1H, Lys-CαH), 3.82 (app-br-s, 1H, Pip-CγH), 3.65 (br-s, 1H, Thr-CβOH), 3.49-3.38 (m, 2H, Lys-CεH), 3.06 (dd, J=14.6, 2.4 Hz, 1H, Pip-CH$_a$), 3.00 (s, 12H, C3"N(CH$_3$)$_2$), 2.85 (app-t, J=13.3 Hz, 1H, Pip-CδH$_b$), 2.79 (d, J=14.4 Hz, 1H, Trp-C3H$_a$), 2.55 (septd, J=6.8, 3.2 Hz, 1H, Val-CβH), 2.48 (app-dp, J=14.5, 2.6 Hz, 1H, Pip-CβH$_a$), 2.20 (dd, J=14.4, 8.1 Hz, 1H, Trp-C3H$_b$), 2.13 (sept, J=6.7 Hz, 1H, Hiv-CβH), 2.01 (ddd, J=15.1, 7.2, 3.4 Hz, 1H, Pip-CβH$_b$), 1.84-1.73 (m, 2H, Lys-CβH$_2$), 1.70-1.61 (m, 2H Lys-CδH$_b$), 1.45-1.33 (m, 2H, Lys-CγH$_2$), 1.17 (d, J=6.5 Hz, 3H, Thr-CγH$_3$), 1.09 (d, J=6.6 Hz, 3H, Hiv-CγH$_3$), 1.01 (d, J=7.2 Hz, 3H, Val-CγH$_3$), 0.99 (d, J=6.8 Hz, 3H, Hiv-CγH$_3$), 0.87 (d, J=6.8 Hz, 3H, Val-CγH$_3$).

$^{13}$C NMR (150.9 MHz, CDCl$_3$, 25° C.): δ 174.3 (Hiv-CO), 173.5 (Val-CO), 173.4 (Pip-CO), 173.2 (2C, Trp-CO, Lys-CO) 172.5 (Thr-CO), 169.2 (C3'), 166.4 (C5'CO), 155.7 (2C, C4a', C5') 153.7 (C4"a), 153.0 (C1"a), 152.7 (C3"), 147.8 (Trp-C7a), 136.5 (C7a'), 133.8 (C6'), 131.5 (Trp-C4a), 130.1 (Trp-C6), 129.3 (C2"), 125.2 (C7'), 124.0 (C4"), 123.4 (Trp-C4), 121.2 (Trp-C5), 112.4 (Trp-C7), 109.5 (C1"), 107.4 (C1'), 98.4 (C4'), 91.0 (Trp-C3a), 86.0 (Trp-C8a), 77.6 (Hiv-Cα), 66.8 (Thr-Cβ), 61.0 (Trp-C2), 58.8 (Pip-CγH), 57.4 (Val-Cα), 55.5 (Lys-Cα), 54.0 (Thr-Cα), 52.7 (Pip-Cδ), 50.3 (Pip-Cα), 40.5 (C3"N(CH$_3$)$_2$), 39.5 (2C, Lys-Cε, Trp-C3), 31.5 (Lys-Cβ), 30.1 (2C, Val-Cβ, Hiv-Cβ), 28.9 (Lys-Cδ), 28.6 (Pip-Cβ), 22.7 (Lys-Cγ), 19.5 (Val-Cγ), 19.0 (Hiv-Cγ), 18.5 (Hiv-Cγ), 17.5 (Thr-Cγ), 16.5 (Val-Cγ).

FTIR (thin film) cm$^{-1}$: 3285 (br-s), 2964 (m), 2930 (m), 2875 (w), 1648 (m), 1598 (s), 1533 (m), 1408 (m), 1348 (m), 1189 (m), 929 (w).

HRMS (ESI) (m/z): calc'd for C$_1$H$_{74}$N$_{10}$NaO$_{14}$ [M+Na]$^+$: 1193.5278, found: 1193.5294.

[α]$_D^{24}$: −36 (c=0.14, MeOH).

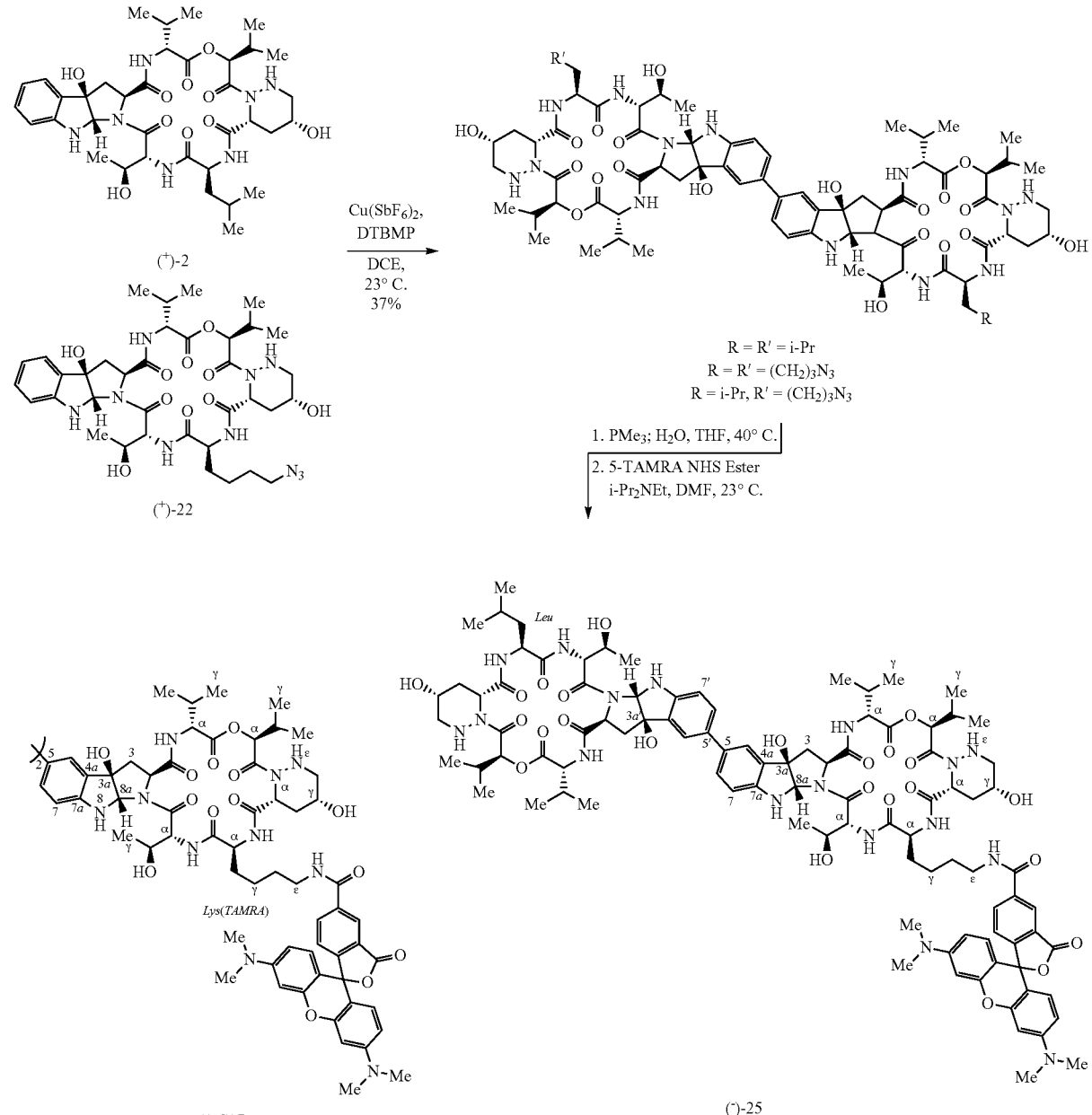

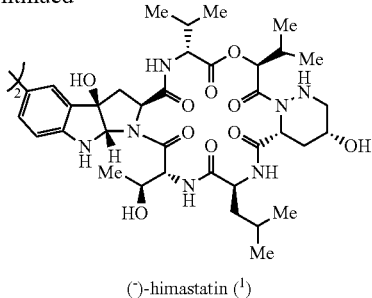

(−)-himastatin (1)

TAMRA Himastatin Heterodimer (−)-25 and TAMRA Himastatin Homodimer (−)-S17:

Dimerization was accomplished according to the procedure described previously for (−)-himastatin (1) from himastatin monomer (+)-2 (7.44 mg, 10.0 μmol, 0.500 equiv) and azido cyclic depsihexapeptide (+)-22 (7.85 mg, 10.0 μmol, 0.500 equiv). Flash column chromatography on silica gel (eluent: 2.7% methanol, 0.3% ammonium hydroxide→4.5% methanol, 0.5% ammonium hydroxide in chloroform) afforded a mixture of hetero- and homodimers (5.67 mg, 37%) as an off-white solid.

A solution of trimethyl phosphine (1.0 M in tetrahydrofuran, 60 μL, 60 μmol, 21 equiv) was added to a pressure flask containing a solution of the above homo- and heterodimers (4.43 mg, 2.90 μmol, 1 equiv) in tetrahydrofuran (300 μL) at 23° C. The reaction vessel was sealed with a Teflon screwcap under an argon atmosphere and was immersed in a preheated oil bath at 40° C. After 16 h, the reaction mixture was cooled to 23° C. and deionized water (5.0 μL) was added. The vessel was then resealed and reheated to 40° C. After 1 h, the reaction mixture was diluted with 10% methanol in dichloromethane and concentrated under reduced pressure to yield a crude mixture which was used directly in the next step without further purification.

5-Carboxy-tetramethylrhodamine N-succinimidyl ester (4.6 mg, 8.7 μmol, 30 equiv) was added as a solid to a solution of the crude mixture and N,N-diisopropylethylamine (10 μL, 58 mol, 20 equiv) in N,N-dimethylformamide (120 μL) at 23° C. After 17 h, the reaction mixture was concentrated under reduced pressure. The resulting residue was purified by semi-preparative HPLC purification (Zorbax® StableBond 80 Å CN, 9.4 mm×250 mm, 5%→95% acetonitrile, 0.1% formic acid in water, 16 min, 5.0 mL/min, 254 nm, $t_R$ ((−)-S17)=8.81 min, (−)-25)=10.34 min, (−)-1)=12.24 min) to afford TAMRA himastatin homodimer (−)-S17 (0.61 mg, 9%) as a pink foam, TAMRA himastatin heterodimer (−)-25 (1.01 mg, 18%) as a pink foam, and (−)-himastatin (1, 0.95 mg, 22%) as a white foam. Spectral data of (−)-himastatin (1) were in agreement with those previously reported in this document. For TAMRA himastatin heterodimer (−)-25, all observable $^{13}$C resonances in $^{13}$C, gHSQC, and gHMBC spectra are given. For TAMRA himastatin homodimer (−)-S17, structural assignments were made using additional information from gCOSY, gHSQC, and gHMBC experiments. Additional $^{13}$C signals were identified from gHSQC, and gHMBC spectra.

TAMRA Himastatin Heterodimer (−)-25

$^1$H NMR (600 MHz, DMSO-$d_6$, 25° C.): δ 8.85 (s, 1H), 8.54-8.38 (m, 3H), 8.25 (s, 1H), 8.14 (d, J=8.1 Hz, 1H), 8.03-7.90 (m, 2H), 7.41 (d, J=5.1 Hz, 2H), 7.35 (d, J=2.1 Hz, 2H), 6.89-6.73 (m, 2H), 6.67 (s, 2H), 6.58-6.41 (m, 2H), 6.18 (d, J=12.7 Hz, 2H), 5.74 (d, J=4.2 Hz, 1H), 5.71 (d, J=4.4 Hz, 1H), 5.64 (app-t, J=6.2 Hz, 2H), 5.24 (s, 1H), 5.14 (d, J=4.2 Hz, 1H), 5.07-4.99 (m, 2H), 4.84 (dd, J=20.3, 6.6 Hz, 2H), 4.73-4.65 (m, 2H), 4.65-4.57 (m, 4H), 4.39-4.33 (m, 6H), 4.18-4.10 (m, 2H), 4.08 (app-p, J=6.4 Hz, 2H), 3.63 (s, 2H), 3.48 (s, 2H), 3.34-3.26 (m, 2H), 2.95 (s, 12H), 2.81 (d, J=11.4 Hz, 4H), 2.35-2.02 (m, 10H), 1.98-1.88 (m, 2H), 1.86-1.76 (m, 1H), 1.68-1.45 (m, 6H), 1.43-1.27 (m, 3H), 1.17-1.10 (m, 6H), 0.99-0.81 (m, 30H).

$^{13}$C NMR (150.9 MHz, DMSO-$d_6$, 25° C.): δ 174.7, 173.1, 172.9, 172.2, 171.7, 171.3, 170.8, 170.3, 147.1, 132.6, 132.6, 131.9, 131.7, 127.4, 127.0, 120.7, 120.5, 111.5, 88.1, 86.1, 74.8, 74.5, 72.9, 72.6, 66.8, 66.4, 63.5, 63.1, 61.1, 60.8, 60.4, 60.1, 59.6, 58.3, 58.0, 57.8, 56.7, 52.9, 52.8, 51.4, 48.7, 48.6, 41.2, 40.1, 39.7, 34.1, 32.3, 30.8, 30.0, 29.3, 29.1, 29.1, 24.6, 23.2, 23.1, 22.5, 20.4, 19.7, 18.9, 18.1.

FTIR (thin film) cm$^{-1}$: 3294 (br-s), 2962 (m), 2931 (m), 2874 (w), 1742 (s), 1650 (m), 1597 (s), 1534 (m), 1409 (m), 1348 (m), 1189 (m), 929 (w).

HRMS (ESI) (m/z): calc'd for $C_{97}H_{126}N_{17}O_{24}$ [M+Na]$^+$: 1912.9156, found: 1912.9153.

$[\alpha]_D^{24}$: −51 (c=0.10, MeOH).

TAMRA Himastatin Homodimer (−)-S17

$^1$H NMR (600 MHz, CDCl$_3$, 25° C.): δ 8.43 (d, J=1.6 Hz, 2H, C4'H), 8.13 (dd, J=8.0, 1.6 Hz, 2H, C6'H), 7.63 (d, J=5.1 Hz, 2H, Lys-NαH), 7.57 (d, J=1.9 Hz, 2H, Trp-C4H), 7.34 (dd, J=8.3, 1.9 Hz, 2H, Trp-C6H), 7.29 (d, J=10.0 Hz, 2H, Val-NH), 7.19-7.15 (m, 4H, C7'H, Thr-NH), 7.08 (app-t, J=5.0 Hz, 2H, Lys-NH), 6.72 (d, J=8.3 Hz, 2H, Trp-C7H), 6.57 (d, J=8.9 Hz, 2H, C2"H$_a$), 6.53 (d, J=8.9 Hz, 2H, C2"H$_b$), 6.48 (d, J=2.5 Hz, 4H, C4"H), 6.40-6.35 (m, 4H, C1"H), 6.16 (br-s, 2H, Trp-C3aOH), 5.85 (s, 2H, Trp-N8H), 5.64 (d, J=8.5 Hz, 2H, Hiv-CαH), 5.40 (d, J=12.7 Hz, 2H, Pip-NεH), 5.22 (s, 2H, Trp-C8aH), 5.21-5.15 (m, 6H, Trp-C2H, Pip-CαH, Pip-CγOH), 4.98 (d, J=10.4 Hz, 2H, Thr-CαH), 4.87 (dd, J=10.1, 3.2 Hz, 2H, Val-CαH), 4.44 (q, J=6.6 Hz, 2H, Thr-CβH), 4.24 (app-q, J=5.9 Hz, 2H, Lys-CαH), 3.82 (app-br-s, 2H, Pip-CγH), 3.64 (s, 2H, Thr-CβOH), 3.48 (app-dq, J=12.8, 6.1 Hz, 2H, Lys-CεH$_a$), 3.37 (app-dq, J=12.4, 6.2 Hz, 2H, Lys-CεH$_b$), 3.06 (d, J=13.9 Hz, 2H, Pip-CδH$_a$), 2.98 (s, 24H, C3"N(CH$_3$)$_2$), 2.85 (app-t, J=13.1 Hz, 2H, Pip-CδH$_b$), 2.79 (d, J=14.4 Hz, 2H, Trp-C3H$_a$), 2.54 (septd, J=6.9, 3.3 Hz, 2H, Val-CβH), 2.48 (d, J=14.9 Hz, 2H, Pip-CβH$_a$), 2.19 (dd, J=14.4, 7.9 Hz, 2H, Trp-C3H$_b$), 2.12 (sept, J=6.7 Hz, 2H, Hiv-CβH), 2.04-1.99 (m, 2H, Pip-CβH$_b$), 1.86-1.79 (m, 2H, Lys-CβH$_a$), 1.75-1.68 (m, 2H, Lys-CβH$_b$), 1.68-1.58 (m, 4H, Lys-CβH$_2$), 1.42-1.34 (m, 4H, Lys-CγH$_2$), 1.17 (d, J=6.5 Hz, 6H, Thr-CγH$_3$), 1.09 (d, J=6.6 Hz, 6H, Hiv-CγH$_3$), 1.00 (d, J=7.0 Hz, 6H, Val-CγH$_3$), 0.99 (d, J=6.7 Hz, 6H, Hiv-CγH$_3$), 0.87 (d, J=6.8 Hz, 6H, Val-CγH$_3$).

$^{13}$C NMR (150.9 MHz, CDCl$_3$, 25° C.): δ 174.3 (Hiv-CO), 173.6 (Val-CO), 173.2 (Pip-CO), 172.9 (3C, Trp-CO,

Lys-CO, Thr-CO), 169.4 (C3'), 166.4 (C5'CO), 155.6 (2C, C4a', C5'), 153.4 (C4"a), 153.0 (C1"a), 146.8 (Trp-C7a), 134.5 (Trp-C5), 134.1 (C6'), 132.0 (Trp-C4a), 128.9 (C2"), 128.4 (Trp-C6), 124.7 (C7'), 123.3 (C4"), 121.4 (Trp-C4), 112.4 (Trp-C7), 109.5 (C1"), 106.7 (C1'), 98.4 (C4'), 91.0 (Trp-C3a), 86.2 (Trp-C8a), 77.3 (Hiv-Cα), 66.5 (Thr-Cβ), 60.8 (Trp-C2), 58.7 (Pip-CγH), 57.1 (Val-Cα), 55.2 (Lys-Cα), 53.8 (Thr-Cα), 52.6 (Pip-Cδ), 50.0 (Pip-Cα), 40.1 (C3"N(CH$_3$)$_2$), 39.5 (Lys-Cε), 39.3 (Trp-Cβ), 31.2 (Lys-Cβ), 29.8 (2C, Val-Cβ, Hiv-Cβ), 28.5 (Lys-Cδ), 28.4 (Pip-Cβ), 22.3 (Lys-Cγ), 19.3 (Val-Cγ), 18.7 (Hiv-Cγ), 18.4 (Hiv-Cγ), 17.3 (Thr-Cγ), 16.4 (Val-Cγ).

FTIR (thin film) cm$^{-1}$: 3268 (br-s), 2964 (m), 2936 (m), 1743 (m), 1648 (s), 1597 (s), 1536 (m), 1408 (m), 1348 (m), 1190 (m), 929 (w).

HRMS (ESI) (m/z): calc'd for C$_{122}$H$_{148}$N$_{20}$O$_{28}$ [M+2H]$^{2+:\ 1170.5380}$, found: 1170.5393.

$[\alpha]_D^{24}$: −48 (c=0.12, MeOH).

Crystal Structure of Glycine Endo-Diketopiperazine Dimer (+)-7h:

Structural parameters for glycine endo-diketopiperazine dimer (+)-7h are freely available from the Cambridge Crystallographic Data Center (CCDC 2099734). Thermal ellipsoids are drawn at 30% probability.

TABLE S5

Crystal data and structure refinement for glycine endo-diketopiperazine dimer (+)-7h

| | |
|---|---|
| Identification code | 092-df_sq |
| Empirical formula | C33.5 H50 N4.5 O4.5 Si1.5 |
| Formula weight | 629.91 |
| Temperature | 100(2) K |
| Wavelength | 1.54178 Å |
| Crystal system | Tetragonal |
| Space group | P4$_3$2$_1$2 |
| Unit cell dimensions | a = 19.5531(7) Å    a = 90°. |
| | b = 19.5531(7) Å    b = 90°. |
| | c = 40.8927(15) Å   g = 90°. |
| Volume | 15634.2(13) Å$^3$ |
| Z | 16 |
| Density (calculated) | 1.070 Mg/m$^3$ |
| Absorption coefficient | 0.987 mm$^{-1}$ |
| F(000) | 5432 |
| Crystal size | 0.404 × 0.185 × 0.110 mm$^3$ |
| Theta range for data collection | 3.196 to 70.079°. |
| Index ranges | −23 <= h <= 23, −23 <= k <= 23, −46 <= l <=48 |
| Reflections collected | 225810 |
| Independent reflections | 14697 [R(int) = 0.0497] |
| Completeness to theta = 67.679° | 99.7% |
| Absorption correction | Semi-empirical from equivalents |
| Max. and min. transmission | 0.7533 and 0.6862 |
| Refinement method | Full-matrix least-squares on F$^2$ |
| Data/restraints/parameters | 14697/1431/997 |
| Goodness-of-fit on F$^2$ | 1.059 |
| Final R indices [I > 2sigma(I)] | R1 = 0.0749, wR2 = 0.2164 |
| R indices (all data) | R1 = 0.0831, wR2 = 0.2301 |
| Absolute structure parameter | 0.038(6) |
| Extinction coefficient | n/a |
| Largest diff. peak and hole | 0.796 and −0.448 e · Å$^{-3}$ |

TABLE S6

Atomic coordinates (×10$^4$) and equivalent isotropic displacement parameters (Å$^2$ × 10$^3$) for glycine endo-diketopiperazine dimer (+)-7h. U(eq) is defined as one third of the trace of the orthogonalized U$^{ij}$ tensor.

| | x | y | z | U(eq) |
|---|---|---|---|---|
| O(2) | 6134(2) | 10599(2) | 7284(1) | 44(1) |
| O(3) | 7275(2) | 8780(2) | 6464(1) | 42(1) |
| O(5) | 10583(2) | 6242(2) | 9365(1) | 49(1) |
| O(6) | 8798(2) | 7406(2) | 10192(1) | 40(1) |
| N(1) | 6586(2) | 10364(2) | 6784(1) | 39(1) |
| N(2) | 6792(2) | 9029(2) | 6952(1) | 34(1) |
| N(3) | 7641(2) | 8222(2) | 7153(1) | 53(1) |
| N(4) | 10381(2) | 6746(2) | 9859(1) | 38(1) |
| N(5) | 9027(2) | 6882(2) | 9710(1) | 32(1) |
| N(6) | 8173(2) | 7690(2) | 9518(1) | 46(1) |
| C(1) | 6614(2) | 8439(2) | 7454(1) | 44(1) |
| O(1) | 5993(2) | 8093(2) | 7486(1) | 56(1) |
| Si(1) | 5869(4) | 7209(4) | 7476(2) | 61(2) |
| C(15) | 5061(6) | 7222(8) | 7211(4) | 76(3) |
| C(16) | 4588(12) | 6673(12) | 7299(7) | 137(7) |
| C(17) | 6046(7) | 6850(6) | 7887(3) | 72(2) |
| C(18) | 5642(12) | 7068(11) | 8173(4) | 94(5) |
| C(19) | 6416(7) | 6756(6) | 7169(4) | 85(3) |
| C(20) | 6525(11) | 6021(9) | 7263(5) | 125(5) |
| Si(1A) | 5729(3) | 7338(3) | 7531(2) | 48(1) |
| C(15A) | 4893(6) | 7169(7) | 7383(4) | 75(3) |
| C(16A) | 4605(9) | 6460(8) | 7422(5) | 88(4) |
| C(17A) | 5262(6) | 7200(6) | 7939(2) | 64(2) |
| C(18A) | 5686(11) | 7251(9) | 8236(4) | 70(4) |
| C(19A) | 6438(5) | 6726(5) | 7488(3) | 63(2) |
| C(20A) | 6242(9) | 5996(6) | 7492(4) | 92(4) |
| C(2) | 6483(3) | 9221(2) | 7488(1) | 49(1) |
| C(3) | 6299(2) | 9426(2) | 7140(1) | 37(1) |
| C(4) | 6338(2) | 10186(2) | 7076(1) | 37(1) |
| C(5) | 6736(2) | 9870(2) | 6526(1) | 44(1) |
| C(6) | 6960(2) | 9174(2) | 6645(1) | 34(1) |
| C(7) | 6929(2) | 8368(2) | 7102(1) | 42(1) |
| C(8) | 7756(2) | 8064(2) | 7478(1) | 42(1) |
| C(9) | 8354(2) | 7806(2) | 7618(1) | 43(1) |
| C(10) | 8364(2) | 7719(2) | 7955(1) | 39(1) |
| C(11) | 7812(2) | 7894(2) | 8155(1) | 36(1) |
| C(12) | 7215(2) | 8140(2) | 8007(1) | 37(1) |
| C(13) | 7183(2) | 8204(2) | 7668(1) | 40(1) |
| C(14) | 6568(3) | 11087(2) | 6686(1) | 52(1) |
| C(21) | 8407(2) | 6652(2) | 9221(1) | 40(1) |
| O(4) | 8027(2) | 6040(2) | 9203(1) | 50(1) |
| Si(2) | 7173(4) | 5926(4) | 9158(2) | 67(2) |
| C(35) | 6903(6) | 6001(7) | 8736(3) | 88(3) |
| C(36) | 7230(9) | 5608(8) | 8477(4) | 109(4) |
| C(37) | 6690(7) | 6606(7) | 9389(4) | 94(3) |
| C(38) | 5916(7) | 6606(9) | 9313(5) | 128(5) |
| C(39) | 7109(9) | 5066(8) | 9375(4) | 75(3) |
| C(40) | 6429(6) | 4686(5) | 9288(3) | 79(3) |
| Si(2A) | 7272(6) | 5820(6) | 9128(2) | 58(2) |
| C(35A) | 7229(10) | 5481(11) | 8692(4) | 85(3) |
| C(36A) | 7847(11) | 5207(10) | 8561(4) | 97(5) |
| C(37A) | 6624(7) | 6517(7) | 9185(4) | 67(3) |
| C(38A) | 6497(11) | 6688(12) | 9557(5) | 104(5) |
| C(39A) | 6975(16) | 5021(13) | 9318(4) | 83(4) |
| C(40A) | 7115(14) | 5005(13) | 9671(5) | 131(7) |
| C(22) | 9170(2) | 6481(3) | 9183(1) | 45(1) |
| C(23) | 9420(2) | 6366(2) | 9533(1) | 36(1) |
| C(24) | 10184(2) | 6454(2) | 9575(1) | 39(1) |
| C(25) | 9906(2) | 6918(2) | 10118(1) | 38(1) |
| C(26) | 9192(2) | 7086(2) | 10011(1) | 34(1) |
| C(27) | 8349(2) | 6981(2) | 9571(1) | 38(1) |
| C(28) | 8030(2) | 7794(2) | 9191(1) | 35(1) |
| C(29) | 7780(2) | 8394(2) | 9048(1) | 37(1) |
| C(30) | 7692(2) | 8397(2) | 8713(1) | 38(1) |
| C(31) | 7870(2) | 7838(2) | 8513(1) | 35(1) |
| C(32) | 8112(2) | 7243(2) | 8664(1) | 36(1) |
| C(33) | 8173(2) | 7222(2) | 9002(1) | 36(1) |
| C(34) | 11110(2) | 6795(3) | 9934(1) | 55(1) |
| O(8) | 3837(2) | −473(2) | 8943(1) | 46(1) |
| O(9) | 2552(2) | 1282(2) | 8145(1) | 46(1) |
| N(7) | 3237(2) | −292(2) | 8476(1) | 40(1) |
| N(8) | 3124(2) | 1067(2) | 8613(1) | 33(1) |
| N(9) | 2347(2) | 1944(2) | 8813(1) | 54(1) |
| C(41) | 3396(2) | 1694(2) | 9095(1) | 40(1) |
| O(7) | 4015(2) | 2061(2) | 9110(1) | 55(1) |

TABLE S6-continued

Atomic coordinates (×10⁴) and equivalent isotropic displacement parameters ($Å^2 \times 10^3$) for glycine endo-diketopiperazine dimer (+)-7h. U(eq) is defined as one third of the trace of the orthogonalized $U^{ij}$ tensor.

|       | x        | y        | z        | U(eq)  |
|-------|----------|----------|----------|--------|
| Si(3) | 4101(2)  | 2932(2)  | 9078(1)  | 49(1)  |
| C(55) | 3922(5)  | 3341(5)  | 9484(2)  | 56(2)  |
| C(56) | 4353(8)  | 3091(8)  | 9761(3)  | 79(3)  |
| C(57) | 5079(5)  | 2927(6)  | 9038(4)  | 72(3)  |
| C(58) | 5385(6)  | 3619(6)  | 9055(3)  | 81(3)  |
| C(59) | 3588(7)  | 3358(6)  | 8754(2)  | 80(3)  |
| C(60) | 4000(13) | 3217(11) | 8413(4)  | 163(7) |
| Si(3A)| 4304(2)  | 2817(2)  | 9195(1)  | 51(1)  |
| C(55A)| 4745(8)  | 2898(8)  | 9610(3)  | 75(3)  |
| C(56A)| 4355(12) | 2953(13) | 9908(4)  | 97(5)  |
| C(57A)| 4968(7)  | 3054(8)  | 8889(3)  | 62(3)  |
| C(58A)| 4911(11) | 3020(10) | 8533(3)  | 103(5) |
| C(59A)| 3581(6)  | 3416(6)  | 9138(4)  | 69(2)  |
| C(60A)| 3749(11) | 4149(7)  | 9085(6)  | 115(6) |
| C(42) | 3555(2)  | 928(2)   | 9130(1)  | 44(1)  |
| C(43) | 3657(2)  | 685(2)   | 8784(1)  | 35(1)  |
| C(44) | 3580(2)  | −79(2)   | 8742(1)  | 37(1)  |
| C(45) | 3016(2)  | 177(2)   | 8216(1)  | 44(1)  |
| C(46) | 2882(2)  | 898(2)   | 8322(1)  | 37(1)  |
| C(47) | 3046(2)  | 1752(2)  | 8752(1)  | 43(1)  |
| C(48) | 2261(2)  | 2091(2)  | 9140(1)  | 41(1)  |
| C(49) | 1671(2)  | 2336(2)  | 9295(1)  | 39(1)  |
| C(50) | 1682(2)  | 2406(2)  | 9630(1)  | 37(1)  |
| C(51) | 2255(2)  | 2218(2)  | 9821(1)  | 33(1)  |
| C(52) | 2836(2)  | 1976(2)  | 9660(1)  | 34(1)  |
| C(53) | 2844(2)  | 1936(2)  | 9320(1)  | 37(1)  |
| C(54) | 3179(3)  | −1013(2) | 8407(1)  | 63(1)  |
| C(1X) | 4456(4)  | −494(4)  | 10834(2) | 103(3) |
| C(2X) | 4112(4)  | −13(4)   | 10570(2) | 87(2)  |
| C(3X) | 4618(3)  | 285(3)   | 10329(2) | 71(2)  |
| C(4X) | 4287(3)  | 736(3)   | 10069(1) | 67(1)  |
| C(5X) | 4789(3)  | 1069(3)  | 9824(1)  | 72(2)  |
| C(6X) | 5140(3)  | 561(3)   | 9599(2)  | 66(1)  |
| C(7X) | 5561(3)  | 870(4)   | 9312(2)  | 82(2)  |

TABLE S7

Bond lengths [Å] and angles [°] glycine endo-diketopiperazine dimer (+)-7h.

| Bond | Length |
|------|--------|
| O(2)—C(4) | 1.236(5) |
| O(3)—C(6) | 1.233(5) |
| O(5)—C(24) | 1.233(5) |
| O(6)—C(26) | 1.237(5) |
| N(1)—C(4) | 1.335(5) |
| N(1)—C(5) | 1.462(5) |
| N(1)—C(14) | 1.469(5) |
| N(2)—C(6) | 1.329(5) |
| N(2)—C(7) | 1.455(5) |
| N(2)—C(3) | 1.457(5) |
| N(3)—C(8) | 1.383(5) |
| N(3)—C(7) | 1.435(6) |
| N(3)—H(3) | 0.87(3) |
| N(4)—C(24) | 1.350(5) |
| N(4)—C(25) | 1.447(5) |
| N(4)—C(34) | 1.461(5) |
| N(5)—C(26) | 1.335(5) |
| N(5)—C(27) | 1.455(5) |
| N(5)—C(23) | 1.460(4) |
| N(6)—C(28) | 1.381(5) |
| N(6)—C(27) | 1.445(5) |
| N(6)—H(6) | 0.88(3) |
| C(1)—O(1) | 1.398(6) |
| C(1)—C(13) | 1.489(6) |
| C(1)—C(2) | 1.557(6) |
| C(1)—C(7) | 1.572(5) |
| O(1)—Si(1A) | 1.573(7) |
| O(1)—Si(1) | 1.744(8) |
| Si(1)—C(17) | 1.851(11) |
| Si(1)—C(19) | 1.874(12) |

TABLE S7-continued

Bond lengths [Å] and angles [°] glycine endo-diketopiperazine dimer (+)-7h.

| Bond | Length |
|------|--------|
| Si(1)—C(15) | 1.917(12) |
| C(15)—C(16) | 1.462(16) |
| C(15)—H(15A) | 0.9900 |
| C(15)—H(15B) | 0.9900 |
| C(16)—H(16A) | 0.9800 |
| C(16)—H(16B) | 0.9800 |
| C(16)—H(16C) | 0.9800 |
| C(17)—C(18) | 1.475(17) |
| C(17)—H(17A) | 0.9900 |
| C(17)—H(17B) | 0.9900 |
| C(18)—H(18A) | 0.9800 |
| C(18)—H(18B) | 0.9800 |
| C(18)—H(18C) | 0.9800 |
| C(19)—C(20) | 1.503(16) |
| C(19)—H(19A) | 0.9900 |
| C(19)—H(19B) | 0.9900 |
| C(20)—H(20A) | 0.9800 |
| C(20)—H(20B) | 0.9800 |
| C(20)—H(20C) | 0.9800 |
| Si(1A)—C(15A) | 1.774(11) |
| Si(1A)—C(19A) | 1.840(11) |
| Si(1A)—C(17A) | 1.921(11) |
| C(15A)—C(16A) | 1.507(15) |
| C(15A)—H(15C) | 0.9900 |
| C(15A)—H(15D) | 0.9900 |
| C(16A)—H(16D) | 0.9800 |
| C(16A)—H(16E) | 0.9800 |
| C(16A)—H(16F) | 0.9800 |
| C(17A)—C(18A) | 1.474(16) |
| C(17A)—H(17C) | 0.9900 |
| C(17A)—H(17D) | 0.9900 |
| C(18A)—H(18D) | 0.9800 |
| C(18A)—H(18E) | 0.9800 |
| C(18A)—H(18F) | 0.9800 |
| C(19A)—C(20A) | 1.479(14) |
| C(19A)—H(19C) | 0.9900 |
| C(19A)—H(19D) | 0.9900 |
| C(20A)—H(20D) | 0.9800 |
| C(20A)—H(20E) | 0.9800 |
| C(20A)—H(20F) | 0.9800 |
| C(2)—C(3) | 1.520(6) |
| C(2)—H(2A) | 0.9900 |
| C(2)—H(2B) | 0.9900 |
| C(3)—C(4) | 1.510(5) |
| C(3)—H(3A) | 1.0000 |
| C(5)—C(6) | 1.510(5) |
| C(5)—H(5A) | 0.9900 |
| C(5)—H(5B) | 0.9900 |
| C(7)—H(7A) | 1.0000 |
| C(8)—C(13) | 1.391(5) |
| C(8)—C(9) | 1.398(6) |
| C(9)—C(10) | 1.387(6) |
| C(9)—H(9A) | 0.9500 |
| C(10)—C(11) | 1.398(5) |
| C(10)—H(10) | 0.9500 |
| C(11)—C(12) | 1.398(6) |
| C(11)—C(31) | 1.475(6) |
| C(12)—C(13) | 1.394(5) |
| C(12)—H(12) | 0.9500 |
| C(14)—H(14A) | 0.9800 |
| C(14)—H(14B) | 0.9800 |
| C(14)—H(14C) | 0.9800 |
| C(21)—O(4) | 1.411(5) |
| C(21)—C(33) | 1.500(6) |
| C(21)—C(22) | 1.538(6) |
| C(21)—C(27) | 1.574(5) |
| O(4)—Si(2A) | 1.568(11) |
| O(4)—Si(2) | 1.694(9) |
| Si(2)—C(35) | 1.810(11) |
| Si(2)—C(37) | 1.885(14) |
| Si(2)—C(39) | 1.907(12) |
| C(35)—C(36) | 1.456(15) |
| C(35)—H(35A) | 0.9900 |
| C(35)—H(35B) | 0.9900 |
| C(36)—H(36A) | 0.9800 |
| C(36)—H(36B) | 0.9800 |
| C(36)—H(36C) | 0.9800 |

TABLE S7-continued

Bond lengths [Å] and angles [°] glycine endo-diketopiperazine dimer (+)-7h.

| | |
|---|---|
| C(37)—C(38) | 1.543(15) |
| C(37)—H(37A) | 0.9900 |
| C(37)—H(37B) | 0.9900 |
| C(38)—H(38A) | 0.9800 |
| C(38)—H(38B) | 0.9800 |
| C(38)—H(38C) | 0.9800 |
| C(39)—C(40) | 1.564(14) |
| C(39)—H(39A) | 0.9900 |
| C(39)—H(39B) | 0.9900 |
| C(40)—H(40A) | 0.9800 |
| C(40)—H(40B) | 0.9800 |
| C(40)—H(40C) | 0.9800 |
| Si(2A)—C(39A) | 1.840(16) |
| Si(2A)—C(37A) | 1.876(14) |
| Si(2A)—C(35A) | 1.902(14) |
| C(35A)—C(36A) | 1.43(3) |
| C(35A)—H(35C) | 0.9900 |
| C(35A)—H(35D) | 0.9900 |
| C(36A)—H(36D) | 0.9800 |
| C(36A)—H(36E) | 0.9800 |
| C(36A)—H(36F) | 0.9800 |
| C(37A)—C(38A) | 1.576(16) |
| C(37A)—H(37C) | 0.9900 |
| C(37A)—H(37D) | 0.9900 |
| C(38A)—H(38D) | 0.9800 |
| C(38A)—H(38E) | 0.9800 |
| C(38A)—H(38F) | 0.9800 |
| C(39A)—C(40A) | 1.466(18) |
| C(39A)—H(39C) | 0.9900 |
| C(39A)—H(39D) | 0.9900 |
| C(40A)—H(40D) | 0.9800 |
| C(40A)—H(40E) | 0.9800 |
| C(40A)—H(40F) | 0.9800 |
| C(22)—C(23) | 1.526(5) |
| C(22)—H(22A) | 0.9900 |
| C(22)—H(22B) | 0.9900 |
| C(23)—C(24) | 1.514(6) |
| C(23)—H(23) | 1.0000 |
| C(25)—C(26) | 1.499(5) |
| C(25)—H(25A) | 0.9900 |
| C(25)—H(25B) | 0.9900 |
| C(27)—H(27) | 1.0000 |
| C(28)—C(33) | 1.388(5) |
| C(28)—C(29) | 1.399(5) |
| C(29)—C(30) | 1.380(6) |
| C(29)—H(29) | 0.9500 |
| C(30)—C(31) | 1.408(5) |
| C(30)—H(30) | 0.9500 |
| C(31)—C(32) | 1.399(6) |
| C(32)—C(33) | 1.389(5) |
| C(32)—H(32) | 0.9500 |
| C(34)—H(34A) | 0.9800 |
| C(34)—H(34B) | 0.9800 |
| C(34)—H(34C) | 0.9800 |
| O(8)—C(44) | 1.235(5) |
| O(9)—C(46) | 1.225(5) |
| N(7)—C(44) | 1.344(5) |
| N(7)—C(54) | 1.444(6) |
| N(7)—C(45) | 1.468(5) |
| N(8)—C(46) | 1.324(5) |
| N(8)—C(43) | 1.460(5) |
| N(8)—C(47) | 1.460(5) |
| N(9)—C(48) | 1.379(5) |
| N(9)—C(47) | 1.440(6) |
| N(9)—H(9) | 0.91(3) |
| C(41)—O(7) | 1.408(5) |
| C(41)—C(53) | 1.493(6) |
| C(41)—C(42) | 1.537(5) |
| C(41)—C(47) | 1.568(6) |
| O(7)—Si(3A) | 1.620(5) |
| O(7)—Si(3) | 1.716(5) |
| Si(3)—C(59) | 1.860(10) |
| Si(3)—C(55) | 1.877(8) |
| Si(3)—C(57) | 1.918(10) |
| C(55)—C(56) | 1.493(13) |
| C(55)—H(55A) | 0.9900 |
| C(55)—H(55B) | 0.9900 |
| C(56)—H(56A) | 0.9800 |
| C(56)—H(56B) | 0.9800 |
| C(56)—H(56C) | 0.9800 |
| C(57)—C(58) | 1.482(14) |
| C(57)—H(57A) | 0.9900 |
| C(57)—H(57B) | 0.9900 |
| C(58)—H(58A) | 0.9800 |
| C(58)—H(58B) | 0.9800 |
| C(58)—H(58C) | 0.9800 |
| C(59)—C(60) | 1.632(16) |
| C(59)—H(59A) | 0.9900 |
| C(59)—H(59B) | 0.9900 |
| C(60)—H(60A) | 0.9800 |
| C(60)—H(60B) | 0.9800 |
| C(60)—H(60C) | 0.9800 |
| Si(3A)—C(59A) | 1.851(12) |
| Si(3A)—C(57A) | 1.863(11) |
| Si(3A)—C(55A) | 1.913(12) |
| C(55A)—C(56A) | 1.442(16) |
| C(55A)—H(55C) | 0.9900 |
| C(55A)—H(55D) | 0.9900 |
| C(56A)—H(56D) | 0.9800 |
| C(56A)—H(56E) | 0.9800 |
| C(56A)—H(56F) | 0.9800 |
| C(57A)—C(58A) | 1.460(14) |
| C(57A)—H(57C) | 0.9900 |
| C(57A)—H(57D) | 0.9900 |
| C(58A)—H(58D) | 0.9800 |
| C(58A)—H(58E) | 0.9800 |
| C(58A)—H(58F) | 0.9800 |
| C(59A)—C(60A) | 1.485(15) |
| C(59A)—H(59C) | 0.9900 |
| C(59A)—H(59D) | 0.9900 |
| C(60A)—H(60D) | 0.9800 |
| C(60A)—H(60E) | 0.9800 |
| C(60A)—H(60F) | 0.9800 |
| C(42)—C(43) | 1.509(5) |
| C(42)—H(42A) | 0.9900 |
| C(42)—H(42B) | 0.9900 |
| C(43)—C(44) | 1.512(5) |
| C(43)—H(43) | 1.0000 |
| C(45)—C(46) | 1.497(6) |
| C(45)—H(45A) | 0.9900 |
| C(45)—H(45B) | 0.9900 |
| C(47)—H(47) | 1.0000 |
| C(48)—C(53) | 1.390(5) |
| C(48)—C(49) | 1.402(6) |
| C(49)—C(50) | 1.377(6) |
| C(49)—H(49) | 0.9500 |
| C(50)—C(51) | 1.414(5) |
| C(50)—H(50) | 0.9500 |
| C(51)—C(52) | 1.396(6) |
| C(51)—C(51)#1 | 1.465(7) |
| C(52)—C(53) | 1.393(5) |
| C(52)—H(52) | 0.9500 |
| C(54)—H(54A) | 0.9800 |
| C(54)—H(54B) | 0.9800 |
| C(54)—H(54C) | 0.9800 |
| C(1X)—C(2X) | 1.580(10) |
| C(1X)—H(1X1) | 0.9800 |
| C(1X)—H(1X2) | 0.9800 |
| C(1X)—H(1X3) | 0.9800 |
| C(2X)—C(3X) | 1.515(9) |
| C(2X)—H(2X1) | 0.9900 |
| C(2X)—H(2X2) | 0.9900 |
| C(3X)—C(4X) | 1.525(8) |
| C(3X)—H(3X1) | 0.9900 |
| C(3X)—H(3X2) | 0.9900 |
| C(4X)—C(5X) | 1.546(8) |
| C(4X)—H(4X1) | 0.9900 |
| C(4X)—H(4X2) | 0.9900 |
| C(5X)—C(6X) | 1.518(8) |
| C(5X)—H(5X1) | 0.9900 |
| C(5X)—H(5X2) | 0.9900 |
| C(6X)—C(7X) | 1.556(8) |
| C(6X)—H(6X1) | 0.9900 |
| C(6X)—H(6X2) | 0.9900 |

TABLE S7-continued

Bond lengths [Å] and angles [°] glycine endo-diketopiperazine dimer (+)-7h.

| | |
|---|---|
| C(7X)—H(7X1) | 0.9800 |
| C(7X)—H(7X2) | 0.9800 |
| C(7X)—H(7X3) | 0.9800 |
| C(4)—N(1)—C(5) | 123.1(3) |
| C(4)—N(1)—C(14) | 119.1(3) |
| C(5)—N(1)—C(14) | 116.3(3) |
| C(6)—N(2)—C(7) | 122.8(3) |
| C(6)—N(2)—C(3) | 123.2(3) |
| C(7)—N(2)—C(3) | 112.0(3) |
| C(8)—N(3)—C(7) | 110.0(4) |
| C(8)—N(3)—H(3) | 118(4) |
| C(7)—N(3)—H(3) | 122(4) |
| C(24)—N(4)—C(25) | 123.0(3) |
| C(24)—N(4)—C(34) | 119.1(3) |
| C(25)—N(4)—C(34) | 117.3(3) |
| C(26)—N(5)—C(27) | 122.7(3) |
| C(26)—N(5)—C(23) | 122.6(3) |
| C(27)—N(5)—C(23) | 112.2(3) |
| C(28)—N(6)—C(27) | 109.6(3) |
| C(28)—N(6)—H(6) | 121(4) |
| C(27)—N(6)—H(6) | 124(4) |
| O(1)—C(1)—C(13) | 116.4(3) |
| O(1)—C(1)—C(2) | 109.0(4) |
| C(13)—C(1)—C(2) | 111.9(4) |
| O(1)—C(1)—C(7) | 112.6(4) |
| C(13)—C(1)—C(7) | 102.6(3) |
| C(2)—C(1)—C(7) | 103.5(3) |
| C(1)—O(1)—Si(1A) | 138.7(4) |
| C(1)—O(1)—Si(1) | 126.8(4) |
| O(1)—Si(1)—C(17) | 109.2(5) |
| O(1)—Si(1)—C(19) | 113.9(6) |
| C(17)—Si(1)—C(19) | 108.7(7) |
| O(1)—Si(1)—C(15) | 96.6(6) |
| C(17)—Si(1)—C(15) | 132.2(7) |
| C(19)—Si(1)—C(15) | 95.6(7) |
| C(16)—C(15)—Si(1) | 112.0(13) |
| C(16)—C(15)—H(15A) | 109.2 |
| Si(1)—C(15)—H(15A) | 109.2 |
| C(16)—C(15)—H(15B) | 109.2 |
| Si(1)—C(15)—H(15B) | 109.2 |
| H(15A)—C(15)—H(15B) | 107.9 |
| C(15)—C(16)—H(16A) | 109.5 |
| C(15)—C(16)—H(16B) | 109.5 |
| H(16A)—C(16)—H(16B) | 109.5 |
| C(15)—C(16)—H(16C) | 109.5 |
| H(16A)—C(16)—H(16C) | 109.5 |
| H(16B)—C(16)—H(16C) | 109.5 |
| C(18)—C(17)—Si(1) | 120.6(12) |
| C(18)—C(17)—H(17A) | 107.2 |
| Si(1)—C(17)—H(17A) | 107.2 |
| C(18)—C(17)—H(17B) | 107.2 |
| Si(1)—C(17)—H(17B) | 107.2 |
| H(17A)—C(17)—H(17B) | 106.8 |
| C(17)—C(18)—H(18A) | 109.5 |
| C(17)—C(18)—H(18B) | 109.5 |
| H(18A)—C(18)—H(18B) | 109.5 |
| C(17)—C(18)—H(18C) | 109.5 |
| H(18A)—C(18)—H(18C) | 109.5 |
| H(18B)—C(18)—H(18C) | 109.5 |
| C(20)—C(19)—Si(1) | 111.2(11) |
| C(20)—C(19)—H(19A) | 109.4 |
| Si(1)—C(19)—H(19A) | 109.4 |
| C(20)—C(19)—H(19B) | 109.4 |
| Si(1)—C(19)—H(19B) | 109.4 |
| H(19A)—C(19)—H(19B) | 108.0 |
| C(19)—C(20)—H(20A) | 109.5 |
| C(19)—C(20)—H(20B) | 109.5 |
| H(20A)—C(20)—H(20B) | 109.5 |
| C(19)—C(20)—H(20C) | 109.5 |
| H(20A)—C(20)—H(20C) | 109.5 |
| H(20B)—C(20)—H(20C) | 109.5 |
| O(1)—Si(1A)—C(15A) | 115.9(6) |
| O(1)—Si(1A)—C(19A) | 110.6(5) |
| C(15A)—Si(1A)—C(19A) | 122.7(7) |
| O(1)—Si(1A)—C(17A) | 112.9(5) |
| C(15A)—Si(1A)—C(17A) | 80.3(7) |
| C(19A)—Si(1A)—C(17A) | 110.5(6) |
| C(16A)—C(15A)—Si(1A) | 118.7(11) |
| C(16A)—C(15A)—H(15C) | 107.6 |
| Si(1A)—C(15A)—H(15C) | 107.6 |
| C(16A)—C(15A)—H(15D) | 107.6 |
| Si(1A)—C(15A)—H(15D) | 107.6 |
| H(15C)—C(15A)—H(15D) | 107.1 |
| C(15A)—C(16A)—H(16D) | 109.5 |
| C(15A)—C(16A)—H(16E) | 109.5 |
| H(16D)—C(16A)—H(16E) | 109.5 |
| C(15A)—C(16A)—H(16F) | 109.5 |
| H(16D)—C(16A)—H(16F) | 109.5 |
| H(16E)—C(16A)—H(16F) | 109.5 |
| C(18A)—C(17A)—Si(1A) | 116.0(10) |
| C(18A)—C(17A)—H(17C) | 108.3 |
| Si(1A)—C(17A)—H(17C) | 108.3 |
| C(18A)—C(17A)—H(17D) | 108.3 |
| Si(1A)—C(17A)—H(17D) | 108.3 |
| H(17C)—C(17A)—H(17D) | 107.4 |
| C(17A)—C(18A)—H(18D) | 109.5 |
| C(17A)—C(18A)—H(18E) | 109.5 |
| H(18D)—C(18A)—H(18E) | 109.5 |
| C(17A)—C(18A)—H(18F) | 109.5 |
| H(18D)—C(18A)—H(18F) | 109.5 |
| H(18E)—C(18A)—H(18F) | 109.5 |
| C(20A)—C(19A)—Si(1A) | 115.6(9) |
| C(20A)—C(19A)—H(19C) | 108.4 |
| Si(1A)—C(19A)—H(19C) | 108.4 |
| C(20A)—C(19A)—H(19D) | 108.4 |
| Si(1A)—C(19A)—H(19D) | 108.4 |
| H(19C)—C(19A)—H(19D) | 107.4 |
| C(19A)—C(20A)—H(20D) | 109.5 |
| C(19A)—C(20A)—H(20E) | 109.5 |
| H(20D)—C(20A)—H(20E) | 109.5 |
| C(19A)—C(20A)—H(20F) | 109.5 |
| H(20D)—C(20A)—H(20F) | 109.5 |
| H(20E)—C(20A)—H(20F) | 109.5 |
| C(3)—C(2)—C(1) | 102.4(3) |
| C(3)—C(2)—H(2A) | 111.3 |
| C(1)—C(2)—H(2A) | 111.3 |
| C(3)—C(2)—H(2B) | 111.3 |
| C(1)—C(2)—H(2B) | 111.3 |
| H(2A)—C(2)—H(2B) | 109.2 |
| N(2)—C(3)—C(4) | 113.5(3) |
| N(2)—C(3)—C(2) | 101.3(3) |
| C(4)—C(3)—C(2) | 114.1(4) |
| N(2)—C(3)—H(3A) | 109.2 |
| C(4)—C(3)—H(3A) | 109.2 |
| C(2)—C(3)—H(3A) | 109.2 |
| O(2)—C(4)—N(1) | 124.0(4) |
| O(2)—C(4)—C(3) | 120.5(4) |
| N(1)—C(4)—C(3) | 115.5(3) |
| N(1)—C(5)—C(6) | 114.8(3) |
| N(1)—C(5)—H(5A) | 108.6 |
| C(6)—C(5)—H(5A) | 108.6 |
| N(1)—C(5)—H(5B) | 108.6 |
| C(6)—C(5)—H(5B) | 108.6 |
| H(5A)—C(5)—H(5B) | 107.5 |
| O(3)—C(6)—N(2) | 123.9(3) |
| O(3)—C(6)—C(5) | 120.9(3) |
| N(2)—C(6)—C(5) | 115.3(3) |
| N(3)—C(7)—N(2) | 114.6(4) |
| N(3)—C(7)—C(1) | 105.4(3) |
| N(2)—C(7)—C(1) | 103.5(3) |
| N(3)—C(7)—H(7A) | 111.0 |
| N(2)—C(7)—H(7A) | 111.0 |
| C(1)—C(7)—H(7A) | 111.0 |
| N(3)—C(8)—C(13) | 111.2(4) |
| N(3)—C(8)—C(9) | 127.7(4) |
| C(13)—C(8)—C(9) | 121.0(4) |
| C(10)—C(9)—C(8) | 117.7(4) |
| C(10)—C(9)—H(9A) | 121.2 |
| C(8)—C(9)—H(9A) | 121.2 |
| C(9)—C(10)—C(11) | 122.6(4) |
| C(9)—C(10)—H(10) | 118.7 |
| C(11)—C(10)—H(10) | 118.7 |
| C(12)—C(11)—C(10) | 118.5(4) |
| C(12)—C(11)—C(31) | 121.3(4) |

TABLE S7-continued

Bond lengths [Å] and angles [°] glycine endo-diketopiperazine dimer (+)-7h.

| Bond | Value |
|---|---|
| C(10)—C(11)—C(31) | 120.2(4) |
| C(13)—C(12)—C(11) | 119.8(4) |
| C(13)—C(12)—H(12) | 120.1 |
| C(11)—C(12)—H(12) | 120.1 |
| C(8)—C(13)—C(12) | 120.2(4) |
| C(8)—C(13)—C(1) | 109.5(3) |
| C(12)—C(13)—C(1) | 130.3(4) |
| N(1)—C(14)—H(14A) | 109.5 |
| N(1)—C(14)—H(14B) | 109.5 |
| H(14A)—C(14)—H(14B) | 109.5 |
| N(1)—C(14)—H(14C) | 109.5 |
| H(14A)—C(14)—H(14C) | 109.5 |
| H(14B)—C(14)—H(14C) | 109.5 |
| O(4)—C(21)—C(33) | 116.0(3) |
| O(4)—C(21)—C(22) | 108.7(3) |
| C(33)—C(21)—C(22) | 113.4(4) |
| O(4)—C(21)—C(27) | 110.9(3) |
| C(33)—C(21)—C(27) | 102.6(3) |
| C(22)—C(21)—C(27) | 104.5(3) |
| C(21)—O(4)—Si(2A) | 137.6(5) |
| C(21)—O(4)—Si(2) | 129.5(4) |
| O(4)—Si(2)—C(35) | 112.4(6) |
| O(4)—Si(2)—C(37) | 110.3(6) |
| C(35)—Si(2)—C(37) | 106.0(8) |
| O(4)—Si(2)—C(39) | 97.5(6) |
| C(35)—Si(2)—C(39) | 119.7(7) |
| C(37)—Si(2)—C(39) | 110.8(9) |
| C(36)—C(35)—Si(2) | 121.5(11) |
| C(36)—C(35)—H(35A) | 106.9 |
| Si(2)—C(35)—H(35A) | 106.9 |
| C(36)—C(35)—H(35B) | 106.9 |
| Si(2)—C(35)—H(35B) | 106.9 |
| H(35A)—C(35)—H(35B) | 106.7 |
| C(35)—C(36)—H(36A) | 109.5 |
| C(35)—C(36)—H(36B) | 109.5 |
| H(36A)—C(36)—H(36B) | 109.5 |
| C(35)—C(36)—H(36C) | 109.5 |
| H(36A)—C(36)—H(36C) | 109.5 |
| H(36B)—C(36)—H(36C) | 109.5 |
| C(38)—C(37)—Si(2) | 113.0(12) |
| C(38)—C(37)—H(37A) | 109.0 |
| Si(2)—C(37)—H(37A) | 109.0 |
| C(38)—C(37)—H(37B) | 109.0 |
| Si(2)—C(37)—H(37B) | 109.0 |
| H(37A)—C(37)—H(37B) | 107.8 |
| C(37)—C(38)—H(38A) | 109.5 |
| C(37)—C(38)—H(38B) | 109.5 |
| H(38A)—C(38)—H(38B) | 109.5 |
| C(37)—C(38)—H(38C) | 109.5 |
| H(38A)—C(38)—H(38C) | 109.5 |
| H(38B)—C(38)—H(38C) | 109.5 |
| C(40)—C(39)—Si(2) | 111.6(10) |
| C(40)—C(39)—H(39A) | 109.3 |
| Si(2)—C(39)—H(39A) | 109.3 |
| C(40)—C(39)—H(39B) | 109.3 |
| Si(2)—C(39)—H(39B) | 109.3 |
| H(39A)—C(39)—H(39B) | 108.0 |
| C(39)—C(40)—H(40A) | 109.5 |
| C(39)—C(40)—H(40B) | 109.5 |
| H(40A)—C(40)—H(40B) | 109.5 |
| C(39)—C(40)—H(40C) | 109.5 |
| H(40A)—C(40)—H(40C) | 109.5 |
| H(40B)—C(40)—H(40C) | 109.5 |
| O(4)—Si(2A)—C(39A) | 116.5(10) |
| O(4)—Si(2A)—C(37A) | 114.4(8) |
| C(39A)—Si(2A)—C(37A) | 110.5(15) |
| O(4)—Si(2A)—C(35A) | 108.7(8) |
| C(39A)—Si(2A)—C(35A) | 95.0(11) |
| C(37A)—Si(2A)—C(35A) | 109.9(9) |
| C(36A)—C(35A)—Si(2A) | 116.6(13) |
| C(36A)—C(35A)—H(35C) | 108.1 |
| Si(2A)—C(35A)—H(35C) | 108.1 |
| C(36A)—C(35A)—H(35D) | 108.1 |
| Si(2A)—C(35A)—H(35D) | 108.1 |
| H(35C)—C(35A)—H(35D) | 107.3 |
| C(35A)—C(36A)—H(36D) | 109.5 |
| C(35A)—C(36A)—H(36E) | 109.5 |
| H(36D)—C(36A)—H(36E) | 109.5 |
| C(35A)—C(36A)—H(36F) | 109.5 |
| H(36D)—C(36A)—H(36F) | 109.5 |
| H(36E)—C(36A)—H(36F) | 109.5 |
| C(38A)—C(37A)—Si(2A) | 112.4(12) |
| C(38A)—C(37A)—H(37C) | 109.1 |
| Si(2A)—C(37A)—H(37C) | 109.1 |
| C(38A)—C(37A)—H(37D) | 109.1 |
| Si(2A)—C(37A)—H(37D) | 109.1 |
| H(37C)—C(37A)—H(37D) | 107.9 |
| C(37A)—C(38A)—H(38D) | 109.5 |
| C(37A)—C(38A)—H(38E) | 109.5 |
| H(38D)—C(38A)—H(38E) | 109.5 |
| C(37A)—C(38A)—H(38F) | 109.5 |
| H(38D)—C(38A)—H(38F) | 109.5 |
| H(38E)—C(38A)—H(38F) | 109.5 |
| C(40A)—C(39A)—Si(2A) | 112.0(15) |
| C(40A)—C(39A)—H(39C) | 109.2 |
| Si(2A)—C(39A)—H(39C) | 109.2 |
| C(40A)—C(39A)—H(39D) | 109.2 |
| Si(2A)—C(39A)—H(39D) | 109.2 |
| H(39C)—C(39A)—H(39D) | 107.9 |
| C(39A)—C(40A)—H(40D) | 109.5 |
| C(39A)—C(40A)—H(40E) | 109.5 |
| H(40D)—C(40A)—H(40E) | 109.5 |
| C(39A)—C(40A)—H(40F) | 109.5 |
| H(40D)—C(40A)—H(40F) | 109.5 |
| H(40E)—C(40A)—H(40F) | 109.5 |
| C(23)—C(22)—C(21) | 104.3(3) |
| C(23)—C(22)—H(22A) | 110.9 |
| C(21)—C(22)—H(22A) | 110.9 |
| C(23)—C(22)—H(22B) | 110.9 |
| C(21)—C(22)—H(22B) | 110.9 |
| H(22A)—C(22)—H(22B) | 108.9 |
| N(5)—C(23)—C(24) | 112.5(3) |
| N(5)—C(23)—C(22) | 101.3(3) |
| C(24)—C(23)—C(22) | 114.0(3) |
| N(5)—C(23)—H(23) | 109.6 |
| C(24)—C(23)—H(23) | 109.6 |
| C(22)—C(23)—H(23) | 109.6 |
| O(5)—C(24)—N(4) | 124.1(4) |
| O(5)—C(24)—C(23) | 120.4(4) |
| N(4)—C(24)—C(23) | 115.4(3) |
| N(4)—C(25)—C(26) | 115.9(3) |
| N(4)—C(25)—H(25A) | 108.3 |
| C(26)—C(25)—H(25A) | 108.3 |
| N(4)—C(25)—H(25B) | 108.3 |
| C(26)—C(25)—H(25B) | 108.3 |
| H(25A)—C(25)—H(25B) | 107.4 |
| O(6)—C(26)—N(5) | 123.5(4) |
| O(6)—C(26)—C(25) | 121.2(3) |
| N(5)—C(26)—C(25) | 115.3(3) |
| N(6)—C(27)—N(5) | 113.8(4) |
| N(6)—C(27)—C(21) | 105.7(3) |
| N(5)—C(27)—C(21) | 103.6(3) |
| N(6)—C(27)—H(27) | 111.1 |
| N(5)—C(27)—H(27) | 111.1 |
| C(21)—C(27)—H(27) | 111.1 |
| N(6)—C(28)—C(33) | 112.3(3) |
| N(6)—C(28)—C(29) | 126.9(3) |
| C(33)—C(28)—C(29) | 120.8(3) |
| C(30)—C(29)—C(28) | 117.7(3) |
| C(30)—C(29)—H(29) | 121.2 |
| C(28)—C(29)—H(29) | 121.2 |
| C(29)—C(30)—C(31) | 122.7(4) |
| C(29)—C(30)—H(30) | 118.7 |
| C(31)—C(30)—H(30) | 118.7 |
| C(32)—C(31)—C(30) | 118.3(3) |
| C(32)—C(31)—C(11) | 121.8(3) |
| C(30)—C(31)—C(11) | 119.9(4) |
| C(33)—C(32)—C(31) | 119.5(3) |
| C(33)—C(32)—H(32) | 120.3 |
| C(31)—C(32)—H(32) | 120.3 |
| C(28)—C(33)—C(32) | 120.9(4) |
| C(28)—C(33)—C(21) | 109.1(3) |
| C(32)—C(33)—C(21) | 129.9(3) |
| N(4)—C(34)—H(34A) | 109.5 |

TABLE S7-continued

Bond lengths [Å] and angles [°] glycine endo-diketopiperazine dimer (+)-7h.

| Bond | Value |
|---|---|
| N(4)—C(34)—H(34B) | 109.5 |
| H(34A)—C(34)—H(34B) | 109.5 |
| N(4)—C(34)—H(34C) | 109.5 |
| H(34A)—C(34)—H(34C) | 109.5 |
| H(34B)—C(34)—H(34C) | 109.5 |
| C(44)—N(7)—C(54) | 120.1(4) |
| C(44)—N(7)—C(45) | 122.6(3) |
| C(54)—N(7)—C(45) | 116.5(3) |
| C(46)—N(8)—C(43) | 123.8(3) |
| C(46)—N(8)—C(47) | 122.7(3) |
| C(43)—N(8)—C(47) | 111.0(3) |
| C(48)—N(9)—C(47) | 109.7(3) |
| C(48)—N(9)—H(9) | 124(4) |
| C(47)—N(9)—H(9) | 121(4) |
| O(7)—C(41)—C(53) | 115.7(3) |
| O(7)—C(41)—C(42) | 108.5(4) |
| C(53)—C(41)—C(42) | 113.4(4) |
| O(7)—C(41)—C(47) | 112.2(4) |
| C(53)—C(41)—C(47) | 102.3(3) |
| C(42)—C(41)—C(47) | 104.0(3) |
| C(41)—O(7)—Si(3A) | 140.7(3) |
| C(41)—O(7)—Si(3) | 125.9(3) |
| O(7)—Si(3)—C(59) | 116.6(4) |
| O(7)—Si(3)—C(55) | 109.7(4) |
| C(59)—Si(3)—C(55) | 109.8(5) |
| O(7)—Si(3)—C(57) | 95.7(4) |
| C(59)—Si(3)—C(57) | 118.6(6) |
| C(55)—Si(3)—C(57) | 105.3(6) |
| C(56)—C(55)—Si(3) | 115.1(8) |
| C(56)—C(55)—H(55A) | 108.5 |
| Si(3)—C(55)—H(55A) | 108.5 |
| C(56)—C(55)—H(55B) | 108.5 |
| Si(3)—C(55)—H(55B) | 108.5 |
| H(55A)—C(55)—H(55B) | 107.5 |
| C(55)—C(56)—H(56A) | 109.5 |
| C(55)—C(56)—H(56B) | 109.5 |
| H(56A)—C(56)—H(56B) | 109.5 |
| C(55)—C(56)—H(56C) | 109.5 |
| H(56A)—C(56)—H(56C) | 109.5 |
| H(56B)—C(56)—H(56C) | 109.5 |
| C(58)—C(57)—Si(3) | 113.3(8) |
| C(58)—C(57)—H(57A) | 108.9 |
| Si(3)—C(57)—H(57A) | 108.9 |
| C(58)—C(57)—H(57B) | 108.9 |
| Si(3)—C(57)—H(57B) | 108.9 |
| H(57A)—C(57)—H(57B) | 107.7 |
| C(57)—C(58)—H(58A) | 109.5 |
| C(57)—C(58)—H(58B) | 109.5 |
| H(58A)—C(58)—H(58B) | 109.5 |
| C(57)—C(58)—H(58C) | 109.5 |
| H(58A)—C(58)—H(58C) | 109.5 |
| H(58B)—C(58)—H(58C) | 109.5 |
| C(60)—C(59)—Si(3) | 105.5(10) |
| C(60)—C(59)—H(59A) | 110.7 |
| Si(3)—C(59)—H(59A) | 110.7 |
| C(60)—C(59)—H(59B) | 110.7 |
| Si(3)—C(59)—H(59B) | 110.7 |
| H(59A)—C(59)—H(59B) | 108.8 |
| C(59)—C(60)—H(60A) | 109.5 |
| C(59)—C(60)—H(60B) | 109.5 |
| H(60A)—C(60)—H(60B) | 109.5 |
| C(59)—C(60)—H(60C) | 109.5 |
| H(60A)—C(60)—H(60C) | 109.5 |
| H(60B)—C(60)—H(60C) | 109.5 |
| O(7)—Si(3A)—C(59A) | 106.6(5) |
| O(7)—Si(3A)—C(57A) | 109.1(5) |
| C(59A)—Si(3A)—C(57A) | 106.9(7) |
| O(7)—Si(3A)—C(55A) | 114.9(6) |
| C(59A)—Si(3A)—C(55A) | 113.8(7) |
| C(57A)—Si(3A)—C(55A) | 105.1(7) |
| C(56A)—C(55A)—Si(3A) | 121.2(13) |
| C(56A)—C(55A)—H(55C) | 107.0 |
| Si(3A)—C(55A)—H(55C) | 107.0 |
| C(56A)—C(55A)—H(55D) | 107.0 |
| Si(3A)—C(55A)—H(55D) | 107.0 |
| H(55C)—C(55A)—H(55D) | 106.8 |
| C(55A)—C(56A)—H(56D) | 109.5 |
| C(55A)—C(56A)—H(56E) | 109.5 |
| H(56D)—C(56A)—H(56E) | 109.5 |
| C(55A)—C(56A)—H(56F) | 109.5 |
| H(56D)—C(56A)—H(56F) | 109.5 |
| H(56E)—C(56A)—H(56F) | 109.5 |
| C(58A)—C(57A)—Si(3A) | 127.2(12) |
| C(58A)—C(57A)—H(57C) | 105.5 |
| Si(3A)—C(57A)—H(57C) | 105.5 |
| C(58A)—C(57A)—H(57D) | 105.5 |
| Si(3A)—C(57A)—H(57D) | 105.5 |
| H(57C)—C(57A)—H(57D) | 106.1 |
| C(57A)—C(58A)—H(58D) | 109.5 |
| C(57A)—C(58A)—H(58E) | 109.5 |
| H(58D)—C(58A)—H(58E) | 109.5 |
| C(57A)—C(58A)—H(58F) | 109.5 |
| H(58D)—C(58A)—H(58F) | 109.5 |
| H(58E)—C(58A)—H(58F) | 109.5 |
| C(60A)—C(59A)—Si(3A) | 117.3(11) |
| C(60A)—C(59A)—H(59C) | 108.0 |
| Si(3A)—C(59A)—H(59C) | 108.0 |
| C(60A)—C(59A)—H(59D) | 108.0 |
| Si(3A)—C(59A)—H(59D) | 108.0 |
| H(59C)—C(59A)—H(59D) | 107.2 |
| C(59A)—C(60A)—H(60D) | 109.5 |
| C(59A)—C(60A)—H(60E) | 109.5 |
| H(60D)—C(60A)—H(60E) | 109.5 |
| C(59A)—C(60A)—H(60F) | 109.5 |
| H(60D)—C(60A)—H(60F) | 109.5 |
| H(60E)—C(60A)—H(60F) | 109.5 |
| C(43)—C(42)—C(41) | 104.2(3) |
| C(43)—C(42)—H(42A) | 110.9 |
| C(41)—C(42)—H(42A) | 110.9 |
| C(43)—C(42)—H(42B) | 110.9 |
| C(41)—C(42)—H(42B) | 110.9 |
| H(42A)—C(42)—H(42B) | 108.9 |
| N(8)—C(43)—C(42) | 101.1(3) |
| N(8)—C(43)—C(44) | 112.3(3) |
| C(42)—C(43)—C(44) | 113.8(3) |
| N(8)—C(43)—H(43) | 109.7 |
| C(42)—C(43)—H(43) | 109.7 |
| C(44)—C(43)—H(43) | 109.7 |
| O(8)—C(44)—N(7) | 123.3(4) |
| O(8)—C(44)—C(43) | 120.1(4) |
| N(7)—C(44)—C(43) | 116.6(3) |
| N(7)—C(45)—C(46) | 115.5(3) |
| N(7)—C(45)—H(45A) | 108.4 |
| C(46)—C(45)—H(45A) | 108.4 |
| N(7)—C(45)—H(45B) | 108.4 |
| C(46)—C(45)—H(45B) | 108.4 |
| H(45A)—C(45)—H(45B) | 107.5 |
| O(9)—C(46)—N(8) | 124.4(4) |
| O(9)—C(46)—C(45) | 120.0(4) |
| N(8)—C(46)—C(45) | 115.6(3) |
| N(9)—C(47)—N(8) | 113.9(4) |
| N(9)—C(47)—C(41) | 106.1(3) |
| N(8)—C(47)—C(41) | 103.7(3) |
| N(9)—C(47)—H(47) | 110.9 |
| N(8)—C(47)—H(47) | 110.9 |
| C(41)—C(47)—H(47) | 110.9 |
| N(9)—C(48)—C(53) | 111.1(4) |
| N(9)—C(48)—C(49) | 127.6(4) |
| C(53)—C(48)—C(49) | 120.7(4) |
| C(50)—C(49)—C(48) | 118.0(4) |
| C(50)—C(49)—H(49) | 121.0 |
| C(48)—C(49)—H(49) | 121.0 |
| C(49)—C(50)—C(51) | 122.5(4) |
| C(49)—C(50)—H(50) | 118.7 |
| C(51)—C(50)—H(50) | 118.7 |
| C(52)—C(51)—C(50) | 118.1(3) |
| C(52)—C(51)—C(51)#1 | 121.9(4) |
| C(50)—C(51)—C(51)#1 | 120.0(4) |
| C(53)—C(52)—C(51) | 120.1(3) |
| C(53)—C(52)—H(52) | 120.0 |
| C(51)—C(52)—H(52) | 120.0 |
| C(48)—C(53)—C(52) | 120.4(4) |
| C(48)—C(53)—C(41) | 109.7(3) |
| C(52)—C(53)—C(41) | 129.8(4) |

TABLE S7-continued

Bond lengths [Å] and angles [°] glycine endo-diketopiperazine dimer (+)-7h.

| | |
|---|---|
| N(7)—C(54)—H(54A) | 109.5 |
| N(7)—C(54)—H(54B) | 109.5 |
| H(54A)—C(54)—H(54B) | 109.5 |
| N(7)—C(54)—H(54C) | 109.5 |
| H(54A)—C(54)—H(54C) | 109.5 |
| H(54B)—C(54)—H(54C) | 109.5 |
| C(2X)—C(1X)—H(1X1) | 109.5 |
| C(2X)—C(1X)—H(1X2) | 109.5 |
| H(1X1)—C(1X)—H(1X2) | 109.5 |
| C(2X)—C(1X)—H(1X3) | 109.5 |
| H(1X1)—C(1X)—H(1X3) | 109.5 |
| H(1X2)—C(1X)—H(1X3) | 109.5 |
| C(3X)—C(2X)—C(1X) | 113.4(6) |
| C(3X)—C(2X)—H(2X1) | 108.9 |
| C(1X)—C(2X)—H(2X1) | 108.9 |
| C(3X)—C(2X)—H(2X2) | 108.9 |
| C(1X)—C(2X)—H(2X2) | 108.9 |
| H(2X1)—C(2X)—H(2X2) | 107.7 |
| C(2X)—C(3X)—C(4X) | 113.6(5) |
| C(2X)—C(3X)—H(3X1) | 108.9 |
| C(4X)—C(3X)—H(3X1) | 108.9 |
| C(2X)—C(3X)—H(3X2) | 108.9 |
| C(4X)—C(3X)—H(3X2) | 108.9 |
| H(3X1)—C(3X)—H(3X2) | 107.7 |
| C(3X)—C(4X)—C(5X) | 115.2(5) |
| C(3X)—C(4X)—H(4X1) | 108.5 |
| C(5X)—C(4X)—H(4X1) | 108.5 |
| C(3X)—C(4X)—H(4X2) | 108.5 |
| C(5X)—C(4X)—H(4X2) | 108.5 |
| H(4X1)—C(4X)—H(4X2) | 107.5 |
| C(6X)—C(5X)—C(4X) | 113.8(5) |
| C(6X)—C(5X)—H(5X1) | 108.8 |
| C(4X)—C(5X)—H(5X1) | 108.8 |
| C(6X)—C(5X)—H(5X2) | 108.8 |
| C(4X)—C(5X)—H(5X2) | 108.8 |
| H(5X1)—C(5X)—H(5X2) | 107.7 |
| C(5X)—C(6X)—C(7X) | 116.2(5) |
| C(5X)—C(6X)—H(6X1) | 108.2 |
| C(7X)—C(6X)—H(6X1) | 108.2 |
| C(5X)—C(6X)—H(6X2) | 108.2 |
| C(7X)—C(6X)—H(6X2) | 108.2 |
| H(6X1)—C(6X)—H(6X2) | 107.4 |
| C(6X)—C(7X)—H(7X1) | 109.5 |
| C(6X)—C(7X)—H(7X2) | 109.5 |
| H(7X1)—C(7X)—H(7X2) | 109.5 |
| C(6X)—C(7X)—H(7X3) | 109.5 |
| H(7X1)—C(7X)—H(7X3) | 109.5 |
| H(7X2)—C(7X)—H(7X3) | 109.5 |

Symmetry Transformations Used to Generate Equivalent Atoms:
1 y,x,−z+2

TABLE S8

Anisotropic displacement parameters ($Å^2 × 10^3$) for glycine endo-diketopiperazine dimer (+)-7h. The anisotropic displacement factor exponent takes the form: $-2p^2 [h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| O(2) | 57(2) | 39(1) | 38(2) | −4(1) | 5(1) | 12(1) |
| O(3) | 52(2) | 45(2) | 29(1) | −9(1) | −1(1) | 12(1) |
| O(5) | 44(2) | 67(2) | 37(2) | −3(1) | 12(1) | 19(1) |
| O(6) | 46(2) | 46(2) | 27(1) | −2(1) | 7(1) | 15(1) |
| N(1) | 51(2) | 30(2) | 36(2) | −2(1) | 4(1) | 3(1) |
| N(2) | 42(2) | 36(2) | 25(2) | −3(1) | −3(1) | 13(1) |
| N(3) | 63(2) | 68(2) | 28(2) | 6(2) | 7(2) | 38(2) |
| N(4) | 33(2) | 44(2) | 39(2) | −1(1) | 4(1) | 5(1) |
| N(5) | 36(2) | 38(2) | 22(1) | −1(1) | 5(1) | 12(1) |
| N(6) | 60(2) | 51(2) | 28(2) | −10(1) | −3(2) | 30(2) |
| C(1) | 50(2) | 42(2) | 38(2) | 8(2) | 10(2) | 15(2) |
| O(1) | 47(2) | 59(2) | 63(2) | 22(2) | −1(2) | 12(1) |
| Si(1) | 53(3) | 57(3) | 74(3) | −7(2) | −11(2) | 6(2) |
| O(15) | 59(5) | 85(6) | 82(6) | −3(6) | −5(5) | 7(5) |
| O(16) | 115(11) | 128(13) | 168(15) | −4(12) | −7(11) | −19(10) |
| O(17) | 77(5) | 57(4) | 82(5) | 16(4) | −15(4) | −10(4) |
| O(18) | 115(10) | 84(12) | 82(9) | −5(8) | −7(7) | −51(8) |
| O(19) | 78(6) | 75(6) | 104(7) | −22(5) | 23(6) | −10(5) |
| C(20) | 125(11) | 115(9) | 135(12) | −18(9) | 17(10) | 15(9) |
| Si(1A) | 52(3) | 41(2) | 51(2) | 12(2) | −16(2) | 3(2) |
| C(15A) | 54(5) | 84(6) | 89(6) | 0(6) | −12(5) | 1(5) |
| C(16A) | 71(7) | 83(8) | 111(11) | 12(8) | 3(8) | 11(6) |
| C(17A) | 68(5) | 60(5) | 63(5) | 13(4) | 3(4) | −6(4) |
| C(18A) | 93(8) | 57(8) | 59(6) | −13(6) | 0(6) | −27(7) |
| C(19A) | 60(4) | 56(4) | 73(5) | 7(4) | −2(4) | 5(4) |
| C(20A) | 98(10) | 74(7) | 104(10) | 11(7) | −2(8) | −3(7) |
| C(2) | 65(3) | 47(2) | 34(2) | 5(2) | 19(2) | 24(2) |
| C(3) | 43(2) | 34(2) | 33(2) | 2(2) | 6(2) | 10(2) |
| C(4) | 40(2) | 37(2) | 34(2) | −4(2) | 2(2) | 6(2) |
| C(5) | 62(3) | 37(2) | 33(2) | −4(2) | 9(2) | 2(2) |
| C(6) | 39(2) | 36(2) | 27(2) | −2(1) | −3(1) | 7(2) |
| C(7) | 56(2) | 38(2) | 31(2) | 1(2) | 4(2) | 18(2) |
| C(8) | 53(2) | 46(2) | 27(2) | 2(2) | 9(2) | 20(2) |
| C(9) | 49(2) | 49(2) | 30(2) | −2(2) | 8(2) | 20(2) |
| C(10) | 48(2) | 37(2) | 30(2) | −4(1) | 4(2) | 11(2) |
| C(11) | 48(2) | 32(2) | 27(2) | −2(1) | 6(2) | 2(2) |
| C(12) | 46(2) | 32(2) | 33(2) | 1(1) | 10(2) | 7(2) |
| C(13) | 49(2) | 38(2) | 32(2) | 3(2) | 8(2) | 14(2) |
| C(14) | 75(3) | 32(2) | 49(2) | −1(2) | 11(2) | −6(2) |
| C(21) | 44(2) | 44(2) | 32(2) | −6(2) | −1(2) | 14(2) |
| O(4) | 68(2) | 36(1) | 48(2) | −2(1) | −11(1) | 7(1) |
| Si(2) | 71(3) | 50(2) | 80(3) | 21(2) | 3(2) | −14(2) |
| C(35) | 90(6) | 90(6) | 84(5) | 13(5) | −19(5) | −32(5) |
| C(36) | 112(9) | 107(9) | 108(9) | −25(8) | 17(8) | −46(7) |
| C(37) | 89(6) | 79(6) | 114(8) | 12(7) | 17(7) | −6(5) |
| C(38) | 95(8) | 128(10) | 159(12) | 44(9) | 14(8) | 1(8) |
| C(39) | 83(6) | 58(5) | 82(6) | 17(5) | −2(5) | −11(4) |
| C(40) | 80(6) | 50(5) | 108(8) | 4(5) | 28(6) | −9(4) |
| Si(2A) | 58(3) | 62(4) | 55(3) | 13(2) | −17(2) | −3(2) |
| C(35A) | 82(7) | 101(8) | 71(6) | −14(6) | −13(6) | −20(6) |
| C(36A) | 128(11) | 99(10) | 63(8) | −35(7) | 29(8) | −47(8) |
| C(37A) | 66(5) | 53(5) | 82(6) | 16(5) | −5(6) | −3(4) |
| C(38A) | 88(11) | 102(11) | 123(11) | −24(10) | 7(9) | 4(9) |
| C(39A) | 92(7) | 66(6) | 93(7) | 14(6) | 4(6) | −13(6) |
| C(40A) | 145(15) | 121(14) | 126(10) | 35(11) | −14(12) | −17(12) |
| C(22) | 49(2) | 60(3) | 27(2) | −12(2) | 2(2) | 23(2) |
| C(23) | 39(2) | 39(2) | 30(2) | −7(2) | 3(2) | 14(2) |
| C(24) | 39(2) | 43(2) | 35(2) | 4(2) | 7(2) | 11(2) |
| C(25) | 38(2) | 43(2) | 32(2) | −3(2) | 5(2) | 3(2) |
| C(26) | 39(2) | 36(2) | 25(2) | 4(1) | 6(1) | 10(1) |
| C(27) | 40(2) | 46(2) | 27(2) | −6(2) | 3(2) | 13(2) |
| C(28) | 38(2) | 42(2) | 25(2) | −7(2) | −1(1) | 13(2) |
| C(29) | 45(2) | 35(2) | 33(2) | −8(2) | 5(2) | 10(2) |
| C(30) | 45(2) | 38(2) | 31(2) | −2(2) | 7(2) | 5(2) |
| C(31) | 41(2) | 35(2) | 29(2) | −3(1) | 6(2) | 2(2) |
| C(32) | 43(2) | 35(2) | 30(2) | −6(1) | 4(2) | 5(2) |
| C(33) | 40(2) | 40(2) | 29(2) | −6(2) | 2(1) | 7(2) |
| C(34) | 34(2) | 69(3) | 63(3) | −7(2) | 4(2) | −2(2) |
| O(8) | 56(2) | 46(2) | 37(2) | 3(1) | −7(1) | 15(1) |
| O(9) | 57(2) | 52(2) | 28(1) | 9(1) | −1(1) | 17(1) |
| N(7) | 49(2) | 36(2) | 36(2) | 4(1) | −6(1) | 2(1) |
| N(8) | 40(2) | 37(2) | 24(1) | 3(1) | 2(1) | 10(1) |
| N(9) | 58(2) | 69(3) | 33(2) | −7(2) | −8(2) | 35(2) |
| C(41) | 44(2) | 39(2) | 37(2) | −5(2) | −4(2) | 7(2) |
| O(7) | 41(2) | 64(2) | 60(2) | −26(2) | 6(1) | 0(1) |
| Si(3) | 38(1) | 65(2) | 43(2) | −13(1) | 2(1) | −7(1) |
| C(55) | 60(4) | 57(4) | 52(4) | −19(3) | 6(3) | −1(3) |
| C(56) | 104(8) | 83(8) | 49(7) | −21(6) | −15(6) | −9(6) |
| C(57) | 50(4) | 82(5) | 85(6) | −1(5) | 17(5) | 0(4) |
| C(58) | 51(5) | 88(7) | 103(8) | 16(6) | 5(5) | −5(5) |
| C(59) | 112(7) | 63(5) | 65(5) | 10(4) | −22(5) | −24(5) |
| C(60) | 203(16) | 164(14) | 122(10) | 45(10) | 17(10) | −24(13) |
| Si(3A) | 50(2) | 52(2) | 52(2) | −12(2) | 14(2) | −5(2) |
| C(55A) | 82(6) | 82(7) | 61(6) | −12(5) | 0(5) | −6(6) |
| C(56A) | 109(11) | 121(13) | 60(9) | 1(10) | 12(9) | −3(10) |
| C(57A) | 47(5) | 83(6) | 57(5) | 11(5) | 11(4) | −5(5) |

TABLE S8-continued

Anisotropic displacement parameters (Å² × 10³) for glycine endo-diketopiperazine dimer (+)-7h. The anisotropic displacement factor exponent takes the form: −2p² [h² a*²U¹¹ + . . . + 2 h k a* b*U¹²].

|       | U¹¹    | U²²    | U³³    | U²³    | U¹³    | U¹²    |
|-------|--------|--------|--------|--------|--------|--------|
| C(58A)| 128(12)| 106(11)| 74(7)  | 5(8)   | 12(8)  | 29(10) |
| C(59A)| 69(5)  | 67(5)  | 70(5)  | −4(5)  | 11(4)  | −4(4)  |
| C(60A)| 121(13)| 66(7)  | 158(15)| 2(9)   | 66(12) | 4(8)   |
| C(42) | 54(2)  | 47(2)  | 32(2)  | −7(2)  | −15(2) | 18(2)  |
| C(43) | 37(2)  | 38(2)  | 30(2)  | 1(1)   | −1(2)  | 6(2)   |
| C(44) | 41(2)  | 39(2)  | 31(2)  | 1(2)   | 2(2)   | 8(2)   |
| C(45) | 59(3)  | 41(2)  | 32(2)  | 4(2)   | −9(2)  | 4(2)   |
| C(46) | 43(2)  | 45(2)  | 23(2)  | 5(2)   | 5(1)   | 9(2)   |
| C(47) | 53(2)  | 42(2)  | 34(2)  | 2(2)   | 2(2)   | 17(2)  |
| C(48) | 51(2)  | 44(2)  | 28(2)  | −3(2)  | −8(2)  | 15(2)  |
| C(49) | 41(2)  | 40(2)  | 36(2)  | 2(2)   | −7(2)  | 13(2)  |
| C(50) | 41(2)  | 37(2)  | 34(2)  | 5(2)   | −2(2)  | 6(2)   |
| C(51) | 35(2)  | 35(2)  | 30(2)  | 3(1)   | −4(1)  | 2(1)   |
| C(52) | 33(2)  | 35(2)  | 33(2)  | 0(1)   | −6(1)  | 2(1)   |
| C(53) | 38(2)  | 36(2)  | 36(2)  | −2(2)  | −4(2)  | 7(2)   |
| C(54) | 89(4)  | 38(2)  | 61(3)  | 1(2)   | −23(3) | −3(2)  |
| C(1X) | 112(6) | 111(6) | 85(5)  | −38(4) | 2(4)   | 26(5)  |
| C(2X) | 93(5)  | 92(5)  | 76(4)  | −17(3) | 6(3)   | 26(4)  |
| C(3X) | 61(3)  | 65(3)  | 88(4)  | −16(3) | −15(3) | 9(3)   |
| C(4X) | 58(3)  | 75(4)  | 68(3)  | −16(3) | −12(2) | 9(3)   |
| C(5X) | 70(3)  | 64(3)  | 80(3)  | 0(3)   | −24(3) | 2(3)   |
| C(6X) | 54(3)  | 60(3)  | 85(4)  | 11(3)  | −15(3) | 0(2)   |
| C(7X) | 69(4)  | 90(4)  | 86(4)  | 35(4)  | −19(3) | −11(3) |

TABLE S9

Hydrogen coordinates (×10⁴) and isotropic displacement parameters (Å² × 10³) for glycine endo-diketopiperazine dimer (+)-7h.

|        | x        | y        | z        | U(eq) |
|--------|----------|----------|----------|-------|
| H(3)   | 7890(30) | 8020(30) | 7006(12) | 64    |
| H(6)   | 8000(30) | 7960(20) | 9668(11) | 56    |
| H(15A) | 4828     | 7668     | 7238     | 91    |
| H(15B) | 5192     | 7174     | 6979     | 91    |
| H(16A) | 4182     | 6697     | 7158     | 206   |
| H(16B) | 4814     | 6230     | 7269     | 206   |
| H(16C) | 4450     | 6724     | 7528     | 206   |
| H(17A) | 6001     | 6347     | 7869     | 86    |
| H(17B) | 6532     | 6946     | 7937     | 86    |
| H(18A) | 5805     | 6827     | 8368     | 141   |
| H(18B) | 5694     | 7562     | 8204     | 141   |
| H(18C) | 5159     | 6959     | 8136     | 141   |
| H(19A) | 6194     | 6777     | 6951     | 102   |
| H(19B) | 6864     | 6989     | 7153     | 102   |
| H(20A) | 6811     | 5796     | 7098     | 187   |
| H(20B) | 6751     | 5999     | 7476     | 187   |
| H(20C) | 6082     | 5788     | 7275     | 187   |
| H(15C) | 4577     | 7491     | 7493     | 90    |
| H(15D) | 4887     | 7282     | 7147     | 90    |
| H(16D) | 4143     | 6444     | 7329     | 132   |
| H(16E) | 4898     | 6132     | 7307     | 132   |
| H(16F) | 4586     | 6341     | 7654     | 132   |
| H(17C) | 4889     | 7541     | 7955     | 76    |
| H(17D) | 5047     | 6742     | 7935     | 76    |
| H(18D) | 5401     | 7173     | 8429     | 105   |
| H(18E) | 6050     | 6906     | 8228     | 105   |
| H(18F) | 5891     | 7708     | 8248     | 105   |
| H(19C) | 6676     | 6822     | 7279     | 76    |
| H(19D) | 6768     | 6808     | 7667     | 76    |
| H(20D) | 6653     | 5712     | 7468     | 138   |
| H(20E) | 6019     | 5888     | 7700     | 138   |
| H(20F) | 5926     | 5902     | 7312     | 138   |
| H(2A)  | 6102     | 9316     | 7641     | 58    |
| H(2B)  | 6898     | 9463     | 7564     | 58    |
| H(3A)  | 5826     | 9261     | 7090     | 44    |
| H(5A)  | 7100     | 10060    | 6385     | 53    |
| H(5B)  | 6322     | 9813     | 6389     | 53    |
| H(7A)  | 6702     | 7991     | 6977     | 50    |

TABLE S9-continued

Hydrogen coordinates (×10⁴) and isotropic displacement parameters (Å² × 10³) for glycine endo-diketopiperazine dimer (+)-7h.

|        | x        | y        | z        | U(eq) |
|--------|----------|----------|----------|-------|
| H(9A)  | 8741     | 7695     | 7488     | 51    |
| H(10)  | 8763     | 7532     | 8054     | 46    |
| H(12)  | 6832     | 8263     | 8138     | 44    |
| H(14A) | 6153     | 11174    | 6559     | 78    |
| H(14B) | 6971     | 11192    | 6554     | 78    |
| H(14C) | 6567     | 11376    | 6882     | 78    |
| H(35A) | 6410     | 5888     | 8730     | 105   |
| H(35B) | 6945     | 6489     | 8676     | 105   |
| H(36A) | 7014     | 5717     | 8267     | 163   |
| H(36B) | 7717     | 5724     | 8467     | 163   |
| H(36C) | 7178     | 5118     | 8522     | 163   |
| H(37A) | 6756     | 6534     | 9627     | 113   |
| H(37B) | 6882     | 7059     | 9333     | 113   |
| H(38A) | 5692     | 6968     | 9440     | 191   |
| H(38B) | 5846     | 6688     | 9080     | 191   |
| H(38C) | 5720     | 6162     | 9373     | 191   |
| H(39A) | 7503     | 4777     | 9312     | 89    |
| H(39B) | 7131     | 5139     | 9615     | 89    |
| H(40A) | 6413     | 4247     | 9404     | 119   |
| H(40B) | 6038     | 4967     | 9354     | 119   |
| H(40C) | 6410     | 4605     | 9052     | 119   |
| H(35C) | 6874     | 5121     | 8684     | 102   |
| H(35D) | 7076     | 5858     | 8548     | 102   |
| H(36D) | 7765     | 5048     | 8337     | 145   |
| H(36E) | 8201     | 5561     | 8559     | 145   |
| H(36F) | 7998     | 4821     | 8696     | 145   |
| H(37C) | 6783     | 6935     | 9072     | 80    |
| H(37D) | 6186     | 6376     | 9084     | 80    |
| H(38D) | 6156     | 7053     | 9575     | 156   |
| H(38E) | 6330     | 6278     | 9670     | 156   |
| H(38F) | 6926     | 6837     | 9658     | 156   |
| H(39C) | 6476     | 4973     | 9282     | 100   |
| H(39D) | 7205     | 4629     | 9212     | 100   |
| H(40D) | 6950     | 4573     | 9762     | 196   |
| H(40E) | 7609     | 5044     | 9707     | 196   |
| H(40F) | 6881     | 5388     | 9777     | 196   |
| H(22A) | 9233     | 6063     | 9049     | 55    |
| H(22B) | 9420     | 6864     | 9079     | 55    |
| H(23)  | 9281     | 5900     | 9608     | 43    |
| H(25A) | 10092    | 7316     | 10239    | 45    |
| H(25B) | 9885     | 6529     | 10272    | 45    |
| H(27)  | 7993     | 6745     | 9706     | 45    |
| H(29)  | 7675     | 8785     | 9176     | 45    |
| H(30)  | 7503     | 8794     | 8613     | 45    |
| H(32)  | 8234     | 6856     | 8536     | 43    |
| H(34A) | 11238    | 6428     | 10085    | 83    |
| H(34B) | 11206    | 7239     | 10035    | 83    |
| H(34C) | 11375    | 6750     | 9731     | 83    |
| H(9)   | 2080(30) | 2120(30) | 8652(11) | 64    |
| H(55A) | 3989     | 3841     | 9462     | 68    |
| H(55B) | 3435     | 3263     | 9540     | 68    |
| H(56A) | 4225     | 3331     | 9962     | 118   |
| H(56B) | 4282     | 2598     | 9790     | 118   |
| H(56C) | 4836     | 3178     | 9712     | 118   |
| H(57A) | 5274     | 2642     | 9215     | 87    |
| H(57B) | 5205     | 2714     | 8827     | 87    |
| H(58A) | 5883     | 3584     | 9033     | 121   |
| H(58B) | 5203     | 3902     | 8877     | 121   |
| H(58C) | 5272     | 3830     | 9265     | 121   |
| H(59A) | 3122     | 3162     | 8744     | 96    |
| H(59B) | 3552     | 3855     | 8797     | 96    |
| H(60A) | 3754     | 3430     | 8231     | 245   |
| H(60B) | 4461     | 3412     | 8428     | 245   |
| H(60C) | 4033     | 2723     | 8375     | 245   |
| H(55C) | 5048     | 2496     | 9634     | 90    |
| H(55D) | 5045     | 3305     | 9599     | 90    |
| H(56D) | 4667     | 2990     | 10095    | 145   |
| H(56E) | 4064     | 3361     | 9898     | 145   |
| H(56F) | 4068     | 2546     | 9934     | 145   |
| H(57C) | 5092     | 3534     | 8939     | 74    |
| H(57D) | 5375     | 2776     | 8945     | 74    |
| H(58D) | 5339     | 3176     | 8433     | 154   |
| H(58E) | 4821     | 2547     | 8466     | 154   |
| H(58F) | 4534     | 3314     | 8460     | 154   |

TABLE S9-continued

Hydrogen coordinates (×10$^4$) and isotropic displacement parameters (Å$^2$ × 10$^3$) for glycine endo-diketopiperazine dimer (+)-7h.

| | x | y | z | U(eq) |
|---|---|---|---|---|
| H(59C) | 3309 | 3257 | 8948 | 82 |
| H(59D) | 3283 | 3385 | 9333 | 82 |
| H(60D) | 3325 | 4411 | 9058 | 172 |
| H(60E) | 4003 | 4324 | 9273 | 172 |
| H(60F) | 4029 | 4195 | 8887 | 172 |
| H(42A) | 3974 | 856 | 9262 | 53 |
| H(42B) | 3170 | 684 | 9236 | 53 |
| H(43) | 4117 | 833 | 8703 | 42 |
| H(45A) | 2593 | −7 | 8117 | 53 |
| H(45B) | 3372 | 184 | 8044 | 53 |
| H(47) | 3281 | 2101 | 8613 | 52 |
| H(49) | 1274 | 2451 | 9172 | 47 |
| H(50) | 1291 | 2588 | 9737 | 45 |
| H(52) | 3225 | 1839 | 9782 | 41 |
| H(54A) | 3525 | −1145 | 8246 | 94 |
| H(54B) | 2722 | −1111 | 8320 | 94 |
| H(54C) | 3249 | −1274 | 8609 | 94 |
| H(1X1) | 4104 | −670 | 10982 | 154 |
| H(1X2) | 4682 | −877 | 10724 | 154 |
| H(1X3) | 4794 | −232 | 10959 | 154 |
| H(2X1) | 3764 | −278 | 10449 | 104 |
| H(2X2) | 3875 | 366 | 10684 | 104 |
| H(3X1) | 4864 | −94 | 10219 | 86 |
| H(3X2) | 4961 | 559 | 10450 | 86 |
| H(4X1) | 4028 | 1104 | 10180 | 80 |
| H(4X2) | 3955 | 456 | 9945 | 80 |
| H(5X1) | 4534 | 1404 | 9689 | 86 |
| H(5X2) | 5142 | 1323 | 9947 | 86 |
| H(6X1) | 4786 | 256 | 9505 | 80 |
| H(6X2) | 5449 | 274 | 9733 | 80 |
| H(7X1) | 5764 | 500 | 9183 | 122 |
| H(7X2) | 5259 | 1144 | 9172 | 122 |
| H(7X3) | 5924 | 1162 | 9400 | 122 |

REFERENCES IN EXAMPLE 2

1. Still, W. C.; Kahn, M.; Mitra, A. *J. Org. Chem.* 1978, 43, 2923.
2. Pangborn, A. B.; Giardello, M. A.; Grubbs, R. H.; Rosen, R. K.; Timmers, F. Organometallics 1996, 15, 1518.
3. Y. Qian, X. Xu, X. Wang, P. J. Zavalij, W. Hu, M. P. Doyle, Rhodium(II)- and copper(II)-catalyzed reactions of enol diazoacetates with nitrones: metal carbene versus Lewis acid directed pathways. *Angew. Chem. Int. Ed.* 51, 5900-5903 (2012).
4. (a) Gottlieb, H. E.; Kotlyar, V.; Nudelman, A. *J. Org. Chem.* 1997, 62, 7512. (b) Fulmer, G. R.; Miller, A. J. M.; Sherden, N. H.; Gottlieb, H. E.; Nudelman, A.; Stoltz, B. M.; Bercaw, J. E.; Goldberg, K. I. *Organometallics* 2010, 29, 2176.
5. Barrow, C. J.; Cai, P.; Snyder, J. K.; Sedlock, D. M.; Sun, H. H.; Cooper, R. WIN 64821, a new competitive antagonist to substance P, isolated from an *Aspergillus* species: structure determination and solution conformation. J. Org. Chem. 1993, 58, 6016-6021.
6. R. P. Bhattacharyya, M. Walker, R. Boykin, S. S. Son, J. Liu, A. C. Hachey, P. Ma, L. Wu, K. Choi, K. C. Cummins, M. Benson, J. Skerry, H. Ryu, S. Y. Wong, M. B. Goldberg, J. Han, V. M. Pierce, L. A. Cosimi, N. Shoresh, J. Livny, J. Beechem, D. T. Hung, Rapid
7. 48 I. Wiegand, K. Hilpert, R. E. W. Hancock, Agar and broth microdilution methods to determine the minimal inhibitory concentration (MIC) of antimicrobial substances. Nat. Protoc. 3, 163-175 (2008).
8. A crystal structure of HmtS was recently determined to 2.0 Å resolution (PDB: 5Z9J). HmtS adopts a prism-shape architecture typical of cytochrome P450 enzymes with 12 α helices, 14 β strands, and a heme prosthetic group in a conserved binding pocket, see Zhang, C.; Lu, M.; Lin, L.; Huang, Z.; Zhang, R.; Wu, X.; Chen, Y. Riboflavin Is Directly Involved in N-Dealkylation Catalyzed by Bacterial Cytochrome P450 Monooxygenases. *ChemBioChem* 2020, 21, 2297-2305.
9. (a) Zhao, B.; Guengerich, F. P.; Bellamine, A.; Lamb, D. C.; Izumikawa, M.; Lei, L.; Podust, L. M.; Sundaramoorthy, M.; Kalaitzis, J. A.; Reddy, L. M.; Kelly, S. L.; Moore, B. S.; Stec, D.; Voehler, M.; Falck, J. R.; Shimada, T.; Waterman, M. R. Binding of Two Flaviolin Substrate Molecules, Oxidative Coupling, and Crystal Structure of *Streptomyces Coelicolor* A3(2) Cytochrome P450 158A2. *J. Biol. Chem.* 2005, 280, 11599-11607. (b) Davis, J. A.; Greene, R. J.; Han, S.; Rock, D. A.; Wienkers, L. C. Formation of Raloxifene Homo-Dimer in CYP3A4, Evidence for Multi-Substrate Binding in a Single Catalytically Competent P450 Active Site. *Arch. Biochem. Biophys.* 2011, 513, 110-118. (c) Saruwatari, T.; Yagishita, F.; Mino, T.; Noguchi, H.; Hotta, K.; Watanabe, K. Cytochrome P450 as Dimerization Catalyst in Diketopiperazine Alkaloid Biosynthesis. *ChemBioChem* 2014, 15, 656-659. (d) Shende, V. V.; Khatri, Y.; Newmister, S. A.; Sanders, J. N.; Lindovska, P.; Yu, F.; Doyon, T. J.; Kim, J.; Movassaghi, M.; Houk, K. N.; Sherman, D. H. Structure and Function of NzeB, a Versatile C-C and C—N Bond Forming Diketopiperazine Dimerase. *J. Am. Chem. Soc.* 2020, DOI: 10.1021/jacs.0c06312.
10. (a) Lin, H.-C.; McMahon, T. C.; Patel, A.; Corsello, M.; Simon, A.; Xu, W.; Zhao, M.; Houk, K. N.; Garg, N. K.; Tang, Y. P450-Mediated Coupling of Indole Fragments To Forge Communesin and Unnatural Isomers. *J. Am. Chem. Soc.* 2016, 138, 4002-4005. (b) Grandner, J. M.; Cacho, R. A.; Tang, Y.; Houk, K. N. Mechanism of the P450-Catalyzed Oxidative Cyclization in the Biosynthesis of Griseofulvin. *ACS Catal.* 2016, 6, 4506-4511. (c) Takahashi, R. H.; Grandner, J. M.; Bobba, S.; Liu, Y.; Beroza, P.; Zhang, D.; Ma, S. Novel Homodimer Metabolites of GDC-0994 via Cytochrome P450-Catalyzed Radical Coupling. *Drug. Metab. Dispos.* 2020, 48, 521-527.
11. Kamenecka, T. M.; Danishefsky, S. J. Discovery through Total Synthesis: A Retrospective on the Himastatin Problem. *Chem. Eur. J.* 2001, 7, 41-63.
12. Literature value: $[\alpha]_D^{25}$=−98.2 (c=1.00, CHCl$_3$), see Kamenecka, T. M.; Danishefsky, S. J. Discovery through Total Synthesis: A Retrospective on the Himastatin Problem. *Chem. Eur. J.* 2001, 7, 41-63.
13. Benco, J. S.; Nienaber, H. A.; McGimpsey, W. G. Synthesis of an Ammonium Ionophore and Its Application in a Planar Ion-Selective Electrode. *Anal. Chem.* 2003, 75, 152-156.
14. J. Kim, J. A. Ashenhurst, M. Movassaghi, Total synthesis of (+)-11,11'-dideoxyverticillin A. *Science.* 324, 238-241 (2009).
15. J. Ma, Z. Wang, H. Huang, M. Luo, D. Zuo, B. Wang, A. Sun, Y.-Q. Cheng, C. Zhang, J. Ju, Biosynthesis of himastatin: assembly line and characterization of three cytochrome p450 enzymes involved in the post-tailoring oxidative steps. Angew. Chem. Int. Ed. 50, 7797-7802 (2011).
16. J. E. Leet, D. R. Schroeder, J. Golik, J. A. Matson, T. W. Doyle, K. S. Lam, S. E. Hill, M. S. Lee, J. L. Whitney, B. S. Krishnan, Himastatin, a new antitumor antibiotic from *Streptomyces hygroscopicus*. III. Structural elucidation. J. Antibiot. 49, 299-311 (1996).

17. R. H. Takahashi, J. M. Grandner, S. Bobba, Y. Liu, P. Beroza, D. Zhang, S. Ma, Novel homodimer metabolites of GDC-0994 via cytochrome p450-catalyzed radical coupling. *Drug. Metab. Dispos.* 48, 521-527 (2020).

18. (a) Literature value: $[\alpha]_D^{25}=+37.5$ (c=0.7, CHCl$_3$), see Kamenecka, T. M.; Danishefsky, S. J. Discovery through Total Synthesis: A Retrospective on the Himastatin Problem. *Chem. Eur. J.* 2001, 7, 41-63. (b) Literature value: $[\alpha]_D^{25}=+64$ (c=1.87, CHCl$_3$), see Ma, J.; Wang, Z.; Huang, H.; Luo, M.; Zuo, D.; Wang, B.; Sun, A.; Cheng, Y.-Q.; Zhang, C.; Ju, J. Biosynthesis of Himastatin: Assembly Line and Characterization of Three Cytochrome P450 Enzymes Involved in the Post-Tailoring Oxidative Steps. *Angew. Chem. Int. Ed.* 2011, 50, 7797-7802.

19. (a) Literature value: $[\alpha]_D^{25}=-33.8$ (c=0.35, MeOH), see Kamenecka, T. M.; Danishefsky, S. J. Discovery through Total Synthesis: A Retrospective on the Himastatin Problem. *Chem. Eur. J.* 2001, 7, 41-63. (b) Literature value: $[\alpha]_D=-34$ (c=0.35, MeOH), see Leet, J. E.; Schroeder, D. R.; Golik, J.; Matson, J. A.; Doyle, T. W.; Lam, K. S.; Hill, S. E.; Lee, M. S.; Whitney, J. L.; Krishnan, B. S. Himastatin, a New Antitumor Antibiotic from *Streptomyces Hygroscopicus*. III. Structural Elucidation. *J. Antibiot.* 1996, 49, 299-311.

20. (a) Leet, J. E.; Schroeder, D. R.; Golik, J.; Matson, J. A.; Doyle, T. W.; Lam, K. S.; Hill, S. E.; Lee, M. S.; Whitney, J. L.; Krishnan, B. S. Himastatin, a New Antitumor Antibiotic from *Streptomyces Hygroscopicus*. III. Structural Elucidation. J. Antibiot. 1996, 49, 299-311. (b) Leet, J. E.; Schroeder, D. R.; Krishnan, B. S.; Matson, J. A. Himastatin, a New Antitumor Antibiotic from *Streptomyces Hygroscopicus*. II. Isolation and Characterization. J. Antibiot. 1990, 43, 961-966.

Example 3

| Compound Formula | Compound Number |
|---|---|
| | (−)-11a  (−)-7a |
| | (−)-11b  (−)-7b |
| | (+)-11c  (+)-7c |
| | (+)-11d  (+)-7d<br>(−)-11d |

-continued

| Compound Formula | Compound Number | |
|---|---|---|
| | endo-(+)-11e, endo-(+)-11f | endo-(+)-7f |
| | exo-(−)-11f, (−)-11e | exo-(−)-7e |
| | endo-(+)-11g | endo-(+)-7h |
| | exo-(+)-11h | exo-(+)-7g |
| | 11i | 7j |
| | 11j | 7i |
| | 11k | 7k |

| Compound Formula | Compound Number | |
|---|---|---|
| | 11m | 7m |
| | 11n | 7n |
| | (−)-26 | (−)-15 |
| | (−)-28 | (−)-17 |

| Compound Formula | Compound Number |
|---|---|
| [structure] | (−)-30   (−)-19 |
| [structure] | (−)-32   (−)-23 |

The synthesis and study of antibiotic natural products with unique structures and mechanisms of action represents a proven strategy to combat the public health crisis posed by antibiotic-resistant bacteria. The natural product himastatin is an antibiotic with an unusual homodimeric structure that presents a significant synthetic challenge. We report the concise total synthesis of himastatin by a newly developed final-stage dimerization strategy that was inspired by a detailed consideration of its biogenesis. Combining our bio-inspired dimerization approach with a modular synthesis enabled expedient access to a number of designed derivatives of himastatin, including synthetic probes that provide insight into its antibiotic activity.

The proliferation of multi-drug resistant pathogenic bacteria is widely recognized as an eminent threat to global health (i, ii). Since their discovery, natural products have served as the primary inspiration for new antibiotics to treat bacterial infections (iii). (−)-Himastatin (1) is a macrocyclic peptide antibiotic with a homodimeric structure isolated from *Streptomyces* himastatinicus (FIG. 1) (iv, v, vi). While (−)-himastatin's (1) mechanism of action is not known, an early investigation demonstrated that its antibiotic activity was reduced in the presence of sodium salts of phospholipids and fatty acids, leading to speculation that (−)-himastatin (1) may target the bacterial membrane (vii). The first member discovered in this family (FIG. S1), (−)-himastatin's (1) homodimeric structure does not show resemblance to any well-characterized antibiotic class, including known membrane-disrupting cyclic peptides. The most striking structural feature of (−)-himastatin (1) is the central C5-C5' linkage between cyclotryptophan residues that is formed in the final biosynthetic step (viii) and is critical for the observed Gram-positive antibiotic activity (ix). Related monomeric natural products, including NW-G01 (S2), show a significant enhancement in antibiotic activity upon enzymatic dimerization (x). Other notable structural features of (−)-himastatin (1) include the alternating sequence of D- and L-amino acids, a depsipeptide linkage, and the piperazic acid residue with γ-hydroxylation.

Danishefsky's landmark synthesis of (−)-himastatin (1), which clarified the Cα stereochemistry of the cyclotryptophan residue, featured an early-stage Stille coupling to form the central C5-C5' linkage followed by bidirectional elaboration of a dimeric cyclotryptophan (ix). Early-stage formation of this linkage was also utilized in total syntheses of the related natural product (−)-chloptosin (S1) by Yao (xi) and Ley (xii), who found that cross-coupling approaches to achieve a more attractive late-stage dimerization that would offer access to heterodimeric derivatives were not successful (xii). Motivated by the unique structure, established synthetic challenge, and antibiotic activity, we became interested in developing a concise total synthesis of (−)-himastatin (1) that would offer rapid access to novel derivatives for chemical biology studies.

The key unaddressed challenge of uniting two complex fragments to form the C5-C5' bond at the center of (−)-himastatin's (1) dimeric structure encouraged us to consider the development of new synthetic methodology. To address the $C_{sp2}$-$C_{sp2}$ linkage present in (−)-himastatin (1), we needed to identify a new strategy that stands apart from our group's prior radical-based approaches to secure $C_{sp3}$-$C_{sp3}$ linkages and $C_{sp3}$-$C_{sp2}$ linkages between similar (xiii) and dissimilar fragments (xiv). We began with a detailed examination of (−)-himastatin's (1) biogenesis from a linear peptide 4 that is cyclized and then subject to oxidative tailoring by three cytochrome p450 enzymes (viii). The final step, catalyzed by HmtS, forges the central C5-C5' bond by oxidative dimerization of (+)-himastatin monomer (2). Based on recent theoretical studies of p450-catalyzed C—C bond formation, we envisioned that this enzymatic dimerization may take place via radical-radical coupling of two cyclotryptophan radicals (FIG. S2) (xv,xvi). These radical species are likely generated in rapid succession via indoline N—H hydrogen-atom abstraction at the heme active site, before undergoing combination in its vicinity (xvi,xvii).

We envisioned that a biogenetically-inspired chemical method for the oxidative dimerization of cyclotryptophans could follow the same radical-radical coupling blueprint. As opposed to hydrogen atom abstraction, we planned to generate an analogous open-shell cyclotryptophan species via single-electron oxidation of the embedded aniline substructure. Consistent with studies of aniline dimerization via single-electron oxidation (xviii,xix,xx), we predicted that the resulting arylamine radical cation would rapidly dimerize at the most accessible position, forming the desired C5-C5' linkage. Late-stage application of this chemistry to dimerization of (+)-himastatin monomer (2) permits a straightforward modular assembly of linear hexadepsipeptide 5 akin to native precursor 4, without the constraints imposed by bidirectional elaboration of a simple dimeric cyclotryptophan (ix,xi,xii). Direct union of complex peptide macrocycles also offers the elusive opportunity to access the first heterodimeric derivatives of (−)-himastatin (1).

Our new dimerization method required the identification of a single-electron oxidant that would target the aniline substructure within a complex cyclotryptophan precursor (xxi). We discovered that stoichiometric silver(I) hexafluoroantimonate, in combination with the non-nucleophilic pyrimidine base TTBP (xxii) in 1,2-dichloroethane, could effect C5-C5' dimerization of cyclotryptophan, cyclotryptamine, and indoline derivatives (FIG. 2A). In each case, a single regioisomer consistent with a symmetric C5-C5' linked homodimer was isolated. Single crystal X-ray diffraction of dimeric endo-diketopiperazine (+)-7h verified the expected connectivity. The use of an aqueous sodium thiosulfate reductive workup was critical for optimal isolation of the products due to their sensitivity toward further oxidation under the reaction conditions (xxiii,xxiv). Notably, we found that exo-configured diketopiperazines 6e and 6g were subject to complete oxidation in approximately half the time of their corresponding endo-derivatives 6f and 6h, respectively. This finding correlates with the increased accessibility of the N1 locus in substrates 6e and 6g, the site of initial oxidation (xxv). Substitution of N1 with a methyl group in the case of indoline 6k did not inhibit the dimerization, consistent with a radical intermediate as opposed to a closed-shell arenium cation (xxvi). In order to expand the range of reagents that could be utilized in more complex applications of our dimerization method, we also investigated the use of copper (II) salts as single-electron oxidants (xx). Cyclotryptophan dimer (−)-7a could be obtained using catalytic copper(II) trifluoromethanesulfonate and silver(I) carbonate as the terminal oxidant, albeit in lower yield (34%, 18% RSM) compared to stoichiometric $AgSbF_6$ (54%).

To investigate the mechanism of this C—C bond forming dimerization reaction, we devised a series of experiments using indoline substrates (FIGS. 2B and S3) (xxiii). When an equimolar mixture of C2-methyl and C2-phenyl indolines 6i and 6j, respectively, were subjected to our dimerization conditions, we observed a statistical mixture of homo- and heterodimers that arise from similar rates of single-electron oxidation (FIG. 2B, green; FIG. S3, eq. 1). However, oxidative dimerization of an equal mixture of indolines 6j and 6k gave predominant (90%) homodimer formation, along with a trace (4%) amount of heterodimer 7n (FIG. S3, eq. 2). When a limiting quantity of oxidant was used, we determined that these indoline substrates were consumed sequentially, with N1-methyl indoline 6k dimerizing selectively over NH indoline 6j (FIG. 2B, blue; FIG. S3 eq. 3). Having observed homodimerization of a more readily oxidized monomer in the presence of a similarly nucleophilic but less readily oxidized monomer, we conclude that C5-C5' bond formation preferentially occurs through radical-radical coupling rather than nucleophilic capture. This conclusion is consistent with the absence of adduct formation in the homodimerization of cyclotryptophan 6a despite the presence of external π-nucleophiles (e.g. methallyltrimethylsilane, dimethylketene silyl acetal, N-trimethylsilylindoline), and is reinforced by prior studies demonstrating that radical-radical coupling between aniline radical cations is fast (k=~$10^7$ $M^{-1} \cdot s_{-1}$ for the dimerization of $PhNMe_2 \cdot^+$) (xviii, xix,xx). We postulate that the high local concentration of radical species near the surface of the oxidant favors their direct combination over nucleophilic pathways (xiv,xx). In the context of our synthetic efforts, the rapid rate and apparent insensitivity of the radical-radical coupling manifold to nucleophilic interference bode well for the application of this chemistry to complex substrates. These findings highlight a possible underlying parallel between our oxidative dimerization methodology and our mechanistic proposal for the biosynthetic dimerization catalyzed by HmtS (FIG. S2), involving successive generation of radical species in close proximity to each other.

For the synthesis of (+)-himastatin monomer (2), we sought to leverage the practical advantages of solid-phase peptide synthesis (xxvii), offering rapid and customizable access to complex peptides by minimizing repetitive purification and isolation steps. In contrast to the reported solution-based approach to intermediates en route to (−)-himastatin (1) (ix), we relied on a hybrid solution-solid phase synthetic strategy. The resin-bound D-threonine 9 (FIG. 3) was elaborated with L-leucine (−)-10 and depsitripeptide fragment (+)-8, the latter being prepared in one step from a depsipeptide block (xxviii) and known Nε,O-protected D-5-hydroxypiperazic acid (ix). The crude depsipentapeptide acid (+)-11 obtained upon cleavage was then coupled with cyclotryptophan (−)-12 (FIG. S4), affording linear hexadepsipeptide (−)-13 in 55% overall yield from threonine resin 9 (xxiii). The efficient hybrid synthetic strategy we have developed enables convergent assembly of intermediate hexadepsipeptide (−)-13 with only a single chromatographic purification, and compares favorably to linear solution-phase synthesis which requires at least 10 separate steps to access an intermediate of similar complexity (ix). Furthermore, our modular strategy allows for conducting difficult couplings in solution (xxviii), and introducing the tryptophan residue as a cyclotryptophan to bypass stereoselectivity concerns that would arise from late-stage oxidation (xxix). The resulting linear peptide (−)-13 was cyclized to (+)-himastatin monomer (2) in 46% overall yield (FIG. 4), affording the immediate biosynthetic precursor to (−)-himastatin (1). All $^1H$ and $^{13}C$ NMR data as well as optical rotation for synthetic monomer (+)-2 were consistent with literature values (viii, ix).

Having accessed (+)-himastatin monomer (2), we focused on the application of our biogenetically inspired oxidative dimerization methodology to complete the total synthesis of (−)-himastatin (1) (FIG. 3). While silver(I) hexafluoroantimonate and copper(II) trifluoromethanesulfonate were effective for the dimerization of simpler cyclotryptophans (FIG. 2), they gave little to no oxidation of the cyclotryptophan incorporated within the more complex (+)-himastatin monomer (2). We hypothesized that aggregation and inactivation of these insoluble oxidants, combined with the lower reactivity of complex macrocyclic peptide substrates, may be responsible for the low conversion, and sought to address the challenge posed by evaluating other single-electron oxidants. Consistent with this hypothesis, insoluble oxidants such as other Ag(I,II) and Cu(II) salts were generally ineffective. However, soluble oxidants including organic radical cations such as magic blue ((4-BrPh)$_3$N.$^+$ SbF$_6$), did provide oxidation, but products derived from nucleophilic substitution of the C—Br bond (S$_N$Ar) by the peptide dominated (xxi). Informed by our prior use of Cu(II) for the dimerization of simpler substrates and in search of an oxidant with both good solubility and low propensity toward nucleophilic capture, we identified copper(II) hexafluoroantimonate. Our isolation of freshly prepared Cu(SbF$_6$)$_2$, commonly used as a soluble Lewis acid catalyst (xxx), provided us with an opportunity to investigate its use as a stoichiometric oxidant. In the event, exposure of (+)-himastatin monomer (2) to Cu(SbF$_6$)$_2$ and DTBMP in 1,2-dichloroethane, afforded (−)-himastatin (1) in 40% yield, with only trace (<5%) amounts of recovered starting material. All spectroscopic data, as well as optical rotation, for synthetic (−)-himastatin (1) were consistent with literature values (vi, ix).

Figure 4:
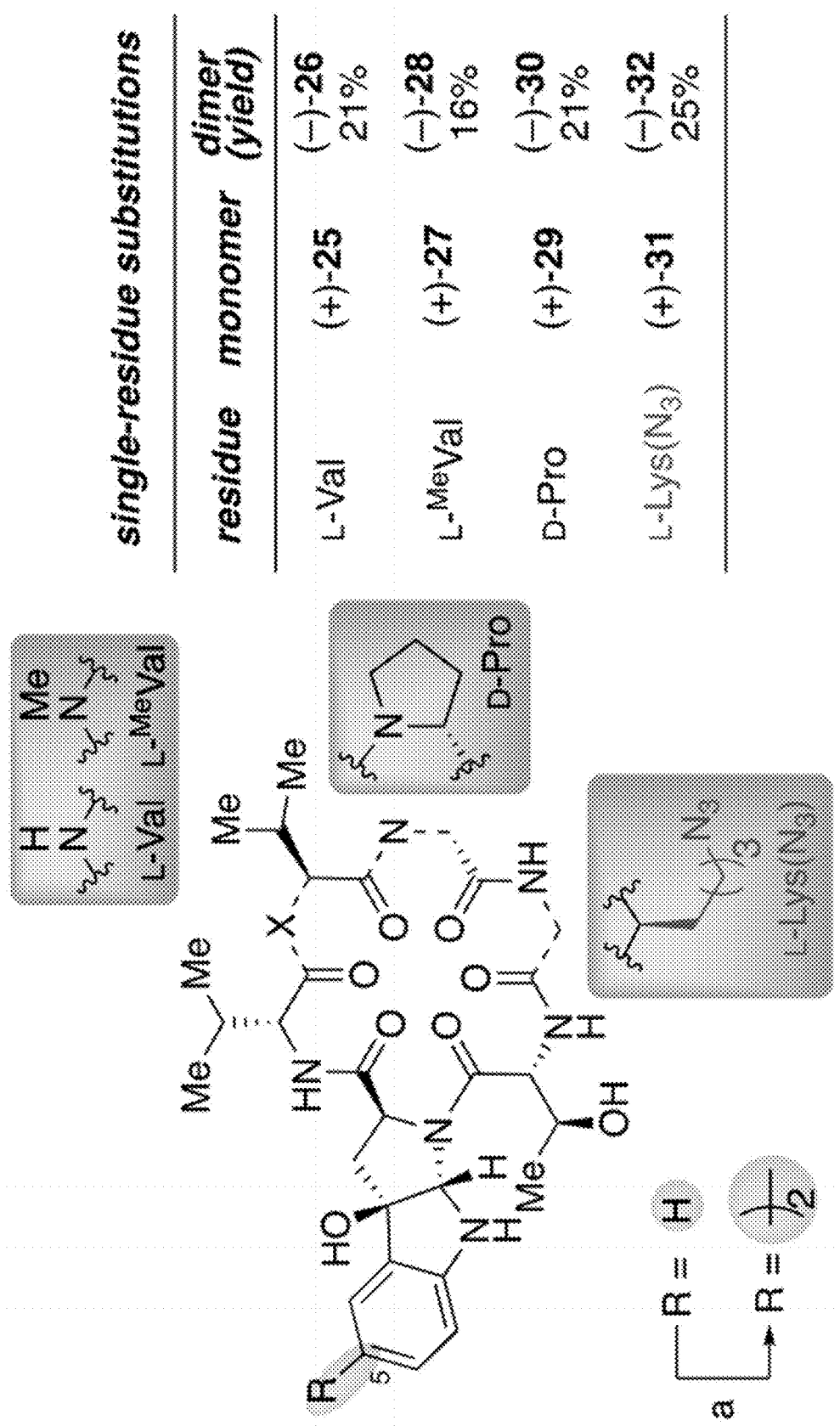
FIG. 4 shows the derivatives of (−)-Himastatin (1) with Single-Residue Substitution[a]. [a]Reagents and conditions: (a) $AgSbF_6$, DTBMP, $ClCH_2CH_2Cl$, 23° C.

Our concise and versatile chemical synthesis of himastatin, featuring a biogenetically inspired final-stage dimerization reaction, presented an opportunity both to interrogate structural characteristics that are important for its bioactivity, and to access synthetic probes for chemical biology studies (FIG. 4). We hypothesized that the alternating sequence of D,L-residues present in the macrocyclic rings of (−)-himastatin (1) could promote self-assembly (xxxi,xxxii), inspiring our preparation of both the enantiomer (ent-(+)-1) and meso derivative of himastatin (1). These stereochemical probes were prepared from precursors of opposite chirality, and in the case of the heterodimer meso-himastatin (1), by dimerization of an equal mixture of monomer 2 enantiomers and separation of the resulting heterodimer (xxiii). Apart from slight variations in the chemical shifts of aromatic $^1$H and $^{13}$C signals, the spectra of meso-himastatin (1) were nearly identical to the corresponding homodimers. We also selected several derivatives with single-residue substitutions to synthesize, each varying a residue that is unique to himastatin amongst related antibiotics. In all cases, our modular hybrid peptide synthesis approach was quickly adapted to introduce the substituted residue, and the resulting monomers were effectively dimerized (21-37% yield) using the conditions developed for the synthesis of (−)-himastatin (1) (FIG. 4A) (xxiii). As an orthogonal mechanistic probe that would permit direct visualization of himastatin's interaction with bacteria, we designed a fluorescent heterodimer that we predicted would retain antibiotic activity (vide infra). TAMRA-himastatin heterodimer (−)-25 was rapidly prepared via the union of himastatin monomer (+)-2 and azidolysine monomer (+)-22 followed by labelling via a reduction-acylation sequence (FIG. 4B). This procedure also provided access to TAMRA-himastatin homodimer (−)-S17 as a useful control (xxiii).

We found that synthetic (−)-himastatin (1) showed antibiotic activity against several Gram-positive species, including antibiotic-resistant strains of public health concern (FIG. 4C, Table S10) (i). Our synthetic (−)-himastatin (1) showed similar MIC values (1-2 µg/mL) to those reported for natural (−)-himastatin (1) in identical species (iv). All monomeric derivatives prepared in this study had MIC values ≥64 µg/mL across all species tested (xxiii), highlighting the critical role of dimerization for antibiotic activity. Our stereochemical probes revealed that the absolute stereochemistry of himastatin has negligible impact on its antibiotic activity; stereoisomers of himastatin (1) were found to have nearly identical MIC values across the B. subtilis, S. aureus, and E. faecalis strains tested. This finding has also been observed amongst enantiomers of certain membrane-targeting cyclic peptides with alternating stereochemistry (xxxiii), and is consistent with antibiotic activity depending on achiral as opposed to diastereomeric interactions that would lead to differential activity of each stereoisomer (e.g. with peptides or receptors) (xxxiv,xxxv). In contrast, we found that ent-(+)-himastatin (1) was 4-8 fold more active in inhibiting the growth of the producing organism, Streptomyces himastatinicus, compared to (−)-himastatin (1). This finding might be explained by the presence of known self-resistance mechanisms that have evolved in other species, such as enzymatic degradation and efflux, which would be expected to show differences between stereoisomers (xxxvi).

The introduction of a strategically positioned functional handle in (−)-himastatin (1) was a key goal of our derivative design that would permit introduction of a fluorescent tag. We focused on L-leucine substitution, given the natural variation of this site among related antibiotics (FIG. S1). Replacement with an O-methyl serine residue (L-Ser(OMe), dimer (−)-21), which is found in (−)-chloptosin (S1), had minimal impact on antibiotic activity. A similar finding was observed upon substitution with L-azidolysine (L-Lys(N$_3$), dimer (−)-23), which offered the conjugation site exploited in our synthesis of fluorescent probes. However, unlike serine and azidolysine homodimers (−)-21 and (−)-23, respectively, the corresponding TAMRA-himastatin homodimer (−)-S17 was inactive (MIC>64 µg/mL) (FIG. S5, Table S10). In addition to TAMRA, homodimeric himastatin analogues derived from other fluorophores were also found to be inactive (FIG. S5). Consistent with our expectation that minimizing the overall perturbation of himastatin's structure to only one half of the dimer may preserve antibiotic activity, we found that the MIC of TAMRA-heterodimer (−)-25 (FIG. 4B) was indeed comparable to that of (−)-himtastatin (1) in Bacillus subtilis (6 vs. 1 µg/mL). Thus, the opportunity for heterodimer formation offered by our biogenetically-inspired late-stage dimerization methodology was instrumental to secure access to a fluorescent himastatin probe (xxxvii), as well as other key derivatives including meso-himastatin (1) that would otherwise be significantly challenging to prepare using chemoenzymatic or bidirectional synthesis (ix,x).

Other structural features specific to (−)-himastatin (1) include a depsipeptide linkage and 5-hydroxypiperazic acid residue. Evaluating the derivatives that we prepared to study these particular structural features, we observed a trend of decreasing antibiotic activity when the ester linkage was replaced with either a secondary amide (−)-15 or tertiary amide (−)-17, consistent with the loss of a hydrogen-bond site (xxxviii). Furthermore, when the 5-hydroxypiperazic acid residue was replaced with a proline residue, antibiotic activity was completely abolished. While proline residues are known to induce turn formation, especially when the adjacent amino acid is of opposite α-stereochemistry, they do not exhibit a rigidifying effect as pronounced as that seen in N-acyl piperazic acid derivatives (xxxix). Consistent with the predicted loss of rigidity upon proline substitution, NMR spectra of homodimer (−)-19 and monomer (+)-18 in various solvents at 23° C. revealed the presence of minor conformers not observed in the spectra of (−)-himastatin (1) or our other derivatives. Taken together, these results provide evidence that structural rigidity, enforced by hydrogen-bonding and conformational restriction, is important to himastatin's antimicrobial mode of action.

Confocal microscopy has been used to observe the biological effects of antibiotics on *B. subtilis*, including the first approved membrane-disrupting lipopeptide, daptomycin (xxxvii). We sought to use our synthetic compounds in conjunction with this experimental approach to further characterize the antibiotic activity of (−)-himastatin (1). Our synthetic heterodimeric probe, TAMRA-himastatin (−)-25, offered an opportunity to directly visualize its interaction with bacteria and monitor cellular localization. When *B. subtilis* cells were treated with TAMRA-himastatin (−)-25, we observed substantial accumulation in the bacterial envelope (FIG. S6A), with little to no intracellular staining seen at sub-lethal concentrations. The most intense sites of staining were observed at bacterial septa, in addition to patches of stain along sidewalls. At lethal concentrations (FIG. S6B), defects such as membrane extrusions coincided with lateral accumulation of TAMRA-himastatin (−)-25. These sites of curvature appear to reflect areas where the antibiotic has induced changes to membrane morphology.

The staining pattern observed with TAMRA-himastatin (−)-25 was similar to that of the membrane stain FM4-64 with unmodified himastatin (1) (FIG. S7). Untreated *B. subtilis* cells have smooth membranes and normal septal rings, but cells treated with a sub-lethal concentration of either enantiomer of himastatin (1) display striking membrane defects, notably patches of membrane thickening. Furthermore, the observed similarity in membrane morphology between himastatin (1) enantiomers appears to be consistent with their similar antibiotic activity. In a separate experiment, we evaluated the timescale by which (−)-himastatin (1) acts on bacteria at lethal concentrations (FIG. S8). When treated with (−)-himastatin (1) at a concentration twice the MIC value, bacterial membranes were permeabilized within 30 minutes, as indicated by influx of the viability stain SYTOX Green.

The observations of our microscopy studies are comparable to those seen with daptomycin despite a lack of structural similarity to himastatin (xxxvii). The membrane defects and localization patterns observed in *B. subtilis* with unmodified (−)-himastatin (1) and our fluorescent himastatin derivative (−)-25, show resemblance to those seen with unmodified and fluorescent forms of daptomycin, respectively (xxxvii). Furthermore, the short timescale of membrane permeabilization following treatment with himastatin (1), like daptomycin, is consistent with a mode of action based on physical perturbations (xxxiii, xxxvii). This mode of action is distinct from other Gram-positive peptide antibiotics, such as vancomycin and teixobactin, that interfere with cell-wall biosynthesis and have longer kill times (xl). Separately, the similarity in MIC values and cellular morphology amongst our series of synthetic himastatin stereoisomers reveals that achiral interactions, for example with the hydrophobic groups of phospholipids (xxxiv,xxxv), are largely responsible for the observed antibiotic activity. In summary, our chemical biology studies using our synthetic probes offer findings that are consistent with the hypothesis that (−)-himastatin's (1) antibiotic activity is dependent on interaction with bacterial membranes (vii). It is evident that (−)-himastatin (1) is a structurally unique member amongst known membrane-disruptors. These antibiotics target an essential bacterial organelle that can be difficult to alter without severe fitness cost (xli).

As society continues to battle multidrug-resistant pathogens, membrane-disrupting antibiotics, like the FDA-approved daptomycin, represent an important frontier in the fight. Our bioinspired strategy for the total synthesis of (−)-himastatin (1) provides rapid access to derivatives and is enabling investigations that point to its antibiotic activity via membrane disruption. This effort aims to facilitate further inquiries to advance our understanding and exploit how himastatin's unique molecular structure contributes to its antibiotic activity.

REFERENCES IN EXAMPLE 3

1. H. W. Boucher, G. H. Talbot, J. S. Bradley, J. E. Edwards, D. Gilbert, L. B. Rice, M. Scheld, B. Spellberg, J. Bartlett, Bad bugs, no drugs: no ESKAPE! An update from the Infectious Diseases Society of America. Clin. Infect. Dis. 48, 1-12 (2009).
2. C. L. Ventola, The antibiotic resistance crisis: part 1: causes and threats. Pharm. Ther. 40, 277-283 (2015).
3. G. D. Wright, Something old, something new: revisiting natural products in antibiotic drug discovery. Can. J. Microbiol. 60, 147-154 (2014).
4. K. S. Lam, G. A. Hesler, J. M. Mattei, S. W. Mamber, S. Forenza, K. Tomita, Himastatin, a new antitumor antibiotic from *Streptomyces hygroscopicus*. I. Taxonomy of producing organism, fermentation and biological activity. J. Antibiot. 43, 956-960 (1990).
5. J. E. Leet, D. R. Schroeder, B. S. Krishnan, J. A. Matson, Himastatin, a new antitumor antibiotic from *Streptomyces hygroscopicus*. II. Isolation and characterization. J. Antibiot. 43, 961-966 (1990).
6. J. E. Leet, D. R. Schroeder, J. Golik, J. A. Matson, T. W. Doyle, K. S. Lam, S. E. Hill, M. S. Lee, J. L. Whitney, B. S. Krishnan, Himastatin, a new antitumor antibiotic from *Streptomyces hygroscopicus*. III. Structural elucidation. J. Antibiot. 49, 299-311 (1996).
7. S. W. Mamber, K. W. Brookshire, B. J. Dean, R. A. Firestone, J. E. Leet, J. A. Matson, S. Forenza, Inhibition of antibacterial activity of himastatin, a new antitumor antibiotic from *Streptomyces hygroscopicus*, by fatty acid sodium salts. Antimicrob. Agents Chemother. 38, 2633-2642 (1994).
8. J. Ma, Z. Wang, H. Huang, M. Luo, D. Zuo, B. Wang, A. Sun, Y.-Q. Cheng, C. Zhang, J. Ju, Biosynthesis of himastatin: assembly line and characterization of three cytochrome p450 enzymes involved in the post-tailoring oxidative steps. Angew. Chem. Int. Ed. 50, 7797-7802 (2011).
9. T. M. Kamenecka, S. J. Danishefsky, Discovery through total synthesis: a retrospective on the himastatin problem. Chem. Eur. J. 7, 41-63 (2001).
10. Z. Guo, P. Li, G. Chen, C. Li, Z. Cao, Y. Zhang, J. Ren, H. Xiang, S. Lin, J. Ju, Y. Chen, Design and biosynthesis of dimeric alboflavusins with biaryl linkages via regiospecific C—C bond coupling. J. Am. Chem. Soc. 140, 18009-18015 (2018).
11. S.-M. Yu, W.-X. Hong, Y. Wu, C.-L. Zhong, Z.-J. Yao, Total synthesis of chloptosin, a potent apoptosis-inducing cyclopeptide. Org. Lett. 12, 1124-1127 (2010).

12. A. J. Oelke, F. Antonietti, L. Bertone, P. B. Cranwell, D. J. France, R. J. M. Goss, T. Hofmann, S. Knauer, S. J. Moss, P. C. Skelton, R. M. Turner, G. Wuitschik, S. V. Ley, Total synthesis of chloptosin: a dimeric cyclohexapeptide. Chem. Eur. J. 17, 4183-4194 (2011).
13. J. Kim, J. A. Ashenhurst, M. Movassaghi, Total synthesis of (+)-11,11'-dideoxyverticillin A. Science. 324, 238-241 (2009).
14. M. Movassaghi, O. K. Ahmad, S. P. Lathrop, Directed heterodimerization: stereocontrolled assembly via solvent-caged unsymmetrical diazene fragmentation. J. Am. Chem. Soc. 133, 13002-13005 (2011).
15. J. M. Grandner, R. A. Cacho, Y. Tang, K. N. Houk, Mechanism of the p450-catalyzed oxidative cyclization in the biosynthesis of griseofulvin. ACS Catal. 6, 4506-4511 (2016).
16. R. H. Takahashi, J. M. Grandner, S. Bobba, Y. Liu, P. Beroza, D. Zhang, S. Ma, Novel homodimer metabolites of GDC-0994 via cytochrome p450-catalyzed radical coupling. Drug. Metab. Dispos. 48, 521-527 (2020).
17. V. V. Shende, Y. Khatri, S. A. Newmister, J. N. Sanders, P. Lindovska, F. Yu, T. J. Doyon, J. Kim, K. N. Houk, M. Movassaghi, D. H. Sherman, Structure and function of NzeB, a versatile C-C and C—N bond-forming diketopiperazine dimerase. J. Am. Chem. Soc. 142, 17413-17424 (2020).
18. D. Larumbe, I. Gallardo, C. P. Andrieux, Anodic oxidation of some tertiary amines. J. Electroanal. Chem. 304, 241-247 (1991).
19. H. Yang, D. O. Wipf, A. J. Bard, Application of rapid scan cyclic voltammetry to a study of the oxidation and dimerization of N,N-dimethylaniline in acetonitrile. J. Electroanal. Chem. 331, 913-924 (1992).
20. M. Kirchgessner, K. Sreenath, K. R. Gopidas, Understanding reactivity patterns of the dialkylaniline radical cation. J. Org. Chem. 71, 9849-9852 (2006).
21. N. G. Connelly, W. E. Geiger, Chemical redox agents for organometallic chemistry. Chem. Rev. 96, 877-910 (1996).
22. D. Crich, M. Smith, Q. Yao, J. Picione, 2,4,6-Tri-tert-butylpyrimidine (TTBP): a cost effective, readily available alternative to the hindered base 2,6-di-tert-butylpyridine and its 4-substituted derivatives in glycosylation and other reactions. Synthesis, 323-326 (2001).
23. Described herein.
24. O. Ivashenko, J. T. van Herpt, P. Rudolf, B. L. Feringa, W. R. Browne, Oxidative electrochemical aryl C-C coupling of spiropyrans. Chem. Commun. 49, 6737-6739 (2013).
25. B. M. Nelson, R. P. Loach, S. Schiesser, M. Movassaghi, Concise total synthesis of (+)-asperazine A and (+)-pestalazine B. Org. Biomol. Chem. 16, 202-207 (2018).
26. P. G. Gassman, G. A. Campbell, R. C. Frederick, Nucleophilic aromatic substitution of anilines via aryl nitrenium ions (anilenium ions). J. Am. Chem. Soc. 94, 3884-3891 (1972).
27. J. S. Albin, B. L. Pentelute, Efficient flow synthesis of human antimicrobial peptides. Aust. J. Chem. 73, 380 (2020).
28. M. M. Nguyen, N. Ong, L. Suggs, A general solid phase method for the synthesis of depsipeptides. Org. Biomol. Chem. 11, 1167-1170 (2013).
29. K. L. Greenman, D. M. Hach, D. L. Van Vranken, Synthesis of Phakellistatin 13 and Oxidation to Phakellistatin 3 and Isophakellistatin 3. Org. Lett. 6, 1713-1716 (2004).
30. S.-K. Chang, P. Selvaraj, "Copper(II) Hexafluoroantimonate" in Encyclopedia of Reagents for Organic Synthesis (Wiley, 2005).
31. P. De Santis, S. Morosetti, R. Rizzo, Conformational analysis of regular enantiomeric sequences. Macromolecules. 7, 52-58 (1974).
32. L. Tomasic, G. P. Lorenzi, Some cyclic oligopeptides with S2n symmetry. Helv. Chim. Acta. 70, 1012-1016 (1987).
33. S. Fernandez-Lopez, H.-S. Kim, E. C. Choi, M. Delgado, J. R. Granja, A. Khasanov, K. Kraehenbuehl, G. Long, D. A. Weinberger, K. M. Wilcoxen, M. R. Ghadiri, Antibacterial agents based on the cyclic D,L-α-peptide architecture. 412, 4 (2001).
34. D. Wade, A. Boman, B. Wåhlin, C. M. Drain, D. Andreu, H. G. Boman, R. B. Merrifield, All-D amino acid-containing channel-forming antibiotic peptides. Proc. Natl. Acad. Sci. 87, 4761-4765 (1990).
35. C. K. Wang, G. J. King, A. C. Conibear, M. C. Ramos, S. Chaousis, S. T. Henriques, D. J. Craik, Mirror images of antimicrobial peptides provide reflections on their functions and amyloidogenic properties. J. Am. Chem. Soc. 138, 5706-5713 (2016).
36. E. Peterson, P. Kaur, Antibiotic Resistance Mechanisms in Bacteria: Relationships Between Resistance Determinants of Antibiotic Producers, Environmental Bacteria, and Clinical Pathogens. Front. Microbiol. 9, 2928 (2018).
37. J. Pogliano, N. Pogliano, J. A. Silverman, Daptomycin-mediated reorganization of membrane architecture causes mislocalization of essential cell division proteins. J. Bacteriol. 194, 4494-4504 (2012).
38. Y. Li, N. P. Lavey, J. A. Coker, J. E. Knobbe, D. C. Truong, H. Yu, Y.-S. Lin, S. L. Nimmo, A. S. Duerfeldt, Consequences of depsipeptide substitution on the ClpP activation activity of antibacterial acyldepsipeptides. ACS Med. Chem. Lett. 8, 1171-1176 (2017).
39. N. Xi, L. B. Alemany, M. A. Ciufolini, Elevated conformational rigidity in dipeptides incorporating piperazic acid derivatives. J. Am. Chem. Soc. 120, 80-86 (1998).
40. L. L. Ling, T. Schneider, A. J. Peoples, A. L. Spoering, I. Engels, B. P. Conlon, A. Mueller, T. F. Schäberle, D. E. Hughes, S. Epstein, M. Jones, L. Lazarides, V. A. Steadman, D. R. Cohen, C. R. Felix, K. A. Fetterman, W. P. Millett, A. G. Nitti, A. M. Zullo, C. Chen, K. Lewis, A new antibiotic kills pathogens without detectable resistance. Nature. 517, 455-459 (2015).
41. M. Roch, P. Gagetti, J. Davis, P. Ceriana, L. Errecalde, A. Corso, A. E. Rosato, Daptomycin resistance in clinical MRSA strains is associated with a high biological fitness cost. Front Microbiol. 8, 2303 (2017).
42. W. C. Still, M. Kahn, A. Mitra, Rapid chromatographic technique for preparative separations with moderate resolution. J. Org. Chem. 43, 2923-2925 (1978).
43. A. B. Pangborn, M. A. Giardello, R. H. Grubbs, R. K. Rosen, F. J. Timmers, Safe and convenient procedure for solvent purification. Organometallics. 15, 1518-1520 (1996).
44. Y. Qian, X. Xu, X. Wang, P. J. Zavalij, W. Hu, M. P. Doyle, Rhodium(II)- and copper(II)-catalyzed reactions of enol diazoacetates with nitrones: metal carbene versus Lewis acid directed pathways. Angew. Chem. Int. Ed. 51, 5900-5903 (2012).
45. H. E. Gottlieb, V. Kotlyar, A. Nudelman, NMR Chemical shifts of common laboratory solvents as trace impurities. J. Org. Chem. 62, 7512-7515 (1997).
46. C. J. Barrow, P. Cai, J. K. Snyder, D. M. Sedlock, H. H. Sun, R. Cooper, WIN 64821, a new competitive antagonist to substance P, isolated from an *Aspergillus* species: structure determination and solution conformation. J. Org. Chem. 58, 6016-6021 (1993).

47 R. P. Bhattacharyya, M. Walker, R. Boykin, S. S. Son, J. Liu, A. C. Hachey, P. Ma, L. Wu, K. Choi, K. C. Cummins, M. Benson, J. Skerry, H. Ryu, S. Y. Wong, M. B. Goldberg, J. Han, V. M. Pierce, L. A. Cosimi, N. Shoresh, J. Livny, J. Beechem, D. T. Hung, Rapid identification and phylogenetic classification of diverse bacterial pathogens in a multiplexed hybridization assay targeting ribosomal RNA. Sci. Rep. 9, 4516 (2019).

48 I. Wiegand, K. Hilpert, R. E. W. Hancock, Agar and broth microdilution methods to determine the minimal inhibitory concentration (MIC) of antimicrobial substances. Nat. Protoc. 3, 163-175 (2008).

49 J. S. Benco, H. A. Nienaber, W. G. McGimpsey, Synthesis of an ammonium ionophore and its application in a planar ion-selective electrode. Anal. Chem. 75, 152-156 (2003).

50 S. Eissler, M. Kley, D. Bächle, G. Loidl, T. Meier, D. Samson, Substitution determination of Fmoc-substituted resins at different wavelengths. J. Pept. Sci. 23, 757-762 (2017).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of the Formula I:

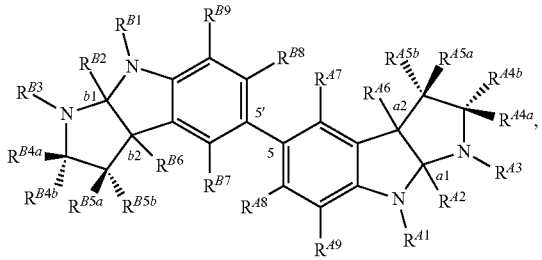

or a tautomer or isotopically labeled compound thereof, or a salt thereof, wherein:

the bond a1 and the bond a2 are syn or anti to each other;
the bond b1 and the bond b2 are syn or anti to each other;
each of $R^{A1}$ and $R^{B1}$ is independently hydrogen, substituted or unsubstituted alkyl, or substituted or unsubstituted phenyl;
each of $R^{A2}$ and $R^{B2}$ is independently hydrogen, substituted or unsubstituted alkyl, or substituted or unsubstituted phenyl;
$R^{A3}$ and $R^{A4a}$ or $R^{A4b}$ are joined with their intervening atoms to form substituted or unsubstituted heterocyclyl; and the remaining one of $R^{A4a}$ and $R^{A4b}$ is hydrogen, substituted or unsubstituted alkyl, substituted or unsubstituted phenyl, —C(=O)OR$^a$, a peptide, or a depsipeptide, wherein each R$^a$ is independently substituted or unsubstituted alkyl, substituted or unsubstituted phenyl, or hydrogen;
$R^{B3}$ and $R^{B4a}$ or $R^{B4b}$ are joined with their intervening atoms to form substituted or unsubstituted heterocyclyl; and the remaining one of $R^{B4a}$ and $R^{B4b}$ is hydrogen, substituted or unsubstituted alkyl, substituted or unsubstituted phenyl, —C(=O)OR$^a$, a peptide, or a depsipeptide, wherein each $R^a$ is independently substituted or unsubstituted alkyl, substituted or unsubstituted phenyl, or hydrogen:

or each of $R^{A3}$ and $R^{B3}$ is hydrogen, substituted or unsubstituted alkyl, substituted or unsubstituted phenyl, —C(=O)$R^a$, —C(=O)O$R^a$, a nitrogen protecting group, a peptide, or a depsipeptide, wherein each $R^a$ is independently substituted or unsubstituted alkyl, substituted or unsubstituted phenyl, or hydrogen; and each of $R^{A4a}$, $R^{A4b}$, $R^{B4a}$, and $R^{B4b}$ is independently hydrogen, substituted or unsubstituted alkyl, substituted or unsubstituted phenyl, a peptide, or a depsipeptide, wherein each $R^a$ is independently substituted or unsubstituted alkyl, substituted or unsubstituted phenyl, or hydrogen;

each of $R^{A5a}$, $R^{B5a}$, $R^{A5b}$, and $R^{B5b}$ is independently hydrogen or substituted or unsubstituted alkyl;

each of $R^{A6}$ and $R^{B6}$ is independently substituted or unsubstituted alkyl, substituted or unsubstituted phenyl, or —O$R^a$, wherein each $R^a$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group; and each of $R^{A7}$, $R^{B7}$, $R^{A8}$, $R^{B8}$, $R^{A9}$, and $R^{B9}$ is independently hydrogen, halogen, substituted or unsubstituted alkyl, or —O$R^a$, wherein each $R^a$ is independently hydrogen or substituted or unsubstituted alkyl;

provided that the compound is not of the formula:

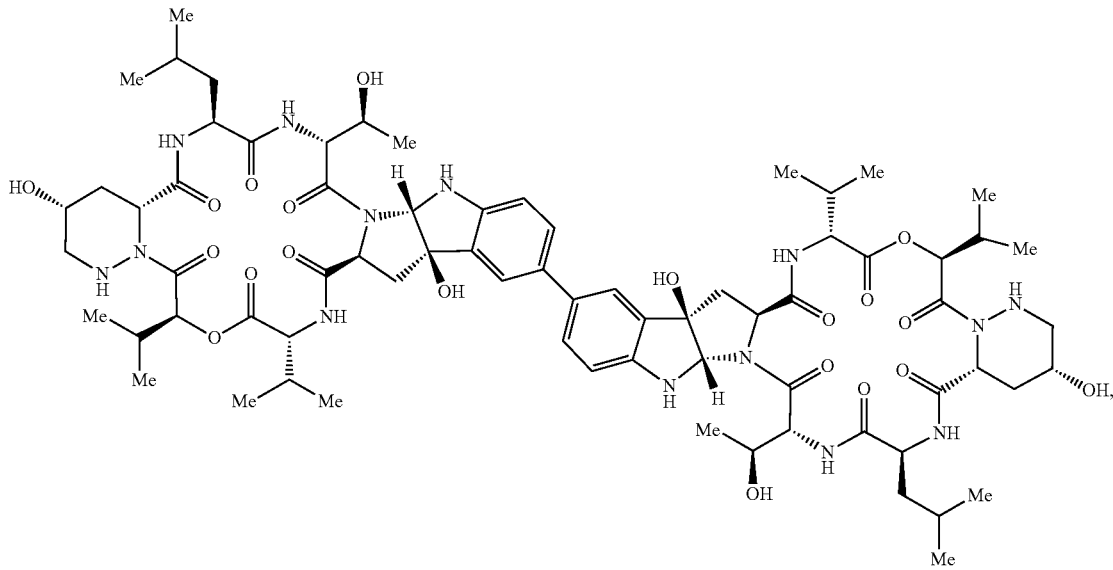

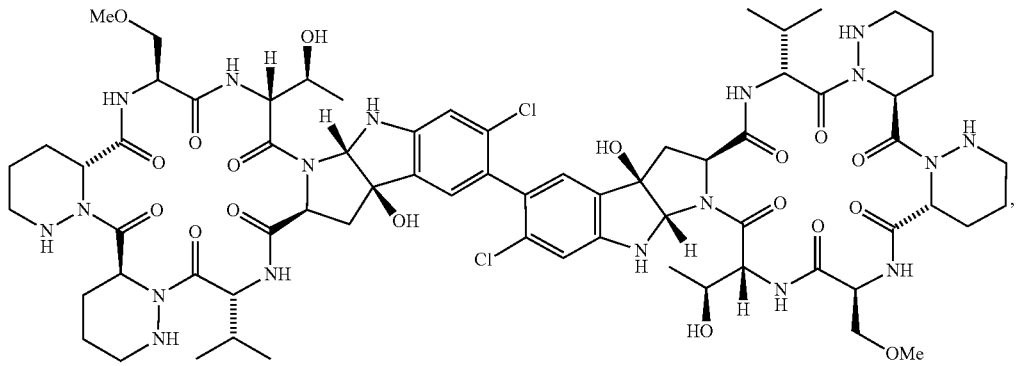

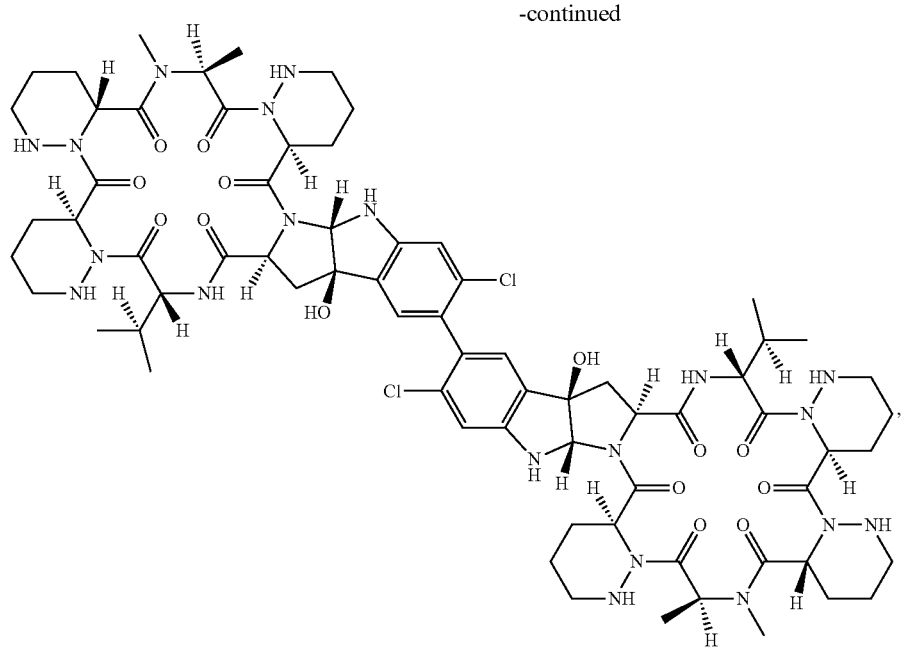
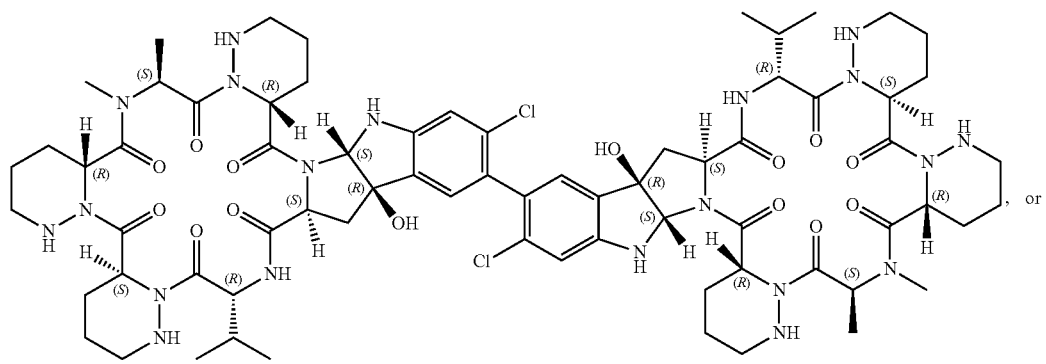
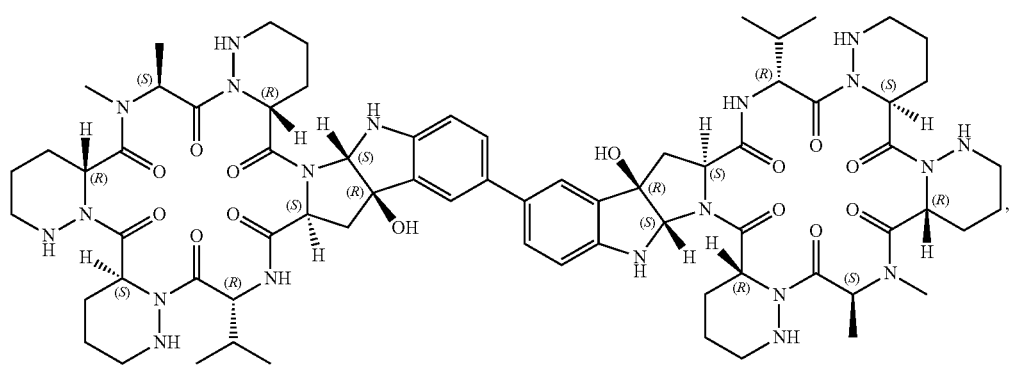
or a tautomer or isotopically labeled compound thereof, or a salt thereof.

2. A process of preparing a compound of claim 1, or a tautomer or isotopically labeled compound thereof, or a salt thereof, the process comprising reacting a compound of the formula:

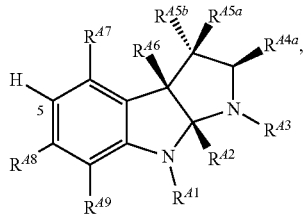

or a tautomer or isotopically labeled compound thereof, or a salt thereof, with a compound of the formula:

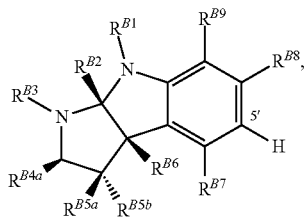

or a tautomer or isotopically labeled compound thereof, or a salt thereof, in the presence of a single-electron oxidant, a base, and a solvent.

3. The compound, tautomer, isotopically labeled compound, or salt of claim 1, wherein Formula I is:

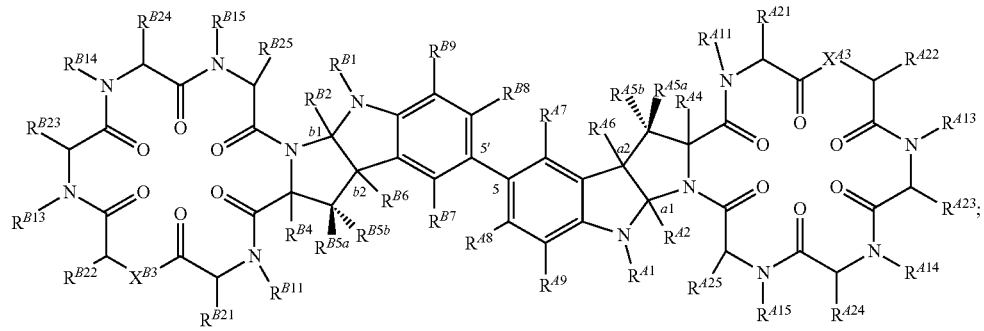

wherein:

$R^{A4}$ is $R^{A4a}$ or $R^{A4b}$;

$R^{B4}$ is $R^{B4a}$ or $R^{B4b}$;

$X^{A3}$ is O or $NR^{A12}$;

$X^{B3}$ is O or $NR^{B12}$;

each of $R^{A11}$, $R^{B11}$, $R^{A12}$, $R^{B12}$, $R^{A13}$, $R^{B13}$, $R^{A14}$, $R^{B14}$, $R^{A15}$, and $R^{B15}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —S(=O)R$^a$, S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), —P(=O)(OR$^a$)$_2$, or a nitrogen protecting group; and each of $R^{A21}$, $R^{B21}$, $R^{A22}$, $R^{B22}$, $R^{A23}$, $R^{B23}$, $R^{A24}$, $R^{B24}$, $R^{A25}$, and $R^{B25}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —OS(=O)$_2$R$^a$, —OS(=O)$_2$OR$^a$, —OS(=O)$_2$N(R$^a$)$_2$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —P(=O)(R$^a$)$_2$, —P(=O)(R$^a$)(OR$^a$), or —P(=O)(OR$^a$)$_2$;

or:

$R^{A11}$ and $R^{A21}$ are joined with their intervening atoms to form substituted or unsubstituted heterocyclyl;

$R^{A21}$ and $R^{A12}$ are joined with their intervening atoms to form substituted or unsubstituted heterocyclyl;

$R^{A12}$ and $R^{A22}$ are joined with their intervening atoms to form substituted or unsubstituted heterocyclyl;

$R^{A22}$ and $R^{A13}$ are joined with their intervening atoms to form substituted or unsubstituted heterocyclyl;

$R^{A13}$ and $R^{A23}$ are joined with their intervening atoms to form substituted or unsubstituted heterocyclyl;

$R^{A23}$ and $R^{A14}$ are joined with their intervening atoms to form substituted or unsubstituted heterocyclyl;

$R^{A14}$ and $R^{A24}$ are joined with their intervening atoms to form substituted or unsubstituted heterocyclyl;

$R^{A24}$ and $R^{A15}$ are joined with their intervening atoms to form substituted or unsubstituted heterocyclyl;

$R^{A15}$ and $R^{A25}$ are joined with their intervening atoms to form substituted or unsubstituted heterocyclyl;

$R^{B11}$ and $R^{B21}$ are joined with their intervening atoms to form substituted or unsubstituted heterocyclyl;

$R^{B21}$ and $R^{B12}$ are joined with their intervening atoms to form substituted or unsubstituted heterocyclyl;

$R^{B12}$ and $R^{B22}$ are joined with their intervening atoms to form substituted or unsubstituted heterocyclyl;
$R^{B22}$ and $R^{B13}$ are joined with their intervening atoms to form substituted or unsubstituted heterocyclyl;
$R^{B13}$ and $R^{B23}$ are joined with their intervening atoms to form substituted or unsubstituted heterocyclyl;
$R^{B23}$ and $R^{B14}$ are joined with their intervening atoms to form substituted or unsubstituted heterocyclyl;
$R^{B14}$ and $R^{B24}$ are joined with their intervening atoms to form substituted or unsubstituted heterocyclyl;
$R^{B24}$ and $R^{B15}$ are joined with their intervening atoms to form substituted or unsubstituted heterocyclyl; and/or
$R^{B15}$ and $R^{B25}$ are joined with their intervening atoms to form substituted or unsubstituted heterocyclyl.

4. The compound, tautomer, isotopically labeled compound, or salt of claim 1, wherein $R^{A1}$ and/or $R^{B1}$ are independently hydrogen or substituted or unsubstituted alkyl.

5. The compound, tautomer, isotopically labeled compound, or salt of claim 1, wherein $R^{A2}$ and/or $R^{B2}$ are independently hydrogen or substituted or unsubstituted alkyl.

6. The compound, tautomer, isotopically labeled compound, or salt of claim 1, wherein $R^{A6}$ and/or $R^{B6}$ are —$OR^a$.

7. The compound, tautomer, isotopically labeled compound, or salt of claim 1, wherein $R^{A7}$ and/or $R^{B7}$ are independently hydrogen, halogen, or substituted or unsubstituted alkyl.

8. The compound, tautomer, isotopically labeled compound, or salt of claim 1, wherein $R^{A8}$ and/or $R^{B8}$ are independently hydrogen, halogen, or substituted or unsubstituted alkyl.

9. The compound, tautomer, isotopically labeled compound, or salt of claim 1, wherein $R^{A9}$ and/or $R^{B9}$ are independently hydrogen, halogen, or substituted or unsubstituted alkyl.

10. The compound, tautomer, isotopically labeled compound, or salt of claim 1, wherein $R^{A3}$ and $R^{A4a}$ or $R^{A4b}$ are joined with their intervening atoms to form substituted or unsubstituted heterocyclyl; and/or $R^{B3}$ and $R^{B4a}$ or $R^{B4b}$ are joined with their intervening atoms to form substituted or unsubstituted heterocyclyl.

11. The compound of claim 1, or a tautomer or isotopically labeled compound thereof, or a salt thereof, wherein the compound is of the formula:

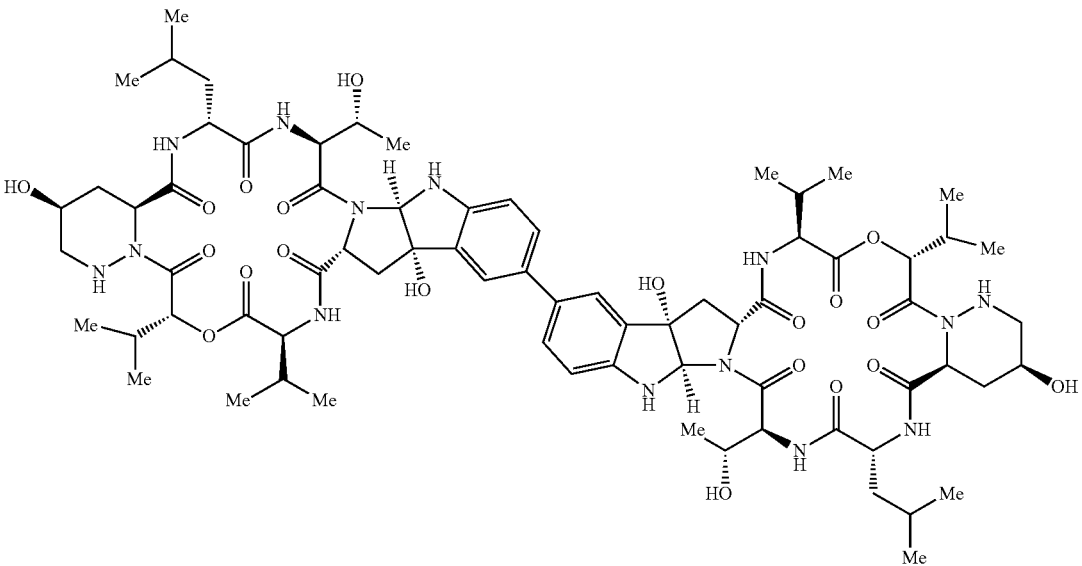 [SMILES: CC(C)C[C@H]1NC(=O)[C@@H]2C[C@H](O)CNN2C(=O)[C@@H](C(C)C)OC(=O)[C@H](C(C)C)NC(=O)[C@H]2C[C@]3(O)c4cc(-c5ccc6c(c5)[C@@]5(O)C[C@@H]7C(=O)N[C@@H](C(C)C)C(=O)O[C@H](C(C)C)C(=O)N8NC[C@@H](O)C[C@H]8C(=O)N[C@H](CC(C)C)C(=O)N[C@@H]([C@@H](C)O)C(=O)N7[C@H]5N6)ccc4N[C@@H]3N2C(=O)[C@H]([C@@H](C)O)NC1=O]

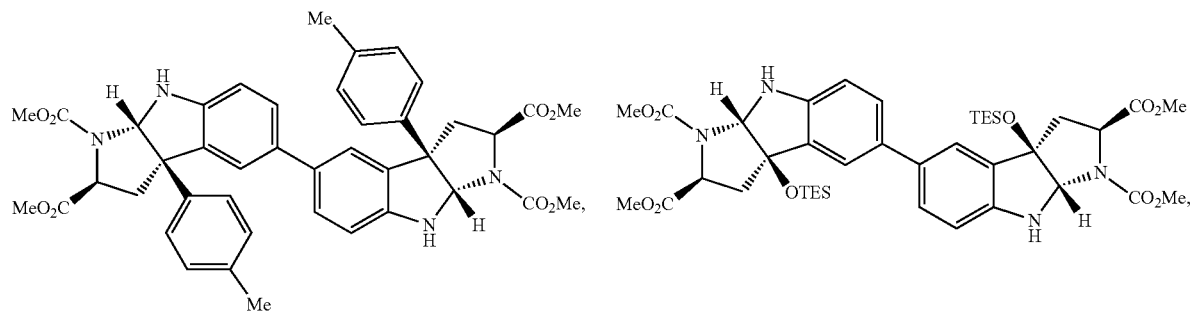

-continued
289
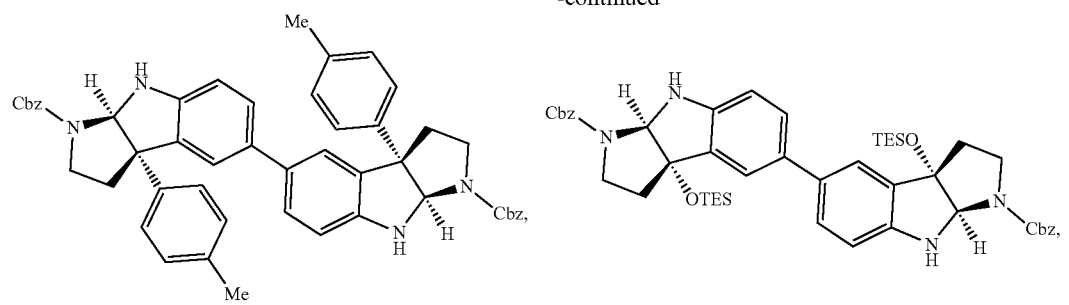
290
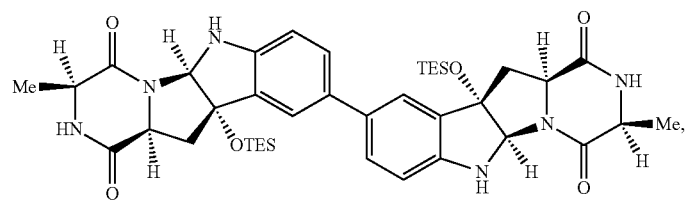
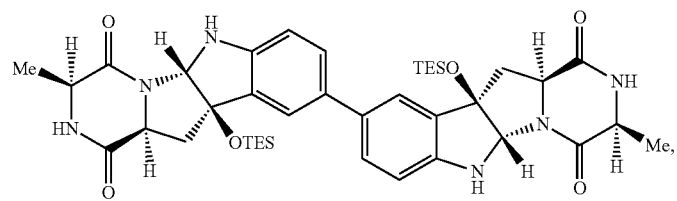
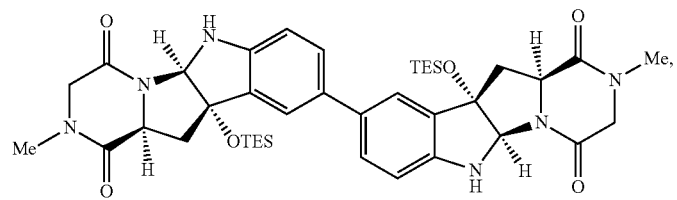
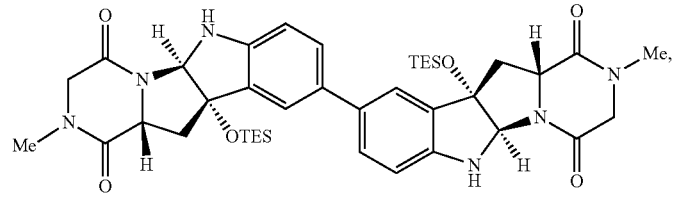
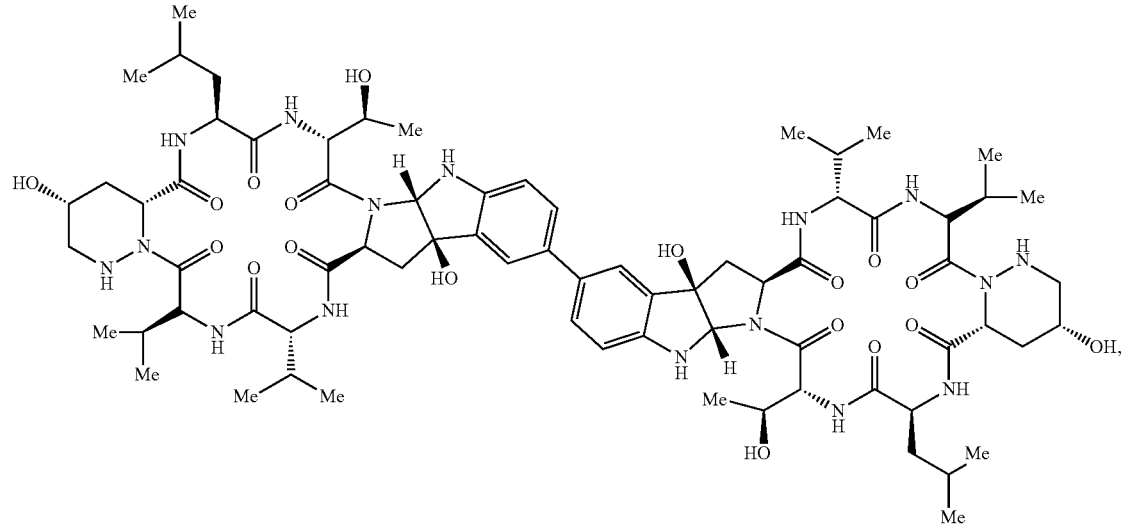

291
292
-continued
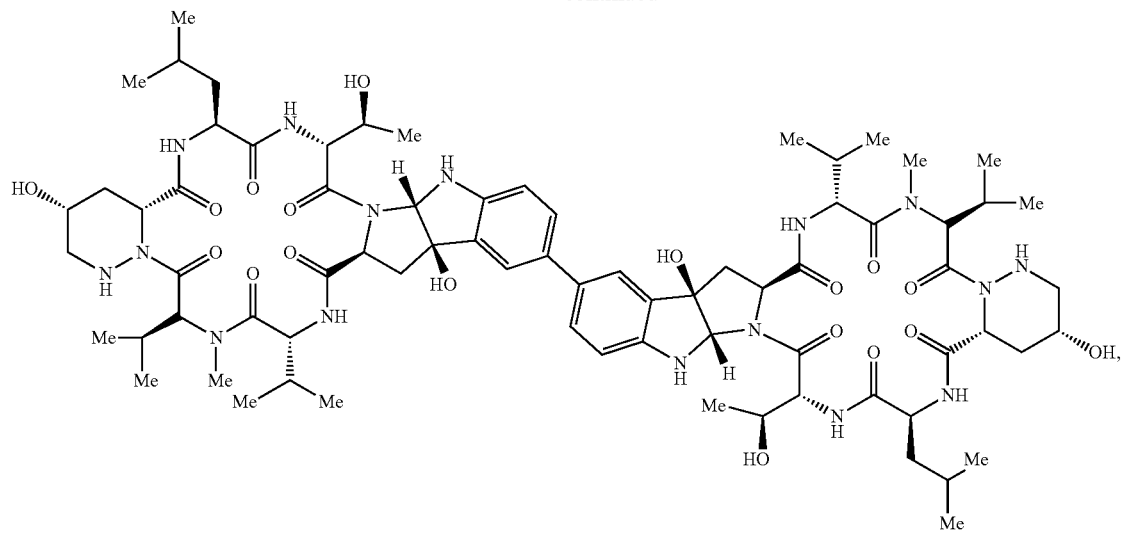
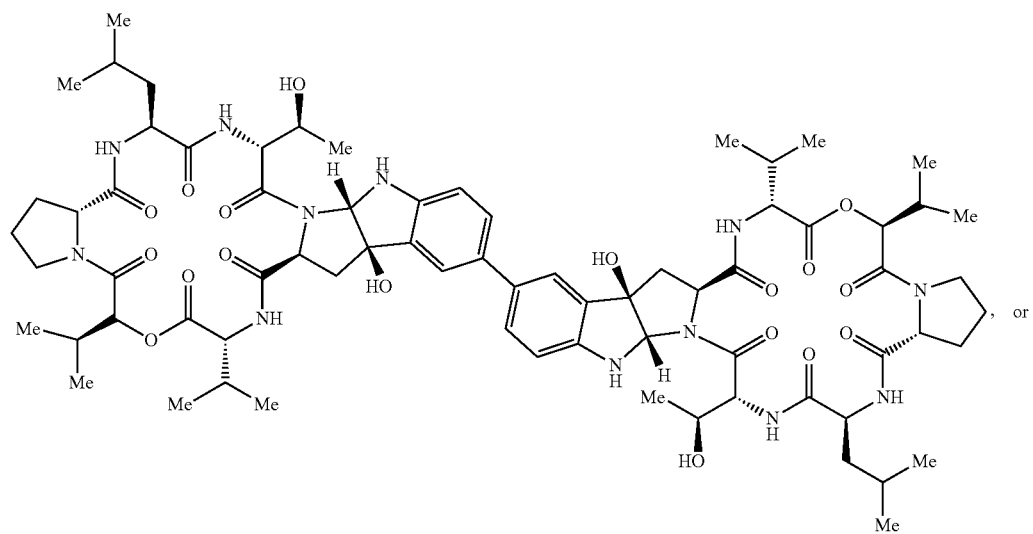
, or
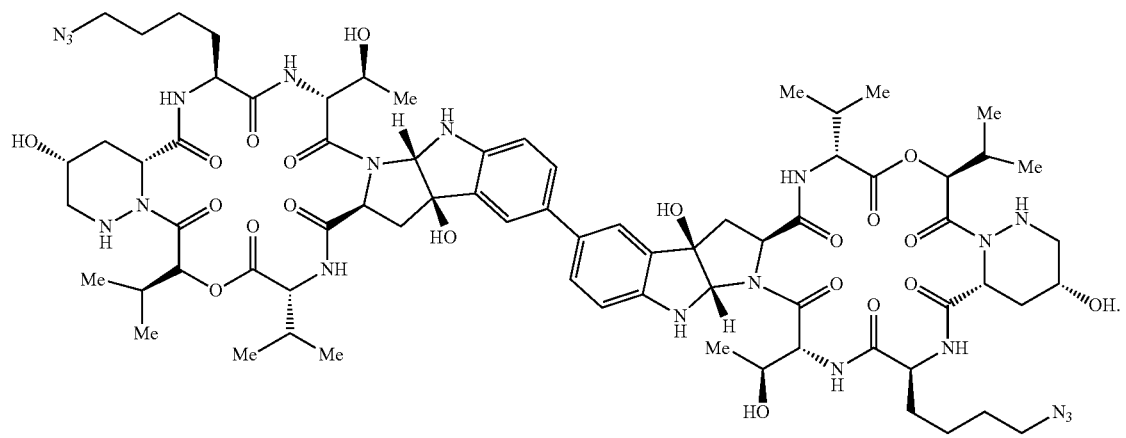

12. The compound of claim 1, or a tautomer or isotopically labeled compound thereof, or a salt thereof, wherein the compound is of the formula:
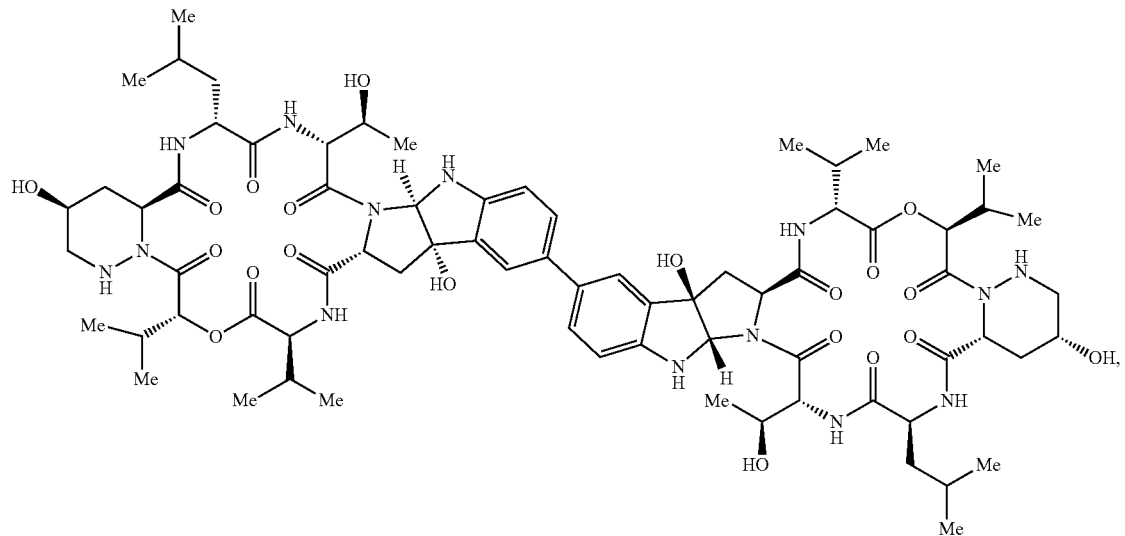
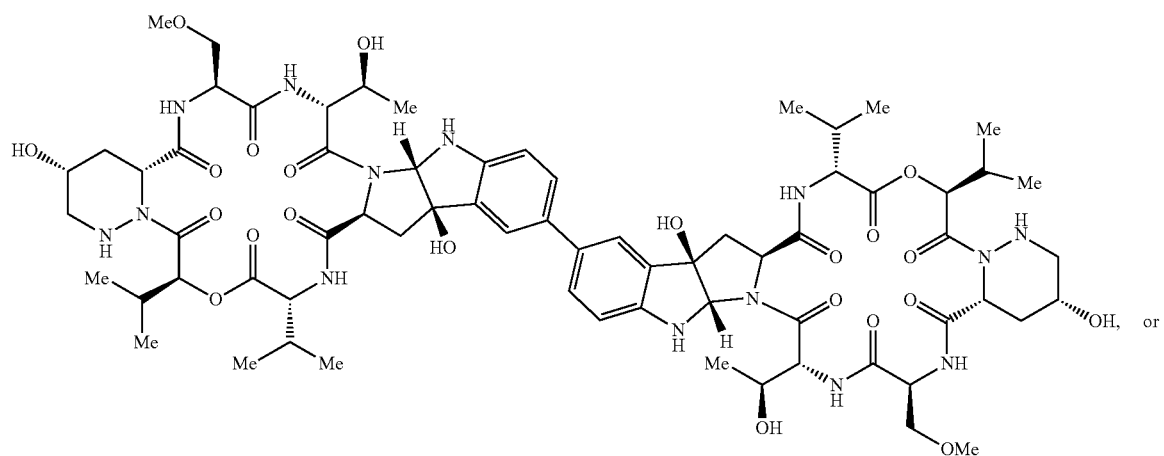
, or -continued
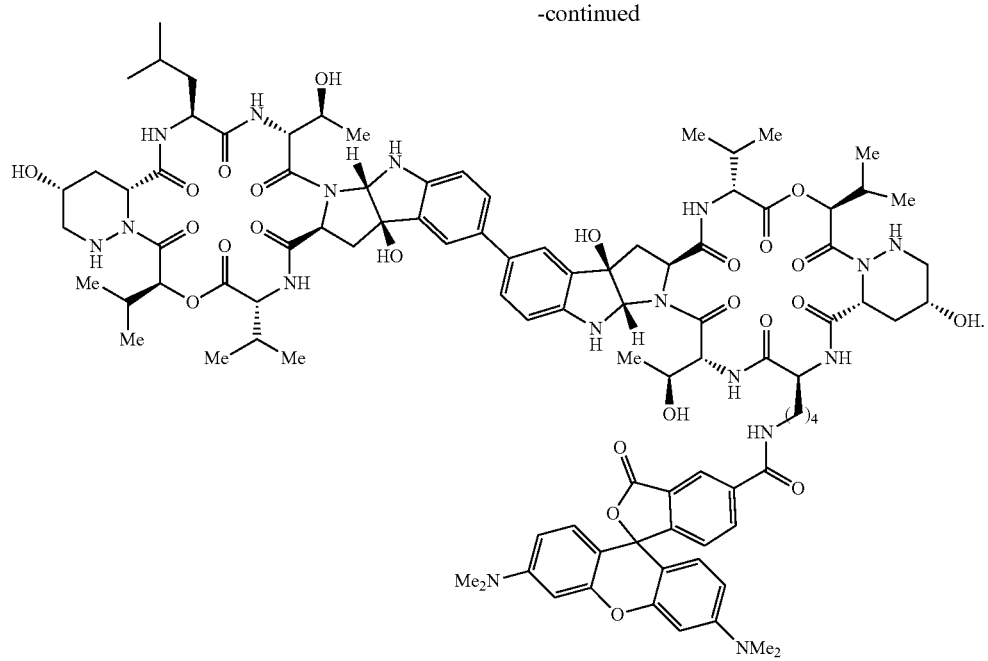
13. The compound of claim 1, or a tautomer or isotopically labeled compound thereof, or a salt thereof, wherein the compound is of the formula:
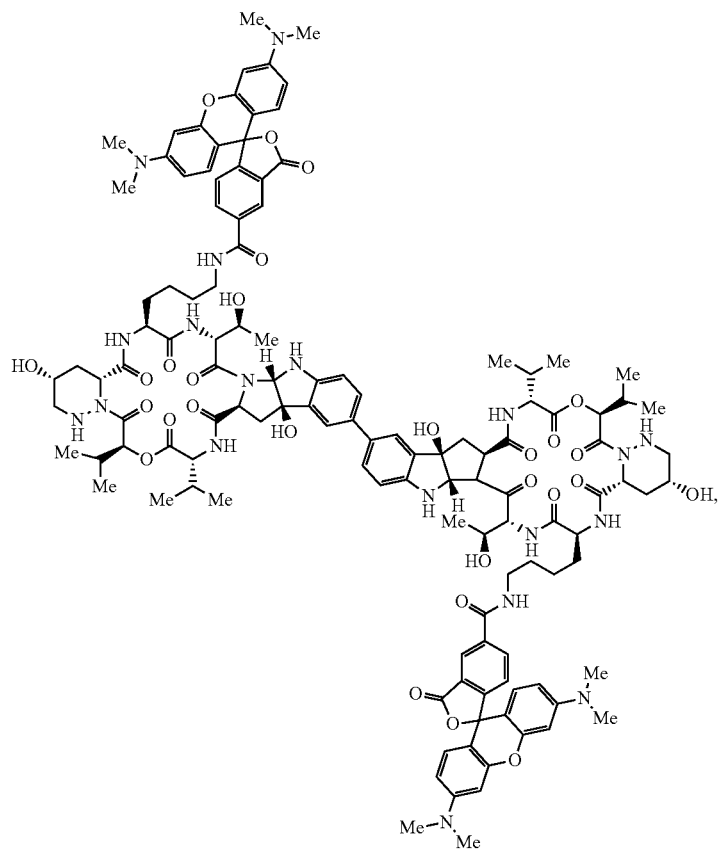

-continued
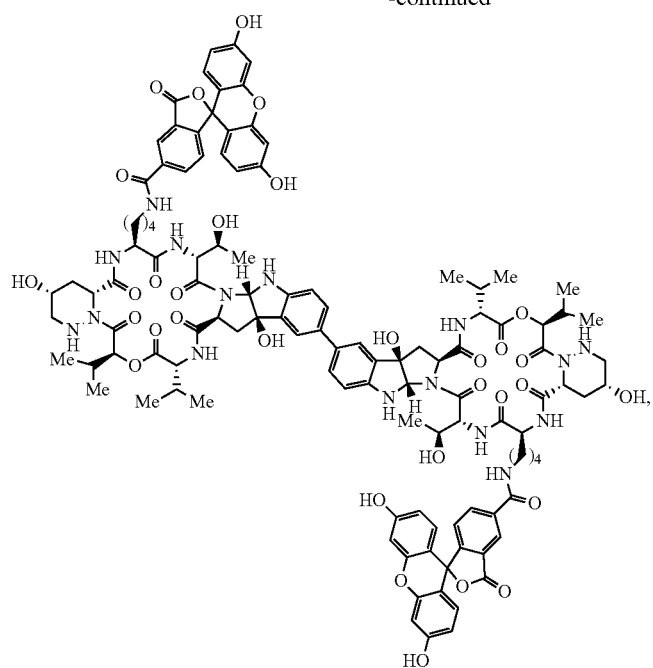
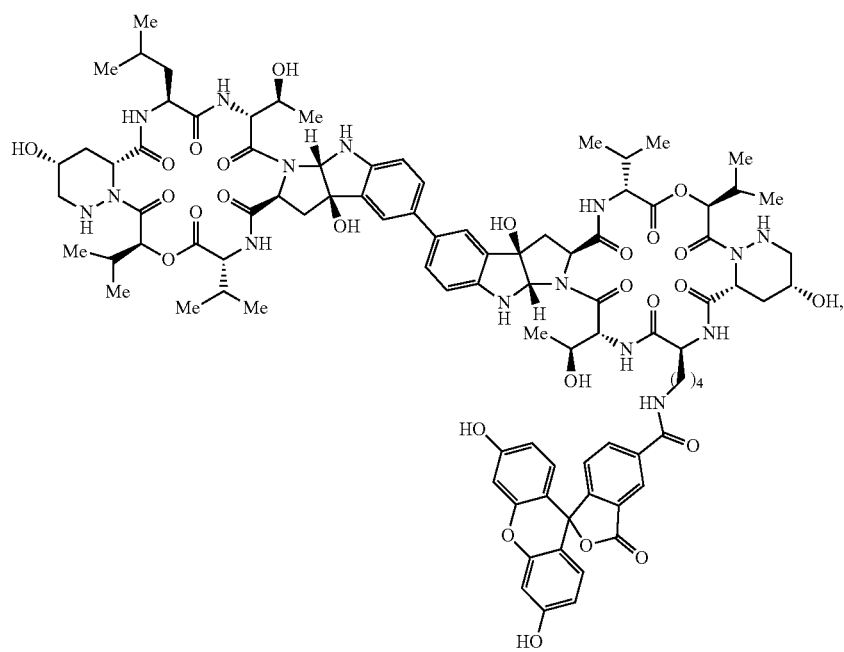

-continued
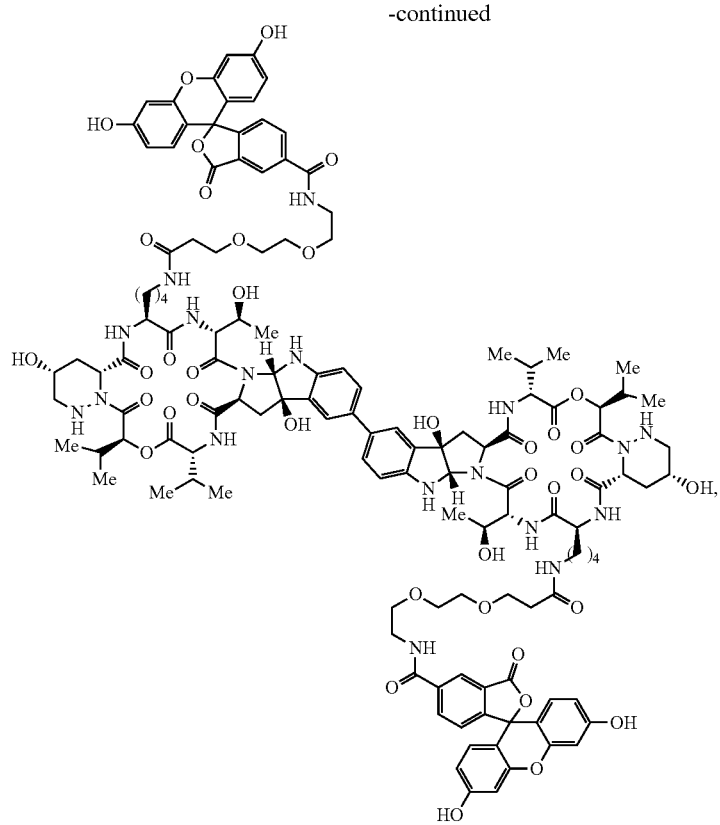
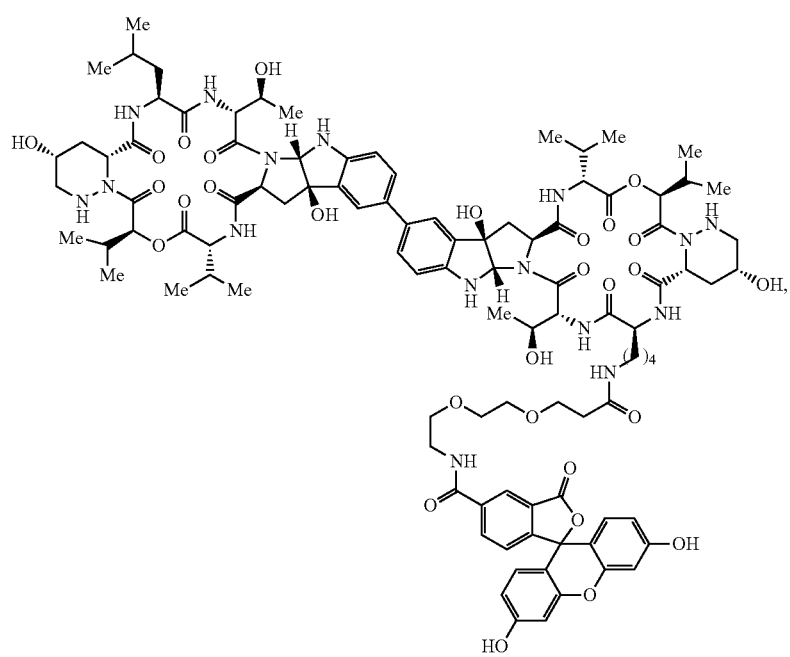

-continued

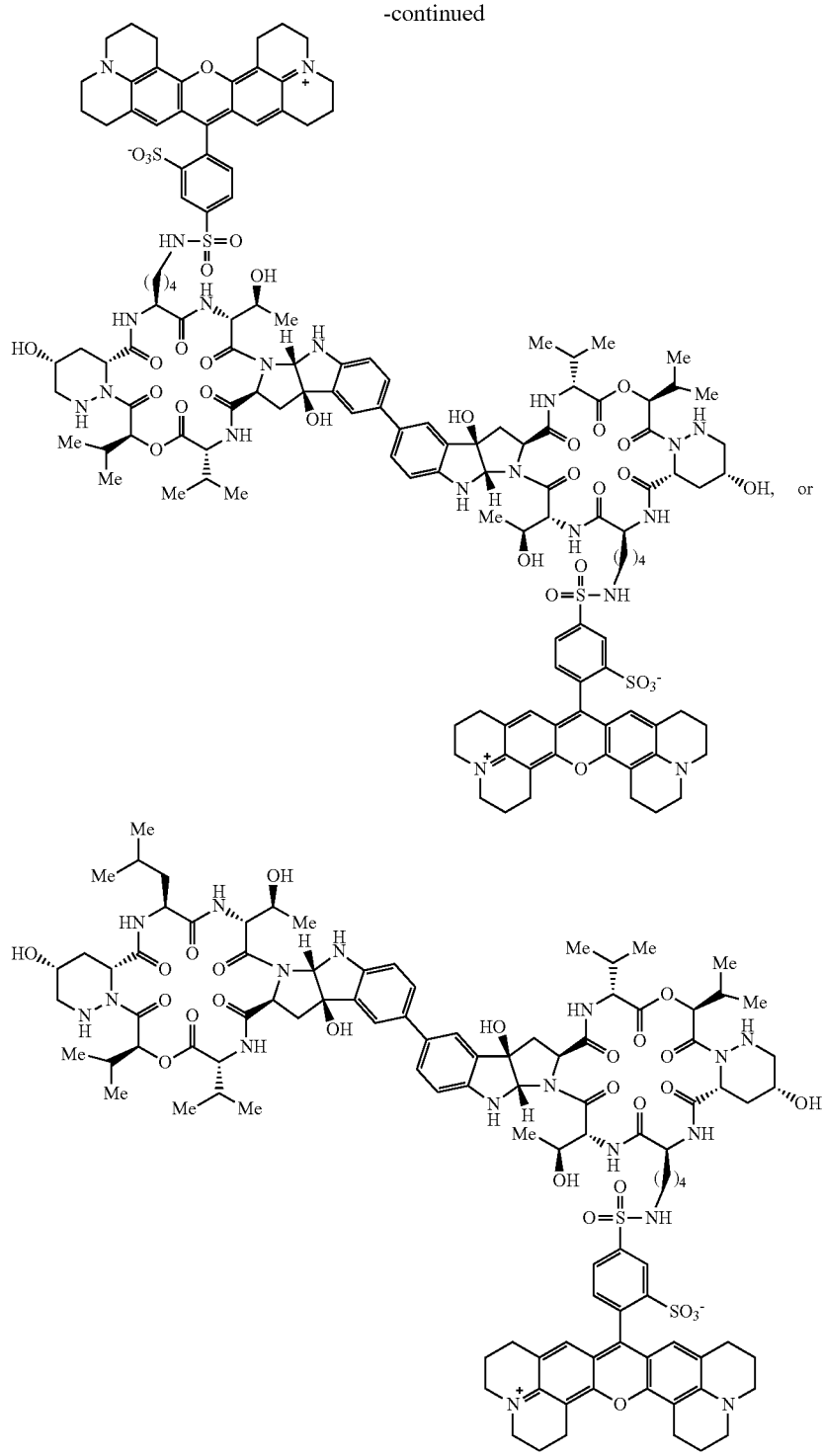

14. A pharmaceutical composition comprising:
   a compound of claim 1, or a tautomer or isotopically labeled compound thereof, or a pharmaceutically acceptable salt thereof; and
   optionally a pharmaceutically acceptable excipient.

15. A kit comprising:
   a compound of claim 1, or a tautomer or isotopically labeled compound thereof, or a pharmaceutically acceptable salt thereof; and
   instructions for using the compound, or a tautomer or isotopically labeled compound thereof, or a pharmaceutically acceptable salt thereof.

16. A method of treating a microbial infection in a subject in need thereof, the method comprising administering to the subject in need thereof an effective amount of a compound of claim 1, or a tautomer or isotopically labeled compound thereof, or a pharmaceutically acceptable salt thereof.

17. The method of claim 16, wherein the microbial infection is a bacterial infection.

18. The method of claim 17, wherein the bacterial infection is a Gram-positive bacterial infection.

19. The method of claim 16, wherein the microbial infection is caused by *Bacillus, Staphylococcus*, or *Enterococcus*.

20. The method of claim 16, wherein the microbial infection is caused by *Bacillus subtilis*, methicillin-resistant *Staphylococcus aureus*, methicillin-sensitive *Staphylococcus aureus*, vancomycin-resistant *Enterococcus faecalis*, or vancomycin-sensitive *Enterococcus faecalis*.

21. The method of claim 16, wherein the subject is a human.

22. The compound, tautomer, isotopically labeled compound, or salt of claim 1, wherein $R^{A6}$ and/or $R^{B6}$ are independently substituted or unsubstituted alkyl or substituted or unsubstituted phenyl.

23. The compound, tautomer, isotopically labeled compound, or salt of claim 1, wherein $R^{A3}$ and $R^{A4a}$ or $R^{A4b}$ are joined with their intervening atoms to form substituted or unsubstituted, 12- to 24-membered, monocyclic heterocyclyl optionally fused independently with one to four substituted or unsubstituted, 3- to 7-membered, monocyclic heterocyclyl; and/or $R^{B3}$ and $R^{B4a}$ or $R^{B4b}$ are joined with their intervening atoms to form substituted or unsubstituted, 12- to 24-membered, monocyclic heterocyclyl optionally fused independently with one to four substituted or unsubstituted, 3- to 7-membered, monocyclic heterocyclyl.

24. The compound, tautomer, isotopically labeled compound, or salt of claim 23, wherein the substituted or unsubstituted, 12- to 24-membered, monocyclic heterocyclyl optionally fused independently with one to four substituted or unsubstituted, 3- to 7-membered, monocyclic heterocyclyl is a cyclic peptide or cyclic depsipeptide.

25. The compound, tautomer, isotopically labeled compound, or salt of claim 1, wherein $R^{A3}$ and $R^{A4a}$ or $R^{A4b}$ are joined with their intervening atoms to form substituted or unsubstituted, 5- to 7-membered, monocyclic heterocyclyl; and/or $R^{B3}$ and $R^{B4a}$ or $R^{B4b}$ are joined with their intervening atoms to form substituted or unsubstituted, 5- to 7-membered, monocyclic heterocyclyl.

26. The compound, tautomer, isotopically labeled compound, or salt of claim 1, wherein $R^{A3}$ and/or $R^{B3}$ are independently —C(=O)O(substituted or unsubstituted alkyl), a nitrogen protecting group, a peptide, or a depsipeptide.

27. The compound, tautomer, isotopically labeled compound, or salt of claim 1, wherein $R^{A4a}$ and/or $R^{B4a}$ are independently —C(=O)O(substituted or unsubstituted alkyl), a peptide, a depsipeptide, or hydrogen.

28. The compound, tautomer, isotopically labeled compound, or salt of claim 1, wherein $R^{A4b}$ and/or $R^{B4b}$ are independently hydrogen, —C(=O)O(substituted or unsubstituted alkyl), a peptide, or a depsipeptide.

29. The compound, tautomer, isotopically labeled compound, or salt of claim 1, wherein $R^{A5a}$ and/or $R^{B5a}$ are hydrogen.

30. The compound, tautomer, isotopically labeled compound, or salt of claim 1, wherein $R^{A5b}$ and/or $R^{B5b}$ are hydrogen.

31. The compound or salt of claim 1.

32. A compound of the formula:

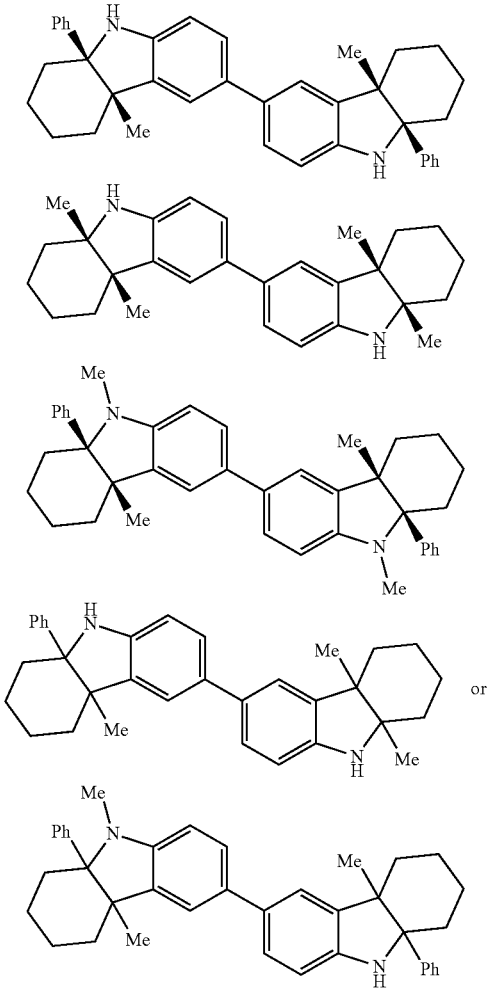

or a tautomer or isotopically labeled compound thereof, or a salt thereof.

33. A pharmaceutical composition comprising:
a compound of claim 32, or a tautomer or isotopically labeled compound thereof, or a pharmaceutically acceptable salt thereof; and
optionally a pharmaceutically acceptable excipient.

34. A method of treating a microbial infection in a subject in need thereof, the method comprising administering to the subject in need thereof an effective amount of a compound of claim 32, or a tautomer or isotopically labeled compound thereof, or a pharmaceutically acceptable salt thereof.

35. The method of claim 34, wherein the microbial infection is a bacterial infection.

36. The method of claim 35, wherein the bacterial infection is a Gram-positive bacterial infection.

37. The method of claim 34, wherein the microbial infection is caused by *Bacillus, Staphylococcus*, or *Enterococcus*.

38. The method of claim 34, wherein the microbial infection is caused by *Bacillus subtilis*, methicillin-resistant *Staphylococcus aureus*, methicillin-sensitive *Staphylococcus aureus*, vancomycin-resistant *Enterococcus faecalis*, or vancomycin-sensitive *Enterococcus faecalis*.

39. The method of claim 34, wherein the subject is a human.

40. A kit comprising:
a compound of claim 32, or a tautomer or isotopically labeled compound thereof, or a pharmaceutically acceptable salt thereof; and
instructions for using the compound, or a tautomer or isotopically labeled compound thereof, or a pharmaceutically acceptable salt thereof.

* * * * *

UNITED STATES PATENT AND TRADEMARK OFFICE
CERTIFICATE OF CORRECTION

PATENT NO. : 12,030,888 B2
APPLICATION NO. : 17/561680
DATED : July 9, 2024
INVENTOR(S) : Mohammad Movassaghi et al.

It is certified that error appears in the above-identified patent and that said Letters Patent is hereby corrected as shown below:

In the Specification

At Column 1, Lines 13-16, please change the sentence:
"This invention was made with government support under Grant No. R01 GM089732 awarded by the National Institutes of Health. The government has certain rights in the invention."
To:
-- This invention was made with government support under GM089732 awarded by the National Institutes of Health. The government has certain rights in the invention. --.

In the Claims

In Claim 3, at Column 285, Line 67, the text:
"S(=O)OR$^a$"
Should be replaced with:
-- –S(=O)OR$^a$ --.

Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 12,030,888 B2

In Claim 12, at Columns 293-294, the first formula:

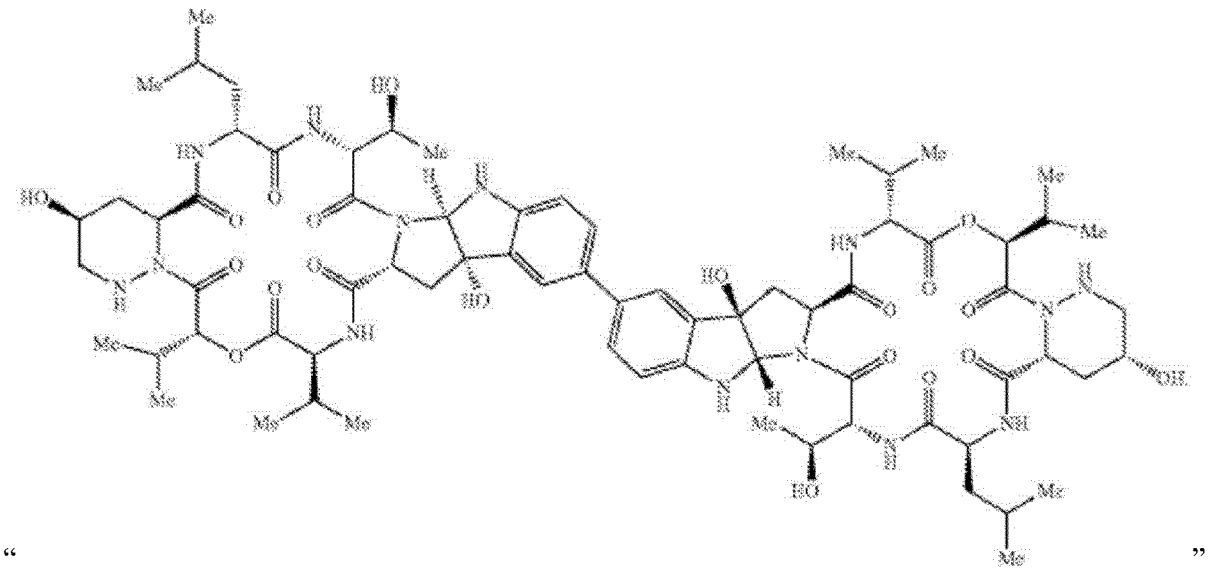

"

"

Should be replaced with:

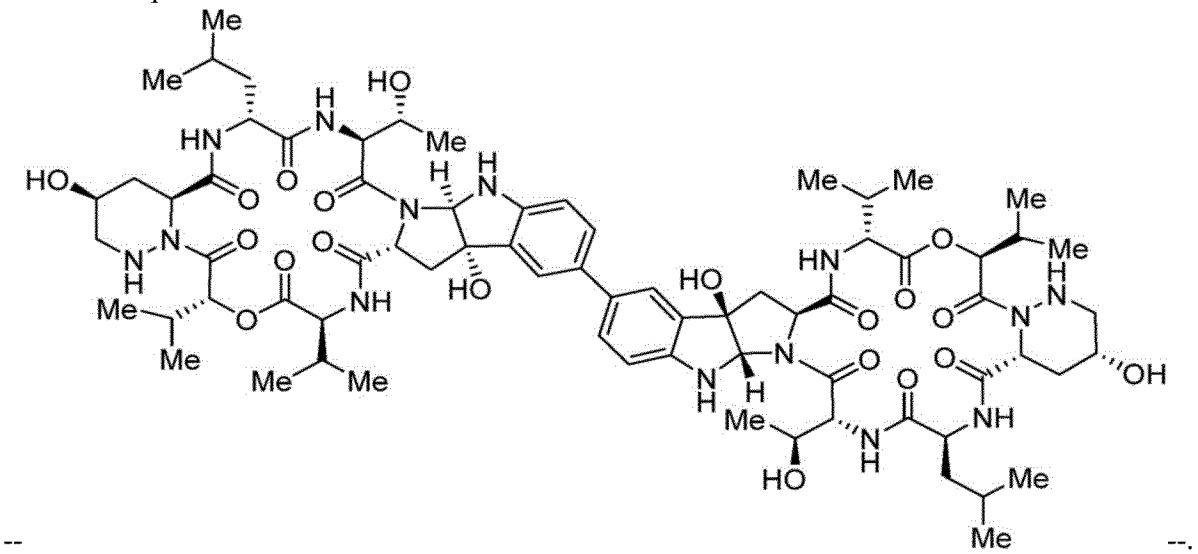

--          --.

CERTIFICATE OF CORRECTION (continued)
U.S. Pat. No. 12,030,888 B2

In Claim 13, at Column 295, the first formula should be replaced with:

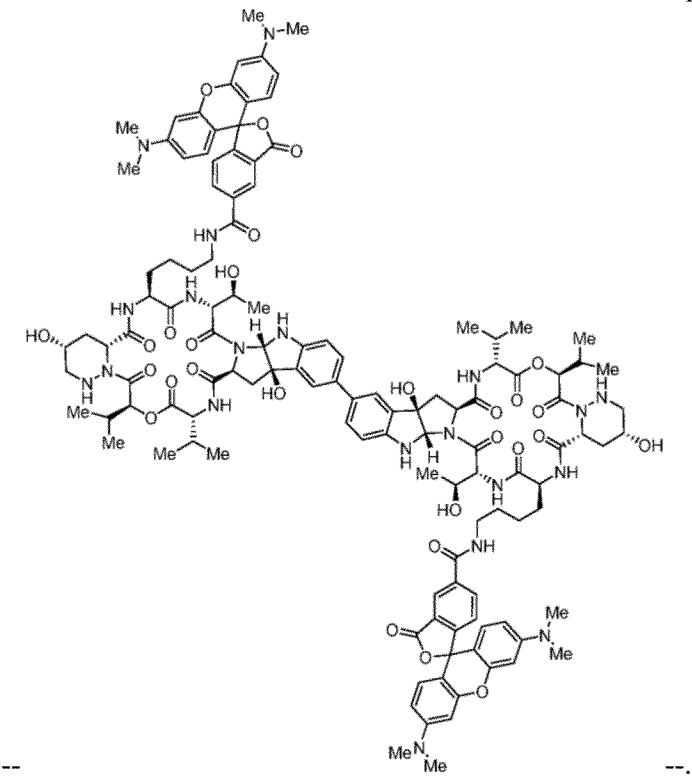

-- --.